US011795210B2

(12) United States Patent
Liu et al.

(10) Patent No.: US 11,795,210 B2
(45) Date of Patent: Oct. 24, 2023

(54) HIV VACCINES AND METHODS OF MAKING AND USING

(71) Applicant: Gilead Sciences, Inc., Foster City, CA (US)

(72) Inventors: Xinan Liu, Shanghai (CN); Azure T. Makadzange, Half Moon Bay, CA (US); Stephen R. Martin, Tiburon, CA (US); Hesham Shehata, Daly City, CA (US); Evguenia Svarovskaia, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 344 days.

(21) Appl. No.: 16/928,571

(22) Filed: Jul. 14, 2020

(65) Prior Publication Data

US 2021/0017255 A1 Jan. 21, 2021

Related U.S. Application Data

(60) Provisional application No. 62/874,712, filed on Jul. 16, 2019.

(51) Int. Cl.
| | | |
|---|---|---|
| C07K 16/10 | (2006.01) | |
| C07K 16/28 | (2006.01) | |
| C12N 15/10 | (2006.01) | |
| A61K 9/14 | (2006.01) | |
| A61K 45/06 | (2006.01) | |

(52) U.S. Cl.
CPC ............ C07K 16/1045 (2013.01); A61K 9/14 (2013.01); A61K 45/06 (2013.01); C07K 16/2818 (2013.01); C07K 16/2827 (2013.01); C12N 15/1082 (2013.01)

(58) Field of Classification Search
None
See application file for complete search history.

(56) References Cited

U.S. PATENT DOCUMENTS

| | | |
|---|---|---|
| 6,303,334 B1 | 10/2001 | Holler et al. |
| 6,440,730 B1 | 8/2002 | Von Laer et al. |
| 6,610,476 B1 | 8/2003 | Chang et al. |
| 7,153,509 B2 | 12/2006 | Haynes et al. |
| 7,172,761 B2 | 2/2007 | Haynes et al. |
| 7,195,768 B2 | 3/2007 | Haynes et al. |
| 7,425,611 B2 | 9/2008 | Lal et al. |
| 7,488,485 B2 | 2/2009 | Narayan et al. |
| 7,612,173 B2 | 11/2009 | Abrecht et al. |
| 7,618,642 B2 | 11/2009 | zur Megede et al. |
| 7,655,235 B2 | 2/2010 | Ertl |
| 7,820,786 B2 | 10/2010 | Thomson et al. |
| 7,935,805 B1 | 5/2011 | Barnett et al. |
| 7,943,375 B2 | 5/2011 | Barnett et al. |
| 7,951,377 B2 | 5/2011 | Korber et al. |
| 7,981,430 B2 | 7/2011 | Hanke et al. |
| 8,000,900 B2 | 8/2011 | Heckerman et al. |
| 8,071,107 B2 | 12/2011 | Haynes et al. |
| 8,119,140 B2 | 2/2012 | Korber et al. |
| 8,119,144 B2 | 2/2012 | Gupta et al. |
| 8,263,394 B2 | 9/2012 | zur Megede et al. |
| 8,452,541 B2 | 5/2013 | Kirovski et al. |
| 8,452,542 B2 | 5/2013 | Zemla et al. |
| 8,478,535 B2 | 7/2013 | Jojic et al. |
| 8,541,230 B2 | 9/2013 | Barnett et al. |
| 8,592,205 B2 | 11/2013 | Pinschewer et al. |
| 8,697,084 B2 | 4/2014 | Weiner et al. |
| 8,735,542 B2 | 5/2014 | Gupta et al. |
| 8,795,685 B2 | 8/2014 | Renard et al. |
| 9,011,873 B2 | 4/2015 | Korber et al. |
| 9,011,875 B2 | 4/2015 | Korber et al. |
| 9,017,691 B2 | 4/2015 | Barouch et al. |
| 9,044,445 B2 | 6/2015 | Korber et al. |
| 9,309,289 B2 | 4/2016 | Pinschewer et al. |
| 9,342,786 B2 | 5/2016 | Krause et al. |
| 9,376,471 B2 | 6/2016 | Weiner et al. |
| 9,492,532 B2 | 11/2016 | Korber et al. |
| 9,501,614 B2 | 11/2016 | Ortoleva |
| 9,670,253 B2 | 6/2017 | Barouch et al. |
| 9,725,768 B2 | 8/2017 | Santos et al. |
| 9,732,121 B2 | 8/2017 | Foung et al. |

(Continued)

FOREIGN PATENT DOCUMENTS

| | | |
|---|---|---|
| EP | 1921146 A1 | 5/2008 |
| EP | 1682666 B1 | 12/2008 |

(Continued)

OTHER PUBLICATIONS

International Preliminary Report on Patentability and Written Opinion dated Jan. 27, 2022 for Intl. Appl. No. PCT/US2020/041945 (7 pages).
Notice of Allowance dated Apr. 20, 2022 for Taiwanese Patent Application No. 109124087 (5 pages).
Office Action and Search Report dated Aug. 20, 2021 for Taiwanese Patent Application No. 109124087 (7 pages).
Abbink P et al. (2018), "Rapid Cloning of Novel Rhesus Adenoviral Vaccine Vectors", Journal of Virology, vol. 92, Issue 6, e01924-17.
Amacker M et al. (2020), "New GMP manufacturing processes to obtain thermostable HIV-1 gp41 virosomes under solid forms for various mucosal vaccination routes", npj Vaccines 5:41.
Apostolico J et al. (2016), "Adjuvants: Classification, Modus Operandi, and Licensing", Journal of Immunology Research, vol. 2016, Article ID 1459394, 16 pgs.

(Continued)

Primary Examiner — Misook Yu
Assistant Examiner — Sarah A Alsomairy

(57) ABSTRACT

Provided are HIV-1 fusion polypeptides, polynucleotides encoding such fusion polypeptides, vectors expressing such fusion polypeptides for use in eliciting an immune response against HIV-1; pharmaceutical and immunogenic compositions and kits comprising such fusion polypeptides, polynucleotides or vectors, and methods of use in treating and/or preventing HIV-1. Further provided are methods for design of antiviral vaccines, including vaccines to elicit an immune response against HIV-1.

12 Claims, 66 Drawing Sheets

Specification includes a Sequence Listing.

(56) References Cited

U.S. PATENT DOCUMENTS

| | | |
|---|---|---|
| 9,821,053 B2 | 11/2017 | Korber et al. |
| 9,833,506 B2 | 12/2017 | Lambkin-Williams et al. |
| 9,844,589 B2 | 12/2017 | Haynes et al. |
| 9,844,590 B2 | 12/2017 | Korber et al. |
| 9,855,329 B2 | 1/2018 | Korber et al. |
| 9,913,895 B2 | 3/2018 | Yamamoto |
| 9,944,952 B2 | 4/2018 | Pinschewer et al. |
| 9,988,425 B2 | 6/2018 | Brander et al. |
| 10,004,800 B2 | 6/2018 | Haynes et al. |
| 10,010,606 B2 | 7/2018 | Korber et al. |
| 10,285,942 B2 | 5/2019 | Luo |
| 10,722,564 B2 | 7/2020 | Pinschewer et al. |
| 11,254,712 B2 * | 2/2022 | Chappell .............. C07K 14/005 |
| 2007/0077257 A1 | 4/2007 | Emini et al. |
| 2010/0047276 A1 | 2/2010 | Heeney et al. |

FOREIGN PATENT DOCUMENTS

| | | | |
|---|---|---|---|
| EP | 1667523 B1 | 11/2012 | |
| EP | 2604695 A1 | 6/2013 | |
| EP | 2238255 B1 | 9/2013 | |
| EP | 3218504 B1 | 7/2020 | |
| JP | 2018-527366 A | 9/2018 | |
| WO | WO-2005028634 A2 * | 3/2005 | ............. A61K 39/12 |
| WO | WO-2009/083210 A1 | 7/2009 | |
| WO | WO-2010/059732 A1 | 5/2010 | |
| WO | WO-2014/160747 A2 | 10/2014 | |
| WO | WO-2015/048785 A2 | 4/2015 | |
| WO | WO-2016/049287 A1 | 3/2016 | |
| WO | WO-2016/054654 A1 | 4/2016 | |
| WO | WO-2016/075250 A1 | 5/2016 | |
| WO | WO-2017/044850 A1 | 3/2017 | |
| WO | WO-2017/048727 A1 | 3/2017 | |
| WO | WO-2017/106638 A1 | 6/2017 | |
| WO | WO-2017/198726 A1 | 11/2017 | |
| WO | WO-2018/075559 A1 | 4/2018 | |
| WO | WO-2018/098362 A1 | 5/2018 | |
| WO | WO-2018/195357 A1 | 10/2018 | |
| WO | WO-2018/208856 A1 | 11/2018 | |
| WO | WO-2018/227030 A1 | 12/2018 | |
| WO | WO-2019/036688 A1 | 2/2019 | |
| WO | WO-2019/050994 A1 | 3/2019 | |
| WO | WO-2019/070730 A1 | 4/2019 | |
| WO | WO-2019/075112 A1 | 4/2019 | |
| WO | WO-2019/104203 A1 | 5/2019 | |
| WO | WO-2019/133853 A1 | 7/2019 | |
| WO | WO-2021/003348 A1 | 1/2021 | |

OTHER PUBLICATIONS

Bahbouhi B et al. (2002), "Effects of L- and D-REKR amino acid-containing peptides on HIV and SIV envelope glycoprotein precursor maturation and HIV and SIV replication", Biochem. J. 366, 863-872.

Bajracharya R et al. (2019), "Recent Advancements in Non-Invasive Formulations for Protein Drug Delivery", Computational and Structural Biotechnolgy Journal 17: 1290-1308.

Chen X et al. (2013), "Fusion Protein Linkers: Property, Design and Functionality", Adv Drug Deliv Rev. 65(10): 1357-1369.

Chng J et al. (2015), "Cleavage efficient 2A peptides for high level monoclonal antibody expression in CHO cells", mAbs 7:2, 403-412.

Donnelly M L L et al. (2001), "The 'cleavage' activities of foot-and-mouth disease virus 2A site-directed mutants and naturally occurring '2A-like' sequences", Journal of General Virology, 82, 1027-1041.

Dorta-Estremera S et al. (2017), "Minimally invasive monitoring of CD4 T cells at multiple mucosal tissues after intranasal vaccination in rhesus macaques", PLoS ONE 12(12): e0188807.

Gaiha G D et al. (2019), "Structural topology defines protective CD8+ T cell epitopes in the HIV proteome", Science 364, 480-484.

Guo J et al. (2018), "Development of novel vaccine vectors: Chimpanzee adenoviral vectors", Human Vaccines & Immunotherapeutics 2018, vol. 14, No. 7, 1679-1685.

Hamid M A et al. (2019), "Enriched HLA-E and CD94/NKG2A interaction limits antitumor CD8+ tumor-infiltrating T lymphocyte responses", Cancer Immunol Res, vol. 7, Issue 8.

Intl. Search Report-Written Opinion dated Nov. 3, 2020 for Intl. Appl. No. PCT/US2020/041945.

Karpenko L I et al. (2012), "Attenuated *Salmonella enteritidis* E23 as a vehicle for the rectal delivery of DNA vaccine coding for HIV-1 polyepitope CTL immunogen", Microbial Biotechnology 5(2), 241-250.

Liu H et al. (2017), "Introducing a cleavable signal peptide enhances the packaging efficiency of lentiviral vectors pseudotyped with Japanese encephalitis virus envelope proteins", Virus Research 229, 9-16.

Martins M A et al. (2017), "Vaccine-induced immune responses against both Gag and Env improve control of simian immunodeficiency virus replication in rectally challenged rhesus macaques", PLOS Pathog 13(7): e1006529.

McMichael A J et al. (2019), "Topological perspective on HIV escape", Science 364 (6439), 438-439.

Ndhlovu Z M et al. (2019), "Augmentation of HIV-specific T cell function by immediate treatment of hyperacute HIV-1 infection", Sci. Transl. Med. 11, eaau0528.

Oconnor G M et al. (2015), "Peptide-Dependent Recognition of HLA-B*57:01 by KIR3DS1", Journal of Virology, vol. 89, No. 10, 5213-5221.

Patterson L J et al. (2012), "Replicating Adenovirus-Simian Immunodeficiency Virus (SIV) Vectors Efficiently Prime SIV-Specific Systemic and Mucosal Immune Responses by Targeting Myeloid Dendritic Cells and Persisting in Rectal Macrophages, Regardless of Immunization Route", Clinical and Vaccine Immunology, vol. 19, No. 5, p. 629-637.

Sanchez-Trincado, J L et al. (2017), "Fundamentals and Methods for T- and B-Cell Epitope Prediction", Journal of Immunology Research, vol. 2017, Article ID 2680160, 14 pgs.

Shah R R et al. (2017), "Overview of Vaccine Adjuvants: Introduction, History, and Current Status", Chapter 1, in Vaccine Adjuvants: Methods and Protocols, Methods in Molecular Biology, vol. 1494.

Trolle T et al. (2016), "The length distribution of class I restricted T cell epitopes is determined by both peptide supply and MHC allele specific binding preference", J Immunol. 196(4): 1480-1487.

Tuyishime S et al. (2018), "Correlates of Protection Against $SIV_{mac251}$ Infection in Rhesus Macaques Immunized With Chimpanzee-Derived Adenovirus Vectors", EBioMedicine 31:25-35.

Wallis J et al. (2019), "Novel approaches for the design, delivery and administration of vaccine technologies", Clinical and Experimental Immunology, 196: 189-204.

Xu H et al. (2017), "Mucosal Vaccination with Heterologous Viral Vectored Vaccine Targeting Subdominant SIV Accessory Antigens Strongly Inhibits Early Viral Replication", EBioMedicine 18:204-215.

Zou C et al. (2019), "Effective Suppression of HIV-1 Replication by Cytotoxic T Lymphocytes Specific for Pol Epitopes in Conserved Mosaic Vaccine Immunogens", Journal of Virology, vol. 93, Issue 7, e02142-18.

Office Action dated Jul. 28, 2023 for Japanese Patent Application No. 2022-502457.

Examination Report dated Feb. 7, 2023 for Canadian Patent Application No. 3,145,791 (8 pages).

Office Action dated Mar. 10, 2023 for Japanese Patent Application No. 2022-502457 (3 pages).

Hepler N L et al. (2014), "IDEPI: Rapid Prediction of HIV-1 Antibody Epitopes and Other Phenotypic Features from Sequence Data Using a Flexible Machine Learning Platform", Plos Comput Biol, vol. 10, No. 9, article No. e1003842 (pp. 1-10).

* cited by examiner

INPUT: Viral Sequence Data Set

↓

1: Identify conserved regions

↓

2: Build multivalent (bivalent) sequences in conserved regions

↓

3: Identify intra-patient diversity within conserved regions

↓

4: Peptide MHC (class I and/or class II) binding prediction

↓

5: Generate longer peptides including MHC I binding segments

↓

6: Add peptide segments including class II epitopes

↓

7: Check cross-recognition with human proteins

↓

8: Rearrange epitopes and conserved region sequences to reduce creation of neoepitope at junctions

*Fig. 1*

1. Conservation analysis to identify conserved regions (> 80% or 90% conservation)

2. Further selection of conserved regions based on conservation and known immunogenicity:
   (i)    include regions > 90% conservation;
   (ii)   remove short segments < 35 bp;
   (iii)  remove weakly immunogenic or non-immunogenic segments; and
   (iv)   for application to HIV: include conserved part of NEF from 3. Build multivalent (bivalent) sequences with conserved walking analysis (CWA) algorithm for each selected region and connect them in the same order as viral reference sequence coordinates by direct fusion or via a linker (*e.g.*, a polyalanine or proteolytic cleavage sequence), as described herein

INTER-patient diversity

| | | | |
|---|---|---|---|
| Patient 1 | QNLQGQMVH | QAISPRTL | NAWVKVVKAF ... |
| Patient 2 | QNLQGQMVH | QAISPRTL | NAWVKVEKAF ... |
| Patient 3 | QNLQGQMVH | QAISPRTL | NAWVKVEKAF ... |
| Patient 4 | QNLQGQMVH | QAISPRTL | NAWVKIVKAF ... |
| Patient 5 | QNLQGQMVH | QAISPRTL | NAWVKVEKAF ... |
| Patient 6 | QNLQGQMVH | QAISPRTL | NAWVKIEKAF ... |
| Patient 7 | QNLQGQMVH | QAISPRTL | NAWVKVVKAF ... |
| Patient 8 | QNIQGQMVH | QAISPRTL | NAWVKIVKAF ... |
| Patient 9 | QNIQGQMVH | QAISPRTL | NAWVKVVKAF ... |
| Patient 10 | PNIQGQMVH | QAISPRTL | NAWVKIVKAF ... |

QAISPRTLN x10

INTRA-patient diversity

| | | | |
|---|---|---|---|
| Patient 1 | | | |
| Virus 1 | QNLQGQMVH | QAISPRTL | NAWVKVVKAF ... |
| Virus 2 | QNLQGQMVH | QATSPRTL | NAWVKVEKAF ... |
| Virus 3 | QNLQGQMVH | QATSPRTL | NAWVKVVKAF ... |
| Virus 4 | QNLQGQMVH | QATSPRTL | NAWVKVVKAF ... |
| Virus 5 | QNLQGQMVH | QAISPRTL | NAWVKVVKAF ... |
| Virus 6 | QNLQGQMVH | QAISPRTL | NAWVKVVKAF ... |
| Virus 7 | QNLQGQMVH | QAISPRTL | NAWVKVVKAF ... |
| Virus 8 | QNLQGQMVH | QAISPRTL | NAWVKVVKAF ... |
| Virus 9 | QNLQGQMVH | QAISPRTL | NAWVKVVKAF ... |
| Virus 10 | QNLQGQMVH | QAISPRTL | NAWVKVVKAF ... |

QAISPRTLN x6
QATSPRTLN x4

*Fig. 6*

| HIV Peptide | HLA Allele | Human Protein 9-mer | Human Protein |
|---|---|---|---|
| HPPQAGPVA | B07:02 | VPLQAGPVQ | sp\|P15822\|ZEP1 |
| | | MPGQAGPVG | sp\|P35247\|SFTPD |
| | | QYRQAGPVI | sp\|Q8NCI6\|GLBL3 |
| | | TATQAGLVF | sp\|P41440\|S19A1 |
| | | HTKQAGLVV | sp\|O00522\|KRIT1 |
| | | GTRQAGLVA | sp\|Q6ZRI0\|OTOG |
| | | VPLQAGPVQ | sp\|P15822\|ZEP1 |

Fig. 8

```
┌─────────────────────────────────────────────┐
│ Conservation Analysis to identify conserved │
│   regions (> 80% or 90% conservation)       │
└─────────────────────────────────────────────┘
                      ↓
┌─────────────────────────────────────────────┐
│   Build multivalent (bivalent) sequences    │
│     with CWA for each conserved region      │
└─────────────────────────────────────────────┘
                      ↓
┌─────────────────────────────────────────────┐
│ *In-silico* HLA binding prediction on all 9-mers in the │
│ sequences built in the previous step. Only keep 9- │
│ mers that have predicted high binding affinity to │
│ specific HLA allele(s) (*e.g.*, HLA-A*0201). │
└─────────────────────────────────────────────┘
                      ↓
┌─────────────────────────────────────────────┐
│    Human proteome analysis on all the       │
│   remaining 9-mers. Remove 9-mers that have │
│    cross-conservation with human peptides.  │
└─────────────────────────────────────────────┘
                      ↓
┌─────────────────────────────────────────────┐
│  Improve arrangement of remaining 9-mers    │
│     to reduce possible junction response    │
└─────────────────────────────────────────────┘
                      ↓
┌─────────────────────────────────────────────┐
│ Add Class II epitopes at the N- and/or C- termini of sequence │
└─────────────────────────────────────────────┘
```

*Fig. 10A*

Conservation Analysis to identify conserved regions (> 80% or 90% conservation)

↓

Building multivalent (bivalent) sequences with CWA for each conserved region

↓

*In-silico* HLA binding prediction on all 9-mers in the sequences built in the previous step. Only keep 9-mers that have predicted high binding affinity to specific HLA allele (*e.g.*, HLA-A*0201).

↓

Human proteome analysis on all the remaining 9-mers. Remove 9-mers have cross-conservation with human peptides.

↓

Flanking the remaining 9-mers with the most conserved 8aa segments upstream and downstream to create 25aa long peptides

↓

Improve arrangement of 25-mers to reduce possible junction response

↓

Add Class II epitopes at the N- and/or C- termini of sequence

*Fig. 10B*

```
┌─────────────────────────────────────────────────────────┐
│   Conservation Analysis to identify conserved           │
│   regions (> 80% or 90% bivalent conservation)          │
└─────────────────────────────────────────────────────────┘
                            ↓
┌─────────────────────────────────────────────────────────┐
│ Build multivalent (bivalent) sequences with CWA for each conserved region │
└─────────────────────────────────────────────────────────┘
                            ↓
┌─────────────────────────────────────────────────────────┐
│   Identify intra-patient 9-mer variants within conserved regions │
│   using deep sequencing data of a target individual     │
└─────────────────────────────────────────────────────────┘
                            ↓
┌─────────────────────────────────────────────────────────┐
│ *In silico* HLA binding prediction on all 9-mer variants. Remove all the │
│ 9-mers in the positions that are associated with potential escape epitopes │
│ for the target individual. In other positions, only keep 9-mers that have │
│ predicted high binding affinity to the target individual's HLA alleles │
└─────────────────────────────────────────────────────────┘
                            ↓
┌─────────────────────────────────────────────────────────┐
│   Human proteome analysis on all the remaining 9-mers.  │
│   Remove 9-mers have cross-conservation with human peptides. │
└─────────────────────────────────────────────────────────┘
                            ↓
┌─────────────────────────────────────────────────────────┐
│ Flanking the remaining 9-mers with the most conserved 8aa │
│ segments upstream and downstream to create 25aa long peptide │
└─────────────────────────────────────────────────────────┘
                            ↓
┌─────────────────────────────────────────────────────────┐
│   Improve arrangement of 25-mers to                     │
│   reduce possible junction response                     │
└─────────────────────────────────────────────────────────┘
                            ↓
┌─────────────────────────────────────────────────────────┐
│ Add Class II epitopes at the N- and/or C- termini of sequence │
└─────────────────────────────────────────────────────────┘
```

*Fig. 13*

```
┌─────────────────────────────────────────────────┐
│   Conservation Analysis to identify conserved   │
│     regions (> 80% or 90% conservation)         │
└─────────────────────────────────────────────────┘
                        ↓
┌─────────────────────────────────────────────────────────────┐
│ Build multivalent (bivalent) sequences with CWA for each conserved region │
└─────────────────────────────────────────────────────────────┘
                        ↓
┌─────────────────────────────────────────────────────────────┐
│ Identify intra-patient 9-mer variants within conserved regions │
│ using deep sequencing data from dataset containing only sequences │
│ from individuals that express target HLA allele (e.g., A*0201) │
└─────────────────────────────────────────────────────────────┘
                        ↓
┌─────────────────────────────────────────────────────────────┐
│ In silico HLA binding prediction on all 9-mer variants. Remove all the 9-mers in │
│ the positions that are associated with potential escape epitopes. In other positions, │
│ only keep 9-mers that have predicted high binding affinity to target HLA allele(s). │
└─────────────────────────────────────────────────────────────┘
                        ↓
┌─────────────────────────────────────────────────────────────┐
│ Human proteome analysis on all the remaining 9-mers. Remove 9-mers │
│ that have cross-recognition/cross-conservation with human peptides. │
└─────────────────────────────────────────────────────────────┘
                        ↓
┌─────────────────────────────────────────────────────────────┐
│ Flanking the remaining 9-mers with the most conserved 8aa │
│ segments upstream and downstream to create 25aa long peptide │
└─────────────────────────────────────────────────────────────┘
                        ↓
┌─────────────────────────────────────────────────────────────┐
│         Improve arrangement of 25-mers to                    │
│         reduce possible junction response                    │
└─────────────────────────────────────────────────────────────┘
                        ↓
┌─────────────────────────────────────────────────────────────┐
│ Add Class II epitopes at the N- and/or C- termini of sequence │
└─────────────────────────────────────────────────────────────┘
```

*Fig. 14*

MRVKEKYQHLWRWGWRWGTMLLGMLMICSATEKLWVTVYYGVPVWKEATTTLFCASDAKAYDTEVHNVWATHACVPTDPNPQEVVLVNVTENFN
                              CSATEKLWVTVYYGVPVWKEATTTL     KAYDTEVHNVWATHACVPTDPNPQE
                                   LWVTVYYGVPVWKE                    NVWATHACV
                                     VTVYYGVPV

MWKNDMVEQMHEDIISLWDQSLKPCVKLTPLCVSLKCTDLKNDTNTNSSSGRMIMEKGEIKNCSFNISTSIRGKVQKEYAFFYKLDIIPIDNDT
                   DQSLKPCVKLTPLCVTLNCTDLRNT
                         KLTPLCVTL

TSYKLTSCNTSVITQACPKVSFEPIPIHYCAPAGFAILKCNNKTFNGTGPCTNVSTVQCTHGIRPVVSTQLLLNGSLAEEEVVIRSVNFTDNAK
                                  GTGPCTNVSTVQCTHGIRPVVSTQL
                                     NVSTVQCTHGIRPVVSTQLLLNGSLAEE
                                           STVQCTHGI

TIIVQLNTSVEINCTRPNNNTRKRIRIQRGPGRAFVTIGKIGNMRQAHCNISRAKWNNTLKQIASKLREQFGNNKTIIFKQSSGGDPEIVTHSF
NCGGEFFYCNSTQLFNSTWFNSTWSTEGSNNTEGSDTITLPCRIKQIINMWQKVGKAMYAPPISGQIRCSSNITGLLLTRDGGNSNNESEIFRP
GGGDMRDNWRSELYKYKVVKIEPLGVAPTKAKRRVVQREKRAVGIGALFLGFLGAAGSTMGAASMTLTVQARQLLSGIVQQQNNLLRAIEAQQH
MRDNWRSELYKYKVV KRRVVQREKRAVGIGAMFLGFLGAAGSTMGAASITLTVQARQLLSGIVQQQNNLLRAIEAQQH

LLQLTVWGIKQLQARILAVERYLKDQQLLGIWGCSGKLICTTAVPWNASWSNKSLEQIWNHTTWMEWDREINNYTSLIHSLIEESQNQQEKNEQ
LLQLTVWGIKQLQARVLAVERYLKDQQLLGIWGCSGKLICTTAVPW
YLKDQQLLGIWGCSGKLICTT
GIWGCSGKL

ELLELDKWASLWNWFNITNWLWYIKLFIMIVGGLVGLRIVFAVLSIVNRVRQGYSPLSFQTHLPTPRGPDRPEGIEEEGGERDRDRSIRLVNGS
LALIWDDLRSLCLFSYHRLRDLLLIVTRIVELLGRRGWEALKYWWNLLQYWSQELKNSAVSLLNATAIAVAEGTDRVIEVVQGACRAIRHIPRR
IRQGLERILL

Fig. 16

```
MGARASVLSGGELDRWEKIRLRPGGKKKYKLKHIVWASRELERFAVNPGLLETSEGCRQILGQLQPSLQTGSEELRSLYNTVATLYCVHQRIEI
MGARASVLSGGELDRWEKIRLRPGGKKKYRLKHIVWASRELERFAVNPGLLET
                              LKHIVWASRELERFAVNPGLLET
                                    ASRELERFAVNPGLLL

KDTKEALDKIEEEQNKSKKKAQQAAADTGHSNQVSQNYPIVQNIQGQMVHQAISPRTLNAWVKVVEEKAFSPEVIPMFSALSEGATPQDLNTML
                              VSQNFPIVQN    ISPRTLNAWVKVVEEKAFSPEVIPMFSALSEGATPQDLNTML
                                        RTLNAWVKV              LSEGATPQDLNTML
                                                                     DLNTML

NTVGGHQAAMQMLKETINEEAAEWDRVHPVHAGPIAPGQMREPRGSDIAGTTSTLQEQIGWMTNNPPIPVGEIYKRWIILGLNKIVRMYSPTSI
NTVGGHQAAMQMLKETINEEAAEWDRLHPVHAGPIAPGQMREPRGSDIAGTTSTLQEQIGWMTNNPPIPVGEIYKRWIILGLNKIVRMYSPTSI
NTVGGHQAAMQ                                         PVGEIYKRWIILGLNKIVRMYSPTSI
NTV                                                       WIILGLNKIVRMYSPTSI

LDIRQGPKEPFRDYVDRFYKTLRAEQASQEVKNWMTETLLVQNANPDCKTILKALGPAATLEEMMTACQGVGGPGHKARVLAEAMSQVTNSATI
LDIRQGPKEPFRDYVDRFYKTLRAEQASQEVKNWMTETLLVQNANPDCKTILKALGPAATLEEMMTACQGVGGPGHKARVLAEAMSQ
 GPKEPFRDYVDRFYKTLRAEQASQEV                    ILKALGPAATLEEMMTACQGVGGPG
      YVDRFYKTLRAEQASQEV                            LGPAATLEEMMTACQGVGGPGHKAR
                                                          ATLEEMMTA
                                                          EMMTACQGV

MMQRGNFRNQ

```
MGGKWSKSSVVIGWPTVRERMRRAEPAADRVGAASRDLEKHGAITSSNTAATNAACAWLEAQEEEEVGFPVTPQVPLRPMTYKAAVDLSHFLKEK
                                                                       EEVGFPVKPQVPLRPMTFKGALDLSHFLREK
                                                                       EEVGFPVKPQVPLRPMTFKGALDLSHFLREK
                                                                                      YKAAVDLSHFLREK

GGLEGLIHSQRRQDILDLWIYHTQGYFPDWQNYTPGPGVRYPLTFGWCYKLVPVEPDKIEEANKGENTSLLHPVSLHGMDDPEREVLEWRFDSR
GGLEG         TQGFFPDWQNYTPE
GGLE                             GPGIRYPLLTFGWCFKLPVEPEKVE
GGLEGAAY                          PGIRFPLTFGWCFKLVPL
                                        LTFGWCFKL

LAFHHVARELHPEYFKNC
```

Fig. 18

```
FFREDLAFLQGKAREFSSEQTRANSPTRRELQVWGRDNNSPSEAGADRQGTVSENFPQVTLWQRPLVTIKIGGQLKEALLDTGADDTVLEEMS
                                                          FPQITLWQRPLVTIKIGGQLKEALLDTGADDTVLEEMN

LPGRWKPKMIGGIGGFIKVRQYDQILIEICGHKAIGTVLVGPTPVNIIGRNLLTQIGCTLNFPISPIETVPVKLKPGMDGPKVKQWPLTEEKIK
LPGRWKPKMIGGIGGFIKVRQYDQ               GTVLVGPTPVNIIGRNLLTQIGCTLNFPISPIETVPVKLKPGMDGPKVKQWPLTEEKIK
LPGKWKPKMIGGIGGFIKVKQYDQ                              NLLTQIGCTLNFPISPIETVPVKLK
                                                              TLNFPISPI

ALVEICTEMEKEGKISKIGPENPYNTPVFAIKKKDSTKWRKLVDFRELNKRTQDFWEVQLGIPHPAGLKKKKSVTVLDVGDAYFSVPLDEDEFRK
ALVEICTEMEKEGKISKIGPENPYNTPVFAIKKKDSTKWRKLVDFRELNKRTQDFWEVQLGIPHPAGLKKKKSVTVLDVGDAYFSVPLDKDFRK
VTVLDVGDAYFSVPLDKDFRK

YTAFTIPSINNETPGIRYQYNVLPQGWKGSPAIFQSSMTKILEPFRKQNPDIVIYQYMDDLYVGSDLEIGQHRTKIEELRQHLLR
YTAFTIPSINNETPGIRYQYNVLPQGWKGSPAIFQSSMT      FRKQNPDIVIYQYMDDLYVGSDLEIGQHR
YTAFTIPS NNETPGIRYQYNVLPQGWKGSPAIF            KQNPDIVIYQYMDDLYVGSDLEIGQ
         YQYNVLPQG                              NPDIVIYQYMDDLYVGSDLEIGQHR
                                                  IVIYQYMDDLYVGSDLEIGQHR
                                                    VIYQYMDD
                                                     YQYMDDLYV
                                                       YMDDLYVGS
```

*Fig. 19A*

```
WGLTTPDKKHQKEPPFLWMGYELHPDKWTVQPIVLPEKDSWTVNDIQKLVGKLNWASQIYPGIKVRQLCKLLRGTKALTEVIPLTEEAELELAE
WGFTTPDKKHQKEPPFLWMGYELHPDKWTVQPIVLPEKDSWTVNDIQKLVGKLNWASQIYPGIKV
WGLTTPDKKHQKDPPFLWMGYELHPDRWTVQPI
      KKHQKEPPFLWMGYELHPDKWTVQP
         KEPPFLWMGYELHPDKWTVQPIVLPEK
              FLWMGYELH
                 ELHPDKWTV
                         IVLPEKDSWTVNDIQKLVGKLNWAS
                            VLPEKDSWTVNDIQKLVGKLNWASQ
                             LPEKDSWTVNDIQKLVGKLNWASQIYPGIKV
                                  SWTVNDIQKLVGKLNWASQIYPGIK
                                       WTVNDIQKL
                                         TVNDIQKLV
                                              KLVGKLNWA

NREILKEPVHGVYYDPSKDLIAEIQKQGQGQWTYQIYQEPFKNLKTGKYARMRGAHTNDVKQLTEAVQKITTESIVIWGKT
PKFKLPIQKETWETWWTEYWQATWIPEWEFVNTPPLVKLWYQLEKEPIVGAETFYVDGAANRETKLGKAGYVTNRGRQKVVTLTDTTNQKTELQ
PKFKLPIQKETWETWWTEYWQATWIPEWEFVNTPPLVKLWYQLEKEPIVGAETFYVDGAANRETK
                 WETWWTEYWQATWIPEWEFVNTPPL
                       WQATWIPEW

AIYLALQDSGLEVNIVTDSQYALGIIQAQPDQSESELVNQIIEQLIKKEKVYLAWVPAHKGIGGNEQVDKLVSAGIRKVLFLDGIDKAQDEHEK
     QDSGLEVNIVTDSQYALGIIQAQPD                    KEKVYLAWVPAHKGIGGNEQVDKLVS
           IVTDSQYAL
```

Fig. 19B

YHSNWRAMASDFNLPPVVAKEIVASCDKCQLKGEAMHGQVDCSPGIWQLDCTHLEGKVILVAVHVASGYIEAEVIPAETGQETAYFLLKLAGRW
VAKEIVASCDKCQLKGEAMHGQVDCSPGIWQLDCTHLEGKIILVAVHVASGYIEAEVIPAETGQETAYFLLKLAGRW
QLKGEAMHGQVDCSPGIWQLDCTHL
QVDCSPGIWQLDCTHLEGKIILVAV
GQVDCSPGI
WQLDCTHLE

PVKTIHTDNGSNFTGATVRAACWWAGIKQEFGIPYNPQSQGVVESMNKELKKIIGQVRDQAEHLKTAVQMAVFIHNFKRKGGIGGYSAGERIVD
PVKT SNFTSTTVKAACWWAGIKQEFGIPY
TVKAACWWAGIKQEFGIPYNPQSQGVVESMNKELKKIIGQVRDQAEHLKTAVQMAVFIHNFKRKGGIGGYSAGERIVD
TVKAACWWAGIKQEFGIPYNPQSQGVVESMNKELKKIIGQVRDQAEHLKTAVQMAVFIHNFKRKGGIGGYSAGERIVD
KAACWWAGI

IIATDIQTKELQKQITKIQNFRVYYRDSRNPLWKGPAKLLWKGEGAVVIQDNSDIKVVPRRKAKIIRDYGKQMAGDDCVASRQDED
IIA AITKIQNFRVYYRDSRDPLWKGPAKLLWKGEGAVVIQDNSDIKVVPRRKAKIIRDYGKQMAGDDCVASRQDED
II ITKLQNFRVYYRDNRDPLWKGPARLLWKGEGAVVIQDNSEIKVVPRRKVKIIRDYGKRMAGDDCVAGRQDED
VYYRDSRDPLWKGPAKLLWKGEGAV AKIIRDYGKQMAGDDCVASRQDED
DPLWKGPAKLLWKGEGAVVIQDNSD KQMAGDDCV
PLWKGPAKLLWKGEGAVVIQDNSDI
PLWKGPAKL
KLLWKGEGA
LLWKGEGAV

*Fig. 21A-B*

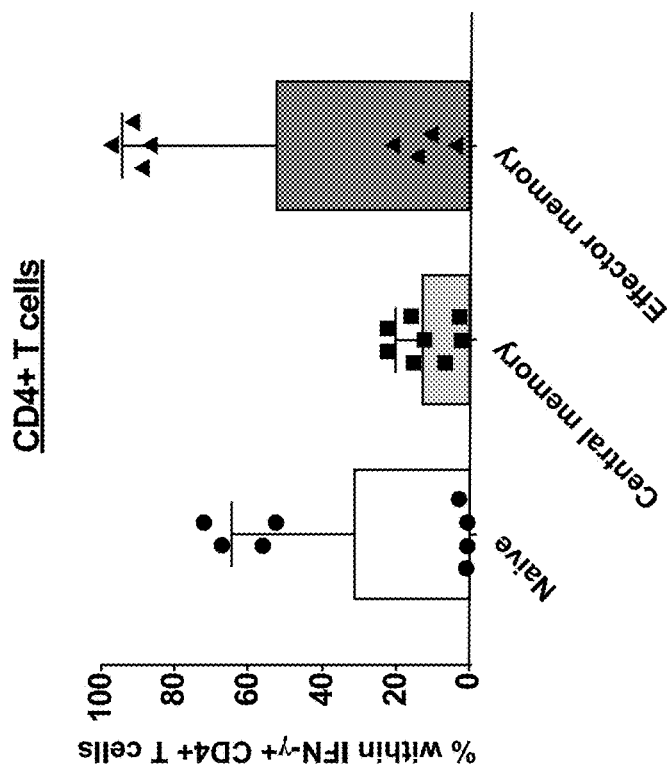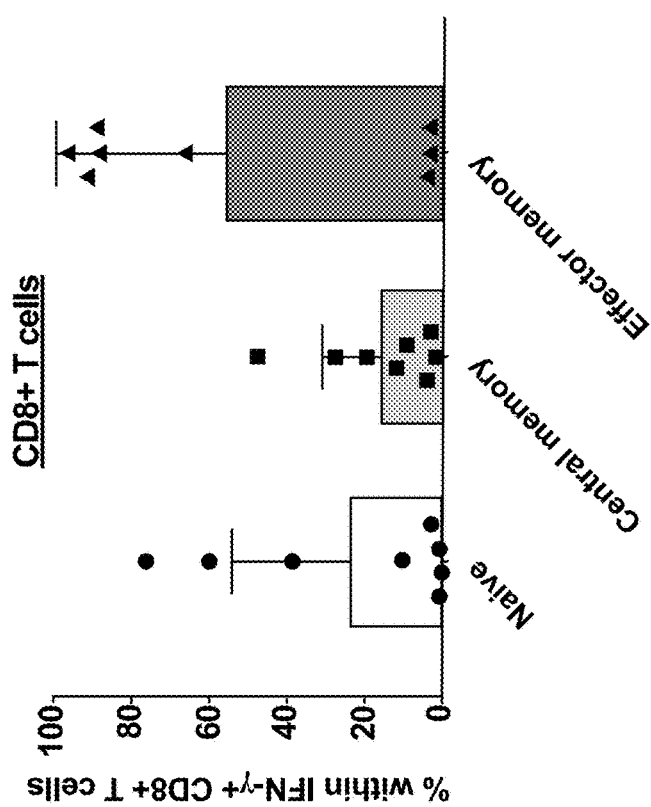
Fig. 30B

HIV VACCINES AND METHODS OF MAKING AND USING

CROSS-REFERENCE TO RELATED APPLICATIONS

This application claims the benefit under 35 U.S.C. § 119(e) of U.S. Provisional Patent Application No. 62/874,712, filed on Jul. 16, 2019, which is hereby incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Jun. 30, 2020, is named 1314_PC_SL.txt and is 446,538 bytes in size.

BACKGROUND

Human immunodeficiency virus type 1 (HIV-1) infection is a serious, life-threatening disease and remains one of the leading causes of morbidity and mortality worldwide, with approximately 36.9 million people infected globally and 1.1 million people infected in the United States (US) (National Center for HIV/AIDS Viral Hepatitis STD & TB Prevention: Division of HIV/AIDS Prevention, HIV in the United States and Dependent Areas. January. 2019; UNAIDS, 2017 Global HIV Statistics. Fact Sheet—July. 2018). Combination antiretroviral therapy (cART) for HIV-1 infection has led to significant improvements in morbidity and mortality by suppressing viral replication, preserving immunologic function, and averting the progression to AIDS. However, despite cART, HIV-1 infection results in chronic immune activation and increased risk of non-AIDS-related morbidity and mortality.

In the early phase of infection, HIV-1 integrates into the genome of memory cluster determinant 4 (CD4) T cells, a subset of which forms a long-lived reservoir of HIV-1 infected cells that persist despite treatment with antiretroviral therapy (ART) (Siliciano, et al., Nature Medicine (2003) 9(6):727-728). Eradication of the viral reservoir is a component of any HIV cure strategy. Immune based therapies can be a further component of a combination approach to HIV cure or ART-free viral remission and can include T cell and antibody-based vaccines, passive administration of antibodies and immune modulators.

The development of HIV T cell specific vaccines has primarily focused in designing immunogens that provide universal coverage by addressing global HIV viral diversity. HIV-1 is defined by 4 groups (group M, N, O and P). Subtypes or clades (labeled A-K) and several cross clade recombinant forms within Group-M cause the majority of human disease. Strategies to design vaccines that address enormous global viral sequence diversity include in-silico designed polyvalent mosaic immunogens that capture common epitope variants within potential T cell epitopes (Fischer, et al., Nat Med, (2007) 13(1):100-6). These may be expressed as full-length artificial proteins or artificial recombinant proteins from regions with a high degree of sequence conservation (Ondondo, et al., Mol Ther, (2016) 24(4):832-42; Barouch, et al., Cell, (2013) 155(3):531-9). Subsequent iterations to the in-silico design algorithm led to the development of a computationally faster graph-based approach known as epigraph (Theiler, et al., Sci Rep, (2016) 6:33987). These design approaches can be used to develop a single global vaccine or be tailored to the clades circulating within a certain population and geography. These approaches focus exclusively on viral diversity, however, and do not consider the host genetic diversity that drives antigen presentation and T cell recognition, and subsequent emergence of immune-driven escape variants.

Antigen specific CD4+ and CD8+ T cells are associated with the control of viremia during acute infection and are associated with slow disease progression and control of viremia in individuals who maintain low viral load in the absence of ART (elite controllers). Antigen specific T cells recognize viral epitopes presented on MHC class I and II molecules. Human leukocyte antigen (HLA) class I alleles have been associated with HIV control in genome wide association studies (GWAS) (Fellay, et al., Science, 2007. 317(5840):944-7; International, H.I.V.C.S., et al., Science, (2010) 330(6010):1551-7). These proteins present antigenic peptides from sequences to induce effector and memory T cells. Current approaches to generating candidate vaccines for HIV-1 have focused on viral sequence diversity without adequately modelling the process of epitope generation across a range of host HLA alleles. This complex process of antigen presentation and T cell priming includes proteosomal cleavage, TAP transport, cross-presentation, MHC binding and peptide-MHC complex stability and ultimately TCR recognition (Yewdell, et al., Nat Rev Immunol, (2003) 3(12):952-61). Consequently, existing methods of generating T cell vaccines have had limited success, e.g., in some cases inducing on average only 4 responses per patient (see, e.g., Priddy, et al., Clin Infect Dis (2008) 46(11):1769-81; Sekaly, et al., J Exp Med. (2008) 205(1): 7-12; and Iaccino, et al., Retrovirology. (2008) 5:56).

In addition, highly variant viruses such as HIV-1 provide unique challenges due to the high level of sequence diversity and a host immune response that drives some of that sequence diversity. The role of the adaptive immune responses in driving diversity in HIV-1 has been well described, and results in changes in virus sequences over time (Goulder, et al., Nature, (2001) 412(6844):334-8; Kelleher, et al., J Exp Med, (2001) 193(3):375-86; Schneidewind, et al., J Virol, (2007) 81(22):12382-93; Kawashima, et al., Nature, (2009) 458(7238):641-5; Leslie, et al., Nat Med, (2004) 10(3):282-9; Phillips, et al., Nature, (1991) 354(6353):453-9). A large proportion of that diversity is driven by cytotoxic T lymphocytes that recognized peptide epitopes presented on MHC class I alleles. The selection pressure exerted by these T cell responses during chronic infection leads to HIV sequence adaptation. This sequence evolution drives the diversity of HIV-1 within individuals and across a population (Kawashima, et al., supra; Phillips, et al., supra). In addition, viral sequences are undergoing mutations that enable them to be hidden from host defenses. These sequences may resemble self-peptides or peptide sequences that induce central or peripheral tolerance. Standard vaccine design approaches may fail to account for viral sequence variants and may lead to inefficient use of vaccine capacity by including sequences that may induce responses that may cross react with self-antigens.

The impact of vaccines on human health cannot be overstated. Most of these are preventative vaccines, however, and have been effective in inducing usually neutralizing antibodies against infectious disease targets. The development of therapeutic vaccines has largely been advanced in cancer immunotherapeutics where the focus has been on developing vaccines that generate antigen specific T cells. Many tumor-associated or tumor-specific antigens are self-antigens and require the design of vaccines that need to overcome immune tolerance. Recent innovations in the identification and prediction of neoantigens that arise from cancer specific mutations, provide potential targets that may not be subject to central or peripheral tolerance mechanisms. Various informatics strategies have been established to support the identification of neoantigens and predict their ability to elicit strong T cell responses (see, e.g., Bulik-Sullivan, et al., Nature Biotech (2019) 37:55-63). In the development of therapeutic vaccines against HIV, the antigenic targets are defined by the virus. Tools to predict the capacity of those viral sequences to be effectively presented and stimulate an immune response are less well-defined. This is relevant within the context of HIV, where a high mutation rate coupled with host immune mediated selection pressure result in the establishment of highly variable quasi-species. We have therefore developed informatics tools that allow for the identification of conserved viral sequences in population-based consensus sequences or by individual deep sequencing of isolates and can predict presentation, priming of T cells and HLA driven escape pathways that are useful in designing HIV vaccine immunogens.

SUMMARY

Provided herein are at least the following embodiments. Additional embodiments are described in the detailed embodiments and examples herein.

Fusion Polypeptides

Embodiment 1: A fusion polypeptide comprising a plurality of polypeptide segments of one or more human immunodeficiency virus-1 (HIV-1) proteins encoded by one or more HIV genes selected from Gag, Nef, Env, Pol, Rev, Tat, Rev, Vif, Vpr and Vpu.

Embodiment 2: The fusion polypeptide of embodiment 1, wherein the plurality of polypeptide segments comprises or consists of only polypeptide segments encoded by HIV-1 genes Env, Gag, Nef and Pol, e.g. does not comprise polypeptide segments encoded by HIV-1 Tat, Rev, Vif, Vpr and/or Vpu genes.

Embodiment 3: The fusion polypeptide of embodiment 1, wherein the plurality of polypeptide segments comprises or consists of only polypeptide segments encoded by HIV-1 genes Gag, Nef and Pol, e.g. does not comprise polypeptide segments encoded by HIV-1 Env, Tat, Rev, Vif, Vpr and/or Vpu genes.

Embodiment 4: The fusion polypeptide of embodiment 1, wherein the plurality of polypeptide segments comprises or consists of only polypeptide segments encoded by HIV-1 genes Gag and Nef, e.g. does not comprise polypeptide segments encoded by HIV-1 Env, Pol, Tat, Rev, Vif, Vpr and/or Vpu genes.

Embodiment 5: The fusion polypeptide of embodiment 1, wherein the plurality of polypeptide segments comprises or consists of only polypeptide segments encoded by HIV-1 genes Pol and Nef, e.g. does not comprise polypeptide segments encoded by HIV-1 Env, Gag, Tat, Rev, Vif, Vpr and/or Vpu genes.

Embodiment 6: The fusion polypeptide of embodiment 1, wherein the plurality of polypeptide segments comprises or consists of only polypeptide segments encoded by HIV-1 genes Pol and Env, e.g. does not comprise polypeptide segments encoded by HIV-1 Gag, Nef, Tat, Rev, Vif, Vpr and/or Vpu genes.

Embodiment 7: The fusion polypeptide of embodiment 1, wherein the plurality of polypeptide segments comprises or consists of only polypeptide segments encoded by HIV-1 Pol gene, e.g. does not comprise polypeptide segments encoded by HIV-1 Env, Gag, Nef, Tat, Rev, Vif, Vpr and/or Vpu genes.

Embodiment 8: The fusion polypeptide of any one of embodiments 1 to 7, wherein the plurality of polypeptide segments does not contain a segment encoded by one, two, three or four of HIV Tat, Rev, Vif, Vpr and Vpu genes.

Embodiment 9: The fusion polypeptide of any one of embodiments 1 to 8, wherein the polypeptide segments are derived from conserved regions in a population of viral proteome sequences.

Embodiment 10: The fusion polypeptide of embodiment 9, wherein the conserved regions are greater than 80%, 81%, 82%, 83%, 84%, 85%, 86%, 87%, 88%, 89%, 90%, 91%, 92%, 93%, 94%, 95%, 96%, 97%, 98% or 99% conserved amongst HIV-1 species in interpatient populations.

Embodiment 11: The fusion polypeptide of any one of embodiments 9 to 10, wherein the conserved regions are conserved amongst one or more of HIV-1 clades A-K, e.g., one or more of clades A, B, C, D and G, or recombinant forms of one or more of HIV-1 clades A-K, and combinations thereof.

Embodiment 12: The fusion polypeptide of any one of embodiments 1 to 11, comprising at least 5 and up to 40 polypeptide segments, e.g. from 5 polypeptide segments and up to 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40 polypeptide segments.

Embodiment 13: The fusion polypeptide of any one of embodiments 1 to 12, wherein each polypeptide segment is at least 8 amino acids in length, and up to about 30, e.g., up to about 50, e.g., up to about 100, e.g., up to about 250 amino acids in length, e.g. from at least 8 amino acids in length up to 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 45, 50, 55, 60, 65, 70, 75, 80, 85, 90, 95, 100, 110, 120, 130, 140, 150, 160, 170, 180, 190, 200, 210, 220, 230, 240 or 250 amino acids in length.

Embodiment 14: The fusion polypeptide of any one of embodiments 1 to 13, wherein the full-length of the fusion polypeptide comprises at least about 350 amino acids and up to about 1000 amino acids, e.g., at least about 350 amino acids and up to about 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 or 1000 amino acids.

Embodiment 15: The fusion polypeptide of any one of embodiments 1 to 13, wherein the full-length of the fusion polypeptide comprises at least about 500 amino acids and up to about 1000 amino acids, e.g., at least about 500 amino acids and up to about 550, 560, 570, 580, 590, 600, 610, 620, 630, 640, 650, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 or 1000 amino acids.

Embodiment 16: The fusion polypeptide of any one of embodiments 1 to 13, wherein the full-length of the fusion polypeptide comprises or consists of only polypeptide segments encoded by HIV-1 genes Gag, Nef and Pol and is at least about 700 amino acids and up to about 800 amino acids, e.g., at least about 700 amino acids and up to about 710, 720, 730, 740, 750, 760, 770, 780, 790 or 800 amino acids in length (e.g., SEQ ID NOs: 345-350, 422-423 are illustrative fusion polypeptides).

Embodiment 17: The fusion polypeptide of any one of embodiments 1 to 13, wherein the full-length of the fusion polypeptide comprises or consists of only polypeptide segments encoded by HIV-1 genes Gag and Nef and is at least about 340 amino acids and up to about 500 amino acids, e.g., at least about 340 amino acids and up to about 350, 360, 370, 380, 390, 400, 410, 420, 430, 440, 450, 460, 470, 480, 490 or 500 amino acids in length, inclusive of an optional N-terminal signal peptide (e.g., SEQ ID NOs: 351-356, 430 are illustrative fusion polypeptides).

Embodiment 18: The fusion polypeptide of any one of embodiments 1 to 13, wherein the full-length of the fusion polypeptide comprises or consists of only polypeptide segments encoded by HIV-1 genes Pol and Env and is at least about 335 amino acids and up to about 970 amino acids, e.g., at least about 335 amino acids and up to about 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960 or 970, amino acids in length, inclusive of an optional N-terminal signal peptide (e.g., SEQ ID NOs: 357-366 are illustrative fusion polypeptides).

Embodiment 19: The fusion polypeptide of any one of embodiments 1 to 13, wherein the full-length of the fusion polypeptide comprises or consists of only polypeptide segments encoded by HIV-1 genes Pol and is at least about 645 amino acids and up to about 675 amino acids, e.g., at least about 645 amino acids and up to about 650, 655, 660, 670, 675 or 680 amino acids in length (e.g., SEQ ID NOs: 407-410 are illustrative fusion polypeptides).

Embodiment 20: The fusion polypeptide of any one of embodiments 1 to 13, wherein the full-length of the fusion polypeptide comprises or consists of only polypeptide segments encoded by HIV-1 genes Env, Gag, Nef and Pol, and is at least about 360 amino acids and up to about 510 amino acids, e.g., at least about 360 amino acids and up to about 370, 380, 390, 400, 410, 420, 430, 440, 450, 460, 470, 480, 490, 500 or 510 amino acids in length, inclusive of an optional N-terminal signal peptide (e.g., SEQ ID NOs: 367-371, 424, 431-435 are illustrative fusion polypeptides).

Embodiment 21: The fusion polypeptide of any one of embodiments 1 to 13, wherein the full-length of the fusion polypeptide comprises or consists of only polypeptide segments encoded by HIV-1 genes Env, Gag, Nef and Pol, and is at least about 760 amino acids and up to about 955 amino acids, e.g., at least about 760 amino acids and up to about 770, 780, 790, 800, 810, 820, 830, 840, 850, 860, 870, 880, 890, 900, 910, 920, 930, 940, 950, 955 amino acids in length, inclusive of an optional N-terminal signal peptide (e.g., SEQ ID NOs: 373-377, 411 are illustrative fusion polypeptides).

Embodiment 22: The fusion polypeptide of any one of embodiments 1 to 14, wherein the full-length of the fusion polypeptide is no longer than 800 amino acids, e.g. no longer than 795, 790, 785, 780, 775, 770, 765, 760, 755, 750, 745, 740, 735, 730, 725, 720, 715, 710, 705 or 700 amino acids.

Embodiment 23: The fusion polypeptide of any one of embodiments 1 to 22, wherein each polypeptide segment comprises or consists of one or more predicted T cell epitopes.

Embodiment 24: The fusion polypeptide of any one of embodiments 1 to 23, comprising one or more polypeptide segments that bind to or are presented by one or more human HLA class I alleles (e.g. 1, 2, 3, 4, 5 or 6 alleles), e.g. within a single subject or amongst multiple patients.

Embodiment 25: The fusion polypeptide of any one of embodiments 1 to 24, comprising one or more polypeptide segments that bind to or are presented by at least one human HLA class I molecule, e.g., by a human A*0201 HLA class I molecule.

Embodiment 26: The fusion polypeptide of any one of embodiments 1 to 25, comprising one or more 8-mer, 9-mer and/or 10-mer polypeptide segments that are presented by one or more human HLA class I alleles (e.g. 1, 2, 3, 4, 5 or 6 alleles), e.g. within a single subject.

Embodiment 27: The fusion polypeptide of any one of embodiments 1 to 25, comprising one or more 25-mer polypeptide segments, each 25-mer polypeptide segment comprising one or more 8-mer, 9-mer and/or 10-mer polypeptide segments that are presented by one or more human HLA class I alleles (e.g. 1, 2, 3, 4, 5 or 6 alleles), e.g. within a single subject.

Embodiment 28: The fusion polypeptide of any one of embodiments 1 to 27, comprising one or more polypeptide segments that are intracellularly processed and presented by one or more human HLA class II alleles (e.g. 1, 2, 3, 4, 5 or 6 alleles), e.g. within a single subject.

Embodiment 29: The fusion polypeptide of any one of embodiments 1 to 28, wherein one or more of the polypeptide segments is abutted or fused to an adjacent segment.

Embodiment 30: The fusion polypeptide of any one of embodiments 1 to 28, wherein one or more of the polypeptide segments is joined to an adjacent segment by one or more peptide linkers.

Embodiment 31: The fusion polypeptide of embodiment 30, wherein the one or more peptide linkers is selected from one or more of a polyalanine linker, a polyglycine linker, a cleavable linker, a flexible linker, a rigid linker, a Nef linking sequence, and combinations thereof.

Embodiment 32: The fusion polypeptide of embodiment 31, wherein the polyalanine linker comprises or consists of 2 or 3 contiguous alanine residues, e.g. AA, AAA (SEQ ID NO: 378), AAY (SEQ ID NO: 379) or AAX (SEQ ID NO: 380), wherein X is any amino acid (e.g. A, C, D, E, F, G, H, I, K, L, M, N, P, Q, R, S, T, V, Y).

Embodiment 33: The fusion polypeptide of embodiment 31, wherein the flexible linker or polyglycine linker comprises or consists of GG, GGS (SEQ ID NO: 419), GSG (SEQ ID NO: 420) or GGGS (SEQ ID NO: 421).

Embodiment 34: The fusion polypeptide of embodiment 31, wherein the cleavable linker is selected from a 2A cleavable peptide (e.g. foot-and-mouth disease virus (F2A), equine rhinitis A virus (E2A), porcine teschovirus-1 (P2A) and Thosea asigna virus (T2A)), a furin recognition/cleavage sequence (e.g. REKR (SEQ ID NO: 382), RRKR (SEQ ID NO: 383), RAKR (SEQ ID NO: 381)), a Nef linking sequence, and combinations, derivatives or variants thereof.

Embodiment 35: The fusion polypeptide of embodiment 34, wherein the cleavable linker comprises or consists of a furin recognition/cleavage site selected from the group consisting of RAKR (SEQ ID NO: 381), REKR (SEQ ID NO: 382) and RRKR (SEQ ID NO: 383).

Embodiment 36: The fusion polypeptide of any one of embodiments 34 to 35, wherein the cleavable linker comprises or consists of the amino acid sequence that is at least 90%, 91%, 92%, 93%, 94%, 95%, 96%, 97%, 98% or at least 99% identical to ATNFSLLKQAGDVEENPGP (SEQ ID NO: 384), APVKQTLNFDLLKLAGDVESNPGP (SEQ ID NO: 385), RAKRAPVKQTLNFDLLKLAGD-VESNPGP (SEQ ID NO: 386), QCTNYALLKLAGD-VESNPGP (SEQ ID NO: 387), or EGRGSLLTCGDVEEN-PGP (SEQ ID NO: 388), or comprises or consists of the amino acid sequence of ATNFSLLKQAGDVEENPGP (SEQ ID NO: 384), APVKQTLNFDLLKLAGDVESNPGP (SEQ ID NO: 385), RAKRAPVKQTLNFDLLKLAGD-VESNPGP (SEQ ID NO: 386), QCTNYALLKLAGD-VESNPGP (SEQ ID NO: 387), or EGRGSLLTCGDVEEN-PGP (SEQ ID NO: 388).

Embodiment 37: The fusion polypeptide of embodiment 31, wherein the Nef linking sequence comprises or consists of an amino acid sequence that is at least 95%, 96%, 97%, 98% or 99% identical to VHAGPIA (SEQ ID NO: 389), VHAGPVA (SEQ ID NO: 390), or GALDI (SEQ ID NO:391), or comprises or consists of an amino acid sequence selected from VHAGPIA (SEQ ID NO: 389), VHAGPVA (SEQ ID NO: 390) and GALDI (SEQ ID NO: 391).

Embodiment 38: The fusion polypeptide of any one of embodiments 1 to 37, wherein the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, polypeptide segments selected from SEQ ID NOs: 1-344.

Embodiment 39: The fusion polypeptide of any one of embodiments 1 to 38, wherein the plurality of polypeptide segments comprises one or more segments of one or more viral proteins, or fragments or subsequences thereof, encoded by the HIV-1 Gag gene.

Embodiment 40: The fusion polypeptide of embodiment 39, wherein the one or more viral proteins encoded by the HIV-1 Gag gene is selected from p7, p17 and p24, and wherein the fusion polypeptide does not comprise any p6 proteins.

Embodiment 41: The fusion polypeptide of any one of embodiments 39 to 40, wherein the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from:
  SEQ ID NOs: 68-146 and 339-342;
  SEQ ID NOs: 68, 69, 72, 73, 74, 75, 76, 77, 80, 81, 82, 83, 84, 85, 86, 87, 88, 89, 92, 93, 101, 102, 103, 104, 109, 110, 115, 116, 125, 126, 127, 128, 129, 130, 131, 132, 133, 134, 135, 136, 139, 140, 141, 142, 143, 144, 145 and 146;
  SEQ ID NOs: 76, 77, 86, 87 and 92-124;
  SEQ ID NOs: 76, 77, 86, 87, 94 and 95;
  SEQ ID NOs: 76, 86 and 94;
  SEQ ID NOs: 77, 87 and 95;
  SEQ ID NOs: 68-79 and 92-124;
  SEQ ID NOs: 70-71, 76-77 and 94-95;
  SEQ ID NOs: 78, 79, 96, 99, 100, 107, 108, 113, 114, 121, 122, 123, 124, 137 and 138;
  SEQ ID NOs: 78, 99, 107, 113, 121, 123 and 137;
  SEQ ID NOs: 78, 79, 90, 91, 97, 98, 99, 100, 105, 106, 107, 108, 111, 112, 113, 114, 117, 118, 119, 120, 121, 122, 123, 124, 137 and 138;
  SEQ ID NOs: 78, 90, 97, 105, 111, 117, 119 and 137; and
  SEQ ID NOs: 78 and 137.

Embodiment 42: The fusion polypeptide of any one of embodiments 39 to 41, wherein the plurality of polypeptide segments comprises at least 2 polypeptide segments, e.g., at least 3, 4, 5, 6, 7, 8, 9, 10, 11, 12, 13, 14, 15, 16, 17, 18, 19, 20, or more, segments comprising or consisting of an HIV-1 Gag amino acid sequence corresponding to amino acid residue positions selected from 31-53, 37-51, 142-166, 175-199, 183-191, 257-282, 257-290, 265-282, 288-313, 288-321, 296-313, 333-357, 337-361, 341-349, 345-353 and 429-444, wherein the amino acid positions are with respect to SEQ ID NO:404.

Embodiment 43: The fusion polypeptide of any one of embodiments 39 to 42, wherein the plurality of polypeptide segments does not comprise 1, 2, 3, 4, 5, or more, polypeptide segments comprising or consisting of an HIV-1 Gag amino acid sequence corresponding to amino acid residue positions selected from 1-30, 54-127, 138-146, 370-428 and 445-500, or subsequences thereof, wherein the amino acid positions are with respect to SEQ ID NO:404.

Embodiment 44: The fusion polypeptide of any one of embodiments 39 to 43, wherein the plurality of polypeptide segments does not comprise 1, 2, 3, 4, 5, or more, polypeptide segments comprising or consisting of an HIV-1 Gag amino acid sequence of any one of SEQ ID NOs: 444-448, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 444-448, or subsequences thereof.

Embodiment 45: The fusion polypeptide of any one of embodiments 1 to 44, wherein the plurality of polypeptide segments comprises one or more segments of the viral protein encoded by the HIV-1 Nef gene.

Embodiment 46: The fusion polypeptide of embodiment 45, wherein the plurality of polypeptide segments comprises at least one polypeptide segment, e.g., at least 2, 3, 4, 5, 6, 7, 8, 9, 10, 11, 12, 13, 14, 15, 16, 17, 18, 19, 20, 21, 22, 23, 24, 25, or more, segments comprising or consisting of an amino acid sequence selected from:
  SEQ ID NOs: 147, 148, 149, 150, 151, 152, 153, 154, 155, 156, 157, 158, 159, 160, 161, 162, 163, 164, 165, 166, 167, 168, 169, 170, 171 and 172;
  SEQ ID NOs: 147, 148, 149, 150, 155, 156, 157, 158, 159, 160, 166, 167, 168, 169, 170 and 171;
  SEQ ID NOs: 149-152;
  SEQ ID NOs: 151 and 152;
  SEQ ID NOs: 149, 150, 151, 152, 159, 160, 161, 162, 163, 164, 166, 167, 168, 169, 170, 171, 172, 173 and 174;
  SEQ ID NOs: 151, 152, 161 and 162;
  SEQ ID NOs: 151 and 152;
  SEQ ID NOs: 153, 154, 172 and 173;
  SEQ ID NOs: 153 and 172;
  SEQ ID NOs: 153, 154, 155, 156, 157, 158, 163, 164, 165, 166, 167, 168, 169, 170, 171, 172 and 173;
  SEQ ID NOs: 153 and 165; and
  SEQ ID NO: 153.

Embodiment 47: The fusion polypeptide of any one of embodiments 45 to 46, wherein the plurality of polypeptide segments comprises at least 2 polypeptide segments, e.g., at least 3, 4, 5, 6, 7, 8, 9, 10, 11, 12, 13, 14, 15, or more, segments comprising or consisting of an HIV-1 Nef amino acid sequence corresponding to amino acid residue positions selected from 64-102, 81-102, 88-97, 91-99, 130-148, 130-154, 134-142, 134-148, 136-148, 137-145, 137-145 and 117-154, wherein the amino acid positions are with respect to SEQ ID NO:405.

Embodiment 48: The fusion polypeptide of any one of embodiments 45 to 47, wherein the plurality of polypeptide segments does not comprise 1, 2, 3, or more, polypeptide segments comprising or consisting of an HIV-1 Nef amino acid sequence corresponding to amino acid residue positions selected from 1-63, 103-116 and 155-206, or subsequences thereof, wherein the amino acid positions are with respect to SEQ ID NO:405.

Embodiment 49: The fusion polypeptide of any one of embodiments 45 to 48, wherein the plurality of polypeptide segments does not comprise 1, 2, 3, or more, polypeptide segments comprising or consisting of an HIV-1 Nef amino acid sequence of any one of SEQ ID NOs: 449-451, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 449-451, or subsequences thereof.

Embodiment 50: The fusion polypeptide of any one of embodiments 1 to 49, wherein the plurality of polypeptide segments comprises or consists of one or more segments of viral proteins encoded by the HIV-1 Gag and Nef genes.

Embodiment 51: The fusion polypeptide of embodiment 50, wherein the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from:
  SEQ ID NOs: 68-79 and 92-124, 149, 150, 151, 152, 159, 160, 161, 162, 163, 164, 166, 167, 168, 169, 170, 171, 172, 173 and 174;
  SEQ ID NOs: 70, 71, 76, 77, 94, 95, 151, 152, 161 and 162;
  SEQ ID NOs: 70, 76, 94, 151 and 161; and
  SEQ ID NOs: 71, 77, 95, 152 and 162.

Embodiment 52: The fusion polypeptide of any one of embodiments 1 to 4 and 8 to 51 comprising or consisting of the following polypeptide segments in sequential order, from N-terminus to C-terminus, optionally joined or connected by one or more linkers:
  SEQ ID NOs: 70, 76, 94, 151 and 161; or
  SEQ ID NOs: 71, 77, 95, 152 and 162.

Embodiment 53: The fusion polypeptide of any one of embodiments 1 to 52, wherein the plurality of polypeptide segments comprises or consists of an amino acid sequence of any one of SEQ ID NOs: 351-356 and 430, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 351-356 and 430.

Embodiment 54: The fusion polypeptide of any one of embodiments 1, 2, 6 and 9 to 53, wherein the plurality of polypeptide segments comprises one or more segments of one or more viral proteins encoded by the HIV-1 Env gene.

Embodiment 55: The fusion polypeptide embodiment 54, wherein the one or more viral proteins encoded by the HIV-1 Env gene is selected from gp120 and gp41.

Embodiment 56: The fusion polypeptide of any one of embodiments 54 to 55, wherein the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from:
  SEQ ID NOs: 1-67 and 338;
  SEQ ID NOs: 2, 3, 8, 9, 13, 14, 17, 18, 23, 24, 25, 26, 28, 29, 31, 32, 33, 34, 35, 36, 37, 38, 39, 40, 43, 44, 45, 46, 47, 48, 49, 50, 51, 52, 53, 54, 55, 56, 58, 59, 62, 63, 64, 65, 66 and 67;
  SEQ ID NOs: 4, 5, 6, 7, 11, 12, 13, 14, 15, 16, 28, 29, 30, 37, 38, 41, 42, 43, 44, 45, 46, 47, 48, 49, 50, 51, 52, 53, 54, 55, 56, 57, 58, 59, 60, 61 and 338;
  SEQ ID NOs: 4, 5, 6, 7, 11, 12, 13, 14, 15, 16, 28, 29, 30, 37, 38, 41 and 42;
  SEQ ID NOs: 28, 29, 30 and 41-56;
  SEQ ID NOs: 28, 29, 41 and 42;
  SEQ ID NOs: 4, 5, 6, 7, 11, 12, 13, 14, 15, 16, 37 and 38;
  SEQ ID NOs: 4, 5, 11, 12, 37 and 38;
  SEQ ID NOs: 6, 7, 15, 16, 21, 22, 30, 60 and 61;
  SEQ ID NOs: 6, 15, 21, 30 and 60;
  SEQ ID NOs: 1, 2, 3, 4, 5, 6, 7, 10, 11, 12, 13, 14, 15, 16, 19, 20, 27, 55, 56, 57, 58, 59, 60, 61 and 338;
  SEQ ID NOs: 1, 10, 19, 27, 55, 56 and 57; and
  SEQ ID NOs: 6, 15 and 60.

Embodiment 57: The fusion polypeptide of any one of embodiments 54 to 56, wherein the plurality of polypeptide segments comprises at least 2 polypeptide segments, e.g., at least 3, 4, 5, 6, 7, 8, 9, 10, 11, 12, 13, 14, or more, segments comprising or consisting of an HIV-1 Env amino acid sequence corresponding to amino acid residue positions selected from 28-52, 34-48, 34-47, 36-44, 59-83, 64-83, 66-83, 67-75, 113-137, 235-259, 586-594, 586-610, 589-606 and 594-602, wherein the amino acid positions are with respect to SEQ ID NO:403.

Embodiment 58: The fusion polypeptide of any one of embodiments 54 to 57, wherein the plurality of polypeptide segments does not comprise 1, 2, 3, 4, 5, 6, or more, polypeptide segments comprising or consisting of an HIV-1 Env amino acid sequence corresponding to amino acid residue positions selected from 1-27, 53-58, 84-112, 138-234, 269-474, 490-501, 611-856, or subsequences thereof, wherein the amino acid positions are with respect to SEQ ID NO:403.

Embodiment 59: The fusion polypeptide of any one of embodiments 54 to 57, wherein the plurality of polypeptide segments does not comprise 1, 2, 3, 4, 5, or more, polypeptide segments comprising or consisting of an HIV-1 Env amino acid sequence of any one of SEQ ID NOs: 437-443, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 437-443, or subsequences thereof.

Embodiment 60: The fusion polypeptide of any one of embodiments 1 to 58, wherein the plurality of polypeptide segments comprises or consists of one or more segments of one or more viral proteins encoded by the HIV-1 Pol gene.

Embodiment 61: The fusion polypeptide of embodiment 60, wherein the one or more viral proteins encoded by the HIV-1 Pol gene is selected from one or more of protease (PR), reverse transcriptase (RT), and integrase (INT).

Embodiment 62: The fusion polypeptide of any one of embodiments 60 to 61, wherein the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from:
  SEQ ID NOs: 174-337 and 343-344;
  SEQ ID NOs: 174, 175, 178, 179, 180, 181, 182, 183, 184, 185, 193, 194, 195, 196, 197, 198, 199, 200, 203, 204, 205, 206, 207, 208, 213, 214, 221, 222, 236, 237, 245, 246, 247, 248, 249, 250, 251, 252, 253, 254, 255, 256, 257, 258, 263, 264, 266, 267, 268, 269, 270, 271, 272, 273, 278, 279, 280, 281, 282, 283, 284, 285, 286, 287, 288, 289, 290, 291, 292, 293, 294, 295, 305, 306, 307, 308, 309, 310, 313, 314, 315, 316, 317, 318, 321 and 322;
  SEQ ID NOs: 180, 181, 182, 183, 184, 185, 186, 187, 190, 191, 192, 193, 194, 195, 196, 221, 222, 294, 295, 296, 297, 298, 299, 300, 301, 305, 306, 307, 308, 311, 312, 321, 322, 323, 324, 325, 326, 327, 328, 329, 330, 331, 332, 333, 334, 335, 336 and 337;
  SEQ ID NOs: 180, 181, 186, 187, 221, 222, 294, 295, 307, 308, 321 and 322;

SEQ ID NOs: 176, 177, 178, 179, 180, 181, 182, 183, 184, 185, 186, 187, 188, 189, 190, 191, 192, 193, 194, 195, 196, 197, 198, 199, 200, 201, 202, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 257, 258, 259, 260, 261, 262, 263, 264, 265, 266, 267, 282, 283, 294, 295, 296, 297, 298, 299, 300, 301, 302, 305, 306, 319, 320, 321, 322, 323, 324, 325, 326, 327, 328, 329, 330, 331, 332, 333, 334, 335, 336 and 337;

SEQ ID NOs: 176, 177, 188, 189, 213, 214, 223, 224, 259, 260, 282, 283, 294, 295, 305, 306, 319 and 320;

SEQ ID NOs: 180, 181, 186, 187, 221, 222, 294, 295, 321 and 322;

SEQ ID NOs: 182-202, 292-302, 305 and 306;

SEQ ID NOs: 188, 189, 294, 295, 305 and 306;

SEQ ID NOs: 176, 177, 178, 179, 180, 181, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 257, 258, 259, 260, 261, 262, 263, 264, 265, 266, 267, 282, 283, 319, 320, 321, 322, 323, 324, 325, 326, 327, 328, 329, 330, 331, 332, 333, 334, 335, 336 and 337;

SEQ ID NOs: 176, 177, 213, 214, 223, 224, 259, 260, 282, 283, 319 and 320;

SEQ ID NOs: 192, 201, 202, 215, 216, 217, 218, 219, 220, 229, 230, 231, 240, 241, 242, 243, 244, 265, 276, 277, 298, 299, 302, 311, 312, 327, 328, 331, 332, 333, 336 and 337;

SEQ ID NOs: 192, 201, 215, 217, 219, 229, 230, 240, 241, 243, 265, 276, 298, 302, 311, 327, 331, 333 and 336;

SEQ ID NOs: 190, 191, 192, 197, 198, 209, 210, 211, 212, 213, 214, 215, 216, 217, 218, 219, 220, 225, 226, 227, 228, 229, 230, 231, 232, 233, 234, 235, 238, 239, 261, 262, 274, 275, 276, 277, 296, 297, 298, 299, 300, 301, 302, 303, 304, 323, 324, 325, 326, 327, 328, 329, 330, 331, 332, 333, 334, 335, 336, 337, 343, 344, 375 and 376;

SEQ ID NOs: 190, 197, 209, 210, 211, 225, 227, 234, 238, 261, 296, 300, 303, 323, 325, 329 and 334; and SEQ ID NOs: 192, 215, 217, 219, 229, 230, 276, 298, 302, 327, 331, 333 and 336.

Embodiment 63: The fusion polypeptide of any one of embodiments 54 to 62, wherein the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from:

SEQ ID NOs: 4, 5, 6, 7, 11, 12, 13, 14, 15, 16, 28, 29, 30, 37, 38, 41, 42, 43, 44, 45, 46, 47, 48, 49, 50, 51, 52, 53, 54, 55, 56, 57, 58, 59, 60, 61, 176, 177, 178, 179, 180, 181, 182, 183, 184, 185, 186, 187, 188, 189, 190, 191, 192, 193, 194, 195, 196, 197, 198, 199, 200, 201, 202, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 257, 258, 259, 260, 261, 262, 263, 264, 265, 266, 267, 282, 283, 294, 295, 296, 297, 298, 299, 300, 301, 302, 305, 306, 319, 320, 321, 322, 323, 324, 325, 326, 327, 328, 329, 330, 331, 332, 333, 334, 335, 336, 337 and 338;

SEQ ID NOs: 4, 5, 6, 7, 11, 12, 13, 14, 15, 16, 28, 29, 30, 37, 38, 41, 42, 176, 177, 188, 189, 213, 214, 223, 224, 259, 260, 282, 283, 294, 295, 305, 306, 319 and 320;

SEQ ID NOs: 28, 29, 30, 41-56, 182-202, 292-302, 305 and 306;

SEQ ID NOs: 28, 29, 41, 42, 188, 189, 294, 295, 305 and 306;

SEQ ID NOs: 4, 5, 6, 7, 11, 12, 13, 14, 15, 16, 37, 38, 176, 177, 178, 179, 180, 181, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 257, 258, 259, 260, 261, 262, 263, 264, 265, 266, 267, 282, 283, 319, 320, 321, 322, 323, 324, 325, 326, 327, 328, 329, 330, 331, 332, 333, 334, 335, 336 and 337; and SEQ ID NOs: 4, 5, 11, 12, 37, 38, 176, 177, 213, 214, 223, 224, 259, 260, 282, 283, 319 and 320.

Embodiment 64: The fusion polypeptide of any one of embodiments 1, 6, 9 to 38 and 54 to 63, comprising or consisting of the following polypeptide segments in sequential order, from N-terminus to C-terminus, optionally joined or connected by one or more linkers:

SEQ ID NOs: 188, 305, 28, 41, 294, 4, 176, 11, 319, 259, 282, 223, 213 and 37;

SEQ ID NOs: 188, 305, 28, 41 and 294;

SEQ ID NOs: 4, 176, 11, 319, 259, 282, 223, 213 and 37;

SEQ ID NOs: 189, 306, 29, 42, 295, 5, 177, 12, 320, 260, 283, 224, 214 and 38;

SEQ ID NOs: 189, 306, 29, 42 and 295;

SEQ ID NOs: 5, 177, 12, 320, 260, 283, 224, 214 and 38;

SEQ ID NOs: 305, 319, 259, 282, 223, 213, 294, 176 and 188;

SEQ ID NOs: 306, 320, 260, 283, 224, 214, 295, 177 and 189;

SEQ ID NOs: 305, 294, 223, 213, 176, 259, 319, 188 and 282;

SEQ ID NOs: 306, 295, 224, 214, 177, 260, 320, 189 and 283;

SEQ ID NOs: 305, 294, 319, 259, 282, 223, 176, and 188;

SEQ ID NOs: 306, 295, 320, 260, 283, 224, 177 and 189;

SEQ ID NOs: 305, 223, 294, 176, 259, 319, 188 and 282; or

SEQ ID NOs: 306, 224, 295, 177, 260, 320, 189 and 283.

Embodiment 65: The fusion polypeptide of any one of embodiments 60 to 64, wherein the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 39, 30, or more, segments comprising or consisting of an HIV-1 Pol amino acid sequence corresponding to amino acid residue positions selected from 144-168, 152-160, 291-315, 326-350, 328-352, 330-354, 333-354, 334-342, 336-344, 338-346, 374-398, 380-404, 382-390, 388-396, 399-423, 400-424, 406-430, 553-577, 642-666, 650-658, 759-783, 767-775, 768-792, 776-784, 834-858, 940-964, 947-971, 948-956, 948-972, 955-963, 956-964, 980-1003 and 988-996, wherein the amino acid positions are with respect to SEQ ID NO:406.

Embodiment 66: The fusion polypeptide of any one of embodiments 60 to 65, wherein the plurality of polypeptide segments does not comprise 1, 2, 3, 4, 5, 6, 7, 8, 9, 10, or more, polypeptide segments comprising or consisting of an HIV-1 Pol amino acid sequence corresponding to amino acid residue positions selected from 1-55, 118-128, 321-325, 355-366, 432-541, 607-641, 667-682, 709-746, 828-833, 921-930, or subsequences thereof, wherein the amino acid positions are with respect to SEQ ID NO:406.

Embodiment 67: The fusion polypeptide of any one of embodiments 60 to 66, wherein the plurality of polypeptide segments does not comprise 1, 2, 3, 4, 5, or more, polypeptide segments comprising or consisting of an HIV-1 Pol amino acid sequence of any one of SEQ ID NOs: 452-461, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 452-461, or subsequences thereof.

Embodiment 68: The fusion polypeptide of any one of embodiments 1, 6 to 38, and 54 to 67, wherein the plurality of polypeptide segments comprises or consists of an amino acid sequence of any one of SEQ ID NOs: 357-366 and 407-410, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 357-366 and 407-410.

Embodiment 69: The fusion polypeptide of any one of embodiments 1, 3 and 8 to 68, wherein the plurality of polypeptide segments comprises or consists of segments of viral proteins encoded by Gag, Nef and Pol genes.

Embodiment 70: The fusion polypeptide of embodiment 69, wherein the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from:
  SEQ ID NOs: 76, 77, 86, 87, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 149, 150, 151, 152, 180, 181, 182, 183, 184, 185, 186, 187, 190, 191, 192, 193, 194, 195, 196, 221, 222, 294, 295, 296, 297, 298, 299, 300, 301, 305, 306, 307, 308, 311, 312, 321, 322, 323, 324, 325, 326, 327, 328, 329, 330, 331, 332, 333, 334, 335, 336, 337, 339, 340, 341 and 342; and
  SEQ ID NOs: 76, 77, 86, 87, 94, 95, 151, 152, 181, 182, 186, 187, 221, 222, 294, 195, 307, 308, 321, 322.

Embodiment 71: The fusion polypeptide of any one of embodiments 69 to 70, comprising or consisting of the following polypeptide segments in sequential order, from N-terminus to C-terminus, optionally joined or connected by one or more linkers:
  SEQ ID NOs: 76, 86, 94, 180, 186, 221, 294, 307, 321 and 151; or
  SEQ ID NOs: 77, 87, 95, 181, 187, 222, 295, 308, 322 and 152.

Embodiment 72: The fusion polypeptide of any one of embodiments 69 to 71, wherein the plurality of polypeptide segments comprises or consists of an amino acid sequence of any one of SEQ ID NOs: 345-350, the sequences in Table 1, and SEQ ID NOs: 422-424, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 345-350, the sequences in Table 1, and SEQ ID NOs: 422-424.

Embodiment 73: The fusion polypeptide of any one of embodiments 1 to 72, wherein the plurality of polypeptide segments comprises or consists of segments of viral proteins encoded by Gag, Pol, Env, and Nef genes, wherein each of the plurality of polypeptide segments can bind to or be presented by a human HLA allele A*0201.

Embodiment 74: The fusion polypeptide of embodiment 73, wherein each of the plurality of polypeptide segments are from 8-35 amino acids in length, e.g. from 9-34 amino acids in length, e.g. from 9-25 amino acids in length.

Embodiment 75: The fusion polypeptide of any one of embodiments 73 to 74, wherein the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from
  SEQ ID NOs: 6, 7, 15, 16, 21, 22, 30, 60, 61, 78, 79, 96, 99, 100, 107, 108, 113, 114, 121, 122, 123, 124, 137, 138, 153, 154, 172, 173, 192, 201, 202, 215, 216, 217, 218, 219, 220, 229, 230, 231, 240, 241, 242, 243, 244, 265, 276, 277, 298, 299, 302, 311, 312, 327, 328, 331, 332, 333, 336, and 337;
  SEQ ID NOs: 6, 15, 21, 30, 60, 78, 99, 107, 113, 121, 123, 137, 153, 172, 192, 201, 215, 217, 219, 229, 230, 240, 241, 243, 265, 276, 298, 302, 311, 327, 331, 333 and 336;
  SEQ ID NOs: 1, 2, 3, 4, 5, 6, 7, 10, 11, 12, 13, 14, 15, 16, 19, 20, 27, 55, 56, 57, 58, 59, 60, 61, 78, 79, 90, 91, 97, 98, 99, 100, 105, 106, 107, 108, 111, 112, 113, 114, 117, 118, 119, 120, 121, 122, 123, 124, 137, 138, 153, 154, 155, 156, 157, 158, 163, 164, 165, 166, 167, 168, 169, 170, 171, 172, 173, 190, 191, 192, 197, 198, 209, 210, 211, 212, 213, 214, 215, 216, 217, 218, 219, 220, 225, 226, 227, 228, 229, 230, 231, 232, 233, 234, 235, 238, 239, 261, 262, 274, 275, 276, 277, 296, 297, 298, 299, 300, 301, 302, 303, 304, 323, 324, 325, 326, 327, 328, 329, 330, 331, 332, 333, 334, 335, 336, 337, 338, 343 and 344;
  SEQ ID NOs: 1, 10, 19, 27, 55, 56, 57, 78, 90, 97, 105, 111, 117, 119, 137, 153, 165, 190, 197, 209, 210, 211, 225, 227, 234, 238, 261, 296, 300, 303, 323, 325, 329 and 334.

Embodiment 76: The fusion polypeptide of any one of embodiments 73 to 75, comprising or consisting of the following polypeptide segments in sequential order, from N-terminus to C-terminus, optionally joined or connected by one or more linkers:
  SEQ ID NOs: 201, 78, 107, 96, 229, 172, 327, 6, 333, 243, 331, 192, 265, 311, 137, 15, 123, 30, 336, 302, 153, 219, 298, 121, 230, 240, 60, 241, 276, 113, 99, 21, 217 and 215;
  SEQ ID NOs: 78, 296, 1, 339, 197, 329, 232, 323, 303, 234, 90, 261, 274, 238, 211, 325, 137, 227, 209, 190, 341, 57, 225, 27, 210, 119, 19, 165, 334, 117, 153, 10, 97 and 300; or
  SEQ ID NOs: 296, 1, 78, 197, 339, 227, 261, 274, 238, 325, 137, 329, 303, 234, 90, 232, 27, 57, 225, 323, 190, 341, 119, 19, 165, 334, 117, 153, 10, 97 and 300.

Embodiment 77: The fusion polypeptide of any one of embodiments 73 to 76, wherein the plurality of polypeptide segments comprises or consists of an amino acid sequence of any one of SEQ ID NOs: 367-377, 411, 431-435, or a sequence that is 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 367-377, 411, 431-435.

Embodiment 78: The fusion polypeptide of any one of embodiments 1 to 77, wherein the fusion polypeptide does not comprise the amino acid sequence YMDD (SEQ ID NO: 462) or YVDD (SEQ ID NO: 463).

Embodiment 79: The fusion polypeptide of embodiment 78, wherein the fusion polypeptide does not comprise one or more amino acid sequences selected from SEQ ID NOs: 215, 216, 217, 218, 219 and 220.

Embodiment 80: The fusion polypeptide of any one of embodiments 78 to 79, wherein the fusion polypeptide does not comprise one or more amino acid sequences selected from SEQ ID NOs: 209, 210, 211, 212, 213, 214, 343 and 344.

Embodiment 81: A fusion polypeptide comprising an amino acid sequence of SEQ ID NOs: 345-352, 357-362, 367, 373, 407-411 or 422-424, or a sequence that is at least 85%, 86%, 87%, 88%, 89%, 90%, 91%, 92%, 93%, 94%, 95%, 96%, 97%, 98%, or 99% identical to any one of SEQ ID NOs: 345-352, 357-362, 367, 373, 407-411, 422-424 and 431-435.

Embodiment 82: The fusion polypeptide of any one of embodiments 1 to 81, comprising an N-terminal signal peptide or leader sequence.

Embodiment 83: The fusion polypeptide of embodiment 82, wherein the signal peptide or leader sequence is from a source protein selected from a serum protein, a cytokine, a chemokine, a chaperone protein, an invariant protein, and a protein that directs proteins to the lysosomal compartment.

Embodiment 84: The fusion polypeptide of any one of embodiments 82 to 83, wherein the signal peptide or leader sequence is from a source protein selected from the group consisting of: colony stimulating factor 2 (CSF2, GM-CSF), tissue type plasminogen activator (PLAT, t-PA), C-C motif chemokine ligand 7 (CCL7, MCP-3), C-X-C motif chemokine ligand 10 (CXCL10, IP-10), catenin beta 1 (CTNNB1), CD74 (p33; DHLAG; HLADG; Ia-GAMMA, invariant chain), serum albumin (ALB), polyubiquitin B/C (UBB/UBC), calreticulin (CALR), vesicular stomatitis virus G protein (VSV-G), lysosomal associated membrane protein 1 (LAMP-1) and lysosomal associated membrane protein 2 (LAMP-2).

Embodiment 85: The fusion polypeptide of any one of embodiments 82 to 84, wherein the signal peptide or leader sequence is selected from an amino acid sequence of any one of SEQ ID NOs: 393-402 and 412-413, or a sequence that is at least 95%, 96%, 97%, 98%, or 99% identical to any one of SEQ ID NOs: 393-402 and 412-413.

Embodiment 86: The fusion polypeptide of any one of embodiments 1 to 85, wherein the fusion polypeptide is recombinantly produced or chemically synthesized.

Embodiment 87: The fusion polypeptide of any one of embodiments 1 to 86, wherein the fusion polypeptide is capable of inducing, promoting or stimulating an immune response in a human.

Embodiment 88: The fusion polypeptide of any one of embodiments 1 to 87, wherein the fusion polypeptide is capable of inducing, promoting or stimulating an immune response against HIV-1 in a human.

Embodiment 89: The fusion polypeptide of any one of embodiments 1 to 88, wherein the fusion polypeptide is capable of inducing, promoting or stimulating proliferation and/or activation of one or more cell types selected from monocyte-derived dendritic cells (DCs), CD8+ T cells and CD4+ T cells.

Polynucleotides, Lipoplexes, Expression Cassettes, Vectors, Host Cells

Embodiment 90: A polynucleotide encoding one or more fusion polypeptides of any one of embodiments 1 to 89.

Embodiment 91: The polynucleotide of embodiment 90, wherein the polynucleotide comprises or is in the form of cDNA, mRNA, self-amplifying RNA (SAM), self-replicating RNA, or self-amplifying replicon RNA (RepRNA).

Embodiment 92: The polynucleotide of embodiment 91, wherein the polynucleotide comprises one or more self-replicating or self-amplifying alphavirus replicons.

Embodiment 93: The polynucleotide of any one of embodiments 90 to 92, comprising a nucleic acid sequence of any one of SEQ ID NOs: 414-418, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 414-418.

Embodiment 94: A lipoplex, e.g., a lipid nanoparticle (LNP), comprising the polynucleotide of any one of embodiments 90 to 93.

Embodiment 95: An expression cassette, comprising a polynucleotide of any one of embodiments 90 to 93 operably linked to one or more regulatory sequences.

Embodiment 96: The expression cassette of embodiment 95, wherein the polynucleotide is operably linked to and under the control of a constitutive promoter.

Embodiment 97: The expression cassette of any of embodiments 95 to 96, wherein the promoter is selected from a CMV promoter, a CAG promoter and an EF1a promoter.

Embodiment 98: A vector comprising one or more polynucleotides of any one of embodiments 90 to 93, or an expression cassette of any one of embodiments 95 to 97.

Embodiment 99: The vector of embodiment 98, wherein the vector is a plasmid vector, a bacterial vector or a viral vector.

Embodiment 100: The vector of any one of embodiments 98 to 99, wherein the vector is a viral vector or a viral expression vector.

Embodiment 101: The vector of any one of embodiments 98 to 100, wherein the viral vector or viral expression vector is from a DNA virus or an RNA virus.

Embodiment 102: The vector of any one of embodiments 98 to 101, wherein the viral vector or viral expression vector is from a virus selected from the group consisting of adenovirus, adeno-associated virus, arenavirus, alphavirus, poxvirus, cytomegalovirus, rhabdovirus, vesicular stomatitis virus, flavivirus, maraba virus and vaccinia virus.

Embodiment 103: The vector of any one of embodiments 98 to 102, wherein the viral vector or the viral expression vector is from a virus from a taxonomical family selected from Adenoviridae, Arenaviridae, Herpesviridae (e.g. Cytomegalovirus), Poxviridae (e.g. Vaccinia virus, e.g. modified vaccinia Ankara (MVA)), Paramyxoviridae (e.g. measles virus), Flaviviridae (e.g. Yellow fever virus), Rhabdoviridae (e.g. Vesiculovirus, e.g. Maraba vesiculovirus), Togaviridae (e.g., Alphavirus).

Embodiment 104: The vector of any one of embodiments 98 to 103, wherein the viral vector or viral expression vector is an arenavirus vector selected from Lymphocytic choriomeningitis mammarenavirus (LCMV), Cali mammarenavirus (a.k.a., Pichinde mammarenavirus or Pichinde arenavirus), Guanarito virus (GTOV), Junin virus (JUNV), Lassa virus (LASV), Lujo virus (LUJV), Machupo virus (MACV), Sabia virus (SABV), and Whitewater Arroyo virus (WWAV).

Embodiment 105: The vector of embodiment 104, wherein the viral vector or viral expression vector is an arenavirus vector selected from Lymphocytic choriomeningitis mammarenavirus (LCMV) or Cali mammarenavirus (a.k.a. Pichinde mammarenavirus or Pichinde arenavirus).

Embodiment 106: The vector of any one of embodiments 98 to 103, wherein the viral vector or viral expression vector is a human adenovirus or a simian adenovirus (e.g., a chimpanzee adenovirus, a gorilla adenovirus or a rhesus adenovirus).

Embodiment 107: The vector of embodiment 106, wherein the viral vector or viral expression vector is an adenovirus vector selected from adenovirus serotype 5 (Ad5), adenovirus serotype 26 (Ad26), adenovirus serotype 34 (Ad34), adenovirus serotype 35 (Ad35), adenovirus serotype 48 (Ad48), chimpanzee adenovirus (e.g. ChAd3 (AdC3), ChAd5 (AdC5), ChAd6 (AdC6), ChAd7 (AdC7), ChAd8 (AdC8), ChAd9 (AdC9), ChAd10 (AdC10), ChAd11

(AdC11), ChAd17 (AdC17), ChAd16 (AdC16), ChAd19 (AdC19), ChAd20 (AdC20), ChAd22 (AdC22), ChAd24 (AdC24), ChAdY25, ChAd26 (AdC26), ChAd28 (AdC28), ChAd30 (AdC30), ChAd31 (AdC31), ChAd37 (AdC37), ChAd38 (AdC38), ChAd43 (AdC43), ChAd44 (AdC44), ChAd55 (AdC55), ChAd63 (AdC63), ChAdV63, ChAd68 (AdC68), ChAd73 (AdC73), ChAd82 (AdC82), ChAd83 (AdC83), ChAd143 (AdC143), ChAd144 (AdC144), ChAd145 (AdC145), ChAd147 (AdC147)), gorilla adenovirus (e.g. GC44, GC45, GC46) and rhesus adenovirus (e.g., RhAd51, RhAd52, RhAd53, RhAd54, RhAd55, RhAd56, RhAd57, RhAd58, RhAd59, RhAd60, RhAd61, RhAd62, RhAd63, RhAd64, RhAd65, RhAd66).

Embodiment 108: The vector of any one of embodiments 98 to 107, wherein the viral vector or viral expression vector is replication defective, replication deficient, replication attenuated or replication competent.

Embodiment 109: The vector of any one of embodiments 98 to 108, wherein the viral vector or viral expression vector is an adenoviral vector comprising one or more polynucleotides that encode one or more fusion proteins comprising an amino acid sequence of any one of any one of SEQ ID NOs: 345-377, 407-411, 422-424, 430-435, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 345-377, 407-411, 422-424, 430-435.

Embodiment 110: The vector of any one of embodiments 98 to 109, wherein the vector comprises two or more polynucleotides encoding two or more fusion proteins that are at least 80%, 81%, 82%, 83%, 84%, 85%, 86%, 87%, 88%, 89%, 90%, 91%, 92%, 93%, 94%, 95%, 96%, 97%, 98%, 99% identical, or 100% identical, to the following amino acid sequences: SEQ ID NOs: 345 and 346; SEQ ID NOs: 347 and 348; SEQ ID NOs: 349 and 350; SEQ ID NOs: 351 and 352; SEQ ID NOs: 430 and 352; SEQ ID NOs: 357 and 358; SEQ ID NOs: 360 and 362; SEQ ID NOs: 359 and 361; SEQ ID NOs: 351 and 357; SEQ ID NOs: 351 and 358; SEQ ID NOs: 351 and 359; SEQ ID NOs: 351 and 360; SEQ ID NOs: 351 and 361; SEQ ID NOs: 351 and 362; SEQ ID NOs: 351 and 407; SEQ ID NOs: 351 and 408; SEQ ID NOs: 351 and 409; SEQ ID NOs: 351 and 410; SEQ ID NOs: 352 and 357; SEQ ID NOs: 352 and 358; SEQ ID NOs: 352 and 359; SEQ ID NOs: 352 and 360; SEQ ID NOs: 352 and 361; SEQ ID NOs: 352 and 362; SEQ ID NOs: 352 and 407; SEQ ID NOs: 352 and 408; SEQ ID NOs: 352 and 409; SEQ ID NOs: 352 and 410; SEQ ID NOs: 430 and 357; SEQ ID NOs: 430 and 358; SEQ ID NOs: 430 and 359; SEQ ID NOs: 430 and 360; SEQ ID NOs: 430 and 361; SEQ ID NOs: 430 and 362; SEQ ID NOs: 407 and 409; SEQ ID NOs: 407 and 408; SEQ ID NOs: 408 and 410; or SEQ ID NOs: 409 and 410.

Embodiment 111: A host cell comprising one or more polynucleotides of any one of embodiments 90 to 93, or one or more vectors of any one of embodiments 98 to 110.

Embodiment 112: The host cell of embodiment 111, wherein the one or more polynucleotides are not integrated into the host cell genome, e.g., are episomal.

Embodiment 113: The host cell of embodiment 111, wherein the one or more polynucleotides are integrated into the host cell genome.

Embodiment 114: The host cell of any one of embodiments 111 to 113, wherein the host cell is a mammalian cell, e.g., a human cell, e.g., a cell line selected from BHK-21, A549, Vero, HEK293 (e.g., HEK293E, HEK293F, HEK293H, HEK293T, Expi293™) cells, MDCK, Caco-2 and Calu-3.

Embodiment 115: The host cell of anyone of embodiments 111 to 114, wherein the host cell is in vitro.

Embodiment 116: The host cell of any one of embodiments 111 to 114, wherein the host cell is in vivo.

Compositions

Embodiment 117: An immunogenic composition comprising one or more of the fusion polypeptides of any one of embodiments 1 to 89, or one or more polynucleotides of any one of embodiments 90 to 93, or one or more vectors of any one of embodiments 98 to 110, and a pharmaceutically acceptable carrier.

Embodiment 118: The immunogenic composition of embodiment 117, comprising two or more of the fusion polypeptides of any one of embodiments 1 to 89, or two or more polynucleotides of any one of embodiments 90 to 93, or two or more vectors of any one of embodiments 98 to 110.

Embodiment 119: The immunogenic composition of any one of embodiments 117 to 118, wherein the one or more polynucleotides comprise or are in the form of DNA, cDNA, mRNA, or self-replicating RNA.

Embodiment 120: The immunogenic composition of any one of embodiments 117 to 118, comprising:
1) One or more fusion polypeptides comprising or consisting of the following polypeptide segments in sequential order, from N-terminus to C-terminus, optionally joined or connected by one or more linkers:
SEQ ID NOs: 70, 76, 94, 151 and 161; or
SEQ ID NOs: 71, 77, 95, 152 and 162; and
2) One or more fusion polypeptides comprising or consisting of the following polypeptide segments in sequential order, from N-terminus to C-terminus, optionally joined or connected by one or more linkers:
SEQ ID NOs: 188, 305, 28, 41, 294, 4, 176, 11, 319, 259, 282, 223, 213 and 37;
SEQ ID NOs: 188, 305, 28, 41 and 294;
SEQ ID NOs: 4, 176, 11, 319, 259, 282, 223, 213 and 37;
SEQ ID NOs: 189, 306, 29, 42, 295, 5, 177, 12, 320, 260, 283, 224, 214, and 38;
SEQ ID NOs: 189, 306, 29, 42 and 295;
SEQ ID NOs: 5, 177, 12, 320, 260, 283, 224, 214 and 38;
SEQ ID NOs: 305, 319, 259, 282, 223, 213, 294, 176 and 188;
SEQ ID NOs: 306, 320, 260, 283, 224, 214, 295, 177 and 189;
SEQ ID NOs: 305, 294, 223, 213, 176, 259, 319, 188 and 282;
SEQ ID NOs: 306, 295, 224, 214, 177, 260, 320, 189 and 283;
SEQ ID NOs: 305, 294, 319, 259, 282, 223, 176, and 188;
SEQ ID NOs: 306, 295, 320, 260, 283, 224, 177 and 189;
SEQ ID NOs: 305, 223, 294, 176, 259, 319, 188 and 282; or
SEQ ID NOs: 306, 224, 295, 177, 260, 320, 189 and 283.

Embodiment 121: The immunogenic composition of any one of embodiments 117 to 120, comprising one or more adenoviral vectors, each adenoviral vector comprising one or more polynucleotides encoding one or more fusion proteins comprising an amino acid sequence of any one of any one of SEQ ID NOs: 345-377, 407-411, 422-424, 430-435, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 345-377, 407-411, 422-424, 430-435.

Embodiment 122: The immunogenic composition of any one of embodiments 117 to 121, comprising one or more viral vectors, each viral vector comprising one or more polynucleotides encoding two or more fusion proteins that are at least 80%, 81%, 82%, 83%, 84%, 85%, 86%, 87%, 88%, 89%, 90%, 91%, 92%, 93%, 94%, 95%, 96%, 97%, 98%, 99% identical, or 100% identical, to the following amino acid sequences: SEQ ID NOs: 345 and 346; SEQ ID NOs: 347 and 348; SEQ ID NOs: 349 and 350; SEQ ID NOs: 351 and 352; SEQ ID NOs: 430 and 352; SEQ ID NOs: 357 and 358; SEQ ID NOs: 360 and 362; SEQ ID NOs: 359 and 361; SEQ ID NOs: 351 and 357; SEQ ID NOs: 351 and 358; SEQ ID NOs: 351 and 359; SEQ ID NOs: 351 and 360; SEQ ID NOs: 351 and 361; SEQ ID NOs: 351 and 362; SEQ ID NOs: 351 and 407; SEQ ID NOs: 351 and 408; SEQ ID NOs: 351 and 409; SEQ ID NOs: 351 and 410; SEQ ID NOs: 352 and 357; SEQ ID NOs: 352 and 358; SEQ ID NOs: 352 and 359; SEQ ID NOs: 352 and 360; SEQ ID NOs: 352 and 361; SEQ ID NOs: 352 and 362; SEQ ID NOs: 352 and 407; SEQ ID NOs: 352 and 408; SEQ ID NOs: 352 and 409; SEQ ID NOs: 352 and 410; SEQ ID NOs: 430 and 357; SEQ ID NOs: 430 and 358; SEQ ID NOs: 430 and 359; SEQ ID NOs: 430 and 360; SEQ ID NOs: 430 and 361; SEQ ID NOs: 430 and 362; SEQ ID NOs: 407 and 409; SEQ ID NOs: 407 and 408; SEQ ID NOs: 408 and 410; or SEQ ID NOs: 409 and 410.

Embodiment 123: The immunogenic composition of any one of embodiments 117 to 122, comprising:
1) One or more fusion polypeptides comprising an amino acid sequence of any one of SEQ ID NOs: 351-356 and 430, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 351-356 and 430; and
2) One or more fusion polypeptides comprising an amino acid sequence of any one of SEQ ID NOs: 357-366 and 407-410, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 357-366 and 407-410.

Embodiment 124: A pharmaceutical composition comprising one or more of the fusion polypeptides of any one of embodiments 1 to 89, or one or more polynucleotides of any one of embodiments 90 to 93, or one or more vectors of any one of embodiments 98 to 110, and a pharmaceutically acceptable carrier.

Embodiment 125: The pharmaceutical composition of embodiment 124, comprising two or more fusion polypeptides, two or more polynucleotides or two or more vectors.

Embodiment 126: The pharmaceutical composition of any one of embodiments 124 to 125, further comprising one or more of an adjuvant, an immunostimulator, a detergent, a micelle-forming agent, and an oil.

Embodiment 127: The pharmaceutical composition of embodiment 126, wherein the immunomodulator is selected from a toll-like receptor (TLR) agonist, a cytokine (e.g., IL-2, IL-7, IL-12, IL-15, IL-18, IL-21, IFN-α, IFN-γ, GM-CSF, FLT3LG, and combinations and functional variants thereof), a non-coding immunostimulatory polynucleotide (e.g., a pathogen-activated molecular pattern (PAMP), a cytosine-phosphate-guanosine (CpG) oligodeoxynucleotide, and an immunostimulatory RNA (isRNA, e.g., CV8102)), an inhibitor of an inhibitory immune checkpoint protein or a stimulator of a stimulatory immune checkpoint protein.

Embodiment 128: The pharmaceutical composition of any one of embodiments 124 to 127, formulated for administration via a route selected from the group consisting of intravenous, intramuscular, intradermal, subcutaneous and mucosal (e.g. buccal, intranasal, intrarectal, intravaginal).

Embodiment 129: The pharmaceutical composition of any one of embodiments 124 to 128, formulated as a liquid.

Embodiment 130: The pharmaceutical composition of any one of embodiments 124 to 128, wherein the composition is lyophilized.

Kits

Embodiment 131: A kit comprising one or more unitary doses of one or more of the fusion polypeptides of any one of embodiments 1 to 89, or one or more polynucleotides of any one of embodiments 90 to 93, or one or more vectors of any one of embodiments 98 to 110, or one or more immunogenic compositions of any one of embodiments 117 to 121, or one or more pharmaceutical compositions of any one of embodiments 124 to 130.

Embodiment 132: The kit of embodiment 131, wherein the one or more unitary doses are in a single container.

Embodiment 133: The kit of embodiment 131, wherein the one or more unitary doses are in two or more separate containers.

Embodiment 134: The kit of any one of embodiments 131 to 133, comprising one or more containers selected from the group consisting of vials, ampules and pre-loaded syringes.

Embodiment 135: The kit of any one of embodiments 131 to 134, comprising one or more containers comprising the one or more fusion polypeptides, one or more polynucleotides or one or more vectors in an aqueous solution.

Embodiment 136: The kit of any one of embodiments 131 to 135, wherein the one or more unitary doses are the same.

Embodiment 137: The kit of any one of embodiments 131 to 135, wherein the one or more unitary doses are the different.

Embodiment 138: The kit of any one of embodiments 131 to 137, comprising one or more unitary doses of one or more viral vectors of any one of embodiments 98 to 110, wherein the unitary doses are in the range of about $10^3$ to about $10^{15}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$, $10^{12}$, $10^{13}$, $10^{14}$ or $10^{15}$ viral FFU or PFU or IU or vp.

Embodiment 139: The kit of any one of embodiments 131 to 138, comprising two or more of the fusion polypeptides of any one of embodiments 1 to 89, or two or more polynucleotides of any one of embodiments 90 to 93, or two or more vectors of any one of embodiments 98 to 110.

Embodiment 140: The kit of embodiment 139, comprising two or more polynucleotides encoding or two or more vectors expressing the fusion polypeptides, the fusion polypeptides comprising:
1) One or more fusion polypeptides comprising or consisting of the following polypeptide segments in sequential order, from N-terminus to C-terminus, optionally joined or connected by one or more linkers:
SEQ ID NOs: 70, 76, 94, 151 and 161; or
SEQ ID NOs: 71, 77, 95, 152 and 162; and
2) One or more fusion polypeptides comprising or consisting of the following polypeptide segments in sequential order, from N-terminus to C-terminus, optionally joined or connected by one or more linkers:
SEQ ID NOs: 188, 305, 28, 41, 294, 4, 176, 11, 319, 259, 282, 223, 213 and 37;
SEQ ID NOs: 188, 305, 28, 41 and 294;

SEQ ID NOs: 4, 176, 11, 319, 259, 282, 223, 213 and 37;
SEQ ID NOs: 189, 306, 29, 42, 295, 5, 177, 12, 320, 260, 283, 224, 214, and 38;
SEQ ID NOs: 189, 306, 29, 42 and 295;
SEQ ID NOs: 5, 177, 12, 320, 260, 283, 224, 214 and 38;
SEQ ID NOs: 305, 319, 259, 282, 223, 213, 294, 176 and 188;
SEQ ID NOs: 306, 320, 260, 283, 224, 214, 295, 177 and 189;
SEQ ID NOs: 305, 294, 223, 213, 176, 259, 319, 188 and 282;
SEQ ID NOs: 306, 295, 224, 214, 177, 260, 320, 189 and 283;
SEQ ID NOs: 305, 294, 319, 259, 282, 223, 176, and 188;
SEQ ID NOs: 306, 295, 320, 260, 283, 224, 177 and 189;
SEQ ID NOs: 305, 223, 294, 176, 259, 319, 188 and 282; or
SEQ ID NOs: 306, 224, 295, 177, 260, 320, 189 and 283.

Embodiment 141: The kit of embodiment 139, comprising two or more polynucleotides encoding or two or more vectors expressing the fusion polypeptides, the fusion polypeptides comprising:

1) One or more fusion polypeptides comprising, one or more polynucleotides encoding or one or more vectors capable of expressing, an amino acid sequence of any one of SEQ ID NOs: 351-356 and 430, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 351-356 and 430; and 2) One or more fusion polypeptides comprising, one or more polynucleotides encoding or one or more vectors capable of expressing, an amino acid sequence of any one of SEQ ID NOs: 357-366 and 407-410, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 357-366 and 407-410.

Embodiment 142: The kit of any one of embodiments 131 to 141, comprising one or more polynucleotides encoding or one or more vectors expressing the fusion polypeptides, the fusion polypeptides comprising or consisting of the following polypeptide segments in sequential order, from N-terminus to C-terminus, optionally joined or connected by one or more linkers:

SEQ ID NOs: 201, 78, 107, 96, 229, 172, 327, 6, 333, 243, 331, 192, 265, 311, 137, 15, 123, 30, 336, 302, 153, 219, 298, 121, 230, 240, 60, 241, 276, 113, 99, 21, 217 and 215;

SEQ ID NOs: 78, 296, 1, 339, 197, 329, 232, 323, 303, 234, 90, 261, 274, 238, 211, 325, 137, 227, 209, 190, 341, 57, 225, 27, 210, 119, 19, 165, 334, 117, 153, 10, 97 and 300; or SEQ ID NOs: 296, 1, 78, 197, 339, 227, 261, 274, 238, 325, 137, 329, 303, 234, 90, 232, 27, 57, 225, 323, 190, 341, 119, 19, 165, 334, 117, 153, 10, 97 and 300.

Embodiment 143: The kit of any one of embodiments 131 to 142, comprising one or more polynucleotides encoding or one or more vectors expressing the fusion polypeptides, the fusion polypeptides comprising or consisting of an amino acid sequence of any one of SEQ ID NOs: 345-377, 411, 422-424 and 430-435, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 345-377, 411, 422-424 and 430-435.

Embodiment 144: The kit of any one of embodiments 131 to 143, comprising one or more adenoviral vectors, each adenoviral vector comprising one or more polynucleotides encoding one or more fusion proteins comprising an amino acid sequence of any one of any one of SEQ ID NOs: 345-377, 407-411, 422-424, 430-435, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 345-377, 407-411, 422-424, 430-435.

Embodiment 145: The kit of any one of embodiments 131 to 144, comprising one or more viral vectors, wherein each viral vector comprises two or more polynucleotides encoding two or more fusion proteins that are at least 80%, 81%, 82%, 83%, 84%, 85%, 86%, 87%, 88%, 89%, 90%, 91%, 92%, 93%, 94%, 95%, 96%, 97%, 98%, 99% identical, or 100% identical, to the following amino acid sequences: SEQ ID NOs: 345 and 346; SEQ ID NOs: 347 and 348; SEQ ID NOs: 349 and 350; SEQ ID NOs: 351 and 352; SEQ ID NOs: 430 and 352; SEQ ID NOs: 357 and 358; SEQ ID NOs: 360 and 362; SEQ ID NOs: 359 and 361; SEQ ID NOs: 351 and 357; SEQ ID NOs: 351 and 358; SEQ ID NOs: 351 and 359; SEQ ID NOs: 351 and 360; SEQ ID NOs: 351 and 361; SEQ ID NOs: 351 and 362; SEQ ID NOs: 351 and 407; SEQ ID NOs: 351 and 408; SEQ ID NOs: 351 and 409; SEQ ID NOs: 351 and 410; SEQ ID NOs: 352 and 357; SEQ ID NOs: 352 and 358; SEQ ID NOs: 352 and 359; SEQ ID NOs: 352 and 360; SEQ ID NOs: 352 and 361; SEQ ID NOs: 352 and 362; SEQ ID NOs: 352 and 407; SEQ ID NOs: 352 and 408; SEQ ID NOs: 352 and 409; SEQ ID NOs: 352 and 410; SEQ ID NOs: 430 and 357; SEQ ID NOs: 430 and 358; SEQ ID NOs: 430 and 359; SEQ ID NOs: 430 and 360; SEQ ID NOs: 430 and 361; SEQ ID NOs: 430 and 362; SEQ ID NOs: 407 and 409; SEQ ID NOs: 407 and 408; SEQ ID NOs: 408 and 410; or SEQ ID NOs: 409 and 410.

Embodiment 146: The kit of any one of embodiments 131 to 145, further comprising one or more unitary doses of one or more additional therapeutic agents.

Embodiment 147: The kit of embodiment 146, comprising one or more agents that activate latent HIV, e.g., one or more latency reversing agents (LRAs).

Embodiment 148: The kit of any one of embodiments 146 to 147, comprising one or more LRAs selected from the group consisting of agonists or activators of one or more toll-like receptors (TLRs), histone deacetylase (HDAC) inhibitors, proteasome inhibitors, protein kinase C (PKC) activators, Smyd2 inhibitors, BET-bromodomain 4 (BRD4) inhibitors, ionomycin, inhibitor of apoptosis proteins (IAP) antagonists, and second mitochondria-derived activator of caspases (SMAC) mimetics.

Embodiment 149: The kit of any one of embodiments 146 to 148, comprising one or more agonists or activators of one or more toll-like receptors (TLRs).

Embodiment 150: The kit of embodiment 149, wherein the TLR agonist or activator is selected from the group consisting of a TLR2 agonist, a TLR3 agonist, a TLR4 agonist, a TLR5 agonist, a TLR7 agonist, a TLR8 agonist and a TLR9 agonist.

Embodiment 151: The kit of any one of embodiments 149 to 150, wherein the TLR7 agonist is selected from the group consisting of GS 9620 (vesatolimod), R848 (Resiquimod), DS-0509, LHC-165 and TMX-101 (imiquimod), and/or wherein the TLR8 agonist is selected from the group consisting of GS-9688, R848 (Resiquimod), CV8102 (dual TLR7/TLR8 agonist) and NKTR-262 (dual TLR7/TLR8 agonist).

Embodiment 152: The kit of any one of embodiments 149 to 151, wherein the TLR9 agonist is selected from the group consisting of AST-008, cobitolimod, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042.

Embodiment 153: The kit of any one of embodiments 146 to 152, comprising one or more interleukin receptor agonists of an interleukin selected from IL-2, IL-7, IL-12, IL-15, IL-18, IL-21, IFN-α, IFN-γ, GM-CSF and FLT3LG.

Embodiment 154: The kit of embodiment 153, comprising one or more cytokines selected from the group consisting of IL-2, IL-7, IL-12, IL-15, IL-18, IL-21, IFN-α, IFN-γ, GM-CSF, FLT3LG, and combinations and functional variants thereof.

Embodiment 155: The kit of any one of embodiments 146 to 154, comprising one or more innate immune activators.

Embodiment 156: The kit of embodiment 155, wherein the one or more innate immune activators comprises a non-coding immunostimulatory polynucleotide (e.g., a pathogen-activated molecular pattern (PAMP), a cytosine-phosphate-guanosine (CpG) oligodeoxynucleotide, and an immunostimulatory RNA (isRNA, e.g., CV8102)), an agonist of a receptor selected from the group consisting of fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2).

Embodiment 157: The kit of any one of embodiments 146 to 156, comprising one or more blockers, antagonists or inhibitors of an inhibitory immune checkpoint protein or receptor and/or one or more activators or agonists of a stimulatory immune checkpoint protein or receptor.

Embodiment 158: The kit of embodiment 157, wherein the one or more immune checkpoint proteins or receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM44); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

Embodiment 159: The kit of any one of embodiments 157 to 158, comprising one or more blockers, antagonists or inhibitors of one or more T-cell inhibitory immune checkpoint proteins or receptors.

Embodiment 160: The kit of embodiment 159, wherein the T-cell inhibitory immune checkpoint proteins or receptors are selected from the group consisting of CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1).

Embodiment 161: The kit of any one of embodiments 157 to 160, comprising one or more agonists or activators of one or more T-cell stimulatory immune checkpoint proteins or receptors.

Embodiment 162: The kit of embodiment 161, wherein the T-cell stimulatory immune checkpoint proteins or receptors are selected from the group consisting of CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155).

Embodiment 163: The kit of any one of embodiments 157 to 162, comprising one or more blockers, antagonists or inhibitors of one or more NK-cell inhibitory immune checkpoint proteins or receptors.

Embodiment 164: The kit embodiment 163, wherein the NK-cell inhibitory immune checkpoint proteins or receptors are selected from the group consisting of killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94).

Embodiment 165: The kit of any one of embodiments 157 to 164, comprising one or more agonists or activators of one or more NK-cell stimulatory immune checkpoint proteins or receptors.

Embodiment 166: The kit of embodiment 165, wherein the NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7).

Embodiment 167: The kit of any one of embodiments 157 to 166, wherein the one or more immune checkpoint inhibitors comprises a proteinaceous inhibitor of PD-L1 (CD274), PD-1 (PDCD1) or CTLA4.

Embodiment 168: The kit of embodiment 167, wherein the proteinaceous inhibitor of CTLA4 is selected from the group consisting of ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1).

Embodiment 169: The kit of embodiment 167, wherein the proteinaceous inhibitor of PD-L1 (CD274) or PD-1 (PDCD1) is selected from the group consisting of pembrolizumab, nivolumab, cemiplimab, pidilizumab, AB122 (zimberelimab), AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034 (balstilimab), JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

Embodiment 170: The kit of any one of embodiments 157 to 169, wherein the one or more immune checkpoint inhibitors comprises a small molecule inhibitor of CD274 (PDL1, PD-L1), programmed cell death 1 (PDCD1, PD1, PD-1) or CTLA4.

Embodiment 171: The kit of embodiment 170, wherein the small molecule inhibitor of CD274 or PDCD1 is selected from the group consisting of GS-4224, GS-4416, INCB086550 and MAX10181.

Embodiment 172: The kit of embodiment 170, wherein the small molecule inhibitor of CTLA4 comprises BPI-002.

Embodiment 173: The kit of any one of embodiments 146 to 172, further comprising one or more anti-viral agents.

Embodiment 174: The kit of embodiment 173, wherein the one or more antiviral agents are selected from the group consisting of HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors and capsid inhibitors.

Methods of Treating or Preventing HIV

Embodiment 175: A method for eliciting an immune response to human immunodeficiency virus (HIV) in a subject in need thereof, comprising administering to the subject the pharmaceutical composition of any one of embodiments 124 to 130, or the immunogenic composition of any one of embodiments 117 to 121.

Embodiment 176: A method of treating or preventing human immunodeficiency virus (HIV) in a subject in need thereof, comprising administering to the subject the pharmaceutical composition of any one of embodiments 124 to 130, the immunogenic composition of any one of embodiments 117 to 121.

Embodiment 177: The method of any one of embodiments 175 to 176, comprising administering a single fusion polypeptide, or a polynucleotide or viral expression vector encoding the fusion polypeptide, wherein the fusion polypeptide comprises two or more multivalent polypeptide segments, e.g., bivalent polypeptide segments.

Embodiment 178: The method of any one of embodiments 175 to 176, wherein two or more fusion polypeptides, or two or more viral expression vectors encoding the fusion polypeptides, are administered to the subject simultaneously or concurrently.

Embodiment 179: The method of any one of embodiments 175 to 178, wherein two or more fusion polypeptides, or two or more polynucleotides or two or more viral expression vectors encoding the fusion polypeptides, are in the form of a bivalent antigen composition.

Embodiment 180: The method of any one of embodiments 175 to 179, comprising administering to the subject:
1) one or more fusion polypeptides, or polynucleotides encoding, or viral expression vectors expressing the fusion polypeptides, the fusion polypeptides comprising or consisting of the following polypeptide segments in sequential order, from N-terminus to C-terminus, optionally joined or connected by one or more linkers:
SEQ ID NOs: 70, 76, 94, 151 and 161; or
SEQ ID NOs: 71, 77, 95, 152 and 162; and 2) one or more fusion polypeptides, or polynucleotides encoding, or viral expression vectors expressing the fusion polypeptides, the fusion polypeptides comprising or consisting of the following polypeptide segments in sequential order, from N-terminus to C-terminus, optionally joined or connected by one or more linkers:
SEQ ID NOs: 188, 305, 28, 41, 294, 4, 176, 11, 319, 259, 282, 223, 213 and 37;
SEQ ID NOs: 188, 305, 28, 41 and 294;
SEQ ID NOs: 4, 176, 11, 319, 259, 282, 223, 213 and 37;
SEQ ID NOs: 189, 306, 29, 42, 295, 5, 177, 12, 320, 260, 283, 224, 214 and 38;
SEQ ID NOs: 189, 306, 29, 42 and 295;
SEQ ID NOs: 5, 177, 12, 320, 260, 283, 224, 214 and 38;
SEQ ID NOs: 305, 319, 259, 282, 223, 213, 294, 176 and 188;
SEQ ID NOs: 306, 320, 260, 283, 224, 214, 295, 177 and 189;
SEQ ID NOs: 305, 294, 223, 213, 176, 259, 319, 188 and 282;
SEQ ID NOs: 306, 295, 224, 214, 177, 260, 320, 189 and 283;
SEQ ID NOs: 305, 294, 319, 259, 282, 223, 176, and 188;
SEQ ID NOs: 306, 295, 320, 260, 283, 224, 177 and 189;
SEQ ID NOs: 305, 223, 294, 176, 259, 319, 188 and 282; or
SEQ ID NOs: 306, 224, 295, 177, 260, 320, 189 and 283.

Embodiment 181: The method of any one of embodiments 175 to 180, comprising administering to the subject:
1) one or more fusion polypeptides, or polynucleotides encoding, or viral expression vectors expressing the fusion polypeptides, the fusion polypeptides comprising or consisting of an amino acid sequence of any one of SEQ ID NOs: 351-356 and 430, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 351-356 and 430; and
2) one or more fusion polypeptides, or polynucleotides encoding, or viral expression vectors expressing the fusion polypeptides, the fusion polypeptides comprising or consisting of an amino acid sequence of any one of SEQ ID NOs: 357-366 and 407-410, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 357-366 and 407-410.

Embodiment 182: The method of any one of embodiments 175 to 178, comprising administering to the subject one or more fusion polypeptides, or polynucleotides encoding, or viral expression vectors expressing the fusion polypeptides, the fusion polypeptides comprising or consisting of the following polypeptide segments in sequential order, from N-terminus to C-terminus, optionally joined or connected by one or more linkers:
SEQ ID NOs: 201, 78, 107, 96, 229, 172, 327, 6, 333, 243, 331, 192, 265, 311, 137, 15, 123, 30, 336, 302, 153, 219, 298, 121, 230, 240, 60, 241, 276, 113, 99, 21, 217 and 215;
SEQ ID NOs: 78, 296, 1, 339, 197, 329, 232, 323, 303, 234, 90, 261, 274, 238, 211, 325, 137, 227, 209, 190, 341, 57, 225, 27, 210, 119, 19, 165, 334, 117, 153, 10, 97 and 300; or
SEQ ID NOs: 296, 1, 78, 197, 339, 227, 261, 274, 238, 325, 137, 329, 303, 234, 90, 232, 27, 57, 225, 323, 190, 341, 119, 19, 165, 334, 117, 153, 10, 97 and 300.

Embodiment 183: The method of any one of embodiments 175 to 182, comprising administering to the subject one or more fusion polypeptides, or polynucleotides encoding, or viral expression vectors expressing the fusion polypeptides, the fusion polypeptides comprising or consisting of an amino acid sequence of any one of SEQ ID NOs: 345-377, 407-411, 422-424, 430-435, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 345-377, 407-411, 422-424, 430-435.

Embodiment 184: The method of any one of embodiments 175 to 183, comprising administering to the subject one or more adenoviral vectors, each adenoviral vector comprising one or more polynucleotides encoding one or more fusion proteins comprising an amino acid sequence of any one of any one of SEQ ID NOs: 345-377, 407-411, 422-424, 430-435, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 345-377, 407-411, 422-424, 430-435.

Embodiment 185: The method of any one of embodiments 175 to 183, comprising administering to the subject one or more viral vectors, wherein each viral vector comprises two or more polynucleotides encoding two or more fusion proteins that are at least 80%, 81%, 82%, 83%, 84%, 85%, 86%, 87%, 88%, 89%, 90%, 91%, 92%, 93%, 94%, 95%, 96%, 97%, 98%, 99% identical, or 100% identical, to the following amino acid sequences: SEQ ID NOs: 345 and 346; SEQ ID NOs: 347 and 348; SEQ ID NOs: 349 and 350; SEQ ID NOs: 351 and 352; SEQ ID NOs: 430 and 352; SEQ ID NOs: 357 and 358; SEQ ID NOs: 360 and 362; SEQ ID NOs: 359 and 361; SEQ ID NOs: 351 and 357; SEQ ID NOs: 351 and 358; SEQ ID NOs: 351 and 359; SEQ ID NOs: 351 and 360; SEQ ID NOs: 351 and 361; SEQ ID NOs: 351 and 362; SEQ ID NOs: 351 and 407; SEQ ID NOs: 351 and 408; SEQ ID NOs: 351 and 409; SEQ ID NOs: 351 and 410; SEQ ID NOs: 352 and 357; SEQ ID NOs: 352 and 358; SEQ ID NOs: 352 and 359; SEQ ID NOs: 352 and 360; SEQ ID NOs: 352 and 361; SEQ ID NOs: 352 and 362; SEQ ID NOs: 352 and 407; SEQ ID NOs: 352 and 408; SEQ ID NOs: 352 and 409; SEQ ID NOs: 352 and 410; SEQ ID NOs: 430 and 357; SEQ ID NOs: 430 and 358; SEQ ID NOs: 430 and 359; SEQ ID NOs: 430 and 360; SEQ ID NOs: 430 and 361; SEQ ID NOs: 430 and 362; SEQ ID NOs: 407 and 409; SEQ ID NOs: 407 and 408; SEQ ID NOs: 408 and 410; or SEQ ID NOs: 409 and 410.

Embodiment 186: The method of any one of embodiments 175 to 185, wherein the subject is infected with HIV-1, is suspected of being infected with HIV-1, or is at risk of being infected with HIV-1.

Embodiment 187: The method of any one of embodiments 175 to 186, wherein the subject is chronically infected with HIV-1.

Embodiment 188: The method of any one of embodiments 175 to 187, wherein the subject is acutely infected with HIV-1.

Embodiment 189: The method of any one of embodiments 175 to 188, wherein the subject has an HIV-1 infection of Fiebig stage IV or earlier, e.g. Fiebig stage III, Fiebig stage II or Fiebig stage I.

Embodiment 190: The method of any one of embodiments 175 to 189, wherein the composition is administered via a route selected from intravenous, intramuscular, intradermal, subcutaneous and mucosal (e.g. buccal, intranasal, intrarectal, intravaginal).

Embodiment 191: The method of any one of embodiments 175 to 190, comprising administering from about $10^3$ to about $10^{15}$ viral focus forming units (FFU) or plaque forming units (PFU) or infectious units (IU) or viral particles (vp), e.g. from about $10^4$ to about 107 viral FFU or PFU or IU or vp, e.g. from about $10^3$ to about $10^4$, $10^5$, $10^6$, $10^7$, $10^8$, $10^9$, $10^{10}$, $10^{11}$, $10^{12}$, $10^{13}$, $10^{14}$ or $10^{15}$ viral FFU or PFU or IU or vp, per administration.

Embodiment 192: The method of any one of embodiments 175 to 191, comprising a prime-boost regimen comprising:
  (i) administering a priming composition at a first time point and administering one or more boosting compositions at one or more subsequent time points (e.g., prime-boost-boost-boost, etc.); or
  (ii) one or more itereations of administering a priming composition at a first time point and administering a boosting composition at a second time point (e.g., prime-boost-prime-boost, etc.).

Embodiment 193: The method of embodiment 192, wherein the administrations of the priming composition and the one or more boosting compositions are spaced at least 1 week, 2 weeks, 3 weeks or 1 month apart, e.g., at least 2, 3, 4, 5 or 6 months, apart.

Embodiment 194: The method of any one of embodiments 192 to 193, wherein the priming composition and the boosting composition comprise the same immunogenic composition.

Embodiment 195: The method of any one of embodiments 192 to 193, wherein the priming composition and the boosting composition comprise different immunogenic compositions.

Embodiment 196: The method of any one of embodiments 192 to 193, wherein the priming composition and the boosting composition comprise the same one or more fusion polypeptides and same polynucleotide or viral expression vector.

Embodiment 197: The method of any one of embodiments 192 to 193, wherein the priming composition and the boosting composition comprise different fusion polypeptides and/or different polynucleotide or viral expression vectors.

Embodiment 198: The method of embodiment 197, comprising priming with a first polynucleotide or viral expression vector, and boosting with a second polynucleotide or viral expression vector.

Embodiment 199: The method of any one of embodiments 192 to 198, wherein the prime-boost regimen comprises:
  a) Priming with a viral expression vector and boosting with a polynucleotide, wherein the polynucleotide is DNA, cDNA, mRNA or self-replicating RNA;
  b) Priming with a polynucleotide, wherein the polynucleotide is DNA, cDNA, mRNA or self-replicating RNA, and boosting with a viral expression vector;
  c) Priming with a first viral expression vector and boosting with a second viral expression vector, wherein the first and second viral expression vectors are from identical, related or unrelated taxonomical families;
  d) Priming with a first replication deficient viral expression vector and boosting with a second replication deficient viral expression vector, wherein the first and second replication deficient viral expression vectors are from identical, related or unrelated taxonomical families;
  e) Priming with a first attenuated deficient viral expression vector and boosting with a second replication attenuated viral expression vector, wherein the first and second replication attenuated viral expression vectors are from identical, related or unrelated taxonomical families;
  f) Priming with a replication deficient viral expression vector and boosting with a replication attenuated viral expression vector;
  g) Priming with a replication attenuated viral expression vector and boosting with a replication deficient viral expression vector;
  h) Priming with a Lymphocytic choriomeningitis mammarenavirus (LCMV) viral expression vector and boosting with a Pichinde mammarenavirus viral expression vector;
  i) Priming with a Pichinde mammarenavirus viral expression vector and boosting with a Lymphocytic choriomeningitis mammarenavirus (LCMV) viral expression vector;
  j) Priming with an arenavirus viral expression vector and boosting with an adenovirus viral expression vector; or
  k) Priming with an adenovirus viral expression vector and boosting with an arenavirus viral expression vector.

Embodiment 200: The method of any one of embodiments 175 to 199, wherein the subject is not receiving antiretroviral therapy (ART) or ART is discontinued prior to administration of the one or more compositions.

Embodiment 201: The method of any one of embodiments 175 to 200, wherein ART is discontinued after one or more administrations of the compositions.

Embodiment 202: The method of any one of embodiments 175 to 201, further comprising administering to the subject one or more additional therapeutic agents, e.g. two, three, four, or more additional therapeutic agents.

Embodiment 203: The method of embodiment 202, comprising co-administering one or more agents that activate latent HIV, e.g., one or more latency reversing agents (LRAs).

Embodiment 204: The method of any one of embodiments 202 to 203, wherein the one or more LRAs are selected from the group consisting of agonists or activators of one or more toll-like receptors (TLRs), histone deacetylase (HDAC) inhibitors, proteasome inhibitors, protein kinase C (PKC) activators, Smyd2 inhibitors, BET-bromodomain 4 (BRD4) inhibitors, ionomycin, inhibitor of apoptosis proteins (IAP) antagonists, and second mitochondria-derived activator of caspases (SMAC) mimetics.

Embodiment 205: The method of any one of embodiments 202 to 204, comprising co-administering one or more agonists or activators of one or more toll-like receptors (TLRs).

Embodiment 206: The method of embodiment 205, wherein the TLR agonist or activator is selected from the group consisting of a TLR2 agonist, a TLR3 agonist, a TLR4 agonist, a TLR5 agonist, a TLR7 agonist, a TLR8 agonist and a TLR9 agonist.

Embodiment 207: The method of any one of embodiments 205 to 206, wherein the TLR7 agonist is selected from the group consisting of GS 9620 (vesatolimod), R848 (Resiquimod), DS-0509, LHC-165 and TMX-101 (imiquimod), and/or wherein the TLR8 agonist is selected from the group consisting of GS-9688, R848 (Resiquimod), CV8102 (dual TLR7/TLR8 agonist) and NKTR-262 (dual TLR7/TLR8 agonist).

Embodiment 208: The method of any one of embodiments 202 to 207, comprising co-administering one or more interleukin receptor agonists of an interleukin selected from IL-2, IL-7, IL-12, IL-15, IL-18, IL-21, IFN-α, IFN-γ, GM-CSF and FLT3LG.

Embodiment 209: The method of embodiment 208, comprising co-administering one or more cytokines selected from the group consisting of IL-2, IL-7, IL-12, IL-15, IL-18, IL-21, IFN-α, IFN-γ, GM-CSF, FLT3LG, and combinations and functional variants thereof.

Embodiment 210: The method of any one of embodiments 202 to 209, comprising co-administering one or more innate immune activators.

Embodiment 211: The method of embodiment 210, wherein the one or more innate immune activators comprises a non-coding immunostimulatory polynucleotide (e.g., a pathogen-activated molecular pattern (PAMP), a cytosine-phosphate-guanosine (CpG) oligodeoxynucleotide, and an immunostimulatory RNA (isRNA, e.g., CV8102)), an agonist of a receptor selected from the group consisting of fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2).

Embodiment 212: The method of any one of embodiments 202 to 211, comprising co-administering one or more antagonists or inhibitors of an inhibitory immune checkpoint protein or receptor and/or one or more activators or agonists of a stimulatory immune checkpoint protein or receptor.

Embodiment 213: The method of embodiment 212, wherein the one or more immune checkpoint proteins or receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript IE (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

Embodiment 214: The method of any one of embodiments 212 of 213, comprising co-administering one or more blockers, antagonists or inhibitors of one or more T-cell inhibitory immune checkpoint proteins or receptors.

Embodiment 215: The method of embodiment 214, wherein the T-cell inhibitory immune checkpoint proteins or receptors are selected from the group consisting of CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1).

Embodiment 216: The method of any one of embodiments 212 of 213, comprising co-administering one or more agonists or activators of one or more T-cell stimulatory immune checkpoint proteins or receptors.

Embodiment 217: The method of embodiment 216, wherein the T-cell stimulatory immune checkpoint proteins or receptors are selected from the group consisting of CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155).

Embodiment 218: The method of any one of embodiments 212 of 213, comprising co-administering one or more blockers, antagonists or inhibitors of one or more NK-cell inhibitory immune checkpoint proteins or receptors.

Embodiment 219: The method of embodiment 218, wherein the NK-cell inhibitory immune checkpoint proteins or receptors are selected from the group consisting of killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94).

Embodiment 220: The method of any one of embodiments 212 of 213, comprising co-administering one or more agonists or activators of one or more NK-cell stimulatory immune checkpoint proteins or receptors.

Embodiment 221: The method of embodiment 220, wherein the NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7).

Embodiment 222: The method of any one of embodiments 212 to 215, wherein the one or more immune checkpoint inhibitors comprises a proteinaceous inhibitor of PD-L1 (CD274), PD-1 (PDCD1) or CTLA4.

Embodiment 223: The method of embodiment 222, wherein the proteinaceous inhibitor of CTLA4 is selected from the group consisting of ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1).

Embodiment 224: The method of embodiment 222, wherein the proteinaceous inhibitor of PD-L1 (CD274) or PD-1 (PDCD1) is selected from the group consisting of pembrolizumab, nivolumab, cemiplimab, pidilizumab, AB122 (zimberelimab), AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034 (balstilimab), JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

Embodiment 225: The method of any one of embodiments 212 to 215, wherein the one or more immune checkpoint inhibitors comprises a small molecule inhibitor of CD274 (PDL1, PD-L1), programmed cell death 1 (PDCD1, PD1, PD-1) or CTLA4.

Embodiment 226: The method of embodiment 225, wherein the small molecule inhibitor of CD274 or PDCD1 is selected from the group consisting of GS-4224, GS-4416, INCB086550 and MAX10181.

Embodiment 227: The method of embodiment 225, wherein the small molecule inhibitor of CTLA4 comprises BPI-002.

Embodiment 228: The method of any one of embodiments 202 to 227, further comprising administering to the subject one or more anti-viral agents.

Embodiment 229: The method of 228, wherein the one or more antiviral agents are selected from the group consisting of HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors and capsid inhibitors.

Embodiment 230: The method of any one of embodiments 202 to 229, further comprising administering to the subject one or more anti-HIV antibodies or antigen-binding fragments thereof.

Embodiment 231: The method of embodiment 230, wherein the one or more anti-HIV antibodies or antigen-binding fragments thereof binds to HIV gp120.

Embodiment 232: The method of any one of embodiments 230 to 231, wherein the anti-HIV antibody or antigen-binding fragment thereof comprises a broadly neutralizing antibody.

Embodiment 233: The method of any one of embodiments 230 to 232, wherein one or more anti-HIV antibodies or antigen-binding fragments thereof that bind, inhibit, and/or neutralize HIV, compete with or comprise VH and VL variable domains of a broadly neutralizing antibody (bNAb) against HIV.

Embodiment 234: The method of any one of embodiments 230 to 233, wherein one or more anti-HIV antibodies or antigen-binding fragments thereof that bind, inhibit, and/or neutralize HIV, bind to an epitope or region of gp120 selected from the group consisting of:
  i. third variable loop (V3) and/or high mannose patch comprising a N332 oligomannose glycan;
  ii. CD4 binding site (CD4bs);
  iii. second variable loop (V2) and/or Env trimer apex;
  iv. gp120/gp41 interface; or
  v. silent face of gp120.

Embodiment 235: The method of any one of embodiments 230 to 234, wherein the antibody or antigen-binding fragment thereof that binds, inhibits, and/or neutralizes HIV, binds to an epitope or region of gp120 in the third variable loop (V3) and/or high mannose patch comprising a N332 oligomannose glycan and competes with or comprises VH and VL regions from an antibody selected from the group consisting of GS-9722, PGT-121, PGT-122, PGT-123, PGT-124, PGT-125, PGT-126, PGT-128, PGT-130, PGT-133, PGT-134, PGT-135, PGT-136, PGT-137, PGT-138, PGT-139, 10-1074, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03.

Embodiment 236: The method of any one of embodiments 230 to 235, wherein the antibody or antigen-binding fragment thereof binds to an epitope or region of gp120 in the CD4 binding site (CD4bs) and competes with or comprises VH and VL regions from an antibody selected from the group consisting of b12, F105, VRC01, VRC07, VRC07-523, VRC03, VRC06, VRC06b01 VRC08, VRC0801, NIH45-46, GS-9723, 3BNC117, 3BNC60, VRC-PG04, PGV04; CH103, 44-VRC13.01, 1NC9, 12A12, N6, N49-P7, NC-Cowl, IOMA, CH235 and CH235.12, N49P6, N49P7, N49P11, N49P9 and N60P25.

Embodiment 237: The method of any one of embodiments 230 to 236, wherein the antibody or antigen-binding fragment thereof that binds, inhibits, and/or neutralizes HIV, binds to an epitope or region of gp120 in the second variable loop (V2) and/or Env trimer apex and competes with or comprises VH and VL regions from an antibody selected from the group consisting of PG9, PG16, PGC14, PGG14, PGT-142, PGT-143, PGT-144, PGT-145, CH01, CH59, PGDM1400, CAP256, CAP256-VRC26.08, CAP256-VRC26.09, CAP256-VRC26.25, PCT64-24E and VRC38.01.

Embodiment 238: The method of any one of embodiments 230 to 237, wherein the antibody or antigen-binding fragment binds to an epitope or region of gp120 in the gp120/gp41 interface and competes with or comprises VH and VL regions from an antibody selected from the group consisting of PGT-151, CAP248-2B, 35O22, 8ANC195, ACS202, VRC34 and VRC34.01.

Embodiment 239: The method of any one of embodiments 230 to 238, wherein the antibody or antigen-binding fragment thereof that binds, inhibits, and/or neutralizes HIV, binds to an epitope or region of the gp120 silent face and competes with or comprises VH and VL regions from antibody selected from the group consisting of VRC-PG05 and SF12.

Embodiment 240: The method of any one of embodiments 230 to 239, wherein the antibody or antigen-binding fragment thereof that binds, inhibits, and/or neutralizes HIV, binds to an epitope or region of gp41 in the membrane proximal region (MPER).

Embodiment 241: The method of any one of embodiments 230 to 240, wherein the antibody or antigen-binding fragment thereof that binds, inhibits, and/or neutralizes HIV, binds to an epitope or region of gp41 in the membrane proximal region (MPER) and competes with or comprises VH and VL regions from an antibody selected from the group consisting of 10E8, 10E8v4, 10E8-5R-100cF, 4E10, DH511.11P, 2F5, 7b2, and LN01.

Embodiment 242: The method of any one of embodiments 230 to 241, wherein the antibody or antigen-binding fragment thereof that binds, inhibits, and/or neutralizes HIV, binds to an epitope or region of the gp41 fusion peptide and competes with or comprises VH and VL regions from an antibody selected from the group consisting of VRC34 and ACS202.

Embodiment 243: The method of any one of embodiments 175 to 242, wherein, after one or more administrations of one or more of the compositions, optionally in combination with one or more additional therapeutic agents, the subject does not exhibit symptoms of HIV or AIDS in the absence of anti-retroviral treatment (ART) for at least 6 months, at least 1 year, at least 2 years, at least 3 years, or more.

Embodiment 244: The method of any one of embodiments 175 to 243, wherein, after one or more administrations of one or more of the compositions, optionally in combination with one or more additional therapeutic agents, the subject has a viral load copies/ml blood of less than 500, e.g. less than 400, less than 300, less than 200, less than 100, less than 50, in the absence of anti-retroviral treatment (ART) for at least 6 months, at least 1 year, at least 2 years, at least 3 years, or more.

Methods of Immunogen Design

Embodiment 245: A method of designing a fusion polypeptide that is capable of eliciting an immune response against one or more viral target antigens, the method comprising:
  a) identifying in silico one or more regions of sequence conservation in a population of polypeptide sequences encoded by a viral gene, the population from an inter-patient virus population; and
  b) identifying in silico the two most prevalent polypeptide sequences from the one or more conserved regions identified in step a), and generating multivalent polypeptide segments from the conserved regions.

Embodiment 246: The method of embodiment 245, wherein the multivalent polypeptide segments are bivalent polypeptide segments.

Embodiment 247: The method of any one of embodiments 245 to 246, further comprising step c): arranging the polypeptide segments into one or more contiguous fusion polypeptides, such that the junctions connecting the polypeptide segments reduce or avoid creating epitopes capable of binding human MHC class I or human MHC class II molecules, e.g., with a predicted binding affinity IC50 value of less than about 1000 nM or having a percentile rank within the top 5% in a population of polypeptide segments.

Embodiment 248: The method of any one of embodiments 245 to 247, further comprising the step of inserting a linker between polypeptide segments junctions predicted to create epitopes capable of binding human MHC class I or human MHC class II molecules.

Embodiment 249: The method of any one of embodiments 245 to 248, comprising after step b) and before step c), the steps of:
  d) within the one or more regions of sequence conservation identified in step a), identifying in silico polypeptide segments predicted to bind to a human MHC class I molecule with an IC50 value of less than about 1000 nM or having a percentile rank within the top 5% in a population of polypeptide segments; and
  e) generating polypeptide segments comprising the one or more regions of sequence conservation identified in step a), and which are predicted to bind to a human MHC class I molecule with an IC50 value of less than about 1000 nM or having a percentile rank within the top 5% in a population of polypeptide segments.

Embodiment 250: The method of any one of embodiments 245 to 249, further comprising after step b) and before step c) the step of reducing or eliminating viral polypeptide 9-mers that have at least 55% (5 of 9 amino acid residues), e.g., at least 65% (6 of 9 amino acid residues), e.g., at least 75% (7 of 9 amino acid residues), e.g., at least 85% (8 of 9 amino acid residues), amino acid sequence identity to a human protein.

Embodiment 251: The method of anyone of embodiments 245 to 250, further comprising after step b) and before step c) the step of providing one or more polypeptide segments known or predicted to bind to a human MHC class II molecule, e.g., with a predicted binding affinity IC50 value of less than about 1000 nM or having a percentile rank within the top 5% in a population of polypeptide segments.

Embodiment 252: The method of any one of embodiments 245 to 251, further comprising after step b) and before step c) the step of identifying within the one or more regions of sequence conservation identified in step a), sequence variance in a second population of polypeptide sequences encoded by the viral gene, the second population from an intrapatient virus population.

Embodiment 253: The method of embodiment 252, wherein the sequence variance from the intrapatient virus population is determined by deep sequencing or next generation sequencing.

Embodiment 254: A method of designing a fusion polypeptide that is capable of eliciting an immune response against one or more viral target antigens, the method comprising:
- a) identifying in silico one or more regions of sequence conservation in a first population of polypeptide sequences encoded by a viral gene, the first population from an interpatient virus population;
- b) identifying in silico the two most prevalent polypeptide sequences from the one or more conserved regions identified in step a);
- c) within the one or more regions of sequence conservation identified in step a), identifying in silico polypeptide segments predicted to bind to a human MHC class I molecule with an IC50 value of less than about 1000 nM or having a percentile rank within the top 5% in a population of polypeptide segments;
- d) generating polypeptide segments comprising the one or more regions of sequence conservation identified in step a), and which are predicted to bind to a human MHC class I molecule with an IC50 value of less than about 1000 nM or having a percentile rank within the top 5% in a population of polypeptide segments;
- e) removing viral polypeptide 9-mer segments generated in step d) determined to have at least 55% (5 of 9 amino acid residues), e.g., at least 65% (6 of 9 amino acid residues), e.g., at least 75% (7 of 9 amino acid residues), e.g., at least 85% (8 of 9 amino acid residues), amino acid sequence identity to a human protein, yielding retained viral polypeptide segments; and
- f) arranging the retained polypeptide segments into one or more contiguous fusion polypeptides, such that the junctions connecting the polypeptide segments avoid or reduce creating epitopes capable of binding human MHC class I or human MHC class II molecules, e.g., with a predicted binding affinity IC50 value of less than about 1000 nM or having a percentile rank within the top 5% in a population of polypeptide segments.

Embodiment 255: A method of designing a fusion polypeptide that is capable of eliciting an immune response against one or more viral target antigens, the method comprising:
- a) identifying in silico one or more regions of sequence conservation in a first population of polypeptide sequences encoded by a viral gene, the first population from an interpatient virus population;
- b) optionally, identifying in silico the two most prevalent polypeptide sequences from the one or more conserved regions identified in step a);
- c) within the one or more regions of sequence conservation identified in step a), identifying sequence variance in a second population of polypeptide sequences encoded by the viral gene, the second population from an intrapatient virus population;
- d) within the one or more regions of sequence conservation identified in step a), identifying in silico polypeptide segments predicted to bind to a human MHC class I molecule with an IC50 value of less than about 1000 nM or having a percentile rank within the top 5% in a population of polypeptide segments;
- e) generating polypeptide segments comprising the one or more regions of sequence conservation identified in step a), and which are predicted to bind to a human MHC class I molecule with an IC50 value of less than about 1000 nM or having a percentile rank within the top 5% in a population of polypeptide segments;
- f) removing viral polypeptide 9-mer segments generated in step e) determined to have at least 55% (5 of 9 amino acid residues), e.g., at least 65% (6 of 9 amino acid residues), e.g., at least 75% (7 of 9 amino acid residues), e.g., at least 85% (8 of 9 amino acid residues), amino acid sequence identity to a human protein, yielding retained viral polypeptide segments;
- g) arranging the retained polypeptide segments into one or more contiguous fusion polypeptides, such that the junctions connecting the polypeptide segments avoid or reduce creating epitopes capable of binding human MHC class I or human MHC class II molecules, e.g., with a predicted binding affinity IC50 value of less than about 1000 nM or having a percentile rank within the top 5% in a population of polypeptide segments.

Embodiment 256: The method of embodiment 255, wherein the sequence variance from the intrapatient virus population is determined by deep sequencing or next generation sequencing.

Embodiment 257: The method of any one of embodiments 254 to 256, further comprising the step of incorporating one or more polypeptide segments known or predicted to bind to a human MHC class II molecule, e.g., with a predicted binding affinity IC50 value of less than about 1000 nM or having a percentile rank within the top 5% in a population of polypeptide segments.

Embodiment 258: The method of any one of embodiments 254 to 257, further comprising the step of inserting a linker between polypeptide segments at junctions predicted to create epitopes capable of binding human MHC class I or human MHC class II molecules.

Embodiment 259: A method for producing a multivalent antigen, the method comprising constructing, in silico, a set of multivalent amino acid sequences within structurally conserved regions of a population of viral proteome sequences by a method comprising
- (a) aligning the population of viral proteome sequences;
- (b) creating, for each sequence in the alignment, a set of 9-amino acid subsequences ("9-mers") starting with the N-terminal amino acid, each subsequence overlapping the preceding subsequence by eight amino acids such that each sequence of length l in the alignment contains (1-8) 9-mers;
- (c) calculating a frequency for each unique 9-mer starting at a position i in each sequence of the alignment and identifying the two or more most common unique 9-mers at each position; (c)(1) wherein frequency is calculated as the number of times the unique 9-mer occurs at position i in the alignment divided by the total number of sequences in the alignment;

(d) calculating a multivalent conservation for each position by summing the proportion of sequences in the alignment containing either of the two or more most common unique 9-mers;
(e) creating an alignment of conserved regions by extracting the sequences in the alignment having a multivalent conservation of greater than 80% or greater than 90%;
(f) determining a frequency for each pair of unique 9-mers at each position in the alignment of conserved regions;
(g) connecting 9-mer pairs in adjacent positions of the alignment of conserved regions that share an overlap of eight amino acids;
(h) creating a directed acyclic graph in which each 9-mer pair is a node and the edges between adjacent nodes are formed from the connected 9-mer pairs in the adjacent positions with the weight of each edge equal to the frequency of the downstream 9-mer pair,
adding a source node and connecting it with all of the nodes in the first position,
adding a sink node and connecting it with all of the nodes in the last position, and
negating all of the weights;
(i) finding an optimal path in the directed acyclic graph from the source node to the sink node where the optimal path is defined in terms of the sum of the frequencies of all 9-mer pairs in the directed acyclic graph;
(j) building a multivalent antigen by connecting two or more 9-mers in adjacent positions within the optimal multivalent 9-mer path if they share an overlap of eight amino acids, thereby creating two or more sequences of connected 9-mers which together form the multivalent antigen; and
(k) optionally, rearranging the polypeptide segments to reduce or avoid the creation of deleterious epitopes at junctions between polypeptide segments.

Embodiment 260: The method of embodiment 259, wherein the multivalent conservation is bivalent conservation and wherein the multivalent antigen is a bivalent antigen.

Embodiment 261: The method of any one of embodiments 259 to 260, wherein in step (a) the conserved regions are further defined by performing one or more of the following steps:
(i) removing segments of fewer than 35 amino acids in length, e.g., from 9 amino acids to 10, 15, 20, 25, 30 or 35 amino acids in length;
(ii) removing segments determined to have less than 90% multivalent (e.g., bivalent) conservation;
(iii) removing segments determined to be weakly immunogenic or non-immunogenic, e.g., as demonstrated in in vitro or in vivo; and/or
(iv) including additional segments determined to be immunogenic, e.g., as demonstrated in in vitro or in vivo.

Embodiment 262: The method of any one of embodiments 259 to 261, wherein the step of rearranging the peptide segments to reduce or avoid creation of deleterious epitopes is performed by a method comprising one or more of in silico HLA binding analysis and human proteome cross-recognition analysis.

Embodiment 263: The method of any one of embodiments 259 to 262, further comprising inserting a linker sequence between one or more adjacent segments.

Embodiment 264: The method of any one of embodiments 259 to 263, wherein the method further comprises improving the multivalent (e.g., bivalent) antigen produced in step (h) by removing junctional 9-mers that bind to a specific HLA allele with a predicted IC50 value of less than about 1000 nM or having a percentile rank within the top 5% in a population of polypeptide segments.

Embodiment 265: The method of any one of embodiments 259 to 264, wherein the method further comprises improving the multivalent (e.g., bivalent) antigen produced in step (h) by removing 9-mers that have at least 55% (5 of 9 amino acid residues), e.g., at least 65% (6 of 9 amino acid residues), e.g., at least 75% (7 of 9 amino acid residues), e.g., at least 85% (8 of 9 amino acid residues), amino acid sequence identity with human peptides or that have the same T cell receptor (TCR) facing residues with human proteins.

Embodiment 266: The method of any one of embodiments 259 to 265, further comprising improving the multivalent (e.g., bivalent) antigen produced in step (h) to generate sufficient T cell epitopes to cover intra-patient viral diversity, the method further comprising the steps of:
a) identifying viral quasi-species variants within a biological sample obtained from a subject; and
b) determining intrapatient amino acid variants from the sequences of the multivalent (e.g., bivalent) antigen produced in step (h) by a method comprising:
(i) determining, at each 9-mer position in the multivalent (e.g., bivalent) antigen, corresponding 9-mer subsequences from the plurality of sequencing reads that completely cover that position;
(ii) extracting 9-mer subsequences; and
(iii) aligning the extracted 9-mer subsequences to the sequences of the multivalent (e.g., bivalent) antigen and determining the presence of any mismatches.

Embodiment 267: The method of embodiment 266, wherein the viral quasi-species are identified by a method comprising sequencing the viral DNA, assembling a plurality of sequencing reads to create a subject consensus sequence; aligning each read in the plurality of reads to the subject consensus sequence; mapping the aligned reads of the subject to a reference sequence to obtain sequence coordinates.

Embodiment 268: The method of any one of embodiments 266 to 267, wherein the biological sample is selected from blood, peripheral blood mononuclear cells (PBMCs), serum, plasma, semen or lymph nodes.

Embodiment 269: The method of any one of embodiments 266 to 268, wherein the subject is acutely infected with HIV-1.

Embodiment 270: The method of any one of embodiments 266 to 269, wherein the subject has an HIV-1 infection of Fiebig stage IV or earlier, e.g. Fiebig stage III, Fiebig stage II or Fiebig stage I.

Embodiment 271: The method of any one of embodiments 266 to 268, wherein the subject is chronically infected with HIV-1.

Embodiment 272: The method of any one of embodiments 266 to 271, wherein the subject has received antiretroviral therapy (ART).

Embodiment 273: The method of any one of embodiments 266 to 271, wherein the subject has not received antiretroviral therapy (ART).

Embodiment 274: The method of any one of embodiments 266 to 273, further comprising excluding sequences with pre-existing escape variants.

Embodiment 275: The method of any one of embodiments 259 to 274, further comprising rearranging the polypeptide segments to reduce or avoid the creation of deleterious epitopes at junctions between polypeptide segments.

Embodiment 276: The method of embodiment 275, wherein the step of rearranging the peptide segments to reduce or avoid creation of deleterious epitopes is performed by a method comprising one or more of in silico HLA binding analysis and human proteome cross-recognition analysis.

Embodiment 277: The method of any one of embodiments 245 to 276, wherein the one or more viral target antigens are from a mammalian virus, e.g., a human virus.

Embodiment 278: The method of any one of embodiments 245 to 277, wherein the one or more viral target antigens are from a virus selected from the group consisting of human immunodeficiency virus (HIV), hepatitis B virus (HBV), human papillomavirus (HPV), herpes simplex virus (HSV), Ebola virus, Zika virus and Chikungunya virus.

Embodiment 279: The method of any one of embodiments any one of embodiments 245 to 278, wherein the interpatient virus population is from a population of patients who have not received antiretroviral therapy (ART).

Embodiment 280: The method of any one of embodiments any one of embodiments 245 to 278, wherein the interpatient virus population is from a population of patients who have received antiretroviral therapy (ART).

Embodiment 281: The method of anyone of embodiments anyone of embodiments 252 to 280, wherein the intrapatient virus population is from a patient who has not received antiretroviral therapy (ART).

Embodiment 282: The method of any one of embodiments any one of embodiments 252 to 280, wherein the intrapatient virus population is from a patient who has received antiretroviral therapy (ART).

Embodiment 283: A fusion polypeptide made according to the method of any one of embodiments 245 to 282, wherein the fusion polypeptide elicits an immune response against a virus in a mammal, e.g., a human.

BRIEF DESCRIPTION OF THE DRAWINGS

FIG. 1 illustrates an 8-step workflow for designing a fusion polypeptide to elicit an antiviral response.

FIG. 2 illustrates a representative methodology of a population-based vaccine construct approach.

FIG. 4A illustrates how "bivalent conservation" can be determined based on the prevalence of the two most common 9-mers among all considered viral sequences in a population. FIG. 4A discloses SEQ ID NOS 475-476, 476-477, 476, 476, 478-479 and 479-480 in the top panel, respectively, in order of appearance. FIG. 4A also discloses "QNLQGQMVH" as SEQ ID NO: 481, "QNIQGQMVH" as SEQ ID NO: 482 and "PNIQGQMVH" as SEQ ID NO: 483 in the bottom panel. FIG. 4B illustrates how the conserved regions are identified based on the "bivalent conservation" distribution across 9-mer positions. HIV-1 Gag p24 was used as the representative protein.

FIG. 5A illustrates unique 9-mers extracted from aligned natural sequences. FIG. 5B illustrates a directed acyclic graph built based on 9-mer pair nodes and their connection. FIG. 5C illustrates how 9-mers in connected 9-mer pairs are connected. When there are two options available for the connection, the ultimate connection is determined by the prevalence of each connection in naturally occurring sequences. FIGS. 5A-5C disclose "IIIIIIIIR" as SEQ ID NO: 467, "GIIIIIIIH" as SEQ ID NO: 473, "AIIIIIIIK" as SEQ ID NO: 474, "GIIIIIIIR" as SEQ ID NO: 484, "GIIIIIII" as SEQ ID NO: 485, "AIIIIIII" as SEQ ID NO: 486, "IIIIIIIK" as SEQ ID NO: 487 and "IIIIIIIH" as SEQ ID NO: 488.

FIG. 6 illustrates interpatient and intrapatient diversity viral sequence analyses. FIG. 6 discloses SEQ ID NOs. 475-476, 476-477, 476, 476, 478-479, 479-480, and 489 in the first column and SEQ ID NOs. 475, 490, 490, 490, 490, 475, 475, 475, 475, 475, 475, 489 and 491 in the second column, all respectively, in order of appearance.

FIG. 8 illustrates the results of human proteome cross-recognition analysis. FIG. 8 discloses the "HIV Peptide" sequence as SEQ ID NO: 492 and the "Human Protein 9-mer" sequences as SEQ ID NOS 493-498 and 493, respectively, in order of appearance.

FIGS. 10A-10B illustrate an approach in which a set of HLA restricted 9-mers is selected from the bivalent constructs and combined to form an HLA restricted vaccine construct. FIG. 10A illustrates a basic methodology of the "short peptide" approach, described in Example 3. FIG. 10B illustrates a basic methodology of the "long peptide" approach, described in Example 3.

FIG. 12A illustrates a method of classifying conserved region positions into four categories. Antiviral vaccine design approaches can be improved by incorporating deep sequencing analysis and MHC class I binding data. FIG. 12A discloses SEQ ID NOs. 499-501, 121, 502-505, 499-501, 121 and 502-510, respectively, in order of appearance. FIG. 12B illustrates approaches of improving current antiviral vaccine design approaches by incorporating deep sequencing analysis and MHC class I binding data into intrapatient sequence analysis.

FIG. 13 illustrates an approach in which deep sequencing data and patient HLA data analyses are included to form an individualized vaccine construct.

FIG. 14 illustrates an approach in which deep sequencing data analysis is included to further improve the HLA restricted vaccine construct described in Example 3.

FIG. 16 illustrates polypeptide segments encoded by the HIV-1 Env gene used in the fusion polypeptide constructs described herein. The Env HIV-1 HXB2 reference polypeptide (SEQ ID NO:403) sequence is underlined. FIG. 16 also discloses SEQ ID NOs. 1, 10, 4, 15, 6, 19, 21, 27-28, 30, 37, 511, 512 and 60, respectively, in order of appearance.

FIG. 17 illustrates polypeptide segments encoded by the HIV-1 Gag gene used in the fusion polypeptide constructs described herein. The Gag HIV-1 HXB2 reference polypeptide (SEQ ID NO:404) sequence is underlined. FIG. 17 also discloses SEQ ID NOs. 70, 76, 78, 87, 94, 96-97, 99, 339, 107, 341, 117, 113, 119, 121, 123 and 137, respectively, in order of appearance.

FIG. 18 illustrates polypeptide segments encoded by the HIV-1 Nef gene used in the fusion polypeptide constructs described herein. The Nef HIV-1 HXB2 reference polypeptide, having a tryptophan (W) at position 124 (SEQ ID NO:405) sequence is underlined. FIG. 18 also discloses SEQ ID NOs. 151, 513, 153, 514, 165, 515 and 172, respectively, in order of appearance.

FIGS. 19A-19C illustrate polypeptide segments encoded by the HIV-1 Pol gene used in the fusion polypeptide constructs described herein. The Pol HIV-1 HXB2 reference polypeptide (SEQ ID NO:406) sequence is underlined. FIGS. 19A-19C also disclose SEQ ID NOs. 176, 188, 181, 190, 192, 516, 209, 517, 197, 210, 201, 211, 213, 518, 217, 219, 223, 222, 225, 227, 229-230, 232, 234, 236, 238, 240-241, 243, 259, 261, 265, 274, 282, 276, 294, 296, 300, 298, 302-303, 305, 519, 311, 319, 322-323, 334, 325, 336, 329, 327, 331 and 333, respectively, in order of appearance.

FIGS. 25A-25B disclose "AAA" as SEQ ID NO: 378.

(prime) or Day 36 (prime-boost). (B) Day 16 (C) Day 36 immunogenicity following immunization was determined by evaluating the frequency of ex vivo peptide specific splenocytes using an IFN-γ ELISPOT assay to detect IFN-γ producing cells. A set of 15-mer peptides overlapping by 11 amino acids that matched the sequences within the vaccine construct as well as the F2A peptide were synthesized and used to stimulate splenocytes in the ELISpot and ICS assays.

Figure 29A:
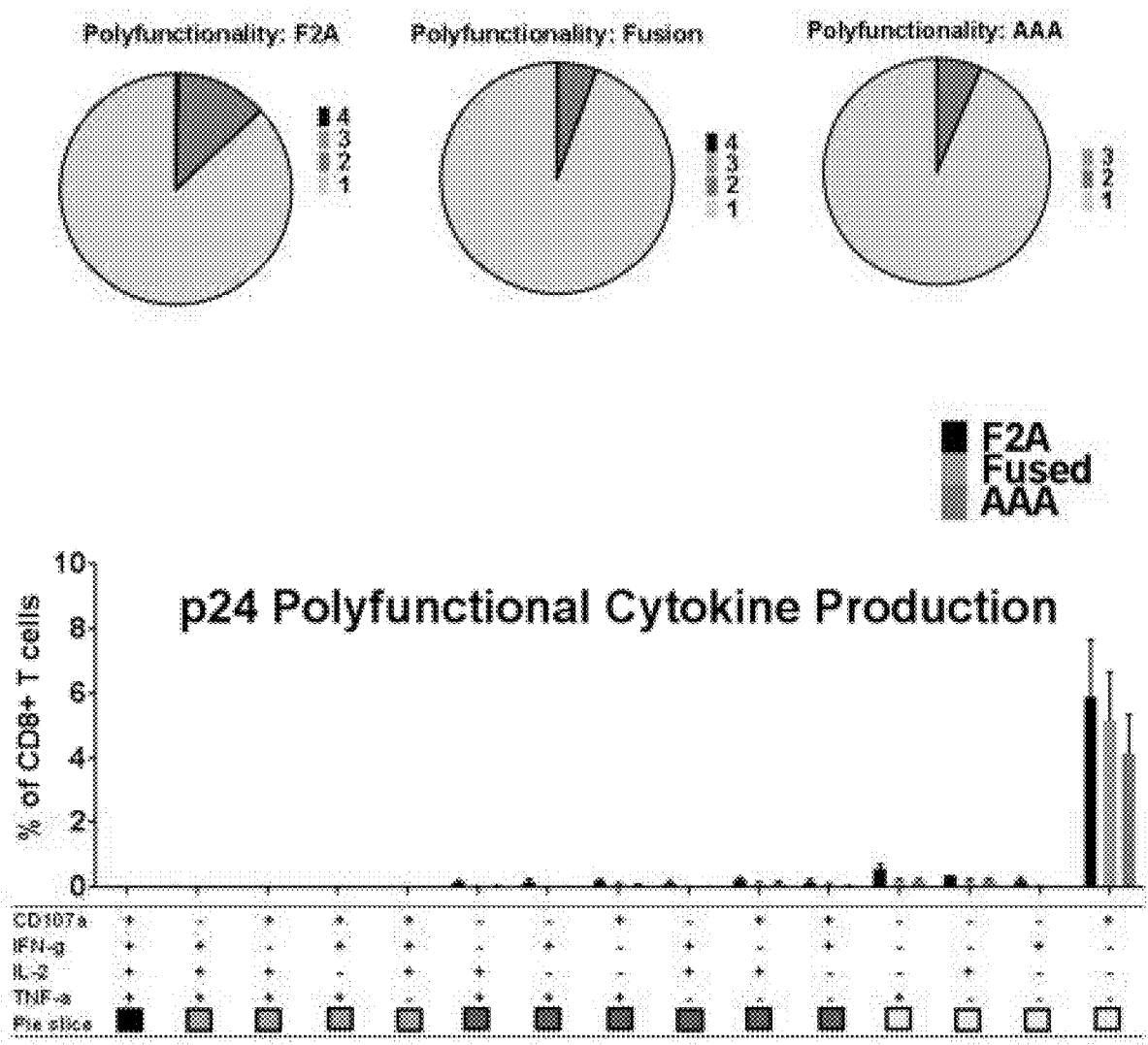
Figure 29B:
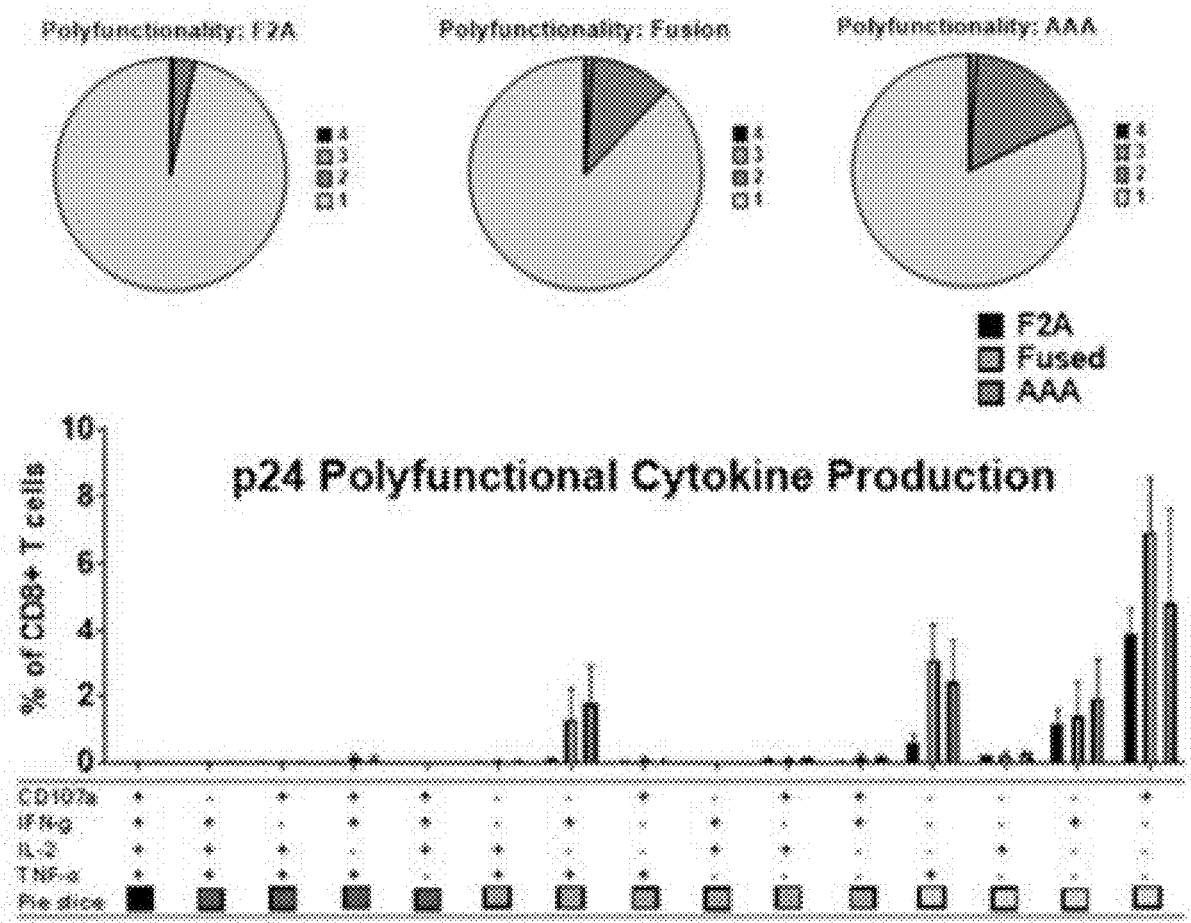

FIGS. 29A-29B illustrate functional profiles of vaccine induced CD8+ T cell responses in Balb/c (A) and C57 BL/6 animals (B). Flow cytometry profiles of CD8+ T cells able to mediate degranulation (CD107a), IFN-γ, IL-2 and TNF-α production were analyzed and the functional composition of responses for animals in each vaccination group are shown. Splenocytes were stimulated with the relevant peptide pool (p24 shown here) for 6 hours and stained as described in methods. The pie chart summarized the data, with each slice of the pie corresponding to the fraction of CD8+ T cells with a given number of functions within the total CD8+ T cell population. All possible combinations of responses are shown on the x-axis, and the percentage of functionally distinct CD8+ T cells within the total population are shown on the y-axis. Mean and SD are shown. FIGS. 29A-29B disclose "AAA" as SEQ ID NO: 378.

Figure 30A:
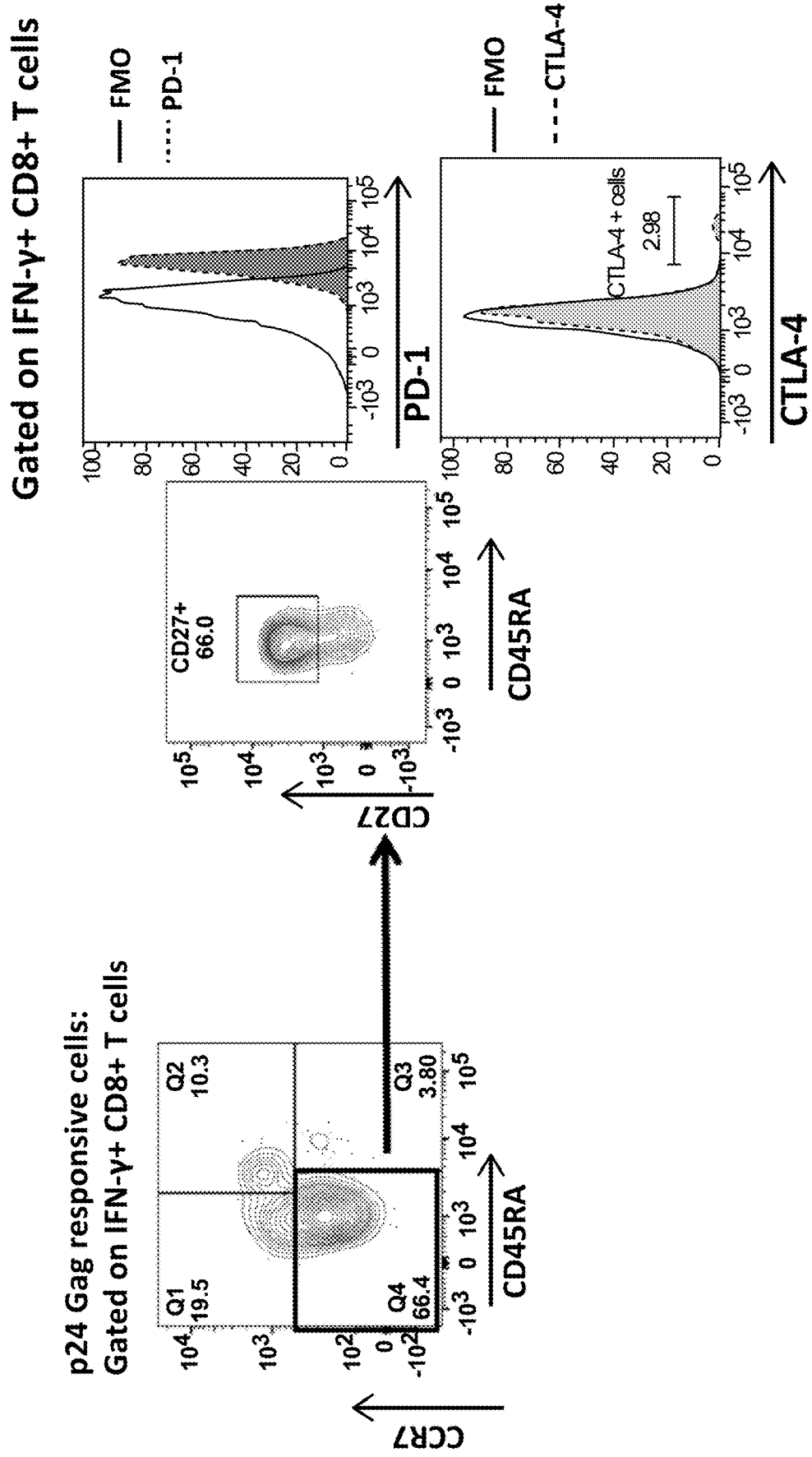

FIGS. 30A-30B illustrate the memory phenotype of IFN-γ producing cells. (A) Flow cytometry plots illustrating the gating strategy to define memory subsets and exhaustion phenotype based on CCR7, CD45RA, CD27, PD-1 and CTLA-4 expression on IFN-γ+CD8+ T cells post re-stimulation with 2 μg/ml Gag p24 peptide pools. (B) The proportion of naive (CCR7+ CD45RA+), effector memory (CCR7– CD45RA–) and central memory cells (CCR7+ CD45RA–) within IFN-γ+CD8+ and IFN-γ+ CD4+ T cells post re-stimulation with 2 μg/ml Gag p24 peptide pools.

Figure 31A:
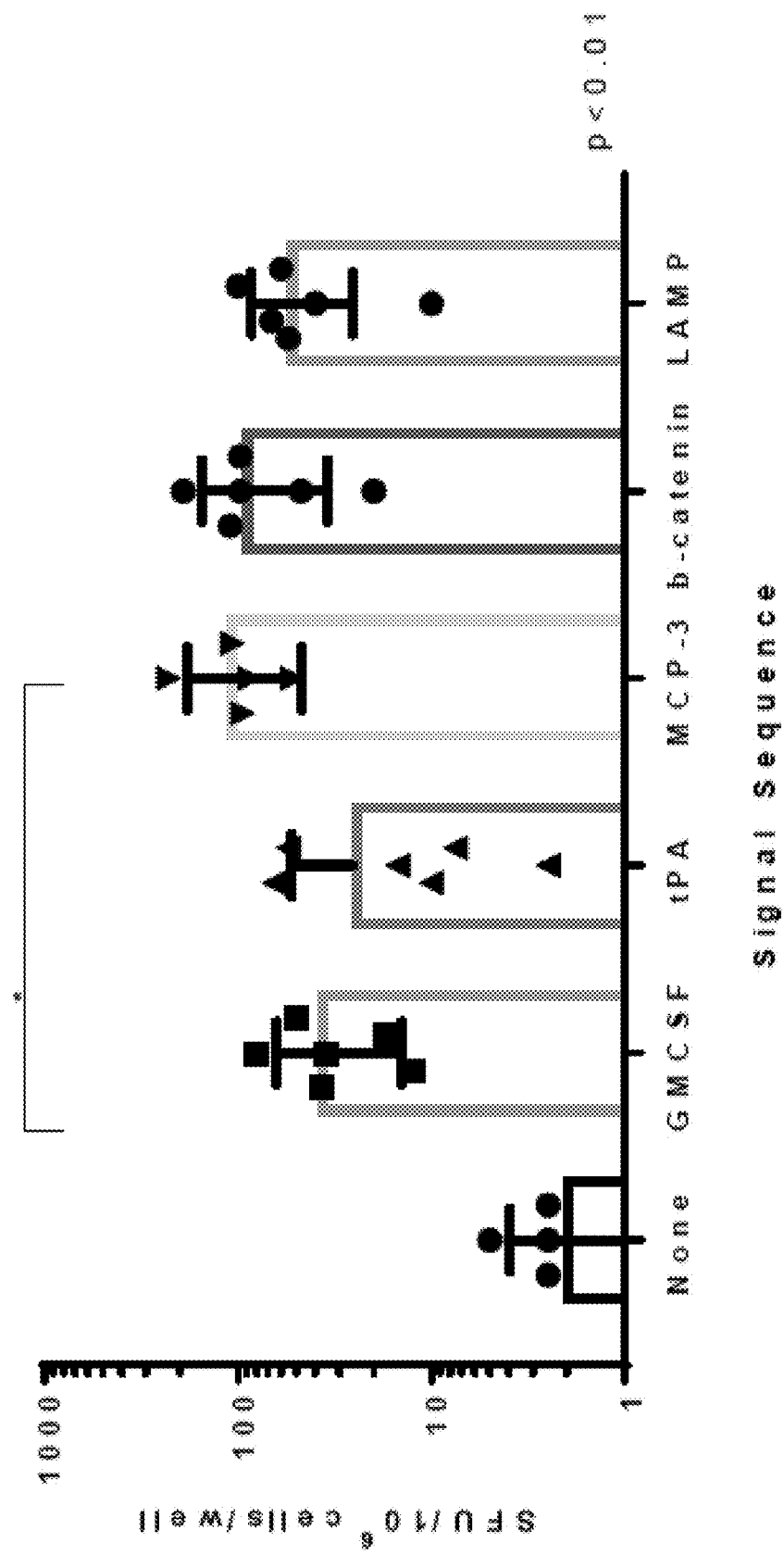
Figure 31B:
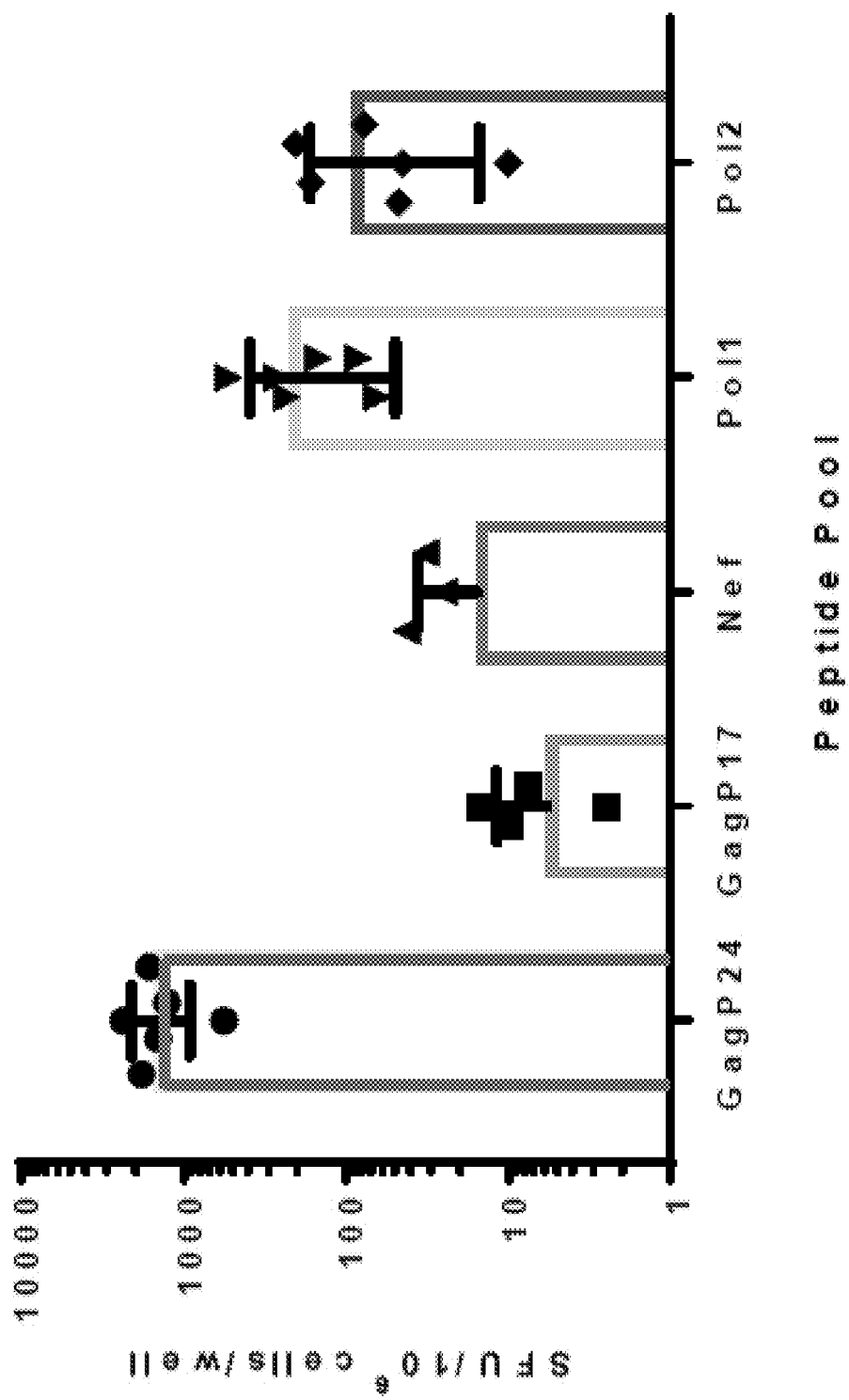

FIGS. 31A-31B. FIG. 31A illustrates that signal sequences differentially enhance immunogenicity of vaccine immunogen (SEQ ID NOs: 369, 370, 371, 368, 367). FIG. 31B illustrates that sequences of HIV-1 conserved regions are immunogenic with GM-CSF signal sequence (SEQ ID NOs: 353, 363).

Figure 32A:
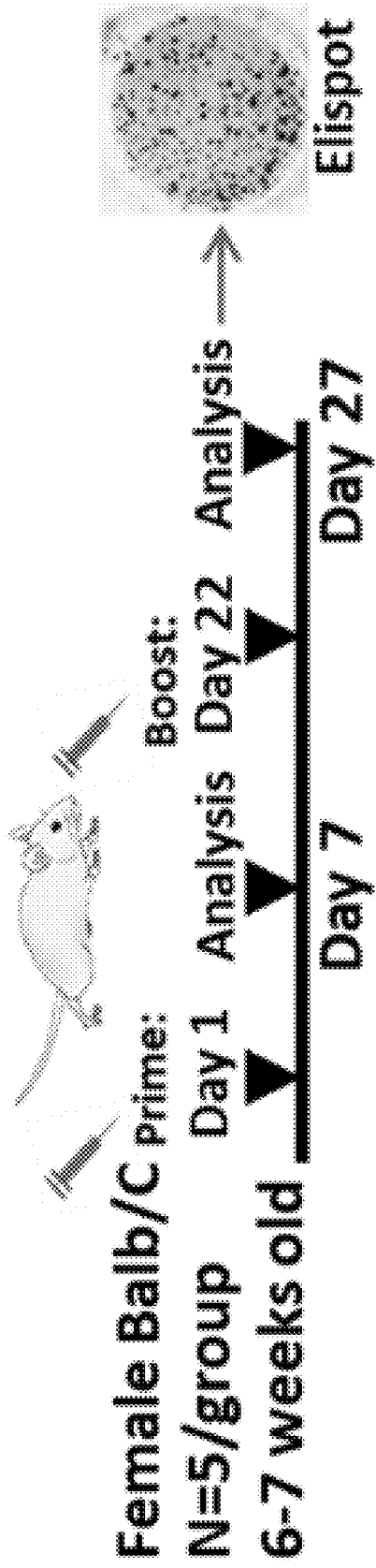
Figure 32B:
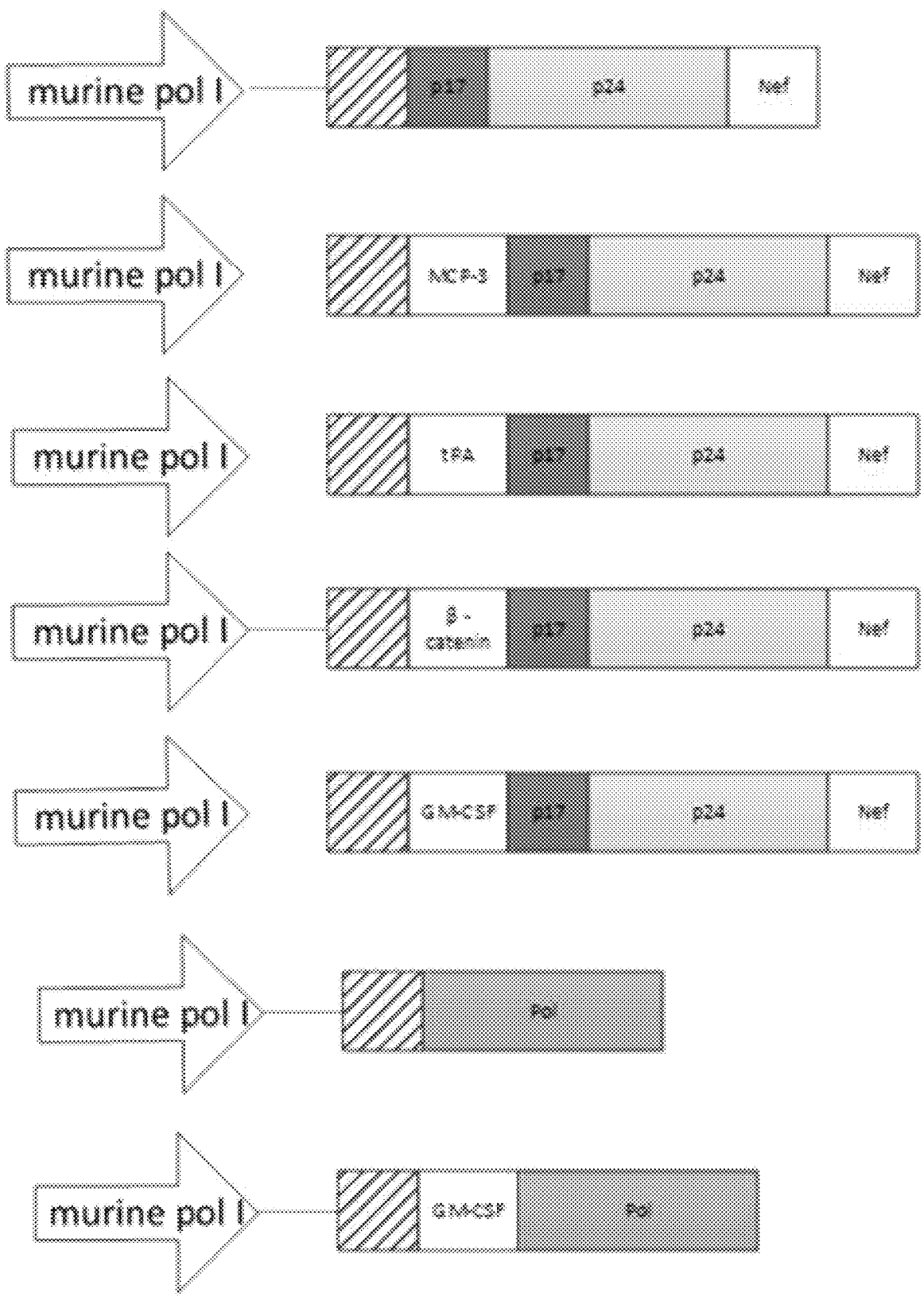
Figure 32C:
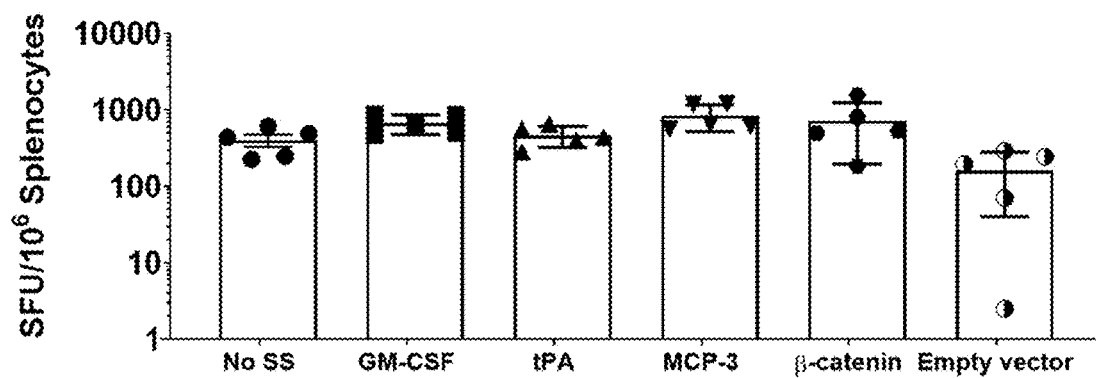
Figure 32D:
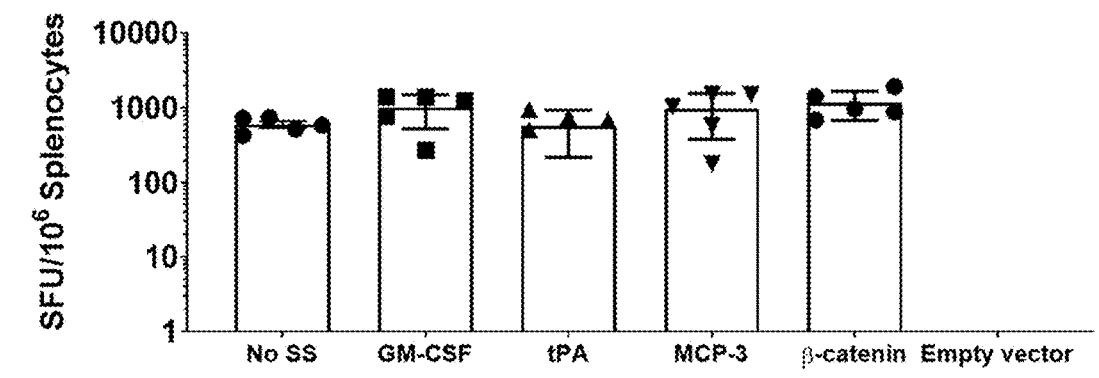
Figure 32E:
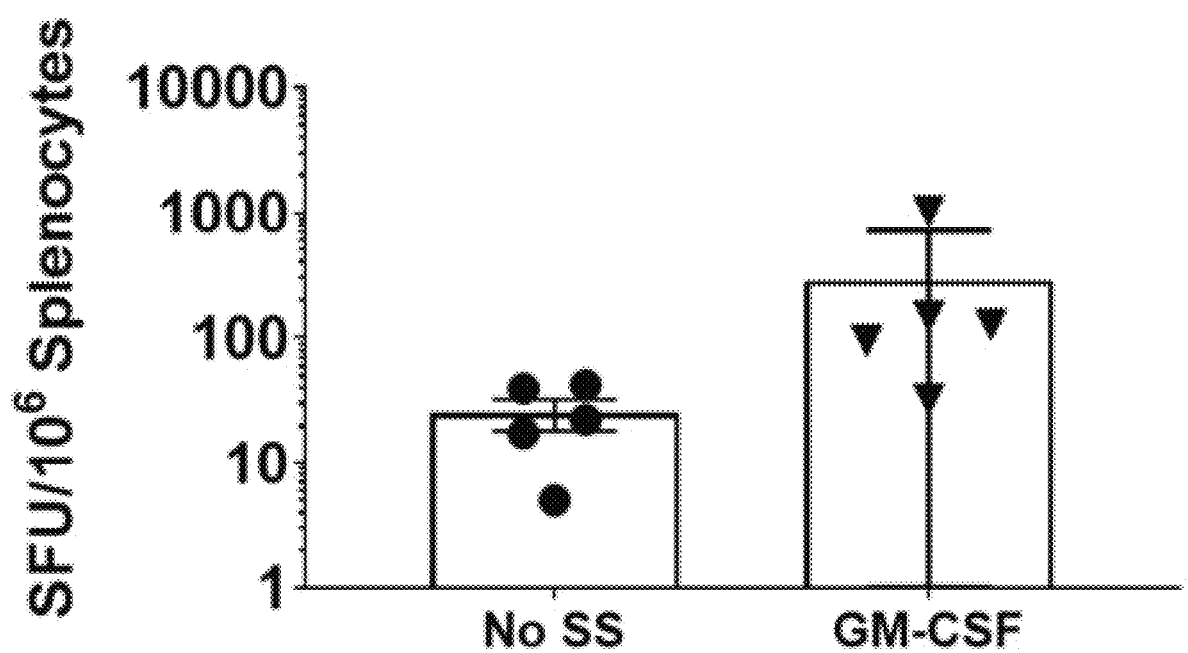

FIGS. 32A-32E. FIG. 32A illustrates immunization and sampling schedule. FIG. 32B illustrates LCMV vectors expressing HIV-1 conserved regions sequences from Gag-Nef fusion protein sequences without a signal sequence (SEQ ID NOs: 357, 430) and with signal sequences from GM-CSF (SEQ ID NOs: 353, 363), t-PA (SEQ ID NO: 354), MCP-3 (SEQ ID NO: 355), β-catenin (SEQ ID NO: 356) used to immunize groups of Balb/c mice. FIGS. 32C-32D illustrate the immunogenicity of vaccine immunogens with different signal sequences to Gag p24 by IFN-γ ELISpot after prime immunization on day 7 (FIG. 32C) and boost on day 27 (FIG. 32D) with LCMV replication incompetent vectors expressing conserved Gag-Nef in the presence or absence of MCP-3, tPA, β-catenin and GM-CSF signal sequences. FIG. 32E represents immunogenicity of Ad5/35 vectors expressing conserved Pol with or without GMCSF signal sequence in female Balb/c on day 7 post immunization. Each point represents one individual mouse. Mean and SD are shown. No statistical significance was observed among the different groups in this analysis.

Figure 33A:
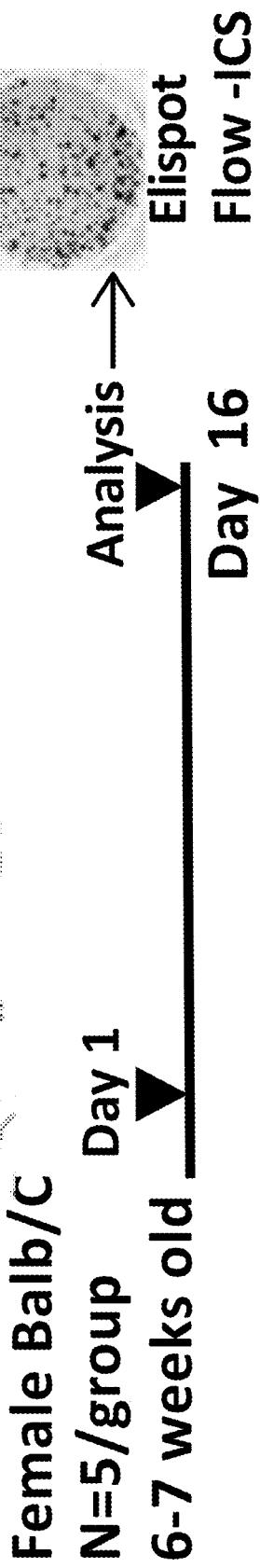
Figure 33B:
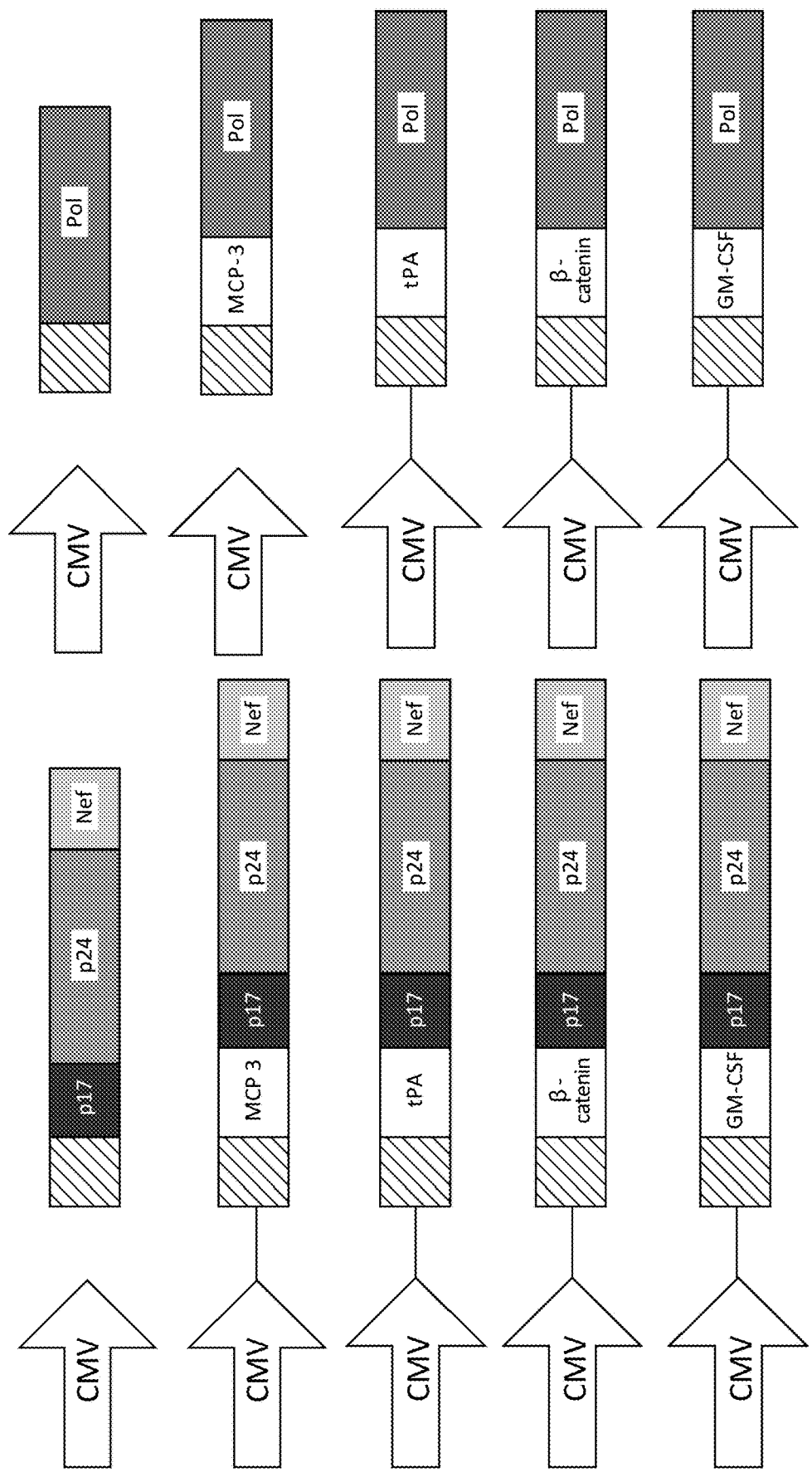
Figure 33C:
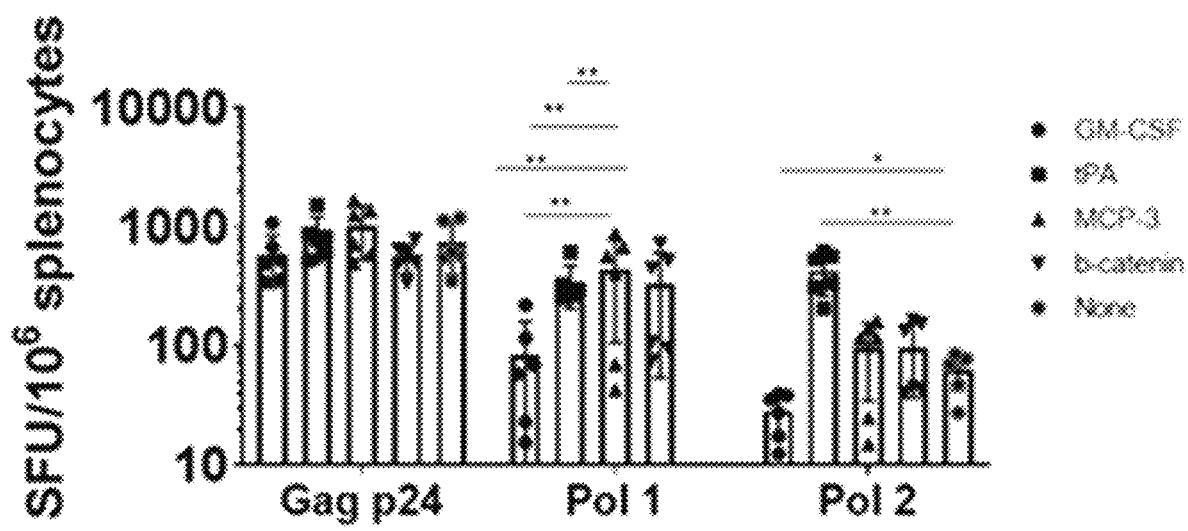
Figure 33D:
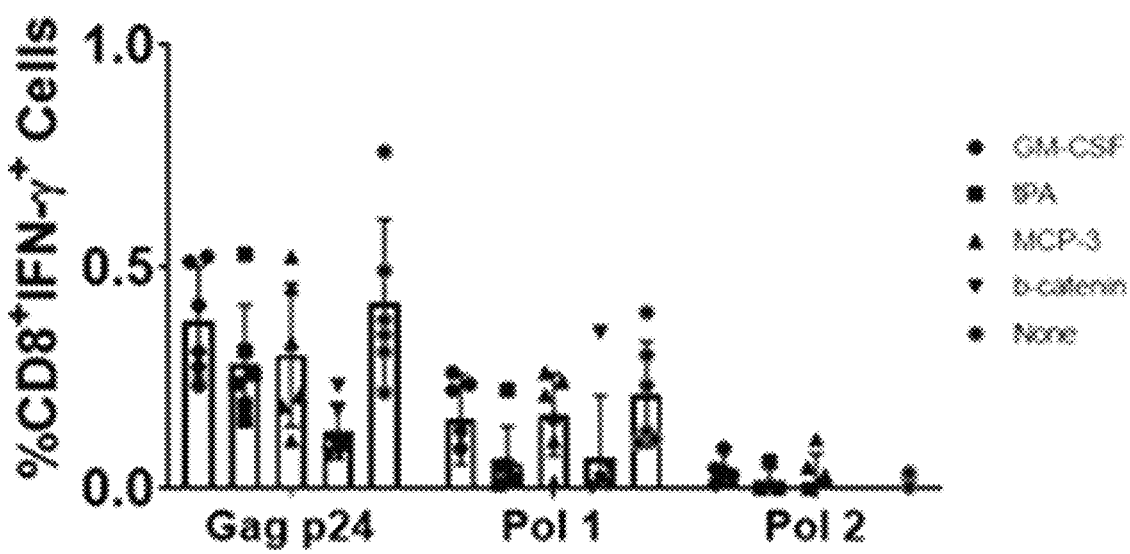

FIGS. 33A-33D. FIG. 32A illustrates immunization and sampling schedule. Groups of Balb/c mice were immunized with FIG. 33B illustrates Ad5/35 vectors expressing HIV-1 conserved regions from Gag-Nef and Pol fusion protein sequences without a signal sequence (SEQ ID NOs: 357, 430) and with signal sequences from GM-CSF (SEQ ID NOs: 353, 363), t-PA (SEQ ID NO: 354), MCP-3 (SEQ ID NO: 355), β-catenin (SEQ ID NO: 356) used to immunize groups of Balb/c mice. Fusion protein sequences are provided in Table J. FIGS. 33C-33D illustrate the immunogenicity of vaccine immunogens with different signal sequences by IFN-γ ELISpot (FIG. 33C) and intracellular IFN-γ+CD8+ T (FIG. 33D) cells by flow cytometry analysis after prime immunization on day 16. Each point represents one individual mouse. Mean and SD are shown. Non-parametric Mann-Whitney tests were used to determine statistical significance between groups. *P≤0.05, **P≤0.001.

Figure 34A:
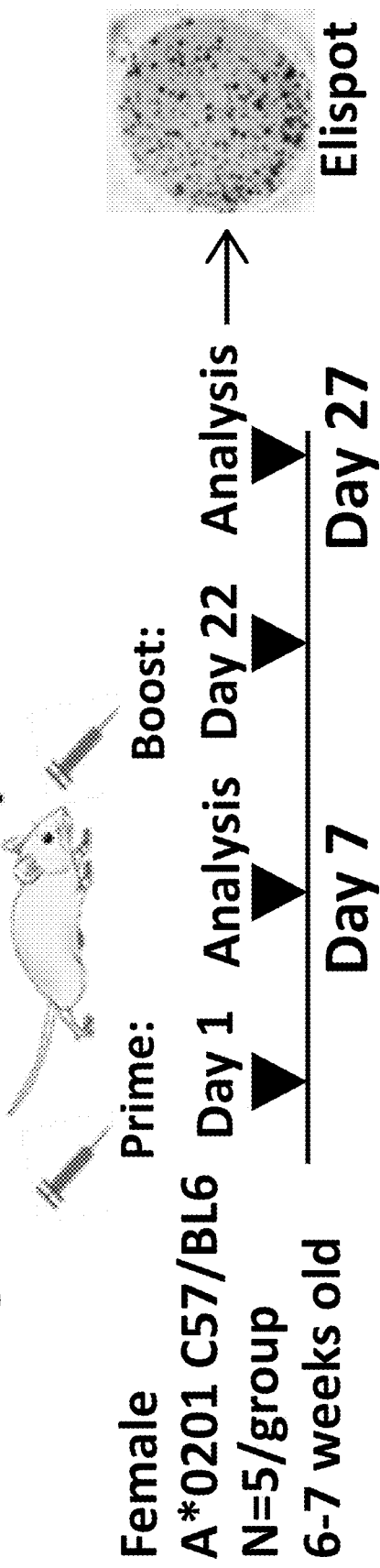
Figure 34B:
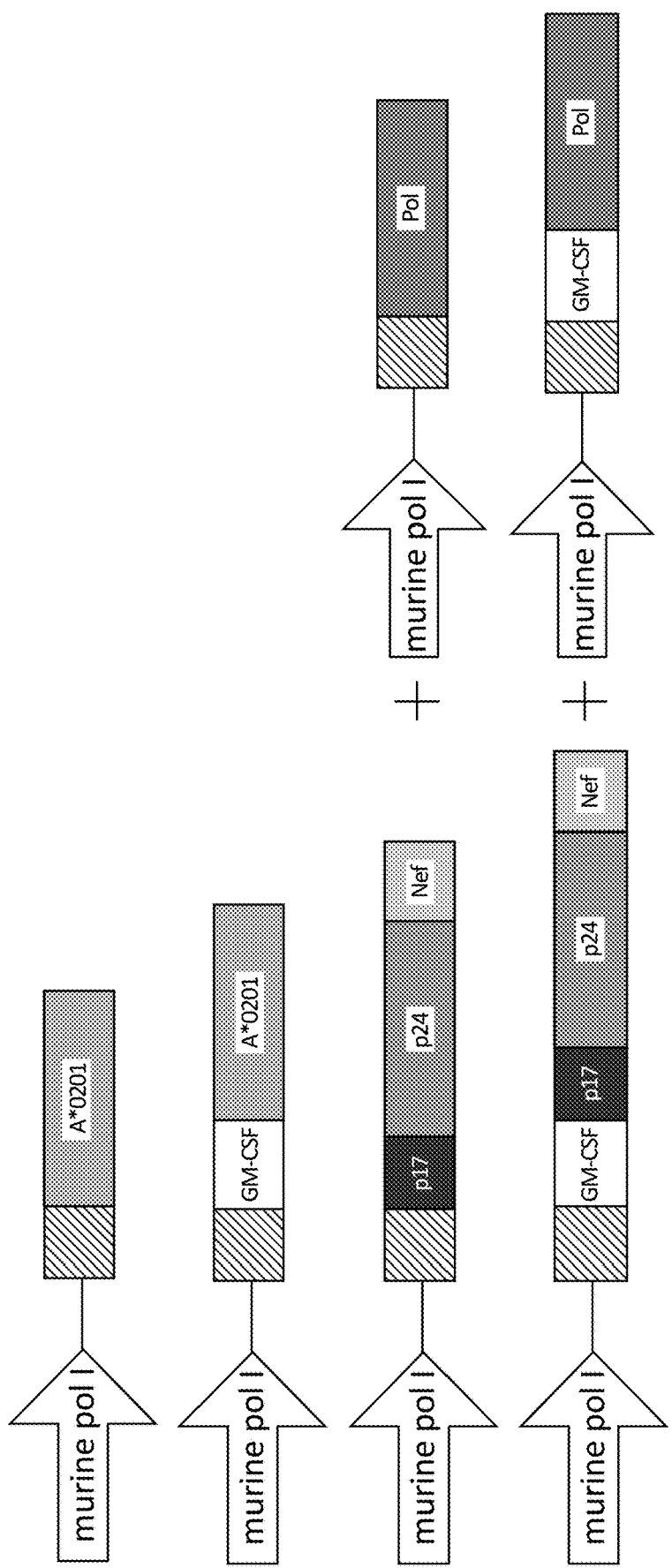
Figure 34C:
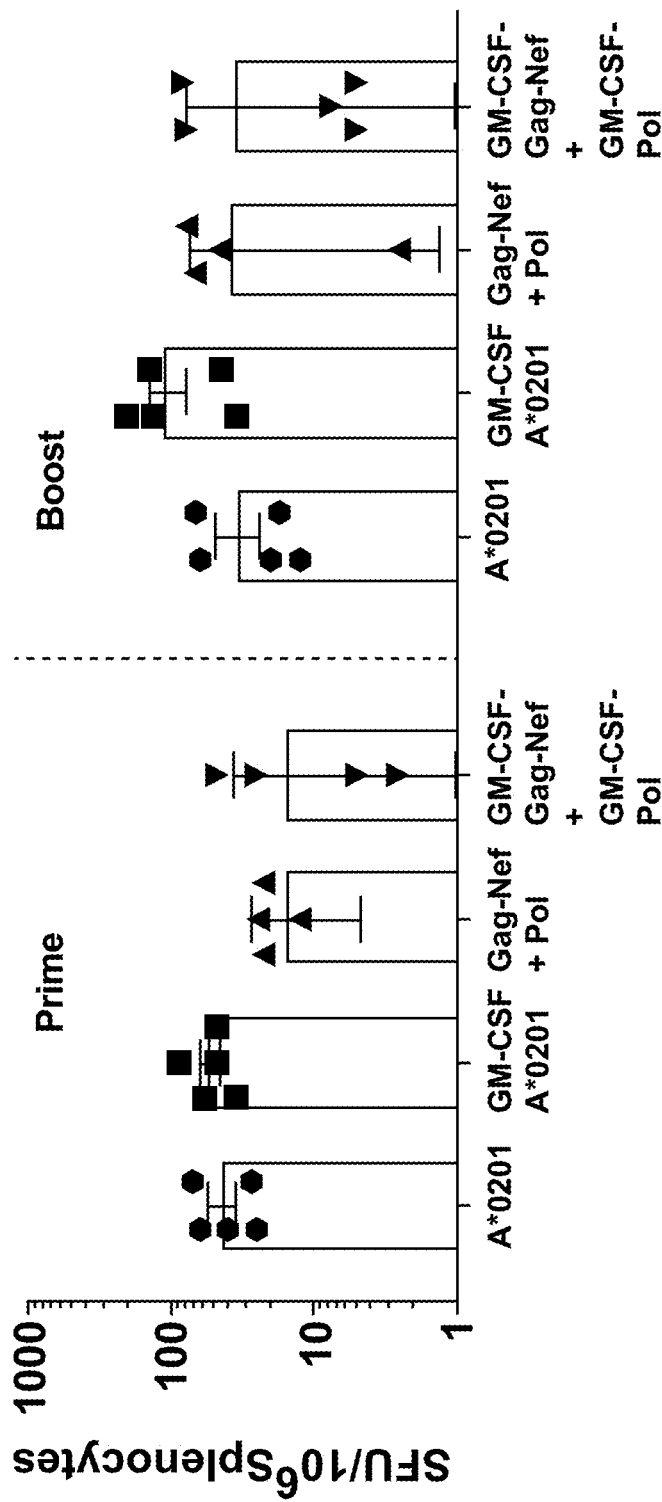
Figure 34D:
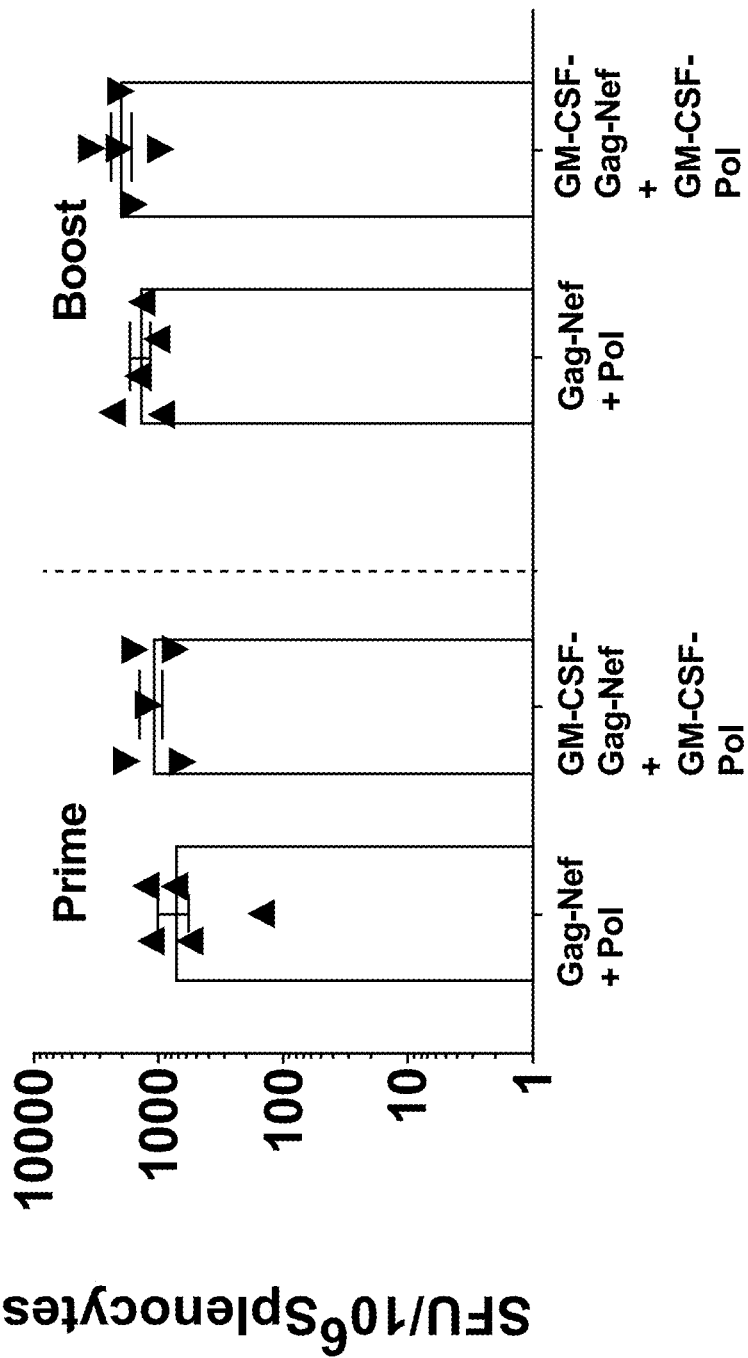

FIGS. 34A-34D illustrate immunogenicity of LCMV vectors containing conserved HIV sequences with and without leader sequences in A*0201-C57/BL6 transgenic mice. FIG. 34A represents the immunization and sampling schedules depicting time points for prime and boost vaccination and assessment of responses by IFN-γ ELISpot. FIG. 34B represents immunogen constructs used for vaccinations, with LCMV vectors expressing A*0201 sequences, in the absence (SEQ ID NOs: 367, 431) or presence (SEQ ID NOs: 368, 432) of GM-CSF signal sequence. Mice were also immunized with LCMV vectors expressing Gag-Nef and Pol fusion protein sequences in the absence (SEQ ID NO: 430+SEQ ID NO: 357) or presence (SEQ ID NO: 353+SEQ ID NO: 363) of GM-CSF signal sequences. Fusion protein sequences are provided in Table J. The A*0201 sequences comprise specific epitope sequences from conserved HIV sequences against A*0201 allele and are placed in the vector as bead in a string arrangement. FIG. 34C represents magnitude of IFN-γ responses against A*0201 peptide pool from both prime and prime/boost vaccinated animals. FIG. 34D represents magnitude of IFN-γ responses against Gag peptide pool from both prime and prime/boost vaccinated animals. In FIGS. 34C-34D: the Y axis represents magnitude of IFN-γ responses against the specific peptide pool stimulus as number of spot-forming units (SFU) per $10^6$ Splenocytes. Peptide specific values were obtained by subtracting no peptide stimulated control to exclude nonspecific responses. The X-axis indicates the individual vaccine constructs used for in vivo priming and boosting against which peptide specific responses were studied. No statistical significance was observed among the different groups in this analysis.

Figure 35A:
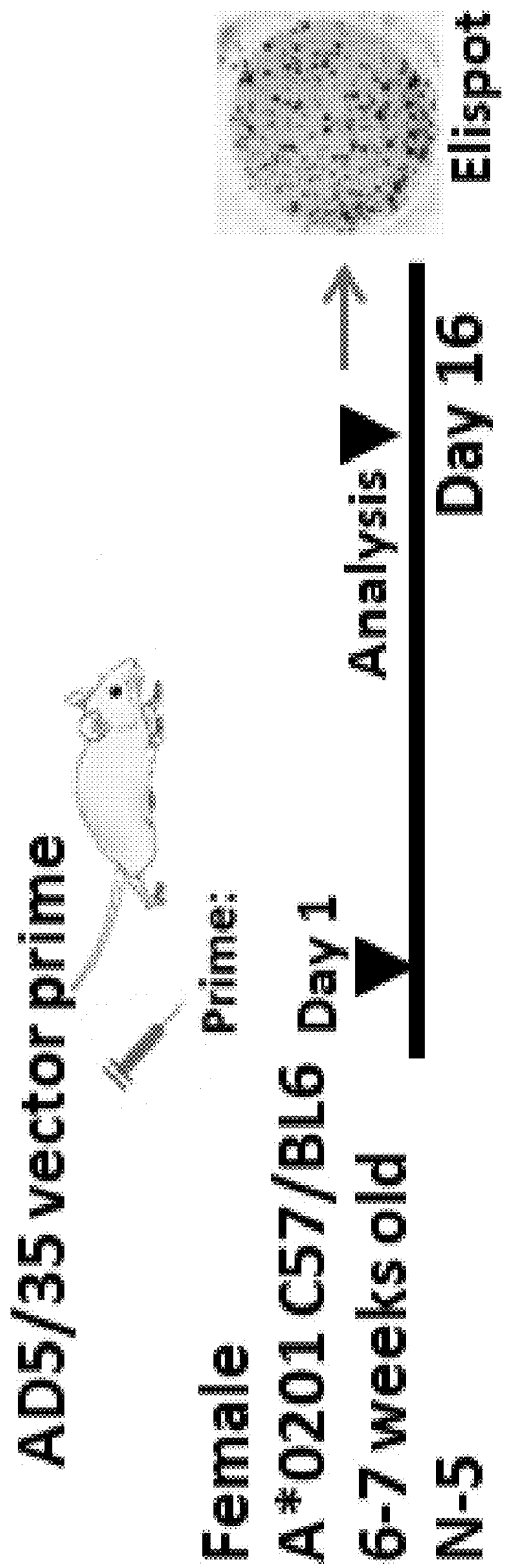
Figure 35B:
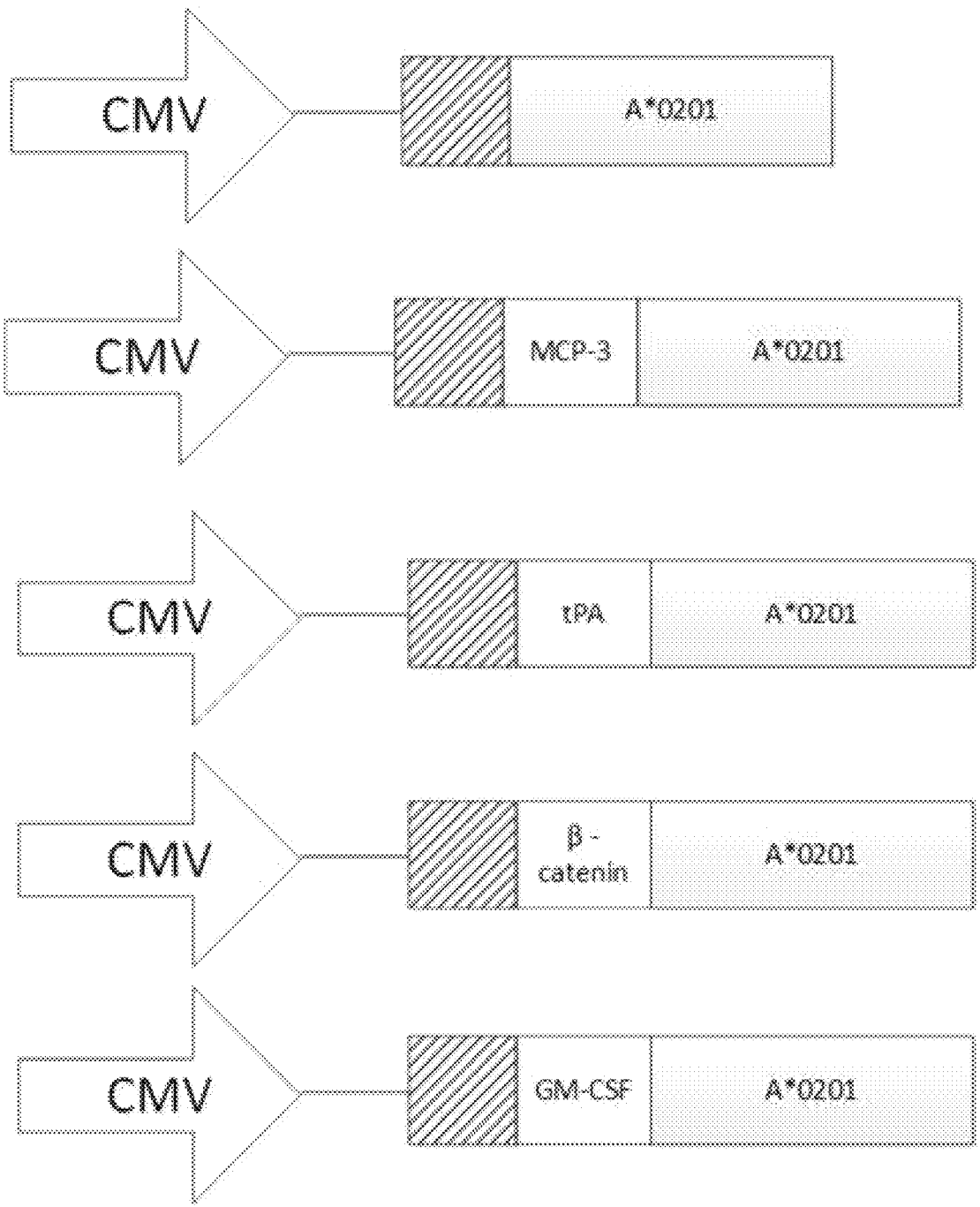
Figure 35C:
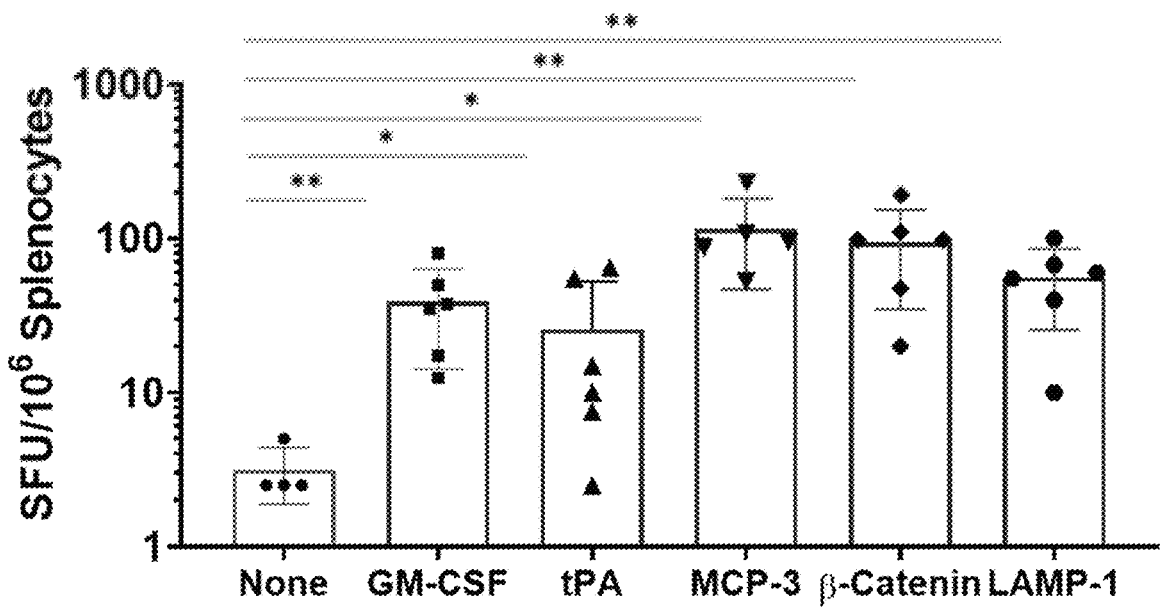
Figure 35D:
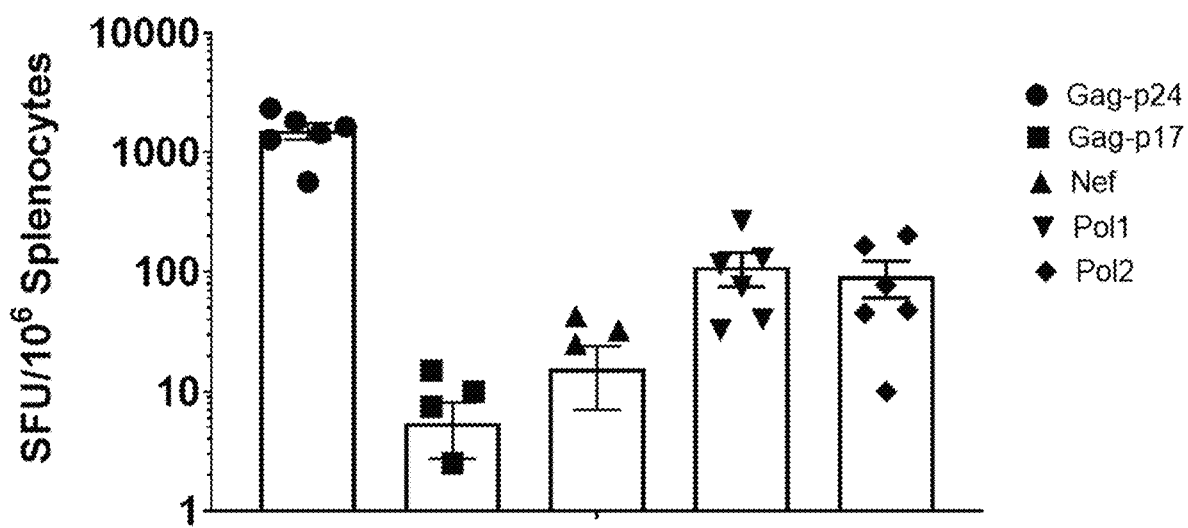
Figure 36A:
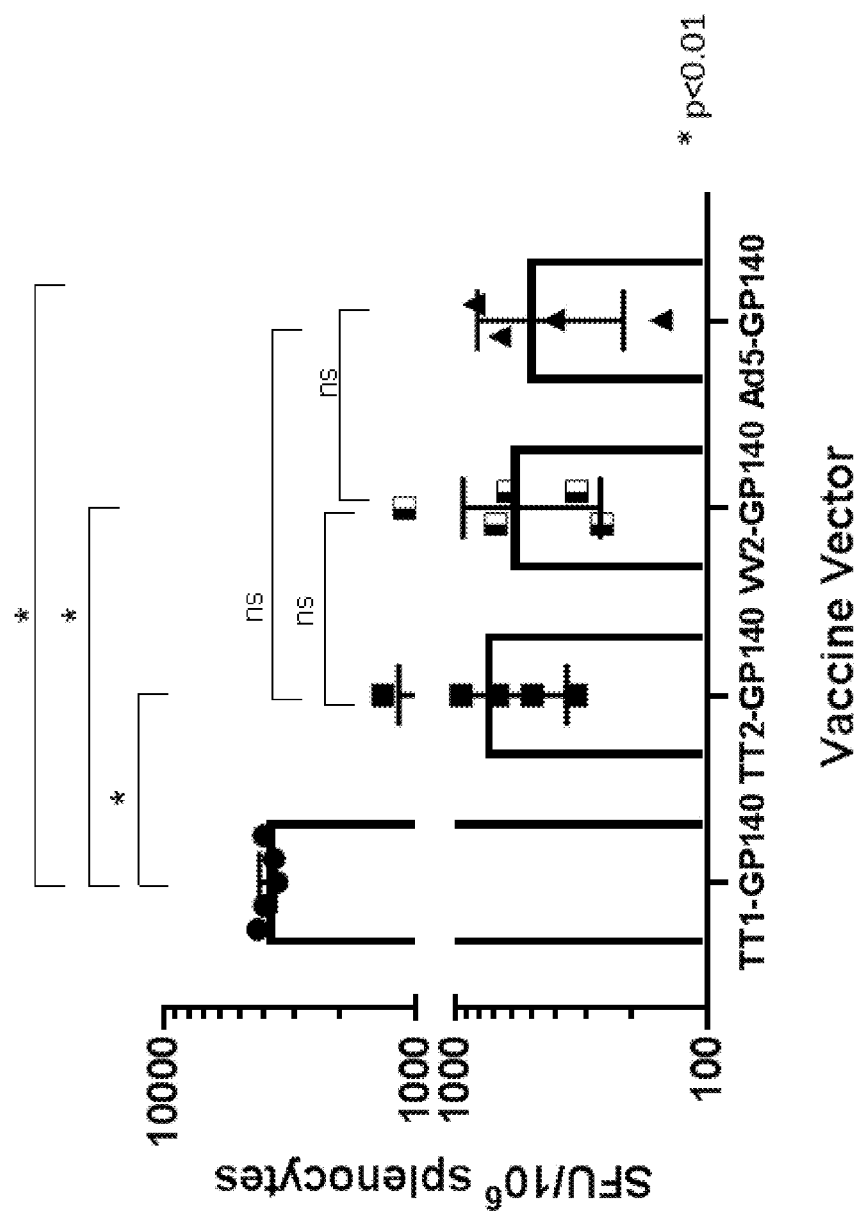
Figure 36B:
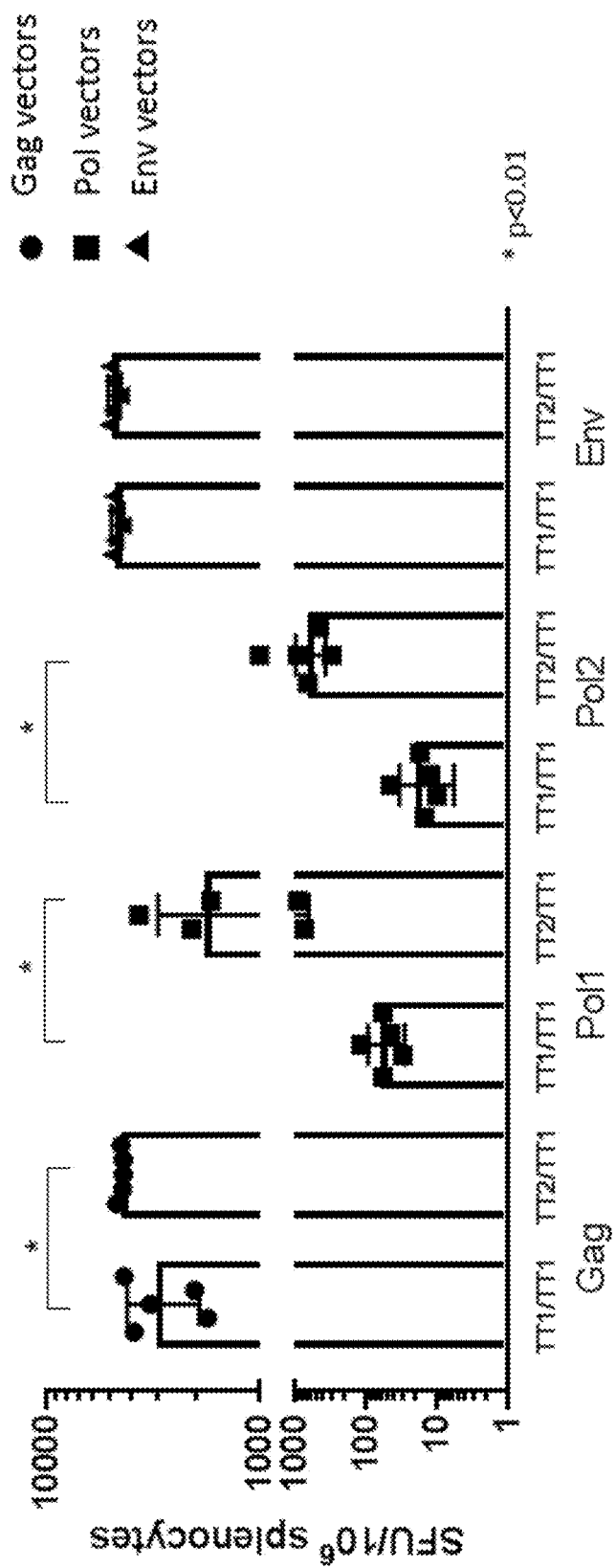
Figure 36C:
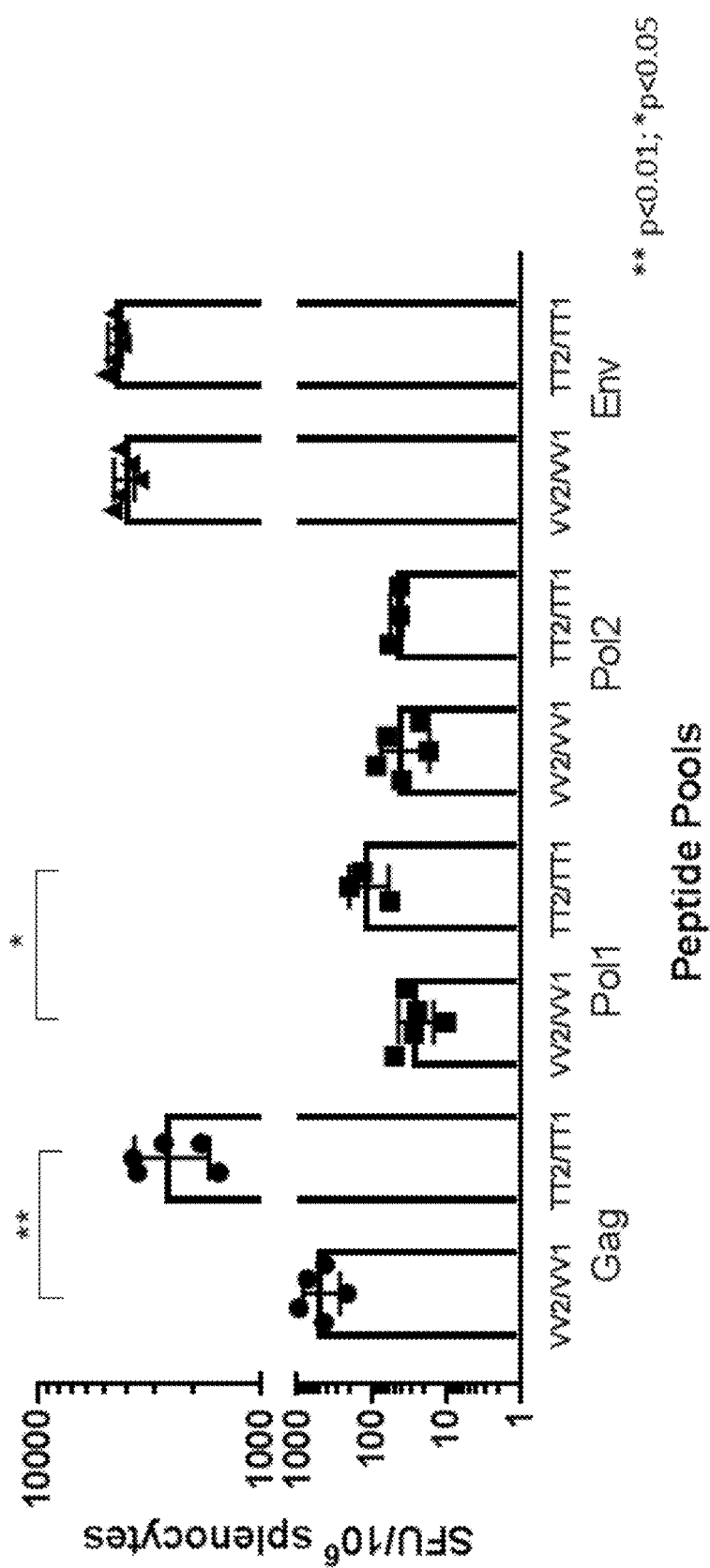
Figure 36D:
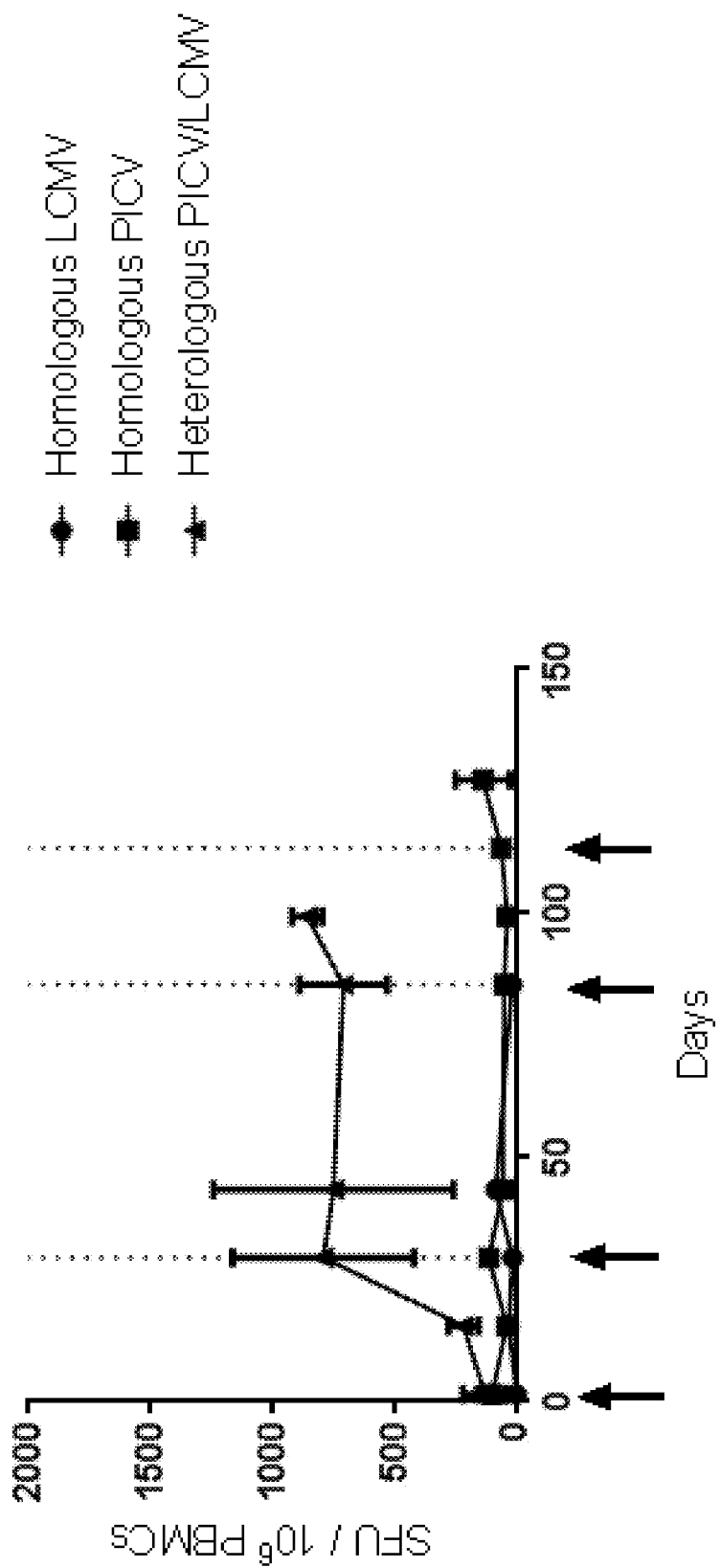
Figure 36E:
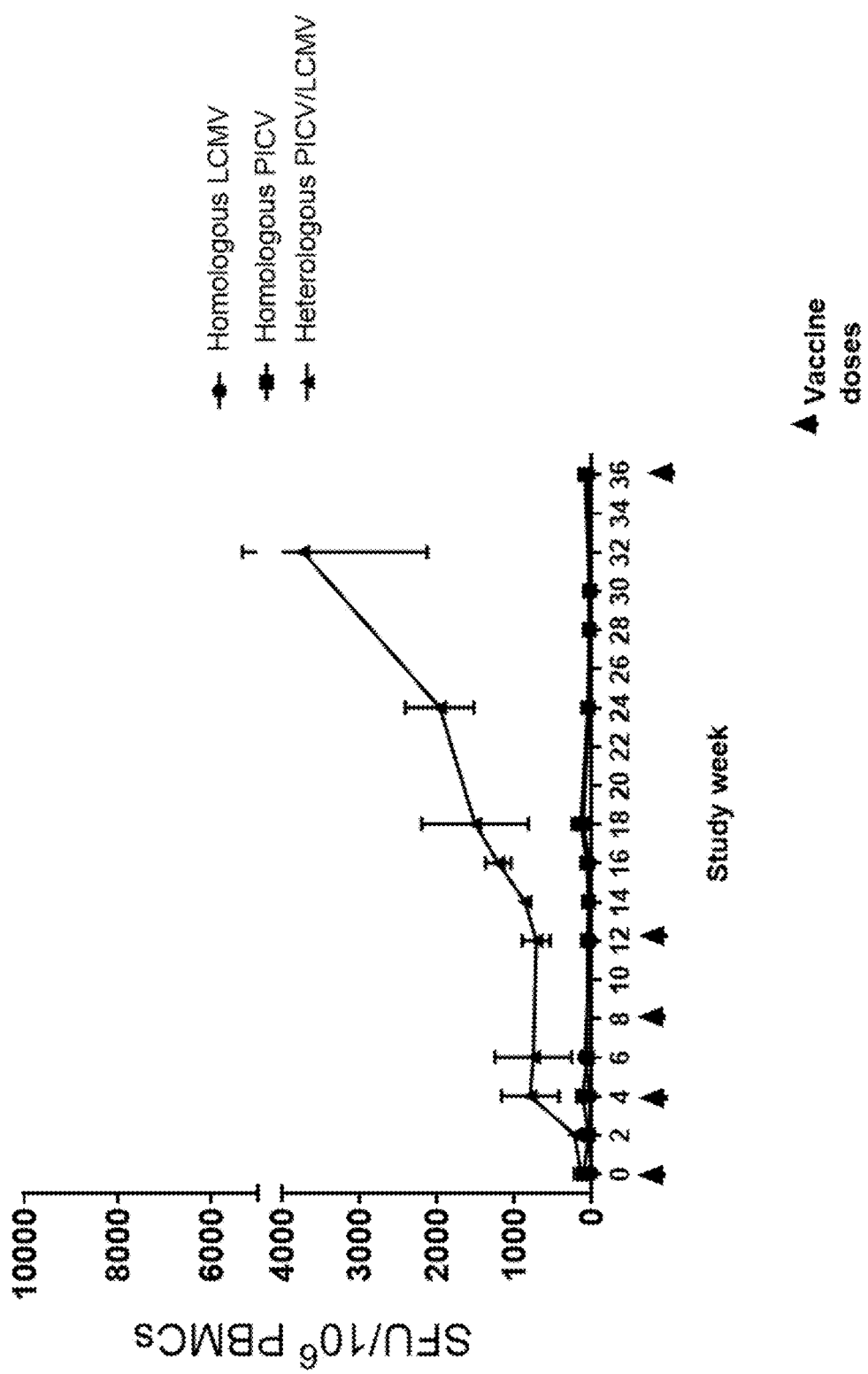

FIGS. 35A-35D illustrate immunogenicity of Ad5/35 vectors containing conserved HIV sequences with and without leader sequences in A*0201-C57/BL6 transgenic mice. FIG. 35A represents the immunization and sampling schedules depicting time points for prime vaccination and assessment of responses by IFN-γ ELISpot. FIG. 35B represents immunogen constructs used for vaccinations, where A*0201 sequences without a signal sequence is (SEQ ID NOs: 367, 431), with GM-CSF signal sequence is (SEQ ID NOs: 368, 432), with tPA signal sequence is (SEQ ID NOs: 369, 433), with MCP-3 signal sequence is (SEQ ID NOs: 370, 434), with β-catenin signal sequence is (SEQ ID NOs: 371, 435), with LAMP-1 N-terminal and C-terminal signal sequences is (SEQ ID NO: 372) and vectors each expressing GM-CSF Gag-Nef and GM-CSF Pol fusion protein sequences (SEQ ID NO: 353+SEQ ID NO: 363) respectively. Fusion protein sequences are provided in Table J. The A*0201 sequences in vectors comprise specific epitope sequences from conserved HIV sequences against A*0201 allele and are cloned in the Ad5/35 vectors as a bead on a string arrangement. FIG. 35C represents magnitude of IFN-γ responses against A*0201 peptide pool from prime vaccinated animals. The Y axis represents magnitude of IFN-γ responses against the A*0201 peptide pool stimulus as number of spot-forming cells (SFC) per $10^6$ splenocytes. Peptide specific values were obtained by subtracting no peptide stimulated control to exclude nonspecific responses. The X-axis indicates the individual vaccine constructs used for in-vivo priming. FIG. 35D represents magnitude of IFN-γ responses against Gag, Nef, Pol-1 and Pol-2 peptide pools in GM-CSF-Gag/Nef+GM-CSF-Pol vaccinated animals. The vector sequences contain conserved sequences as a whole; not just the A*0201 epitope specific sequences. The Y axis represents magnitude of IFN-γ responses in GM-CSF-Gag/Nef+GM-CSCF-Pol vaccine primed animals and X axis represents specific peptide pools used in stimulation. Each bar represents stimulation with peptide pools from Gag p24, Gag p17, Nef, Pol-1 (protease/RT) and Pol-2 (integrase) responses. Responses are represented as spot forming units (SFU) per $10^6$ Splenocytes. Peptide specific values were obtained by subtracting no peptide stimulated control to exclude nonspecific responses. Non-parametric Mann-Whitney tests were used to determine statistical significance between groups. *P≤0.05, **P≤0.001.

FIGS. 36A-36E illustrate various prime and prime-boost regimens using arenavirus LCMV and Pichinde (PICV) arenavirus vectors. (A) C57Bl/6 mice were immunized with a single prime with tri-segmented replication attenuated LCMV (TT1), tri-segmented replication attenuated PICV (TT2), replication defective PICV (VV2) and adenovirus vectors expressing SIVsme543 gp140. (B) Homologous and heterologous prime boost regimens with tri-segmented replication attenuated LCMV (TT1) or tri-segmented replication attenuated PICV (TT2) vectors expressing Gag, Pol-1/Pol-2 and Env (gp140). (C) Comparison of heterologous prime-boost, first priming with tri-segmented replication attenuated PICV (TT2) or replication defective PICV (VV2) and then boosting with replication defective LCMV (VV1) and tri-segmented replication attenuated LCMV (TT1) vectors expressing SIV antigens. Mice received a single immunization at each time point consisting of three (tri-segmented replication attenuated) or four (replication deficient) arenavirus vectors mixed in a 1:1:1:1 ratio. (D) Immunization of rhesus macaques with replication attenuated arenavirus vectors expressing SIVsme543 Gag as homologous LCMV or PICV and heterologous PICV prime and LCMV boost. Four intravenous immunizations we administered on Days 1, 29, 85 and 113. (E) Summary of longitudinal follow-up immune responses by IFN-γ ELISpot in rhesus macaques immunized with replication attenuated arenavirus vectors expressing SIVsme543 Gag as homologous LCMV or PICV and heterologous PICV prime and LCMV boost. The responses observed in (E) are an extension of the responses observed in (D).

FIGS. 37A-37F. (A) Illustrates protocol established for moDC-T cell priming assay followed by individual epitope using 384 well ELISPOT assays. (B) Represents the gender, viral loads and HLA diversity characteristics currently available for 10 aviremic HIV-1 patient donors completed in this analysis. (C) Represents viral vector sequences in the absence of signal sequences to evaluate if vaccination enhances the breadth of response evaluated in (D). (D) Comparison of the breadth of responses (number of independent epitopes) induced post priming with moDCs transduced with Ad5/35 vectors expressing conserved regions within Gag-Nef and Pol-Env. (E) Characterization of the breadth of immune responses targeted to different HIV-1 antigens with empty vectors (pre-vaccine) and conserved regions vaccines with different signal sequences (SEQ ID NOs. 353, 363, 354, 355, 356, 429 and 357). (F) Breadth of responses defined as number of de novo recognized peptide pools (excluding pre-existing baseline responses) and magnitude of responses assessed by IFN-γ ELISpot assay on day 10 following co-culture of PBMCs with vaccine vector transduced autologous moDCs expressing conserved regions constructs with different signal sequences. Each point represents one donor. Mean and SD are shown.

DETAILED DESCRIPTION

1. Introduction

Provided herein are fusion polypeptides comprising a plurality of polypeptide or peptide segments and related compositions, including immunogenic compositions and pharmaceutical compositions, as well as methods for making the fusion polypeptides and methods for their use to elicit an immunogenic response to a human immunodeficiency virus (HIV-1) in a subject in need thereof. As used herein, an "immunogen" is a substance, such as an antigen, that elicits an immune response or is capable of eliciting an immune response. Also provided are polynucleotides encoding the fusion polypeptides described herein, as well as vectors comprising same.

Provided herein are fusion polypeptides designed to induce an antiviral immune response. The vaccine constructs described herein were designed to provide mathematically-determined improved coverage of predicted T cell epitopes ("PTE") using the most highly conserved predicted epitopes within a source set of viral proteome sequences. As a paradigm for the methods of designing antiviral immunogens, fusion polypeptides encoded by one, two, three, or four, of the HIV-1 Gag, Pol, Env, and Nef genes were used. The methods described herein both retain the positional information of the PTE's within the source set of sequences and construct a bivalent set of sequences to improve coverage of conserved PTEs. The result is an initial bivalent vaccine construct that advantageously improves or increases highly conserved PTEs that are most likely to be highly similar to conserved epitopes in the naturally occurring sequences in proteins expressed by viral species amongst a population of patients and within an individual patient, due to both the retained positional information. In addition, the use of only highly conserved PTE sequences amongst HIV-1 species in interpatient and intrapatient populations reduces the likelihood of escape mutants because the highly conserved sequences are more likely to contribute viral structure and function.

Further provided are computational approaches for designing antiviral vaccine immunogens for a highly variable virus, such as HIV-1. The antiviral vaccine immunogen design methods incorporate deep sequencing data from individual patient samples with variable sequences and analyze the sequence diversity in the context of host HLA diversity to develop antiviral vaccines for therapeutic and preventative use. The antiviral immunogens can be designed to provide coverage at an individual level, for a group of individuals with a defined set of HLA alleles, or for broad population coverage. In the herein described vaccine immunogen design methods, we define a computational approach for targeting conserved regions within a vaccine sequence using bulk population sequences, e.g., from public databases and internally developed databases. Further, using individual patient deep sequence data we define sequence variability for each potential T cell epitope within the conserved regions. Moreover, we identify regions that may serve as actual epitopes based on likelihood of presentation by the individual host's set of HLA alleles. The likelihood of binding to host HLA defined by publicly available and internally-developed databases, was used to develop deep learning models that model peptide binding per allele. This can be coupled with in-silico, published and/or experimental in-vitro T cell priming data that can define the potential impact of antigen variants in modulating TCR recognition or identify a peptide as an escape variant. These data are used to design a set of peptide immunogens that contain the epitopes and associated epitope variants. The epitope sequences are concatenated or connected in series into a single fusion polypeptide, either directly fused or linked via a linker sequence. Peptide segments are joined in a computationally determined sequential order from N-terminus to C-terminus that reduces or eliminates the creation of junctional epitopes that may mimic human self-antigens and have undesirable effects (e.g., eliciting an autoimmune response or a tolerogenic response).

Unlike similar graph-based approaches to vaccine design, the approaches described herein build segments of connected PTE's using only adjacent PTE's that are also adjacent in the natural sequences. In addition, the present methods first build a bivalent construct consisting of two polypeptides matched to improve or increase coverage at each PTE position in the viral proteome. The bivalent construct itself may be used as a vaccine, as in the constructs described in Examples 1 and 2 below, or it may serve as the basis for a further construct, such as the HLA-restricted construct described in Example 3 or individualized construct described in Examples 4 and 5, below. The bivalent constructs designed by analysis of population-based sequences (e.g., interpatient diversity) identifies population-based conserved sequences that may contribute to viral structure and function and can serve as a template for defining conservation within intrapatient sequences, which information can be applied to build an individualized vaccine construct.

The methods described herein can begin with the identification of conserved region bivalent sequences, using a process referred to herein as the "Conservation Analysis" or "Conservation Algorithm." The methods further can comprise a step of building a bivalent vaccine construct having maximal epitope coverage while retaining the positional information of the PTE's from the natural sequences, using a process referred to referred to herein as a "Conserved Walking Algorithm" or "CWA."

Therapeutic vaccines based on the induction of T cell responses are being readily evaluated and showing efficacy within the context of cancer vaccines. These vaccines are typically epitope based and can be tailored to an individual's HLA alleles as well as their specific tumor antigen (see, e.g., Tran, et al., *Science*, (2014) 344(6184):641-5). We have developed vaccine sequences that may target sub-populations based on the population prevalence of certain HLA alleles or may be specifically tailored to an individual's range of HLA alleles.

2. Fusion Polypeptides Useful to Promote Immune Response Against Human Immunodeficiency Virus-1 (HIV-1)

Provided herein are fusion polypeptides comprising a plurality of polypeptide or peptide segments encoded by one or more HIV-1 genes. A 'segment' of a fusion polypeptide described herein is a contiguous sequence of at least 8 amino acids with respect to a reference sequence, for example HIV-1 HXB2 reference sequences for Env, Gag, Nef and Pol polypeptides, provided herein as SEQ ID NOs: 403-406, respectively. The polypeptides described herein are 'fusion' polypeptides in the sense that they are assembled from connected or concatenated polypeptide or peptide segments of two or more HIV-1 proteins. With respect to the HIV-1 protein reference sequences, the polypeptide or peptide segments may correspond to discontinuous sequences of the same HIV-1 protein or different HIV-1 proteins. Generally, the fusion polypeptides are non-naturally occurring, and can be synthetic or recombinantly produced.

a. Polypeptide Segments

With respect to the HIV-1 genes encoding the polypeptide segments used to assemble the herein described fusion polypeptides, in various embodiments, the fusion polypeptides comprise a plurality of polypeptide segments of one or more human immunodeficiency virus-1 (HIV-1) proteins encoded by one or more, e.g. two or more, three or more, four or more, HIV-1 genes selected from Gag, Nef, Env, Pol, Vpu, Vpr and Vif, e.g., two or more, three or more, four or more, HIV-1 genes selected from Gag, Nef, Env, Pol, and Vif. In some embodiments, the plurality of polypeptide segments is comprised of only polypeptide segments encoded by HIV-1 genes Env, Gag, Nef and Pol, e.g., does not comprise polypeptide segments encoded by HIV-1 Tat, Rev, Vif, Vpr and/or Vpu genes. In some embodiments, the plurality of polypeptide segments is comprised of only polypeptide segments encoded by HIV-1 genes Gag, Nef and Pol, e.g., does not comprise polypeptide segments encoded by HIV-1 Env, Tat, Rev, Vif, Vpr and/or Vpu genes. In some embodiments, the plurality of polypeptide segments is comprised of only polypeptide segments encoded by HIV-1 genes Gag and Nef, e.g., does not comprise polypeptide segments encoded by HIV-1 Env, Pol, Tat, Rev, Vif, Vpr and/or Vpu genes. In some embodiments, the plurality of polypeptide segments is comprised of only polypeptide segments encoded by HIV-1 genes Pol and Nef, e.g., does not comprise polypeptide segments encoded by HIV-1 Env, Gag, Tat, Rev, Vif, Vpr and/or Vpu genes. In some embodiments, the plurality of polypeptide segments is comprised of only polypeptide segments encoded by HIV-1 genes Pol and Env, e.g., does not comprise polypeptide segments encoded by HIV-1 Gag, Nef, Tat, Rev, Vif, Vpr and/or Vpu genes. In some embodiments, the plurality of polypeptide segments is comprised of only polypeptide segments encoded by HIV-1 Pol gene, e.g., does not comprise polypeptide segments encoded by HIV-1 Env, Gag, Nef, Tat, Rev, Vif, Vpr and/or Vpu genes. In various embodiments, the plurality of polypeptide segments does not contain a segment encoded by one, two, three or four of HIV Tat, Rev, Vif, Vpr and/or Vpu genes.

With respect to the number of polypeptide segments assembled, connected, linked or concatenated into a single fusion polypeptide, in various embodiments, the fusion polypeptides are comprised of at least 5 and up to 40 polypeptide segments, e.g., from 5 polypeptide segments and up to 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39 or 40 polypeptide segments. As appropriate, the polypeptide segments can be arranged in the same order or according to a different order than in the naturally occurring proteins.

With respect to the regions of the polypeptides encoded by an HIV-1 gene selected as polypeptide segments to include in the fusion polypeptides, in various embodiments, the polypeptide segments are derived from conserved regions in a population of viral proteome sequences. In some embodiments, the conserved regions are greater than 80%, e.g., greater than 81%, 82%, 83%, 84%, 85%, 86%, 87%, 88%, 89%, 90%, 91%, 92%, 93%, 94%, 95%, 96%, 97%, 98% or 99% conserved amongst HIV-1 species, e.g., as determined in interpatient and/or intrapatient populations. As used herein, conserved regions in a polypeptide encoded by an HIV-1 gene refers to the percentage of sequences in a population of sequences containing identical amino acid segments or subsequences e.g., (segments 9 amino acids in length or 9-mers) as the most prevalent one in a predetermined amino acid segment or subsequence position, where an amino acid segment or subsequence position is determined with respect to a reference sequence, e.g., HIV-1 HXB2 polypeptide sequences, e.g., SEQ ID NOs: 403-406. In various embodiments, the conserved regions are conserved amongst one or more of HIV-1 clades within Group M, e.g., one or more of HIV-1 clades A-K, e.g., one or more of clades A, B, C, D and G, e.g., amongst HIV-1 Group M, clade B, and recombinant forms thereof, e.g., CRF01_AE. In some embodiments, the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, polypeptide segments selected from SEQ ID NOs: 1-344, e.g., polypeptide segments identified in Table B. In some embodiments, the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, polypeptide segments selected from SEQ ID NOs: 2, 3, 8, 9, 13, 14, 17, 18, 23, 24, 25, 26, 28, 29, 31, 32, 33, 34, 35, 36, 37, 38, 39, 40, 43, 44, 45, 46, 47, 48, 49, 50, 51, 52, 53, 54, 55, 56, 58, 59, 62, 63, 64, 65, 66, 67, 68, 69, 72, 73, 74, 75, 76, 77, 80, 81, 82, 83, 84, 85, 86, 87, 88, 89, 92, 93, 101, 102, 103, 104, 109, 110, 115, 116, 125, 126, 127, 128, 129, 130, 131, 132, 133, 134, 135, 136, 139, 140, 141, 142, 143, 144, 145, 146, 147, 148, 149, 150, 155, 156, 157, 158, 159, 160, 166, 167, 168, 169, 170, 171, 174, 175, 178, 179, 180, 181, 182, 183, 184, 185, 193, 194, 195, 196, 197, 198, 199, 200, 203, 204, 205, 206, 207, 208, 213, 214, 221, 222, 236, 237, 245, 246, 247, 248, 249, 250, 251, 252, 253, 254, 255, 256, 257, 258, 263, 264, 266, 267, 268, 269, 270, 271, 272, 273, 278, 279, 280, 281, 282, 283, 284, 285, 286, 287, 288, 289, 290, 291, 292, 293, 294, 295, 305, 306, 307, 308, 309, 310, 313, 314, 315, 316, 317, 318, 321 and 322, e.g., polypeptide segments identified in Table C. The start and end positions are with respect to HIV-1 HXB2 reference polypeptides, GenBank Accession No. K03455 (ncbi.nlm.nih.gov/nuccore/K03455), provided herein as SEQ ID NOs: 403-406 and identified in Table A.

TABLE A

HIV-1 HXB2 reference sequences

| SEQ ID NO: | GENE | SEQUENCE |
|---|---|---|
| 403 | Env | MRVKEKYQHLWRWGWRWGTMLLGMLMICSATEKLWVTVYYGVPVWKEATTTLFCASDAKAYDT EVHNVWATHACVPTDPNPQEVVLVNVTENFNMWKNDMVEQMHEDIISLWDQSLKPCVKLTPLC VSLKCTDLKNDTNTNSSSGRMIMEKGEIKNCSFNISTSIRGKVQKEYAFFYKLDIIPIDNDTT SYKLTSCNTSVITQACPKVSFEPIPIHYCAPAGFAILKCNNKTFNGTGPCTNVSTVQCTHGIR PVVSTQLLLNGSLAEEEVVIRSVNFTDNAKTIIVQLNTSVEINCTRPNNNTRKRIRIQRGPGR AFVTIGKIGNMRQAHCNISRAKWNNTLKQIASKLREQFGNNKTIIFKQSSGGDPEIVTHSFNC GGEFFYCNSTQLFNSTWENSTWSTEGSNNTEGSDTITLPCRIKQIINMWQKVGKAMYAPPISG QIRCSSNITGLLLTRDGGNSNNESEIFRPGGGDMRDNWRSELYKYKVVKIEPLGVAPTKAKRR VVQREKRAVGIGALFLGFLGAAGSTMGAASMTLTVQARQLLSGIVQQQNNLLRAIEAQQHLLQ LTVWGIKQLQARILAVERYLKDQQLLGIWGCSGKLICTTAVPWNASWSNKSLEQIWNHTTWME WDREINNYTSLIHSLIEESQNQQEKNEQELLELDKWASLWNWFNITNWLWYIKLFIMIVGGLV GLRIVFAVLSIVNRVRQGYSPLSFQTHLPTPRGPDRPEGIEEEGGERDRDRSIRLVNGSLALI WDDLRSLCLFSYHRLRDLLLIVTRIVELLGRRGWEALKYWWNLLQYWSQELKNSAVSLLNATA IAVAEGTDRVIEVVQGACRAIRHIPRRIRQGLERILL |
| 404 | Gag | MGARASVLSGGELDRWEKIRLRPGGKKKYKLKHIVWASRELERFAVNPGLLETSEGCRQILGQ LQPSLQTGSEELRSLYNTVATLYCVHQRIEIKDTKEALDKIEEEQNKSKKKAQQAAADTGHSN QVSQNYPIVQNIQGQMVHQAISPRTLNAWVKVVEEKAFSPEVIPMFSALSEGATPQDLNTMLN TVGGHQAAMQMLKETINEEAAEWDRVHPVHAGPIAPGQMREPRGSDIAGTTSTLQEQIGWMTN NPPIPVGEIYKRWIILGLNKIVRMYSPTSILDIRQGPKEPFRDYVDRFYKTLRAEQASQEVKN WMTETLLVQNANPDCKTILKALGPAATLEEMMTACQGVGGPGHKARVLAEAMSQVTNSATIMM QRGNFRNQRKIVKCFNCGKEGHTARNCRAPRKKGCWKCGKEGHQMKDCTERQANFLGKIWPSY KGRPGNFLQSRPEPTAPPEESFRSGVETTTPPQKQEPIDKELYPLTSLRSLFGNDPSSQ |
| 405 | Nef | MGGKWSKSSVIGWPTVRERMRRAEPAADRVGAASRDLEKHGAITSSNTAATNAACAWLEAQEE EEVGFPVTPQVPLRPMTYKAAVDLSHFLKEKGGLEGLIHSQRRQDILDLWIYHTQGYFPDWQN YTPGPGVRYPLTFGWCYKLVPVEPDKIEEANKGENTSLLHPVSLHGMDDPEREVLEWRFDSRL AFHHVARELHPEYFKNC |
| 406 | Pol | FFREDLAFLQGKAREFSSEQTRANSPTRRELQVWGRDNNSPSEAGADRQGTVSFNFPQVTLWQ RPLVTIKIGGQLKEALLDTGADDTVLEEMSLPGRWKPKMIGGIGGFIKVRQYDQILIEICGHK AIGTVLVGPTPVNIIGRNLLTQIGCTLNFPISPIETVPVKLKPGMDGPKVKQWPLTEEKIKAL VEICTEMEKEGKISKIGPENPYNTPVFAIKKKDSTKWRKLVDFRELNKRTQDFWEVQLGIPHP AGLKKKKSVTVLDVGDAYFSVPLDEDFRKYTAFTIPSINNETPGIRYQYNVLPQGWKGSPAIF QSSMTKILEPFRKQNPDIVIYQYMDDLYVGSDLEIGQHRTKIEELRQHLLRWGLTTPDKKHQK EPPFLWMGYELHPDKWTVQPIVLPEKDSWTVNDIQKLVGKLNWASQIYPGIKVRQLCKLLRGT KALTEVIPLTEEAELELAENREILKEPVHGVYYDPSKDLIAEIQKQGQGQWTYQIYQEPFKNL KTGKYARMRGAHTNDVKQLTEAVQKITTESIVIWGKTPKFKLPIQKETWETWWTEYWQATWIP EWEFEVNTPPLVKLWYQLEKEPIVGAETFYVDGAANRETKLGKAGYVTNRGRQKVVTLTDTTNQ KTELQAIYLALQDSGLEVNIVTDSQYALGIIQAQPDQSESELVNQIIEQLIKKEKVYLAWVPA HKGIGGNEQVDKLVSAGIRKVLFLDGIDKAQDEHEKYHSNWRAMASDFNLPPVVAKEIVASCD KCQLKGEAMHGQVDCSPGIWQLDCTHLEGKVILVAVHVASGYIEAEVIPAETGQETAYFLLKL AGRWPVKTIHTDNGSNFTGATVRAACWWAGIKQEFGIPYNPQSQGVVESMNKELKKIIGQVRD QAEHLKTAVQMAVFIHNFKRKGGIGGYSAGERIVDIIATDIQTKELQKQITKIQNFRVYYRDS RNPLWKGPAKLLWKGEGAVVIQDNSDIKVVPRRKAKIIRDYGKQMAGDDCVASRQDED |

TABLE B

| SEQ ID NO | Gene | Start | End | Sequence |
|---|---|---|---|---|
| 1 | Env | 28 | 52 | CSATEKLWVTVYYGVPVWKEATTTL |
| 2 | Env | 34 | 48 | LWVTVYYGVPVWKEA |
| 3 | Env | 34 | 48 | LWVTIYYGVPVWKDA |
| 4 | Env | 34 | 47 | LWVTVYYGVPVWKE |
| 5 | Env | 34 | 47 | LWVTIYYGVPVWKD |
| 6 | Env | 36 | 44 | VTVYYGVPV |
| 7 | Env | 36 | 44 | VTIYYGVPV |
| 8 | Env | 48 | 61 | ATTTLFCASDAKAY |
| 9 | Env | 48 | 61 | ANTTLFCASDAKGY |
| 10 | Env | 59 | 83 | KAYDTEVHNVWATHACVPTDPNPQE |
| 11 | Env | 64 | 83 | AHNVWATHACVPTDPNPQE |
| 12 | Env | 64 | 83 | VHNIWATHACVPTDPSPQE |
| 13 | Env | 65 | 83 | HNVWATHACVPTDPNPQE |
| 14 | Env | 65 | 83 | HNIWATHACVPTDPSPQE |
| 15 | Env | 67 | 75 | NVWATHACV |
| 16 | Env | 67 | 75 | NIWATHACV |
| 17 | Env | 107 | 129 | DIISLWDQSLKPCVKLTPLCVTL |
| 18 | Env | 107 | 129 | DIISLWDESLKPCVKLTPICVTL |
| 19 | Env | 113 | 137 | DQSLKPCVKLTPLCVTLNCTDLRNT |
| 20 | Env | 113 | 137 | DESLKPCVKLTPICVTLNCTDLRNT |
| 21 | Env | 121 | 129 | KLTPLCVTL |
| 22 | Env | 121 | 129 | KLTPICVTL |
| 23 | Env | 209 | 226 | SFEPIPIHYCAPAGFAIL |
| 24 | Env | 209 | 226 | TFEPIPIHYCTPAGFAIL |
| 25 | Env | 220 | 228 | PAGFAILKC |
| 26 | Env | 220 | 228 | PAGFALLKC |
| 27 | Env | 235 | 259 | GTGPCTNVSTVQCTHGIRPVVSTQL |
| 28 | Env | 241 | 268 | NVSTVQCTHGIRPVVSTQLLLNGSLAEE |
| 29 | Env | 241 | 268 | NISTVQCTHGIKPVVSTQLLLNGSLAEK |
| 30 | Env | 243 | 251 | STVQCTHGI |
| 31 | Env | 376 | 386 | FNCGGEFFYCN |
| 32 | Env | 376 | 386 | FNCRGEFFYCN |
| 33 | Env | 430 | 439 | VGKAMYAPPI |
| 34 | Env | 430 | 439 | VGRAMYAPPI |
| 35 | Env | 472 | 481 | GGDMRDNWRS |
| 36 | Env | 472 | 481 | GGNMKDNWRS |
| 37 | Env | 475 | 489 | MRDNWRSELYKYKVV |
| 38 | Env | 475 | 489 | MKDNWRSELYRYKVV |

TABLE B-continued all polypeptide segments

| SEQ ID NO | Gene | Start | End | Sequence |
|---|---|---|---|---|
| 39 | Env | 501 | 511 | AKRRVVQREKR |
| 40 | Env | 501 | 511 | ARRRVVQREKR |
| 41 | Env | 502 | 606 | KRRVVQREKRAVGIGAMFLGFLGAAGSTMGAASITLTVQARQLLSGIVQQQNNLLRAIEAQQHLLQLTVWGIKQLQARVLAVERYLKDQQLLGIWGCSGKLICTT |
| 42 | Env | 502 | 606 | RRRVVQREKRAIGLGAVFLGFLGTAGSTMGAASMTLTVQARLLLSGIVQQQSNLLRAIEAQQHMLQLTVWGIKQLQARILAVERYLRDQQLLGIWGCSGRLICTT |
| 43 | Env | 519 | 534 | FLGFLGAAGSTMGAAS |
| 44 | Env | 519 | 534 | FLGFLGTAGSTMGAAA |
| 45 | Env | 533 | 606 | ASITLIVQARQLLSGIVQQQNNLLRAIEAQQHLLQLTVWGIKQLQARVLAVERYLKDQQLLGIWGCSGKLICIT |
| 46 | Env | 533 | 606 | ASMTLTVQARLLLSGIVQQQSNLLRAIEAQQHMLQLTVWGIKQLQARILAVERYLRDQQLLGIWGCSGRLICIT |
| 47 | Env | 536 | 556 | TLTVQARQLLSGIVQQQNNLL |
| 48 | Env | 536 | 556 | TLTVQARLLLSGIVQQQSNLL |
| 49 | Env | 554 | 564 | NLLRAIEAQQH |
| 50 | Env | 554 | 564 | NLLKAIEAQQH |
| 51 | Env | 558 | 584 | AIEAQQHLLQLTVWGIKQLQARVLAVE |
| 52 | Env | 558 | 584 | AIEAQQHMLQLTVWGIKQLQARILAVE |
| 53 | Env | 584 | 592 | ERYLKDQQL |
| 54 | Env | 584 | 592 | ERYLRDQQL |
| 55 | Env | 586 | 594 | YLKDQQLLG |
| 56 | Env | 586 | 594 | YLRDQQLLG |
| 57 | Env | 586 | 610 | YLKDQQLLGIWGCSGKLICTTAVPW |
| 338 | Env | 586 | 610 | YLRDQQLLGLWGCSGKLICPTAVPW |
| 58 | Env | 589 | 606 | DQQLLGIWGCSGKLICTT |
| 59 | Env | 589 | 606 | DQQLLGLWGCSGKLICPT |
| 60 | Env | 594 | 602 | GIWGCSGKL |
| 61 | Env | 594 | 602 | GLWGCSGKL |
| 62 | Env | 678 | 688 | WLWYIKIFIMI |
| 63 | Env | 678 | 688 | WLWYIRIFIMI |
| 64 | Env | 684 | 697 | IFIMIVGGLIGLRI |
| 65 | Env | 684 | 697 | LFIMIVGGLVGLRI |
| 66 | Env | 705 | 719 | VNRVRQGYSPLSFQT |
| 67 | Env | 705 | 719 | VNRVRKGYSPLSFQI |
| 68 | Gag | 1 | 11 | MGARASVLSGG |
| 69 | Gag | 1 | 11 | MGARASILSGG |
| 70 | Gag | 1 | 53 | MGARASVLSGGELDRWEKIRLRPGGKKKYRLKHIVWASRELERFAVNPGLLET |
| 71 | Gag | 1 | 53 | MGARASILSGGKLDKWEKIRLRPGGRKKYKLKHIVWASRELERFAVNPGLLET |
| 72 | Gag | 13 | 25 | LDRWEKIRLRPGG |

TABLE B-continued all polypeptide segments

| SEQ ID NO | Gene | Start | End | Sequence |
|---|---|---|---|---|
| 73 | Gag | 13 | 25 | LDKWEKIRLRPMG |
| 74 | Gag | 19 | 27 | IRLRPGGKK |
| 75 | Gag | 19 | 27 | IRLRPGGRK |
| 76 | Gag | 31 | 53 | LKHIVWASRELERFAVNPGLLET |
| 77 | Gag | 31 | 53 | LKHLVWASRELERFALNPGLLET |
| 78 | Gag | 37 | 51 | ASRELERFAVNPGLL |
| 79 | Gag | 37 | 51 | ASRELERFALNPGLL |
| 80 | Gag | 70 | 78 | TGSEELKSL |
| 81 | Gag | 70 | 78 | TGSEELRSL |
| 82 | Gag | 96 | 104 | DTKEALDKI |
| 83 | Gag | 96 | 104 | DTKEALEKI |
| 84 | Gag | 99 | 107 | EALDKIEEE |
| 85 | Gag | 99 | 107 | EALEKIEEE |
| 86 | Gag | 128 | 137 | VSQNYPIVQN |
| 87 | Gag | 128 | 137 | VSQNFPIVQN |
| 88 | Gag | 133 | 363 | PIVQNLQGQMVHQAISPRTLNAWVKVVEEKAFSPEVIPMFSALSEGATPQDLN TMLNTVGGHQAAMQMLKETINEEAAEWDRLHPVHAGPIAPGQMREPRGSDIAG TTSTLQEQIGWMTNNPPIPVGEIYKRWIILGLNKIVRMYSPTSILDIRQGPKE PERDYVDREYKTLRAEQASQEVKNWMTETLLVQNANPDCKTILKALGPAATLE EMMTACQGVGGPGHKARVL |
| 89 | Gag | 133 | 363 | PIVQNIQGQMVHQPISPRTLNAWVKVIEEKAFSPEVIPMFTALSEGATPHDLN TMLNTIGGHQAAMQMLKDTINEEAAEWDRVHPVHAGPVAPGQMRDPRGSDIAG TTSNLQEQIGWMTSNPPIPVGDIYKRWIIMGLNKIVRMYSPVSILDIKQGPKE PFRDYVDRFYRTLRAEQASQDVKNWMTETLLVQNSNPDCKTILKALGPATLE EMMSACQGVGGPSHKARVL |
| 90 | Gag | 142 | 166 | MVHQAISPRTLNAWVKVVEEKAFSP |
| 91 | Gag | 142 | 166 | MVHQPISPRTLNAWVKVIEEKAFSP |
| 92 | Gag | 147 | 217 | ISPRTLNAWVKVVEEKAFSPEVIPMFSALSEGATPQDLNTMLNTVGGHQAAMQ MLKETINEEAAEWDRLHP |
| 93 | Gag | 147 | 217 | LSPRTLNAWVKVIEEKAFSPEVIPMFTALSEGATPHDLNTMLNTIGGHQAAMQ MLKDTINEEAAEWDRVHP |
| 94 | Gag | 147 | 369 | ISPRTLNAWVKVVEEKAFSPEVIPMFSALSEGATPQDLNTMLNTVGGHQAAMQ MLKETINEEAAEWDRLHPVHAGPIAPGQMREPRGSDIAGTTSTLQEQIGWMTN NPPIPVGEIYKRWIILGLNKIVRMYSPTSILDIRQGPKEPFRDYVDREYKTLR AEQASQEVKNWMTETLLVQNANPDCKTILKALGPAATLEEMMTACQGVGGPGH KARVLAEAMSQ |
| 95 | Gag | 147 | 369 | LSPRTLNAWVKVIEEKAFSPEVIPMFTALSEGATPHDLNTMLNTIGGHQAAMQ MLKDTINEEAAEWDRVHPVHAGPVAPGQMRDPRGSDIAGSTSTLQEQIAWMTN NPPIPVGDIYKRWIIMGLNKIVRMYSPVSILDIKQGPKEPFRDYVDRFYRTLR AEQASQDVKNWMTETLLVQNSNPDCKTILKALGPATLEEMMSACQGVGGPSH KARVLAEAMCQ |
| 96 | Gag | 150 | 158 | RTLNAWVKV |
| 97 | Gag | 175 | 199 | LSEGATPQDLNTMLNTVGGHQAAMQ |
| 98 | Gag | 175 | 199 | LSEGATPHDLNTMLNTIGGHQAAMQ |
| 99 | Gag | 183 | 191 | DLNTMLNTV |
| 100 | Gag | 183 | 191 | DLNTMLNTI |
| 101 | Gag | 225 | 251 | PGQMREPRGSDIAGTTSTLQEQIGWMT |

TABLE B-continued all polypeptide segments

| SEQ ID NO | Gene | Start | End | Sequence |
|---|---|---|---|---|
| 102 | Gag | 225 | 251 | PGQMRDPRGSDIAGSTSTLQEQIAWMT |
| 103 | Gag | 253 | 285 | NPPIPVGEIYKRWIILGLNKIVRMYSPTSILDI |
| 104 | Gag | 253 | 285 | NPPIPVGDIYKRWIIMGLNKIVRMYSPVSILDI |
| 339 | Gag | 257 | 282 | PVGEIYKRWIILGLNKIVRMYSPTSI |
| 340 | Gag | 257 | 282 | PVGDIYKRWIIMGLNKIVRMYSPVSI |
| 105 | Gag | 257 | 290 | PVGEIYKRWIILGLNKIVRMYSPTSILDIRQGPK |
| 106 | Gag | 257 | 290 | PVGDIYKRWIIMGLNKIVRMYSPVSILDIKQGPK |
| 107 | Gag | 265 | 282 | WIILGLNKIVRMYSPTSI |
| 108 | Gag | 265 | 282 | WIIMGLNKIVRMYSPVSI |
| 109 | Gag | 281 | 314 | SILDIRQGPKEPFRDYVDRFYKTLRAEQASQEVK |
| 110 | Gag | 281 | 314 | SILDIKQGPKEPFRDYVDRFYRTLRAEQASQDVK |
| 341 | Gag | 288 | 313 | GPKEPFRDYVDRFYKTLRAEQASQEV |
| 342 | Gag | 288 | 313 | GPKEPFRDYVDRFYRTLRAEQASQDV |
| 111 | Gag | 288 | 321 | GPKEPFRDYVDRFYKTLRAEQASQEVKNWMTETL |
| 112 | Gag | 288 | 321 | GPKEPFRDYVDRFYRTLRAEQASQDVKNWMTETL |
| 113 | Gag | 296 | 313 | YVDRFYKTLRAEQASQEV |
| 114 | Gag | 296 | 313 | YVDRFYRTLRAEQASQDV |
| 115 | Gag | 311 | 369 | QEVKNWMTETLLVQNANPDCKTILKALGPAATLEEMMTACQGVGGPGHKARVLAEAMSQ |
| 116 | Gag | 311 | 369 | QDVKNWMTETLLVQNSNPDCKTILKALGPGATLEEMMSACQGVGGPSHKARVLAEAMCQ |
| 117 | Gag | 333 | 357 | ILKALGPAATLEEMMTACQGVGGPG |
| 118 | Gag | 333 | 357 | ILKALGPGATLEEMMSACQGVGGPS |
| 119 | Gag | 337 | 361 | LGPAATLEEMMTACQGVGGPGHKAR |
| 120 | Gag | 337 | 361 | LGPGATLEEMMSACQGVGGPSHKAR |
| 121 | Gag | 341 | 349 | ATLEEMMTA |
| 122 | Gag | 341 | 349 | ATLEEMMSA |
| 123 | Gag | 345 | 353 | EMMTACQGV |
| 124 | Gag | 345 | 353 | EMMSACQGV |
| 125 | Gag | 391 | 400 | KCFNCGKEGH |
| 126 | Gag | 391 | 400 | KCFNCGREGH |
| 127 | Gag | 402 | 410 | ARNCRAPRK |
| 128 | Gag | 402 | 410 | AKNCRAPRK |
| 129 | Gag | 402 | 440 | ARNCRAPRKKGCWKCGKEGHQMKDCTERQANFLGKIWPS |
| 130 | Gag | 402 | 440 | AKNCRAPRKRGCWKCGREGHQMKDCNERQANFLGKVWPS |
| 131 | Gag | 404 | 417 | NCRAPRKKGCWKCG |
| 132 | Gag | 404 | 417 | NCRAPRKRGCWKCG |
| 133 | Gag | 412 | 430 | GCWKCGKEGHQMKDCTERQ |

TABLE B-continued all polypeptide segments

| SEQ ID NO | Gene | Start | End | Sequence |
|---|---|---|---|---|
| 134 | Gag | 412 | 430 | GCWKCGREGHQMKDCNERQ |
| 135 | Gag | 424 | 440 | KDCTERQANFLGKIWPS |
| 136 | Gag | 424 | 440 | KDCNERQANFLGKVWPS |
| 137 | Gag | 429 | 444 | RQANFLGKIWPSHKGR |
| 138 | Gag | 429 | 444 | RQANFLGKVWPSHNGR |
| 139 | Gag | 442 | 453 | KGRPGNFLQSRP |
| 140 | Gag | 442 | 453 | NGRPGNFLQNRP |
| 141 | Gag | 488 | 497 | SLRSLFGNDP |
| 142 | Gag | 488 | 497 | SLKSLFGNDP |
| 143 | Gag | 491 | 499 | SLFGNDPSS |
| 144 | Gag | 491 | 499 | SLFGNDPLS |
| 145 | Gag | | | LKHIVWASRELERFAVNPGLLETVSQNYPIVQN |
| 146 | Gag | | | LKHLVWASRELERFALNPGLLETVSQNFPIVQN |
| 147 | Nef | 29 | 37 | GVGAVSRDL |
| 148 | Nef | 29 | 37 | GVGAASRDL |
| 149 | Nef | 64 | 82 | EEVGFPVRPQVPLRPMTYK |
| 150 | Nef | 64 | 82 | EEVGFPVKPQVPLRPMTFK |
| 151 | Nef | 64 | 99 | EEVGFPVKPQVPLRPMTFKGALDLSHFLREKGGLEG |
| 152 | Nef | 64 | 99 | EEVGFPVRPQVPLRPMTYKGALDLSHFLKEKGGLEG |
| 153 | Nef | 81 | 102 | YKAAVDLSHFLREKGGLEGAAY |
| 154 | Nef | 81 | 102 | YKGALDLSHFLKEKGGLEGAAY |
| 155 | Nef | 88 | 97 | SHFLKEKGGL |
| 156 | Nef | 88 | 97 | SHFLREKGGL |
| 157 | Nef | 91 | 99 | LKEKGGLEG |
| 158 | Nef | 91 | 99 | LREKGGLEG |
| 159 | Nef | 117 | 132 | TQGYFPDWQNYTPGPG |
| 160 | Nef | 117 | 132 | TQGFFPDWQNYTPEPG |
| 161 | Nef | 117 | 148 | TQGFFPDWQNYTPEPGIRFPLTFGWCFKLVPL |
| 162 | Nef | 117 | 148 | TQGYFPDWQNYTPGPGTRYPLTFGWCFKLVPV |
| 163 | Nef | 130 | 148 | EPGIRFPLTFGWCFKLVPL |
| 164 | Nef | 130 | 148 | GPGTRYPLTFGWCFKLVPV |
| 165 | Nef | 130 | 154 | GPGIRYPLLTFGWCFKLPVEPEKVE |
| 166 | Nef | 134 | 142 | RYPLTFGWC |
| 167 | Nef | 134 | 142 | RFPLTFGWC |
| 168 | Nef | 134 | 148 | RYPLTFGWCFKLVPV |
| 169 | Nef | 134 | 148 | RFPLTFGWCFKLVPL |
| 170 | Nef | 136 | 148 | PLTFGWCFKLVPV |
| 171 | Nef | 136 | 148 | PLCFGWCFKLVPL |

TABLE B-continued all polypeptide segments

| SEQ ID NO | Gene | Start | End | Sequence |
|---|---|---|---|---|
| 172 | Nef | 137 | 145 | LTFGWCFKL |
| 173 | Nef | 137 | 145 | LCFGWCFKL |
| 174 | Pol | 56 | 67 | FPQITLWQRPLV |
| 175 | Pol | 56 | 67 | LPQITLWQRPIV |
| 176 | Pol | 56 | 117 | FPQITLWQRPLVTIKIGGQLKEALLDTGADDTVLEEMNLPGRWKPKMIGGIGGFIKVRQYDQ |
| 177 | Pol | 56 | 117 | LPQITLWQRPIVTIKIGGQIKEALLDTGADDTVLEDMNLPGKWKPKMIGGIGGFIKVKQYDQ |
| 178 | Pol | 72 | 91 | GGQLKEALLDTGADDTVLEE |
| 179 | Pol | 72 | 91 | GGQIKEALLDTGADDTVLED |
| 180 | Pol | 94 | 117 | LPGRWKPKMIGGIGGFIKVRQYDQ |
| 181 | Pol | 94 | 117 | LPGKWKPKMIGGIGGFIKVKQYDQ |
| 182 | Pol | 129 | 260 | GTVLVGPTPVNIIGRNLLTQIGCTLNFPISPIETVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKS |
| 183 | Pol | 129 | 260 | GTVLIGPTPVNIIGRNLLTQLGCTLNFPISPIDTVPVKLKPGMDGPRVKQWPLTEEKIKALIEICTEMEKEGKISRIGPENPYNTPIFAIKKKDGTKWRKLVDFRELNKKTQDFWEVQLGIPHPSGLKKKKS |
| 184 | Pol | 129 | 277 | GTVLVGPTPVNIIGRNLLTQIGCTLNFPISPIETVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKSVTVLDVGDAYFSVPLDK |
| 185 | Pol | 129 | 277 | GTVLIGPTPVNIIGRNLLTQLGCTLNFPISPIDTVPVKLKPGMDGPRVKQWPLTEEKIKALIEICTEMEKEGKISRIGPENPYNTPIFAIKKKDGTKWRKLVDFRELNKKTQDFWEVQLGIPHPSGLKKKKSVTILDVGDAYFSIPLDK |
| 186 | Pol | 129 | 289 | GTVLVGPTPVNIIGRNLLTQIGCTLNFPISPIETVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKSVTVLDVGDAYFSVPLDKDFRKYTAFTIPS |
| 187 | Pol | 129 | 289 | GTVLIGPTPVNIIGRNLLTQLGCTLNFPISPIDTVPVKLKPGMDGPRVKQWPLTEEKIKALIEICTEMEKEGKISRIGPENPYNTPIFAIKKKDGTKWRKLVDFRELNKKTQDFWEVQLGIPHPSGLKKKKSVTVLDIGDAYFSVPLDKEFRKYTAFTVPS |
| 188 | Pol | 129 | 320 | GTVLVGPTPVNIIGRNLLTQIGCTLNFPISPIETVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKSVTVLDVGDAYFSVPLDKDFRKYTAFTIPSINNETPGIRYQYNVLPQGWKGSPAIFQSSMT |
| 189 | Pol | 129 | 320 | GTVLIGPTPVNIIGRNLLTQLGCTLNFPISPIDTVPVKLKPGMDGPRVKQWPLTEEKIKALIEICTEMEKEGKISRIGPENPYNTPIFAIKKKDGTKWRKLVDFRELNKKTQDFWEVQLGIPHPSGLKKKKSVTVLDIGDAYFSVPLDKEFRKYTAFTVPSTNNETPGVRYQYNVLPMGWKGSPAIFQCSMT |
| 190 | Pol | 144 | 168 | NLLTQIGCTLNFPISPIETVPVKLK |
| 191 | Pol | 144 | 168 | NLLTQLGCTLNFPISPIDTVPVKLK |
| 192 | Pol | 152 | 160 | TLNFPISPI |
| 193 | Pol | 254 | 277 | GLKKKKSVTVLDVGDAYFSVPLDK |
| 194 | Pol | 254 | 277 | GLKKNKSVTVLDVGDAYFSIPLDK |
| 195 | Pol | 278 | 289 | DFRKYTAFTIPS |
| 196 | Pol | 278 | 289 | EFRKYTAFTVPS |
| 197 | Pol | 291 | 315 | NNETPGIRYQYNVLPQGWKGSPAIF |

TABLE B-continued all polypeptide segments

| SEQ ID NO | Gene | Start | End | Sequence |
|---|---|---|---|---|
| 198 | Pol | 291 | 315 | NNETPGVRYQYNVLPMGWKGSPAIF |
| 199 | Pol | 291 | 320 | NNETPGIRYQYNVLPQGWKGSPAIFQSSMT |
| 200 | Pol | 291 | 320 | NNETPGVRYQYNVLPMGWKGSPAIFQCSMT |
| 201 | Pol | 299 | 307 | YQYNVLPQG |
| 202 | Pol | 299 | 307 | YQYNVLPMG |
| 203 | Pol | 315 | 323 | FQSSMTKIL |
| 204 | Pol | 315 | 323 | FQCSMTKIL |
| 205 | Pol | 318 | 327 | SMTKILEPFR |
| 206 | Pol | 318 | 327 | SMTKILDPFR |
| 207 | Pol | 322 | 330 | ILEPFRKQN |
| 208 | Pol | 322 | 330 | ILDPFRKQN |
| 209 | Pol | 326 | 350 | FRKQNPDIVIYQYMDDLYVGSDLEI |
| 343 | Pol | 326 | 350 | FRKQNPDIVIYQYVDDLYVGSDLEI |
| 210 | Pol | 328 | 352 | KQNPDIVIYQYMDDLYVGSDLEIGQ |
| 344 | Pol | 328 | 352 | KQNPDIVIYQYVDDLYVGSDLEIEQ |
| 211 | Pol | 330 | 354 | NPDIVIYQYMDDLYVGSDLEIGQHR |
| 212 | Pol | 330 | 354 | NPDIVIYQYVDDLYVGSDLEIEQHR |
| 213 | Pol | 333 | 354 | IVIYQYMDDLYVGSDLEIGQHR |
| 214 | Pol | 333 | 354 | IVIYQYVDDLYVGSDLEIEQHR |
| 215 | Pol | 334 | 342 | VIYQYMDDL |
| 216 | Pol | 334 | 342 | VIYQYVDDL |
| 217 | Pol | 336 | 344 | YQYMDDLYV |
| 218 | Pol | 336 | 344 | YQYVDDLYV |
| 219 | Pol | 338 | 346 | YMDDLYVGS |
| 220 | Pol | 338 | 346 | YVDDLYVGS |
| 221 | Pol | 367 | 399 | WGFTTPDKKHQKEPPFLWMGYELHPDKWTVQPI |
| 222 | Pol | 367 | 399 | WGLTTPDKKHQKDPPFLWMGYELHPDRWTVQPI |
| 223 | Pol | 367 | 431 | WGFTTPDKKHQKEPPFLWMGYELHPDKWTVQPIVLPEKDSWTVNDIQKLVGKLNWASQIYPGIKV |
| 224 | Pol | 367 | 431 | WGLTTPDKKHQKDPPFLWMGYELHPDRWTVQPIELPEKESWTVNDIQKLIGKLNWASQIYAGIKV |
| 225 | Pol | 374 | 398 | KKHQKEPPFLWMGYELHPDKWTVQP |
| 226 | Pol | 374 | 398 | KKHQKDPPFLWMGYELHPDRWTVQP |
| 227 | Pol | 380 | 404 | PPFLWMGYELHPDKWTVQPIVLPEK |
| 228 | Pol | 380 | 404 | PPFLWMGYELHPDRWTVQPIELPEK |
| 229 | Pol | 382 | 390 | FLWMGYELH |
| 230 | Pol | 388 | 396 | ELHPDKWTV |
| 231 | Pol | 388 | 396 | ELHPDRWTV |
| 232 | Pol | 399 | 423 | IVLPEKDSWTVNDIQKLVGKLNWAS |

TABLE B-continued all polypeptide segments

| SEQ ID NO | Gene | Start | End | Sequence |
|---|---|---|---|---|
| 233 | Pol | 399 | 423 | IELPEKESWTVNDIQKLIGKLNWAS |
| 234 | Pol | 400 | 424 | VLPEKDSWTVNDIQKLVGKLNWASQ |
| 235 | Pol | 400 | 424 | ELPEKESWTVNDIQKLIGKLNWASQ |
| 236 | Pol | 401 | 431 | LPEKDSWTVNDIQKLVGKLNWASQIYPGIKV |
| 237 | Pol | 401 | 431 | LPEKESWTVNDIQKLIGKLNWASQIYAGIKV |
| 238 | Pol | 406 | 430 | SWTVNDIQKLVGKLNWASQIYPGIK |
| 239 | Pol | 406 | 430 | SWTVNDIQKLIGKLNWASQIYAGIK |
| 240 | Pol | 407 | 415 | WTVNDIQKL |
| 241 | Pol | 408 | 416 | TVNDIQKLV |
| 242 | Pol | 408 | 416 | TVNDIQKLI |
| 243 | Pol | 414 | 422 | KLVGKLNWA |
| 244 | Pol | 414 | 422 | KLIGKLNWA |
| 245 | Pol | 434 | 442 | LCKLLRGTK |
| 246 | Pol | 434 | 442 | LCKLLRGAK |
| 247 | Pol | 453 | 471 | EAELELAENREILKEPVHG |
| 248 | Pol | 453 | 471 | EAEIELAENREILREPVHG |
| 249 | Pol | 467 | 478 | EPVHGVYYDPSK |
| 250 | Pol | 467 | 478 | EPVHGAYYDPSK |
| 251 | Pol | 490 | 511 | GQWTYQIYQEPFKNLKTGKYAR |
| 252 | Pol | 490 | 511 | GQWSYQIYQEPYKNLKTGKYAK |
| 253 | Pol | 515 | 530 | AHTNDVKQLTEAVQKI |
| 254 | Pol | 515 | 530 | AHTNDVRQLTEAVQKV |
| 255 | Pol | 535 | 544 | IVIWGKTPKF |
| 256 | Pol | 535 | 544 | IVIWGKIPKF |
| 257 | Pol | 542 | 554 | PKFKLPIQKETWE |
| 258 | Pol | 542 | 554 | PKFRLPIQKETWD |
| 259 | Pol | 542 | 606 | PKFKLPIQKETWETWWTEYWQATWIPEWEFVNTPPLVKLWYQLEKEPIVGAETFYVDGAANRETK |
| 260 | Pol | 542 | 606 | PKFRLPIQKETWDTWWTDYWQATWIPEWEFTNTPPLVKLWYQLETEPIAGVETFYVDGASNRETK |
| 261 | Pol | 553 | 577 | WETWWTEYWQATWIPEWEFVNTPPL |
| 262 | Pol | 553 | 577 | WDTWWTDYWQATWIPEWEFTNTPPL |
| 263 | Pol | 559 | 589 | EYWQATWIPEWEFVNTPPLVKLWYQLEKEPI |
| 264 | Pol | 559 | 589 | DYWQATWIPEWEFTNTPPLVKLWYQLETEPI |
| 265 | Pol | 561 | 569 | WQATWIPEW |
| 266 | Pol | 591 | 606 | GAETFYVDGAANRETK |
| 267 | Pol | 591 | 606 | GVETFYVDGASNRETK |
| 268 | Pol | 625 | 637 | TDTTNQKTELQAI |

TABLE B-continued all polypeptide segments

| SEQ ID NO | Gene | Start | End | Sequence |
|---|---|---|---|---|
| 269 | Pol | 625 | 637 | ADTTNQKTELHAI |
| 270 | Pol | 636 | 644 | AIHLALQDS |
| 271 | Pol | 636 | 644 | AIYLALQDS |
| 272 | Pol | 639 | 671 | LALQDSGLEVNIVTDSQYALGIIQAQPDKSESE |
| 273 | Pol | 639 | 671 | LALQDSGSEVNIVTDSQYAIGIIQAQPDRSESE |
| 274 | Pol | 642 | 666 | QDSGLEVNIVTDSQYALGIIQAQPD |
| 275 | Pol | 642 | 666 | QDSGSEVNIVTDSQYAIGIIQAQPD |
| 276 | Pol | 650 | 658 | IVTDSQYAL |
| 277 | Pol | 650 | 658 | IVTDSQYAI |
| 278 | Pol | 673 | 681 | VSQIIEQLI |
| 279 | Pol | 673 | 681 | VNQIIEQLI |
| 280 | Pol | 675 | 684 | QIIEQLIKKE |
| 281 | Pol | 675 | 684 | QIIEQLINKE |
| 282 | Pol | 683 | 708 | KEKVYLAWVPAHKGIGGNEQVDKLVS |
| 283 | Pol | 683 | 708 | KEKIYLAWVPAHKGIGGNEQIDKLVS |
| 284 | Pol | 710 | 725 | GIRKVLFLDGIDKAQE |
| 285 | Pol | 710 | 725 | GIRRVLFLDGIEKAQD |
| 286 | Pol | 727 | 735 | HEKYHSNWR |
| 287 | Pol | 727 | 735 | HEKYHNNWR |
| 288 | Pol | 737 | 745 | MASDFNLPP |
| 289 | Pol | 737 | 745 | MASDFNIPP |
| 290 | Pol | 741 | 753 | FNLPPVVAKEIVA |
| 291 | Pol | 741 | 753 | FNLPPIVAKEIVA |
| 292 | Pol | 741 | 827 | FNLPPVVAKEIVASCDKCQLKGEAMHGQVDCSPGIWQLDCTHLEGKIILVAVHVASGYIEAEVIPAETGQETAYFLLKLAGRWPVKT |
| 293 | Pol | 741 | 827 | FNLPPIVAKEIVACCDKCQLKGEAIHGQVDCSPGVWQLDCTHLEGKVILVAVHVASGYIEAEIIPTETGQETAYFILKLAGRWPVTT |
| 294 | Pol | 747 | 827 | VAKEIVASCDKCQLKGEAMHGQVDCSPGIWQLDCTHLEGKIILVAVHVASGYIEAEVIPAETGQETAYFLLKLAGRWPVKT |
| 295 | Pol | 747 | 827 | VAKEIVACCDKCQLKGEAIHGQVDCSPGVWQLDCTHLEGKVILVAVHVASGYMEAEVIPTETGQETAYFILKLAGRWPVTT |
| 296 | Pol | 759 | 783 | QLKGEAMHGQVDCSPGIWQLDCTHL |
| 297 | Pol | 759 | 783 | QLKGEAIHGQVDCSPGVWQLDCTHL |
| 298 | Pol | 767 | 775 | GQVDCSPGI |
| 299 | Pol | 767 | 775 | GQVDCSPGV |
| 300 | Pol | 768 | 792 | QVDCSPGIWQLDCTHLEGKIILVAV |
| 301 | Pol | 768 | 792 | QVDCSPGVWQLDCTHLEGKVILVAV |
| 302 | Pol | 776 | 784 | WQLDCTHLE |
| 303 | Pol | 834 | 858 | SNFTSTTVKAACWWAGIKQEFGIPY |
| 304 | Pol | 834 | 858 | SNFTSTAVKAACWWAGVKQEFGIPY |

TABLE B-continued all polypeptide segments

| SEQ ID NO | Gene | Start | End | Sequence |
|---|---|---|---|---|
| 305 | Pol | 840 | 919 | TVKAACWWAGIKQEFGIPYNPQSQGVVESMNKELKKIIGQVRDQAEHLKTAVQMAVFIHNFKRKGGIGGYSAGERIVDII |
| 306 | Pol | 840 | 919 | AVKAACWWAGVKQEFGIPYHPQSQGVVESMNNELKKIIGQIRDQAEQLKTAVQMAVLIHNFKRKGGIGEYSAGERIIDII |
| 307 | Pol | 840 | 920 | TVKAACWWAGIKQEFGIPYNPQSQGVVESMNKELKKIIGQVRDQAEHLKTAVQMAVFIHNFKRKGGIGGYSAGERIVDIIA |
| 308 | Pol | 840 | 920 | AVKAACWWAGVKQEFGIPYHPQSQGVVESMNNELKKIIGQIRDQAEQLKTAVQMAVLIHNFKRKGGIGEYSAGERIIDIIA |
| 309 | Pol | 840 | 1003 | TVKAACWWAGIKQEFGIPYNPQSQGVVESMNKELKKIIGQVRDQAEHLKTAVQMAVFIHNFKRKGGIGGYSAGERIVDIIATDIQTKELQKQIIKIQNFRVYYRDSRDPLWKGPAKLLWKGEGAVVIQDNSDIKVVPRRKAKIIRDYGKQMAGDDCVASRQDED |
| 310 | Pol | 840 | 1003 | AVKAACWWAGVKQEFGIPYNTQSQGVVESMNNELKKIIGQIRDQAEHLKTAVQMAVLIHNFKRKGGIGEYSAGERIIDIIATDIQTRELQKQIIKLQNFRVYYRDNRDPLWKGPARLLWKGEGAVVIQDNSEIKVVPRRKVKIIRDYGKRMAGDDCVAGRQDED |
| 311 | Pol | 842 | 850 | KAACWWAGI |
| 312 | Pol | 842 | 850 | KAACWWAGV |
| 313 | Pol | 917 | 925 | DIIATDIQT |
| 314 | Pol | 917 | 925 | DIIASDIQT |
| 315 | Pol | 922 | 930 | DIQTKELQK |
| 316 | Pol | 922 | 930 | DIQTRELQK |
| 317 | Pol | 924 | 932 | QTKELQKQI |
| 318 | Pol | 924 | 932 | QTRELQKQI |
| 319 | Pol | 931 | 1003 | AITKIQNFRVYYRDSRDPLWKGPAKLLWKGEGAVVIQDNSDIKVVPRRKAKIIRDYGKQMAGDDCVASRQDED |
| 320 | Pol | 931 | 1003 | AITKLQNFRVYYRDNRDPLWKGPARLLWKGEGAVVIQDNSEIKVVPRRKVKIIRDYGKRMAGDDCVAGRQDED |
| 321 | Pol | 932 | 1003 | ITKIQNFRVYYRDSRDPLWKGPAKLLWKGEGAVVIQDNSDIKVVPRRKAKIIRDYGKQMAGDDCVASRQDED |
| 322 | Pol | 932 | 1003 | ITKLQNFRVYYRDNRDPLWKGPARLLWKGEGAVVIQDNSEIKVVPRRKVKIIRDYGKRMAGDDCVAGRQDED |
| 323 | Pol | 940 | 964 | VYYRDSRDPLWKGPAKLLWKGEGAV |
| 324 | Pol | 940 | 964 | VYYRDNRDPLWKGPARLLWKGEGAV |
| 325 | Pol | 947 | 971 | DPLWKGPAKLLWKGEGAVVIQDNSD |
| 326 | Pol | 947 | 971 | DPLWKGPARLLWKGEGAVVIQDNSE |
| 327 | Pol | 948 | 956 | PLWKGPAKL |
| 328 | Pol | 948 | 956 | PLWKGPARL |
| 329 | Pol | 948 | 972 | PLWKGPAKLLWKGEGAVVIQDNSDI |
| 330 | Pol | 948 | 972 | PLWKGPARLLWKGEGAVVIQDNSEI |
| 331 | Pol | 955 | 963 | KLLWKGEGA |
| 332 | Pol | 955 | 963 | RLLWKGEGA |
| 333 | Pol | 956 | 964 | LLWKGEGAV |
| 334 | Pol | 980 | 1003 | AKIIRDYGKQMAGDDCVASRQDED |

TABLE B-continued all polypeptide segments

| SEQ ID NO | Gene | Start | End | Sequence |
|---|---|---|---|---|
| 335 | Pol | 980 | 1003 | VKIIRDYGKRMAGDDCVAGRQDED |
| 336 | Pol | 988 | 996 | KQMAGDDCV |
| 337 | Pol | 988 | 996 | KRMAGDDCV |

TABLE C polypeptide segments in conserved regions of HIV-1 proteins

| SEQ ID NO: | Gene | Start | End | Length | Sequence |
|---|---|---|---|---|---|
| 2 | Env | 34 | 48 | 15 | LWVTVYYGVPVWKEA |
| 3 | Env | 34 | 48 | 15 | LWVTIYYGVPVWKDA |
| 8 | Env | 48 | 61 | 14 | ATTTLFCASDAKAY |
| 9 | Env | 48 | 61 | 14 | ANTTLFCASDAKGY |
| 13 | Env | 66 | 83 | 18 | HNVWATHACVPTDPNPQE |
| 14 | Env | 66 | 83 | 18 | HNIWATHACVPTDPSPQE |
| 17 | Env | 107 | 129 | 23 | DIISLWDQSLKPCVKLTPLCVTL |
| 18 | Env | 107 | 129 | 23 | DIISLWDESLKPCVKLTPICVTL |
| 23 | Env | 209 | 226 | 18 | SFEPIPIHYCAPAGFAIL |
| 24 | Env | 209 | 226 | 18 | TFEPIPIHYCTPAGFAIL |
| 25 | Env | 220 | 228 | 9 | PAGFAILKC |
| 26 | Env | 220 | 228 | 9 | PAGFALLKC |
| 28 | Env | 241 | 268 | 28 | NVSTVQCTHGIRPVVSTQLLLNGSLAEE |
| 29 | Env | 241 | 268 | 28 | NISTVQCTHGIKPVVSTQLLLNGSLAEK |
| 31 | Env | 376 | 386 | 11 | FNCGGEFFYCN |
| 32 | Env | 376 | 386 | 11 | FNCRGEFFYCN |
| 33 | Env | 430 | 439 | 10 | VGKAMYAPPI |
| 34 | Env | 430 | 439 | 10 | VGRAMYAPPI |
| 35 | Env | 472 | 481 | 10 | GGDMRDNWRS |
| 36 | Env | 472 | 481 | 10 | GGNMKDNWRS |
| 37 | Env | 475 | 489 | 15 | MRDNWRSELYKYKVV |
| 38 | Env | 475 | 489 | 15 | MKDNWRSELYRYKVV |
| 39 | Env | 501 | 511 | 11 | AKRRVVQREKR |
| 40 | Env | 501 | 511 | 11 | ARRRVVQREKR |
| 43 | Env | 519 | 534 | 16 | FLGFLGAAGSTMGAAS |
| 44 | Env | 519 | 534 | 16 | FLGFLGTAGSTMGAAA |
| 45 | Env | 533 | 606 | 74 | ASITLTVQARQLLSGIVQQQNNLLRAIEAQQHLLQLTVWGIKQLQARVLAVERYLKDQQLLGIWGCSGKLICTT |
| 46 | Env | 533 | 606 | 74 | ASMTLTVQARLLLSGIVQQQSNLLRAIEAQQHMLQLTVWGIKQLQARILAVERYLRDQQLLGIWGCSGRLICTT |
| 47 | Env | 536 | 556 | 21 | TLTVQARQLLSGIVQQQNNLL |

TABLE C-continued polypeptide segments in conserved regions of HIV-1 proteins

| SEQ ID NO: | Gene | Start | End | Length | Sequence |
|---|---|---|---|---|---|
| 48 | Env | 536 | 556 | 21 | TLTVQARLLLSGIVQQQSNLL |
| 49 | Env | 554 | 564 | 11 | NLLRAIEAQQH |
| 50 | Env | 554 | 564 | 11 | NLLKAIEAQQH |
| 51 | Env | 558 | 584 | 27 | AIEAQQHLLQLTVWGIKQLQARVLAVE |
| 52 | Env | 558 | 584 | 27 | AIEAQQHMLQLTVWGIKQLQARILAVE |
| 53 | Env | 584 | 592 | 9 | ERYLKDQQL |
| 54 | Env | 584 | 592 | 9 | ERYLRDQQL |
| 55 | Env | 586 | 594 | 9 | YLKDQQLLG |
| 56 | Env | 586 | 594 | 9 | YLRDQQLLG |
| 58 | Env | 589 | 606 | 18 | DQQLLGIWGCSGKLICTT |
| 59 | Env | 589 | 606 | 18 | DQQLLGLWGCSGKLICPT |
| 62 | Env | 678 | 688 | 11 | WLWYIKIFIMI |
| 63 | Env | 678 | 688 | 11 | WLWYIRIFIMI |
| 64 | Env | 684 | 697 | 14 | IFIMIVGGLIGLRI |
| 65 | Env | 684 | 697 | 14 | LFIMIVGGLVGLRI |
| 66 | Env | 705 | 719 | 15 | VNRVRQGYSPLSFQT |
| 67 | Env | 705 | 719 | 15 | VNRVRKGYSPLSFQI |
| 68 | Gag | 1 | 11 | 11 | MGARASVLSGG |
| 69 | Gag | 1 | 11 | 11 | MGARASILSGG |
| 72 | Gag | 13 | 25 | 13 | LDRWEKIRLRPGG |
| 73 | Gag | 13 | 25 | 13 | LDKWEKIRLRPMG |
| 74 | Gag | 19 | 27 | 9 | IRLRPGGKK |
| 75 | Gag | 19 | 27 | 9 | IRLRPGGRK |
| 76 | Gag | 31 | 53 | 23 | LKHIVWASRELERFAVNPGLLET |
| 77 | Gag | 31 | 53 | 23 | LKHLVWASRELERFALNPGLLET |
| 80 | Gag | 70 | 78 | 9 | TGSEELKSL |
| 81 | Gag | 70 | 78 | 9 | TGSEELRSL |
| 82 | Gag | 96 | 104 | 9 | DTKEALDKI |
| 83 | Gag | 96 | 104 | 9 | DTKEALEKI |
| 84 | Gag | 99 | 107 | 9 | EALDKIEEE |
| 85 | Gag | 99 | 107 | 9 | EALEKIEEE |
| 86 | Gag | 128 | 137 | 10 | VSQNYPIVQN |
| 87 | Gag | 128 | 137 | 10 | VSQNFPIVQN |
| 88 | Gag | 133 | 363 | 231 | PIVQNLQGQMVHQAISPRTLNAWVKVVEEKAFSPEVIPMFSALSEGATPQDLN TMLNTVGGHQAAMQMLKETINEEAAEWDRLHPVHAGPIAPGQMREPRGSDIAG TTSTLQEQIGWMTNNPPIPVGEIYKRWIILGLNKIVRMYSPTSILDIRQGPKE PFRDYVDRFYKTLRAEQASQEVKNWMTETLLVQNANPDCKTILKALGPAATLE EMMTACQGVGGPGHKARVL |

TABLE C-continued polypeptide segments in conserved regions of HIV-1 proteins

| SEQ ID NO: | Gene | Start | End | Length | Sequence |
|---|---|---|---|---|---|
| 89 | Gag | 133 | 363 | 231 | PIVQNIQGQMVHQPISPRTLNAWVKVIEEKAFSPEVIPMFTALSEGATPHDLN TMLNTIGGHQAAMQMLKDTINEEAAEWDRVHPVHAGPVAPGQMRDPRGSDIAG TTSNLQEQIGWMTSNPPIPVGDIYKRWIIMGLNKIVRMYSPVSILDIKQGPKE PFRDYVDRFYRTLRAEQASQDVKNWMTETLLVQNSNPDCKTILKALGPGATLE EMMSACQGVGGPSHKARVL |
| 92 | Gag | 147 | 217 | 71 | ISPRTLNAWVKVVEEKAFSPEVIPMFSALSEGATPQDLNTMLNTVGGHQAAMQ MLKETINEEAAEWDRLHP |
| 93 | Gag | 147 | 217 | 71 | LSPRTLNAWVKVIEEKAFSPEVIPMFTALSEGATPHDLNTMLNTIGGHQAAMQ MLKDTINEEAAEWDRVHP |
| 101 | Gag | 225 | 251 | 27 | PGQMREPRGSDIAGTTSTLQEQIGWMT |
| 102 | Gag | 225 | 251 | 27 | PGQMRDPRGSDIAGSTSTLQEQIAWMT |
| 103 | Gag | 253 | 285 | 33 | NPPIPVGEIYKRWIILGLNKIVRMYSPTSILDI |
| 104 | Gag | 253 | 285 | 33 | NPPIPVGDIYKRWIIMGLNKIVRMYSPVSILDI |
| 109 | Gag | 281 | 314 | 34 | SILDIRQGPKEPFRDYVDRFYKTLRAEQASQEVK |
| 110 | Gag | 281 | 314 | 34 | SILDIKQGPKEPFRDYVDRFYRTLRAEQASQDVK |
| 115 | Gag | 311 | 369 | 59 | QEVKNWMTETLLVQNANPDCKTILKALGPAATLEEMMTACQGVGGPGHKARVL AEAMSQ |
| 116 | Gag | 311 | 369 | 59 | QDVKNWMTEILLVQNSNPDCKTILKALGPGATLEEMMSACQGVGGPSHKARVL AEAMCQ |
| 125 | Gag | 391 | 400 | 10 | KCFNCGKEGH |
| 126 | Gag | 391 | 400 | 10 | KCFNCGREGH |
| 127 | Gag | 402 | 410 | 9 | ARNCRAPRK |
| 128 | Gag | 402 | 410 | 9 | AKNCRAPRK |
| 129 | Gag | 402 | 440 | 39 | ARNCRAPRKKGCWKCGKEGHQMKDCTERQANFLGKIWPS |
| 130 | Gag | 402 | 440 | 39 | AKNCRAPRKRGCWKCGREGHQMKDCNERQANFLGKVWPS |
| 131 | Gag | 404 | 417 | 14 | NCRAPRKKGCWKCG |
| 132 | Gag | 404 | 417 | 14 | NCRAPRKRGCWKCG |
| 133 | Gag | 412 | 430 | 19 | GCWKCGKEGHQMKDCTERQ |
| 134 | Gag | 412 | 430 | 19 | GCWKCGREGHQMKDCNERQ |
| 135 | Gag | 424 | 440 | 17 | KDCTERQANFLGKIWPS |
| 136 | Gag | 424 | 440 | 17 | KDCNERQANFLGKVWPS |
| 139 | Gag | 442 | 453 | 12 | KGRPGNFLQSRP |
| 140 | Gag | 442 | 453 | 12 | NGRPGNFLQNRP |
| 141 | Gag | 488 | 497 | 10 | SLRSLFGNDP |
| 142 | Gag | 488 | 497 | 10 | SLKSLFGNDP |
| 143 | Gag | 491 | 499 | 9 | SLFGNDPSS |
| 144 | Gag | 491 | 499 | 9 | SLFGNDPLS |
| 145 | Gag | | | | LKHIVWASRELERFAVNPGLLETVSQNYPIVQN |
| 146 | Gag | | | | LKHLVWASRELERFALNPGLLETVSQNFPIVQN |
| 147 | Nef | 29 | 37 | 9 | GVGAVSRDL |
| 148 | Nef | 29 | 37 | 9 | GVGAASRDL |
| 149 | Nef | 64 | 82 | 19 | EEVGFPVRPQVPLRPMTYK |

TABLE C-continued polypeptide segments in conserved regions of HIV-1 proteins

| SEQ ID NO: | Gene | Start | End | Length | Sequence |
|---|---|---|---|---|---|
| 150 | Nef | 64 | 82 | 19 | EEVGFPVKPQVPLRPMTFK |
| 155 | Nef | 88 | 97 | 10 | SHFLKEKGGL |
| 156 | Nef | 88 | 97 | 10 | SHFLREKGGL |
| 157 | Nef | 91 | 99 | 9 | LKEKGGLEG |
| 158 | Nef | 91 | 99 | 9 | LREKGGLEG |
| 159 | Nef | 117 | 132 | 16 | TQGYFPDWQNYTPGPG |
| 160 | Nef | 117 | 132 | 16 | TQGFFPDWQNYTPEPG |
| 166 | Nef | 134 | 142 | 9 | RYPLTFGWC |
| 167 | Nef | 134 | 142 | 9 | RFPLTFGWC |
| 168 | Nef | 134 | 148 | 15 | RYPLTFGWCFKLVPV |
| 169 | Nef | 134 | 148 | 15 | RFPLTFGWCFKLVPL |
| 170 | Nef | 136 | 148 | 13 | PLTFGWCFKLVPV |
| 171 | Nef | 136 | 148 | 13 | PLCFGWCFKLVPL |
| 174 | Pol | 56 | 67 | 12 | FPQITLWQRPLV |
| 175 | Pol | 56 | 67 | 12 | LPQITLWQRPIV |
| 178 | Pol | 72 | 91 | 20 | GGQLKEALLDTGADDTVLEE |
| 179 | Pol | 72 | 91 | 20 | GGQIKEALLDTGADDTVLED |
| 180 | Pol | 94 | 117 | 24 | LPGRWKPKMIGGIGGFIKVRQYDQ |
| 181 | Pol | 94 | 117 | 24 | LPGKWKPKMIGGIGGFIKVKQYDQ |
| 182 | Pol | 129 | 260 | 132 | GTVLVGPTPVNIIGRNLLTQIGCTLNFPISPIETVPVKLKPGMDGPKVKQWPL TEEKIKALVEICTEMEKEGKISKIGPENPYNTPVFAIKKKDSTKWRKLVDFRE LNKRIQDFWEVQLGIPHPAGLKKKKS |
| 183 | Pol | 129 | 260 | 132 | GTVLIGPTPVNIIGRNLLTQLGCTLNFPISPIDTVPVKLKPGMDGPRVKQWPL TEEKIKALIEICTEMEKEGKISRIGPENPYNTPIFAIKKKDGTKWRKLVDFRE LNKKTQDFWEVQLGIPHPSGLKKKKS |
| 184 | Pol | 129 | 277 | 149 | GTVLVGPTPVNIIGRNLLTQIGCTLNFPISPIETVPVKLKPGMDGPKVKQWPL TEEKIKALVEICTEMEKEGKISKIGPENPYNTPVFAIKKKDSTKWRKLVDFRE LNKRTQDFWEVQLGIPHPAGLKKKKSVTVLDVGDAYFSVPLDK |
| 185 | Pol | 129 | 277 | 149 | GTVLIGPTPVNIIGRNLLTQLGCTLNFPISPIDTVPVKLKPGMDGPRVKQWPL TEEKIKALIEICTEMEKEGKISRIGPENPYNTPIFAIKKKDGTKWRKLVDFRE LNKKTQDFWEVQLGIPHPSGLKKKKSVTILDVGDAYFSIPLDK |
| 193 | Pol | 254 | 277 | 24 | GLKKKKSVTVLDVGDAYFSVPLDK |
| 194 | Pol | 254 | 277 | 24 | GLKKNKSVTVLDVGDAYFSIPLDK |
| 195 | Pol | 278 | 289 | 12 | DFRKYTAFTIPS |
| 196 | Pol | 278 | 289 | 12 | EFRKYTAFTVPS |
| 197 | Pol | 291 | 315 | 25 | NNETPGIRYQYNVLPQGWKGSPAIF |
| 198 | Pol | 291 | 315 | 25 | NNETPGVRYQYNVLPMGWKGSPAIF |
| 199 | Pol | 291 | 320 | 30 | NNETPGIRYQYNVLPQGWKGSPAIFQSSMT |
| 200 | Pol | 291 | 320 | 30 | NNETPGVRYQYNVLPMGWKGSPAIFQCSMT |
| 203 | Pol | 315 | 323 | 9 | FQSSMTKIL |
| 204 | Pol | 315 | 323 | 9 | FQCSMTKIL |

TABLE C-continued polypeptide segments in conserved regions of HIV-1 proteins

| SEQ ID NO: | Gene | Start | End | Length | Sequence |
|---|---|---|---|---|---|
| 205 | Pol | 318 | 327 | 10 | SMTKILEPFR |
| 206 | Pol | 318 | 327 | 10 | SMTKILDPFR |
| 207 | Pol | 322 | 330 | 9 | ILEPFRKQN |
| 208 | Pol | 322 | 330 | 9 | ILDPFRKQN |
| 213 | Pol | 333 | 354 | 22 | IVIYQYMDDLYVGSDLEIGQHR |
| 214 | Pol | 333 | 354 | 22 | IVIYQYVDDLYVGSDLEIEQHR |
| 221 | Pol | 367 | 399 | 33 | WGFTTPDKKHQKEPPFLWMGYELHPDKWTVQPI |
| 222 | Pol | 367 | 399 | 33 | WGLTTPDKKHQKDPPFLWMGYELHPDRWTVQPI |
| 236 | Pol | 401 | 431 | 31 | LPEKDSWTVNDIQKLVGKLNWASQIYPGIKV |
| 237 | Pol | 401 | 431 | 31 | LPEKESWTVNDIQKLIGKLNWASQIYAGIKV |
| 245 | Pol | 434 | 442 | 9 | LCKLLRGTK |
| 246 | Pol | 434 | 442 | 9 | LCKLLRGAK |
| 247 | Pol | 453 | 471 | 19 | EAELELAENREILKEPVHG |
| 248 | Pol | 453 | 471 | 19 | EAEIELAENREILREPVHG |
| 249 | Pol | 467 | 478 | 12 | EPVHGVYYDPSK |
| 250 | Pol | 467 | 478 | 12 | EPVHGAYYDPSK |
| 251 | Pol | 490 | 511 | 22 | GQWTYQIYQEPFKNLKTGKYAR |
| 252 | Pol | 490 | 511 | 22 | GQWSYQIYQEPYKNLKTGKYAK |
| 253 | Pol | 515 | 530 | 16 | AHTNDVKQLTEAVQKI |
| 254 | Pol | 515 | 530 | 16 | AHTNDVRQLTEAVQKV |
| 255 | Pol | 535 | 544 | 10 | IVIWGKTPKF |
| 256 | Pol | 535 | 544 | 10 | IVIWGKIPKF |
| 257 | Pol | 542 | 554 | 13 | PKFKLPIQKETWE |
| 258 | Pol | 542 | 554 | 13 | PKFRLPIQKETWD |
| 263 | Pol | 559 | 589 | 31 | EYWQATWIPEWEFVNTPPLVKLWYQLEKEPI |
| 264 | Pol | 559 | 589 | 31 | DYWQATWIPEWEFTNTPPLVKLWYQLETEPI |
| 266 | Pol | 591 | 606 | 16 | GAETFYVDGAANRETK |
| 267 | Pol | 591 | 606 | 16 | GVETFYVDGASNRETK |
| 268 | Pol | 625 | 637 | 13 | TDTTNQKTELQAI |
| 269 | Pol | 625 | 637 | 13 | ADTTNQKTELHAI |
| 270 | Pol | 636 | 644 | 9 | AIHLALQDS |
| 271 | Pol | 636 | 644 | 9 | AIYLALQDS |
| 272 | Pol | 639 | 671 | 33 | LALQDSGLEVNIVTDSQYALGIIQAQPDKSESE |
| 273 | Pol | 639 | 671 | 33 | LALQDSGSEVNIVTDSQYAIGIIQAQPDRSESE |
| 278 | Pol | 673 | 681 | 9 | VSQIIEQLI |
| 279 | Pol | 673 | 681 | 9 | VNQIIEQLI |
| 280 | Pol | 675 | 684 | 10 | QIIEQLIKKE |
| 281 | Pol | 675 | 684 | 10 | QIIEQLINKE |

TABLE C-continued polypeptide segments in conserved regions of HIV-1 proteins

| SEQ ID NO: | Gene | Start | End | Length | Sequence |
|---|---|---|---|---|---|
| 282 | Pol | 683 | 708 | 26 | KEKVYLAWVPAHKGIGGNEQVDKLVS |
| 283 | Pol | 683 | 708 | 26 | KEKIYLAWVPAHKGIGGNEQIDKLVS |
| 284 | Pol | 710 | 725 | 16 | GIRKVLFLDGIDKAQE |
| 285 | Pol | 710 | 725 | 16 | GIRRVLFLDGIEKAQD |
| 286 | Pol | 727 | 735 | 9 | HEKYHSNWR |
| 287 | Pol | 727 | 735 | 9 | HEKYHNNWR |
| 288 | Pol | 737 | 745 | 9 | MASDFNLPP |
| 289 | Pol | 737 | 745 | 9 | MASDFNIPP |
| 290 | Pol | 741 | 753 | 13 | FNLPPVVAKEIVA |
| 291 | Pol | 741 | 753 | 13 | FNLPPIVAKEIVA |
| 292 | Pol | 741 | 827 | 87 | FNLPPVVAKEIVASCDKCQLKGEAMHGQVDCSPGIWQLDCTHLEGKIILVAVHVASGYIEAEVIPAETGQETAYFLLKLAGRWPVKT |
| 293 | Pol | 741 | 827 | 87 | FNLPPIVAKEIVACCDKCQLKGEAIHGQVDCSPGVWQLDCTHLEGKVILVAVHVASGYIEAEIIPTETGQETAYFILKLAGRWPVTT |
| 294 | Pol | 747 | 827 | 81 | VAKEIVASCDKCQLKGEAMHGQVDCSPGIWQLDCTHLEGKIILVAVHVASGYIEAEVIPAETGQETAYFLLKLAGRWPVKT |
| 295 | Pol | 747 | 827 | 81 | VAKEIVACCDKCQLKGEAIHGQVDCSPGVWQLDCTHLEGKVILVAVHVASGYMEAEVIPTETGQETAYFILKLAGRWPVTT |
| 305 | Pol | 840 | 919 | 80 | TVKAACWWAGIKQEFGIPYNPQSQGVVESMNKELKKIIGQVRDQAEHLKTAVQMAVFIHNFKRKGGIGGYSAGERIVDII |
| 306 | Pol | 840 | 919 | 80 | AVKAACWWAGVKQEFGIPYHPQSQGVVESMNNELKKIIGQIRDQAEQLKTAVQMAVLIHNFKRKGGIGEYSAGERIIDII |
| 307 | Pol | 840 | 920 | 81 | TVKAACWWAGIKQEFGIPYNPQSQGVVESMNKELKKIIGQVRDQAEHLKTAVQMAVFIHNFKRKGGIGGYSAGERIVDIIA |
| 308 | Pol | 840 | 920 | 81 | AVKAACWWAGVKQEFGIPYHPQSQGVVESMNNELKKIIGQIRDQAEQLKTAVQMAVLIHNFKRKGGIGEYSAGERIIDIIA |
| 309 | Pol | 840 | 1003 | 164 | TVKAACWWAGIKQEFGIPYNPQSQGVVESMNKELKKIIGQVRDQAEHLKTAVQMAVFIHNFKRKGGIGGYSAGERIVDIIATDIQTKELQKQIIKIQNFRVYYRDSRDPLWKGPAKLLWKGEGAVVIQDNSDIKVVPRRKAKIIRDYGKQMAGDDCVASRQDED |
| 310 | Pol | 840 | 1003 | 164 | AVKAACWWAGVKQEFGIPYNTQSQGVVESMNNELKKIIGQIRDQAEHLKTAVQMAVLIHNFKRKGGIGEYSAGERIIDIIATDIQTRELQKQIIKLQNFRVYYRDNRDPLWKGPARLLWKGEGAVVIQDNSEIKVVPRRKVKIIRDYGKRMAGDDCVAGRQDED |
| 313 | Pol | 917 | 925 | 9 | DIIATDIQT |
| 314 | Pol | 917 | 925 | 9 | DIIASDIQT |
| 315 | Pol | 922 | 930 | 9 | DIQTKELQK |
| 316 | Pol | 922 | 930 | 9 | DIQTRELQK |
| 317 | Pol | 924 | 932 | 9 | QTKELQKQI |
| 318 | Pol | 924 | 932 | 9 | QTRELQKQI |
| 321 | Pol | 932 | 1003 | 72 | ITKIQNFRVYYRDSRDPLWKGPAKLLWKGEGAVVIQDNSDIKVVPRRKAKIIRDYGKQMAGDDCVASRQDED |
| 322 | Pol | 932 | 1003 | 72 | ITKLQNFRVYYRDNRDPLWKGPARLLWKGEGAVVIQDNSEIKVVPRRKVKIIRDYGKRMAGDDCVAGRQDED |

With respect to the range of lengths of the individual polypeptide or peptide segments, in various embodiments, each polypeptide segment is at least 8 amino acids in length, and up to about 250 amino acids in length, e.g., from at least 8 amino acids in length up to 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 45, 50, 55, 60, 65, 70, 75, 80, 85, 90, 95, 100, 110, 120, 130, 140, 150, 160, 170, 180, 190, 200, 210, 220, 230, 240 or 250 amino acids in length. In various embodiments, each polypeptide segment is at least 8 amino acids in length, and up to about 35 amino acids in length, e.g., from at least 8 amino acids in length up to 9, 10, 11, 12, 13, 14, 15, 16, 17, 18, 19, 20, 21, 22, 23, 24, 25, 26, 27, 28, 29, 30, 31, 32, 34 or 35 amino acids in length. In various embodiments, each polypeptide segment is at least 15 amino acids in length, and up to about 30 amino acids in length, e.g., from at least 15 amino acids in length up to 16, 17, 18, 19, 20, 21, 22, 23, 24, 25, 26, 27, 28, 29 or 30 amino acids in length.

With respect to the length of the full-length fusion polypeptide, in various embodiments, in some embodiments, the full-length of the fusion polypeptide comprises at least about 350 amino acids and up to about 1000 amino acids, e.g., at least about 350 amino acids and up to about 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 or 1000 amino acids. With respect to the length of the full-length fusion polypeptide, in various embodiments, in some embodiments, the full-length of the fusion polypeptide comprises at least about 350 amino acids and up to about 800 amino acids, e.g., at least about 350 amino acids and up to about 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 670, 680, 690, 700, 710, 720, 730, 740, 750, 760, 770, 780, 790, or 800 amino acids. In some embodiments, the full-length of the fusion polypeptide is no longer than 800 amino acids, e.g., no longer than 795, 790, 785, 780, 775, 770, 765, 760, 755, 750, 745, 740, 735, 730, 725, 720, 715, 710, 705 or 700 amino acids.

Generally, the fusion polypeptides are immunogenic, in that they are capable of eliciting an immune response in a human, e.g., against HIV-1. In some embodiments, the fusion polypeptides, optionally in combination with one or more additional therapeutic agents, e.g., as described herein, are capable of eliciting a protective or a therapeutically effective immune response in a human against HIV-1, e.g., capable of either preventing HIV-1 infection in an uninfected individual, or in therapeutic contexts, capable of eliciting an immune response sufficient to induce immune mediated control of HIV-1 or eradicate HIV-1 in an infected individual. The immunogenicity of the fusion polypeptides can be evaluated and demonstrated, in in vitro and in vivo assays, as described herein. For example, immunogenicity of the fusion polypeptides can be demonstrated by an in vitro assay, including CD4+ and/or CD8+ T-cell activation (e.g., including cytokine expression and target killing assays) or proliferation assays. The T-cells can be activated by exposure to antigen presenting cells (APCs) (such as dendritic cells, e.g., monocyte-derived dendritic cells) that have been transfected with a polynucleotide encoding the fusion polypeptide. Such assays are known in the art and described herein. The immunogenicity of the fusion polypeptides can also be demonstrated in in vivo animal models, for example, by administering to mice, e.g., transgenic for one or more human HLA molecules (available from Jackson Laboratories or Taconic), or non-human primates, and evaluating CD4+ and/or CD8+ T-cell activation (e.g., including serum cytokine levels) or proliferation. In various embodiments, one, two, three, or more, of each polypeptide segment comprises or consists of one or more predicted T cell epitopes, e.g., as computationally or experimentally determined. In some embodiments, the fusion polypeptide comprises one or more polypeptide segments that bind to or are presented by one or more human HLA class I and/or class II alleles (e.g. 1, 2, 3, 4, 5 or 6 alleles), e.g. within a single subject or amongst multiple subjects. In some embodiments, the fusion polypeptide comprises one or more polypeptide segments that bind to or are presented by at least by a human A*0201 HLA class I molecule. In some embodiments, the fusion polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more, 8-mer, 9-mer and/or 10-mer polypeptide segments that bind to or are presented by one or more human HLA class I and/or class II alleles (e.g. 1, 2, 3, 4, 5 or 6 alleles), e.g. within a single subject. In some embodiments, the fusion polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more polypeptide segments, each 15-30 amino acids in length, that are intracellularly processed and presented by one or more human HLA class I and/or class II alleles (e.g. 1, 2, 3, 4, 5 or 6 alleles), e.g. within a single subject.

Concatenating Polypeptide Segments

As appropriate, the one or more of the polypeptide segments can be directly abutted or fused to an adjacent segment, or can be joined, connected or linked to an adjacent segment by one or more peptide linkers. In various embodiments, the one or more peptide linkers is selected from one or more of a polyalanine linker, a polyglycine linker, a cleavable linker, a flexible linker, a rigid linker, a Nef linking sequence, and combinations thereof, e.g., within a linker or within a full-length fusion polypeptide. Illustrative fusion protein linkers that can be used in the present fusion polypeptides to connect one or more polypeptide segments are described, e.g., in Chen, et al., *Adv Drug Deliv Rev.* (2013) 65(10): 1357-1369. In some embodiments, the polyalanine linker comprises or consists of 2 or 3 contiguous alanine residues, e.g. AA, AAA (SEQ ID NO: 378), AAY (SEQ ID NO: 379) or AAX, wherein X is any amino acid (e.g., A, C, D, E, F, G, H, I, K, L, M, N, P, Q, R, S, T, V, Y) (SEQ ID NO: 380). In some embodiments, a polyglycine linker is used, e.g., GGS (SEQ ID NO: 419), GSG (SEQ ID NO: 420) or GGGS (SEQ ID NO:421).

In some embodiments, the cleavable linker is selected from a 2A cleavable peptide. Illustrative 2A cleavable peptides that can be used in the present fusion polypeptides to connect one or more polypeptide segments are described, e.g., in Donnelly, et al., *J. Gen. Virol* (2001), 82, 1027-1041 and Chng, et al., mAbs (2015) 7:2, 403-412. Illustrative cleavable peptides that can be used to link one or more polypeptide segments include without limitation 2A cleavage sequences (e.g., foot-and-mouth disease virus (F2A), equine rhinitis A virus (E2A), porcine teschovirus-1 (P2A) and Thosea asigna virus (T2A)), and furin recognition/cleavage sequences (e.g. REKR (SEQ ID NO: 382), RRKR (SEQ ID NO: 383), RAKR (SEQ ID NO: 381)). In certain embodiments, a furin recognition/cleavage sequence (e.g., REKR (SEQ ID NO: 382), RRKR (SEQ ID NO: 383), RAKR (SEQ ID NO: 381)) is combined or fused with a 2A cleavable peptide (e.g., foot-and-mouth disease virus (F2A), equine rhinitis A virus (E2A), porcine teschovirus-1 (P2A) and Thosea asigna virus (T2A)) in a single linker. See, e.g., Chng, et al., mAbs (2015) 7:2, 403-412. In various embodiments, the 2A cleavable linker comprises or consists of the amino acid sequence that is at least 90%, 91%, 92%, 93%, 94%, 95%, 96%, 97%, 98% or at least 99% identical to ATNFSLLKQAGDVEENPGP (SEQ ID NO: 384), APVKQTLNFDLLKLAGDVESNPGP (SEQ ID NO: 385), RAKRAPVKQTLNFDLLKLAGDVESNPGP (SEQ ID NO: 386), QCTNYALLKLAGDVESNPGP (SEQ ID NO: 387), or EGRGSLLTCGDVEENPGP (SEQ ID NO: 388), or comprises or consists of the amino acid sequence of ATNFSLLKQAGDVEENPGP (SEQ ID NO: 384), APVKQTLNFDLLKLAGDVESNPGP (SEQ ID NO: 385), RAKRAPVKQTLNFDLLKLAGDVESNPGP (SEQ ID NO: 386), QCTNYALLKLAGDVESNPGP (SEQ ID NO: 387), or EGRGSLLTCGDVEENPGP (SEQ ID NO: 388). As appropriate, in certain embodiments, a furin recognition/cleavage sequence can be positioned either at the N-terminus or the C-terminus of a 2A linker. In some embodiments, the cleavable linker comprises or consists of a furin recognition/cleavage site selected from the group consisting of RAKR (SEQ ID NO: 381), REKR (SEQ ID NO: 382) and RRKR (SEQ ID NO: 383). REKR (SEQ ID NO: 382) is a naturally occurring cleavable linker in HIV and SIV envelope glycoprotein precursor (Bahbouhi, et al., *Biochem. J.* (2002) 366, 863-872). In some embodiments, the fusion polypeptide comprises one or more Nef linking sequence comprises or consists of an amino acid sequence that is at least 95%, 96%, 97%, 98% or 99% identical to VHAGPIA (SEQ ID NO: 389), VHAGPVA (SEQ ID NO: 390), or GALDI (SEQ ID NO:391), or comprises or consists of an amino acid sequence selected from VHAGPIA (SEQ ID NO: 389), VHAGPVA (SEQ ID NO: 390) and GALDI (SEQ ID NO: 391). Illustrative linkers that can be used to link or connect one or more polypeptide segments in a fusion polypeptide are provided in Table D.

TABLE D illustrative linkers for connecting polypeptide segments

| SEQ ID NO: | NAME | SEQUENCE |
|---|---|---|
|  | poly-alanine (2) | AA |
| 378 | poly-alanine (3) | AAA |
| 379 | poly-alanine-Tyr | AAY |
| 380 | poly-alanine-XXX | AAX (X = any amino acid) |
| 381 | furin recognition site | RAKR |
| 382 | furin recognition site | REKR |
| 383 | furin recognition site | RRKR |
| 384 | P2A | ATNFSLLKQAGDVEENPGP |
| 385 | F2A | APVKQTLNFDLLKLAGDVESNPGP |
| 386 | F2A + furin recognition site | RAKRAPVKQTLNFDLLKLAGDVESNPGP |
| 387 | E2A | QCTNYALLKLAGDVESNPGP |
| 388 | T2A | EGRGSLLTCGDVEENPGP |
| 389 | Nef natural sequence link | VHAGPIA |
| 390 | Nef natural sequence link | VHAGPVA |
| 391 | Nef natural sequence link | GALDI |
| 392 | Nef natural sequence link | GALDL |
| 419 | poly-glycine | GGS |
| 420 | poly-glycine | GSG |
| 421 | Gly3Ser | GGGS |

Polypeptide Segments Encoded by HIV-1 Gail Gene

In various embodiments, the fusion polypeptide comprises one or more segments of one or more viral proteins, or fragments or subsequences thereof, encoded by the HIV-1 Gag gene. In some embodiments, the one or more viral proteins encoded by the HIV-1 Gag gene is selected from p17 (N-terminal matrix), p24 (capsid), p7 (nucleocapsid) and p6 (C-terminus). In some embodiments, the one or more viral proteins encoded by the HIV-1 Gag gene does not comprise any p6 components. In some embodiments, the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from: SEQ ID NOs: 68-146 and 339-342; SEQ ID NOs: 68, 69, 72, 73, 74, 75, 76, 77, 80, 81, 82, 83, 84, 85, 86, 87, 88, 89, 92, 93, 101, 102, 103, 104, 109, 110, 115, 116, 125, 126, 127, 128, 129, 130, 131, 132, 133, 134, 135, 136, 139, 140, 141, 142, 143, 144, 145 and 146; SEQ ID NOs: 76, 77, 86, 87 and 92-124; SEQ ID NOs: 76, 77, 86, 87, 94 and 95; SEQ ID NOs: 76, 86 and 94; SEQ ID NOs: 77, 87 and 95; SEQ ID NOs: 68-79 and 92-124; SEQ ID NOs: 70-71, 76-77 and 94-95; SEQ ID NOs: 78, 79, 96, 99, 100, 107, 108, 113, 114, 121, 122, 123, 124, 137 and 138; SEQ ID NOs: 78, 99, 107, 113, 121, 123 and 137; SEQ ID NOs: 78, 79, 90, 91, 97, 98, 99, 100, 105, 106, 107, 108, 111, 112, 113, 114, 117, 118, 119, 120, 121, 122, 123, 124, 137 and 138; SEQ ID NOs: 78, 90, 97, 105, 111, 117, 119 and 137; and SEQ ID NOs: 78 and 137.

In some embodiments, the fusion polypeptide comprises at least 2 polypeptide segments, e.g., at least 3, 4, 5, 6, 7, 8, 9, 10, 11, 12, 13, 14, 15, 16, 17, 18, 19, 20, or more, segments comprising or consisting of an HIV-1 Gag amino acid sequence corresponding to amino acid residue positions selected from 31-53, 37-51, 142-166, 175-199, 183-191, 257-282, 257-290, 265-282, 288-313, 288-321, 296-313, 333-357, 337-361, 341-349, 345-353 and 429-444, wherein the amino acid positions are with respect to SEQ ID NO:404. In certain embodiments, the fusion polypeptide does not comprise 1, 2, 3, 4, 5, or more, polypeptide segments comprising or consisting of an HIV-1 Gag amino acid sequence corresponding to amino acid residue positions selected from 1-30, 54-127, 138-146, 370-428 and 445-500, or subsequences thereof, wherein the amino acid positions are with respect to SEQ ID NO:404. In some embodiments, the plurality of polypeptide segments does not, or the herein described fusion proteins do not, comprise 1, 2, 3, 4, 5, or more, polypeptide segments comprising or consisting of an HIV-1 Gag amino acid sequence of any one of SEQ ID NOs: 444-448, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 444-448, or subsequences thereof (Table K). Illustrative polypeptide segments encoded by the HIV-1 Gag gene and incorporated into the herein described fusion polypeptides (e.g., determined to be from conserved regions, predicted to bind to human HLA A*0201 and/or known to be immunogenic) are depicted as aligned to the HIV-1 HXB2 Gag reference polypeptide in FIG. 18. As used herein, numbering of a given amino acid polymer or nucleic acid polymer "corresponds to", is "corresponding to" or is "relative to" the numbering of a selected or reference amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer.

Polypeptide Segments Encoded by HIV-1 Nef Gene

In some embodiments, the fusion polypeptide comprises one or more segments of the viral protein encoded by the HIV-1 Nef gene. In some embodiments, the plurality of polypeptide segments comprises at least one polypeptide segment, e.g., at least 2, 3, 4, 5, 6, 7, 8, 9, 10, 11, 12, 13, 14, 15, 16, 17, 18, 19, 20, 21, 22, 23, 24, 25, or more, segments comprising or consisting of an amino acid sequence selected from: SEQ ID NOs: 147, 148, 149, 150, 151, 152, 153, 154, 155, 156, 157, 158, 159, 160, 161, 162, 163, 164, 165, 166, 167, 168, 169, 170, 171 and 172; SEQ ID NOs: 147, 148, 149, 150, 155, 156, 157, 158, 159, 160, 166, 167, 168, 169, 170 and 171; SEQ ID NOs: 149-152; SEQ ID NOs: 151-152; SEQ ID NOs: 149, 150, 151, 152, 159, 160, 161, 162, 163, 164, 166, 167, 168, 169, 170, 171, 172, 173 and 174; SEQ ID NOs: 151, 152, 161 and 162; SEQ ID NOs: 151 and 152; SEQ ID NOs: 153, 154, 172 and 173; SEQ ID NOs: 153 and 172; SEQ ID NOs: 153, 154, 155, 156, 157, 158, 163, 164, 165, 166, 167, 168, 169, 170, 171, 172 and 173; SEQ ID NOs: 153 and 165; and SEQ ID NO: 153.

In some embodiments, the fusion polypeptide comprises at least 2 polypeptide segments, e.g., at least 3, 4, 5, 6, 7, 8, 9, 10, 11, 12, 13, 14, 15, or more, segments comprising or consisting of an HIV-1 Nef amino acid sequence corresponding to amino acid residue positions selected from 64-102, 81-102, 88-97, 91-99, 130-148, 130-154, 134-142, 134-148, 136-148, 137-145, 137-145 and 117-154, wherein the amino acid positions are with respect to SEQ ID NO:405. In certain embodiments, the fusion polypeptide does not comprise 1, 2, 3, or more, polypeptide segments comprising or consisting of an HIV-1 Nef amino acid sequence corresponding to amino acid residue positions selected from 1-63, 103-116 and 155-206, or subsequences thereof, wherein the amino acid positions are with respect to SEQ ID NO:405. In some embodiments, the plurality of polypeptide segments does not, or the herein described fusion proteins do not, comprise 1, 2, 3, or more, polypeptide segments comprising or consisting of an HIV-1 Nef amino acid sequence of any one of SEQ ID NOs: 449-451, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 449-451, or subsequences thereof (Table K). Illustrative polypeptide segments encoded by the HIV-1 Nef gene and incorporated into the herein described fusion polypeptides (e.g., determined to be from conserved regions, predicted to bind to human HLA A*0201 and/or known to be immunogenic) are depicted as aligned to the HIV-1 HXB2 Nef reference polypeptide in FIG. 19.

Fusion Polypeptides Having Polypeptide Segments Encoded by HIV-1 Gag and Nef Genes In some embodiments, the fusion polypeptide comprises or consists of one or more segments of viral proteins encoded by the HIV-1 Gag and Nef genes, e.g., does not comprise one or more polypeptide segments encoded by the HIV-1 Env, Pol, Tat, Rev, Vif, Vpr or Vpu genes. In some embodiments, the fusion polypeptide comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from: SEQ ID NOs: 68-79 and 92-124, 149, 150, 151, 152, 159, 160, 161, 162, 163, 164, 166, 167, 168, 169, 170, 171, 172, 173 and 174; SEQ ID NOs: 70, 71, 76, 77, 94, 95, 151, 152, 161 and 162; SEQ ID NOs: 70, 76, 94, 151 and 161; and SEQ ID NOs: 71, 77, 95, 152 and 162. Polypeptide segments included in fusion polypeptides having polypeptide segments encoded by HIV-1 Gag and Nef genes are listed in Table E.

TABLE E polypeptide segments in GagNef fusion polypeptides (e.g., SEQ ID NOs: 353-356)

| SEQ ID NO: | Gene | Start | End | SEQUENCE |
|---|---|---|---|---|
| 68 | Gag | 1 | 11 | MGARASVLSGG |
| 69 | Gag | 1 | 11 | MGARASILSGG |
| 70 | Gag | 1 | 53 | MGARASVLSGGELDRWEKIRLRPGGKKKYRLKHIVWASRELERFAVNPGLLET |
| 71 | Gag | 1 | 53 | MGARASILSGGKLDKWEKIRLRPGGRKKYKLKHIVWASRELERFAVNPGLLET |
| 72 | Gag | 13 | 25 | LDRWEKIRLRPGG |
| 73 | Gag | 13 | 25 | LDKWEKIRLRPMG |
| 74 | Gag | 19 | 27 | IRLRPGGKK |
| 75 | Gag | 19 | 27 | IRLRPGGRK |
| 76 | Gag | 31 | 53 | LKHIVWASRELERFAVNPGLLET |
| 77 | Gag | 31 | 53 | LKHLVWASRELERFALNPGLLET |
| 78 | Gag | 37 | 51 | ASRELERFAVNPGLL |
| 79 | Gag | 37 | 51 | ASRELERFALNPGLL |
| 92 | Gag | 147 | 217 | ISPRTLNAWVKVVEEKAFSPEVIPMFSALSEGATPQDLNTMLNTVGGHQAAMQMLKETINEEAAEWDRLHP |
| 93 | Gag | 147 | 217 | LSPRTLNAWVKVIEEKAFSPEVIPMFTALSEGATPHDLNTMLNTIGGHQAAMQMLKDTINEEAAEWDRVHP |
| 94 | Gag | 147 | 369 | ISPRTLNAWVKVVEEKAFSPEVIPMFSALSEGATPQDLNTMLNTVGGHQAAMQMLKETINEEAAEWDRLHPVHAGPIAPGQMREPRGSDIAGTTSTLQEQIGWMTNNPPIPVGEIYKRWIILGLNKIVRMYSPTSILDIRQGPKEPFRDYVDRFYKTLRAEQASQEVKNWMTETLLVQNANPDCKTILKALGPAATLEEMMTACQGVGGPGHKARVLAEAMSQ |
| 95 | Gag | 147 | 369 | LSPRILNAWVKVIEEKAFSPEVIPMFTALSEGATPHDLNTMLNTIGGHQAAMQMLKDTINEEAAEWDRVHPVHAGPVAPGQMRDPRGSDIAGSTSTLQEQIAWMTNNPPIPVGDIYKRWIIMGLNKIVRMYSPVSILDIKQGPKEPFRDYVDRFYRTLRAEQASQDVKNWMTETLLVQNSNPDCKTILKALGPGATLEEMMSACQGVGGPSHKARVLAEAMCQ |
| 96 | Gag | 150 | 158 | RTLNAWVKV |
| 97 | Gag | 175 | 199 | LSEGATPQDLNTMLNTVGGHQAAMQ |
| 98 | Gag | 175 | 199 | LSEGATPHDLNTMLNTIGGHQAAMQ |
| 99 | Gag | 183 | 191 | DLNTMLNTV |
| 100 | Gag | 183 | 191 | DLNTMLNTI |
| 101 | Gag | 225 | 251 | PGQMREPRGSDIAGTTSTLQEQIGWMT |
| 102 | Gag | 225 | 251 | PGQMRDPRGSDIAGSTSTLQEQIAWMT |
| 103 | Gag | 253 | 285 | NPPIPVGEIYKRWIILGLNKIVRMYSPTSILDI |
| 104 | Gag | 253 | 285 | NPPIPVGDIYKRWIIMGLNKIVRMYSPVSILDI |
| 339 | Gag | 257 | 282 | PVGEIYKRWIILGLNKIVRMYSPTSI |
| 340 | Gag | 257 | 282 | PVGDIYKRWIIMGLNKIVRMYSPVSI |
| 105 | Gag | 257 | 290 | PVGEIYKRWIILGLNKIVRMYSPTSILDIRQGPK |
| 106 | Gag | 257 | 290 | PVGDIYKRWIIMGLNKIVRMYSPVSILDIKQGPK |
| 107 | Gag | 265 | 282 | WIILGLNKIVRMYSPTSI |
| 108 | Gag | 265 | 282 | WIIMGLNKIVRMYSPVSI |
| 109 | Gag | 281 | 314 | SILDIRQGPKEPFRDYVDRFYKTLRAEQASQEVK |
| 110 | Gag | 281 | 314 | SILDIKQGPKEPFRDYVDRFYRTLRAEQASQDVK |
| 341 | Gag | 288 | 313 | GPKEPFRDYVDRFYKTLRAEQASQEV |
| 342 | Gag | 288 | 313 | GPKEPFRDYVDRFYRTLRAEQASQDV |

TABLE E-continued polypeptide segments in GagNef fusion polypeptides (e.g., SEQ ID NOs: 353-356)

| SEQ ID NO: | Gene | Start | End | SEQUENCE |
|---|---|---|---|---|
| 111 | Gag | 288 | 321 | GPKEPFRDYVDRFYKTLRAEQASQEVKNWMTETL |
| 112 | Gag | 288 | 321 | GPKEPFRDYVDRFYRTLRAEQASQDVKNWMTETL |
| 113 | Gag | 296 | 313 | YVDRFYKTLRAEQASQEV |
| 114 | Gag | 296 | 313 | YVDRFYRTLRAEQASQDV |
| 115 | Gag | 311 | 369 | QEVKNWMTETLLVQNANPDCKTILKALGPAATLEEMMTACQGVGGPGHKARVLAEAMSQ |
| 116 | Gag | 311 | 369 | QDVKNWMTETLLVQNSNPDCKTILKALGPGATLEEMMSACQGVGGPSHKARVLAEAMCQ |
| 117 | Gag | 333 | 357 | ILKALGPAATLEEMMTACQGVGGPG |
| 118 | Gag | 333 | 357 | ILKALGPGATLEEMMSACQGVGGPS |
| 119 | Gag | 337 | 361 | LGPAATLEEMMTACQGVGGPGHKAR |
| 120 | Gag | 337 | 361 | LGPGATLEEMMSACQGVGGPSHKAR |
| 121 | Gag | 341 | 349 | ATLEEMMTA |
| 122 | Gag | 341 | 349 | ATLEEMMSA |
| 123 | Gag | 345 | 353 | EMMTACQGV |
| 124 | Gag | 345 | 353 | EMMSACQGV |
| 149 | Nef | 64 | 82 | EEVGFPVRPQVPLRPMTYK |
| 150 | Nef | 64 | 82 | EEVGFPVKPQVPLRPMTFK |
| 151 | Nef | 64 | 99 | EEVGFPVKPQVPLRPMTFKGALDLSHFLREKGGLEG |
| 152 | Nef | 64 | 99 | EEVGFPVRPQVPLRPMTYKGALDLSHFLKEKGGLEG |
| 159 | Nef | 117 | 132 | TQGYFPDWQNYTPGPG |
| 160 | Nef | 117 | 132 | TQGFFPDWQNYTPEPG |
| 161 | Nef | 117 | 148 | TQGFFPDWQNYTPEPGIRFPLTFGWCFKLVPL |
| 162 | Nef | 117 | 148 | TQGYFPDWQNYTPGPGTRYPLTFGWCFKLVPV |
| 163 | Nef | 130 | 148 | EPGIRFPLTFGWCFKLVPL |
| 164 | Nef | 130 | 148 | GPGTRYPLTFGWCFKLVPV |
| 166 | Nef | 134 | 142 | RYPLTFGWC |
| 167 | Nef | 134 | 142 | RFPLTFGWC |
| 168 | Nef | 134 | 148 | RYPLTFGWCFKLVPV |
| 169 | Nef | 134 | 148 | RFPLTFGWCFKLVPL |
| 170 | Nef | 136 | 148 | PLTFGWCFKLVPV |
| 171 | Nef | 136 | 148 | PLCFGWCFKLVPL |
| 172 | Nef | 137 | 145 | LTFGWCFKL |
| 173 | Nef | 137 | 145 | LCFGWCFKL |

In some embodiments, the fusion polypeptide comprises or consists of the following polypeptide segments in sequential order, from N-terminus to C-terminus, optionally joined or connected by one or more linkers: SEQ ID NOs: 70, 76, 94, 151 and 161; or SEQ ID NOs: 71, 77, 95, 152 and 162.

In some embodiments, the fusion polypeptide comprises or consists of an amino acid sequence of any one of SEQ ID NOs: 351-356 and 430, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 351-356 and 430.

Modifications may be made in the structure of the fusion polypeptides and polynucleotides encoding such fusion polypeptides, described herein, and still obtain a functional molecule that encodes a variant or derivative polypeptide with desirable (e.g., immunogenic) characteristics. When it is desired to alter the amino acid sequence of a polypeptide to create an equivalent, or even an improved, variant or portion of a fusion polypeptide described herein, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed fusion polypeptides, or corresponding DNA sequences that encode such fusion polypeptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 Methods in Enzymology vol. 183, Academic Press, Inc., San Diego, CA; Higgins, D. G. and Sharp, P. M. (1989) CABIOS 5: 151-153; Myers, E. W. and Muller W. (1988) CABIOS 4:11-17; Robinson, E. D. (1971) Comb. Theor 77: 105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, CA; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides described herein. Software for performing BLAST analyses is publicly available through the National Center for Biotechnology Information (blast.ncbi.nlm.nih.gov/Blast.cgi).

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff (1989) Proc. Natl. Acad. Sci. USA 89: 10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

A "polypeptide variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences described herein and evaluating one or more biological activities of the polypeptide as described herein and/or using any of a number of techniques well known in the art. The term "variant" may also refer to any naturally occurring or engineered molecule comprising one or more nucleotide or amino acid mutations.

Polypeptide Segments Encoded by HIV-1 Env Gene

In some embodiments, the fusion polypeptides comprise one or more segments of one or more viral proteins encoded by the HIV-1 Env gene. In certain embodiments, the one or more viral proteins encoded by the HIV-1 Env gene is selected from gp120 and gp41.

Figure 20:
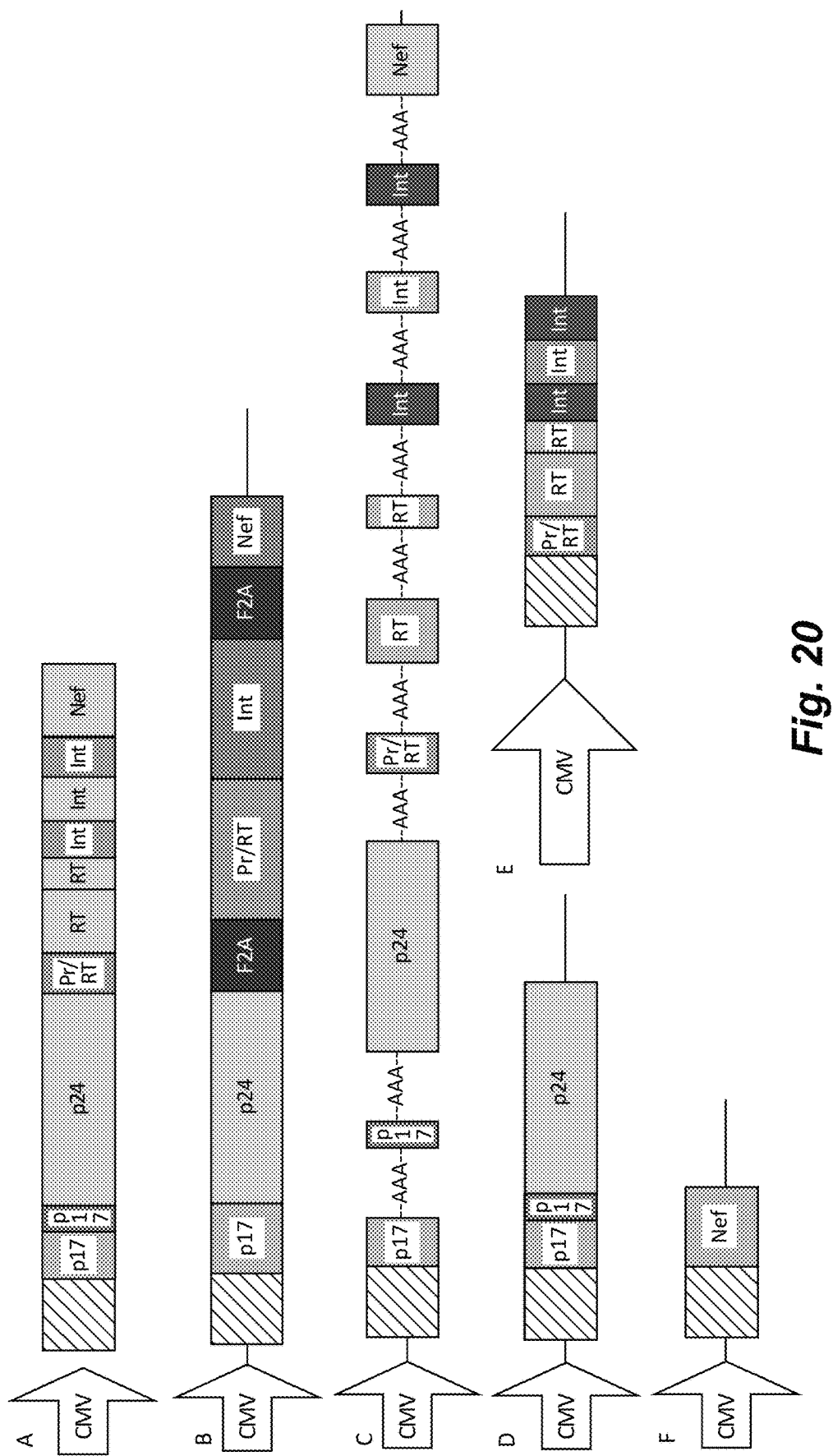
FIG. 20 illustrates modified vaccine expression cassettes for expressing the fusion polypeptides in adenoviral expression vectors, in this example, under the control of a CMV promoter. To determine an approach to combining conserved regions, candidate viral vector vaccines were constructed for expression of polypeptide segments of computationally defined conserved regions, and regions combined as (A) fusion polypeptide construct (SEQ ID NOs: 345/346); (B) with a processing spacer containing the F2A proteolytic cleavage site (SEQ ID NO:349/350; (C) flexible linker (e.g., AAA (SEQ ID NO: 378)) (SEQ ID NOs: 347/348); (D) fusion polypeptide with p17 and p24 conserved regions only; (E) fusion polypeptide with Protease, RT, Integrase conserved regions only; and (F) Nef only construct (SEQ ID NOs: 151/152).

In various embodiments, the fusion polypeptide comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from: SEQ ID NOs: 1-67 and 338; SEQ ID NOs: 2, 3, 8, 9, 13, 14, 17, 18, 23, 24, 25, 26, 28, 29, 31, 32, 33, 34, 35, 36, 37, 38, 39, 40, 43, 44, 45, 46, 47, 48, 49, 50, 51, 52, 53, 54, 55, 56, 58, 59, 62, 63, 64, 65, 66 and 67; SEQ ID NOs: 4, 5, 6, 7, 11, 12, 13, 14, 15, 16, 28, 29, 30, 37, 38, 41, 42, 43, 44, 45, 46, 47, 48, 49, 50, 51, 52, 53, 54, 55, 56, 57, 58, 59, 60, 61 and 338; SEQ ID NOs: 4, 5, 6, 7, 11, 12, 13, 14, 15, 16, 28, 29, 30, 37, 38, 41 and 42; SEQ ID NOs: 28, 29, 30 and 41-56; SEQ ID NOs: 28, 29, 41 and 42; SEQ ID NOs: 4, 5, 6, 7, 11, 12, 13, 14, 15, 16, 37 and 38; SEQ ID NOs: 4, 5, 11, 12, 37 and 38; SEQ ID NOs: 6, 7, 15, 16, 21, 22, 30, 60 and 61; SEQ ID NOs: 6, 15, 21, 30 and 60; SEQ ID NOs: 1, 2, 3, 4, 5, 6, 7, 10, 11, 12, 13, 14, 15, 16, 19, 20, 27, 55, 56, 57, 58, 59, 60, 61 and 338; SEQ ID NOs: 1, 10, 19, 27, 55, 56 and 57; and SEQ ID NOs: 6, 15 and 60.

In various embodiments, the fusion polypeptide comprises at least 2 polypeptide segments, e.g., at least 3, 4, 5, 6, 7, 8, 9, 10, 11, 12, 13, 14, or more, segments comprising or consisting of an HIV-1 Env amino acid sequence corresponding to amino acid residue positions selected from 28-52, 34-48, 34-47, 36-44, 59-83, 64-83, 66-83, 67-75, 113-137, 235-259, 586-594, 586-610, 589-606 and 594-602, wherein the amino acid positions are with respect to SEQ ID NO:403. In certain embodiments, the fusion polypeptide does not comprise 1, 2, 3, 4, 5, 6, or more, polypeptide segments comprising or consisting of an HIV-1 Env amino acid sequence corresponding to amino acid residue positions selected from 1-27, 53-58, 84-112, 138-234, 269-474, 490-501, 611-856, or subsequences thereof, wherein the amino acid positions are with respect to SEQ ID NO:403. In some embodiments, the plurality of polypeptide segments does not, or the herein described fusion proteins do not, comprise 1, 2, 3, 4, 5, or more, polypeptide segments comprising or consisting of an HIV-1 Env amino acid sequence of any one of SEQ ID NOs: 437-443, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 437-443, or subsequences thereof (Table K). Illustrative polypeptide segments encoded by the HIV-1 Env gene and incorporated into the herein described fusion polypeptides (e.g., determined to be from conserved regions, predicted to bind to human HLA A*0201 and/or known to be immunogenic) are depicted as aligned to the HIV-1 HXB2 Env reference polypeptide in FIG. 17.

Polypeptide Segments Encoded by HIV-1 Pol Gene

In some embodiments, the fusion polypeptides comprise of one or more segments of one or more viral proteins encoded by the HIV-1 Pol gene. In various embodiments, the one or more viral proteins encoded by the HIV-1 Pol gene is selected from one or more of protease (PR), reverse transcriptase (RT), and integrase (INT).

In some embodiments, the plurality of polypeptide segments comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from: SEQ ID NOs: 174-337 and 343-344; SEQ ID NOs: 174, 175, 178, 179, 180, 181, 182, 183, 184, 185, 193, 194, 195, 196, 197, 198, 199, 200, 203, 204, 205, 206, 207, 208, 213, 214, 221, 222, 236, 237, 245, 246, 247, 248, 249, 250, 251, 252, 253, 254, 255, 256, 257, 258, 263, 264, 266, 267, 268, 269, 270, 271, 272, 273, 278, 279, 280, 281, 282, 283, 284, 285, 286, 287, 288, 289, 290, 291, 292, 293, 294, 295, 305, 306, 307, 308, 309, 310, 313, 314, 315, 316, 317, 318, 321, and 322; SEQ ID NOs: 180, 181, 182, 183, 184, 185, 186, 187, 190, 191, 192, 193, 194, 195, 196, 221, 222, 294, 295, 296, 297, 298, 299, 300, 301, 305, 306, 307, 308, 311, 312, 321, 322, 323, 324, 325, 326, 327, 328, 329, 330, 331, 332, 333, 334, 335, 336 and 337; SEQ ID NOs: 180, 181, 186, 187, 221, 222, 294, 295, 307, 308, 321 and 322; SEQ ID NOs: 176, 177, 178, 179, 180, 181, 182, 183, 184, 185, 186, 187, 188, 189, 190, 191, 192, 193, 194, 195, 196, 197, 198, 199, 200, 201, 202, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 257, 258, 259, 260, 261, 262, 263, 264, 265, 266, 267, 282, 283, 294, 295, 296, 297, 298, 299, 300, 301, 302, 305, 306, 319, 320, 321, 322, 323, 324, 325, 326, 327, 328, 329, 330, 331, 332, 333, 334, 335, 336 and 337; SEQ ID NOs: 176, 177, 188, 189, 213, 214, 223, 224, 259, 260, 282, 283, 294, 295, 305, 306, 319, and 320; SEQ ID NOs: 180, 181, 186, 187, 221, 222, 294, 295, 321 and 322; SEQ ID NOs: 182-202, 292-302, 305, 306; SEQ ID NOs: 188, 189, 294, 295, 305, 306; SEQ ID NOs: 176, 177, 178, 179, 180, 181, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 257, 258, 259, 260, 261, 262, 263, 264, 265, 266, 267, 282, 283, 319, 320, 321, 322, 323, 324, 325, 326, 327, 328, 329, 330, 331, 332, 333, 334, 335, 336 and 337; SEQ ID NOs: 176, 177, 213, 214, 223, 224, 259, 260, 282, 283, 319 and 320; SEQ ID NOs: 192, 201, 202, 215, 216, 217, 218, 219, 220, 229, 230, 231, 240, 241, 242, 243, 244, 265, 276, 277, 298, 299, 302, 311, 312, 327, 328, 331, 332, 333, 336 and 337; SEQ ID NOs: 192, 201, 215, 217, 219, 229, 230, 240, 241, 243, 265, 276, 298, 302, 311, 327, 331, 333 and 336; SEQ ID NOs: 190, 191, 192, 197, 198, 209, 210, 211, 212, 213, 214, 215, 216, 217, 218, 219, 220, 225, 226, 227, 228, 229, 230, 231, 232, 233, 234, 235, 238, 239, 261, 262, 274, 275, 276, 277, 296, 297, 298, 299, 300, 301, 302, 303, 304, 323, 324, 325, 326, 327, 328, 329, 330, 331, 332, 333, 334, 335, 336, 337, 343, 344, 375 and 376; SEQ ID NOs: 190, 197, 209, 210, 211, 225, 227, 234, 238, 261, 296, 300, 303, 323, 325, 329, 334; and SEQ ID NOs: 192, 215, 217, 219, 229, 230, 276, 298, 302, 327, 331, 333 and 336.

In some embodiments, the fusion polypeptide comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 39, 30, or more, segments comprising or consisting of an HIV-1 Pol amino acid sequence corresponding to amino acid residue positions selected from 144-168, 152-160, 291-315, 326-350, 328-352, 330-354, 333-354, 334-342, 336-344, 338-346, 374-398, 380-404, 382-390, 388-396, 399-423, 400-424, 406-430, 553-577, 642-666, 650-658, 759-783, 767-775, 768-792, 776-784, 834-858, 940-964, 947-971, 948-956, 948-972, 955-963, 956-964, 980-1003 and 988-996, wherein the amino acid positions are with respect to SEQ ID NO:406. In certain embodiments, the fusion polypeptide does not comprise 1, 2, 3, 4, 5, 6, 7, 8, 9, 10, or more, polypeptide segments comprising or consisting of an HIV-1 Pol amino acid sequence corresponding to amino acid residue positions selected from 1-55, 118-128, 321-325, 355-366, 432-541, 607-641, 667-682, 709-746, 828-833, 921-930, or subsequences thereof, wherein the amino acid positions are with respect to SEQ ID NO:406. In some embodiments, the plurality of polypeptide segments does not, or the herein described fusion proteins do not, comprise 1, 2, 3, 4, 5, or more, polypeptide segments comprising or consisting of an HIV-1 Pol amino acid sequence of any one of SEQ ID NOs: 452-461, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 452-461, or subsequences thereof (Table K). Illustrative polypeptide segments encoded by the HIV-1 Pol gene and incorporated into the herein described fusion polypeptides (e.g., determined to be from conserved regions, predicted to bind to human HLA A*0201 and/or known to be immunogenic) are depicted as aligned to the HIV-1 HXB2 Pol reference polypeptide in FIGS. 20A-C.

In some embodiments, a fusion polypeptide comprising polypeptide segments encoded by the HIV-1 Pol gene does not comprise the amino acid sequence or motif YMDD (SEQ ID NO: 462) or YVDD (SEQ ID NO: 463). In some embodiments, the fusion polypeptide does not comprise one or more amino acid sequences selected from SEQ ID NOs: 215, 216, 217, 218, 219 and 220. In some embodiments, the fusion polypeptide does not comprise one or more amino acid sequences selected from SEQ ID NOs: 209, 210, 211, 212, 213, 214, 343 and 344.

Fusion Polypeptides Having Polypeptide Segments Encoded by HIV-1 Env and Pol Genes In some embodiments, the fusion polypeptide comprises or consists of one or more segments of viral proteins encoded by the HIV-1 Env and Pol genes, e.g., does not comprise one or more polypeptide segments encoded by the HIV-1 Gag, Nef, Tat, Rev, Vif, Vpr or Vpu genes.

In some embodiments, the fusion polypeptide comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from: SEQ ID NOs: 4, 5, 6, 7, 11, 12, 13, 14, 15, 16, 28, 29, 30, 37, 38, 41, 42, 43, 44, 45, 46, 47, 48, 49, 50, 51, 52, 53, 54, 55, 56, 57, 58, 59, 60, 61, 176, 177, 178, 179, 180, 181, 182, 183, 184, 185, 186, 187, 188, 189, 190, 191, 192, 193, 194, 195, 196, 197, 198, 199, 200, 201, 202, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 257, 258, 259, 260, 261, 262, 263, 264, 265, 266, 267, 282, 283, 294, 295, 296, 297, 298, 299, 300, 301, 302, 305, 306, 319, 320, 321, 322, 323, 324, 325, 326, 327, 328, 329, 330, 331, 332, 333, 334, 335, 336, 337 and 338; SEQ ID NOs: 4, 5, 6, 7, 11, 12, 13, 14, 15, 16, 28, 29, 30, 37, 38, 41, 42, 176, 177, 188, 189, 213, 214, 223, 224, 259, 260, 282, 283, 294, 295, 305, 306, 319 and 320; SEQ ID NOs: 28, 29, 30, 41-56, 182-202, 292-302, 305 and 306; SEQ ID NOs: 28, 29, 41, 42, 188, 189, 294, 295, 305 and 306; SEQ ID NOs: 4, 5, 6, 7, 11, 12, 13, 14, 15, 16, 37, 38, 176, 177, 178, 179, 180, 181, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 257, 258, 259, 260, 261, 262, 263, 264, 265, 266, 267, 282, 283, 319, 320, 321, 322, 323, 324, 325, 326, 327, 328, 329, 330, 331, 332, 333, 334, 335, 336 and 337; and SEQ ID NOs: 4, 5, 11, 12, 37, 38, 176, 177, 213, 214, 223, 224, 259, 260, 282, 283, 319 and 320. Polypeptide segments included in fusion polypeptides having polypeptide segments encoded by HIV-1 Env and Pol genes are listed in Table F.

In some embodiments, the fusion polypeptide comprises the following polypeptide segments in sequential order, from N-terminus to C-terminus, optionally joined or connected by one or more linkers: SEQ ID NOs: 188, 305, 28, 41, 294, 4, 176, 11, 319, 259, 282, 223, 213 and 37; SEQ ID NOs: 188, 305, 28, 41 and 294; SEQ ID NOs: 4, 176, 11, 319, 259, 282, 223, 213 and 37; SEQ ID NOs: 189, 306, 29, 42, 295, 5, 177, 12, 320, 260, 283, 224, 214 and 38; SEQ ID NOs: 189, 306, 29, 42 and 295; SEQ ID NOs: 5, 177, 12, 320, 260, 283, 224, 214 and 38; SEQ ID NOs: 305, 319, 259, 282, 223, 213, 294, 176 and 188; SEQ ID NOs: 306, 320, 260, 283, 224, 214, 295, 177 and 189; SEQ ID NOs: 305, 294, 223, 213, 176, 259, 319, 188 and 282; SEQ ID NOs: 306, 295, 224, 214, 177, 260, 320, 189 and 283; SEQ ID NOs: 305, 294, 319, 259, 282, 223, 176, and 188; SEQ ID NOs: 306, 295, 320, 260, 283, 224, 177 and 189; SEQ ID NOs: 305, 223, 294, 176, 259, 319, 188 and 282; or SEQ ID NOs: 306, 224, 295, 177, 260, 320, 189 and 283.

In some embodiments, the fusion polypeptide comprises or consists of an amino acid sequence of any one of SEQ ID NOs: 357-366 and 407-410, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 357-366 and 407-410.

Fusion Polypeptides Having Polypeptide Segments Encoded by HIV-1 Gag, Nef and Pol Genes In some embodiments, the fusion polypeptide comprises or consists of one or more segments of viral proteins encoded by the HIV-1 Gag, Nef and Pol genes, e.g., does not comprise one or more polypeptide segments encoded by the HIV-1 Env, Tat, Rev, Vif, Vpr or Vpu genes.

In some embodiments, the fusion polypeptide comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from: SEQ ID NOs: 76, 77, 86, 87, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 149, 150, 151, 152, 180, 181, 182, 183, 184, 185, 186, 187, 190, 191, 192, 193, 194, 195, 196, 221, 222, 294, 295, 296, 297, 298, 299, 300, 301, 305, 306, 307, 308, 311, 312, 321, 322, 323, 324, 325, 326, 327, 328, 329, 330, 331, 332, 333, 334, 335, 336, 337, 339, 340, 341 and 342; and SEQ ID NOs: 76, 77, 86, 87, 94, 95, 151, 152, 181, 182, 186, 187, 221, 222, 294, 195, 307, 308, 321, 322. Polypeptide segments included in fusion polypeptides having polypeptide segments encoded by HIV-1 Gag, Nef and Pol genes are listed in Table G.

In some embodiments, the fusion polypeptide comprises the following polypeptide segments in sequential order, from N-terminus to C-terminus, optionally joined or connected by one or more linkers: SEQ ID NOs: 76, 86, 94, 180, 186, 221, 294, 307, 321 and 151; or SEQ ID NOs: 77, 87, 95, 181, 187, 222, 295, 308, 322 and 152.

In some embodiments, the fusion polypeptide comprises or consists of an amino acid sequence of any one of SEQ ID NOs: 345-350, the sequences in Table 1, and SEQ ID NOs: 422-424, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 345-350, the sequences in Table 1, and SEQ ID NOs: 422-424.

TABLE F polypeptide segments in Pol/PolEnv fusion polypeptides (e.g., SEQ ID NOs: 357-366, 407-410))

| SEQ ID NO: | Gene | Start | End | Sequence |
|---|---|---|---|---|
| 4 | Env | 34 | 47 | LWVTVYYGVPVWKE |
| 5 | Env | 34 | 47 | LWVTIYYGVPVWKD |
| 6 | Env | 36 | 44 | VTVYYGVPV |
| 7 | Env | 36 | 44 | VTIYYGVPV |
| 11 | Env | 65 | 83 | AHNVWATHACVPTDPNPQE |
| 12 | Env | 65 | 83 | VHNIWATHACVPTDPSPQE |
| 13 | Env | 66 | 83 | HNVWATHACVPTDPNPQE |
| 14 | Env | 66 | 83 | HNIWATHACVPTDPSPQE |
| 15 | Env | 67 | 75 | NVWATHACV |
| 16 | Env | 67 | 75 | NIWATHACV |
| 28 | Env | 241 | 268 | NVSTVQCTHGIRPVVSTQLLLNGSLAEE |
| 29 | Env | 241 | 268 | NISTVQCTHGIKPVVSTQLLLNGSLAEK |
| 30 | Env | 243 | 251 | STVQCTHGI |
| 37 | Env | 475 | 489 | MRDNWRSELYKYKVV |
| 38 | Env | 475 | 489 | MKDNWRSELYRYKVV |
| 41 | Env | 502 | 606 | KRRVVQREKRAVGIGAMFLGFLGAAGSTMGAASITLTVQARQLLSGIVQQQNNLLRAIEAQQHLLQLTVWGIKQLQARVLAVERYLKDQQLLGIWGCSGKLICTT |
| 42 | Env | 502 | 606 | RRRVVQREKRAIGLGAVFLGFLGTAGSTMGAASMTLTVQARLLLSGIVQQQSNLLRAIEAQQHMLQLTVWGIKQLQARILAVERYLRDQQLLGIWGCSGRLICTT |
| 43 | Env | 519 | 534 | FLGFLGAAGSTMGAAS |
| 44 | Env | 519 | 534 | FLGFLGTAGSTMGAAA |
| 45 | Env | 533 | 606 | ASITLTVQARQLLSGIVQQQNNLLRAIEAQQHLLQLTVWGIKQLQARVLAVERYLKDQQLLGIWGCSGKLICTT |
| 46 | Env | 533 | 606 | ASMTLTVQARLLLSGIVQQQSNLLRAIEAQQHMLQLTVWGIKQLQARILAVERYLRDQQLLGIWGCSGRLICTT |
| 47 | Env | 536 | 556 | TLTVQARQLLSGIVQQQNNLL |
| 48 | Env | 536 | 556 | TLTVQARLLLSGIVQQQSNLL |
| 49 | Env | 554 | 564 | NLLRAIEAQQH |
| 50 | Env | 554 | 564 | NLLKAIEAQQH |
| 51 | Env | 558 | 584 | AIEAQQHLLQLTVWGIKQLQARVLAVE |
| 52 | Env | 558 | 584 | AIEAQQHMLQLTVWGIKQLQARILAVE |
| 53 | Env | 584 | 592 | ERYLKDQQL |
| 54 | Env | 584 | 592 | ERYLRDQQL |
| 55 | Env | 586 | 594 | YLKDQQLLG |
| 56 | Env | 586 | 594 | YLRDQQLLG |
| 57 | Env | 586 | 610 | YLKDQQLLGIWGCSGKLICTTAVPW |
| 338 | Env | 586 | 610 | YLRDQQLLGLWGCSGKLICPTAVPW |
| 58 | Env | 589 | 606 | DQQLLGIWGCSGKLICTT |
| 59 | Env | 589 | 606 | DQQLLGLWGCSGKLICPT |
| 60 | Env | 594 | 602 | GIWGCSGKL |
| 61 | Env | 594 | 602 | GLWGCSGKL |

TABLE F-continued polypeptide segments in Pol/PolEnv fusion polypeptides (e.g., SEQ ID NOs: 357-366, 407-410))

| SEQ ID NO: | Gene | Start | End | Sequence |
|---|---|---|---|---|
| 176 | Pol | 56 | 117 | FPQITLWQRPLVTIKIGGQLKEALLDTGADDTVLEEMNLPGRWKPKMIGGIGGFIKVRQYDQ |
| 177 | Pol | 56 | 117 | LPQITLWQRPIVTIKIGGQIKEALLDTGADDTVLEDMNLPGKWKPKMIGGIGGFIKVKQYDQ |
| 178 | Pol | 72 | 91 | GGQLKEALLDTGADDTVLEE |
| 179 | Pol | 72 | 91 | GGQIKEALLDTGADDTVLED |
| 180 | Pol | 94 | 117 | LPGRWKPKMIGGIGGFIKVRQYDQ |
| 181 | Pol | 94 | 117 | LPGKWKPKMIGGIGGFIKVKQYDQ |
| 182 | Pol | 129 | 260 | GTVLVGPTPVNIIGRNLLTQIGCTLNFPISPIETVPVKLKPGMDGPKVKQWPLTEEKIKALVEICTEMEKEGKIS KIGPENPYNTPVFAIKKKDSTKWRKLVDFRELNKRIQDFWEVQLGIPHPAGLKKKKS |
| 183 | Pol | 129 | 260 | GTVLIGPTPVNIIGRNLLTQLGCTLNFPISPIDTVPVKLKPGMDGPRVKQWPLTEEKIKALIEICTEMEKEGKIS RIGPENPYNTPIFAIKKKDGTKWRKLVDFRELNKKTQDFWEVQLGIPHPSGLKKKKS |
| 184 | Pol | 129 | 277 | GTVLVGPTPVNIIGRNLLTQIGCTLNFPISPIETVPVKLKPGMDGPKVKQWPLTEEKIKALVEICTEMEKEGKIS KIGPENPYNTPVFAIKKKDSTKWRKLVDFRELNKRTQDFWEVQLGIPHPAGLKKKKSVTVLDVGDAYFSVPLDK |
| 185 | Pol | 129 | 277 | GTVLIGPTPVNIIGRNLLTQLGCTLNFPISPIDTVPVKLKPGMDGPRVKQWPLTEEKIKALIEICTEMEKEGKIS RIGPENPYNTPIFAIKKKDGTKWRKLVDFRELNKKTQDFWEVQLGIPHPSGLKKKKSVTILDVGDAYFSIPLDK |
| 186 | Pol | 129 | 289 | GTVLVGPTPVNIIGRNLLTQIGCTLNFPISPIETVPVKLKPGMDGPKVKQWPLTEEKIKALVEICTEMEKEGKIS KIGPENPYNTPVFAIKKKDSTKWRKLVDFRELNKRTQDFWEVQLGIPHPAGLKKKKSVTVLDVGDAYFSVPLDKD FRKYTAFTIPS |
| 187 | Pol | 129 | 289 | GTVLIGPTPVNIIGRNLLTQLGCTLNFPISPIDTVPVKLKPGMDGPRVKQWPLTEEKIKALIEICTEMEKEGKIS RIGPENPYNTPIFAIKKKDGTKWRKLVDFRELNKKTQDFWEVQLGIPHPSGLKKKKSVTVLDIGDAYFSVPLDKE FRKYTAFTVPS |
| 188 | Pol | 129 | 320 | GTVLVGPTPVNIIGRNLLTQIGCTLNFPISPIETVPVKLKPGMDGPKVKQWPLTEEKIKALVEICTEMEKEGKIS KIGPENPYNTPVFAIKKKDSTKWRKLVDFRELNKRIQDFWEVQLGIPHPAGLKKKKSVTVLDVGDAYFSVPLDKD FRKYTAFTIPSINNETPGIRYQYNVLPQGWKGSPAIFQSSMT |
| 189 | Pol | 129 | 320 | GTVLIGPTPVNIIGRNLLTQLGCTLNFPISPIDTVPVKLKPGMDGPRVKQWPLTEEKIKALIEICTEMEKEGKIS RIGPENPYNTPIFAIKKKDGTKWRKLVDFRELNKKTQDFWEVQLGIPHPSGLKKKKSVTVLDIGDAYFSVPLDKE FRKYTAFTVPSTNNETPGVRYQYNVLPMGWKGSPAIFQCSMT |
| 190 | Pol | 144 | 168 | NLLTQIGCTLNFPISPIETVPVKLK |
| 191 | Pol | 144 | 168 | NLLTQLGCTLNFPISPIDTVPVKLK |
| 192 | Pol | 152 | 160 | TLNFPISPI |
| 193 | Pol | 254 | 277 | GLKKKKSVTVLDVGDAYFSVPLDK |
| 194 | Pol | 254 | 277 | GLKKNKSVTVLDVGDAYFSIPLDK |
| 195 | Pol | 278 | 289 | DFRKYTAFTIPS |
| 196 | Pol | 278 | 289 | EFRKYTAFTVPS |
| 197 | Pol | 291 | 315 | NNETPGIRYQYNVLPQGWKGSPAIF |
| 198 | Pol | 291 | 315 | NNETPGVRYQYNVLPMGWKGSPAIF |
| 199 | Pol | 291 | 320 | NNETPGIRYQYNVLPQGWKGSPAIFQSSMT |
| 200 | Pol | 291 | 320 | NNETPGVRYQYNVLPMGWKGSPAIFQCSMT |
| 201 | Pol | 299 | 307 | YQYNVLPQG |
| 202 | Pol | 299 | 307 | YQYNVLPMG |
| 213 | Pol | 333 | 354 | IVIYQYMDDLYVGSDLEIGQHR |
| 214 | Pol | 333 | 354 | IVIYQYVDDLYVGSDLEIEQHR |
| 215 | Pol | 334 | 342 | VIYQYMDDL |
| 216 | Pol | 334 | 342 | VIYQYVDDL |

TABLE F-continued polypeptide segments in Pol/PolEnv fusion polypeptides (e.g., SEQ ID NOs: 357-366, 407-410))

| SEQ ID NO: | Gene | Start | End | Sequence |
|---|---|---|---|---|
| 217 | Pol | 336 | 344 | YQYMDDLYV |
| 218 | Pol | 336 | 344 | YQYVDDLYV |
| 219 | Pol | 338 | 346 | YMDDLYVGS |
| 220 | Pol | 338 | 346 | YVDDLYVGS |
| 221 | Pol | 367 | 399 | WGFTTPDKKHQKEPPFLWMGYELHPDKWTVQPI |
| 222 | Pol | 367 | 399 | WGLTTPDKKHQKDPPFLWMGYELHPDRWTVQPI |
| 223 | Pol | 367 | 431 | WGFTTPDKKHQKEPPFLWMGYELHPDKWTVQPIVLPEKDSWTVNDIQKLVGKLNWASQIYPGIKV |
| 224 | Pol | 367 | 431 | WGLTTPDKKHQKDPPFLWMGYELHPDRWTVQPIELPEKESWTVNDIQKLIGKLNWASQIYAGIKV |
| 225 | Pol | 374 | 398 | KKHQKEPPFLWMGYELHPDKWTVQP |
| 226 | Pol | 374 | 398 | KKHQKDPPFLWMGYELHPDRWTVQP |
| 227 | Pol | 380 | 404 | PPFLWMGYELHPDKWTVQPIVLPEK |
| 228 | Pol | 380 | 404 | PPFLWMGYELHPDRWTVQPIELPEK |
| 229 | Pol | 382 | 390 | FLWMGYELH |
| 230 | Pol | 388 | 396 | ELHPDKWTV |
| 231 | Pol | 388 | 396 | ELHPDRWTV |
| 232 | Pol | 399 | 423 | IVLPEKDSWTVNDIQKLVGKLNWAS |
| 233 | Pol | 399 | 423 | IELPEKESWTVNDIQKLIGKLNWAS |
| 234 | Pol | 400 | 424 | VLPEKDSWTVNDIQKLVGKLNWASQ |
| 235 | Pol | 400 | 424 | ELPEKESWTVNDIQKLIGKLNWASQ |
| 236 | Pol | 401 | 431 | LPEKDSWTVNDIQKLVGKLNWASQIYPGIKV |
| 237 | Pol | 401 | 431 | LPEKESWTVNDIQKLIGKLNWASQIYAGIKV |
| 238 | Pol | 406 | 430 | SWTVNDIQKLVGKLNWASQIYPGIK |
| 239 | Pol | 406 | 430 | SWTVNDIQKLIGKLNWASQIYAGIK |
| 240 | Pol | 407 | 415 | WTVNDIQKL |
| 241 | Pol | 408 | 416 | TVNDIQKLV |
| 242 | Pol | 408 | 416 | TVNDIQKLI |
| 243 | Pol | 414 | 422 | KLVGKLNWA |
| 244 | Pol | 414 | 422 | KLIGKLNWA |
| 257 | Pol | 542 | 554 | PKFKLPIQKETWE |
| 258 | Pol | 542 | 554 | PKFRLPIQKETWD |
| 259 | Pol | 542 | 606 | PKFKLPIQKETWETWWTEYWQATWIPEWEFVNTPPLVKLWYQLEKEPIVGAETFYVDGAANRETK |
| 260 | Pol | 542 | 606 | PKFRLPIQKETWDTWWIDYWQATWIPEWEFTNTPPLVKLWYQLETEPIAGVETFYVDGASNRETK |
| 261 | Pol | 553 | 577 | WETWWTEYWQATWIPEWEFVNTPPL |
| 262 | Pol | 553 | 577 | WDTWWTDYWQATWIPEWEFTNTPPL |
| 263 | Pol | 559 | 589 | EYWQATWIPEWEFVNTPPLVKLWYQLEKEPI |
| 264 | Pol | 559 | 589 | DYWQATWIPEWEFTNTPPLVKLWYQLETEPI |
| 265 | Pol | 561 | 569 | WQATWIPEW |
| 266 | Pol | 591 | 606 | GAETFYVDGAANRETK |

TABLE F-continued polypeptide segments in Pol/PolEnv fusion polypeptides (e.g., SEQ ID NOs: 357-366, 407-410))

| SEQ ID NO: | Gene | Start | End | Sequence |
|---|---|---|---|---|
| 267 | Pol | 591 | 606 | GVETFYVDGASNRETK |
| 282 | Pol | 683 | 708 | KEKVYLAWVPAHKGIGGNEQVDKLVS |
| 283 | Pol | 683 | 708 | KEKIYLAWVPAHKGIGGNEQIDKLVS |
| 294 | Pol | 747 | 827 | VAKEIVASCDKCQLKGEAMHGQVDCSPGIWQLDCTHLEGKIILVAVHVASGYIEAEVIPAETGQETAYFLLKLAGRWPVKT |
| 295 | Pol | 747 | 827 | VAKEIVACCDKCQLKGEAIHGQVDCSPGVWQLDCTHLEGKVILVAVHVASGYMEAEVIPTETGQETAYFILKLAGRWPVTT |
| 296 | Pol | 759 | 783 | QLKGEAMHGQVDCSPGIWQLDCTHL |
| 297 | Pol | 759 | 783 | QLKGEAIHGQVDCSPGVWQLDCTHL |
| 298 | Pol | 767 | 775 | GQVDCSPGI |
| 299 | Pol | 767 | 775 | GQVDCSPGV |
| 300 | Pol | 768 | 792 | QVDCSPGIWQLDCTHLEGKIILVAV |
| 301 | Pol | 768 | 792 | QVDCSPGVWQLDCTHLEGKVILVAV |
| 302 | Pol | 776 | 784 | WQLDCTHLE |
| 305 | Pol | 840 | 919 | TVKAACWWAGIKQEFGIPYNPQSQGVVESMNKELKKIIGQVRDQAEHLKTAVQMAVFIHNFKRKGGIGGYSAGERIVDII |
| 306 | Pol | 840 | 919 | AVKAACWWAGVKQEFGIPYHPQSQGVVESMNNELKKIIGQIRDQAEQLKTAVQMAVLIHNFKRKGGIGEYSAGERIIDII |
| 319 | Pol | 931 | 1003 | AITKIQNFRVYYRDSRDPLWKGPAKLLWKGEGAVVIQDNSDIKVVPRRKAKIIRDYGKQMAGDDCVASRQDED |
| 320 | Pol | 931 | 1003 | AITKLQNFRVYYRDNRDPLWKGPARLLWKGEGAVVIQDNSEIKVVPRRKVKIIRDYGKRMAGDDCVAGRQDED |
| 321 | Pol | 932 | 1003 | ITKIQNFRVYYRDSRDPLWKGPAKLLWKGEGAVVIQDNSDIKVVPRRKAKIIRDYGKQMAGDDCVASRQDED |
| 322 | Pol | 932 | 1003 | ITKLQNFRVYYRDNRDPLWKGPARLLWKGEGAVVIQDNSEIKVVPRRKVKIIRDYGKRMAGDDCVAGRQDED |
| 323 | Pol | 940 | 964 | VYYRDSRDPLWKGPAKLLWKGEGAV |
| 324 | Pol | 940 | 964 | VYYRDNRDPLWKGPARLLWKGEGAV |
| 325 | Pol | 947 | 971 | DPLWKGPAKLLWKGEGAVVIQDNSD |
| 326 | Pol | 947 | 971 | DPLWKGPARLLWKGEGAVVIQDNSE |
| 327 | Pol | 948 | 956 | PLWKGPAKL |
| 328 | Pol | 948 | 956 | PLWKGPARL |
| 329 | Pol | 948 | 972 | PLWKGPAKLLWKGEGAVVIQDNSDI |
| 330 | Pol | 948 | 972 | PLWKGPARLLWKGEGAVVIQDNSEI |
| 331 | Pol | 955 | 963 | KLLWKGEGA |
| 332 | Pol | 955 | 963 | RLLWKGEGA |
| 333 | Pol | 956 | 964 | LLWKGEGAV |
| 334 | Pol | 980 | 1003 | AKIIRDYGKQMAGDDCVASRQDED |
| 335 | Pol | 980 | 1003 | VKIIRDYGKRMAGDDCVAGRQDED |
| 336 | Pol | 988 | 996 | KQMAGDDCV |
| 337 | Pol | 988 | 996 | KRMAGDDCV |

TABLE G polypeptide segments in first iteration fusion polypeptides (e.g., SEQ ID NOs: 345-350)

| SEQ ID NO: | Gene | Start | End | Sequence |
|---|---|---|---|---|
| 76 | Gag | 31 | 53 | LKHIVWASRELERFAVNPGLLET |
| 77 | Gag | 31 | 53 | LKHLVWASRELERFALNPGLLET |
| 86 | Gag | 128 | 137 | VSQNYPIVQN |
| 87 | Gag | 128 | 137 | VSQNFPIVQN |
| 92 | Gag | 147 | 217 | ISPRTLNAWVKVVEEKAFSPEVIPMFSALSEGATPQDLNTMLNTVGGHQAAMQMLKETINEEAAEWDRLHP |
| 93 | Gag | 147 | 217 | LSPRTLNAWVKVIEEKAFSPEVIPMFTALSEGATPHDLNTMLNTIGGHQAAMQMLKDTINEEAAEWDRVHP |
| 94 | Gag | 147 | 369 | ISPRTLNAWVKVVEEKAFSPEVIPMFSALSEGATPQDLNTMLNTVGGHQAAMQMLKETINEEAAEWDRLHPVHAGPIAPGQMREPRGSDIAGTTSTLQEQIGWMTNNPPIPVGEIYKRWIILGLNKIVRMYSPTSILDIRQGPKEPFRDYVDRFYKTLRAEQASQEVKNWMTETLLVQNANPDCKTILKALGPAATLEEMMTACQGVGGPGHKARVLAEAMSQ |
| 95 | Gag | 147 | 369 | LSPRTLNAWVKVIEEKAFSPEVIPMFTALSEGATPHDLNTMLNTIGGHQAAMQMLKDTINEEAAEWDRVHPVHAGPVAPGQMRDPRGSDIAGSTSTLQEQIAWMTNNPPIPVGDIYKRWIIMGLNKIVRMYSPVSILDIKQGPKEPFRDYVDRFYRTLRAEQASQDVKNWMTETLLVQNSNPDCKTILKALGPGATLEEMMSACQGVGGPSHKARVLAEAMCQ |
| 96 | Gag | 150 | 158 | RTLNAWVKV |
| 97 | Gag | 175 | 199 | LSEGATPQDLNTMLNTVGGHQAAMQ |
| 98 | Gag | 175 | 199 | LSEGATPHDLNTMLNTIGGHQAAMQ |
| 99 | Gag | 183 | 191 | DLNTMLNTV |
| 100 | Gag | 183 | 191 | DLNTMLNTI |
| 101 | Gag | 225 | 251 | PGQMREPRGSDIAGTTSTLQEQIGWMT |
| 102 | Gag | 225 | 251 | PGQMRDPRGSDIAGSTSTLQEQIAWMT |
| 103 | Gag | 253 | 285 | NPPIPVGEIYKRWIILGLNKIVRMYSPTSILDI |
| 104 | Gag | 253 | 285 | NPPIPVGDIYKRWIIMGLNKIVRMYSPVSILDI |
| 339 | Gag | 257 | 282 | PVGEIYKRWIILGLNKIVRMYSPTSI |
| 340 | Gag | 257 | 282 | PVGDIYKRWIIMGLNKIVRMYSPVSI |
| 105 | Gag | 257 | 290 | PVGEIYKRWIILGLNKIVRMYSPTSILDIRQGPK |
| 106 | Gag | 257 | 290 | PVGDIYKRWIIMGLNKIVRMYSPVSILDIKQGPK |
| 107 | Gag | 265 | 282 | WIILGLNKIVRMYSPTSI |
| 108 | Gag | 265 | 282 | WIIMGLNKIVRMYSPVSI |
| 109 | Gag | 281 | 314 | SILDIRQGPKEPFRDYVDRFYKTLRAEQASQEVK |
| 110 | Gag | 281 | 314 | SILDIKQGPKEPFRDYVDRFYRTLRAEQASQDVK |
| 341 | Gag | 288 | 313 | GPKEPERDYVDRFYKTLRAEQASQEV |
| 342 | Gag | 288 | 313 | GPKEPERDYVDRFYRTLRAEQASQDV |
| 111 | Gag | 288 | 321 | GPKEPERDYVDRFYKTLRAEQASQEVKNWMTETL |
| 112 | Gag | 288 | 321 | GPKEPERDYVDRFYRTLRAEQASQDVKNWMTETL |
| 113 | Gag | 296 | 313 | YVDRFYKTLRAEQASQEV |
| 114 | Gag | 296 | 313 | YVDRFYRTLRAEQASQDV |
| 115 | Gag | 311 | 369 | QEVKNWMTETLLVQNANPDCKTILKALGPAATLEEMMTACQGVGGPGHKARVLAEAMSQ |
| 116 | Gag | 311 | 369 | QDVKNWMTETLLVQNSNPDCKTILKALGPGATLEEMMSACQGVGGPSHKARVLAEAMCQ |
| 117 | Gag | 333 | 357 | ILKALGPAATLEEMMTACQGVGGPG |
| 118 | Gag | 333 | 357 | ILKALGPGATLEEMMSACQGVGGPS |
| 119 | Gag | 337 | 361 | LGPAATLEEMMTACQGVGGPGHKAR |

TABLE G-continued polypeptide segments in first iteration fusion polypeptides (e.g., SEQ ID NOs: 345-350)

| SEQ ID NO: | Gene | Start | End | Sequence |
|---|---|---|---|---|
| 120 | Gag | 337 | 361 | LGPGATLEEMMSACQGVGGPSHKAR |
| 121 | Gag | 341 | 349 | ATLEEMMTA |
| 122 | Gag | 341 | 349 | ATLEEMMSA |
| 123 | Gag | 345 | 353 | EMMTACQGV |
| 124 | Gag | 345 | 353 | EMMSACQGV |
| 149 | Nef | 64 | 82 | EEVGFPVRPQVPLRPMTYK |
| 150 | Nef | 64 | 82 | EEVGFPVKPQVPLRPMTFK |
| 151 | Nef | 64 | 99 | EEVGFPVKPQVPLRPMTFKGALDLSHFLREKGGLEG |
| 152 | Nef | 64 | 99 | EEVGFPVRPQVPLRPMTYKGALDLSHFLKEKGGLEG |
| 180 | Pol | 94 | 117 | LPGRWKPKMIGGIGGFIKVRQYDQ |
| 181 | Pol | 94 | 117 | LPGKWKPKMIGGIGGFIKVKQYDQ |
| 182 | Pol | 129 | 260 | GTVLVGPTPVNIIGRNLLTQIGCTLNFPISPIETVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKS |
| 183 | Pol | 129 | 260 | GTVLIGPTPVNIIGRNLLTQLGCTLNFPISPIDTVPVKLKPGMDGPRVKQWPLTEEKIKALIEICTEMEKEGKISRIGPENPYNTPIFAIKKKDGTKWRKLVDFRELNKKTQDFWEVQLGIPHPSGLKKKKS |
| 184 | Pol | 129 | 277 | GTVLVGPTPVNIIGRNLLTQIGCTLNFPISPIETVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKSVTVLDVGDAYFSVPLDK |
| 185 | Pol | 129 | 277 | GTVLIGPTPVNIIGRNLLTQLGCTLNFPISPIDTVPVKLKPGMDGPRVKQWPLTEEKIKALIEICTEMEKEGKISRIGPENPYNTPIFAIKKKDGTKWRKLVDFRELNKKTQDFWEVQLGIPHPSGLKKKKSVTILDVGDAYFSIPLDK |
| 186 | Pol | 129 | 289 | GTVLVGPTPVNIIGRNLLTQIGCTLNFPISPIETVPVKLKPGMDGPKVKQWPLTEEKIKALVEICTEMEKEGKISKIGPENPYNTPVFAIKKKDSTKWRKLVDFRELNKRIQDFWEVQLGIPHPAGLKKKKSVTVLDVGDAYFSVPLDKDFRKYTAFTIPS |
| 187 | Pol | 129 | 289 | GTVLIGPTPVNIIGRNLLTQLGCTLNFPISPIDTVPVKLKPGMDGPRVKQWPLTEEKIKALIEICTEMEKEGKISRIGPENPYNTPIFAIKKKDGTKWRKLVDFRELNKKTQDFWEVQLGIPHPSGLKKKKSVTVLDIGDAYFSVPLDKEFRKYTAFTVPS |
| 190 | Pol | 144 | 168 | NLLTQIGCTLNFPISPIETVPVKLK |
| 191 | Pol | 144 | 168 | NLLTQLGCTLNFPISPIDTVPVKLK |
| 192 | Pol | 152 | 160 | TLNFPISPI |
| 193 | Pol | 254 | 277 | GLKKKKSVTVLDVGDAYFSVPLDK |
| 194 | Pol | 254 | 277 | GLKKNKSVTVLDVGDAYFSIPLDK |
| 195 | Pol | 278 | 289 | DFRKYTAFTIPS |
| 196 | Pol | 278 | 289 | EFRKYTAFTVPS |
| 221 | Pol | 367 | 399 | WGFTTPDKKHQKEPPFLWMGYELHPDKWTVQPI |
| 222 | Pol | 367 | 399 | WGLTTPDKKHQKDPPFLWMGYELHPDRWTVQPI |
| 294 | Pol | 747 | 827 | VAKEIVASCDKCQLKGEAMHGQVDCSPGIWQLDCTHLEGKIILVAVHVASGYIEAEVIPAETGQETAYFLLKLAGRWPVKT |
| 295 | Pol | 747 | 827 | VAKEIVACCDKCQLKGEAIHGQVDCSPGVWQLDCTHLEGKVILVAVHVASGYMEAEVIPTETGQETAYFILKLAGRWPVTT |
| 296 | Pol | 759 | 783 | QLKGEAMHGQVDCSPGIWQLDCTHL |
| 297 | Pol | 759 | 783 | QLKGEAIHGQVDCSPGVWQLDCTHL |
| 298 | Pol | 767 | 775 | GQVDCSPGI |
| 299 | Pol | 767 | 775 | GQVDCSPGV |

TABLE G-continued polypeptide segments in first iteration fusion polypeptides (e.g., SEQ ID NOs: 345-350)

| SEQ ID NO: | Gene | Start | End | Sequence |
|---|---|---|---|---|
| 300 | Pol | 768 | 792 | QVDCSPGIWQLDCTHLEGKIILVAV |
| 301 | Pol | 768 | 792 | QVDCSPGVWQLDCTHLEGKVILVAV |
| 305 | Pol | 840 | 919 | TVKAACWWAGIKQEFGIPYNPQSQGVVESMNKELKKIIGQVRDQAEHLKTAVQMAVFIHNFKRKGGIGGYSAGERIVDII |
| 306 | Pol | 840 | 919 | AVKAACWWAGVKQEFGIPYHPQSQGVVESMNNELKKIIGQIRDQAEQLKTAVQMAVLIHNFKRKGGIGEYSAGERIIDII |
| 307 | Pol | 840 | 920 | TVKAACWWAGIKQEFGIPYNPQSQGVVESMNKELKKIIGQVRDQAEHLKTAVQMAVFIHNFKRKGGIGGYSAGERIVDIIA |
| 308 | Pol | 840 | 920 | AVKAACWWAGVKQEFGIPYHPQSQGVVESMNNELKKIIGQIRDQAEQLKTAVQMAVLIHNFKRKGGIGEYSAGERIIDIIA |
| 311 | Pol | 842 | 850 | KAACWWAGI |
| 312 | Pol | 842 | 850 | KAACWWAGV |
| 321 | Pol | 932 | 1003 | ITKIQNFRVYYRDSRDPLWKGPAKLLWKGEGAVVIQDNSDIKVVPRRKAKIIRDYGKQMAGDDCVASRQDED |
| 322 | Pol | 932 | 1003 | ITKLQNFRVYYRDNRDPLWKGPARLLWKGEGAVVIQDNSEIKVVPRRKVKIIRDYGKRMAGDDCVAGRQDED |
| 323 | Pol | 940 | 964 | VYYRDSRDPLWKGPAKLLWKGEGAV |
| 324 | Pol | 940 | 964 | VYYRDNRDPLWKGPARLLWKGEGAV |
| 325 | Pol | 947 | 971 | DPLWKGPAKLLWKGEGAVVIQDNSD |
| 326 | Pol | 947 | 971 | DPLWKGPARLLWKGEGAVVIQDNSE |
| 327 | Pol | 948 | 956 | PLWKGPAKL |
| 328 | Pol | 948 | 956 | PLWKGPARL |
| 329 | Pol | 948 | 972 | PLWKGPAKLLWKGEGAVVIQDNSDI |
| 330 | Pol | 948 | 972 | PLWKGPARLLWKGEGAVVIQDNSEI |
| 331 | Pol | 955 | 963 | KLLWKGEGA |
| 332 | Pol | 955 | 963 | RLLWKGEGA |
| 333 | Pol | 956 | 964 | LLWKGEGAV |
| 334 | Pol | 980 | 1003 | AKIIRDYGKQMAGDDCVASRQDED |
| 335 | Pol | 980 | 1003 | VKIIRDYGKRMAGDDCVAGRQDED |
| 336 | Pol | 988 | 996 | KQMAGDDCV |
| 337 | Pol | 988 | 996 | KRMAGDDCV |

Fusion Polypeptides Having Polypeptide Segments Encoded by HIV-1 Env, Gag, Nef and Pol, and Predicted to Bind to or be Presented by Human HLA A*0201 Molecules As described herein, we have designed fusion polypeptides having a plurality of polypeptide segments that have been computationally predicted to bind to or be presented by human HLA A*0201 molecules. Generally, the selected or included polypeptide segments in such fusion polypeptides comprise polypeptide segments encoded by HIV-1 Env, Gag, Nef and Pol genes (e.g., do not comprise one or more polypeptide segments encoded by the HIV-1 Tat, Rev, Vif, Vpr or Vpu genes), and which are predicted to bind to a human HLA A*0201 molecule with an IC50 value of less than about 1,000 nM. In certain embodiments, the selected or included polypeptide segments in such fusion polypeptides comprise polypeptide segments encoded by HIV-1 Env, Gag, Nef and Pol genes (e.g., do not comprise one or more polypeptide segments encoded by the HIV-1 Tat, Rev, Vif, Vpr or Vpu genes), and which are predicted to bind to a human HLA A*0201 molecule with a percentile rank within the top 5% in a population of polypeptide segments. In some embodiments, the fusion polypeptide comprises or consists of segments of viral proteins encoded by Gag, Pol, Env, and Nef genes, wherein each of the plurality of polypeptide segments can bind to or be presented by a human HLA allele A*0201.

In some embodiments, each of the plurality of polypeptide segments are from 8-35 amino acids in length, e.g. from 9-34 amino acids in length, e.g. from 9-25 amino acids in length.

In some embodiments, the fusion polypeptide comprises at least 2 polypeptide segments, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, or more, segments comprising or consisting of an amino acid sequence selected from: SEQ ID NOs: 6, 7, 15, 16, 21, 22, 30, 60, 61, 78, 79, 96, 99, 100, 107, 108, 113, 114, 121, 122, 123, 124, 137, 138, 153, 154, 172, 173, 192, 201, 202, 215, 216, 217, 218, 219, 220, 229, 230, 231, 240, 241, 242, 243, 244, 265, 276, 277, 298, 299, 302, 311, 312, 327, 328, 331, 332, 333, 336, and 337; SEQ ID NOs: 6, 15, 21, 30, 60, 78, 99, 107, 113, 121, 123, 137, 153, 172, 192, 201, 215, 217, 219, 229, 230, 240, 241, 243, 265, 276, 298, 302, 311, 327, 331, 333 and 336; SEQ ID NOs: 1, 2, 3, 4, 5, 6, 7, 10, 11, 12, 13, 14, 15, 16, 19, 20, 27, 55, 56, 57, 58, 59, 60, 61, 78, 79, 90, 91, 97, 98, 99, 100, 105, 106, 107, 108, 111, 112, 113, 114, 117, 118, 119, 120, 121, 122, 123, 124, 137, 138, 153, 154, 155, 156, 157, 158, 163, 164, 165, 166, 167, 168, 169, 170, 171, 172, 173, 190, 191, 192, 197, 198, 209, 210, 211, 212, 213, 214, 215, 216, 217, 218, 219, 220, 225, 226, 227, 228, 229, 230, 231, 232, 233, 234, 235, 238, 239, 261, 262, 274, 275, 276, 277, 296, 297, 298, 299, 300, 301, 302, 303, 304, 323, 324, 325, 326, 327, 328, 329, 330, 331, 332, 333, 334, 335, 336, 337, 338, 343 and 344; SEQ ID NOs: 1, 10, 19, 27, 55, 56, 57, 78, 90, 97, 105, 111, 117, 119, 137, 153, 165, 190, 197, 209, 210, 211, 225, 227, 234, 238, 261, 296, 300, 303, 323, 325, 329 and 334. Polypeptide segments included in fusion polypeptides having polypeptide segments encoded by HV-1 Env, Gag, Nef and Pol genes, and predicted to bind to or be presented by human HLA A*0201 molecules are listed in Table H.

TABLE H polypeptide segments in A*0201 binding fusion polypeptides (e.g., SEQ ID NOs: 367-377, 411)

| SEQ ID NO: | Gene | Start | End | Sequence |
|---|---|---|---|---|
| 1 | Env | 28 | 52 | CSATEKLWVTVYYGVPVWKEATTTL |
| 2 | Env | 34 | 48 | LWVTVYYGVPVWKEA |
| 3 | Env | 34 | 48 | LWVTIYYGVPVWKDA |
| 4 | Env | 34 | 47 | LWVTVYYGVPVWKE |
| 5 | Env | 34 | 47 | LWVTIYYGVPVWKD |
| 6 | Env | 36 | 44 | VTVYYGVPV |
| 7 | Env | 36 | 44 | VTIYYGVPV |
| 10 | Env | 59 | 83 | KAYDIEVHNVWATHACVPTDPNPQE |
| 11 | Env | 64 | 83 | AHNVWATHACVPTDPNPQE |
| 12 | Env | 64 | 83 | VHNIWATHACVPTDPSPQE |
| 13 | Env | 66 | 83 | HNVWATHACVPTDPNPQE |
| 14 | Env | 66 | 83 | HNIWATHACVPTDPSPQE |
| 15 | Env | 67 | 75 | NVWATHACV |
| 16 | Env | 67 | 75 | NIWATHACV |
| 19 | Env | 113 | 137 | DQSLKPCVKLTPLCVTLNCTDLRNT |
| 20 | Env | 113 | 137 | DESLKPCVKLTPICVTLNCTDLRNT |
| 27 | Env | 235 | 259 | GTGPCTNVSTVQCTHGIRPVVSTQL |
| 55 | Env | 586 | 594 | YLKDQQLLG |
| 56 | Env | 586 | 594 | YLRDQQLLG |
| 57 | Env | 586 | 610 | YLKDQQLLGIWGCSGKLICTTAVPW |
| 338 | Env | 586 | 610 | YLRDQQLLGLWGCSGKLICPTAVPW |
| 58 | Env | 589 | 606 | DQQLLGIWGCSGKLICTT |
| 59 | Env | 589 | 606 | DQQLLGLWGCSGKLICPT |
| 60 | Env | 594 | 602 | GIWGCSGKL |
| 61 | Env | 594 | 602 | GLWGCSGKL |
| 78 | Gag | 37 | 51 | ASRELERFAVNPGLL |
| 79 | Gag | 37 | 51 | ASRELERFALNPGLL |
| 90 | Gag | 142 | 166 | MVHQAISPRTLNAWVKVVEEKAFSP |
| 91 | Gag | 142 | 166 | MVHQPISPRTLNAWVKVIEEKAFSP |
| 97 | Gag | 175 | 199 | LSEGATPQDLNTMLNTVGGHQAAMQ |
| 98 | Gag | 175 | 199 | LSEGATPHDLNTMLNTIGGHQAAMQ |
| 99 | Gag | 183 | 191 | DLNTMLNTV |
| 100 | Gag | 183 | 191 | DLNTMLNTI |
| 339 | Gag | 257 | 282 | PVGEIYKRWIILGLNKIVRMYSPTSI |
| 340 | Gag | 257 | 282 | PVGDIYKRWIIMGLNKIVRMYSPVSI |
| 107 | Gag | 265 | 282 | WIILGLNKIVRMYSPTSI |
| 108 | Gag | 265 | 282 | WIIMGLNKIVRMYSPVSI |
| 341 | Gag | 288 | 313 | GPKEPFRDYVDRFYKTLRAEQASQEV |
| 342 | Gag | 288 | 313 | GPKEPFRDYVDRFYRTLRAEQASQDV |
| 113 | Gag | 296 | 313 | YVDRFYKTLRAEQASQEV |
| 114 | Gag | 296 | 313 | YVDRFYRTLRAEQASQDV |
| 117 | Gag | 333 | 357 | ILKALGPAATLEEMMTACQGVGGPG |
| 118 | Gag | 333 | 357 | ILKALGPGATLEEMMSACQGVGGPS |
| 119 | Gag | 337 | 361 | LGPAATLEEMMTACQGVGGPGHKAR |
| 120 | Gag | 337 | 361 | LGPGATLEEMMSACQGVGGPSHKAR |
| 121 | Gag | 341 | 349 | ATLEEMMTA |
| 122 | Gag | 341 | 349 | ATLEEMMSA |
| 123 | Gag | 345 | 353 | EMMTACQGV |
| 124 | Gag | 345 | 353 | EMMSACQGV |
| 137 | Gag | 429 | 444 | RQANFLGKIWPSHKGR |
| 138 | Gag | 429 | 444 | RQANFLGKVWPSHNGR |
| 153 | Nef | 81 | 102 | YKAAVDLSHFLREKGGLEGAAY |
| 154 | Nef | 81 | 102 | YKGALDLSHFLKEKGGLEGAAY |
| 155 | Nef | 88 | 97 | SHFLKEKGGL |

TABLE H-continued polypeptide segments in A*0201 binding fusion polypeptides (e.g., SEQ ID NOs: 367-377, 411)

| SEQ ID NO: | Gene | Start | End | Sequence |
|---|---|---|---|---|
| 156 | Nef | 88 | 97 | SHFLREKGGL |
| 157 | Nef | 91 | 99 | LKEKGGLEG |
| 158 | Nef | 91 | 99 | LREKGGLEG |
| 163 | Nef | 130 | 148 | EPGIRFPLTFGWCFKLVPL |
| 164 | Nef | 130 | 148 | GPGTRYPLTFGWCFKLVPV |
| 165 | Nef | 130 | 154 | GPGIRYPLLTFGWCFKLPVEPEKVE |
| 166 | Nef | 134 | 142 | RYPLTFGWC |
| 167 | Nef | 134 | 142 | RFPLTFGWC |
| 168 | Nef | 134 | 148 | RYPLTFGWCFKLVPV |
| 169 | Nef | 134 | 148 | RFPLTFGWCFKLVPL |
| 170 | Nef | 136 | 148 | PLTFGWCFKLVPV |
| 171 | Nef | 136 | 148 | PLCFGWCFKLVPL |
| 172 | Nef | 137 | 145 | LTFGWCFKL |
| 173 | Nef | 137 | 145 | LCFGWCFKL |
| 190 | Pol | 144 | 168 | NLLTQIGCTLNFPISPIETVPVKLK |
| 191 | Pol | 144 | 168 | NLLTQLGCTLNFPISPIDTVPVKLK |
| 192 | Pol | 152 | 160 | TLNFPISPI |
| 197 | Pol | 291 | 315 | NNETPGIRYQYNVLPQGWKGSPAIF |
| 198 | Pol | 291 | 315 | NNETPGVRYQYNVLPMGWKGSPAIF |
| 209 | Pol | 326 | 350 | FRKQNPDIVIYQYMDDLYVGSDLEI |
| 343 | Pol | 326 | 350 | FRKQNPDIVIYQYVDDLYVGSDLEI |
| 210 | Pol | 328 | 352 | KQNPDIVIYQYMDDLYVGSDLEIGQ |
| 344 | Pol | 328 | 352 | KQNPDIVIYQYVDDLYVGSDLEIEQ |
| 211 | Pol | 330 | 354 | NPDIVIYQYMDDLYVGSDLEIGQHR |
| 212 | Pol | 330 | 354 | NPDIVIYQYVDDLYVGSDLEIEQHR |
| 213 | Pol | 333 | 354 | IVIYQYMDDLYVGSDLEIGQHR |
| 214 | Pol | 333 | 354 | IVIYQYVDDLYVGSDLEIEQHR |
| 215 | Pol | 334 | 342 | VIYQYMDDL |
| 216 | Pol | 334 | 342 | VIYQYVDDL |
| 217 | Pol | 336 | 344 | YQYMDDLYV |
| 218 | Pol | 336 | 344 | YQYVDDLYV |
| 219 | Pol | 338 | 346 | YMDDLYVGS |
| 220 | Pol | 338 | 346 | YVDDLYVGS |
| 225 | Pol | 374 | 398 | KKHQKEPPFLWMGYELHPDKWTVQP |
| 226 | Pol | 374 | 398 | KKHQKDPPFLWMGYELHPDRWTVQP |
| 227 | Pol | 380 | 404 | PPFLWMGYELHPDKWTVQPIVLPEK |
| 228 | Pol | 380 | 404 | PPFLWMGYELHPDRWTVQPIELPEK |
| 229 | Pol | 382 | 390 | FLWMGYELH |
| 230 | Pol | 388 | 396 | ELHPDKWTV |
| 231 | Pol | 388 | 396 | ELHPDRWTV |
| 232 | Pol | 399 | 423 | IVLPEKDSWTVNDIQKLVGKLNWAS |
| 233 | Pol | 399 | 423 | IELPEKESWTVNDIQKLIGKLNWAS |
| 234 | Pol | 400 | 424 | VLPEKDSWTVNDIQKLVGKLNWASQ |
| 235 | Pol | 400 | 424 | ELPEKESWTVNDIQKLIGKLNWASQ |
| 238 | Pol | 406 | 430 | SWTVNDIQKLVGKLNWASQIYPGIK |
| 239 | Pol | 406 | 430 | SWTVNDIQKLIGKLNWASQIYAGIK |
| 261 | Pol | 553 | 577 | WETWWTEYWQATWIPEWEFVNTPPL |
| 262 | Pol | 553 | 577 | WDTWWTDYWQATWIPEWEFTNTPPL |
| 274 | Pol | 642 | 666 | QDSGLEVNIVTDSQYALGIIQAPD |
| 275 | Pol | 642 | 666 | QDSGSEVNIVTDSQYAIGIIQAPD |
| 276 | Pol | 650 | 658 | IVTDSQYAL |
| 277 | Pol | 650 | 658 | IVTDSQYAI |
| 296 | Pol | 759 | 783 | QLKGEAMHGQVDCSPGIWQLDCTHL |
| 297 | Pol | 759 | 783 | QLKGEAIHGQVDCSPGVWQLDCTHL |
| 298 | Pol | 767 | 775 | GQVDCSPGI |
| 299 | Pol | 767 | 775 | GQVDCSPGV |
| 300 | Pol | 768 | 792 | QVDCSPGIWQLDCTHLEGKIILVAV |
| 301 | Pol | 768 | 792 | QVDCSPGVWQLDCTHLEGKVILVAV |
| 302 | Pol | 776 | 784 | WQLDCTHLE |
| 303 | Pol | 834 | 858 | SNFTSTIVKAACWWAGIKQEFGIPY |
| 304 | Pol | 834 | 858 | SNFTSTAVKAACWWAGVKQEFGIPY |
| 323 | Pol | 940 | 964 | VYYRDSRDPLWKGPAKLLWKEGAV |
| 324 | Pol | 940 | 964 | VYYRDNRDPLWKGPARLLWKEGAV |
| 325 | Pol | 947 | 971 | DPLWKGPAKLLWKEGAVVIQDNSD |
| 326 | Pol | 947 | 971 | DPLWKGPARLLWKEGAVVIQDNSE |
| 327 | Pol | 948 | 956 | PLWKGPAKL |
| 328 | Pol | 948 | 956 | PLWKGPARL |
| 329 | Pol | 948 | 972 | PLWKGPAKLLWKGEGAVVIQDNSDI |
| 330 | Pol | 948 | 972 | PLWKGPARLLWKGEGAVVIQDNSEI |
| 331 | Pol | 955 | 963 | KLLWKGEGA |
| 332 | Pol | 955 | 963 | RLLWKGEGA |
| 333 | Pol | 956 | 964 | LLWKGEGAV |
| 334 | Pol | 980 | 1003 | AKIIRDYGKQMAGDDCVASRQDED |

TABLE H-continued polypeptide segments in A*0201 binding fusion polypeptides (e.g., SEQ ID NOs: 367-377, 411)

| SEQ ID NO: | Gene | Start | End | Sequence |
|---|---|---|---|---|
| 335 | Pol | 980 | 1003 | VKIIRDYGKRMAGDDCVAGRQDED |
| 336 | Pol | 988 | 996 | KQMAGDDCV |
| 337 | Pol | 988 | 996 | KRMAGDDCV |

In some embodiments, the fusion polypeptide comprises the following polypeptide segments in sequential order, from N-terminus to C-terminus, optionally joined or connected by one or more linkers: SEQ ID NOs: 201, 78, 107, 96, 229, 172, 327, 6, 333, 243, 331, 192, 265, 311, 137, 15, 123, 30, 336, 302, 153, 219, 298, 121, 230, 240, 60, 241, 276, 113, 99, 21, 217 and 215; SEQ ID NOs: 78, 296, 1, 339, 197, 329, 232, 323, 303, 234, 90, 261, 274, 238, 211, 325, 137, 227, 209, 190, 341, 57, 225, 27, 210, 119, 19, 165, 334, 117, 153, 10, 97 and 300; or SEQ ID NOs: 296, 1, 78, 197, 339, 227, 261, 274, 238, 325, 137, 329, 303, 234, 90, 232, 27, 57, 225, 323, 190, 341, 119, 19, 165, 334, 117, 153, 10, 97 and 300.

In some embodiments, the fusion polypeptide comprises an amino acid sequence of any one of SEQ ID NOs: 367-377 and 411, or a sequence that is 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 367-377 and 411.

Signal or Leader Sequences

In various embodiments, the fusion polypeptides comprise a signal sequence or signal peptide, e.g., to direct intracellular trafficking of the fusion polypeptide to a proteasomal or lysosomal compartment. In various embodiments, fusion polypeptide comprises a signal sequence at the N-terminus and/or the C-terminus. In some embodiments, the fusion polypeptide comprises an N-terminal signal peptide or leader sequence. In various embodiments, the signal peptide or leader sequence is from a source protein selected from a serum protein, a cytokine, a chemokine, a chaperone protein, an invariant protein, and a protein that directs proteins to the lysosomal compartment. In some embodiments, the signal peptide or leader sequence is from a source protein selected from the group consisting of colony stimulating factor 2 (CSF2, GM-CSF), tissue type plasminogen activator (PLAT, t-PA), C-C motif chemokine ligand 7 (CCL7, MCP-3), C-X-C motif chemokine ligand 10 (CXCL10, IP-10), catenin beta 1 (CTNNB1), CD74 (p33; DHLAG; HLADG; Ia-GAMMA, invariant chain), serum albumin (ALB), polyubiquitin B/C (UBB/UBC), calreticulin (CALR), vesicular stomatitis virus G protein (VSV-G), lysosomal associated membrane protein 1 (LAMP-i) and lysosomal associated membrane protein 2 (LAMP-2). In certain embodiments, the fusion polypeptide comprises N-terminal and C-terminal signal sequences from LAMP-1, e.g., SEQ ID NOs: 399 and 412, respectively. In various embodiments, the signal peptide or leader sequence is selected from an amino acid sequence of any one of SEQ ID NOs: 393-402 and 412-413, or a sequence that is at least 95%, 96%, 97%, or 98%, or 99% identical to any one of SEQ ID NOs: 393-402 and 412-413. Illustrative signal sequences that can be used in the present fusion polypeptides are provided in Table I.

TABLE I signal sequences

| SEQ ID NO: | source protein name | SEQUENCE |
|---|---|---|
| 393 | CSF2, GM-CSF | MWLQSLLLLGTVACSISV |
| 394 | PLAT, t-PA | MDAMKRGLCCVLLLCGAVFVSAR |
| 395 | CD74 | MHRRRSRSCREDQKPV |
| 396 | albumin | KWVTFISLLFLFSSAYS |
| 397 | p-catenin | MRKAAVSHWQQQSYLDSGIHSGATTTAPSLS |
| 398 | CCL7, MCP-3 | MNPSAAVIFCLILLGLSGTQGILDMAQPVGI NTSTTCCYRFINKKIPKQRLESYRRTTSSHC PREAVIFKTKLDKEICADPTQKWVQDFMKHL DKKTQTPKLASAGA |
| 399 | LA4P-1 N-terminal | MAPRSARRPLLLLLLLLLGLMHCASAAMFM VKNGNGTACIMANFSAAFSVNYDTKSGPKNM TLDLPSDATVVLNRSSCGKENTSDPSLVIAF GRGHTLTLNFTRNATRYSVQLMSFVYNLSDT HLFPNASSKEIKTVESITDIRADIDKKYRCV SGTQVHMNNVTVTLHDATIQAYLSNSSFSRG ETRCEQDRPSPTTAPPAPPSPSPSPVPKSPS VDKYNVSGTNGTCLLASMGLQLNLTYERKDN TTVTRLLNINPNKTSASGSCGAHLVTLELHS EGTTVLLFQFGMNASSSRFFLQGIQLNT1LP DARDPAFKAANGSLRALQATVGNSYKCNAEE HVRVTKAFSVNIFKVWVQAFKVEGGQFGSVE ECLLDENSLEDI |
| 412 | LAMP-1 C-terminal | GSEFTLIPIAVGGALAGLVIVLIAYLVGRKR SHAGYQTI |
| 400 | ubiquitin | MQIFVKTLTGKTITLEVEPSDTIENVKAKIQ DKEGIPPDQQRLIFAGKQLEDGRTLSDYNIQ KESTLHLVLRLRGG |
| 401 | calreticulin | MLLSVPLLLGLLGLAVA |
| 402 | VSV-G | MKCLLYLAFLFIGVNC |
| 413 | CXCL10, IP-10 | MNQTAILICCLIFLTLSGIQG |

Illustrative fusion polypeptides, with and without signal sequences, which have been designed and assembled according to the herein described methods, are provided in Table J.

In various embodiments, the fusion polypeptides described herein do not comprise 1, 2, 3, 4, 5, or more, or any or all, polypeptide segments comprising or consisting of an HIV-1 amino acid sequence of SEQ ID NOs: 437-461, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to an amino acid sequence of SEQ ID NOs: 437-461, or subsequences thereof. Amino acid sequences that can be excluded from (i.e., not included in) the herein described fusion polypeptides in certain embodiments are provided in Table K.

Further provided are methods for making a fusion polypeptide, pharmaceutical composition, immunogenic composition or vaccine composition comprising same. In some implementations, the methods comprise constructing the fusion polypeptides using peptide synthesis. In some implementations, the methods comprise constructing, using synthetic or recombinant DNA technology, polynucleotides encoding each of the polypeptides of the bivalent antigen and expressing the polypeptides from an expression vector. In some implementations, the methods may further comprise inserting the polynucleotides into one or more vectors and expressing the encoded polypeptides in a cell.

TABLE J immunogenic fusion polypeptides comprising HIV-1 polypeptide segments ("AAA" is SEQ ID NO: 378, "AAY" is SEQ ID NO: 379, "YMDD" is SEQ ID NO: 462 and "REKR" is SEQ ID NO: 382)

| SEQ ID NO: | Linker/ Signal peptide | HIV-1 Genes | SEQUENCE |
|---|---|---|---|
| 345 | AAA/ none | Gag, Pol, Nef | LKHIVWASRELERFAVNPGLLETAAAVSQNYPIVQNAAAISPRTLNAWVKVVEEKAFSPEVIPMFSALSEGATPQDLNTMLN TVGGHQAAMQMLKETINEEAAEWDRLHPVHAGPIAPGQMREPRGSDIAGTTSTLQEQIGWMTNNPPIPVGEIYKRWIILGLN KIVRMYSPTSILDIRQGPKEPFRDYVDRFYKTLRAEQASQEVKNWMTETLLVQNANPDCKTILKALGPAATLEEMMTACQGV GGPGHKARVLAEAMSQAAALPGRWKPKMIGGIGGFIKVRQYDQAAAGTVLVGPTPVNIIGRNLLTQIGCTLNFPISPIETVP VKLKPGMDGPKVKQWPLTEEKIKALVEICTEMEKEGKISKIGPENPYNTPVFAIKKKDSTKWRKLVDFRELNKRTQDFWEVQ LGIPHPAGLKKKKSVTVLDVGDAYFSVPLDKDFRKYTAFTIPSAAAWGFTTPDKKHQKEPPFLWMGYELHPDKWIVQPIAAA VAKEIVASCDKCQLKGEAMHGQVDCSPGIWQLDCTHLEGKIILVAVHVASGYIEAEVIPAETGQETAYFLLKLAGRWPVKTA AATVKAACWWAGIKQEFGIPYNPQSQGVVESMNKELKKIIGQVRDQAEHLKTAVQMAVFIHNFKRKGGIGGYSAGERIVDII AAAAITKIQNFRVYYRDSRDPLWKGPAKLLWKGEGAVVIQDNSDIKVVPRRKAKIIRDYGKQMAGDDCVASRQDEDAAAEEV GFPVKPQVPLRPMTFKGALDLSHFLREKGGLEG |
| 346 | AAA/ none | Gag, Pol, Nef | LKHLVWASRELERFALNPGLLETAAAVSQNFPIVQNAAALSPRILNAWVKVIEEKAFSPEVIPMFTALSEGATPHDLNTMLN TIGGHQAAMQMLKDTINEEAAEWDRVHPVHAGPVAPGQMRDPRGSDIAGSTSTLQEQIAWMTNNPPIPVGDIYKRWIIMGLN KIVRMYSPVSILDIKQGPKEPFRDYVDRFYRTLRAEQASQDVKNWMTETLLVQNSNPDCKTILKALGPGATLEEMMSACQGV GGPSHKARVLAEAMCQAAALPGKWKPKMIGGIGGFIKVKQYDQAAAGTVLIGPTPVNIIGRNLLTQLGCTLNFPISPIDTVP VKLKPGMDGPRVKQWPLTEEKIKALIEICTEMEKEGKISRIGPENPYNTPIFAIKKKDGTKWRKLVDFRELNKKTQDFWEVQ LGIPHPSGLKKKKSVTVLDIGDAYFSVPLDKEFRKYTAFTVPSAAAWGLTTPDKKHQKDPPFLWMGYELHPDRWTVQPIAAA VAKEIVACCDKCQLKGEAIHGQVDCSPGVWQLDCTHLEGKVILVAVHVASGYMEAEVIPTETGQETAYFILKLAGRWPVTTA AAAVKAACWWAGVKQEFGIPYHPQSQGVVESMNNELKKIIGQIRDQAEQLKTAVQMAVLIHNFKRKGGIGEYSAGERIIDII AAAAITKLQNFRVYYRDNRDPLWKGPARLLWKGEGAVVIQDNSEIKVVPRRKVKIIRDYGKRMAGDDCVAGRQDEDAAAEEV GFPVRPQVPLRPMTYKGALDLSHFLKEKGGLEG |
| 347 | F2A/ none | Gag, Pol, Nef | LKHIVWASRELERFAVNPGLLETVSQNYPIVQNISPRTLNAWVKVVEEKAFSPEVIPMFSALSEGATPQDLNTMLNTVGGHQ AAMQMLKETINEEAAEWDRLHPVHAGPIAPGQMREPRGSDIAGTTSTLQEQIGWMTNNPPIPVGEIYKRWIILGLNKIVRMY SPTSILDIRQGPKEPFRDYVDRFYKTLRAEQASQEVKNWMTETLLVQNANPDCKTILKALGPAATLEEMMTACQGVGGPGHK ARVLAEAMSQRAKRAPVKQTLNFDLLKLAGDVESNPGPLPGRWKPKMIGGIGGFIKVRQYDQGTVLVGPTPVNIIGRNLLTQ IGCTLNFPISPIETVPVKLKPGMDGPKVKQWPLTEEKIKALVEICTEMEKEGKISKIGPENPYNTPVFAIKKKDSTKWRKLV DFRELNKRTQDFWEVQLGIPHPAGLKKKKSVTVLDVGDAYFSVPLDKDFRKYTAFTIPSWGFTTPDKKHQKEPPFLWMGYEL HPDKWTVQPIVAKEIVASCDKCQLKGEAMHGQVDCSPGIWQLDCTHLEGKIILVAVHVASGYIEAEVIPAETGQETAYFLLK LAGRWPVKTTVKAACWWAGIKQEFGIPYNPQSQGVVESMNKELKKIIGQVRDQAEHLKTAVQMAVFIHNFKRKGGIGGYSAG ERIVDIIAITKIQNFRVYYRDSRDPLWKGPAKLLWKGEGAVVIQDNSDIKVVPRRKAKIIRDYGKQMAGDDCVASRQDEDRA KRAPVKQTLNFDLLKLAGDVESNPGPEEVGFPVKPQVPLRPMTFKGALDLSHFLREKGGLEG |
| 348 | F2A/ none | Gag, Pol, Nef | LKHLVWASRELERFALNPGLLETVSQNFPIVQNLSPRTLNAWVKVIEEKAFSPEVIPMFTALSEGATPHDLNTMLNTIGGHQ AAMQMLKDTINEEAAEWDRVHPVHAGPVAPGQMRDPRGSDIAGSTSTLQEQIAWMTNNPPIPVGDIYKRWIIMGLNKIVRMY SPVSILDIKQGPKEPFRDYVDRFYRTLRAEQASQDVKNWMTETLLVQNSNPDCKTILKALGPGATLEEMMSACQGVGGPSHK ARVLAEAMCQRAKRAPVKQTLNFDLLKLAGDVESNPGPLPGKWKPKMIGGIGGFIKVKQYDQGTVLIGPTPVNIIGRNLLTQ LGCTLNFPISPIDTVPVKLKPGMDGPRVKQWPLTEEKIKALIEICTEMEKEGKISRIGPENPYNTPIFAIKKKDGIKWRKLV DFRELNKKTQDFWEVQLGIPHPSGLKKKKSVTVLDIGDAYFSVPLDKEFRKYTAFTVPSWGLTTPDKKHQKDPPFLWMGYEL HPDRWTVQPIVAKEIVACCDKCQLKGEAIHGQVDCSPGVWQLDCTHLEGKVILVAVHVASGYMEAEVIPTETGQETAYFILK LAGRWPVTTAVKAACWWAGVKQEFGIPYHPQSQGVVESMNNELKKIIGQIRDQAEQLKTAVQMAVLIHNFKRKGGIGEYSAG ERIIIDIIAITKLQNFRVYYRDNRDPLWKGPARLLWKGEGAVVIQDNSEIKVVPRRKVKIIRDYGKRMAGDDCVAGRQDEDRA KRAPVKQTLNFDLLKLAGDVESNPGPEEVGFPVRPQVPLRPMTYKGALDLSHFLKEKGGLEG |
| 349 | Fusion/ none | Gag, Pol, Nef | LKHIVWASRELERFAVNPGLLETVSQNYPIVQNISPRTLNAWVKVVEEKAFSPEVIPMFSALSEGATPQDLNTMLNIVGGHQ AAMQMLKETINEEAAEWDRLHPVHAGPIAPGQMREPRGSDIAGTTSTLQEQIGWMTNNPPIPVGEIYKRWIILGLNKIVRMY SPTSILDIRQGPKEPFRDYVDRFYKTLRAEQASQEVKNWMTETLLVQNANPDCKTILKALGPAATLEEMMTACQGVGGPGHK ARVLAEAMSQLPGRWKPKMIGGIGGFIKVRQYDQGTVLVGPTPVNIIGRNLLTQIGCTLNFPISPIETVPVKLKPGMDGPKV KQWPLTEEKIKALVEICTEMEKEGKISKIGPENPYNTPVFAIKKKDSTKWRKLVDFRELNKRTQDFWEVQLGIPHPAGLKKK KSVTVLDVGDAYFSVPLDKDFRKYTAFTIPSWGFTTPDKKHQKEPPFLWMGYELHPDKWTVQPIVAKEIVASCDKCQLKGEA MHGQVDCSPGIWQLDCTHLEGKIILVAVHVASGYIEAEVIPAETGQETAYFLLKLAGRWPVKTIVKAACWWAGIKQEFGIPY NPQSQGVVESMNKELKKIIGQVRDQAEHLKTAVQMAVFIHNFKRKGGIGGYSAGERIVDIIAITKIQNFRVYYRDSRDPLWK GPAKLLWKGEGAVVIQDNSDIKVVPRRKAKIIRDYGKQMAGDDCVASRQDEDEEVGFPVKPQVPLRPMTFKGALDLSHFLRE KGGLEG |
| 350 | Fusion/ none | Gag, Pol, Nef | LKHLVWASRELERFALNPGLLETVSQNFPIVQNLSPRTLNAWVKVIEEKAFSPEVIPMFTALSEGATPHDLNTMLNTIGGHQ AAMQMLKDTINEEAAEWDRVHPVHAGPVAPGQMRDPRGSDIAGSTSTLQEQIAWMTNNPPIPVGDIYKRWIIMGLNKIVRMY SPVSILDIKQGPKEPFRDYVDRFYRTLRAEQASQDVKNWMTETLLVQNSNPDCKTILKALGPGATLEEMMSACQGVGGPSHK ARVLAEAMCQLPGKWKPKMIGGIGGFIKVKQYDQGTVLIGPTPVNIIGRNLLTQLGCTLNFPISPIDTVPVKLKPGMDGPRV KQWPLTEEKIKALIEICTEMEKEGKISRIGPENPYNTPIFAIKKKDGTKWRKLVDFRELNKKTQDFWEVQLGIPHPSGLKKK KSVTVLDIGDAYFSVPLDKEFRKYTAFTVPSWGLTTPDKKHQKDPPFLWMGYELHPDRWTVQPIVAKEIVACCDKCQLKGEA IHGQVDCSPGVWQLDCTHLEGKVILVAVHVASGYMEAEVIPTETGQETAYFILKLAGRWPVTTAVKAACWWAGVKQEFGIPY HPQSQGVVESMNNELKKIIGQIRDQAEQLKTAVQMAVLIHNFKRKGGIGEYSAGERIIDIIAITKLQNFRVYYRDNRDPLWK GPARLLWKGEGAVVIQDNSEIKVVPRRKVKIIRDYGKRMAGDDCVAGRQDEDEEVGFPVRPQVPLRPMTYKGALDLSHFLKE KGGLEG |
| 351 | AA/ none | Gag, Nef | MGARASVLSGGELDRWEKIRLRPGGKKKYRLKHIVWASRELERFAVNPGLLETAAISPRTLNAWVKVVEEKAFSPEVIPMFS ALSEGATPQDLNTMLNTVGGHQAAMQMLKETINEEAAEWDRLHPVHAGPIAPGQMREPRGSDIAGTTSTLQEQIGWMTNNPP IPVGEIYKRWIILGLNKIVRMYSPTSILDIRQGPKEPFRDYVDRFYKTLRAEQASQEVKNWMTETLLVQNANPDCKTILKAL GPAATLEEMMTACQGVGGPGHKARVLAEAMSQEEVGFPVKPQVPLRPMTFKGALDLSHFLREKGGLEGTQGFFPDWQNYTPE PGIRFPLTFGWCFKLVPL |

TABLE J-continued immunogenic fusion polypeptides comprising HIV-1 polypeptide segments ("AAA" is SEQ ID NO: 378, "AAY" is SEQ ID NO: 379, "YMDD" is SEQ ID NO: 462 and "REKR" is SEQ ID NO: 382)

| SEQ ID NO: | Linker/ Signal peptide | HIV-1 Genes | SEQUENCE |
|---|---|---|---|
| 430 | AA/ none | Gag, Nef | MGARASVLSGGELDRWEKIRLRPGGKKKYRLKHIVWASRELERFAVNPGLLETLKHIVWASRELERFAVNPGLLETAAISPR TLNAWVKVVEEKAFSPEVIPMFSALSEGATPQDLNTMLNTVGGHQAAMQMLKETINEEAAEWDRLHPVHAGPIAPGQMREPR GSDIAGTTSTLQEQIGWMTNNPPIPVGEIYKRWIILGLNKIVRMYSPTSILDIRQGPKEPERDYVDRFYKTLRAEQASQEVK NWMTETLLVQNANPDCKTILKALGPAATLEEMMTACQGVGGPGHKARVLAEAMSQEEVGFPVKPQVPLRPMTFKGALDLSHF LREKGGLEGTQGFFPDQNYTPEPGIRFPLTFGWCFKLVPL |
| 352 | AA/ None | Gag, Nef | LSPRTLNAWVKVIEEKAFSPEVIPMFTALSEGATPHDLNTMLNTIGGHQAAMQMLKDTINEEAAEWDRVHPVHAGPVAPGQM RDPRGSDIAGSTSTLQEEQIAWMTNNPPIPVGDIYKRWIIMGLNKIVRMYSPVSILDIKQGPKEPFRDYVDRFYRTLRAEQAS QDVKNWMTETLLVQNSNPDCKTILKALGPGATLEEMMSACQGVGGPSHKARVLAEAMCQMGARASILSGGKLDKWEKIRLRP GGRKKYKLKHIVWASRELERFAVNPGLLETEEVGFPVRPQVPLRPMTYKGALDLSHFLKEKGGLEGTQGFYFPDWQNYTPGPG TRYPLTFGWCFKLVPV |
| 353 | AA/ GM-CSF | Gag, Nef | MWLQSLLLLGTVACSISVMGARASVLSGGELDRWEKIRLRPGGKKKYRLKHIVWASRELERFAVNPGLLETLKHIVWASREL ERFAVNPGLLETAAISPRTLNAWVKVVEEKAFSPEVIPMFSALSEGATPQDLNTMLNTVGGHQAAMQMLKETINEEAAEWDR LHPVHAGPIAPGQMREPRGSDIAGTTSTLQEQIGWMTNNPPIPVGEIYKRWIILGLNKIVRMYSPTSILDIRQGPKEPERDY VDRFYKTLRAEQASQEVKNWMTETLLVQNANPDCKTILKALGPAATLEEMMTACQGVGGPGHKARVLAEAMSQEEVGFPVKP QVPLRPMTFKGALDLSHFLREKGGLEGTQGFFPDQNYTPEPGIRFPLTFGWCFKLVPL |
| 354 | AA/ t-PA | Gag, Nef | MDAMKRGLCCVLLLCGAVFVSARMGARASVLSGGELDRWEKIRLRPGGKKKYRLKHIVWASRELERFAVNPGLLETLKHIVW ASRELERFAVNPGLLETAAISPRTLNAWVKVVEEKAFSPEVIPMFSALSEGATPQDLNTMLNTVGGHQAAMQMLKETINEEA AEWDRLHPVHAGPIAPGQMREPRGSDIAGTTSTLQEQIGWMTNNPPIPVGEIYKRWIILGLNKIVRMYSPTSILDIRQGPKE PFRDYVDRFYKTLRAEQASQEVKNWMTETLLVQNANPDCKTILKALGPAATLEEMMTACQGVGGPGHKARVLAEAMSQEEVG FPVKPQVPLRPMTFKGALDLSHFLREKGGLEGTQGFFPDQNYTPEPGIRFPLTFGWCFKLVPL |
| 355 | AA/ MCP-3 | Gag, Nef | MNPSAAVIFCLILLGLSGTQGILDMAQPVGINTSTTCCYRFINKKIPKQRLESYRRTTSSHCPREAVIFKTKLDKEICADPT QKWVQDFMKHLDKKTQTPKLASAGAMGARASVLSGGELDRWEKIRLRPGGKKKYRLKHIVWASRELERFAVNPGLLETLKHI VWASRELERFAVNPGLLETAAISPRTLNAWVKVVEEKAFSPEVIPMFSALSEGATPQDLNTMLNTVGGHQAAMQMLKETINE EAAEWDRLHPVHAGPIAPGQMREPRGSDIAGTTSTLQEQIGWMTNNPPIPVGEIYKRWIILGLNKIVRMYSPTSILDIRQGP KEPFRDYVDRFYKTLRAEQASQEVKNWMTETLLVQNANPDCKTILKALGPAATLEEMMTACQGVGGPGHKARVLAEAMSQEE VGFPVKPQVPLRPMTFKGALDLSHFLREKGGLEGTQGFFPDQNYTPEPGIRFPLTFGWCFKLVPL |
| 356 | AA/β-catenin | Gag, Nef | MRKAAVSHWQQQSYLDSGIHSGATTTAPSLSMGARASVLSGGELDRWEKIRLRPGGKKKYRLKHIVWASRELERFAVNPGLL ETLKHIVWASRELERFAVNPGLLETAAISPRTLNAWVKVVEEKAFSPEVIPMFSALSEGATPQDLNTMLNTVGGHQAAMQML KETINEEAAEWDRLHPVHAGPIAPGQMREPRGSDIAGTTSTLQEQIGWMTNNPPIPVGEIYKRWIILGLNKIVRMYSPTSIL DIRQGPKEPFRDYVDRFYKTLRAEQASQEVKNWMTETLLVQNANPDCKTILKALGPAATLEEMMTACQGVGGPGHKARVLAE AMSQEEVGFPVKPQVPLRPMTFKGALDLSHFLREKGGLEGTQGFFPDQNYTPEPGIRFPLTFGWCFKLVPL |
| 357 | AA/ none | Pol, Env | GTVLVGPTPVNIIGRNLLTQIGCTLNFPISPIETVPVKLKPGMDGPKVKQWPLTEEKIKALVEICTEMEKEGKISKIGPENP YNTPVFAIKKKDSTKWRKLVDFRELNKRTQDFWEVQLGIPHPAGLKKKKSVTVLDVGDAYFSVPLDKDFRKYTAFTIPSINN ETPGIRYQYNVLPQGWKGSPAIFQSSMTTVKAACWWAGIKQEFGIPYNPQSQGVVESMNKELKKIIGQVRDQAEHLKTAVQM AVFIHNFKRKGGIGGYSAGERIVDIINSTVQCTHGIRPVVSTQLLLNGSLAEEKRRVVQREKRAVGIGAMFLGFLGAAGST MGAASITLTVQARQLLSGIVQQQNNLLRAIEAQQHLLQLTVWGIKQLQARVLAVERYLKDQQLLGIWGCSGKLICTTVAKEI VASCDKCQLKGEAMHGQVDCSPGIWQLDCTHLEGKIILVAVHVASGYIEAEVIPAETGQETAYFLLKLAGRWPVKTLWVTVY YGVPVWKEAAFPQITLWQRPLVTIKIGGQLKEALLDTGADDTVLEEMNLPGRWKPKMIGGIGGFIKVRQYDQAAAAHNVWAT HACVPTDPNPQEAITKIQNFRVYYRDSRDPLWKGPAKLLWKGEGAVVIQDNSDIKVVPRRKAKIIRDYGKQMAGDDCVASRQ DEDPKFKLPIQKETWETWWTEYWQATWIPEWEFVNTPPLVKLWYQLEKEPIVGAETFYVDGAANRETKAAKEKVYLAWVPAH KGIGGNEQVDKLVSWGFTTPDKKHQKEPPFLWMGYELHPDKWTVQPIVLPEKDSWTVNDIQKLVGKLNWASQIYPGIKVIVI YQYMDDLYVGSDLEIGQHRMRDNWRSELYKYKVV |
| 358 | AA/ none | Pol, Env | AVKAACWWAGVKQEFGIPYHPQSQGVVESMNNELKKIIGQIRDQAEQLKTAVQMAVLIHNFKRKGGIGEYSAGERIIDIIRR RVVQREKRAIGLGAVFLGFLGTAGSTMGAASMTLTVQARLLLSGIVQQQSNLLRAIEAQQHMLQLTVWGIKQLQARILAVER YLRDQQLLGIWGCSGRLICTTVAKEIVACCDKCQLKGEAIHGQVDCTHLEGKIVILVAVHVASGYMEAEVIPTE TGQETAYFILKLAGRWPVTTNISTVQCTHGIKPVVSTQLLLNGSLAEKWGLTTPDKKHQKDPPFLWMGYELHPDRWTVQPIE LPEKESWTVNDIQKLIGKLNWASQIYAGIKVIVIYQYVDDLYVGSDLEIEQHRPKFRLPIQKETWDTWWTDYWQATWIPEWE FTNTPPLVKLWYQLETEPIAGVETFYVDGASNRETKLPQITLWQRPIVTIKIGGQIKEALLDTGADDTVLEDMNLPGKWKPK MIGGIGGFIKVRDQAALWVTIYYGVPVWKDVHNIWATHACVPTDPSPQEAITKLQNFRVYYRDNRDPLWKGPARLLWKGE GAVVIQDNSEIKVVPRRKVKIIRDYGKRMAGDDCVAGRQDEDGTVLIGPTPVNIIGRNLLTQLGCTLNFPISPIDTVPVKLK PGMDGPRVKQWPLTEEKIKALIEICTEMEKEGKISRIGPENPYNTPIFAIKKKDGTKWRKLVDFRELNKKTQDFWEVQLGIP HPSGLKKKKSVTVLDIGDAYFSVPLDKEFRKYTAFTVPSTNNETPGVRYQYNVLPMGWKSPAIFQCSMTKEKIYLAWVPAH KGIGGNEQIDKLVSMKDNWRSELYRYKVV |
| 359 | AA/ none | Pol, Env | GTVLVGPTPVNIIGRNLLTQIGCTLNFPISPIETVPVKLKPGMDGPKVKQWPLTEEKIKALVEICTEMEKEGKISKIGPENP YNTPVFAIKKKDSTKWRKLVDFRELNKRTQDFWEVQLGIPHPAGLKKKKSVTVLDVGDAYFSVPLDKDFRKYTAFTIPSINN ETPGIRYQYNVLPQGWKGSPAIFQSSMTTVKAACWWAGIKQEFGIPYNPQSQGVVESMNKELKKIIGQVRDQAEHLKTAVQM AVFIHNFKRKGGIGGYSAGERIVDIINSTVQCTHGIRPVVSTQLLLNGSLAEEKRRVVQREKRAVGIGAMFLGFLGAAGST MGAASITLTVQARQLLSGIVQQQNNLLRAIEAQQHLLQLTVWGIKQLQARVLAVERYLKDQQLLGIWGCSGKLICTTVAKEI VASCDKCQLKGEAMHGQVDCSPGIWQLDCTHLEGKIILVAVHVASGYIEAEVIPAETGQETAYFLLKLAGRWPVKT |
| 360 | AA/ none | Pol, Env | LWVTVYYGVPVWKEAAFPQITLWQRPLVTIKIGGQLKEALLDTGADDTVLEEMNLPGRWKPKMIGGIGGFIKVRQYDQAAAA HNVWATHACVPTDPNPQEAITKIQNFRVYYRDSRDPLWKGPAKLLWKGEGAVVIQDNSDIKVVPRRKAKIIRDYGKQMAGDD CVASRQDEDPKFKLPIQKETWETWWTEYWQATWIPEWEFVNTPPLVKLWYQLEKEPIVGAETFYVDGAANRETKAAKEKVYL AWVPAHKGIGGNEQVDKLVSWGFTTPDKKHQKEPPFLWMGYELHPDKWTVQPIVLPEKDSWTVNDIQKLVGKLNWASQIYPG IKVIVIYQYMDDLYVGSDLEIGQHRMRDNWRSELYKYKVV |

TABLE J-continued immunogenic fusion polypeptides comprising HIV-1 polypeptide segments ("AAA" is SEQ ID NO: 378, "AAY" is SEQ ID NO: 379, "YMDD" is SEQ ID NO: 462 and "REKR" is SEQ ID NO: 382)

| SEQ ID NO: | Linker/ Signal peptide | HIV-1 Genes | SEQUENCE |
|---|---|---|---|
| 361 | AA/ none | Pol, Env | AVKAACWWAGVKQEFGIPYHPQSQGVVESMNNELKKIIGQIRDQAEQLKTAVQMAVLIHNFKRKGGIGEYSAGERIIDIIRR RVVQREKRAIGLGAVFLGFLGTAGSTMGAASMILTVQARLLLSGIVQQQSNLLRAIEAQQHMLQLTVWGIKQLQARILAVER YLRDQQLLGIWGCSGRLICTTVAKEIVACCDKCQLKGEAIHGQVDCSPGVWQLDTHLEGKVILVAVHVASGYMEAEVIPTE TGQETAYFILKLAGRWPVTTNISTVQCTHGIKPVVSTQLLLNGSLAEKWGLTTPDKKHQKDPPFLWMGYELHPDRWTVQPIE LPEKESWTVNDIQKLIGKLNWASQIYAGIKVIVIYQYVDDLYVGSDLEIEQHRPKFRLPIQKETWDTWWIDYWQATWIPEWE FTNTPPLVKLWYQLETEPIAGVETFYVDGASNRETKLPQITLWQRPIVTIKIGGGQIKEALLDTGADDTVLEDMNLPGKWKPK MIGGIGGFIKVKQYDQAA |
| 362 | AA/ none | Pol, Env | LWVTIYYGVPVWKDVHNIWATHACVPTDPSPQEAITKLQNFRVYYRDNRDPLWKGPARLLWKGEGAVVIQDNSEIKVVPRRK VKIIRDYGKRMAGDDCVAGRQDEDGTVLIGPTPVNIIGRNLLTQLGCTLNFPISPIDTVPVKLKPGMDGPRVKQWPLTEEKI KALIEICTEMEKEGKISRIGPENPYNTPIFAIKKKDGTKWRKLVDFRELNKKTQDFWEVQLGIPHPSGLKKKKSVTVLDIGD AYFSVPLDKEFRKYTAFTVPSTNNETPGVRYQYNVLPMGWKGSPAIFQCSMTKEKIYLAWVPAHKGIGGNEQIDKLVSMKDN WRSELYRYKVV |
| 363 | AA/ GM-CSF | Pol, Env | MWLQSLLLLGTVACSISVGTVLVGPTPVNIIGRNLLTQIGCTLNFPISPIETVPVKLKPGMDGPKVKQWPLTEEKIKALVEI CTEMEKEGKISKIGPENPYNTPVFAIKKKDSTKWRKLVDFRELNKRTQDFWEVQLGIPHPAGLKKKKSVTVLDVGDAYFSVP LDKDFRKYTAFTIPSINNETPGIRYQYNVLPQGWKGSPAIFQSSMTTVKAACWWAGIKQEFGIPYNPQSQGVVESMNKELKK IIGQVRDQAEHLKTAVQMAVFIHNFKRKGGIGGYSAGERIVDIINVSTVQCTHGIRPVVSTQLLLNGSLAEEKRRVVQREKR AVGIGAMPLGFLGAAGSTMGAASITLTVQARQLLSGIVQQQNNLLRAIEAQQHLLQLTVWGIKQLQARVLAVERYLKDQQLL GIWGCSGKLICTTVAKEIVASCDKCQLKGEAMHGQVDCSPGIWQLDCTHLEGKIILVAVHVASGYIEAEVIPAETGQETAYF LLKLAGRWPVKTLWVTVYYGVPVWKEAAFPQITLWQRPLVTIKIGGQLKEALLDTGADDTVLEEMNLPGRWKPKMIGGIGGF IKVRQYDQAAAAHNVWATHACVPTDPNPQEAITKIQNFRVYYRDSRDPLWKGPAKLLWKGEGAVVIQDNSDIKVVPRRKAKI IRDYGKQMAGDDCVASRQDEDPKFKLPIQKETWETWWTEYWQATWIPEWEEVNTPPLVKLWYLEKEPIVGAETFYVDGAAN RETKAAKEKVYLAWVPAHKGIGGNEQVDKLVSWGFTTPDKKHQKEPPFLWMGYELHPDKWTVQPIVLPEKDSWTVNDIQKLV GKLNWASQIYPGIKVIVIYQYMDDLYVGSDLEIGQHRMRDNWRSELYKYKVV |
| 364 | AA/ t-PA | Pol, Env | MDAMKRGLCCVLLLCGAVFVSARGTVLVGPTPVNIIGRNLLTQIGCTLNFPISPIETVPVKLKPGMDGPKVKQWPLTEEKIK ALVEICTEMEKEGKISKIGPENPYNTPVFAIKKKDSTKWRKLVDFRELNKRTQDFWEVQLGIPHPAGLKKKKSVIVLDVGDA YFSVPLDKDFRKYTAFTIPSINNETPGIRYQYNVLPQGWKGSPAIFQSSMTTVKAACWWAGIKQEFGIPYNPQSQGVVESMN KELKKIIGQVRDQAEHLKTAVQMAVFIHNFKRKGGIGGYSAGERIVDIINVSTVQCTHGIRPVVSTQLLLNGSLAEEKRRVV QREKRAVGIGAMFLGFLGAAGSTMGAASITLTVQARQLLSGIVQQQNNLLRAIEAQQHLLQLTVWGIKQLQARVLAVERYLK DQQLLGIWGCSGKLICTTVAKEIVASCDKCQLKGEAMHGQVDCSPGIWQLDCTHLEGKIILVAVHVASGYIEAEVIPAETGQ ETAYFLLKLAGRWPVKTLWVTVYYGVPVWKEAAFPQITLWQRPLVTIKIGGQLKEALLDTGADDTVLEEMNLPGRWKPKMIG GIGGFIKVRQYDQAAAAHNVWATHACVPTDPNPQEAITKIQNFRVYYRDSRDPLWKGPAKLLWKGEGAVVIQDNSDIKVVPR RKAKIIRDYGKQMAGDDCVASRQDEDPKFKLPIQKETWETWWTEYWQATWIPEWEFVNTPPLVKLWYLEKEPIVGAETFYV DGAANRETKAAKEKVYLAWVPAHKGIGGNEQVDKLVSWGFTTPDKKHQKEPPFLWMGYELHPDKWTVQPIVLPEKDSWTVND IQKLVGKLNWASQIYPGIKVIVIYQYMDDLYVGSDLEIGQHRMRDNWRSELYKYKVV |
| 365 | AA/ MCP-3 | Pol, Env | MNPSAAVIFCLILLGLSGTQGILDMAQPVGINTSTTCCYRFINKKIPKQRLESYRRTTSSHCPREAVIFKTKLDKEICADPT QKWVQDFMKHLDKKTQTPKLASAGAGTVLVGPTPVNIIGRNLLTQIGCTLNFPISPIETVPVKLKPGMDGPKVKQWPLTEEK IKALVEICTEMEKEGKISKIGPENPYNTPVFAIKKKDSTKWRKLVDFRELNKRTQDFWEVQLGIPHPAGLKKKKSVTVLDVG DAYFSVPLDKDFRKYTAFTIPSINNETPGIRYQYNVLPQGWKGSPAIFQSSMTTVKAACWWAGIKQEFGIPYNPQSQGVVES MNKELKKIIGQVRDQAEHLKTAVQMAVFIHNFKRKGGIGGYSAGERIVDIINVSTVQCTHGIRPVVSTQLLLNGSLAEEKRR VVQREKRAVGIGAMFLGELGAAGSTMGAASITLTVQARQLLSGIVQQQNNLLRAIEAQQHLLQLTVWGIKQLQARVLAVERY LKDQQLLGIWGCSGKLICTTVAKEIVASCDKCQLKGEAMHGQVDCSPGIWQLDCTHLEGKIILVAVHVASGYIEAEVIPAET GQETAYFLLKLAGRWPVKTLWVTVYYGVPVWKEAAFPQITLWQRPLVTIKIGGQLKEALLDTGADDTVLEEMNLPGRWKPKM IGGIGGFIKVRQYDQAAAAHNVWATHACVPTDPNPQEAITKIQNFRVYYRDSRDPLWKGPAKLLWKGEGAVVIQDNSDIKVV PRRKAKIIRDYGKQMAGDDCVASRQDEDPKFKLPIQKETWETWWTEYWQATWIPEWEFVNTPPLVKLWYLEKEPIVGAETF YVDGAANRETKAAKEKVYLAWVPAHKGIGGNEQVDKLVSWGFTTPDKKHQKEPPFLWMGYELHPDKWTVQPIVLPEKDSWTV NDIQKLVGKLNWASQIYPGIKVIVIYQYMDDLYVGSDLEIGQHRMRDNWRSELYKYKVV |
| 366 | AA/β-catenin | Pol, Env | MRKAAVSHWQQQSYLDSGIHSGATTTAPSLSGTVLVGPTPVNIIGRNLLTQIGCTLNFPISPIETVPVKLKPGMDGPKVKQW PLTEEKIKALVEICTEMEKEGKISKIGPENPYNTPVFAIKKKDSTKWRKLVDFRELNKRTQDFWEVQLGIPHPAGLKKKKSV TVLDVGDAYFSVPLDKDFRKYTAFTIPSINNETPGIRYQYNVLPQGWKGSPAIFQSSMTTVKAACWWAGIKQEFGIPYNPQS QGVVESMNKELKKIIGQVRDQAEHLKTAVQMAVFIHNFKRKGGIGGYSAGERIVDIINVSTVQCTHGIRPVVSTQLLLNGSL AEEKRRVVQREKRAVGIGAMFLGELGAAGSTMGAASITLTVQARQLLSGIVQQQNNLLRAIEAQQHLLQLTVWGIKQLQARV LAVERYLKDQQLLGIWGCSGKLICTTVAKEIVASCDKCQLKGEAMHGQVDCSPGIWQLDCTHLEGKIILVAVHVASGYIEAE VIPAETGQETAYFLLKLAGRWPVKTLWVTVYYGVPVWKEAAFPQITLWQRPLVTIKIGGQLKEALLDTGADDTVLEEMNLPG RWKPKMIGGIGGFIKVRQYDQAAAAHNVWATHACVPTDPNPQEAITKIQNFRVYYRDSRDPLWKGPAKLLWKGEGAVVIQDN SDIKVVPRRKAKIIRDYGKQMAGDDCVASRQDEDPKFKLPIQKETWETWWTEYWQATWIPEWEFVNTPPLVKLWYLEKEPI VGAETFYVDGAANRETKAAKEKVYLAWVPAHKGIGGNEQVDKLVSWGFTTPDKKHQKEPPFLWMGYELHPDKWTVQPIVLPE KDSWTVNDIQKLVGKLNWASQIYPGIKVIVIYQYMDDLYVGSDLEIGQHRMRDNWRSELYKYKVV |
| 407 | AA/ none | Pol | TVKAACWWAGIKQEFGIPYNPQSQGVVESMNKELKKIIGQVRDQAEHLKTAVQMAVFIHNFKRKGGIGGYSAGERIVDIIAI TKIQNFRVYYRDSRDPLWKGPAKLLWKGEGAVVIQDNSDIKVVPRRKAKIIRDYGKQMAGDDCVASRQDEDPKFKLPIQKET WETWWTEYWQATWIPEWEFVNTPPLVKLWYLEKEPIVGAETFYVDGAANRETKAAKEKVYLAWVPAHKGIGGNEQVDKLVS WGFTTPDKKHQKEPPFLWMGYELHPDKWTVQPIVLGKLNWASQIYPGIKVIVIYQYMDDLYVGSDLE IGQHRVAKEIVASCDKCQLKGEAMHGQVDCSPGIWQLDCTHLEGKIILVAVHVASGYIEAEVIPAETGQETAYFLLKLAGRW PVKTAAFPQITLWQRPLVTIKIGGQLKEALLDTGADDTVLEEMNLPGRWKPKMIGGIGGFIKVRQYDQGTVLVGPTPVNIIG RNLLTQIGCTLNFPISPIETVPVKLKPGMDGPKVKQWPLTEEKIKALVEICTEMEKEGKISKIGPENPYNTPVFAIKKKDST KWRKLVDFRELNKRTQDFWEVQLGIPHPAGLKKKKSVTVLDVGDAYFSVPLDKDFRKYTAFTIPSINNETPGIRYQYNVLPQ GWKGSPAIFQSSMT |

TABLE J-continued immunogenic fusion polypeptides comprising HIV-1 polypeptide segments ("AAA" is SEQ ID NO: 378, "AAY" is SEQ ID NO: 379, "YMDD" is SEQ ID NO: 462 and "REKR" is SEQ ID NO: 382)

| SEQ ID NO: | Linker/ Signal peptide | HIV-1 Genes | SEQUENCE |
|---|---|---|---|
| 408 | AA, AAY/ none | Pol | AVKAACWWAGVKQEFGIPYHPQSQGVVESMNNELKKIIGQIRDQAEQLKTAVQMAVLIHNFKRKGGIGEYSAGERIIDIIVA KEIVACCDKCQLKGEAIHGQVDCSPGVWQLDCTHLEGKVILVAVHVASGYMEAEVIPTETGQETAYFILKLAGRWPVTTWGL TTPDKKHQKDPPFLWMGYELHPDRWTVQPIELPEKESWTVNDIQKLIGKLNWASQIYAGIKVIVIYQYVDDLYVGSDLEIEQ HRLPQITLWQRPIVTIKIGGQIKEALLDTGADDTVLEDMNLPGKWKPKMIGGIGGFIKVKQYDQPKFRLPIQKETWDTWWTD YWQATWIPEWEFTNTPPLVKLWYQLETEPIAGVETFYVDGASNRETKAAYAITKLQNFRVYYRDNRDPLWKGPARLLWKGEG AVVIQDNSEIKVVPRRKVKIIRDYGKRMAGDDCVAGRQDEDGTVLIGPTPVNIIGRNLLTQLGCTLNFPISPIDTVPVKLKP GMDGPRVKQWPLTEEKIKALIEICTEMEKEGKISRIGPENPYNTPIFAIKKKDGTKWRKLVDFRELNKKTQDFWEVQLGIPH PSGLKKKKSVTVLDIGDAYFSVPLDKEFRKYTAFTVPSTNNETPGVRYQYNVLPMGWKGSPAIFQCSMTKEKIYLAWVPAHK GIGGNEQIDKLVS |
| 409 | AA/ none | Pol/ no YMDD | TVKAACWWAGIKQEFGIPYNPQSQGVVESMNKELKKIIGQVRDQAEHLKTAVQMAVFIHNFKRKGGIGGYSAGERIVDIIVA KEIVASCDKCQLKGEAMHGQVDCSPGIWQLDCTHLEGKIILVAVHVASGYIEAEVIPAETGQETAYFLLKLAGRWPVTKAIT KIQNFRVYYRDSRDPLWKGPAKLLWKGEGAVVIQDNSDIKVYPRRKAKIIRDYGKQMAGDDCVASRQDEDPKFKLPIQKETW ETWWTEYWQATWIPEWEFVNTPPLVKLWYQLEKEPIVGAETFYVDGAANRETKAAKEKVYLAWVPAHKGIGGNEQVDKLVSW GFTTPDKKHQKEPPFLWMGYELHPDKWTVQPIVLPEKDSWTVNDIQKLVGKLNWASQIYPGIKVAAFPQITLWQRPLVTIKI GGQLKEALLDTGADDTVLEEMNLPGRWKPKMIGGIGGFIKVRQYDQGTVLVGPTPVNIIGRNLLTQIGCTLNFPISPIETVP VKLKPGMDGPKVKQWPLTEEKIKALVEICTEMEKEGKISKIGPENPYNTPVFAIKKKDSTKWRKLVDFRELNKRTQDFWEVQ LGIPHPAGLKKKKSVTVLDVGDAYFSVPLDKDFRKYTAFTIPSINNETPGIRYQYNVLPQGWKGSPAIFQSSMT |
| 410 | AA, AAY/ none | Pol | AVKAACWWAGVKQEFGIPYHPQSQGVVESMNNELKKIIGQIRDQAEQLKTAVQMAVLIHNFKRKGGIGEYSAGERIIDIIWG LTTPDKKHQKDPPFLWMGYELHPDRWTVQPIELPEKESWTVNDIQKLIGKLNWASQIYAGIKVAAYVAKEIVACCDKCQLKG EAIHGQVDCSPGVWQLDCTHLEGKVILVAVHVASGYMEAEVIPTETGQETAYFILKLAGRWPVTTLPQITLWQRPIVTIKIG GQIKEALLDTGADDTVLEDMNLPGKWKPKMIGGIGGFIKVKQYDQPKERLPIQKETWDTWWIDYWQATWIPEWEFTNTPPLV KLWYQLETEPIAGVETFYVDGASNRETKAAYAITKLQNFRVYYRDNRDPLWKGPARLLWKGEGAVVIQDNSEIKVVPRRKVK IIRDYGKRMAGDDCVAGRQDEDGTVLIGPTPVNIIGRNLLTQLGCTLNFPISPIDTVPVKLKPGMDGPRVKQWPLTEEKIKA LIEICTEMEKEGKISRIGPENPYNTPIFAIKKKDGTKWRKLVDFRELNKKTQDFWEVQLGIPHPSGLKKKKSVTVLDIGDAY FSVPLDKEFRKYTAFTVPSTNNETPGVRYQYNVLPMGWKGSPAIFQCSMTKEKIYLAWVPAHKGIGGNEQIDKLVS |
| 367 | AA, AAA/ none | Gag, Pol, Nef, Env | YQYNVLPQGASRELERFAVNPGLLWIILGLNKIVRMYSPTSIAARTLNAWVKVFLWMGYELHLTFGWCFKLPLWKGPAKLVT VYYGVPVAALLWKGEGAVAAAKLVGKLNWAKLLWKGEGATLNFPPISPIWQATWIPEWKAACWWAGIRQANFLGKIWPSHKGR NVWATHACVAAEMMTACQGVSTVQCTHGIAAKQMAGDDCVAAWQLDCTHLEYKAAVDLSHFLREKGGLEGAAYYMDDLYVGS GQVDCSPGIATLEEMMTAELHPDKWTVWTVNDIQKLGIWGCSGKLTVNDIQKLVIVTDSQYALYVDRFYKTLRAEQASQEVD LNTMLNTVKLTPLCVTLYQYMDDLYVVIYQYMDDL |
| 431 | AA, AAA/ none | Gag, Pol, Nef, Env | YQYNVLPQGASRELERFAVNPGLLWIILGLNKIVRMYSPTSIAARTLNAWVKVFLWMGYELHLTFGWCFKLPLWKGPAKLVT VYYGVPVAALLWKGEGAVAAAKLVGKLNWAKLLWKGEGATLNFPPISPIWQATWIPEWKAACWWAGIRQANFLGKIWPSHKGR NVWATHACVAAEMMTACQGVSTVQCTHGIAAKQMAGDDCVAAWQLDCTHLEYKAAVDLSHFREKGGLEGAAYYMDDLYVGS GQVDCSPGIATLEEMMTAELHPDKWTVWTVNDIQKLGIWGCSGKLTVNDIQKLVIVTDSQYALYVDRFYKTLYVDRFYKTLR AEQASQEVDLNTMLNTVKLTPLCVTLYQYMDDLYVVIYQYMDDLWIILGLNKI |
| 368 | AA, AAA/ GM-CSF | Env, Gag, Nef, Pol | MWLQSLLLLGTVACSISVYQYNVLPQGASRELERFAVNPGLLWIILGLNKIVRMYSPTSIAARTLNAWVKVFLWMGYELHLT FGWCFKLPLWKGPAKLVTVYYGVPVAALLWKGEGAVAAAKLVGKLNWAKLLWKGEGATLNFPPISPIWQATWIPEWKAACWWA GIRQANFLGKIWPSHKGRNVWATHACVAAEMMTACQGVSTVQCTHGIAAKQMAGDDCVAAWQLDCTHLEYKAAVDLSHFLRE KGGLEGAAYYMDDLYVGSGQVDCSPGIATLEEMMTAELHPDKWTVWTVNDIQKLGIWGCSGKLTVNDIQKLVIVTDSQYALY VDRFYKTLRAEQASQEVDLNTMLNTVKLTPLCVTLYQYMDDLYVVIYQYMDDL |
| 432 | AA, AAA/ GM-CSF | Env, Gag, Nef, Pol | MWLQSLLLLGTVACSISVYQYNVLPQGASRELERFAVNPGLLWIILGLNKIVRMYSPTSIAARTLNAWVKVFLWMGYELHLT FGWCFKLPLWKGPAKLVTVYYGVPVAALLWKGEGAVAAAKLVGKLNWAKLLWKGEGATLNFPPISPIWQATWIPEWKAACWWA GIRQANFLGKIWPSHKGRNVWATHACVAAEMMTACQGVSTVQCTHGIAAKQMAGDDCVAAWQLDCTHLEYKAAVDLSHFLRE KGGLEGAAYYMDDLYVGSGQVDCSPGIATLEEMMTAELHPDKWTVWTVNDIQKLGIWGCSGKLTVNDIQKLVIVTDSQYALY VDRFYKTLYVDRFYKTLRAEQASQEVDLNTMLNTVKLTPLCVTLYQYMDDLYVVIYQYMDDLWIILGLNKI |
| 369 | AA, AAA/ t-PA | Env, Gag, Nef, Pol | MDAMKRGLCCVLLLCGAVFVSARYQYNVLPQGASRELERFAVNPGLLWIILGLNKIVRMYSPTSIAARTLNAWVKVFLWMGY ELHLTFGWCFKLPLWKGPAKLVTVYYGVPVAALLWKGEGAVAAAKLVGKLNWAKLLWKGEGATLNFPPISPIWQATWIPEWKA ACWWAGIRQANFLGKIWPSHKGRNVWATHACVAAEMMTACQGVSTVQCTHGIAAKQMAGDDCVAAWQLDCTHLEYKAAVDLS HFREKGGLEGAAYYMDDLYVGSGQVDCSPGIATLEEMMTAELHPDKWTVWTVNDIQKLGIWGCSGKLTVNDIQKLVIVTDS QYALYVDRFYKTLRAEQASQEVDLNTMLNTVKLTPLCVTLYQYMDDLYVVIYQYMDDL |
| 433 | AA, AAA/ t-PA | Env, Gag, Nef, Pol | MDAMKRGLCCVLLLCGAVFVSARYQYNVLPQGASRELERFAVNPGLLWIILGLNKIVRMYSPTSIAARTLNAWVKVFLWMGY ELHLTFGWCFKLPLWKGPAKLVTVYYGVPVAALLWKGEGAVAAAKLVGKLNWAKLLWKGEGATLNFPPISPIWQATWIPEWKA ACWWAGIRQANFLGKIWPSHKGRNVWATHACVAAEMMTACQGVSTVQCTHGIAAKQMAGDDCVAAWQLDCTHLEYKAAVDLS HFREKGGLEGAAYYMDDLYVGSGQVDCSPGIATLEEMMTAELHPDKWTVWTVNDIQKLGIWGCSGKLTVNDIQKLVIVTDS QYALYVDRFYKTLYVDRFYKTLRAEQASQEVDLNTMLNTVKLTPLCVTLYQYMDDLYVVIYQYMDDLWIILGLNKI |
| 370 | AA, AAA/ MCP-3 | Env, Gag, Nef, Pol | MNPSAAVIFCLILLGLSGTQGILDMAQPVGINTSTTCCYRFINKKIPKQRLESYRRTTSSHCPREAVIFKTKLDKEICADPT QKWVQDFMKHLDKKTQTPKLASAGAYQYNVLPQGASRELERFAVNPGLLWIILGLNKIVRMYSPTSIAARTLNAWVKVFLWM GYELHLTFGWCFKLPLWKGPAKLVTVYYGVPVAALLWKGEGAVAAAKLVGKLNWAKLLWKGEGATLNFPPISPIWQATWIPEW KAACWWAGIRQANFLGKIWPSHKGRNVWATHACVAAEMMTACQGVSTVQCTHGIAAKQMAGDDCVAAWQLDCTHLEYKAAVD LSHFREKGGLEGAAYYMDDLYVGSGQVDCSPGIATLEEMMTAELHPDKWTVWTVNDIQKLGIWGCSGKLTVNDIQKLVIVT DSQYALYVDRFYKTLRAEQASQEVDLNTMLNTVKLTPLCVTLYQYMDDLYVVIYQYMDDL |

TABLE J-continued immunogenic fusion polypeptides comprising HIV-1 polypeptide segments ("AAA" is SEQ ID NO: 378, "AAY" is SEQ ID NO: 379, "YMDD" is SEQ ID NO: 462 and "REKR" is SEQ ID NO: 382)

| SEQ ID NO: | Linker/ Signal peptide | HIV-1 Genes | SEQUENCE |
|---|---|---|---|
| 434 | AA, AAA/ MCP-3 | Env, Gag, Nef, Pol | MNPSAAVIFCLILLLGLSGTQGILDMAQPVGINTSTTCCYRFINKKIPKQRLESYRRTTSSHCPREAVIFKTKLDKEICADPT QKWVQDFMKHLDKKTQTPKLASAGAYQYNVLPQGASRELERFAVNPGLLWIILGLNKIVRMYSPTSIAARTLNAWVKVFLWM GYELHLTFGWCFKLPLWKGPAKLVTVYYGVPVAALLWKGEGAVAAAKLVGKLNWAKLLWKGEGATLNFPISPIWQATWIPEW KAACWWAGIRQANFLGKIWPSHKGRNVWATHACVAAEMMTACQGVSTVQCTHGIAAKQMAGDDCVAAWQLDCTHLEYKAAVD LSHFLREKGGLEGAAYYMDDLYVGSGQVDCSPGIATLEEMMTAELHPDKWTVWTVNDIQKLGIWGCSGKLTVNDIQKLVIVT DSQYALYVDRFYKTLYVDRFYKTLRAEQASQEVDLNTMLNTVKLTPLCVTLYQYMDDLYVVIYQYMDDLWIILGLNKI |
| 371 | AA, AAA/ β-catenin | Env, Gag, Nef, Pol | MRKAAVSHWQQQSYLDSGIHSGATTTAPSLSYQYNVLPQGASRELERFAVNPGLLWIILGLNKIVRMYSPTSIAARTLNAWV KVFLWMGYELHLTFGWCFKLPLWKGPAKLVTVYYGVPVAALLWKGEGAVAAAKLVGKLNWAKLLWKGEGATLNFPISPIWQA TWIPEWKAACWWAGIRQANFLGKIWPSHKGRNVWATHACVAAEMMTACQGVSTVQCTHGIAAKQMAGDDCVAAWQLDCTHLE YKAAVDLSHFLREKGGLEGAAYYMDDLYVGSGQVDCSPGIATLEEMMTAELHPDKWTVWTVNDIQKLGIWGCSGKLTVNDIQ KLVIVTDSQYALYVDRFYKTLRAEQASQEVDLNTMLNTVKLTPLCVTLYQYMDDLYVVIYQYMDDL |
| 435 | AA, AAA/ p-catenin | Env, Gag, Nef, Pol | MRKAAVSHWQQQSYLDSGIHSGATTTAPSLSYQYNVLPQGASRELERFAVNPGLLWIILGLNKIVRMYSPTSIAARTLNAWV KVFLWMGYELHLTFGWCFKLPLWKGPAKLVTVYYGVPVAALLWKGEGAVAAAKLVGKLNWAKLLWKGEGATLNFPISPIWQA TWIPEWKAACWWAGIRQANFLGKIWPSHKGRNVWATHACVAAEMMTACQGVSTVQCTHGIAAKQMAGDDCVAAWQLDCTHLE YKAAVDLSHFLREKGGLEGAAYYMDDLYVGSGQVDCSPGIATLEEMMTAELHPDKWTVWTVNDIQKLGIWGCSGKLTVNDIQ KLVIVTDSQYALYVDRFYKTLYVDRFYKTLRAEQASQEVDLNTMLNTVKLTPLCVTLYQYMDDLYVVIYQYMDDLWIILGLN KI |
| 424 | REKR/ none | Env, Gag, Nef, Pol | IRTLNAWVKVREKRDLNTMLNTVREKRWIILGLNKIREKRYVDRFYKTLREKRATLEEMMTAREKREMMTACQGVREKRTLN FPISPIREKRYQYNVLPQGREKRVIYQYMDDLREKRYQYMDDLYVREKRYMDDLYVGSREKRFLWMGYELHREKRELHPDKW TVREKRWTVNDIQKLREKRTVNDIQKLVREKRKLVGKLNWAREKRWQATWIPEWREKRIVTDSQYALREKRG TABLE J-continued immunogenic fusion polypeptides comprising HIV-1 polypeptide segments ("AAA" is SEQ ID NO: 378, "AAY" is SEQ ID NO: 379, "YMDD" is SEQ ID NO: 462 and "REKR" is SEQ ID NO: 382)

| SEQ ID NO: | Linker/ Signal peptide | HIV-1 Genes | SEQUENCE |
|---|---|---|---|
| | | | GGPGHKARDQSLKPCVKLTPLCVTLNCTDLRNTGPGIRYPLLTFGWCFKLPVEPEKVEAKIIRDYGKQMAGDDCVASRQDED ILKALGPAATLEEMMTACQGVGGPGYKAAVDLSHFLREKGGLEGAAYAAKAYDTEVHNVWATHACVPTDPNPQEAAALSEGA TPQDLNTMLNTVGGHQAAMQQVDCSPGIWQLDCTHLEGKIILVAV |
| 375 | AA, AAA/ t-PA | Env, Gag, Nef, Pol | MDAMKRGLCCVLLLCGAVFVSARASRELERFAVNPGLLQLKGEAMHGQVDCSPGIWQLDCTHLCSATEKLWVTVYYGVPVWK EATTTLPVGEIYKRWIILGLNKIVRMYSPTSINNETPGIRYQYNVLPQGWKGSPAIFAAPLWKGPAKLLWKGEGAVVIQDNS DIAAIVLPEKDSWTVNDIQKLVGKLNWASVYYRDSRDPLWKGPAKLLWKGEGAVSNFTSTTVKAACWWAGIKQEFGIPYVLP EKDSWTVNDIQKLVGKLNWASQMVHQAISPRTLNAWVKVVEEKAFSPAAWETWWTEYWQATWIPEWEFVNTPPLQDSGLEVN IVTDSQYALGIIQAQPDSWTVNDIQKLVGKLNWASQTYPGIKNPDIVIYQYMDDLYVGSDLEIGQHRAADPLWKGPAKLLWK GEGAVVIQDNSDRQANFLGKIWPSHKGRAAPPFLWMGYELHPDKWTVQPIVLPEKFRKQNPDIVIYQYMDDLYVGSDLEINL LTQIGCTLNFPISPIETVPVKLKGPKEPPFRDYVDRFYKTLRAEQASQEVYLKDQQLLGIWGCSGKLICTTAVPWAAAKKHQK EPPPFLWMGYELHPDKWTVQPGTGPCTNVSTVQCTHGIRPVVSTQLKQNPDIVIYQYMDDLYVGSDLEIGQLGPAATLEEMMT ACQGVGGPGHKARDQSLKPCVKLTPLCVTLNCTDLRNTGPGIRYPLLTFGWCFKLPVEPEKVEAKIIRDYGKQMAGDDCVAS RQDEDILKALGPAATLEEMMTACQGVGGPGYKAAVDLSHFLREKGGLEGAAYAAKAYDTEVHNVWATHACVPTDPNPQEAAA LSEGATPQDLNTMLNTVGGHQAAMQQVDCSPGIWQLDCTHLEGKIILVAV |
| 376 | AA, AAA/ MCP-3 | Env, Gag, Nef, Pol | MNPSAAVIFCLILLGLSGTQGILDMAQPVGINTSTTCCYRFINKKIPKQRLESYRRTTSSHCPREAVIFKTKLDKEICADPT QKWVQDFMKHLDKKTQTPKLASAGAASRELERFAVNPGLLQLKGEAMHGQVDCSPGIWQLDCTHLCSATEKLWVTVYYGVPV WKEATTTLPVGEIYKRWIILGLNKIVRMYSPTSINNETPGIRYQYNVLPQGWKGSPAIFAAPLWKGPAKLLWKGEGAVVIQD NSDIAAIVLPEKDSWTVNDIQKLVGKLNWASVYYRDSRDPLWKGPAKLLWKGEGAVSNFTSTTVKAACWWAGIKQEFGIPYV LPEKDSWTVNDIQKLVGKLNWASQMVHQAISPRTLNAWVKVVEEKAFSPAAWETWWTEYWQATWIPEWEFVNTPPLQDSGLE VNIVTDSQYALGIIQAQPDSWTVNDIQKLVGKLNWASQIYPGIKNPDIVIYQYMDDLYVGSDLEIGQHRAADPLWKGPAKLL WKGEGAVVIQDNSDRQANFLGKIWPSHKGRAAPPFLWMGYELHPDKWTVQPIVLPEKFRKQNPDIVIYQYMDDLYVGSDLEI NLLTQIGCTLNFPISPIETVPVKLKGPKEPPFRDYVDRFYKTLRAEQASQEVYLKDQQLLGIWGCSGKLICTTAVPWAAAKKH QKEPPPFLWMGYELHPDKWTVQPGTGPCTNVSTVQCTHGIRPVVSTQLKQNPDIVIYQYMDDLYVGSDLEIGQLGPAATLEEM MTACQGVGGPGHKARDQSLKPCVKLTPLCVTLNCTDLRNTGPGIRYPLLTFGWCFKLPVEPEKVEAKIIRDYGKQMAGDDCV ASRQDEDILKALGPAATLEEMMTACQGVGGPGYKAAVDLSHFLREKGGLEGAAYAAKAYDTEVHNVWATHACVPTDPNPQEA AALSEGATPQDLNTMLNTVGGHQAAMQQVDCSPGIWQLDCTHLEGKIILVAV |
| 377 | AA, AAA/β- catenin | Env, Gag, Nef, Pol | MRKAAVSHWQQQSYLDSGIHSGATTTAPSLSASRELERFAVNPGLLQLKGEAMHGQVDCSPGIWQLDCTHLCSATEKLWVTV YYGVPVWKEATTTLPVGEIYKRWIILGLNKIVRMYSPTSINNETPGIRYQYNVLPQGWKGSPAIFAAPLWKGPAKLLWKGEG AVVIQDNSDIAAIVLPEKDSWTVNDIQKLVGKLNWASVYYRDSRDPLWKGPAKLLWKGEGAVSNFTSTTVKAACWWAGIKQE FGIPYVLPEKDSWTVNDIQKLVGKLNWASQMVHQAISPRTLNAWVKVVEEKAFSPAAWETWWTEYWQATWIPEWEFVNTPPL QDSGLEVNIVTDSQYALGIIQAQPDSWTVNDIQKLVGKLNWASQIYPGIKNPDIVIYQYMDDLYVGSDLEIGQHRAADPLWK GPAKLLWKGEGAVVIQDNSDRQANFLGKIWPSHKGRAAPPFLWMGYELHPDKWTVQPIVLPEKFRKQNPDIVIYQYMDDLYV GSDLEINLLTQIGCTLNFPISPIETVPVKLKGPKEPPFRDYVDRFYKTLRAEQASQEVYLKDQQLLGIWGCSGKLICTTAVPW AAAKKHQKEPPPFLWMGYELHPDKWTVQPGTGPCTNVSTVQCTHGIRPVVSTQLKQNPDIVIYQYMDDLYVGSDLEIGQLGPA ATLEEMMTACQGVGGPGHKARDQSLKPCVKLTPLCVTLNCTDLRNTGPGIRYPLLTFGWCFKLPVEPEKVEAKIIRDYGKQM AGDDCVASRQDEDILKALGPAATLEEMMTACQGVGGPGYKAAVDLSHFLREKGGLEGAAYAAKAYDTEVHNVWATHACVPTD PNPQEAAALSEGATPQDLNTMLNTVGGHQAAMQQVDCSPGIWQLDCTHLEGKIILVAV |
| 422 | AA, AAY/ none | Gag, Nef, Pol | ICGHKAIGTVLVGPTPVNIIGRNLLTQLGCTLNFPISPIETVPVKLKPGMDGPKVKQWPLTEEKIKALDPLWKGPAKLLWKG EGAVVIQDNSDIKAAIIRDYGKQMAAAYSDIAGTTSTLQEQITWMTNNPPIPVGEIYKRWIILGLNKIVRMYSPVS ILDIRQGPKEPFRDYVDRFYKTLRAEQASQEVKNWMTETLLVQNANPDCKTILKALGPAATLEEMMTACQGVGGPGHKARVL AEAMSQVTNSATLNKRTQDFWEVQLGIPHPAGLKKKKSNFTSTTVKAACWWAGIKQEFGIPYNPQSAYFSVPLDKEFRKYTA FTIPSINNEDTVLEEMNLPGKWKPKMIGGIGGFIKVRQYDQISKIGPENPYNTPIFAIKKKDSTKWAAGKKKYRLKHLVWVS RELERFAVNPGGKKKYRLKHLVWASRELERFAVNPGAEHLKTAVQMAVFIHNFKRKGGIGGAAGQMVHQAISPRTLNAWVKV VEEKAFSPEVIPMFSALAEGATPQDLNTMLNTVGGHQARWIILGLNKTVRMSPVSILDIRQGPKEPFRDYVDRFYKTLRAE QASQEVKNWMTETLLVQNANPDCKTILKALGPAATLEEMMTACQGVGGPGHKARVLAEAMSQVTNSATQLKGEAMHGQVDCS PGIWQLDCTHLEGKVILVAVHVASGYIEAEVIPAETGQETAYFLLKLAGR |
| 423 | AA/ none | Gag, Nef, Pol | SNFTSTTVKVACWWAGIKQEFGIPYAASNFTSTTVKAACWWAGVKQEFGIPYAASNFTSTTVKAACWWAGIKQEFGIPYPLR PMTYKAAVDLSHFLKEKGGLEGPLRPMTYKAAVDLSHFLKEKGGLEGPLRPMTYKAAFDLSFFLKEKGGLEGPLRPMTYKAA FDLSFFLKEKGGLEGLRPMTYKAAFDLSHFLKEKGGLEGPLRPMTYKGALDLSHFLKEKGGLEGLREAMHGQVDCSPGI WQLDCTHLEEKIILVAVHVASGYIEAEVIPAETGQETAYMVHQAISPRTLNAWVKVVEEKAFSPLDCTHLEGKVILVAVHVA SGYIEAEICGHKAIGTVLVGPTPVNIIGRNLLTQIGCTLNFPISPIETVPVKLKDPLWKGPAKLLWKGEGAVVIQDNSDIDP LWKGPAKLLWKGEGVVVIQDNSDIMVHQAISPRTLNALVKVVEEKAFSPICGHKAIGTVLVGSTPVNIIGRNLL |

TABLE K

HIV-1 sequence segments that may be excluded from the present fusion proteins

| SEQ ID NO: | HIV-1 Gene | start | end | SEQUENCE |
|---|---|---|---|---|
| 437 | Env | 1 | 27 | MRVKEKYQHLWRWGWRWGTMLLGMLMI |
| 438 | Env | 53 | 58 | FCASDA |

TABLE K-continued

HIV-1 sequence segments that may be excluded from the present fusion proteins

| SEQ ID NO: | HIV-1 Gene | start | end | SEQUENCE |
|---|---|---|---|---|
| 439 | Env | 84 | 112 | VVLVNVTENFNMWKNDMVEQMHEDIISLW |
| 440 | Env | 138 | 234 | NTNSSSGRMIMEKGEIKNCSFNISTSIRGKVQKEYAFFYKLDIIPIDNDTTSYKLTSCNTSVITQACPKVSFEPIPIHYCAPAGFAILKCNNKTFN |
| 441 | Env | 269 | 474 | EVVIRSVNFTDNAKTIIVQLNTSVEINCTRPNNNTRKRIRIQRGPGRAFVTIGKIGNMRQAHCNISRAKWNNTLKQIASKLREQFGNNKTIIFKQSSGGDPEIVTHSFNCGGEFFYCNSTQLFNSTWFNSTWSTEGSNNTEGSDTITLPCRIKQIINMWQKVGKAMYAPPISGQIRCSSNITGLLLTRDGGNSNNESEIFRPGGGD |
| 442 | Env | 490 | 501 | KIEPLGVAPTKA |
| 443 | Env | 611 | 856 | NASWSNKSLEQIWNHTTWMEWDREINNYTSLIHSLIEESQNQQEKNEQELLELDKWASLWNWFNITNWLWYIKLFIMIVGGLVGLRIVFAVLSIVNRVRQGYSPLSFQTHLPTPRGPDRPEGIEEEGGERDRDRSIRLVNGSLALIWDDLRSLCLFSYHRLRDLLLIVTRIVELLGRRGWEALKYWWNLLQYWSQELKNSAVSLLNATAIAVAEGTDRVIEVVQGACRAIRHIPRRIRQGLERILL |
| 444 | Gag | 1 | 30 | MGARASVLSGGELDRWEKIRLRPGGKKKYK |
| 445 | Gag | 54 | 127 | SEGCRQILGQLQPSLQTGSEELRSLYNTVATLYCVHQRIEIKDTKEALDKIEEEQNKSKKKAQQAAADTGHSNQ |
| 446 | Gag | 138 | 146 | IQGQMVHQA |
| 447 | Gag | 370 | 428 | VTNSATIMMQRGNFRNQRKIVKCFNCGKEGHTARNCRAPRKKGCWKCGKEGHQMKDCTE |
| 448 | Gag | 445 | 500 | PGNFLQSRPEPTAPPEESFRSGVETTTPPQKQEPIDKELYPLTSLRSLFGNDPSSQ |
| 449 | Nef | 1 | 63 | MGGKWSKSSVIGWPTVRERMRRAEPAADRVGAASRDLEKHGAITSSNTAATNAACAWLEAQEE |
| 450 | Nef | 103 | 116 | LIHSQRRQDILDLWIYH |
| 451 | Nef | 155 | 206 | PGVRYPLTFGWCYKLVPVEPDKIEEANKGENTSLLHPVSLHGMDDPEREVLEWRFDSRLAFHHVARELHPEYFKNC |
| 452 | Pol | 1 | 55 | FFREDLAFLQGKAREFSSEQTRANSPTRRELQVWGRDNNSPSEAGADRQGTVSFN |
| 453 | Pol | 118 | 128 | ILIEICGHKAI |
| 454 | Pol | 321 | 325 | KILEP |
| 455 | Pol | 355 | 366 | TKIEELRQHLLR |
| 456 | Pol | 432 | 541 | QLCKLLRGTKALTEVIPLTEEAELELAENREILKEPVHGVYYDPSKDLIAEIQKQGQGQWTYQIYQEPFKNLKIGKYARMRGAHTNDVKQLTEAVQKITTESIVIWGKT |
| 457 | Pol | 607 | 641 | LGKAGYVTNRGRQKVVTLTDTTNQKTELQAIYLAL |
| 458 | Pol | 667 | 682 | QSESELVNQIIEQLIK |
| 459 | Pol | 709 | 746 | GIRKVLFLDGIDKAQDEHEKYHSNWRAMASDFNLPPV |
| 460 | Pol | 828 | 833 | IHTDNG |
| 461 | Pol | 921 | 930 | TDIQTKELQK |

3. Polynucleotides Encoding the Fusion Polypeptides

Provided are polynucleotides encoding the fusion polypeptides, described herein, vectors comprising such polynucleotides, and host cells (e.g., human cells, mammalian cells, yeast cells, plant cells, insect cells, bacterial cells, e.g., *E. coli*) comprising such polynucleotides or expression vectors. Provided herein are polynucleotides comprising nucleotide sequence(s) encoding any of the fusion polypeptides provided herein, as well as expression cassettes and vector(s) comprising such polynucleotide sequences, e.g., expression vectors for their efficient expression in host cells, e.g., mammalian cells. In various embodiments, the polynucleotide is a DNA, a cDNA, an mRNA, a self-amplifying RNA (SAM), a self-replicating RNA, or a self-amplifying replicon RNA (RepRNA). In some embodiments, the polynucleotide comprises an alphavirus self-replicating or self-amplifying replicon RNA (RepRNA). Self-replicating RNA and self-amplifying replicon RNA as modes of vaccine delivery are described, e.g., by Tews, et al., *Methods Mol Biol*. (2017) 1499: 15-35; Démoulins, et al., *Methods Mol Biol*. (2017) 1499: 37-75; Englezou, et al., *Mol Ther Nucleic Acids*. (2018) 12:118-134; McCollough, et al., *Vaccines* (Basel). (2014) 2(4):735-54; and McCollough, et al., *Mol Ther Nucleic Acids*. (2014) 3:e173.

The terms "polynucleotide" and "nucleic acid molecule" interchangeably refer to a polymeric form of nucleotides and includes both sense and anti-sense strands of RNA, cDNA, genomic DNA, and synthetic forms and mixed polymers of the above. As used herein, the term nucleic acid molecule may be interchangeable with the term polynucleotide. In some embodiments, a nucleotide refers to a ribonucleotide, deoxynucleotide or a modified form of either type of nucleotide, and combinations thereof. The terms also include without limitation, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-biased polynucleotides for improved expression in a desired viral expression vector or host cell.

A "substitution," as used herein, denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. "Isolated nucleic acid encoding an polypeptide segment or encoding a fusion polypeptide" refers to one or more nucleic acid molecules encoding such polypeptide segments or fusion polypeptides, including such nucleic acid molecule(s) in a single vector or separate vectors, and such nucleic acid molecule(s) present at one or more locations in a host cell.

A "polynucleotide variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences described herein and evaluating one or more biological activities of the encoded polypeptide as described herein and/or using any of a number of techniques well known in the art.

In some embodiments, the nucleic acid molecule is codon-biased to enhance expression in a desired host cell, e.g., in human cells, mammalian cells, yeast cells, plant cells, insect cells, or bacterial cells, e.g., E. coli cells. Accordingly, provided are polynucleotides encoding a fusion polypeptide, described herein, wherein the polynucleotides are codon-biased, comprise replacement heterologous signal sequences, and/or have mRNA instability elements eliminated. Methods to generate codon-biased nucleic acids can be carried out by adapting the methods described in, e.g., U.S. Pat. Nos. 5,965,726; 6,174,666; 6,291,664; 6,414,132; and 6,794,498. Preferred codon usage for expression of the fusion polypeptides comprising HIV-1 polypeptide segments from desired viral expression vectors and/or in desired host cells is provided, e.g., at kazusa.or.jp/codon/; and genscript.com/tools/codon-frequency-table.

In some embodiments, the polynucleotide encoding a fusion polypeptide, as described herein, has at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence selected from the group consisting of SEQ ID NOs: 414-418, as provided in Table L.

As appropriate, in certain embodiments, the 3'-end of the polynucleotide encoding the fusion polypeptides described herein comprises one or multiple tandem stop codons, e.g., two or more tandem TAG ("amber"), TAA ("ochre") or TGA ("opal" or "umber") stop codons. The multiple tandem stop codons can be the same or different.

Further provided are expression cassettes, comprising a polynucleotide encoding a fusion polypeptide, as described herein, operably linked to one or more regulatory sequences. In some embodiments, the polynucleotide is operably linked to and under the control of a constitutive promoter. In some embodiments, the promoter is selected from cytomegalovirus major immediate-early (CMV), the CMV enhancer fused to the chicken beta-actin promoter (CAG), human elongation factor-1α (HEF-1α), mouse cytomegalovirus (mouse CMV), Chinese hamster elongation factor-1α (CHEF-1α), and phosphoglycerate kinase (PGK).

TABLE L

Polynucleotides encoding fusion polypeptides ("REKR" is SEQ ID NO: 382)

| SEQ ID NO: | HIV-1 GENES/ FEATURES | SEQUENCE |
|---|---|---|
| 414 | Gag, Nef | ATGGGAGCTAGAGCTAGCGTGCTGAGCGGAGGAGAACTCGATCGCTGGGAAAAGATCAGACTGAGACCAGGAGGCAAGA AGAAGTACAGACTGAAGCACATCGTCTGGGCTTCTAGAGAACTGGAAAGATTCGCCGTGAATCCAGGACTGCTGGAAAC ACTGAAGCACATTGTCTGGGCTAGCAGAGAACTGGAGAGATTTGCCGTGAATCCAGGACTGCTGGAAACAGCAGCTATC TCTCCTAGAACACTGAACGCTTGGGTGAAAGTGGTGGAGGAAAAGGCCTTTAGCCCAGAAGTGATCCCTATGTTTAGCG CCCTGTCAGAAGGAGCTACACCTCAGGATCTGAACACCATGCTGAACACAGTGGGAGGACATCAGGCAGCTATGCAGAT GCTGAAGGAGACAATTAACGAAGAAGCCGCCGAGTGGGATAGACTGCATCCAGTGCACGCAGGACCTATTGCTCCAGGA CAGATGAGAGAGCCTAGAGGAAGCGATATCGCAGGAACAACATCTACACTGCAGGAGCAGATCGGTTGGATGACCAATA ATCCTCCTATCCCAGTGGGCGAAATCTATAAGCGCTGGATCATCCTGGGACTGAACAAGATCGTGAGGATGTACAGCCC TACCAGCATCCTGGATATCAGACAGGGACCTAAGGAGCCTTTCAGAGATTACGTGGACAGGTTCTACAAGCACACTGAGA GCCGAACAGGCTTCTCAGGAGGTGAAGAATTGGATGACCGAGACACTGCTGGTGCAGAACGCTAATCCAGATTGCAAGA CAATTCTGAAAGCTCTGGGACCAGCCGCTACACTGGAAGAGATGATGACCGCTTGTCAGGGAGTGGGAGGACCAGGACA TAAAGCTAGAGTGCTGGCAGAAGCCATGTCTCAGGAAGAAGTGGGATTCCCAGTGAAACCTCAGGTGCCTCTGAGACCT ATGACCTTTAAGGGAGCTCTGGACCTGTCTCACTTCCTGAGAGAAAAGGGAGGACTGGAAGGAACACAGGGATTTTTCC CAGATCAGAATTACACACCAGAGCCAGGAATCAGATTCCCTCTGACATTCGGTTGGTGCTTCAAACTGGTGCCTCTG |

TABLE L-continued

Polynucleotides encoding fusion polypeptides ("REKR" is SEQ ID NO: 382)

| SEQ ID NO: | HIV-1 GENES/ FEATURES | SEQUENCE |
|---|---|---|
| 415 | PolEnv | GGAACAGTGCTGGTGGGACCTACTCCAGTGAATATCATCGGAAGGAACCTGCTGACACAGATTGGTTGTACCCTGAACT<br>TCCCTATCTCTCCTATCGAGACAGTGCCAGTGAAACTGAAGCCAGGAATGGATGGACCTAAAGTCAAGCAGTGGCCTCT<br>GACAGAAGAGAAGATCAAAGCCCTGGTGGAGATTTGCACCGAGATGGAGAAGGAGGGAAAGATCAGCAAGATCGGCCCA<br>GAGAATCCTTACAACACCCCAGTGTTCGCCATCAAGAAGAAGGATAGCACCAAGTGGAGAAAGCTGGTGGATTTCAGGG<br>AGCTGAACAAGAGAACCCAGGATTTTTGGGAGGTGCAGCTGGGTATTCCACATCCTGCCGGACTGAAAAAGAAGAAAG<br>CGTGACAGTGCTGGACGTGGGAGACGCTTATTTCAGCGTGCCTCTGGATAAGGACTTCAGAAAGTACACCGCCTTCACC<br>ATCCCTTCTATCAACAACGAGACCCAGGAATCAGATACCAGTACAACGTGCTGCCTCAAGGTTGGAAAGGATCTCCAG<br>CCATCTTTCAGAGCAGCATGACAACAGTGAAGGCAGCTTGTTGGTGGGCAGGAATTAAGCAGGAGTTCGGCATCCCTTA<br>CAATCCTCAGTCTCAGGGAGTGGTGGAATCTATGAACAAGGAGCTGAAGAAGATCATCGGACAGGTGAGAGATCAGGCC<br>GAACATCTGAAGACAGCAGTGCAAATGGCCGTGTTCATCCACAACATTCAAGAGAAAGGGCGGCATTGGAGGCTATTCTG<br>CCGGAGAGAGAATTGTGGACATCATCAACGTGTCAACAGTCCAGTGTACACACGGAATCAGACCAGTCGTGTCTACACA<br>ACTGCTGCTGAACGGATCTCTGGCCGAAGAGAAGAGAAGAGTGGTGCAGAGAGAGAAAAGAGCAGTGGGAATCGGAGCT<br>ATGTTTCTGGGATTTCTGGGCGCAGCAGGATCTACAATGGGAGCAGCTTCTATCACACTGACAGTGCAGGCTAGACAAC<br>TGCTGAGCGGAATTGTGCAGCAGCAGAATAACCTGCTGAGAGCTATCGAAGCTCAGCAACATCTGCTGCAACTCACCGT<br>CTGGGGAATTAAGCAACTGCAAGCTAGAGTGCTGGCAGTGGAAAGATACCTGAAGGATCAGCAACTGCTGGGAATTTGG<br>GGTTGCTCAGGCAAGCTGATTTGCACAACCGTGGCCAAAGAGATTGTGGCTTCTTGCGACAAGTGTCAGCTGAAAGGAG<br>AAGCTATGCACGGACAAGTGGATTGTTCTCCAGGAATTTGGCAGCTGGATTGTACACACCTGGAGGGAAAGATTATTCT<br>GGTGGCAGTGCACGTGGCCAGCGGATATATTGAAGCCGAGGTGATTCCAGCAGAAACAGGACAGGAGAAACAGCCTATTT<br>CTCCTGAAACTGGCAGGTAGGTGGCCAGTGAAAACCCTCTGGGTGACAGTGTACTACGGAGTCCCAGTCTGGAAAGAAG<br>CAGCTTTCCCTCAGATTACTCTCTGGCAGAGACCTCTGGTGACAATCAAGATCGGCGGACAGCTGAAAGAAGCTCTGCT<br>GGATACAGGAGCAGACGATACAGTGCTGGAAGAAATGAACCTGCCAGGTAGATGGAAGCCTAAGATGATCGGAGGCATC<br>GGAGGATTCATCAAGGTGAGACAGTACGACCAAGCAGCAGCAGCTCATAACGTCTGGGCTACACACGCTTGCGTGCCTA<br>CAGATCCTAATCCTCAGGAAGCCATCACCAAGATCCAGAATTTCAGGGTGTACTACAGGGACAGCAGAGATCCTCTCTG<br>GAAAGGACCAGCTAAACTGCTGTGGAAAGGAGAAGGAGCAGTGGTGATCCAGGATAACAGCGACATCAAGGTGGTGCCT<br>AGAAGAAAGGCCAAGATCATCAGGGACTACGGAAAGCAAATGGCAGGAGACGATTGCGTGGCTTCTAGACAGGACGAGG<br>ATCCCAAGTTCAAGCTGCCTATTCAGAAGGAGACTTGGGAGACTTGGTGGACAGATATTGGCAAGCAACTTGGATCCC<br>CGAGTGGGAATTTGTGAATACCCCTCCTCTGGTCAAGCTCTGGTATCAGCTGGAAAAGGAGCCTATCGTGGGAGCCGAA<br>ACATTTTACGTGGACGGAGCAGCTAATAGAGAGACAAAAGCCGCCAAGGAGAAAGTGTATCTGGCTTGGGTGCCAGCTC<br>ATAAAGGAATCGGAGGAAACGAGCAGGTGGATAAACTGGTGTCTTGGGCTTTACCACACCAGATAAGAAGCACCAGAA<br>GGAGCCACCATTTCTCTGGATGGGATACGAACTGCACCCAGATAAGTGGACAGTCCAGCCTATTGTGCTGCCAGAAAAG<br>GACTCTTGGACAGTGAACGACATCCAGAAACTGGTGGGAAAGCTGAATTGGGCCTCTCAGATCTACCCAGGCATCAAGG<br>TGATCGTGATCTACCAGTACATGGACGATCTGTACGTGGGATCAGATCTGGAGATCGGACAGCACAGAATGAGGGACAA<br>TTGGAGAAGCGAGCTGTACAAGTACAAGGTGGTG |
| 416 | Env, Gag, Nef, Pol | TACCAGTATAACGTGCTGCCTCAGGGAGCTTCTAGAGAACTGGAGAGATTCGCAGTGAACCCAGGACTCCTC<br>TGGATTATCCTGGGACTGAACAAGATCGTGAGGATGTACTCTCCTACCTCTATTGCCGCTAGAACACTGAAC<br>GCTTGGGTGAAGGTCTTCCTCTGGATGGGATACGAACTGCATCTGACCTTTGTTGGTGCTTTAAGCTCCCT<br>CTCTGGAAAGGACCAGCTAAGCTGGTGACAGTGTATTACGGAGTGCCAGTGGCAGCTCTCCTCTGGAAAGGA<br>GAAGGAGCAGTGGCAGCAGCTAAACTGGTGGGAAAGCTGAATTGGGCCAAACTCCTCTGGAAGGAGAAGGA<br>GCCACCCTGAATTTTCCTATCAGCCCTATTTGGCAGGCTACTTGGATTCCAGAGTGGAAAGCAGCTTGTTGG<br>TGGGCAGGAATCAGACAGGCCAACTTCCTGGGCAAGATTTGGCCTTCTCACAAAGGAAGAAACGTCTGGGCT<br>ACACACGCTTGCGTGGCAGCAGAAATGATGACAGCTTGTCAGGGAGTGTCTACAGTCCAGTGTACACACGGA<br>ATCGCAGCTAAACAGATGGCAGGAGACGATTGCGTGGCAGCTTGGCAGCTGGATTGTACACACCTGGAGTAC<br>AAGGCAGCAGTGGATCTGTCTCACTTTCTGAGAGAAAAAGGAGGACTGGAAGGAGCAGCTTACTACATGGAC<br>GATCTGTACGTGGGATCAGGACAGGTGGATTGTTCACCAGGAATCGCTACACTGGAGGAAATGATGACCGCA<br>GAACTGCATCCAGATAAGTGGACCGTCTGGACAGTGAACGATATCCAGAAGCTGGGCATTTGGGGTTGTAGC<br>GGAAAACTGACCGTGAACGATATCCAGAAGCTGGTGATCTCAGTACGCTCTGTACGTGGAC<br>AGATTCTACAAGACCCTGTACGTGGACAGGTTCTACAAGACACTGAGAGCCGAACAGGCTTCTCAGGAAGTG<br>GATCTGAACACCATGCTGAACACCGTGAAACTGACACCTCTCTGCGTGACACTGTATCAGTACATGGACGAC<br>CTGTACGTGGTGATCTACCAGTACATGGACGATCTCTGGATCATCCTGGGACTGAACAAGATCG |
| 417 | Env, Gag, Nef, Pol/ REKR linkers | AGAACACTGAACGCTTGGGTGAAGGTGAGAGAGAAGAGAGACCTGAACACCATGCTGAACACCGTGAGAGAA<br>AAGAGGTGGATCATCCTGGGACTGAACAAGATCAGGGAGAAGAGGTACGTGGACAGGTTCTACAAGACACTG<br>AGAGAGAAGAGAGCCACACTGGAAGAGATGATGACCGCTAGAGAGAAGAGAGAGATGATGACCGCTTGTCAG<br>GGAGTGACAGAGAAGAGAACCCTGAACTTCCCCATCTCTCCTATCAGGGAGAAGAGGTACCAGTACAACGTG<br>CTGCCTCAGGGAAGAGAAAAGAGAGTGATCTACCAGTACATGGACGACCTGAGAGAGAAGAGGTACCAGTAC<br>ATGGACGATCTGTACGTGAGGGAAGAGAACATGGACGACCTGTACGTGGGATCAAGAGAAGAAGAGATTC<br>CTCTGGATGGGCTACGAGCTGCATAGAGAGAAGAGAGAGCTGCACCCAGATAAGTGGACAGTGAGAGAAAAG<br>CGCTGGACAGTGAACGACATCCAGAAGCTGAGAGAGAAGAGGCAGTGAACGACATCCAGAAGCTGGTGAGA<br>GAGAGGAAGCTGGTGGGAAAACTGAATTGGGCTGCAGGGAAAAGGGTGGCAGGCTACTTGGATTCCAGAG<br>TGGAGAGAAGAGGATCGTGACAGATAGCCAGTACGCTCTGAGAGAGAAAAGGACAGGTGGATTGCTCT<br>CCAGGAATCAGAGAGAAGAGATGGCAGCTGGATTGTACACACCTGGAGAGAGAGAAGAGGAAAGCAGCTTGT<br>TGGTGGGCAGGAATTCGGGAAAAAGACCTCTCTGGAAAGGACCAGCCAAGCTGAGAGAGAAGAGAAAACTC<br>CTCTGGAAGGGCGAAGGAGCTAGAGAAAAGAGACTCCTCTGGAAGGAGAAGGCCAGTGAGAGAGAAGAGA<br>AAACAGATGGCCGGAGACGATTGCGTGAGAGAAAAGAGAGTGACCGTGTATTACGGAGTGCCAGTGAGAGAA<br>AAGAGAAAGCGTCTGGGCTACACACGCTTGCGTGAGAGAGAAGAGAAAGCTGACACCTCTGTGCGTGACACTG<br>AGAGAAAAGAGAAGCACCGTGCAGTGTACACACGGAATTAGGGAGAAGAGAGGCATTTGGGTTGTTCAGGA<br>AAGCTGAGCAAGAGGCTGACATTCGGTTGGTGTTTCAAGCTGAGGGAGAAGAGGCCTCTAGAGAACTG<br>GAGAGATTCGCAGTGAATCCAGGACTGCTGAGAGAAAAGCGCTGGATTATCCTGGGACTGAACAAGATCGTG<br>AGGATGTACAGCCCTACAAGCATCAGAGAGAAGAGGTACGTGGACAGATTCTACAAGACCCTGAGAGCCGAA<br>CAGGCATCTCAGGAAGTGAGAGAGAAGAGAAGGCAGGCTAACTTCCTGGGAAAGATTTGGCCTAGCCACAAG<br>GAAGAAGAGAAGAGAGATACAAGGCCGCAGTGGATCTGTCTCACTTTCTGAGAGAGAAAGGAGGACTGGAA<br>GGAGGA |

TABLE L-continued

Polynucleotides encoding fusion polypeptides ("REKR" is SEQ ID NO: 382)

| SEQ ID NO: | HIV-1 GENES/ FEATURES | SEQUENCE |
|---|---|---|
| 418 | Env, Gag, Nef, Pol/ REKR linkers; LAMP-1 N-term & C-term signal sequences | ATGGCTCCTAGAAGCGCTAGAAGACCTCTGCTGCTGCTGCTGCTGCTGCTGCTGGGACTGATGCATTGC GCTTCAGCAGCTATGTTCATGGTGAAGAACGGCAACGGAACAGCTTGTATCATGGCCAATTTCAGCGCCGCT TTTAGCGTGAATTACGACACCAAGAGCGGACCTAAGAACATGACACTGGATCTGCCTTCAGACGCTACAGTG GTGCTGAATAGAAGCTCTTGCGGAAAGGAGAATACCTCCGATCCTTCTCTGGTGATCGCTTTTGGCAGAGGA CACACACTGACACTGAACTTCACCAGAAACGCCACCAGATACTCAGTGCAGCTGATGAGCTTCGTGTACAAC CTGAGCGATACCCATCTGTTTCCTAACGCTAGCAGCAAGGAGATCAAGACAGTGGAGTCTATCACCGACATC AGAGCCGATATCGACAAGAAATACCGCTGCGTGTCAGGAACACAGGTGCACATGAACAACGTGACAGTGACA CTGCACGACGCCACAATTCAGGCCTATCTGAGCAATAGCAGCTTTAGCAGAGGCGAAACTAGGTGTGAGCAG GATAGACCTTCTCCTACAACAGCTCCTCCAGCTCCTCCTTCTCCTTCTCCTTCTCCAGTGCCTAAATCTCCT AGCGTGGATAAGTACAACGTGAGCGGAACAAACGGCACTTGTCTGCTGGCTTCTATGGGACTGCAGCTGAAT CTGACATACGAGAGGAAGGACAACACCACAGTGACAAGACTGCTGAACATCAACCCCAACAAAACAAGCGCT AGCGGATCTTGCGGAGCTCATCTGGTGACACTGGAACTGCATTCAGAGGGAACAACAGTGCTGCTGTTTCAG TTCGGAATGAACGCCTCTAGCAGCAGATTCTTCCTGCAGGGTATTCAGCTGAATACACCTGCTGCCAGATGCT AGAGATCCAGCCTTTAAAGCCGCTAATGGATCTCTGAGAGCTCTGCAGCCTACAGTGGGAAATAGCTACAAG TGCAACGCCGAAGAACACGTGAGAGTGACAAAAGCCTTCAGCGTGAACATCTTTAAGGTCTGGGTGCAGGCA TTTAAAGTGGAGGGAGGCCAGTTTGGAAGCGTCGAAGAGTGTCTGCTGGACGAAAATAGCCTGGAAGACATC AGAACACTGAACGCTTGGGTGAAGGTGAGAGAGAAGAGAGACCTGAACACCATGCTGAACACCGTGAGAGAA AAGAGGTGGATCATCCTGGGACTGAACAAGATCAGGGAGAAGGGTACGTGGACAGGTTCTACAAGACACTG AGAGAGAAGAGAGCCACACTGGAAGAGATGATGACCGCTAGAGAGAAGAGAGAGATGATGACCGCTTGTCAG GGAGTGAGAGAGAAGAGAACCCTGAACTTCCCCATCTCTCCTATCAGGGAGAAGAGGTACCAGTACAACGTG CTGCCTCAGGGAAGAGAAAAGAGAGTGATCTACCAGTACATGGACGACCTGAGAGAGAAGAGGTACCAGTAC ATGGACGATCTGTACGTGAGGGAGAAGAGATCATGGACGACCTGTACGTGGGATCAAGAGAGAAGAGATTC CTCTGGATGGGCTACGAGCTGCATAGAGAGAAGAGAGAGCTGCACCCAGATAAGTGGACAGTGAGAGAAAAG CGCTGGACAGTGAACGACATCCAGAAGCTGAGAGAGAAGAGGACAGTGAACGACATCCAGAAGCTGGTGAGA GAGAAGAGGAAGCTGGTGGGAAAACTGAATTGGGCTAGGGAAAAAAGGTGGCAGGCTACTTGGATTCCAGAG TGGAGAGAGAAGAGGATCGTGACAGATAGCCAGTACGCTCTGAGAGAGAAAAGAGGACAGGTGGATTGCTCT CCAGGAATCAGAGAGAAGAGATGGCAGCTGGATTGTACACACCTGGAGAGAGAGAAGAGGAAAGCAGCTTGT TGGTGGGCAGGAATTCGGGAAAAAAGACCTCTCTGGAAAGGACCAGCCAAGCTGAGAGAGAAGAGAAAACTC CTCTGGAAGGGCGAAGGAGCTAGAGAAAAGAGACTCCTCTGGAAAGGAGAAGGCGCAGTGAGAGAGAAGAGA AAACAGATGGCCGGAGACGATTGCGTGAGAGAAAAGAGAGTGACCGTGTATTACGGAGTGCCAGTGAGAGAA AAGAGAAACGTCTGGGCTACACACGCTTGCGTGAGAGAGAAGAAAGCTGACACCTCTGTGCGTGACACTG AGAGAAAAGAGAAGCACCGTGCAGTGTACACACGGAATTAGGGAGAAGAGAGGCATTTGGGGTTGTTCAGGA AAGCTGAGAGAGAAGAGGCTGACATTCGGTTGGTGTTTCAAGCTGAGGGAGAAGAGAGCCTCTAGAGAACTG GAGAGATTCGCAGTGAATCCAGGACTGCTGAGAGAAAAGCGCTGGATTATCCTGGGACTGAACAAGATCGTG AGGATGTACAGCCCTACAAGCATCAGAGAGAAGAGGTACGTGGACAGATTCTACAAGACCCTGAGAGCCGAA CAGGCATCTCAGGAAGTGAGAGAGAAGAGAAGGCAGGCTAACTTCCTGGGAAAGATTTGGCCTAGCCACAAG GGAAGAAGAGAGAAGAGATACAAGGCCGCAGTGGATCTGTCTCACTTTCTGAGAGAGAAAGGAGGACTGGAA GGAGGAAGCGAGTTTACCCTGATTCCAATTGCCGTGGGAGGAGCTCTGGCAGGACTGGTGATTGTGCTGATC GCATACCTGGTGGGAAGAAAGAGATCTCACGCCGGATATCAGACCATC |

4. Vectors and Host Cells

Further provided are vectors comprising one or more polynucleotides encoding one or more of the fusion polypeptides, described herein, or an expression cassette comprising such polynucleotides. A vector can be of any type, for example, a recombinant vector such as an expression vector. Vectors include without limitation, plasmids, cosmids, bacterial artificial chromosomes (BAC) and yeast artificial chromosomes (YAC) and vectors derived from bacteriophages or plant or animal (including human) viruses. Vectors can comprise an origin of replication recognized by the proposed host cell and in the case of expression vectors, promoter and other regulatory regions recognized by the host cell. In additional embodiments, a vector comprises one or more polynucleotides encoding one or more fusion polypeptides of the disclosure operably linked to a promoter and optionally additional regulatory elements. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome. Vectors include without limitation, those suitable for recombinant production of the fusion polypeptides disclosed herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Some vectors are suitable for delivering the nucleic acid molecule or polynucleotide of the present application. Certain vectors are capable of directing the expression of nucleic acids to which they are operatively linked. Such vectors are referred to herein as expression vectors.

The term "operably linked" refers to two or more nucleic acid sequence elements that are usually physically linked and are in a functional relationship with each other. For instance, a promoter is operably linked to a coding sequence if the promoter is able to initiate or regulate the transcription or expression of a coding sequence, in which case, the coding sequence should be understood as being "under the control of" the promoter.

The choice of the vector is dependent on the recombinant procedures followed and the host used. Introduction of vectors into host cells can be effected by inter alia calcium phosphate transfection, DEAE-dextran-mediated transfection, lipofectamine transfection, electroporation, virus infection, or via administration to a subject, as described herein. Vectors may be autonomously replicating or may replicate together with the chromosome into which they have been integrated. In certain embodiments, the vectors contain one or more selection markers. The choice of the markers may depend on the host cells of choice. These include without limitation, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the fusion polypeptides described herein, operably linked to one or more nucleic acid molecules encoding proteins or peptides that can be used to isolate the fusion polypeptides ("purification tags"), are also covered by the disclosure. These proteins or peptides include without limitation, FLAG-tag (DYKDDDDKL; SEQ ID NO: 436), glutathione-S-transferase, maltose binding protein, metal-binding polyhistidine, green fluorescent protein, luciferase and beta-galactosidase.

In other embodiments, the vector that is used is pcDNA™3.1+(ThermoFisher, MA).

In some embodiments, the vector is viral vector. As appropriate, the viral vector can be a DNA virus or a RNA virus, including a self-replicating RNA virus. Self-replicating RNA viruses include Alphaviruses, and are described, e.g., in Lundstrom, *Molecules*. (2018) 23(12). pii: E3310 (PMID: 30551668); and Ljungberg, et al., *Expert Rev Vaccines*. (2015) 14(2):177-94). In various embodiments, the viral vector is from a virus selected from the group consisting of adenovirus, adeno-associated virus, arenavirus, alphavirus, self-replicating alphavirus, poxvirus, cytomegalovirus, rhabdovirus, vesicular stomatitis virus, flavivirus, maraba virus and vaccinia virus. In some embodiments, the viral vector is from a viral family selected from the group consisting of: Adenoviridae (e.g., Adenovirus, adeno-associated virus), Arenaviridae (e.g., lymphocytic choriomeningitis mammarenavirus, Cali mammarenavirus (a.k.a., Pichinde mammarenavirus), Herpesviridae (e.g., Cytomegalovirus, Herpesvirus, e.g., HSV-1), Parvoviridae (e.g., Parvovirus H1), Poxviridae (e.g. Vaccinia virus, e.g. modified vaccinia Ankara (MVA)), Paramyxoviridae (e.g. measles virus), Flaviviridae (e.g. Yellow fever virus), Reoviridae (e.g., Reovirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesiculovirus, including Maraba vesiculovirus and Vesicular stomatitis virus (VSV)), Togaviridae (e.g., Alphavirus, e.g., self-replicating Alphavirus; Sindbis virus), Enteroviridae (e.g., Echovirus). Illustrative modified vaccinia viral vectors of use for expressing the present fusion polypeptides are described, e.g., in WO 2019/134049.

In some embodiments, the viral expression vector is an arenavirus vector selected from Lymphocytic choriomeningitis mammarenavirus (LCMV)(NCBI:txid11623), Cali mammarenavirus (a.k.a., Pichinde mammarenavirus or Pichinde arenavirus) (NCBI:txid2169993), Guanarito virus (GTOV) (NCBI:txid45219), Argentinian mammarenavirus (a.k.a., Junin virus (JUNV))(NCBI:txid2169991), Lassa virus (LASV)(NCBI:txid11620), Lujo virus (LUJV)(NCBI:txid649188), Machupo virus (MACV)(NCBI:txid11628), Brazilian mammarenavirus (a.k.a., Sabia virus (SABV)) (NCBI:txid2169992), and Whitewater Arroyo virus (WWAV)(NCBI:txid46919). In some embodiments, the viral expression vector is an arenavirus vector selected from Lymphocytic choriomeningitis mammarenavirus (LCMV) or Cali mammarenavirus (a.k.a., Pichinde mammarenavirus or Pichinde arenavirus). Illustrative arenavirus vectors that can be used as delivery and expression vehicles for the herein described fusion polypeptides are described, e.g., in WO 2009/083210; WO 2015/183895; WO 2016/075250; WO 2017/198726; and U.S. Pat. No. 9,943,585.

In some embodiments, the viral expression vector is an adenovirus vector, e.g., from a human adenovirus or a simian adenovirus (e.g., a chimpanzee adenovirus, a gorilla adenovirus or a rhesus monkey adenovirus). In various embodiments, the adenovirus vector is selected from adenovirus serotype 5 (Ad5), adenovirus serotype 26 (Ad26), adenovirus serotype 34 (Ad34), adenovirus serotype 35 (Ad35), adenovirus serotype 48 (Ad48), chimpanzee adenovirus (e.g. ChAd3 (AdC3), ChAd5 (AdC5), ChAd6 (AdC6), ChAd7 (AdC7), ChAd8 (AdC8), ChAd9 (AdC9), ChAd10 (AdC10), ChAd11 (AdC11), ChAd17 (AdC17), ChAd16 (AdC16), ChAd19 (AdC19), ChAd20 (AdC20), ChAd22 (AdC22), ChAd24 (AdC24), ChAdY25 (AdC25), ChAd26 (AdC26), ChAd28 (AdC28), ChAd30 (AdC30), ChAd31 (AdC31), ChAd37 (AdC37), ChAd38 (AdC38), ChAd43 (AdC43), ChAd44 (AdC44), ChAd55 (AdC55), ChAd63 (AdC63), ChAdV63, ChAd68 (AdC68), ChAd73 (AdC73), ChAd82 (AdC82), ChAd83 (AdC83), ChAd143 (AdC143), ChAd144 (AdC144), ChAd145 (AdC145), ChAd147 (AdC147)), gorilla adenovirus (e.g. GC44, GC45, GC46) and rhesus adenovirus (e.g., RhAd51, RhAd52, RhAd53, RhAd54, RhAd55, RhAd56, RhAd57, RhAd58, RhAd59, RhAd60, RhAd61, RhAd62, RhAd63, RhAd64, RhAd65, RhAd66). Illustrative Chimpanzee, Gorilla and Rhesus monkey adenovirus vectors that can be used as delivery and expression vehicles for the herein described fusion polypeptides are described, e.g., in WO 2019/076880; WO 2019/076877; Andrabi et al., (2019) *Cell Reports* 27:2426-2441Guo, et al., *Hum Vaccin Immunother*. (2018) 14(7): 1679-1685; Abbink, et al., *J Virol*. (2015) 89(3):1512-22; and Abbink, et al., *J Virol*. (2018) 92(6). pii: e01924-17.

In various embodiments, the viral expression vector is incapable of replication (i.e.., replication defective or replication deficient), has reduced or diminished capacity for replication, e.g., in comparison to a wild-type viral vector (i.e., replication attenuated) or is replication competent.

In various embodiments, the viral vector or viral expression vector is an adenoviral vector comprising one or more polynucleotides that encode one or more fusion proteins comprising an amino acid sequence of any one of any one of SEQ ID NOs: 345-377, 407-411, 422-424, 430-435, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 345-377, 407-411, 422-424, 430-435.

In various embodiments, the viral vector or viral expression vector comprises two or more polynucleotides encoding two or more fusion proteins that are at least 80%, 81%, 82%, 83%, 84%, 85%, 86%, 87%, 88%, 89%, 90%, 91%, 92%, 93%, 94%, 95%, 96%, 97%, 98%, 99% identical, or 100% identical, to the following amino acid sequences: SEQ ID NOs: 345 and 346; SEQ ID NOs: 347 and 348; SEQ ID NOs: 349 and 350; SEQ ID NOs: 351 and 352; SEQ ID NOs: 430 and 352; SEQ ID NOs: 357 and 358; SEQ ID NOs: 360 and 362; SEQ ID NOs: 359 and 361; SEQ ID NOs: 351 and 357; SEQ ID NOs: 351 and 358; SEQ ID NOs: 351 and 359; SEQ ID NOs: 351 and 360; SEQ ID NOs: 351 and 361; SEQ ID NOs: 351 and 362; SEQ ID NOs: 351 and 407; SEQ ID NOs: 351 and 408; SEQ ID NOs: 351 and 409; SEQ ID NOs: 351 and 410; SEQ ID NOs: 352 and 357; SEQ ID NOs: 352 and 358; SEQ ID NOs: 352 and 359; SEQ ID NOs: 352 and 360; SEQ ID NOs: 352 and 361; SEQ ID NOs: 352 and 362; SEQ ID NOs: 352 and 407; SEQ ID NOs: 352 and 408; SEQ ID NOs: 352 and 409; SEQ ID NOs: 352 and 410; SEQ ID NOs: 430 and 357; SEQ ID NOs: 430 and 358; SEQ ID NOs: 430 and 359; SEQ ID NOs: 430 and 360; SEQ ID NOs: 430 and 361; SEQ ID NOs: 430 and 362; SEQ ID NOs: 407 and 409; SEQ ID NOs: 407 and 408; SEQ ID NOs: 408 and 410; or SEQ ID NOs: 409 and 410.

In some embodiments, the vector further comprises a polynucleotide encoding a cytokine or functional variant thereof, or a non-coding immunostimulatory polynucleotide. In some embodiments, the vector further comprises a polynucleotide encoding a cytokine selected from the group consisting of IL-2, IL-7, IL-12, IL-15, IL-18, IL-21, IFN-α, IFN-γ, colony stimulating factor 2 (CSF2; a.k.a., GM-CSF), fms related receptor tyrosine kinase 3 ligand (FLT3LG), and combinations and functional variants thereof. Co-expression and/or co-administration of a cytokine with a vaccine is described, e.g., by Elizaga, et al. (2018) *PLoS One* 13(9): e0202753 (IL-12); Buchbinder, et al., (2017) *PLoS One* 12(7):e0179597 (GM-CSF); Abaitua, et al., *Virus Res* (2006) 116(1-2):11-20 (IL12+IFN-γ); Oudard, et al., *Cancer Immunol Immunother* (2011) February; 60(2):261-71 (IL-2+IFN-α). In some embodiments, the vector further comprises a non-coding immunostimulatory polynucleotide selected from a pathogen-activated molecular pattern (PAMP), a cytosine-phosphate-guanosine (CpG) oligodeoxynucleotide, and an immunostimulatory RNA (isRNA). Illustrative isRNA include CV8102 (CureVac) and others, described in e.g., WO2016170176.

Further provided are host cells comprising one or more polynucleotides encoding one or more of the fusion polypeptides or one or more vectors expressing the fusion polypeptides, as described herein. Any of a variety of host cells can be used. In one embodiment, a host cell is a prokaryotic cell, for example, *E. coli*. In another embodiment, a host cell is a eukaryotic cell, for example, a yeast cell, a plant cell, an insect cell, a mammalian cell, such as a Chinese Hamster Ovary (CHO)-based or CHO-origin cell line (e.g., CHO-S, CHO DG44, ExpiCHO™, CHOZN® ZFN-modified GS–/– CHO cell line, CHO-K1, CHO-K1a), COS cells, BHK cells, NSO cells or Bowes melanoma cells. Examples of human host cells are, inter alia, HeLa, 911, AT1080, A549 and HEK293 (e.g., HEK293E, HEK293F, HEK293H, HEK293T, Expi293™). In addition, the fusion polypeptides can be expressed in a yeast cell such as *Pichia* (see, e.g., Powers et al., *J Immunol Methods.* 251:123-35 (2001)), *Hanseula*, or *Saccharomyces*.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As appropriate, the host cells can be stably or transiently transfected with one or more polynucleotides encoding one or more fusion polypeptides, as described herein. As appropriate, the host cells can be infected with one or more vectors expressing one or more fusion polypeptides, as described herein. In some embodiments, the host cells are capable of being infected with and propagating one or more replication attenuated or replication competent vectors expressing one or more fusion polypeptides, as described herein. Illustrative cells useful for infecting with and/or propagating viral vectors include without limitation BHK-21, A549, Vero and HEK293 (e.g., HEK293E, HEK293F, HEK293H, HEK293T, Expi293™) cells. In certain embodiments, the host cells express the Coxsackievirus and adenovirus receptor (CAR), e.g., MDCK, Caco-2 or Calu-3 host cells. In certain embodiments, the polynucleotides integrate into the genome of the host cell.

5. Pharmaceutical Compositions/Immunogenic Compositions

Provided are pharmaceutical compositions or immunogenic compositions comprising one or more of the fusion polypeptides, as described herein, or a polynucleotide encoding one or more of the fusion polypeptides, as described herein, or a viral expression vector comprising one or more of such polynucleotides, and a pharmaceutically acceptable diluent, carrier or excipient. Generally, the pharmaceutical compositions described herein are immunogenic. In certain embodiments, the pharmaceutical composition comprises a therapeutically effective amount of the one or more fusion polypeptides, or one or more polynucleotides encoding one or more of the fusion polypeptides, or one or more viral expression vectors containing one or more of the polynucleotides encoding one or more of the fusion polypeptides.

Various pharmaceutically acceptable diluents, carriers, and excipients, and techniques for the preparation and use of pharmaceutical compositions will be known to those of skill in the art in light of the present disclosure. Illustrative pharmaceutical compositions and pharmaceutically acceptable diluents, carriers, and excipients are also described in, e.g., Loyd V. Allen Jr (Editor), "Remington: The Science and Practice of Pharmacy," 22$^{nd}$ Edition, 2012, Pharmaceutical Press; Brunton, Knollman and Hilal-Dandan, "Goodman and Gilman's The Pharmacological Basis of Therapeutics," 13th Edition, 2017, McGraw-Hill Education/Medical; McNally and Hastedt (Editors), "Protein Formulation and Delivery, 2nd Edition, 2007, CRC Press; Banga, "Therapeutic Peptides and Proteins: Formulation, Processing, and Delivery Systems," 3rd Edition, 2015, CRC Press; Lars Hovgaard, Frokjaer and van de Weert (Editors), "Pharmaceutical Formulation Development of Peptides and Proteins," 2nd Edition, 2012, CRC Press; Carpenter and Manning (Editors), "Rational Design of Stable Protein Formulations: Theory and Practice," 2002, Springer (Pharmaceutical Biotechnology (Book 13)); Meyer (Editor), "Therapeutic Protein Drug Products: Practical Approaches to Formulation in the Laboratory, Manufacturing, and the Clinic, 2012, Woodhead Publishing.

In certain embodiments, the polynucleotides or vectors are formulated into lipid nanoparticles. For example, in some embodiments where the fusion polypeptides are expressed from self-replicating or self-amplifying RNA molecules, the self-replicating or self-amplifying RNA can be formulated into lipoplexes, such as lipid nanoparticles (LNPs). As used herein, a "lipoplex" refers to cationic liposomes that are nonviral (synthetic) lipid carriers of DNA. As used herein, the term "lipid nanoparticle" refers to one or more spherical nanoparticles with an average diameter of between about 10 to about 1000 nanometers, and which comprise a solid lipid core matrix that can solubilize lipophilic molecules. In certain embodiments, the lipid core is stabilized by surfactants (e.g., emulsifiers), and can comprise one or more of triglycerides (e.g., tristearin), diglycerides (e.g., glycerol bahenate), monoglycerides (e.g., glycerol monostearate), fatty acids (e.g., stearic acid), steroids (e.g., cholesterol), and waxes (e.g., cetyl palmitate), including combinations thereof. Lipid nanoparticles are described, for example, in Petrilli et al., Curr Pharm Biotechnol.

15:847-55, 2014; and U.S. Pat. Nos. 6,217,912; 6,881,421; 7,402,573; 7,404,969; 7,550,441; 7,727,969; 8,003,621; 8,691,750; 8,871,509; 9,017,726; 9,173,853; 9,220,779; 9,227,917; and 9,278,130, each of which is incorporated by reference in its entirety. In one embodiment, a self-replicating or self-amplifying RNA molecule encoding one or more of the fusion polypeptides described herein is formulated or condensed into polyethylenimine (PEI)-polyplex delivery vehicles, e.g., as described in Demoulins, et al., Nanomedicine. (2016) April; 12(3):711-722 and Demoulins, et al., *J Control Release.* (2017) November 28; 266:256-271, which can be nanoparticulate.

In embodiments where the fusion polypeptides are expressed from a viral expression vector, the viral expression vector can be formulated for the desired route of administration, e.g., as an isotonic pharmaceutically acceptable aqueous solution for intravenous, intramuscular, subcutaneous or intradermal administration. In some embodiments, the viral expression vector can be formulated for mucosal, e.g., buccal, intranasal or intrarectal delivery. Illustrative formulations for viral expression vectors that can be used in the herein described pharmaceutical compositions and methods are described, e.g., in Manfredsson and Benskey, editors, "Viral Vectors for Gene Therapy: Methods and Protocols (Methods in Molecular Biology)," 2019, Book 1937 in Methods in Molecular Biology Series, Humana Press; WO 2017/013169 (formulation of Adenoviral vectors in an aqueous mixture or freeze dried composition in the presence of amorphous sugar and low salt concentration); and Kumru, et al., *J Pharm Sci.* (2018) November; 107(11): 2764-2774 (aqueous formulations buffered in Tris and containing proline, lactose, and mannitol as stabilizing additives). Formulation of arenavirus vectors is described, e.g., in WO 2009/083210; WO 2016/075250 and WO 2017/198726. In certain embodiments, the viral expression vectors are delivered via microneedle-mediated delivery, e.g., as described in Zaric, et al., *Expert Opin Drug Deliv.* (2017) October; 14(10):1177-1187. Intranasal viral vaccination by administration of viral particles to the nares is described, e.g., in Dorta-Estremera, et al., *PLoS One.* 2017 Dec. 8; 12(12):e0188807. Intrarectal viral vaccination by administration of viral particles to the rectum is described, e.g., in Patterson, et al., *Clin Vaccine Immunol.* (2012) May; 19(5): 629-37.

In some embodiments, each carrier, diluent or excipient is "acceptable" in the sense of being compatible with the other ingredients of the pharmaceutical composition and not injurious to the subject. Often, the pharmaceutically acceptable carrier is an aqueous pH-buffered solution. Some examples of materials which can serve as pharmaceutically-acceptable carriers, diluents or excipients include: water; buffers, e.g., a buffer having a pKa in the range of about 6.0 to about 8.0, e.g., a physiologically acceptable buffer, e.g., selected from phosphate, carbonate, bicarbonate, citrate, maleate, glycine-glycine, HEPES, HEPPSO, HEPPS, imidazole, BICINE, TRICINE, Tris, and BIS-Tris; sugars, such as lactose, trehalose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Hank's solution, Ringer's solution; ethyl alcohol; phosphate buffer solutions; amino acids (e.g., charged amino acids, including without limitation, aspartate, asparagine, glutamate, glutamine, histidine, arginine, lysine); and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Solid and semi-solid formulations that can be used for intravaginal or intrarectal (e.g., in the form of a troche, a pessary or a suppository) delivery of viral expression vectors, virosomes or virus-like particles (VLPs) is described, e.g., in Brown, et al., *PLoS One.* 2017 Aug. 17; 12(8):e0183510; Brown, et al., *PLoS One.* 2016 Mar. 10; 11(3):e0151184; and Amacker, et al., *npj Vaccines* 5, 41 (2020).

In one particular formulation, an arenavirus vector (e.g., a LCMV or Pichinde mammarenavirus vector) described herein is formulated in an isotonic aqueous solution comprising a biologically compatible buffer having a pKa in the range of about 6.0 to about 8.0 (e.g., HEPES and NaCl), at a neutral or near-neutral pH and a non-ionic surfactant (e.g., PLURONIC® F68 (a.k.a., poloxamer 188)). In one particular formulation, an arenavirus vector (e.g., a LCMV or Pichinde mammarenavirus vector) described herein is formulated in an isotonic aqueous solution comprising HEPES buffer at pH 7.4, NaCl, and PLURONIC® F68 (a.k.a., poloxamer 188). Schleiss, et al. (*Clin Vaccine Immunol.* 2017 Jan. 5; 24(1):e00300-16) describes an LCMV formulating LCMV vectors in a diluent of 25 mM HEPES, 150 mM NaCl, 0.01% PLURONIC® F68; pH 7.4), which can be used to formulate the herein described arenavirus vectors. A final concentration of 10% sorbitol was added before freezing below −60° C.

The formulation of and delivery methods of pharmaceutical compositions will generally be adapted according to the site and the disease to be treated. Exemplary formulations include without limitation, those suitable for parenteral administration, e.g., intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. In some embodiments, the pharmaceutical compositions are formulated for parenteral, e.g., intravenous, subcutaneous, or oral administration. In some embodiments, the pharmaceutical compositions are formulated for mucosal, e.g., buccal, intranasal, intrarectal and/or intravaginal administration.

In certain embodiments, pharmaceutical compositions are sterile. In certain embodiments, the pharmaceutical composition has a pH in the range of 4.5 to 8.5, 4.5 to 6.5, 6.5 to 8.5, or a pH of about 5.0, about 5.5, about 6.0, about 6.5, about 7.0, about 7.5, about 8.0 or about 8.5. In one embodiment, the pharmaceutical composition has an osmolarity in the range of 240-260 or 250-330 mOsmol/L. In certain embodiments, the pharmaceutical composition is isotonic or near isotonic.

In some embodiments, the pharmaceutical compositions are liquids or solids. In some embodiments, the pharmaceutical composition comprises an aqueous solution. In some embodiments, the pharmaceutical composition is lyophilized or is a frozen liquid.

In some embodiments, the pharmaceutical composition further comprises one or more additional therapeutic agents, e.g., a second therapeutic agent, or second and third therapeutic agents, for use in combination therapies, as described herein.

In certain embodiments, the pharmaceutical composition further comprises an adjuvant. Illustrative adjuvants that can be co-formulated or co-administered with the herein described fusion polypeptides, polynucleotides encoding such fusion polypeptides and vectors expressing such fusion polypeptides include without limitation cytokines, chemokines, immune costimulatory molecules, toll-like receptor agonists or inhibitors of immune suppressive pathways, as described herein, and in Li, et al., *Curr Issues Mol Biol.* (2017) 22:17-40. Other adjuvants that can be co-formulated or co-administered with the herein described fusion polypeptides, polynucleotides encoding such fusion polypeptides and vectors expressing such fusion polypeptides include without limitation mineral salts (e.g., aluminum salts (e.g., alum), calcium phosphate, incomplete Freunds's adjuvant), lipid particles (e.g., MF59, cochleates, virus-like particles), microparticles (e.g., virosomes, polylactic acid (PLA), poly[lactide-coglycolide] (PLG)), immune potentiators (e.g., dsRNA:Poly(I:C), Poly-IC:LC, Monophosphoryl lipid A (MPL), LPS, Flagellin, Imidazoquinolines: imiquimod (R837), resiquimod (848), CpG oligodeoxynucleotides (ODN), Muramyl dipeptide (MDP), Saponins (QS-21)), and mucosal adjuvants (e.g., Cholera toxin (CT), Heat-labile enterotoxin (LTK3 and LTR72), Chitosan). Adjuvants that can be co-formulated or co-administered with the herein described fusion polypeptides, polynucleotides encoding such fusion polypeptides and vectors expressing such fusion polypeptides are summarized in Apostólico, et al., *J Immunol Res.* (2016) 2016:1459394.

In certain embodiments, the pharmaceutical composition further comprises an immunomodulator. Illustrative immunomodulators that can be co-formulated or co-administered with the herein described fusion polypeptides, polynucleotides encoding such fusion polypeptides and vectors expressing such fusion polypeptides include without limitation toll-like receptor agonists and small molecule immune checkpoint inhibitors. Example TLR7 agonists that can be co-formulated or co-administered include without limitation AL-034, DSP-0509, GS-9620 (vesatolimod), LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854 and RG-7795. Illustrative TLR7/TLR8 agonists that can be co-formulated or co-administered include CV8102, NKTR-262, telratolimod and BDB-001. Example TLR8 agonists that can be co-formulated or co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052. Example TLR9 agonists that can be co-formulated or co-administered include without limitation AST-008, cobitolimod, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of small molecule inhibitors of CD274 or PDCD1 that can be co-formulated or co-administered include without limitation GS-4224, GS-4416, INCB086550 and MAX10181. An example small molecule inhibitor of CTLA4 that can be co-formulated or co-administered includes BPI-002.

In some embodiments, the pharmaceutical compositions or immunogenic compositions comprise mixtures of two or more fusion polypeptides, two or more polynucleotides encoding such fusion polypeptides, or two or more vectors expressing such fusion polypeptides. For example, in certain embodiments, the mixtures comprise bivalent pairs of fusion polypeptides, as described herein. In some embodiments, the pharmaceutical composition comprises two or more fusion polypeptides, two or more polynucleotides encoding such fusion polypeptides, or two or more vectors expressing such fusion polypeptides, the fusion polypeptides comprising or consisting of the following polypeptide segments in sequential order, from N-terminus to C-terminus, optionally joined or connected by one or more linkers: SEQ ID NOs: 70, 76, 94, 151 and 161; and SEQ ID NOs: 71, 77, 95, 152 and 162. In some embodiments, the pharmaceutical composition comprises two or more fusion polypeptides, two or more polynucleotides encoding such fusion polypeptides, or two or more vectors expressing such fusion polypeptides, the fusion polypeptides comprising or consisting of the following polypeptide segments in sequential order, from N-terminus to C-terminus, optionally joined or connected by one or more linkers: SEQ ID NOs: 188, 305, 28, 41, 294, 4, 176, 11, 319, 259, 282, 223, 213 and 37; SEQ ID NOs: 188, 305, 28, 41 and 294; SEQ ID NOs: 4, 176, 11, 319, 259, 282, 223, 213 and 37; SEQ ID NOs: 189, 306, 29, 42, 295, 5, 177, 12, 320, 260, 283, 224, 214 and 38; SEQ ID NOs: 189, 306, 29, 42 and 295; SEQ ID NOs: 5, 177, 12, 320, 260, 283, 224, 214 and 38; SEQ ID NOs: 305, 319, 259, 282, 223, 213, 294, 176 and 188; SEQ ID NOs: 306, 320, 260, 283, 224, 214, 295, 177 and 189; SEQ ID NOs: 305, 294, 223, 213, 176, 259, 319, 188 and 282; SEQ ID NOs: 306, 295, 224, 214, 177, 260, 320, 189 and 283; SEQ ID NOs: 305, 294, 319, 259, 282, 223, 176, and 188; SEQ ID NOs: 306, 295, 320, 260, 283, 224, 177 and 189; SEQ ID NOs: 305, 223, 294, 176, 259, 319, 188 and 282; and SEQ ID NOs: 306, 224, 295, 177, 260, 320, 189 and 283. In some embodiments, the pharmaceutical composition comprises two or more fusion polypeptides, two or more polynucleotides encoding such fusion polypeptides, or two or more vectors expressing such fusion polypeptides, the fusion polypeptides comprising or consisting of the following polypeptide segments in sequential order, from N-terminus to C-terminus, optionally joined or connected by one or more linkers: SEQ ID NOs: 76, 86, 94, 180, 186, 221, 294, 307, 321 and 151; and SEQ ID NOs: 77, 87, 95, 181, 187, 222, 295, 308, 322 and 152.

In some embodiments, the pharmaceutical composition or immunogenic composition comprises two or more fusion polypeptides, two or more polynucleotides encoding such fusion polypeptides, or two or more vectors expressing such fusion polypeptides, the fusion polypeptides comprising or consisting of an amino acid sequence of any one of SEQ ID NOs: 351-356 and 430, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 351-356 and 430. In some embodiments, the pharmaceutical composition or immunogenic composition comprises two or more fusion polypeptides, two or more polynucleotides encoding such fusion polypeptides, or two or more vectors expressing such fusion polypeptides, the fusion polypeptides comprising or consisting of an amino acid sequence of any one of SEQ ID NOs: 357-366 and 407-410, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 357-366 and 407-410.

In some embodiments, the pharmaceutical composition or immunogenic composition comprises two or more fusion polypeptides, two or more polynucleotides encoding such fusion polypeptides, or two or more vectors expressing such fusion polypeptides, the fusion polypeptides comprising or consisting of an amino acid sequence of any one of SEQ ID NOs: 345-350, the sequences in Table 1, and SEQ ID NOs: 422-424, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 345-350, the sequences in Table 1, and SEQ ID NOs: 422-424.

In some embodiments, the pharmaceutical compositions or immunogenic compositions comprise a first fusion polypeptide or polynucleotide encoding such fusion polypeptide or a vector expressing such fusion polypeptide, the fusion polypeptide comprising one or more polypeptide segments encoded by HIV-1 Gag and Nef genes and a second fusion polypeptide or polynucleotide encoding such fusion polypeptide or viral expression vector expressing such fusion polypeptide, the fusion polypeptide comprising one or more polypeptide segments encoded by HIV-1 Pol or Pol and Env genes. In some embodiments, the pharmaceutical composition or immunogenic composition comprises (1) one or more fusion polypeptides or one or more polynucleotides encoding such fusion polypeptides or one or more vectors expressing such fusion polypeptides, the fusion polypeptide comprising or consisting of the following polypeptide segments in sequential order, from N-terminus to C-terminus, optionally joined or connected by one or more linkers: SEQ ID NOs: 70, 76, 94, 151 and 161; or SEQ ID NOs: 71, 77, 95, 152 and 162; and (2) one or more fusion polypeptides or one or more polynucleotides encoding such fusion polypeptides or one or more vectors expressing such fusion polypeptides, the fusion polypeptide comprising or consisting of the following polypeptide segments in sequential order, from N-terminus to C-terminus, optionally joined or connected by one or more linkers: SEQ ID NOs: 188, 305, 28, 41, 294, 4, 176, 11, 319, 259, 282, 223, 213 and 37; SEQ ID NOs: 188, 305, 28, 41 and 294; SEQ ID NOs: 4, 176, 11, 319, 259, 282, 223, 213 and 37; SEQ ID NOs: 189, 306, 29, 42, 295, 5, 177, 12, 320, 260, 283, 224, 214 and 38; SEQ ID NOs: 189, 306, 29, 42 and 295; SEQ ID NOs: 5, 177, 12, 320, 260, 283, 224, 214 and 38; SEQ ID NOs: 305, 319, 259, 282, 223, 213, 294, 176 and 188; SEQ ID NOs: 306, 320, 260, 283, 224, 214, 295, 177 and 189; SEQ ID NOs: 305, 294, 223, 213, 176, 259, 319, 188 and 282; SEQ ID NOs: 306, 295, 224, 214, 177, 260, 320, 189 and 283; SEQ ID NOs: 305, 294, 319, 259, 282, 223, 176, and 188; SEQ ID NOs: 306, 295, 320, 260, 283, 224, 177 and 189; SEQ ID NOs: 305, 223, 294, 176, 259, 319, 188 and 282; or SEQ ID NOs: 306, 224, 295, 177, 260, 320, 189 and 283. In some embodiments, the pharmaceutical composition or immunogenic composition comprises (1) one or more fusion polypeptides or one or more polynucleotides encoding such fusion polypeptides or one or more vectors expressing such fusion polypeptides, the fusion polypeptide comprising an amino acid sequence of any one of SEQ ID NOs: 351-356 and 430, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 351-356 and 430; and (2) one or more fusion polypeptides or one or more polynucleotides encoding such fusion polypeptides or one or more vectors expressing such fusion polypeptides, the fusion polypeptide comprising an amino acid sequence of any one of SEQ ID NOs: 357-366 and 407-410, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 357-366 and 407-410.

In some embodiments, the pharmaceutical composition or immunogenic composition comprises one or more viral vectors, each viral vector comprising one or more polynucleotides encoding two or more fusion proteins that are at least 80%, 81%, 82%, 83%, 84%, 85%, 86%, 87%, 88%, 89%, 90%, 91%, 92%, 93%, 94%, 95%, 96%, 97%, 98%, 99% identical, or 100% identical, to the following amino acid sequences: SEQ ID NOs: 345 and 346; SEQ ID NOs: 347 and 348; SEQ ID NOs: 349 and 350; SEQ ID NOs: 351 and 352; SEQ ID NOs: 430 and 352; SEQ ID NOs: 357 and 358; SEQ ID NOs: 360 and 362; SEQ ID NOs: 359 and 361; SEQ ID NOs: 351 and 357; SEQ ID NOs: 351 and 358; SEQ ID NOs: 351 and 359; SEQ ID NOs: 351 and 360; SEQ ID NOs: 351 and 361; SEQ ID NOs: 351 and 362; SEQ ID NOs: 351 and 407; SEQ ID NOs: 351 and 408; SEQ ID NOs: 351 and 409; SEQ ID NOs: 351 and 410; SEQ ID NOs: 352 and 357; SEQ ID NOs: 352 and 358; SEQ ID NOs: 352 and 359; SEQ ID NOs: 352 and 360; SEQ ID NOs: 352 and 361; SEQ ID NOs: 352 and 362; SEQ ID NOs: 352 and 407; SEQ ID NOs: 352 and 408; SEQ ID NOs: 352 and 409; SEQ ID NOs: 352 and 410; SEQ ID NOs: 430 and 357; SEQ ID NOs: 430 and 358; SEQ ID NOs: 430 and 359; SEQ ID NOs: 430 and 360; SEQ ID NOs: 430 and 361; SEQ ID NOs: 430 and 362; SEQ ID NOs: 407 and 409; SEQ ID NOs: 407 and 408; SEQ ID NOs: 408 and 410; or SEQ ID NOs: 409 and 410.

In some embodiments, the pharmaceutical composition or immunogenic composition comprises a fusion polypeptide, a polynucleotide encoding such polypeptide or a vector expressing such fusion polypeptide, the fusion polypeptide comprising or consisting of the following polypeptide segments in sequential order, from N-terminus to C-terminus, optionally joined or connected by one or more linkers: SEQ ID NOs: 201, 78, 107, 96, 229, 172, 327, 6, 333, 243, 331, 192, 265, 311, 137, 15, 123, 30, 336, 302, 153, 219, 298, 121, 230, 240, 60, 241, 276, 113, 99, 21, 217 and 215; SEQ ID NOs: 78, 296, 1, 339, 197, 329, 232, 323, 303, 234, 90, 261, 274, 238, 211, 325, 137, 227, 209, 190, 341, 57, 225, 27, 210, 119, 19, 165, 334, 117, 153, 10, 97 and 300; or SEQ ID NOs: 296, 1, 78, 197, 339, 227, 261, 274, 238, 325, 137, 329, 303, 234, 90, 232, 27, 57, 225, 323, 190, 341, 119, 19, 165, 334, 117, 153, 10, 97 and 300. In some embodiments, the pharmaceutical composition or immunogenic composition comprises a fusion polypeptide, a polynucleotide encoding such polypeptide or a vector expressing such fusion polypeptide, the fusion polypeptide comprising or consisting of an amino acid sequence of any one of SEQ ID NOs: 367-377, 411, 422-424 and 431-435, or a sequence that is 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 367-377, 411, 422-424 and 431-435.

6. Methods of Treatment

Further provided are methods for treating or preventing an HIV infection or a related disease or disorder in a subject in need thereof (e.g., a human subject), comprising providing to a subject in need thereof an effective amount of one or more fusion polypeptides, as described herein, or one or more polynucleotides encoding one or more fusion polypeptides, as described herein, or one or more vectors expressing one or more fusion polypeptides, as described herein. As used herein, the term "subject" refers to a mammal. The mammal can be any mammal, for example, a human, a non-human primate (e.g., a macaque), a rodent (e.g., mouse, rat, guinea pig), a dog, a cat, or a domesticated animal such as a cow, a horse, a goat, a camel, a sheep or a pig. The term "patient" refers to a human subject. As used herein, the term "effective amount" in the context of the administration of a therapy to a subject refers to the amount of a therapy that achieves a desired prophylactic or therapeutic effect. The polynucleotide may be present in a vector, e.g., a viral vector, as described herein. In some embodiments, the related disease or disorder is caused by infection with HIV. In other embodiments, it is acquired immune deficiency syndrome (AIDS). In certain embodiments, the subject is a virologically suppressed HIV-infected mammal, while in other embodiments, the subject is a treatment-naïve HIV-infected mammal or a treatment experienced HIV-infected subject that is not virologically suppressed. In certain embodiments, a treatment-naïve subject has a viral load between <50 copies/mL and $10^8$ copies/ml. In certain embodiments, a virologically suppressed subject has a viral load <50 copies/ml. In another embodiment, the subject is a mammal, e.g., a human. In certain embodiments, the subject has been diagnosed with an HIV, e.g., HIV-1 or HIV-2, infection or a related disease or disorder, e.g., AIDS, or is considered at risk for developing an HIV, e.g., HIV-1 or HIV-2, infection or a related disease or disorder, e.g., AIDS. Subjects at risk for HIV-related diseases or disorders include patients who have come into contact with an infected person or who have been exposed to HIV in some other way. Administration of a prophylactic agent can occur prior to the manifestation of symptoms characteristic of HIV-related disease or disorder, such that a disease or disorder is prevented or, alternatively, delayed in its progression.

In some embodiments, the subject is chronically infected with HIV-1. In some embodiments, the subject is acutely infected with HIV-1, e.g., has an HIV-1 infection of Fiebig stage IV or earlier, e.g. Fiebig stage III, Fiebig stage II or Fiebig stage I. In some embodiments, the subject is not receiving antiretroviral therapy (ART) or ART is discontinued prior to administration of the one or more compositions. In some embodiments, ART is discontinued after one or more administrations of the compositions. In some embodiments, ART is administered concurrently with administration of one or more fusion polypeptides, as described herein, or one or more polynucleotides encoding one or more fusion polypeptides, as described herein, or one or more vectors expressing one or more fusion polypeptides, as described herein.

Also provided are methods for preventing or inhibiting an increase in HIV virus titer, virus replication, virus proliferation or an amount of an HIV viral DNA, HIV proviral DNA, or HIV viral protein in a subject (e.g., a human subject). In one embodiment, the method comprises providing to the subject in need thereof an amount of an one or more fusion polypeptides, as described herein, or one or more polynucleotides encoding one or more fusion polypeptides, as described herein, or one or more vectors expressing one or more fusion polypeptides, as described herein, effective to prevent an increase in HIV titer, virus replication, or an amount of an HIV protein of one or more HIV strains or isolates in the subject. In certain embodiments, the method further comprises measuring an amount of HIV viral or proviral DNA or protein at one or more time points, e.g., before and after the subject in provided with one or more fusion polypeptides, as described herein, or one or more polynucleotides encoding one or more fusion polypeptides, as described herein, or one or more vectors expressing one or more fusion polypeptides, as described herein. Methods and biomarkers for determining an amount of HIV viral or proviral DNA or protein in a subject are known and available in the art, and described for example, in Siliciano, J. D. et al., Curr Opin. HIV AIDS, 5(6):491-7 (2010), and Rouzioux, C. et al., Curr Opin HIV AIDS, 8(3):170-5 (2013).

In some embodiments, one or more fusion polypeptides, as described herein, or one or more polynucleotides encoding one or more fusion polypeptides, as described herein, or one or more vectors expressing one or more fusion polypeptides, as described herein, may be used in, for example, methods of inhibiting certain viruses such as HIV isolates described herein, prophylactic inhibiting or preventing infections of certain viruses such as HIV isolates described herein, detection of certain viruses such as HIV isolates described herein in a sample, inhibiting certain viruses such as HIV isolates described herein, or diagnosis of certain viruses such as HIV isolates described herein.

For in vivo treatment of mammalian subject, e.g., humans, the subject may be administered or provided a pharmaceutical composition comprising one or more fusion polypeptides, as described herein, or one or more polynucleotides encoding one or more fusion polypeptides, as described herein, or one or more vectors expressing one or more fusion polypeptides, as described herein. When used for in vivo therapy, the one or more fusion polypeptides, as described herein, or one or more polynucleotides encoding one or more fusion polypeptides, as described herein, or one or more vectors expressing one or more fusion polypeptides, as described herein, are typically administered or provided to the patient in therapeutically effective amounts (i.e., amounts that eliminate or reduce the patient's viral burden and/or viral reservoir). The one or more fusion polypeptides, as described herein, or one or more polynucleotides encoding one or more fusion polypeptides, as described herein, or one or more vectors expressing one or more fusion polypeptides, as described herein, are administered or provided to a mammalian subject, e.g., a human, in accord with known methods, such as, but not limited to, intravenous administration, e.g., as a bolus or by continuous infusion over a period of time, by intramuscular, intraperitoneal, intracerebrospinal, subcutaneous, intraarticular, intrasynovial, intrathecal, oral, topical, or inhalation routes. The one or more fusion polypeptides, as described herein, or one or more polynucleotides encoding one or more fusion polypeptides, as described herein, or one or more vectors expressing one or more fusion polypeptides, as described herein, may be administered parenterally, when possible, at the target cell site, or intravenously. In one embodiment, administration of the one or more fusion polypeptides, as described herein, or one or more polynucleotides encoding one or more fusion polypeptides, as described herein, or one or more vectors expressing one or more fusion polypeptides, as described herein, to the subject is via an intravenous route. In another embodiment, administration of the one or more fusion polypeptides, as described herein, or one or more polynucleotides encoding one or more fusion polypeptides, as described herein, or one or more vectors expressing one or more fusion polypeptides, as described herein, to the subject is via a subcutaneous route. In additional embodiments, pharmaceutical compositions of the disclosure are administered to a subject systemically, parenterally, or locally (e.g., mucosally, including buccal, intrarectal and/or intravaginal routes).

In certain embodiments, the present disclosure provides a method for treating an HIV infection, comprising administering to a human subject in need thereof a therapeutically effective amount of one or more fusion polypeptides, as described herein, or one or more polynucleotides encoding one or more fusion polypeptides, as described herein, or one or more vectors expressing one or more fusion polypeptides, as described herein. In some embodiments, the present disclosure provides a method for preventing an HIV infection, comprising administering to a human subject in need thereof a therapeutically effective amount of one or more fusion polypeptides, as described herein, or one or more polynucleotides encoding one or more fusion polypeptides, as described herein, or one or more vectors expressing one or more fusion polypeptides, as described herein.

In various embodiments, the methods comprise administering a single fusion polypeptide, or a polynucleotide or viral expression vector encoding the fusion polypeptide, wherein the fusion polypeptide comprises two or more multivalent polypeptide segments, e.g., bivalent polypeptide segments. In some embodiments, two or more fusion polypeptides, or two or more viral expression vectors encoding the fusion polypeptides, are administered to the subject simultaneously or concurrently. In some embodiments, the two or more fusion polypeptides, or two or more polynucleotides or two or more viral expression vectors encoding the fusion polypeptides, are in the form of a bivalent antigen composition.

In some embodiments, the methods entail administering to the subject: (1) one or more fusion polypeptides, or polynucleotides encoding, or viral expression vectors expressing the fusion polypeptides, the fusion polypeptides comprising or consisting of the following polypeptide segments in sequential order, from N-terminus to C-terminus, optionally joined or connected by one or more linkers: SEQ ID NOs: 70, 76, 94, 151 and 161; or SEQ ID NOs: 71, 77, 95, 152 and 162; and (2) one or more fusion polypeptides, or polynucleotides encoding, or viral expression vectors expressing the fusion polypeptides, the fusion polypeptides comprising or consisting of the following polypeptide segments in sequential order, from N-terminus to C-terminus, optionally joined or connected by one or more linkers: SEQ ID NOs: 188, 305, 28, 41, 294, 4, 176, 11, 319, 259, 282, 223, 213 and 37; SEQ ID NOs: 188, 305, 28, 41 and 294; SEQ ID NOs: 4, 176, 11, 319, 259, 282, 223, 213 and 37; SEQ ID NOs: 189, 306, 29, 42, 295, 5, 177, 12, 320, 260, 283, 224, 214 and 38; SEQ ID NOs: 189, 306, 29, 42 and 295; SEQ ID NOs: 5, 177, 12, 320, 260, 283, 224, 214 and 38; SEQ ID NOs: 305, 319, 259, 282, 223, 213, 294, 176 and 188; SEQ ID NOs: 306, 320, 260, 283, 224, 214, 295, 177 and 189; SEQ ID NOs: 305, 294, 223, 213, 176, 259, 319, 188 and 282; SEQ ID NOs: 306, 295, 224, 214, 177, 260, 320, 189 and 283; SEQ ID NOs: 305, 294, 319, 259, 282, 223, 176, and 188; SEQ ID NOs: 306, 295, 320, 260, 283, 224, 177 and 189; SEQ ID NOs: 305, 223, 294, 176, 259, 319, 188 and 282; or SEQ ID NOs: 306, 224, 295, 177, 260, 320, 189 and 283.

In some embodiments, the methods entail administering to the subject: (1) one or more fusion polypeptides, or polynucleotides encoding, or viral expression vectors expressing the fusion polypeptides, the fusion polypeptides comprising or consisting of an amino acid sequence of any one of SEQ ID NOs: 351-356 and 430, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 351-356 and 430; and (2) one or more fusion polypeptides, or polynucleotides encoding, or viral expression vectors expressing the fusion polypeptides, the fusion polypeptides comprising or consisting of an amino acid sequence of any one of SEQ ID NOs: 357-366 and 407-410, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 357-366 and 407-410.

In some embodiments, the method comprises administering to the subject one or more viral vectors, wherein each viral vector comprises two or more polynucleotides encoding two or more fusion proteins that are at least 80%, 81%, 82%, 83%, 84%, 85%, 86%, 87%, 88%, 89%, 90%, 91%, 92%, 93%, 94%, 95%, 96%, 97%, 98%, 99% identical, or 100% identical, to the following amino acid sequences: SEQ ID NOs: 345 and 346; SEQ ID NOs: 347 and 348; SEQ ID NOs: 349 and 350; SEQ ID NOs: 351 and 352; SEQ ID NOs: 430 and 352; SEQ ID NOs: 357 and 358; SEQ ID NOs: 360 and 362; SEQ ID NOs: 359 and 361; SEQ ID NOs: 351 and 357; SEQ ID NOs: 351 and 358; SEQ ID NOs: 351 and 359; SEQ ID NOs: 351 and 360; SEQ ID NOs: 351 and 361; SEQ ID NOs: 351 and 362; SEQ ID NOs: 351 and 407; SEQ ID NOs: 351 and 408; SEQ ID NOs: 351 and 409; SEQ ID NOs: 351 and 410; SEQ ID NOs: 352 and 357; SEQ ID NOs: 352 and 358; SEQ ID NOs: 352 and 359; SEQ ID NOs: 352 and 360; SEQ ID NOs: 352 and 361; SEQ ID NOs: 352 and 362; SEQ ID NOs: 352 and 407; SEQ ID NOs: 352 and 408; SEQ ID NOs: 352 and 409; SEQ ID NOs: 352 and 410; SEQ ID NOs: 430 and 357; SEQ ID NOs: 430 and 358; SEQ ID NOs: 430 and 359; SEQ ID NOs: 430 and 360; SEQ ID NOs: 430 and 361; SEQ ID NOs: 430 and 362; SEQ ID NOs: 407 and 409; SEQ ID NOs: 407 and 408; SEQ ID NOs: 408 and 410; or SEQ ID NOs: 409 and 410.

In some embodiments, the methods entail administering to the subject one or more fusion polypeptides, or polynucleotides encoding, or viral expression vectors expressing the fusion polypeptides, the fusion polypeptides comprising or consisting of the following polypeptide segments in sequential order, from N-terminus to C-terminus, optionally joined or connected by one or more linkers: SEQ ID NOs: 201, 78, 107, 96, 229, 172, 327, 6, 333, 243, 331, 192, 265, 311, 137, 15, 123, 30, 336, 302, 153, 219, 298, 121, 230, 240, 60, 241, 276, 113, 99, 21, 217 and 215; SEQ ID NOs: 78, 296, 1, 339, 197, 329, 232, 323, 303, 234, 90, 261, 274, 238, 211, 325, 137, 227, 209, 190, 341, 57, 225, 27, 210, 119, 19, 165, 334, 117, 153, 10, 97 and 300; or SEQ ID NOs: 296, 1, 78, 197, 339, 227, 261, 274, 238, 325, 137, 329, 303, 234, 90, 232, 27, 57, 225, 323, 190, 341, 119, 19, 165, 334, 117, 153, 10, 97 and 300.

In some embodiments, the methods entail administering to the subject one or more fusion polypeptides, or polynucleotides encoding, or viral expression vectors expressing the fusion polypeptides, the fusion polypeptides comprising or consisting of an amino acid sequence of any one of SEQ ID NOs: 367-377, 411, 422-424 and 431-435, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 367-377, 411, 422-424 and 431-435.

In some embodiments, the methods entail administering one or more viral expression vectors that express one or more of the fusion polypeptides. In various embodiments, the methods entail administering from about $10^3$ to about $10^{12}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$, $10^{12}$, $10^{13}$, $10^{14}$ or $10^{15}$ viral FFU or PFU or IU or vp, per administration.

In various embodiments, the methods implement a prime-boost regimen. In various embodiments, the prime-boost regimen comprises administering a priming composition at a first time point and administering one or more boosting compositions at one or more subsequent time points (e.g., prime-boost-boost-boost, etc.). In various embodiments, the prime-boost regimen comprises one or more iterations of administering a priming composition at a first time point and administering a boosting composition at a second time point (e.g., prime-boost-prime-boost, etc.). Implementing a prime-boost regimen comprises one or more iterations of administering a priming composition at a first time point and administering a boosting composition at a second time point (e.g., prime-boost-prime-boost, etc.) can facilitate an immune response predominantly focused or trained on the fusion polypeptides, and reduce or avoid inducing an immune response focused or trained on the vector backbone and/or vector specific proteins. In some embodiments, the administrations of the priming composition and the one or more boosting compositions are spaced at least 1 week, 2 weeks, 3 weeks or 1 month apart, e.g., at least 2, 3, 4, 5 or 6 months, apart. In some embodiments, the priming composition and the boosting composition comprise the same immunogenic composition. In some embodiments, the priming composition and the boosting composition comprise different immunogenic compositions. In some embodiments, the priming composition and the boosting composition comprise the same one or more fusion polypeptides and same polynucleotide or viral expression vector. In some embodiments, the priming composition and the boosting composition comprise different fusion polypeptides and the same polynucleotide or viral expression vectors. In some embodiments, the priming composition and the boosting composition comprise the same fusion polypeptides and different polynucleotide or viral expression vectors. In some embodiments, the methods entail priming with a first polynucleotide or viral expression vector, and boosting with a second polynucleotide or viral expression vector.

In various embodiments, the prime-boost regimen comprises:
a) Priming with a viral expression vector and boosting with a polynucleotide, wherein the polynucleotide is DNA, cDNA, mRNA or self-replicating RNA;
b) Priming with a polynucleotide, wherein the polynucleotide is DNA, cDNA, mRNA or self-replicating RNA, and boosting with a viral expression vector;
c) Priming with a first viral expression vector and boosting with a second viral expression vector, wherein the first and second viral expression vectors are from identical, related or unrelated taxonomical families;
d) Priming with a first replication deficient viral expression vector and boosting with a second replication deficient viral expression vector, wherein the first and second replication deficient viral expression vectors are from identical, related or unrelated taxonomical families;
e) Priming with a first attenuated deficient viral expression vector and boosting with a second replication attenuated viral expression vector, wherein the first and second replication attenuated viral expression vectors are from identical, related or unrelated taxonomical families;
f) Priming with a replication deficient viral expression vector and boosting with a replication attenuated viral expression vector;
g) Priming with a replication attenuated viral expression vector and boosting with a replication deficient viral expression vector;
h) Priming with a Lymphocytic choriomeningitis mammarenavirus (LCMV) viral expression vector and boosting with a Pichinde mammarenavirus viral expression vector;
i) Priming with a Pichinde mammarenavirus viral expression vector and boosting with a Lymphocytic choriomeningitis mammarenavirus (LCMV) viral expression vector;
j) Priming with an arenavirus viral expression vector and boosting with an adenovirus viral expression vector; or
k) Priming with an adenovirus viral expression vector and boosting with an arenavirus viral expression vector.

In some embodiments, after one or more administrations of the one or more fusion polypeptides, as described herein, or one or more polynucleotides encoding one or more fusion polypeptides, as described herein, or one or more vectors expressing one or more fusion polypeptides, as described herein, optionally with one or more additional therapeutic agents, described herein, the subject does not exhibit symptoms of HIV or AIDS in the absence of anti-retroviral treatment (ART) for at least 6 months, at least 1 year, at least 2 years, at least 3 years, or more. In some embodiments, after one or more administrations of the binding molecule, the subject has a viral load of copies/ml blood of less than 500, e.g., less than 400, less than 300, less than 200, less than 100, less than 50, in the absence of anti-retroviral treatment (ART) for at least 6 months, at least 1 year, at least 2 years, at least 3 years, or more.

7. Combination Therapies

In certain embodiments, a method for treating or preventing an HIV infection in a human having or at risk of having the infection is provided, comprising administering to the human a therapeutically effective amount of one or more fusion polypeptides, or polynucleotides encoding or vectors expressing such fusion polypeptides, as disclosed herein, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In various embodiments, of one or more fusion polypeptides, or polynucleotides encoding or vectors expressing such fusion polypeptides, as disclosed herein, are administered in combination with one or more (e.g., one, two, three, one or two, or one to three) additional therapeutic agents.

In certain embodiments, the provided are methods for treating an HIV infection, comprising administering to a patient in need thereof a therapeutically effective amount of a compound disclosed herein, or a pharmaceutically acceptable salt thereof, in combination with a therapeutically effective amount of one or more (e.g., one, two, three, one or two, or one to three) additional therapeutic agents which are suitable for treating an HIV infection.

In certain embodiments, one or more fusion polypeptides, or polynucleotides encoding or vectors expressing such fusion polypeptides, as disclosed herein, is co-formulated with one, two, three, four, or more additional therapeutic agents, and a pharmaceutically acceptable carrier. In certain embodiments, one or more fusion polypeptides, or polynucleotides encoding or vectors expressing such fusion polypeptides, as disclosed herein, or a pharmaceutically acceptable salt thereof, is combined with two additional therapeutic agents. As appropriate, the one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a one or more fusion polypeptides, or polynucleotides encoding or vectors expressing such fusion polypeptides, as disclosed herein, are administered with one or more additional therapeutic agents. Co-administration of a compound disclosed herein with one or more additional therapeutic agents generally refers to simultaneous or concurrent, or sequential, administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the one or more fusion polypeptides, or polynucleotides encoding or vectors expressing such fusion polypeptides, as disclosed herein, may be administered within seconds, minutes, or hours of the administration of the one or more additional therapeutic agents. In some embodiments, a unit dose of a one or more fusion polypeptides, or polynucleotides encoding or vectors expressing such fusion polypeptides, as disclosed herein, is administered first, followed within seconds or minutes by administration of a unit dose of one or more additional therapeutic agents. Alternatively, a unit dose of one or more additional therapeutic agents is administered first, followed by administration of a unit dose of a one or more fusion polypeptides, or polynucleotides encoding or vectors expressing such fusion polypeptides, as disclosed herein, within seconds or minutes. In other embodiments, a unit dose of one or more fusion polypeptides, or polynucleotides encoding or vectors expressing such fusion polypeptides, as disclosed herein, is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of one or more fusion polypeptides, or polynucleotides encoding or vectors expressing such fusion polypeptides, as disclosed herein.

In certain embodiments, one or more fusion polypeptides, or polynucleotides encoding or vectors expressing such fusion polypeptides, as disclosed herein, is combined with one or more additional therapeutic agents in a unitary dosage form for simultaneous or concurrent administration to a patient, for example as an aqueous formulation for intravenous, intramuscular, intradermal or subcutaneous administration. In certain embodiments, one or more fusion polypeptides, or polynucleotides encoding or vectors expressing such fusion polypeptides, as disclosed herein, is combined with one or more additional therapeutic agents in a unitary dosage form for simultaneous or concurrent administration to a patient, for example as an intrarectal suppository.

In certain embodiments, the one or more fusion polypeptides, or polynucleotides encoding or vectors expressing such fusion polypeptides, as disclosed herein, can be co-formulated or co-administered with one or more other compounds useful for treating HIV. In certain embodiments, the co-formulation or co-administration can comprise another active agent for treating HIV, such as an anti-HIV antibody, a toll-like receptor (TLR) agonist, an immune checkpoint inhibitor, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, the one or more active agents are suitable for once daily dosing, weekly dosing, monthly dosing, every 3 months dosing, every four months dosing, bi-annual dosing, or annual dosing, as appropriate.

In some embodiments, the one or more fusion polypeptides, or polynucleotides encoding or vectors expressing such fusion polypeptides, as disclosed herein, and the one or more additional therapeutic agents may be an anti-HIV agent. In some instances, the additional therapeutic agent can be HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, HIV Tat or Rev inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, HIV-1 Nef modulators, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

Combination Drugs

In certain embodiments, the one or more fusion polypeptides, or polynucleotides encoding or vectors expressing such fusion polypeptides, as disclosed herein, are combined or co-administered with an HIV combination drug. Examples of combination drugs that can be employed with an agent of this disclosure include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY (bictegravir+emtricitabine+tenofovir alafenamide), DOVATO, TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; cabotegravir+rilpivirine; elpida (elsulfavirine; VM-1500; VM-1500A).

Examples of other drugs for treating HIV that can be combined with the one or more fusion polypeptides, or polynucleotides encoding or vectors expressing such fusion polypeptides, as disclosed herein, include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

In certain embodiments, the one or more fusion polypeptides, or polynucleotides encoding or vectors expressing such fusion polypeptides, as disclosed herein, are combined or co-administered with an HIV protease inhibitor. Examples of HIV protease inhibitors that can be combined with an agent of this disclosure include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, and TMC-310911.

HIV Reverse Transcriptase Inhibitors

In certain embodiments, the one or more fusion polypeptides, or polynucleotides encoding or vectors expressing such fusion polypeptides, as disclosed herein, are combined or co-administered with a non-nucleoside or non-nucleotide inhibitor. Examples of HIV non-nucleoside or non-nucleotide inhibitors of reverse transcriptase that can be combined with an agent of this disclosure include dapivirine, delavirdine, delavirdine mesylate, doravirine, efavirenz, etravirine, lentinan, nevirapine, rilpivirine, ACC-007, AIC-292, KM-023, PC-1005, and elsulfavirine (VM-1500.).

In certain embodiments, the one or more fusion polypeptides, or polynucleotides encoding or vectors expressing such fusion polypeptides, as disclosed herein, are combined or co-administered with an HIV nucleoside or nucleotide inhibitor. Examples of HIV nucleoside or nucleotide inhibitors of reverse transcriptase that can be combined with an agent of this disclosure include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8591, MK-858, VM-2500 and KP-1461.

HIV Integrase Inhibitors

In certain embodiments, the one or more fusion polypeptides, or polynucleotides encoding or vectors expressing such fusion polypeptides, as disclosed herein, are combined or co-administered with an HIV integrase inhibitor. Examples of HIV integrase inhibitors that can be combined with an agent of this disclosure include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T 169, VM-3500 and cabotegravir.

In certain embodiments, the one or more fusion polypeptides, or polynucleotides encoding or vectors expressing such fusion polypeptides, as disclosed herein, are combined or co-administered with a HIV non-catalytic site, or allosteric, integrase inhibitor (NCINI). Examples of HIV non-catalytic site, or allosteric, integrase inhibitors (NCINI) that can be combined with an agent of this disclosure include CX-05045, CX-05168, and CX-14442.

HIV Entry Inhibitors

In certain embodiments, the one or more fusion polypeptides, or polynucleotides encoding or vectors expressing such fusion polypeptides, as disclosed herein, are combined or co-administered with an HIV entry inhibitor. Examples of HIV entry (fusion) inhibitors that can be combined with an agent of this disclosure include cenicriviroc, CCR5 inhibitors, gp41 inhibitors, CD4 attachment inhibitors, gp120 inhibitors, and CXCR4 inhibitors.

In certain embodiments, the one or more fusion polypeptides, or polynucleotides encoding or vectors expressing such fusion polypeptides, as disclosed herein, are combined or co-administered with a CCR5 inhibitor. Examples of CCR5 inhibitors that can be combined with an agent of this disclosure include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu).

In certain embodiments, the one or more fusion polypeptides, or polynucleotides encoding or vectors expressing such fusion polypeptides, as disclosed herein, are combined or co-administered with a gp41 inhibitor. Examples of gp41 inhibitors that can be combined with an agent of this disclosure include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

In certain embodiments, the one or more fusion polypeptides, or polynucleotides encoding or vectors expressing such fusion polypeptides, as disclosed herein, are combined or co-administered with a CD4 attachment inhibitor. Examples of CD4 attachment inhibitors that can be combined with an agent of this disclosure include ibalizumab and CADA analogs.

In certain embodiments, the one or more fusion polypeptides, or polynucleotides encoding or vectors expressing such fusion polypeptides, as disclosed herein, are combined or co-administered with a gp120 inhibitor. Examples of gp120 inhibitors that can be combined with an agent of this disclosure include Radha-108 (receptol) 3B3-PE38, BanLec, bentonite-based nanomedicine, fostemsavir tromethamine, IQP-0831, and BMS-663068.

In certain embodiments, the one or more fusion polypeptides, or polynucleotides encoding or vectors expressing such fusion polypeptides, as disclosed herein, are combined or co-administered with a CXCR4 inhibitor. Examples of CXCR4 inhibitors that can be combined with an agent of this disclosure include plerixafor, ALT-1188, N15 peptide, and vMIP (Haimipu).

In certain embodiments, the one or more fusion polypeptides, or polynucleotides encoding or vectors expressing such fusion polypeptides, as disclosed herein, are combined or co-administered with a HIV maturation inhibitor. Examples of HIV maturation inhibitors that can be combined with an agent of this disclosure include BMS-955176, GSK-3640254 and GSK-2838232.

Latency Reversing Agents

In certain embodiments, the one or more fusion polypeptides, or polynucleotides encoding or vectors expressing such fusion polypeptides, as disclosed herein, are combined or co-administered with a latency reversing agent (LRA). Examples of latency reversing agents that can be combined with an agent of this disclosure include toll-like receptor (TLR) agonists (including TLR7 agonists, e.g., GS-9620), histone deacetylase (HDAC) inhibitors, proteasome inhibitors such as velcade, protein kinase C (PKC) activators, Smyd2 inhibitors, BET-bromodomain 4 (BRD4) inhibitors, ionomycin, IAP antagonists (inhibitor of apoptosis proteins, such as APG-1387, LBW-242), Second mitochondria-derived activator of caspases (SMAC; NCBI Gene ID: 56616) mimetics (including ciapavir, BI-891065, TL32711, LCL161, GDC-0917, HGS1029, AT-406), PMA, SAHA (suberanilohydroxamic acid, or suberoyl, anilide, and hydroxamic acid), NIZ-985, IL-15 modulating antibodies (including IL-15, IL-15 fusion proteins and IL-15 receptor agonists), JQ1, disulfiram, amphotericin B, and ubiquitin inhibitors such as largazole analogs, APH-0812, and GSK-343. Examples of PKC activators include indolactam, prostratin, ingenol B, and DAG-lactones.

Histone Deacetylase (HDAC) Inhibitors

In certain embodiments, the one or more fusion polypeptides, or polynucleotides encoding or vectors expressing such fusion polypeptides, as disclosed herein, are combined or co-administered with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, romidepsin, SHP-141, valproic acid (VAL-001), vorinostat, tinostamustine, remetinostat, entinostat.

Capsid Inhibitor

In certain embodiments, the one or more fusion polypeptides, or polynucleotides encoding or vectors expressing such fusion polypeptides, as disclosed herein, are combined or co-administered with a capsid inhibitor. Examples of capsid inhibitors that can be combined with an agent of this disclosure include capsid polymerization inhibitors or capsid disrupting compounds, HIV nucleocapsid p7 (NCp7) inhibitors such as azodicarbonamide, HIV p24 capsid protein inhibitors, GS-6207 (lenacapavir), GS-CA1, AVI-621, AVI-101, AVI-201, AVI-301, and AVI-CAN1-15 series, and compounds described in this patent (GSK W2019/087016).

Immune Checkpoint Modulators

In certain embodiments, the one or more fusion polypeptides, or polynucleotides encoding or vectors expressing such fusion polypeptides, as disclosed herein, are combined or co-administered with one or more blockers, antagonists or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu, et al., J Exp Clin Cancer Res. (2018) 37:110). In various embodiments, the immune checkpoint proteins or receptors regulate NK cell responses (e.g., reviewed in Davis, et al., Semin Immunol. (2017) 31:64-75 and Chiossone, et al., Nat Rev Immunol. (2018) 18(11):671-688).

Examples of immune checkpoint proteins or receptors include without limitation CD27 (NCBI Gene ID: 939), CD70 (NCBI Gene ID: 970), CD40 (NCBI Gene ID: 958), CD40LG (NCBI Gene ID: 959), CD47 (NCBI Gene ID: 961), CD48 (SLAMF2; NCBI Gene ID: 962), transmembrane and immunoglobulin domain containing 2 (TMIGD2, CD28H; NCBI Gene ID: 126259), CD84 (LY9B, SLAMF5; NCBI Gene ID: 8832), CD96 (NCBI Gene ID: 10225), CD160 (NCBI Gene ID: 11126), MS4A1 (CD20; NCBI Gene ID: 931), CD244 (SLAMF4; NCBI Gene ID: 51744); CD276 (B7H3; NCBI Gene ID: 80381); V-set domain containing T cell activation inhibitor 1 (VTCN1, B7H4; NCBI Gene ID: 79679); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943), TNFSF8 (CD30L; NCBI Gene ID: 944); TNFRSF10A (CD261, DR4, TRAILR1; NCBI Gene ID: 8797), TNFRSF9 (CD137; NCBI Gene ID: 3604), TNFSF9 (CD137L; NCBI Gene ID: 8744); TNFRSF10B (CD262, DR5, TRAILR2; NCBI Gene ID: 8795), TNFRSF10 (TRAIL; NCBI Gene ID: 8743); TNFRSF14 (HVEM, CD270; NCBI Gene ID: 8764), TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608), TNFSF13B (BAFF; NCBI Gene ID: 10673); TNFRSF18 (GITR; NCBI Gene ID: 8784), TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L; NCBI Gene ID: 29126); programmed cell death 1 (PDCD1, PD1, PD-1; CD279; NCBI Gene ID: 5133); cytotoxic T-lymphocyte associated protein 4 (CTLA4, CD152; NCBI Gene ID: 1493); CD80 (B7-1; NCBI Gene ID: 941), CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAET1E; ULBP4; NCBI Gene ID: 135250); retinoic acid early transcript 1G (RAET1G; ULBP5; NCBI Gene ID: 353091); retinoic acid early transcript 1L (RAET1L; ULBP6; NCBI Gene ID: 154064); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1, KIR, CD158E1; NCBI Gene ID: 3811) (e.g., Lirilumab (IPH2102/BMS-986015), IPH-4102); and killer cell lectin like receptor D1 (KLRD1; NCBI Gene ID: 3824).

In certain embodiments, the one or more fusion polypeptides, or polynucleotides encoding or vectors expressing such fusion polypeptides, as disclosed herein, are combined or co-administered with one or more blockers, antagonists or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). Lirilumab is an illustrative antibody that binds to and blocks KIR2DL1/2L3 receptors. In various embodiments, the fusion polypeptides, polynucleotides, vectors, LNPs, immunogenic compositions and/or pharmaceutical compositions, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., J Exp Clin Cancer Res. (2018) 37:110.

In certain embodiments, the one or more fusion polypeptides, or polynucleotides encoding or vectors expressing such fusion polypeptides, as disclosed herein, are combined or co-administered with one or more blockers, antagonists or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2

(KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A), e.g., monalizumab (IPH2201); and killer cell lectin like receptor D1 (KLRD1, CD94). In various embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., Semin Immunol. (2017) 31:64-75; Fang, et al., Semin Immunol. (2017) 31:37-54; and Chiossone, et al., Nat Rev Immunol. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AB122 (zimberelimab), AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034 (balstilimab), JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM4-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In certain embodiments, the one or more fusion polypeptides, or polynucleotides encoding or vectors expressing such fusion polypeptides, as disclosed herein, are combined or co-administered with anti-TIGIT antibodies, such as etigilimab, BMS-986207, tiragolumab (a.k.a., MTIG-7192A; RG-6058; RO 7092284), AGEN1307, AGEN1327, AGEN1777, COM-902, IBI-939, AB154, MG1131 and EOS884448 (EOS-448).

TNF Receptor Superfamily (TNFRSF) Member Agonists or Activators

In certain embodiments, the one or more fusion polypeptides, or polynucleotides encoding or vectors expressing such fusion polypeptides, as disclosed herein, are combined or co-administered with one or more agonists of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1B, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRATLR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, W2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1B, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi- and Tri-Specific Natural Killer (NK)-Cell Engagers

In certain embodiments, the one or more fusion polypeptides, or polynucleotides encoding or vectors expressing such fusion polypeptides, as disclosed herein, are combined or co-administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BBAs appropriate, the anti-CD16 binding bi-specific molecules may or may not have an Fc. Illustrative bi-specific NK-cell engagers that can be co-administered target CD16 and one or more HIV-associated antigens as described herein. BiKEs and TriKEs are described, e.g., in Felices, et al., Methods Mol Biol. (2016) 1441:333-346; Fang, et al., Semin Immunol. (2017) 31:37-54. Examples of a trispecific NK cell engager (TRiKE) include OXS-3550, and CD16-IL-15-B7H3 TriKe.

Indoleamine-Pyrrole-2,3-Dioxygenase (IDO1) Inhibitors

In various embodiments, the one or more fusion polypeptides, or polynucleotides encoding or vectors expressing such fusion polypeptides, as disclosed herein, are combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Toll-Like Receptor (TLR) Agonists

In certain embodiments, the one or more fusion polypeptides, or polynucleotides encoding or vectors expressing such fusion polypeptides, as disclosed herein, are combined or co-administered with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation AL-034, DSP-0509, GS-9620 (vesatolimod), LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Illustrative dual TLR7/TLR8 agonists that can be co-administered include CV8102, NKTR-262, telratolimod and BDB-001. Example TLR8 agonists that can be co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008, cobitolimod, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonist include rintatolimod, poly-ICLC, RIBOXXON®, Apoxxim, RIBOXXIM®, IPH-33, MCT-465, MCT-475, and ND-1.1. Examples of TLR4 agonist include G-100, and GSK-1795091. In some embodiments, the TLR agonist is a non-coding immunostimulatory polynucleotide selected from a pathogen-activated molecular pattern (PAMP), a cytosine-phosphate-guanosine (CpG) oligodeoxynucleotide, and an immunostimulatory RNA (isRNA, e.g., CV8102).

STING Agonists, RIG-I and NOD2 Modulators

In certain embodiments, the one or more fusion polypeptides, or polynucleotides encoding or vectors expressing such fusion polypeptides, as disclosed herein, are combined or co-administered with a stimulator of interferon genes (STING) receptor (a.k.a., stimulator of interferon response cGAMP interactor 1 (STING1); transmembrane protein 173 (TMEM173); NCBI Gene ID: 340061) agonist. In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

In some embodiments, the additional therapeutic agent is an agonist of DExD/H-box helicase 58 (DDX58; a.k.a., RIG-I, RIG1, RIGI, RLR-1, SGMRT2; NCBI Gene ID: 23586). Illustrative RIG-I agonists include inarigivir soproxil (SB-9200; GS-9992); SB-40, SB-44, CV8102, ORI-7246, ORI-9350, ORI-7537, ORI-9020, ORI-9198, ORI-7170, RGT-100 and KIN1148, described by Hemann, et al., J Immunol May 1, 2016, 196 (1 Supplement) 76.1. Additional RIG-I agonists are described, e.g., in Elion, et al., Cancer Res. (2018) 78(21):6183-6195; and Liu, et al., J Virol. (2016) 90(20):9406-19. RIG-I agonists are commercially available, e.g., from Invivogen (invivogen.com). In some embodiments, the agents described herein are combined with a nucleotide binding oligomerization domain containing 2 (NOD2; NCBI Gene ID: 64127) agonist, such as inarigivir soproxil (SB-9200; GS-9992) and IR-103.

LAG-3 and TIM-3 Inhibitors

In certain embodiments, the one or more fusion polypeptides, or polynucleotides encoding or vectors expressing such fusion polypeptides, as disclosed herein, are combined or co-administered with an anti-TIM-3 (hepatitis A virus cellular receptor 2; HAVCR2; CD366, HAVcr-2, KIM-3, SPTCL, TIM3, TIMD-3, TIMD3, Tim-3; NCBI Gene ID: 84868) antibody, such as TSR-022, LY-3321367, MBG-453, INCAGN-2390.

In certain embodiments, the one or more fusion polypeptides, or polynucleotides encoding or vectors expressing such fusion polypeptides, as disclosed herein, are combined or co-administered with anti-LAG-3 (lymphocyte-activating 3; LAG3; CD223; NCBI Gene ID: 3902) antibody, such as relatlimab (ONO-4482), LAG-525, MK-4280, REGN-3767, INCAGN2385.

Interleukin or Cytokine Receptor Agonists

In certain embodiments, the one or more fusion polypeptides, or polynucleotides encoding or vectors expressing such fusion polypeptides, as disclosed herein, are combined or co-administered with a cytokine (e.g., interleukin) receptor agonist, such as IL-2, IL-7, IL-15, IL-10, IL-12, IL-18, IL-21, IFN-α, IFN-γ, GM-CSF, fms related receptor tyrosine kinase 3 (FLT3) receptor agonists, and combinations thereof. Examples of IL-2 receptor agonists that can be co-administered include proleukin (aldesleukin, IL-2); pegylated IL-2 (e.g., NKTR-214); modified variants of IL-2 (e.g., THOR-707), bempegaldesleukin, AIC-284, ALKS-4230, CUI-101, Neo-2/15. Examples of IL-15 receptor agonists that can be co-administered include ALT-803 (nogapendekin alfa), NKTR-255, and hetIL-15, interleukin-15/Fc fusion protein, AM-0015, NIZ-985, SO-C101, IL-15 Synthorin (pegylated Il-15), P-22339, and an IL-15-PD-1 fusion protein N-809. Examples of IL-7 receptor agonist that can be co-administered include CYT-107.

Examples of additional immune-based therapies that can be combined with an agent of this disclosure include interferon alfa; interferon alfa-2b; interferon alfa-n3; pegylated interferon alfa; interferon gamma; fms related tyrosine kinase 3 (FLT3) agonists (e.g., GS-3583, CDX-301); gepon; normferon, peginterferon alfa-2a, peginterferon alfa-2b, RPI-MN.

Phosphatidylinositol 3-Kinase (PI3K) Inhibitors

In some embodiments, the immunogenic polypeptides, polynucleotides encoding such polypeptides, vectors, LNPs and immunogenic compositions comprising such polypeptides or polynucleotides, as described herein, are combined or co-administered with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments, the PI3K inhibitor is a pan-PI3K inhibitor. Examples of PI3K inhibitors include without limitation, ACP-319, AEZA-129, AMG-319, AS252424, AZD8186, BAY 1082439, BEZ235, bimiralisib (PQR309), buparlisib (BKM120), BYL719 (alpelisib), carboxyamidotriazole orotate (CTO), CH5132799, CLR-457, CLR-1401, copanlisib (BAY 80-6946), DS-7423, duvelisib (IPI-145), fimepinostat (CUDC-907), gedatolisib (PF-05212384), GDC-0032, GDC-0084 (RG7666), GDC-0077, pictilisib (GDC-0941), GDC-0980, GSK2636771, GSK2269577, idelalisib (Zydelig®), INCB040093, INCB50465, IPI-443, IPI-549, KAR4141, LY294002, LY3023414, NERLYNX® (neratinib), nemiralisib (GSK2269557), omipalisib (GSK2126458, GSK458), OXY111A, panulisib (P7170, AK151761), PA799, perifosine (KRX-0401), Pilaralisib (SAR245408; XL147), puquitinib mesylate (XC-302), SAR260301, seletalisib (UCB-5857), serabelisib (INK-1117, MLN-1117, TAK-117), SF1126, sonolisib (PX-866), RG7604, rigosertib sodium (ON-01910 sodium), RP5090, tenalisib (RP6530), RV-1729, SRX3177, taselisib, TG100115, umbralisib (TGR-1202), TGX221, voxtalisib (SAR245409), VS-5584, WX-037, X-339, X-414, XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Alpha-4/Beta-7 Antagonists

In certain embodiments, the one or more fusion polypeptides, or polynucleotides encoding or vectors expressing such fusion polypeptides, as disclosed herein, are combined or co-administered with an alpha-4/beta-7 antagonist. Examples of Integrin alpha-4/beta-7 antagonists that can be combined with an agent of this disclosure include PTG-100, TRK-170, abrilumab, etrolizumab, carotegrast methyl, and vedolizumab.

Inhibitor of CD47

In various embodiments, the one or more fusion polypeptides, or polynucleotides encoding or vectors expressing such fusion polypeptides, as disclosed herein, are combined or co-administered with an inhibitor of CD47 (IAP, MER6, OA3; NCBI Gene ID: 961; UniProt Q08722) or an agent that disrupts the binding of CD47 to SIRPα. Examples of CD47 inhibitors include without limitation to anti-CD47 mAbs (Vx-1004), anti-human CD47 mAbs (CNTO-7108), CC-90002, CC-90002-ST-001, humanized anti-CD47 antibody (Hu5F9-G4; magrolimab), NI-1701, NI-1801, RCT-1938, ALX-148, TTI-621, RRx-001, DSP-107, VT-1021, TTI-621, TTI-622, IMM-02 and SGN-CD47M, as well as CD47 targeting agents described in Intl. Patent Publ. Nos. WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188 and WO2020009725.

Examples bi-specific antibodies targeting CD47 that can be combined or co-administered include without limitation IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33). Examples of anti-CD47 antibodies, such as IBI-188, TJC-4, SHR-1603, HLX-24, LQ-001, IMC-002, ZL-1201, IMM-01, B6H12, GenSci-059, TAY-018, PT-240, 1F8-GMCSF, SY-102, KD-015.

HIV Targeting Antibodies

Examples of HIV antibodies, bispecific antibodies, and "antibody-like" therapeutic proteins that can be combined with an agent of this disclosure include DARTs®, DUO-BODIES, BITES®, XmAbs®, TandAbs®, Fab derivatives, bNAbs (broadly neutralizing HIV-1 antibodies), TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66.

In certain embodiments, the co-administered antibody or antigen-binding fragment thereof, or an antigen-binding molecule, is or is derived from human neutralizing antibodies (e.g., monoclonal) that target HIV-1. A "neutralizing antibody" is one that can neutralize the ability of HIV to initiate and/or perpetuate an infection in a host and/or in target cells in vitro. The disclosure provides neutralizing monoclonal human antibodies, wherein the antibody recognizes an antigen from HIV, e.g., a gp120 polypeptide. In certain embodiments, a "neutralizing antibody" may inhibit the entry of HIV-1 virus, e.g., SF162 and/or JR-CSF, with a neutralization index >1.5 or >2.0 (Kostrikis L G et al., J. Viro., 70(1): 445-458 (1996)).

In some embodiments, the co-administered antibody or antigen-binding fragment thereof, or an antigen-binding molecule, is or is derived from human broadly neutralizing antibodies (e.g., monoclonal) that target HIV-1. By "broadly neutralizing antibodies" are meant antibodies that neutralize more than one HIV-1 virus species (from diverse clades and different strains within a clade) in a neutralization assay. A broad neutralizing antibody may neutralize at least 2, 3, 4, 5, 6, 7, 8, 9 or more different strains of HIV-1, the strains belonging to the same or different clades. Illustrative broadly neutralizing antibodies (bNAbs) which can be co-administered as an additional therapeutic agent in a combination therapy are described, e.g., in U.S. Pat. Nos. 8,673,307; 9,493,549; 9,783,594; and WO 2012/154312; WO2012/158948; WO 2013/086533; WO 2013/142324; WO2014/063059; WO 2014/089152; WO 2015/048462; WO 2015/103549; WO 2015/117008; WO2016/014484; WO 2016/154003; WO 2016/196975; WO 2016/149710; WO2017/096221; WO 2017/133639; WO 2017/133640, which are hereby incorporated herein by reference in their entireties for all purposes. Illustrative bNAbs that can be co-administered include without limitation 12A12, 12A21, NIH45-46, bANC131, 8ANC134, IB2530, INC9, 8ANC195, 8ANC196, 10-259, 10-303, 10-410, 10-847, 10-996, 10-1074, 10-1121, 10-1130, 10-1146, 10-1341, 10-1369, and 10-1074GM. Additional examples include those described in Sajadi, et al., Cell. (2018) 173(7):1783-1795; Sajadi, et al., J Infect Dis. (2016) 213(1):156-64; Klein et al., Nature, 492(7427): 118-22 (2012), Horwitz et al., Proc Natl Acad Sci USA, 110(41): 16538-43 (2013), Scheid, et al., Science, 333: 1633-1637 (2011), Scheid, et al., Nature, 458:636-640 (2009), Eroshkin et al, Nucleic Acids Res., 42 (Database issue):D1 133-9 (2014), Mascola et al., Immunol Rev., 254(1):225-44 (2013), such as 2F5, 4E10, M66.6, CAP206-CH12, 10E81 (all of which bind the MPER of gp41); PG9, PG16, CH01-04 (all of which bind V1V2-glycan), 2G12 (which binds to outer domain glycan); b12, HJ16, CH103-106, VRC01-03, VRC-PG04, 04b, VRC-CH30-34, 3BNC62, 3BNC89, 3BNC91, 3BNC95, 3BNC104, 3BNC176, and 8ANC131 (all of which bind to the CD4 binding site), which are hereby incorporated herein by reference in their entireties for all purposes.

In some embodiments, the one or more fusion polypeptides, or polynucleotides encoding or vectors expressing such fusion polypeptides, as disclosed herein, are combined or co-administered with a broadly neutralizing antibody (bNAb)) that binds to an epitope or region of gp120 selected from the group consisting of: (i) the third variable loop (V3) and/or high mannose patch comprising a N332 oligomannose glycan; (ii) second variable loop (V2) and/or Env trimer apex; (iii) CD4 binding site (CD4bs); (iv) gp120/gp41 interface; or (v) silent face of gp120. The foregoing epitopes or regions of gp120 bound by broadly neutralizing antibodies are described, e.g., in McCoy, *Retrovirology* (2018) 15:70; Sok and Burton, *Nat Immunol.* 2018 19(11):1179-1188; Possas, et al., *Expert Opin Ther Pat.* 2018 July; 28(7):551-560; and Stephenson and Barouch, *Curr HIV/AIDS Rep* (2016) 13:31-37, which are hereby incorporated herein by reference in their entirety for all purposes.

In some embodiments, the one or more fusion polypeptides, or polynucleotides encoding or vectors expressing such fusion polypeptides, as disclosed herein, are combined or co-administered with a broadly neutralizing antibody (bNAb)) that binds to an epitope or region of gp120 in the third variable loop (V3) and/or high mannose patch comprising a N332 oligomannose glycan and competes with or comprises VH and VL regions from an antibody selected from the group consisting of GS-9722, PGT-121.60, PGT-121.66, PGT-121, PGT-122, PGT-123, PGT-124, PGT-125, PGT-126, PGT-128, PGT-130, PGT-133, PGT-134, PGT-135, PGT-136, PGT-137, PGT-138, PGT-139, 10-1074, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03. Additional broadly neutralizing antibodies that bind to gp120 in the third variable loop (V3) and/or high mannose patch comprising a N332 oligomannose glycan and which can be used as the second antibody or antigen-binding fragment thereof are described, e.g., in WO 2012/030904; WO 2014/063059; WO 2016/149698; WO 2017/106346; WO 2018/075564, WO 2018/125813 and WO 2018/237148, which are hereby incorporated herein by reference in their entireties for all purposes.

In some embodiments, the one or more fusion polypeptides, or polynucleotides encoding or vectors expressing such fusion polypeptides, as disclosed herein, are combined or co-administered with a broadly neutralizing antibody (bNAb)) that binds to an epitope or region of gp120 in the CD4 binding site (CD4bs) and competes with or comprises CDRs and/or VH and VL regions from an antibody selected from the group consisting of b12, F105, VRC01, VRC07, VRC07-523, VRC03, VRC06, VRC06b01 VRC08, VRC0801, NIH45-46, GS-9723, 3BNC117, 3BNC60, VRC-PG04, PGV04; CH103, 44-VRC13.01, 1NC9, 12A12, N6, N49-P7, NC-Cow1, IOMA, CH235 and CH235.12, N49P6, N49P7, N49P11, N49P9 and N60P25.

In some embodiments, the one or more fusion polypeptides, or polynucleotides encoding or vectors expressing such fusion polypeptides, as disclosed herein, are combined or co-administered with a broadly neutralizing antibody (bNAb)) that binds to an epitope or region of gp120 in the second variable loop (V2) and/or Env trimer apex and competes with or comprises VH and VL regions from an antibody selected from the group consisting of PG9, PG16, PGC14, PGG14, PGT-142, PGT-143, PGT-144, PGT-145, CH01, CH59, PGDM1400, CAP256, CAP256-VRC26.08, CAP256-VRC26.09, CAP256-VRC26.25, PCT64-24E and VRC38.01. Additional broadly neutralizing antibodies that bind to gp120 in the second variable loop (V2) and/or Env trimer apex and which can be used as the second antibody or antigen-binding fragment thereof are described, e.g., in WO 2010/107939; WO 2012/030904; WO 2018/075564 and WO 2018/125813, which are hereby incorporated herein by reference in their entireties for all purposes.

In some embodiments the one or more fusion polypeptides, or polynucleotides encoding or vectors expressing such fusion polypeptides, as disclosed herein, are combined or co-administered with a broadly neutralizing antibody (bNAb)) that binds to an epitope or region of gp120 in the gp120/gp41 interface and competes with or comprises VH and VL regions from an antibody selected from the group consisting of PGT-151, CAP248-2B, 35022, 8ANC195, ACS202, VRC34 and VRC34.01. Additional broadly neutralizing antibodies that bind to gp120 in the gp120/gp41 interface and which can be used as the second antibody or antigen-binding fragment thereof are described, e.g., in WO 2011/038290; WO 2012/030904 and WO2017/079479, which are hereby incorporated herein by reference in their entireties for all purposes.

In some embodiments, the one or more fusion polypeptides, or polynucleotides encoding or vectors expressing such fusion polypeptides, as disclosed herein, combined or co-administered with a broadly neutralizing antibody (bNAb)) that binds to an epitope or region of the gp120 silent face and competes with or comprises VH and VL regions from an antibody selected from the group consisting of VRC-PG05 and SF12. See, e.g., Schoofs, et al., "Broad and Potent Neutralizing Antibodies Recognize the Silent Face of the HIV Envelope," *Immunity* (2019) May 14. pii: S1074-7613(19)30194-3 (PMID 31126879).

In some embodiments, the one or more fusion polypeptides, or polynucleotides encoding or vectors expressing such fusion polypeptides, as disclosed herein, are combined or co-administered with a broadly neutralizing antibody (bNAb)) that binds to an epitope or region of gp41 in the membrane proximal region (MPER). Additional broadly neutralizing antibodies that bind to gp41 in the MPER and which can be used as the second antibody or antigen-binding fragment thereof are described, e.g., in WO 2011/034582; WO 2011/038290; WO 2011/046623 and WO 2013/070776, which are hereby incorporated herein by reference in their entireties for all purposes.

In some embodiments, the one or more fusion polypeptides, or polynucleotides encoding or vectors expressing such fusion polypeptides, as disclosed herein, are combined or co-administered with a broadly neutralizing antibody (bNAb)) that binds to an epitope or region of gp41 in the membrane proximal region (MPER) and competes with or comprises VH and VL regions from an antibody selected from the group consisting of 10E8, 10E8v4, 10E8-5R-100cF, 4E10, DH511.11P, 2F5, 7b2, and LN01.

In some embodiments, the one or more fusion polypeptides, or polynucleotides encoding or vectors expressing such fusion polypeptides, as disclosed herein, are combined or co-administered with a broadly neutralizing antibody (bNAb)) that binds to an epitope or region of the gp41 fusion peptide and competes with or comprises VH and VL regions from an antibody selected from the group consisting of VRC34 and ACS202.

Examples of additional antibodies that can be co-administered include bavituximab, UB-421, BF520.1, CH01, CH59, C2F5, C4E10, C2F5+C2G12+C4E10, 3BNC117, 3BNC117-LS, 3BNC60, DH270.1, DH270.6, D1D2, 10-1074-LS, GS-9722, DH411-2, BG18, PGT145, PGT121, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDXO10 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDXO10 (ipilimumab), VRCO1, VRC-O1-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7, VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100cF, 4E10, DH511.11P, 2F5, 7b2, and LN01.

Example of HIV bispecific and trispecific antibodies include MGD014, B12BiTe, TMB-bispecific, SAR-441236, VRC-01/PGDM-1400/10E8v4, 10E8.4/iMab, 10E8v4/PGT121-VRC01.

In some embodiments, the bNAbs can be expressed in vivo in the patient. Examples of in vivo delivered bNAbs include AAV8-VRC07; mRNA encoding anti-HIV antibody VRCO1; and engineered B-cells encoding 3BNC117 (Hartweger et al, J. Exp. Med. 2019, 1301).

Pharmacokinetic Enhancers

In certain embodiments, the one or more fusion polypeptides, or polynucleotides encoding or vectors expressing such fusion polypeptides, as disclosed herein, are combined with a pharmacokinetic enhancer. Examples of pharmacokinetic enhancers that can be combined with an agent of this disclosure include cobicistat and ritonavir.

Additional Therapeutic Agents

Examples of additional therapeutic agents that can be combined with the one or more fusion polypeptides, or polynucleotides encoding or vectors expressing such fusion polypeptides, as disclosed herein, include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

In certain embodiments, the one or more fusion polypeptides, or polynucleotides encoding or vectors expressing such fusion polypeptides, as disclosed herein, are combined with an HIV vaccine. Examples of HIV vaccines that can be combined with an agent of this disclosure include peptide vaccines, recombinant subunit protein vaccines, live vector vaccines, DNA vaccines, CD4-derived peptide vaccines, vaccine combinations, adenoviral vector vaccines (an adenoviral vector such as Ad5, Ad26 or Ad35), simian adenovirus (chimpanzee, gorilla, rhesus i.e. rhAd), adeno-associated virus vector vaccines, Chimpanzee adenoviral vaccines (e.g., ChAdOXI, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, venezuelan equine encephalitis virus and sindbis virus; (see Lauer, Clinical and Vaccine Immunology, 2017, DOI: 10.1128/CVI.00298-16); LNP formulated mRNA based therapeutic vaccines; LNP-formulated self-replicating RNA/self-amplifying RNA vaccines.

Examples of HIV vaccines that can be co-administered include: rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), Paxvax, EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADVO14-00-VP, INO-6145, JNJ-9220, gp145 C.6980; eOD-GT8 60mer based vaccine, PD-201401, env (A, B, C, A/E)/gag (C) DNA Vaccine, gp120 (A, B, C, A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, arenavirus vector-based vaccines (e.g., described in WO 2009/083210; WO 2015/183895; WO 2016/075250; WO 2017/198726; and U.S. Pat. No. 9,943,585), MVA-BN HIV-1 vaccine regimen, UBI HIV gp120, mRNA based prophylactic vaccines, and TBL-1203HI.

Birth Control (Contraceptive) Combination Therapy

In certain embodiments, the agents described herein are combined with a birth control or contraceptive regimen. Therapeutic agents used for birth control (contraceptive) that can be combined with an agent of this disclosure include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In one embodiment, an agent disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY (bictegravir+emtricitabine+tenofovir alafenamide), adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the one or more fusion polypeptides, or polynucleotides encoding or vectors expressing such fusion polypeptides, as disclosed herein, are combined with an HIV nucleoside or nucleotide inhibitor of reverse transcriptase and an HIV non-nucleoside inhibitor of reverse transcriptase. In another specific embodiment, an agent disclosed herein, or a pharmaceutical composition thereof, is combined with an HIV nucleoside or nucleotide inhibitor of reverse transcriptase, and an HIV protease inhibiting compound. In an additional embodiment, an agent disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In certain embodiments, an agent disclosed herein, or a pharmaceutical composition thereof, is combined with at least one HIV nucleoside inhibitor of reverse transcriptase, an integrase inhibitor, and a pharmacokinetic enhancer. In another embodiment, an agent disclosed herein, or a pharmaceutical composition thereof, is combined with two HIV nucleoside or nucleotide inhibitors of reverse transcriptase.

In a certain embodiment, the one or more fusion polypeptides, or polynucleotides encoding or vectors expressing such fusion polypeptides, as disclosed herein, are combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In another embodiment, the one or more fusion polypeptides, or polynucleotides encoding or vectors expressing such fusion polypeptides, as disclosed herein, are combined with tenofovir, tenofovir disoproxil, tenofovir disoproxil fumarate, tenofovir alafenamide, or tenofovir alafenamide hemifumarate.

In yet another embodiment, the one or more fusion polypeptides, or polynucleotides encoding or vectors expressing such fusion polypeptides, as disclosed herein, are combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In another embodiment, the one or more fusion polypeptides, or polynucleotides encoding or vectors expressing such fusion polypeptides, as disclosed herein, are combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

the one or more fusion polypeptides, or polynucleotides encoding or vectors expressing such fusion polypeptides, as disclosed herein, are combined with a first additional therapeutic agent (a contraceptive) selected from the group consisting of cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

In certain embodiments, the one or more fusion polypeptides, or polynucleotides encoding or vectors expressing such fusion polypeptides, as disclosed herein, are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of dendritic cell therapy include AGS-004. CCR5 gene editing agents include SB-728T. CCR5 gene inhibitors include Cal-1. In some embodiments, C34-CCR5/C34-CXCR4 expressing CD4-positive T-cells are co-administered with the one or more fusion polypeptides. In some embodiments, the agents described herein are co-administered with AGT-103-transduced autologous T-cell therapy or AAV-eCD4-Ig gene therapy.

Gene Editors

In certain embodiments, the one or more fusion polypeptides, or polynucleotides encoding or vectors expressing such fusion polypeptides, as disclosed herein, are combined with a gene editor, e.g., an HIV targeted gene editor. In various embodiments, the genome editing system can be selected from the group consisting of: a CRISPR/Cas9 complex, a zinc finger nuclease complex, a TALEN complex, a homing endonucleases complex, and a meganuclease complex. An illustrative HIV targeting CRISPR/Cas9 system includes without limitation EBT-101.

CAR-T-Cell Therapy

In some embodiments, the agents described herein can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include VC-CAR-T, CMV-N6-CART, anti-CD4 CART-cell therapy, CD4 CAR+C34-CXCR4+CCR5 ZFN T-cells, autologous hematopoietic stem cells genetically engineered to express a CD4 CAR and the C46 peptide.

TCR-T-Cell Therapy

In certain embodiments, the one or more fusion polypeptides, or polynucleotides encoding or vectors expressing such fusion polypeptides, as disclosed herein, are combined with a population of TCR-T-cells. TCR-T-cells are engineered to target HIV derived peptides present on the surface of virus-infected cells, for example ImmTAV.

B-Cell Therapy

In certain embodiments, the one or more fusion polypeptides, or polynucleotides encoding or vectors expressing such fusion polypeptides, as disclosed herein, are combined with a population of B cells genetically modified to express broadly neutralizing antibodies, such as 3BNC117 (Hartweger et al, J. Exp. Med. 2019, 1301, Moffett et al., Sci. Immunol. 4, eaax0644 (2019) 17 May 2019).

8. Kits

Further provided are kits comprising one or more unitary doses of one or more of the fusion polypeptides, as described herein, or one or more polynucleotides encoding such fusion polypeptides, as described herein, or one or more vectors expressing such fusion polypeptides, as described herein. In some embodiments, the kit comprises two or more unitary doses of one or more of the fusion polypeptides, as described herein, or two or more polynucleotides encoding such fusion polypeptides, as described herein, or two or more vectors expressing such fusion polypeptides, as described herein. In some embodiments, the one or more unitary doses are in a single container. In some embodiments, the one or more unitary doses are in two or more separate containers. In certain embodiments, the unitary doses can be the same or different, e.g., can comprise the same or different unitary doses, e.g., can comprise polypeptides, polynucleotides, vectors or combinations thereof.

In various embodiments, the kit comprises one or more pharmaceutical packs or one or more containers (e.g., vials, ampules, pre-loaded syringes) containing one or more of the ingredients of the pharmaceutical compositions described herein, such as one or more of the fusion polypeptides, as described herein, or one or more polynucleotides encoding such fusion polypeptides, as described herein, or one or more vectors expressing such fusion polypeptides, as described herein. In various embodiments, the kit comprises one or more containers comprising the one or more of the fusion polypeptides, as described herein, or one or more polynucleotides encoding such fusion polypeptides, as described herein, or one or more vectors expressing such fusion polypeptides, as described herein, in an aqueous solution. In various embodiments, the kit comprises one or more containers comprising the one or more of the fusion polypeptides, as described herein, or one or more polynucleotides encoding such fusion polypeptides, as described herein, or one or more vectors expressing such fusion polypeptides, as described herein, in lyophilized form.

In some embodiments, the kit comprises one or more unitary doses of one or more viral vectors capable of expressing the fusion polypeptides. In some embodiments, the unitary doses of the one or more viral vectors are in the range of about $10^3$ to about $10^{12}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$, $10^{12}$, $10^{13}$, $10^{14}$ or $10^{15}$ viral FFU or PFU or IU or vp, per administration.

In some embodiments, the kit comprises two or more polynucleotides encoding or two or more viral vectors expressing the fusion polypeptides, the fusion polypeptides comprising: (1) One or more fusion polypeptides comprising or consisting of the following polypeptide segments in sequential order, from N-terminus to C-terminus, optionally joined or connected by one or more linkers: SEQ ID NOs: 70, 76, 94, 151 and 161; or SEQ ID NOs: 71, 77, 95, 152 and 162; and (2) One or more fusion polypeptides comprising or consisting of the following polypeptide segments in sequential order, from N-terminus to C-terminus, optionally joined or connected by one or more linkers: SEQ ID NOs: 188, 305, 28, 41, 294, 4, 176, 11, 319, 259, 282, 223, 213 and 37; SEQ ID NOs: 188, 305, 28, 41 and 294; SEQ ID NOs: 4, 176, 11, 319, 259, 282, 223, 213 and 37; SEQ ID NOs: 189, 306, 29, 42, 295, 5, 177, 12, 320, 260, 283, 224, 214 and 38; SEQ ID NOs: 189, 306, 29, 42 and 295; SEQ ID NOs: 5, 177, 12, 320, 260, 283, 224, 214 and 38; SEQ ID NOs: 305, 319, 259, 282, 223, 213, 294, 176 and 188; SEQ ID NOs: 306, 320, 260, 283, 224, 214, 295, 177 and 189; SEQ ID NOs: 305, 294, 223, 213, 176, 259, 319, 188 and 282; SEQ ID NOs: 306, 295, 224, 214, 177, 260, 320, 189 and 283; SEQ ID NOs: 305, 294, 319, 259, 282, 223, 176, and 188; SEQ ID NOs: 306, 295, 320, 260, 283, 224, 177 and 189; SEQ ID NOs: 305, 223, 294, 176, 259, 319, 188 and 282; or SEQ ID NOs: 306, 224, 295, 177, 260, 320, 189 and 283.

In some embodiments, the kit comprises two or more polynucleotides encoding or two or more viral vectors expressing the fusion polypeptides, the fusion polypeptides comprising: (1) One or more fusion polypeptides comprising an amino acid sequence of any one of SEQ ID NOs: 351-356 and 430, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 351-356 and 430; and (2) One or more fusion polypeptides comprising an amino acid sequence of any one of SEQ ID NOs: 357-366 and 407-410, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to anyone of SEQ ID NOs: 357-366 and 407-410.

In some embodiments, the kit comprises one or more viral vectors, wherein each viral vector comprises two or more polynucleotides encoding two or more fusion proteins that are at least 80%, 81%, 82%, 83%, 84%, 85%, 86%, 87%, 88%, 89%, 90%, 91%, 92%, 93%, 94%, 95%, 96%, 97%, 98%, 99% identical, or 100% identical, to the following amino acid sequences: SEQ ID NOs: 345 and 346; SEQ ID NOs: 347 and 348; SEQ ID NOs: 349 and 350; SEQ ID NOs: 351 and 352; SEQ ID NOs: 430 and 352; SEQ ID NOs: 357 and 358; SEQ ID NOs: 360 and 362; SEQ ID NOs: 359 and 361; SEQ ID NOs: 351 and 357; SEQ ID NOs: 351 and 358; SEQ ID NOs: 351 and 359; SEQ ID NOs: 351 and 360; SEQ ID NOs: 351 and 361; SEQ ID NOs: 351 and 362; SEQ ID NOs: 351 and 407; SEQ ID NOs: 351 and 408; SEQ ID NOs: 351 and 409; SEQ ID NOs: 351 and 410; SEQ ID NOs: 352 and 357; SEQ ID NOs: 352 and 358; SEQ ID NOs: 352 and 359; SEQ ID NOs: 352 and 360; SEQ ID NOs: 352 and 361; SEQ ID NOs: 352 and 362; SEQ ID NOs: 352 and 407; SEQ ID NOs: 352 and 408; SEQ ID NOs: 352 and 409; SEQ ID NOs: 352 and 410; SEQ ID NOs: 430 and 357; SEQ ID NOs: 430 and 358; SEQ ID NOs: 430 and 359; SEQ ID NOs: 430 and 360; SEQ ID NOs: 430 and 361; SEQ ID NOs: 430 and 362; SEQ ID NOs: 407 and 409; SEQ ID NOs: 407 and 408; SEQ ID NOs: 408 and 410; or SEQ ID NOs: 409 and 410.

In some embodiments, the kit comprises one or more polynucleotides encoding or one or more viral vectors expressing the fusion polypeptides, the fusion polypeptides comprising or consisting of the following polypeptide segments in sequential order, from N-terminus to C-terminus, optionally joined or connected by one or more linkers: SEQ ID NOs: 201, 78, 107, 96, 229, 172, 327, 6, 333, 243, 331, 192, 265, 311, 137, 15, 123, 30, 336, 302, 153, 219, 298, 121, 230, 240, 60, 241, 276, 113, 99, 21, 217 and 215; SEQ ID NOs: 78, 296, 1, 339, 197, 329, 232, 323, 303, 234, 90, 261, 274, 238, 211, 325, 137, 227, 209, 190, 341, 57, 225, 27, 210, 119, 19, 165, 334, 117, 153, 10, 97 and 300; or SEQ ID NOs: 296, 1, 78, 197, 339, 227, 261, 274, 238, 325, 137, 329, 303, 234, 90, 232, 27, 57, 225, 323, 190, 341, 119, 19, 165, 334, 117, 153, 10, 97 and 300.

In some embodiments, the kit comprises one or more polynucleotides encoding or one or more viral vectors expressing the fusion polypeptides, the fusion polypeptides comprising or consisting of an amino acid sequence of any one of SEQ ID NOs: 367-377, 411, 422-424 and 431-435, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 367-377, 411, 422-424 and 431-435.

In some embodiments, the kit further comprises one or more unitary doses of one or more additional therapeutic agents. For example, in some embodiments, the kit comprises one or more agonists or activators of one or more toll-like receptors (TLRs). In some embodiments, the TLR agonist or activator is selected from the group consisting of a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from the group consisting of GS 9620 (vesatolimod), R848 (Resiquimod), DS-0509, LHC-165 and TMX-101 (imiquimod), and/or wherein the TLR8 agonist is selected from the group consisting of GS-9688, R848 (Resiquimod), CV8102 (dual TLR7/TLR8 agonist) and NKTR-262 (dual TLR7/TLR8 agonist). In some embodiments, the TLR9 agonist is selected from the group consisting of AST-008, cobitolimod, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD- 1419, lefitolimod (MGN-1703), CYT-003, CYT-003-QbG10, tilsotolimod and PUL-042. In some embodiments, the TLR agonist is a non-coding immunostimulatory polynucleotide selected from a pathogen-activated molecular pattern (PAMP), a cytosine-phosphate-guanosine (CpG) oligodeoxynucleotide, and an immunostimulatory RNA (isRNA, e.g., CV8102).

In some embodiments, the kit comprises one or more interleukin receptor agonists of an interleukin selected from IL-2, IL-7, IL-12, IL-15, IL-18, IL-21, IFN-α, IFN γ, colony stimulating factor 2 (CSF2; a.k.a., GM-CSF) and FLT3LG, e.g., one or more cytokines selected from the group consisting of IL-2, IL-7, IL-12, IL-15, IL-18, IL-21, IFN-α, IFN-γ, GM-CSF, FLT3LG, and combinations and functional variants thereof.

In some embodiments, the kit comprises one or more antagonists or inhibitors of an inhibitory immune checkpoint protein or receptor and/or one or more activators or agonists of a stimulatory immune checkpoint protein or receptor. In some embodiments, the one or more immune checkpoint proteins or receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript IE (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7). In some embodiments, the kit comprises one or more blockers, antagonists or inhibitors of one or more T-cell inhibitory immune checkpoint proteins or receptors. In some embodiments, the T-cell inhibitory immune checkpoint proteins or receptors are selected from the group consisting of CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). Lirilumab is an illustrative antibody that binds to and blocks KIR2DL1/2L3 receptors. In some embodiments, the kit comprises one or more agonists or activators of one or more T-cell stimulatory immune checkpoint proteins or receptors. In some embodiments, the T-cell stimulatory immune checkpoint proteins or receptors are selected from the group consisting of CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the kit comprises one or more blockers, antagonists or inhibitors of one or more NK-cell inhibitory immune checkpoint proteins or receptors. In some embodiments, the NK-cell inhibitory immune checkpoint proteins or receptors are selected from the group consisting of killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A), e.g., monalizumab (IPH2201); and killer cell lectin like receptor D1 (KLRD1, CD94). In some embodiments, the kit comprises one or more agonists or activators of one or more NK-cell stimulatory immune checkpoint proteins or receptors. In some embodiments, the NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7). In some embodiments, the one or more immune checkpoint inhibitors comprises a proteinaceous inhibitor of PD-L1 (CD274), PD-1 (PDCD1) or CTLA4. In some embodiments, the proteinaceous inhibitor of CTLA4 is selected from the group consisting of ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the proteinaceous inhibitor of PD-L1 (CD274) or PD-1 (PDCD1) is selected from the group consisting of pembrolizumab, nivolumab, cemiplimab, pidilizumab, AB122 (zimberelimab), AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034 (balstilimab), JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM4-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the one or more immune checkpoint inhibitors comprises a small molecule inhibitor of CD274 (PDL1, PD-L1), programmed cell death 1 (PDCD1, PD1, PD-1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

In some embodiments, the kit comprises one or more anti-viral agents. In some embodiments, the one or more antiviral agents are selected from the group consisting of HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, and capsid inhibitors.

Optionally associated with such container(s) can be a notice in the form prescribed by a governmental agency regulating the manufacture, use or sale of pharmaceuticals or biological products, which notice reflects approval by the agency of manufacture, use or sale for human administration.

9. Methods of Designing Fusion Polypeptides Useful to Promote Antiviral Immune Responses Provided are methods for designing a vaccine construct or an immunogen that is capable of eliciting an immune response in a human against one or more viral antigens. The immunogenic fusion polypeptides are designed employing a combination of computational, experiential and manual steps, and can be used to elicit an immune response against a highly variable virus. The design methods can be applied to creating an immunogen capable of inducing an immune response in a human against one or more viral antigens of a desired target virus, including without limitation human immunodeficiency virus (HIV), hepatitis B virus (HBV), human papillomavirus (HPV), herpes simplex virus (HSV), Ebola virus, Zika virus and Chikungunya virus. In different implementations, the methods provide a vaccine construct designed for (1) maximum epitope coverage of a broad-based population, referred to herein as a "population" construct or antigen; (2) maximum epitope coverage for a group of individuals sharing a defined set of HLA alleles, referred to herein as an "HLA-restricted" construct or antigen; or (3) maximum epitope coverage for an infected individual's virus by accounting for intra-patient variability in the virus, including the individual's unique complement of viral 'quasi species', referred to herein as a "personalized" construct or antigen. Preferably, the segments comprising each of the constructs represent one or more MHC class I and/or MHC class II T cell epitopes. Accordingly, the segments may be referred to herein as population, HLA-restricted, or personalized epitopes that can be combined and assembled into immunogenic fusion polypeptides.

Most of the steps can be performed in silico, but some steps can be performed manually (e.g., inclusion and/or exclusion selections of certain polypeptide sequences; selection of linker or linkers) and may incorporate information based on experimental data (e.g., experimentally determined MHC class II epitopes). The input information is a viral sequence data set (e.g., for HIV, internal and publicly available HIV population data sets). As summarized in the flow chart of FIG. 1 and Table M below, the vaccine design methods involve at least 2, e.g., at least 3, 4, 5, 6, 7 or 8 of the steps of: 1. Identify conserved regions. All 9 amino acid segments (9-mers) are considered in naturally occurring viral sequences as potential T-cell epitopes. 9-mer positions having a conservation of at least 80% across interpatient viral populations, are identified as conserved regions and included for further analysis. 2. Build bivalent sequences from conserved regions. This can be done by employing a graph-based algorithm. 9-mers are assembled from conserved regions to include the maximum number of naturally occurring 9-mers. 3. Identify intra-patient diversity within conserved regions. This can be done using deep sequencing data. 4. Predict binding of identified polypeptide segments to human MHC alleles. 5. Generate longer peptide segments (e.g. 15 to 26 amino acids in length) including the polypeptide segments predicted to bind to human MHC class I molecules. 6. Include polypeptide segments predicted or shown to bind to MHC class II. 7. Evaluate and eliminate polypeptide segments having high sequence identity with (e.g., cross-recognition) host (e.g., human, dog, cat, horse) proteins. 8. Arrange polypeptide segments to reduce or avoid the creation of human-recognizable neoepitopes at junctions. This can be done by evaluating 9-mers around junctions for MHC class I binding and cross-recognition with host (e.g., human, dog, cat, horse) proteins.

TABLE M

Different Immunogen Design Approaches

| | | No deep sequencing data analysis | | Example 3 single/multiple allele | | Deep sequencing data analysis Example 5 | |
|---|---|---|---|---|---|---|---|
| Step | Step Description | Example 1 Population-based | Example 2 Population-based | Short peptide (9-mers) approach | Long peptide (15-30-mers) approach | Single/multiple allele long peptide | Example 4 Individual |
| 1 | Identify conserved regions | Y* | Y | Y | Y | Y | Y |
| 2 | Build bivalent sequences | Y | Y | Y | Y | Y | Y |
| 3 | Intra-patient diversity | N | N | N | N | Y | Y |
| 4 | MHC class I binding prediction | N | N | Y | Y | Y | Y |
| 5 | Long peptides for improved presentation | N | N | N | Y | Y | Y |
| 6 | Add class II epitopes | N | N | Y | Y | Y | Y |
| 7 | Cross-recognition analysis | N | N | Y | Y | Y | Y |
| 8 | Junctional response analysis | N | Y | Y | Y | Y | Y |

*Y: yes, included in method variation; N: no not included in method variation

In addition to improving epitope coverage, the methods described herein further provide for selecting the most immunogenic epitopes from among the population, HLA-restricted, or personalized epitopes that are identified for incorporation into a final vaccine construct. In one aspect, these methods comprise screening a set of candidate polypeptide segments of a population, HLA-restricted, or personalized construct for MHC peptide binding affinity. MHC binding affinity can be predicted using one or more algorithms. Exemplary predictive algorithms include NetMHC (Vita et al. Nucleic Acids Res 2015 43:D405-D412), NetMHCpan (Andreatta and Nielsen Bioinformatics 2016 32:511-517), and MHCflurry (O'Donnell et al. Cell Syst 2018 7:12-132). Other T-cell epitope prediction tools are publicly available and are described, for example in Sanchez-Trincado et al. J. Immunology Res. 2017 Article ID 2680160. Additional methods for identifying MHC binding peptides include those employing machine learning tools, for example, as described in U.S. Pat. No. 10,055,540, WO 2019/104203 and the "EDGE" tool described in Bulik-Sullivan et al. Nature Biotechnology 2019 37:55.

In some implementations, the disclosure provides methods for producing a bivalent population or HLA-restricted construct designed both to capture the unique diversity of a viral proteome (e.g., HIV proteome) by providing mathematically determined and improved coverage of all potential T cell epitopes and to ensure that the epitopes in each polypeptide of the pair of constructed polypeptides retain the positional information of the original input viral sequences, e.g., by retaining the same order of the polypeptide segments as found in the naturally occurring viral proteome. The epitopes of the resulting pair of polypeptides will therefore more closely resemble those of the naturally occurring viral sequences, increasing the likelihood of their eliciting a relevant T cell response.

In some implementations, the disclosure provides methods for producing a bivalent HLA-restricted construct designed to capture the host genetic diversity driving antigen processing and T cell recognition by modeling epitope generation across a range of host HLA alleles.

Generally, the methods described here comprise initially providing a set of mathematically determined and improved potential T cell epitopes ("PTE") in terms of their coverage of all PTEs in a population of viral proteome sequences, using a graph-based approach. Unlike similar graph-based approaches to vaccine design, the approach described here builds segments of connected PTE's using only adjacent PTE's that are also adjacent in the natural sequences. This provides constructs that retain the positional information of the PTE's within the source set of sequences. Also unlike other graph-based approaches, the methods described here simultaneously build a bivalent construct to provide maximal coverage of the most highly conserved PTEs in the population. The result is an initial bivalent vaccine construct that advantageously maximizes highly conserved PTEs that are most likely to be highly similar to conserved epitopes in the natural sequences. Further advantageously, the use of only the most highly conserved PTEs reduces the likelihood of escape mutants because the highly conserved sequences are more likely to be essential for viral function.

The initial bivalent construct produced by these methods may itself be used as a vaccine, or it may serve as the basis for a further construct, such as an HLA-restricted construct or a personalized construct, as described in more detail below.

The methods described herein generally begin with the identification of a conserved region bivalent sequences, using a process referred to herein as the "Conservation Analysis" or "Conservation Algorithm". The methods further generally comprise a step of building a bivalent vaccine construct having maximal epitope coverage while retaining the positional information of the PTE's from the natural sequences, using a process referred to referred to herein as a "Conserved Walking Algorithm" or "CWA". Thus, in some implementations, an initial step in the method is identifying a set of all conserved regions in a viral proteome for a selected set of viral genes. In implementations for designing a fusion polypeptide to elicit an immune response against HIV-1, the set of HIV-1 viral genes is selected from two or more of Gag, Pol, Env, and Nef. In some implementations, the set of viral genes consists of Gag, Pol, Env, and Nef. In some implementations, the set of viral genes consists of Gag, Pol and Nef. In some implementations, the set of viral genes consists of Gag and Nef or Pol and Env, or solely Pol.

In accordance with the methods described here, a population of viral proteome sequences is first aligned to a reference sequence, for example, the HIV reference sequence HXB2 identified by GenBank No. Accession K03455. Reference sequences for polypeptides encoded by the Env, Gag, Nef and Pol genes are provided herein as SEQ ID NOs: 403-406, respectively. The initial input or 'source' population of viral proteome sequences consists of sequences obtained from naturally occurring viruses. Such sequences are publicly available, for example, from the HIV Databases maintained by the Los Alamos National Laboratory, the U.S. Dept. of Health and Human Services, and the National Institutes of Health. In some implementations of the methods described herein, the source viral sequences may consist of sequences corresponding to a specific viral group and/or clade. In some implementations, in order to improve the identification of conserved regions and sequences, the input viral sequences may be restricted to a single viral clade and/or group. In some implementations, the input viral sequences are restricted to Group M clade B sequences.

The alignment of the source viral sequences to the reference sequence may be accomplished using a multiple alignment algorithm, for example, the fast Fourier transform algorithm, MAFFT. Katoh et al. 2002 Nucleic Acids Res. 30 (14):3059-66. The base MAFFT software is publicly available and distributed, e.g., under the Berkeley Software Distribution (BSD) license.

Next, the Conservation Algorithm is applied to the aligned sequences. For each sequence in the alignment, starting from the first amino acid position, the method shifts one amino acid position at a time and creates all possible amino acid segments that are 9 amino acids in length, referred to herein as "9-mers". The algorithm thus creates, for each sequence in the alignment, a set of 9-amino acid subsequences ("9-mers") starting with the N-terminal amino acid, each subsequence overlapping the preceding subsequence by eight amino acids such that each sequence of length l in the alignment contains (l-8) 9-mers.

Next, for each 9-mer position, the method identifies the two most common unique 9-mers and their prevalence in the aligned set of source viral proteome sequences. Stated another way, starting at position i the two most common unique 9-mers at each position are identified based on their frequency, calculated as the number of times the unique 9-mer occurs at position i in the alignment divided by the total number of sequences in the alignment.

Computationally, each sequence of length l, contains l-8 9-mers. We define all the 9-mers starting at position i as $s_{ij}$ and frequency as $f_{ij}$, j=1, 2, 3, . . . m. In total there are m unique 9-mers at position i. Each two unique 9-mers ($s_{iu}$, $s_{iv}$) can constitute a 9-mer pair and its frequency is $f_{iu}+f_{iv}$. And each 9-mer itself can constitute a 9-mer pair as ($s_{iu}$, $s_{iu}$) and its frequency is $f_{iu}$. Thus, in total, there are m+(m−1)+(m−2)+ . . . +2+1=m*(m+1)/2 9-mer pairs at each position.

The method then calculates the bivalent conservation for each 9-mer position by summing up the proportions of aligned set of source viral proteome sequences containing either of the two most common 9-mers. To do this, a "bivalent conservation" is calculated for each position by summing the proportion of sequences in the alignment containing either of the two most common unique 9-mers. As used herein, "bivalent conservation" refers to the percentage of sequences containing exactly the same 9 amino acid segments (9-mers) as either of the two most prevalent ones in a 9-mer position.

Next, a new alignment of conserved regions is created by extracting the sequences in the alignment having a desired bivalent conservation, for example, a bivalent conservation of greater than 80% or greater than 90%, meaning that the two most common 9-mers at position i account for more than 80% or more than 90% of the 9-mers at that position in the new alignment of conserved regions. Stated another way, the method identifies the conserved regions in the new alignment as those in which the sum of the frequencies of the two most common 9-mers at each position is greater than a certain cutoff, e.g., greater than 80% or greater than 90%. Thus, the method also calculates the frequency of each pair of unique 9-mers at each position in the new alignment of conserved regions.

In some implementations, further selection criteria may be applied to the conserved regions, such as restricting to regions having greater than 90% conservation and removing short segments of less than 35 amino acids.

Using this modified set of conserved regions, certain implementations of the method apply the CWA to build bivalent sequence constructs. The CWA connects 9-mer pairs in adjacent positions of the alignment of conserved regions that share an overlap of eight amino acids.

Computationally, each 9-mer s contains 9 amino acids, we write s[x:y] to represent the amino acid subsequence from position x to y, y−x+1 amino acids in total:

$$s_{iu}[2:9]==s_{i+lp}[1:8] \text{ and } s_{iv}[2:9]==s_{i+lq}[1:8]$$

or $$s_{iu}[2:9]==s_{i+lq}[1:8] \text{ and } s_{iv}[2:9]==s_{i+lp}[1:8].$$

Next, the algorithm builds a directed acyclic graph in which each 9-mer pair is a node and the edges between adjacent nodes are formed from the connected 9-mer pairs in the adjacent positions with the weight of each edge equal to the frequency of the downstream 9-mer pair. This directed acyclic graph is a positional De Brujin graph. Such graphs have been described in connection with assemblies of next generation sequencing data, for example as described in Ronen et al., Bioinformatics 2012 28:188-196. The method further adds a source node, connecting it with all of the nodes in the first position; and a sink node, connecting it with all of the nodes in the last position. The weights are then negated and the optimal path is found from the source node to the sink node, where the optimal path is defined as the path that has the largest sum of the frequencies of all 9-mer pairs among all the paths from the source node to the sink node. The task of finding the optimal path is performed, for example, using the Bellman-Ford algorithm. Generally, the Bellman-Ford algorithm computes the shortest paths from a single source vertex to all of the other vertices in a weighted directed graph which is made up of a set of vertices connected by edges, where the edges have a direction associated with them. The computational steps can be summarized as follows:

(4-1) Treat each 9-mer pair as a node, and build edges between adjacent nodes in Step 3;
(4-2) Adding a source node and connect it with all the nodes at the 1st position;
(4-3) Adding a sink node and connect it with all the nodes at the last position;
(4-4) Weight of each edge equals to the frequency of downstream 9-mer pair;
(4-5) Negating all the weights and finding the optimal path using the Bellman-Ford algorithm.

A further step of the method is to build bivalent vaccine sequences based on the optimal bivalent 9-mer pair path and connect two 9-mers in adjacent positions within the optimal bivalent 9-mer pair path if they share an overlap of 8 amino acids. A bivalent construct is built by connecting two 9-mers in adjacent positions within the optimal bivalent 9-mer path if they share an overlap of eight amino acids, thereby creating two sequences of connected 9-mers which together form the bivalent construct. The connected adjacent 9-mer pairs all have an 8 amino acid overlap, so they will be assembled into two sequences. For example, one 9-mer pair (AIIIIIIIS (SEQ ID NO: 464), MIIIIIIII (SEQ ID NO: 465)) can be connected with another 9-mer pair (IIIIIIISK (SEQ ID NO: 466), IIIIIIIIR (SEQ ID NO: 467)) and make two sequences (bivalent sequences): AIIIIIIISK (SEQ ID NO: 468) and MIIIIIIIIR (SEQ ID NO: 469).

Computationally, the methodology can be described as a positional De Brujin graph based bivalent vaccine sequence design algorithm comprising the following 5 basic steps:

Step 1: align all the population sequences.

Step 2: for each 9-mer position, pull out all the unique 9-mers and their frequencies, and build 9-mer pair sets with frequencies. Each sequence of length l, contains l-8 9-mers. We define all the 9-mers starting at position i as $s_{ij}$ and frequency as $f_{ij}$, j=1, 2, 3, ... m. In total there are m unique 9-mers at position i. Each two unique 9-mers ($s_{iu}$, $s_{iv}$) can constitute a 9-mer pair and its frequency is $f_{iu}+f_{iv}$. And each 9-mer itself can constitute a 9-mer pair as ($s_{iu}$, $s_{iu}$) and its frequency is $f_{iu}$. Thus, in total, there are m+(m−1)+(m−2)+ ... +2+1=m*(m+1)/2 9-mer pairs at each position.

Step 3: connect 9-mer pairs in adjacent positions if they do not have any conflicting amino acids. As used herein, "conflicting amino acid residues" refers to different amino acid residues at overlapped positions between two 9-mers. Each 9-mer s contains 9 amino acids, we write s[x:y] to represent the amino acid subsequence from position x to y, y-x+1 amino acids in total:

$$s_{iu}[2:9]==s_{i+lp}[1:8] \text{ and } s_{iv}[2:9]==s_{i+lq}[1:8]$$

or $$s_{iu}[2:9]==s_{i+lq}[1:8] \text{ and } s_{iv}[2:9]==s_{i+lp}[1:8]$$

Step 4: find the optimal path from the 1st 9-mer position to the last position in terms of the sum of the frequencies of all the 9-mers within the path. The basic idea is to model the maximum coverage bivalent vaccine construction problem as a classic graph theory problem where the solution is finding the minimum path in a directed acyclic graph.

Step 5: build bivalent vaccine sequences based on the optimal bivalent 9-mer pair path and connect two 9-mers in adjacent positions within the optimal bivalent 9-mer pair path if they share an overlap of 8 amino acids. Take for example the following cases:

Case 1: if $s_{iu}[2:9]=s_{i+lp}[1:8]$ and $s_{iv}[2:9]=s_{i+lq}[1:8]$, connect $s_{iu}$ with $s_{i+lp}$ and $s_{iv}$ with $S_{i+lq}$;

Case 2: if $s_{iu}[2:9]=s_{i+lq}[1:8]$ and $s_{iv}[2:9]=s_{i+lp}[1:8]$, connect $s_{iu}$ with $S_{i+lq}$ and $s_{iv}$ with $s_{i+lp}$;

Case 3: if $s_{iu}[2:9]=s_{i+lp}[1:8]$ and $s_{iv}[2:9]=s_{i+lq}[1:8]$ and $s_{iu}[2:9]=s_{i+lq}[1:8]$ and $s_{iv}[2:9]=s_{i+lp}[1:8]$, the selection of connection is based on the prevalence of the two connections in natural sequences:

Denote the prevalence of the co-existence of $s_{ix}$ and $s_{i+ly}$ in input sequences as $C_{ixy}$;

If $C_{iup}+C_{ivq}>C_{iuq}+C_{ivp}$, connect $s_{iu}$ with $s_{i+lp}$ and $s_{iv}$ with $s_{i+lq}$;

If $C_{iuq}+C_{ivp}>C_{iup}+C_{iuq}$, connect $s_{iu}$ with $s_{i+lq}$ and $s_{iv}$ with $s_{i+lp}$;

If $C_{iup}+C_{ivq}=C_{iuq}+C_{ivp}$, backtrack and combine the prevalence of the co-existence of 9-mer pairs in positions i−1 and i until the 1$^{st}$ position. If there is no difference between two different connections, randomly pick one.

HLA-Restricted Constructs

In some implementations, the vaccine construct (e.g., monovalent, bivalent or multivalent) may be designed to increase probability of binding to or presentation by a specific HLA allele or set of HLA alleles. In accordance with this implementation, the MHC binding affinities for each 9-mer in the multivalent (e.g., bivalent) polypeptide can be predicted using a tool such as NetMHC or MHCflurry, and 9-mers that do not bind with high affinity to a specific HLA allele of interest can be excluded. These tools are publicly available and are described, for example, in Lundegarrd et al. Nucleic Acids Res. 2008 Jul. 1; 36(Web Server issue): W509-12 and O'Donnell et al. Cell Systems 2018 7:129-132. Additional publicly available T-cell epitope prediction tools can be used in the herein described viral vaccine design methods and are described in, e.g., Sanchez-Trincado, et al., *J Immunol Res* (2017) 2017:2680160 (PMID: 29445754). Prediction tools for identifying MHC class I binding epitopes include, e.g., MAPPP, PEPVAC, EPISOPT, BIMAS, Propred-1, EpiJen, IEDB-MHCI, Net MHC, NetMHCpan, nHLApred, NetCTL and WAPP. Prediction tools for identifying MHC class II binding epitopes include, e.g., EpiDOCK, PREDIVAC, EpiTOP, TEPITOPE, Propred, IEDB-MHCII, IL4pred, MHC2PRED, NetMHCII and NetMHCIIpan. Prediction tools for identifying MHC class I and/or MHC class II binding epitopes include, e.g., MotifScan, Rankpep, SYFPEITHI, Vaxign, MHCPred, MULTIPRED2, SVMHC and SVRMHC.

In some implementations, the construct is further improved by performing a human proteome cross-recognition analysis, for example by a method comprising searching all of the 9-mers in the construct against a human proteome database such as UniProt to identify any 9-mers having a certain amino acid sequence identity with human peptides, e.g., at least 5 residues, or that share T cell receptor (TCR) facing residues with human proteins. Any such 9-mers may then be excluded from the construct. All remaining 9-mers are then combined, for example using a "beads on a string" approach, linking multiple epitopes in a single contiguous fusion polypeptide. See, e.g., Negahdaripour, et al., *Infect Genet Evol.* (2018) 58:96-109; Schubert, et al., *Genome Med.* 2016 Jan. 26; 8(1):9; Bounds, et al., *Hum Vaccin Immunother.* 2017 Dec. 2; 13(12):2824-2836; Toes, et al., *Proc Natl Acad Sci USA.* (1997) 94(26):14660-5; and Whitton, et al., *J Virol.* 1993 January; 67(1):348-52. In an alternate implementation, each of the remaining 9-mers is flanked with the most conserved 8 amino acid segments upstream and downstream to create 25 amino acid long peptides and all of the 25-mers are combined, for example using a "beads on a string" approach.

In some implementations, the polypeptide segments may optionally be rearranged to reduce or avoid deleterious junctional responses, for example by performing an HLA binding analysis, a human proteome cross-recognition analysis, or both, with respect to the junctional segments. Illustrative methods for reducing junction epitope presentation for neoantigens, in the context of designing anticancer vaccines, are described in WO 2019/104203.

In some implementations, the conserved regions are further defined by performing one or more of the following steps in silico: (i) removing short polypeptide segments, e.g., polypeptide segments of 35 or fewer amino acids in length, e.g., 9-35 amino acids in length; (ii) removing segments that are weakly immunogenic or non-immunogenic in humans; (iii) removing segments that are less than 90% conserved, in certain instances, less than 80% conserved, amongst a predetermined population of sequences; (iv) including additional segments from HIV-1 proteins, e.g., Env, Gag, Nef and Pol, that are known to be immunogenic in humans (see, e.g., epitope maps at hiv.lanl.gov/content/immunology/maps/maps.html; Fischer, et al., *Nat Med*. (2007) 13(1):100-6; and Addo, et al., *J Virol*, (2003) 77(3):2081-92).

In some implementations, adjacent polypeptide segments may optionally be separated with a linker sequence, as described above. In some implementations, the linker sequence or sequences comprise a cleavable linker, optionally further comprising an additional linker sequence located adjacent to the cleavable linker. The additional linker may be another cleavable linker, a polyalanine linker, a polyglycine linker, a flexible linker, or a rigid linker, as described above and herein. In some embodiments, a furin recognition site precedes or is positioned N-terminal to a 2A cleavable linker. In a specific implementation, where the linker sequence comprises a foot-and-mouth disease virus (FMDV) cleavable peptide, FMDV 2A, or derivative thereof, the additional linker sequence may be a REKR sequence (SEQ ID NO: 382), or derivative thereof. In some implementations, the linker is selected from a short polyalanine peptide, for example a peptide consisting of from 2 to 4 alanine residues (SEQ ID NO: 470), or having the sequence AAY (SEQ ID NO: 379) or AAX (SEQ ID NO: 380), where X is any amino acid residue.

In some implementations, the linker is inserted between each adjacent conserved region of the bivalent polypeptide. In some implementations, e.g., when no deleterious junctional epitope is created, no linker is inserted between adjacent segments of the same protein in the polypeptide. A linker can be inserted between adjacent segments of different proteins.

Personalized Constructs

In some implementations, the disclosure further provides methods for producing a personalized construct. Generally, the personalized construct begins with a population-based vaccine construct that defines conserved regions and considers the sequence diversity of a subject's own viral isolates (DNA or RNA) in order to modify the segments of the reference population in order to generate sufficient T cell epitopes to cover the intra-patient viral diversity. Thus, the methods provide a final vaccine construct whose polypeptide sequence accounts for the viral diversity of the virus infecting a particular patient. To do this, the methods comprise analyzing individual patient deep sequencing data to define intra-patient viral sequence variability within each position of the conserved regions covered by the bivalent vaccine construct obtained using the methods described above. In essence, the method comprises identifying viral quasi-species variants existing within the subject and modifying the initial bivalent vaccine construct to reflect this diversity and further reduce the risk of escape mutants while improving for presentation by the individual's HLA alleles.

In an initial step, deep sequencing reads are assembled to create a subject-specific consensus sequence that is mapped to a reference sequence, such as HXB2. At each 9-mer position within the conserved regions covered by the corresponding sequences in the reference construct, i.e., the population construct prepared according to the methods described above, corresponding subsequences from a plurality of sequencing reads that completely covers that position are extracted and converted into 9 amino acid sequences (9-mers). Next, 9-mers in those positions that are covered by a sufficiently large number of sequencing reads, e.g., at least about 1000 reads, are extracted provide that they are present in at least a threshold proportion of the covered sequencing reads, e.g., at least about 1%. The extracted 9-mer subsequences are aligned to the sequences of the reference bivalent construct and mismatches are determined.

In some implementations, the method further comprises identifying regions that may serve as actual epitopes based on likelihood of presentation by the individual host's set of HLA alleles. The likelihood of binding to host HLA may be ascertained using predictive algorithms. Such algorithms have been designed, for example, using publicly available databases to develop deep learning models that model peptide binding per allele. This may be coupled with in-silico, published and/or experimental in-vitro T cell priming data that can define the potential impact of antigen variants in modulating T cell receptor (TCR) recognition or identify a peptide as an escape variant.

In some implementations, the method further comprises excluding sequences with pre-existing escape variants. For example, where an intra-patient 9-mer variant that is known or has been experimentally defined as an escape variant is also predicted to bind MHC, as determined using a tool such as NetMHC, NetMHCpan, MHCflurry, or other similar tools as discussed above, it may be excluded. In addition, any 9-mer variants that are not included in the bivalent vaccine construct, but map to a location covered by that construct, are identified and if the 9-mer variant is predicted to have low-binding affinity to the subject's HLA allele, the 9-mer location may need to be removed from bivalent vaccine construct in order to avoid escape. Possible escape variants for exclusion can also be determined, for example, using existing knowledge of escape variants, peptide prediction models, immunopeptidome analysis and in vitro T cell recognition data.

As discussed above, the method comprises analyzing viral proteome sequences obtained from an infected subject. In some implementations, the method may optionally further comprise a step of obtaining a sample of viral RNA or DNA from the subject. The sample may be plasma sample or a blood sample, for example a sample containing or enriched for peripheral blood mononuclear cells (PBMC) or lymphoid tissue. The sample may be obtained from the subject before anti-retroviral therapy ("preART") or after ART. The sample may comprise one or more of plasma viral RNA, proviral DNA, intact proviral viral DNA, and reservoir outgrowth virus. In some implementations, the sample is obtained from HIV-infected treatment-naïve subjects. In some implementations, the sample is obtained from subjects following ART.

In some implementations, the methods may further comprise isolating viral RNA or DNA from a biological sample obtained from the subject, for example a serum sample, and sequencing the viral DNA.

The sequencing step may further comprise the assembly of a plurality of sequencing reads to create a subject consensus sequence; aligning each read in the plurality of reads to the subject consensus sequence; and mapping the aligned reads of the subject to a reference sequence to obtain sequence coordinates. The reference sequence may be, for example, the HIV reference sequence HXB2 identified by GenBank No. Accession K03455. Polypeptide sequences for HXB2 reference proteins Env, Gag, Nef and Pol are provided herein as SEQ ID NOs: 403-406.

EXAMPLES

The following examples are offered to illustrate, but not to limit the claimed invention.

Example 1

Illustrated Implementation of the Conservation Analysis and Conserved Walking Analysis (CWA) to Generate a Bivalent Vaccine Construct This Example describes the design of population-based bivalent polypeptide constructs by a specific implementation of the Conservation Analysis and CWA to generate a bivalent vaccine construct based on conserved protein regions encoded by the HIV-1 Env, Gag, Nef and/or Pol genes.

First, the method identifies a set of all conserved regions in a viral proteome for a selected set of viral genes. In this example, the set of viral genes consisted of HIV-1 Gag, Pol, and Nef.

Figure 3:
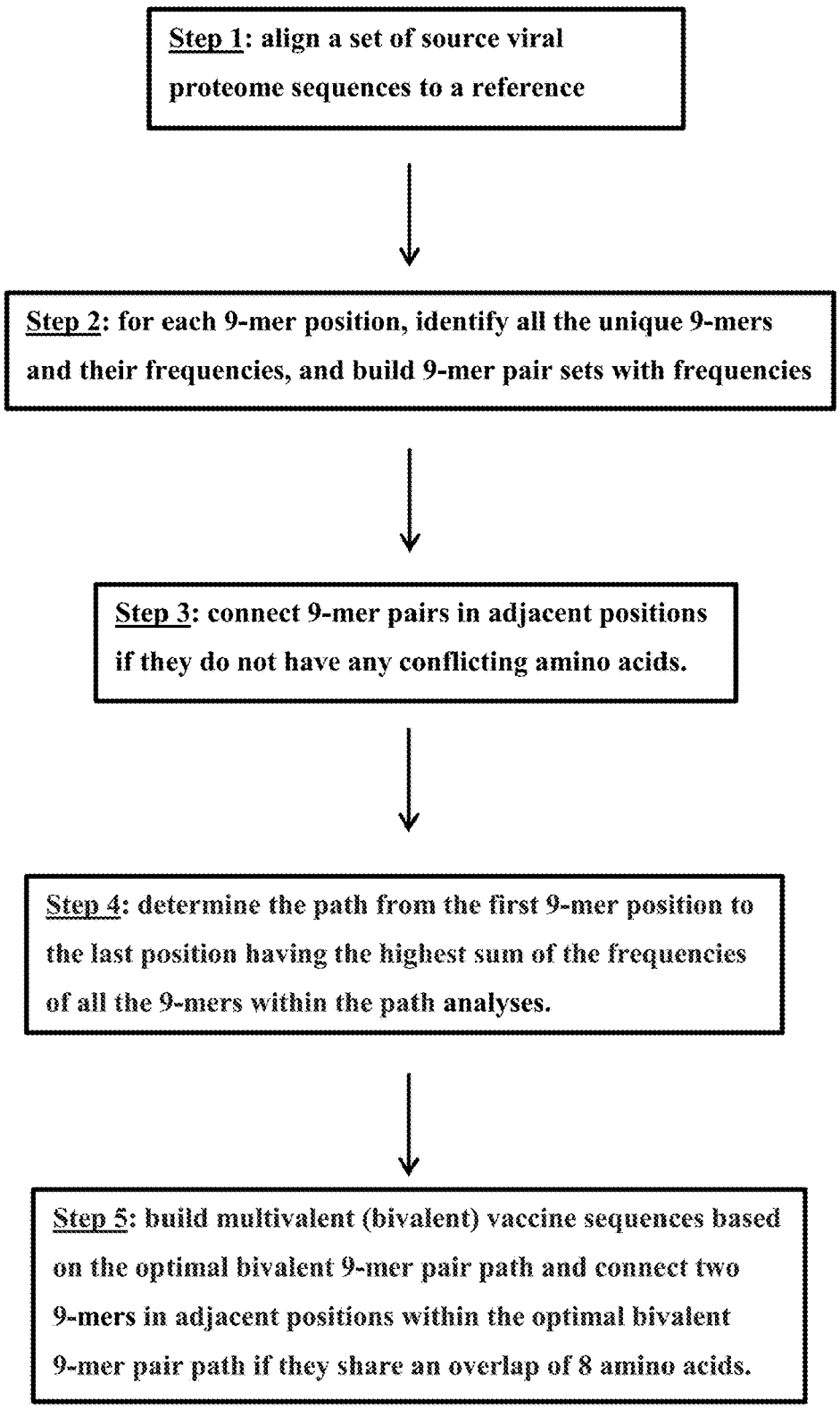
FIG. 3 illustrates the steps of the conserved walking analysis (CWA) algorithm, as described herein.

Computationally, the combination of the Conservation Algorithm and the CWA can be described as a positional De Brujin graph based bivalent vaccine sequence design algorithm comprising the following 5 basic steps, illustrated in FIG. 3:

Step 1: Align a Set of Source Viral Proteome Sequences to a Reference Sequence

In Step 1, a source population of viral proteome sequences is aligned to a reference sequence. In this example, the reference sequence used was the HIV-1 HXB2, identified by GenBank No. Accession K03455. The amino acid sequences of HXB2 reference polypeptides Env, Gag, Nef and Pol are provided herein as SEQ ID NOs: 403, 404, 405 and 406, respectively. The source population of viral proteome sequences consists of sequences obtained from naturally occurring viruses. Such sequences are publicly available, for example, from the HIV Databases maintained by the Los Alamos National Laboratory, the U.S. Dept. of Health and Human Services, and the National Institutes of Health (hiv.lanl.gov), which was the database used for the source population of sequences in this example. For the purposes of illustration, we focused our analysis on a subset of the viral sequences, here, sequences of Group M Clade B. The alignment was performed using a multiple alignment algorithm, specifically a fast Fourier transform algorithm, MAFFT. Katoh, et al. (2002) *Nucleic Acids Res.* 30 (14): 3059-66. The base MAFFT software is publicly available and distributed, e.g., under the Berkeley Software Distribution (BSD) license.

Step 2: For Each 9-Mer Position, Pull Out all the Unique 9-Mers and their Frequencies, and Build 9-Mer Pair Sets with Frequencies In Step 2, we apply the Conservation Algorithm to the set of aligned sequences. For each sequence in the alignment, starting from the first amino acid of the N-terminus, the algorithm shifts one amino acid position at a time to create a set of all possible amino acid segments that are 9 amino acids in length, referred to as "9-mers." The algorithm thus creates, for each sequence in the alignment, a set of 9-amino acid subsequences ("9-mers") starting with the N-terminal amino acid, each subsequence overlapping the preceding subsequence by eight amino acids such that each sequence of length l in the alignment contains (l-8) 9-mers.

Next, for each 9-mer position, the method identifies the two most common unique 9-mers and their prevalence in the aligned set of source viral proteome sequences. Stated another way, starting at position i the two most common unique 9-mers at each position are identified based on their frequency, calculated as the number of times the unique 9-mer occurs at position i in the alignment divided by the total number of sequences in the alignment.

Computationally, each sequence of length l, contains l-8 9-mers. We define all the 9-mers starting at position i as $s_{ij}$ and frequency as $f_{ij}$, j=1, 2, 3, . . . m. In total there are m unique 9-mers at position i. Each two unique 9-mers ($s_{iu}$, $s_{iv}$) can constitute a 9-mer pair and its frequency is $f_{iu}+f_{iv}$. And each 9-mer itself can constitute a 9-mer pair as ($s_{iu}$, $s_{iu}$) and its frequency is $f_{iu}$. Thus, in total, there are m*(m+1)/2 9-mer pairs at each position.

The method then calculates the bivalent conservation for each 9-mer position by summing up the proportions of aligned set of source viral proteome sequences containing either of the two most common 9-mers. To do this, a "bivalent conservation" is calculated for each position by summing the proportion of sequences in the alignment containing either of the two most common unique 9-mers.

Next, a new alignment of conserved regions is created by extracting the sequences in the alignment having a desired bivalent conservation. In this example, we used a bivalent conservation of greater than 80% or greater than 90%, meaning that the two most common 9-mers at position i account for more than 80% or more than 90% of the 9-mers at that position in the new alignment of conserved regions. Stated another way, the method identifies the conserved regions in the new alignment as those in which the sum of the frequencies of the two most common 9-mers at each position is greater than a certain cutoff, e.g., greater than 80% or greater than 90%. Thus, the method also calculates the frequency of each pair of unique 9-mers at each position in the new alignment of conserved regions.

Figure 4A:
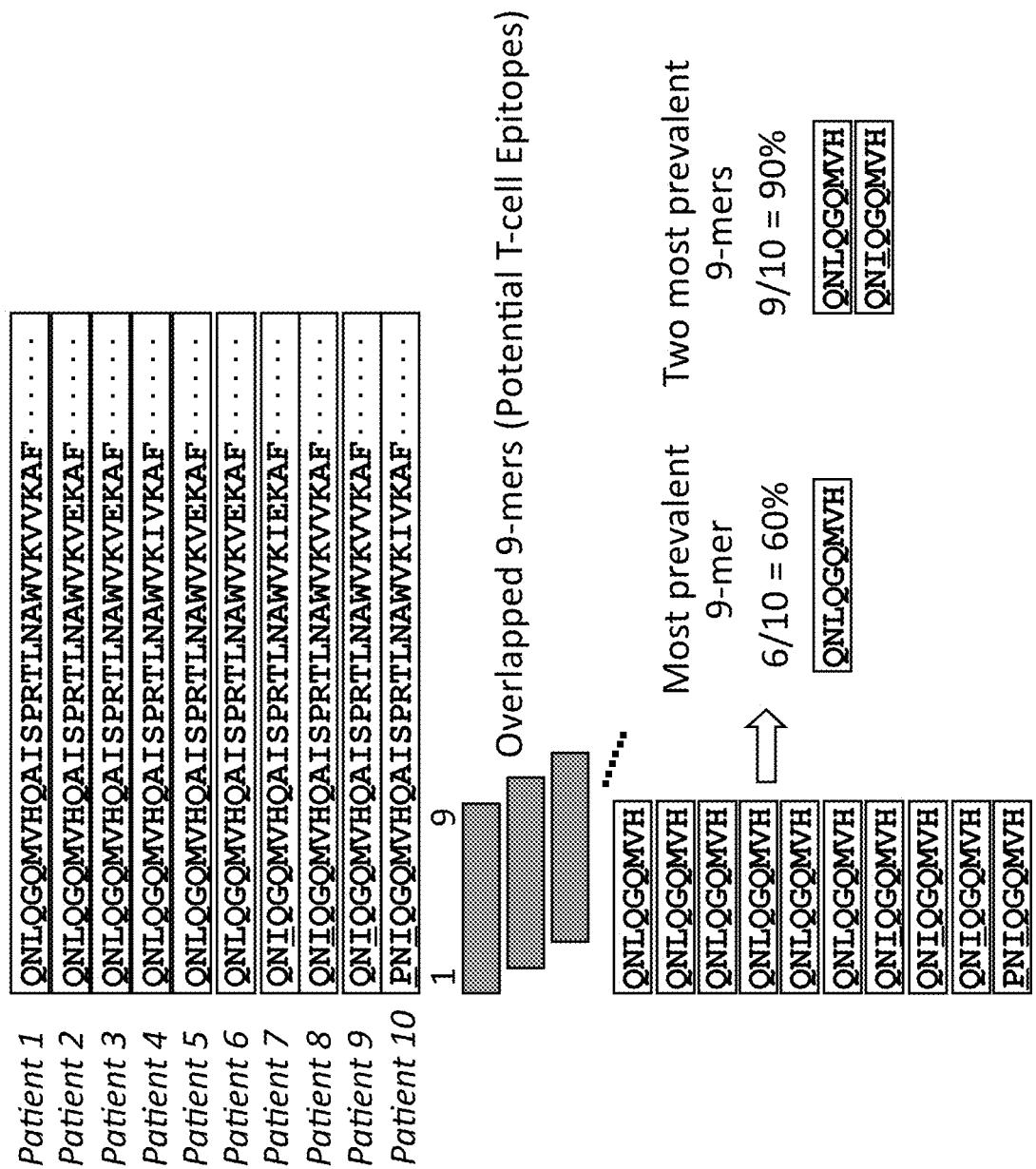
FIGS. 4A-4B.

This is illustrated graphically in FIG. 4A. FIG. 4A shows a hypothetical set of 10 input natural sequences, each having a single amino acid variation within the first 9-mer. Across the set of 10 sequences, the 9-mer having an "L" at the third amino acid position occurs 6 times, the 9-mer having an "I" at that location occurs 3 times, and the 9-mer having an "I" at that location but a different amino acid in the first position occurs once. Thus, the Conservation Algorithm selects the two most prevalent 9-mers which together account for 90% of the possible 9-mers at that position in the population of aligned sequences.

Figure 4B:
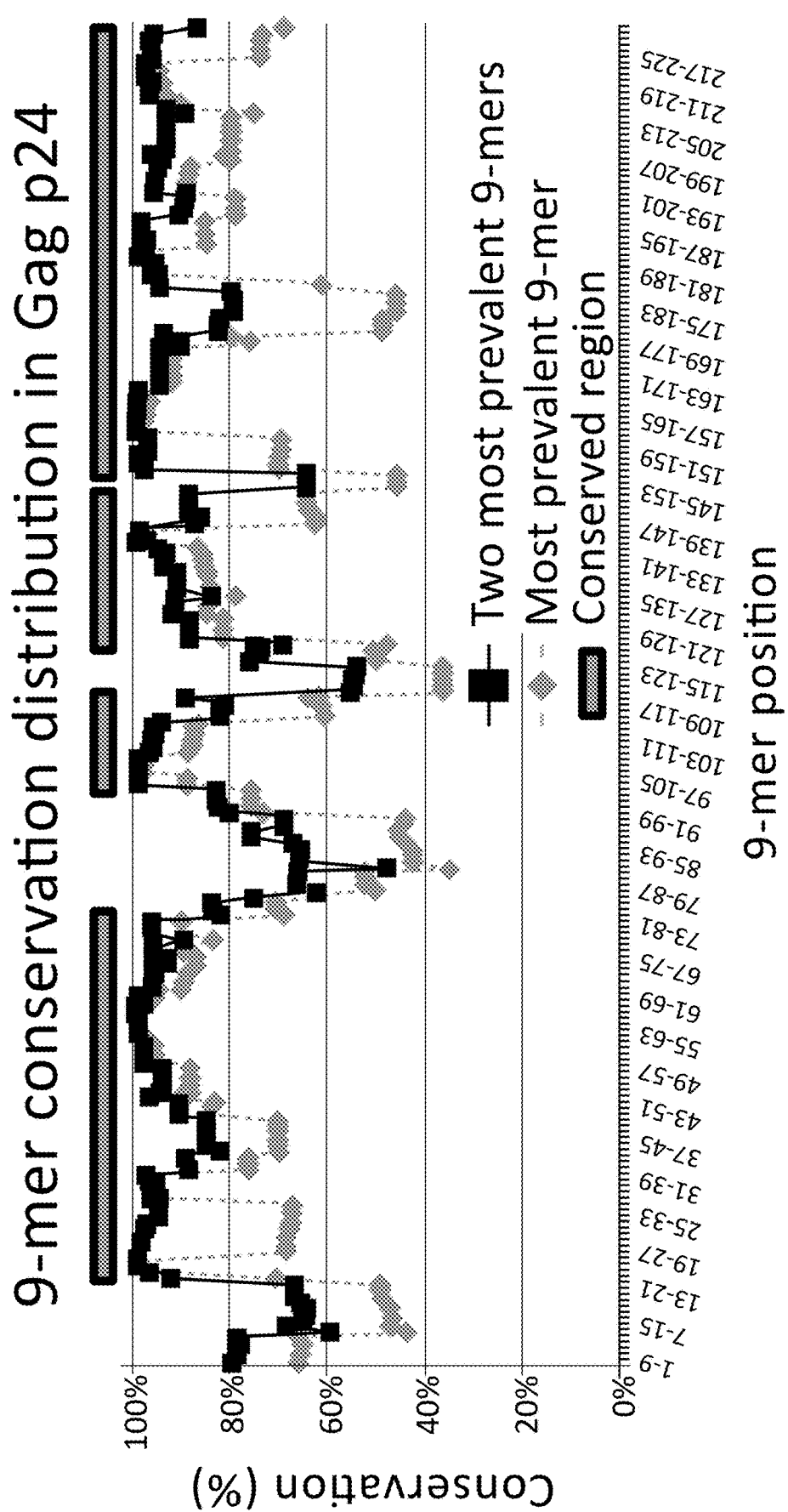

Using this analysis, the distribution of highly conserved 9-mers at each position across all of the protein sequences in the population can be determined. This is illustrated graphically in FIG. 4B. The plot shows the conservation distribution for proteins encoded by the Gag gene p24 protein in 9,846 Group M Clade B input sequences obtained from the Los Alamos HIV Sequence database. The y-axis shows bivalent conservation and the x-axis shows the location of the 9-mer relative to the reference sequence, Gag p24 from HXB2. Across the top of the graph the horizontal bars depict conserved regions as those having at least 80% bivalent conservation using the two most prevalent 9-mers at each position. The dark gray line with the squares plots the bivalent conservation at each position using the two most prevalent 9-mers while the light gray line with the diamonds shows conservation using only the most prevalent 9-mer at each position. This analysis demonstrates that the use of the two most prevalent 9-mers improves the identification of structurally conserved sequences with an input population.

We next applied further selection criteria to define the conserved regions, including restricting to regions having greater than 90% bivalent conservation and removing short segments of less than 35 amino acids, e.g., segments 9-35 amino acids in length.

We also included some additional segments from certain regions having at least 80% bivalent conservation and known to be highly immunogenic, in particular, the region of Nef corresponding to amino acids 64-99 of the reference sequence HXB2_K03455 (see, e.g., epitope maps at hiv.lanl.gov/content/immunology/maps/maps.html; Fischer, et al., *Nat Med*. (2007) 13(1):100-6; and Addo, et al., *J Virol*, (2003) 77(3):2081-92).

Step 3: Connect 9-Mer Pairs in Adjacent Positions if they do not have any Conflicting Amino Acids.

Using this modified set of conserved regions, we applied the CWA to build bivalent sequence constructs. The CWA connects 9-mer pairs in adjacent positions of the alignment of conserved regions that share an overlap of eight amino acids.

Computationally, each 9-mer s contains 9 amino acids, we write s[x:y] to represent the amino acid subsequence from position x to y, y-x+1 amino acids in total:

$s_{iu}[2:9]==s_{i+1p}[1:8]$ and $s_{iv}[2:9]==s_{i+1q}[1:8]$ or $s_{iu}[2:9]==s_{i+1q}[1:8]$ and $s_{iv}[2:9]==s_{i+1p}[1:8]$.

Step 4: Find the Optimal Path from the First 9-Mer Position to the Last Position in Terms of the Sum of the Frequencies of all the 9-Mers within the Path.

In Step 4, the algorithm builds a directed acyclic graph in which each 9-mer pair is a node and the edges between adjacent nodes are formed from the connected 9-mer pairs in the adjacent positions with the weight of each edge equal to the frequency of the downstream 9-mer pair. This directed acyclic graph is a positional De Brujin graph. Such graphs have been described in connection with assemblies of next generation sequencing data, for example as described in Ronen et al., *Bioinformatics* (2012) 28:188-196.

In the present example, we add a source node and connect it with all of the nodes in the first position; and we add a sink node and connect it with all of the nodes in the last position. In a directed graph, a source node is a node that only has out flow and a sink node is a node that only has in flow. Here, the source node is a dummy node that connects to all the 9-mer pair nodes in the first position, and the sink node is a dummy node that connects to all the 9-mer pair nodes in the last position.

We then negate all of the weights and find the optimal path from the source node to the sink node, where the optimal path is defined in terms of the sum of the frequencies of all 9-mer pairs. The task of finding the optimal path is performed, for example, using the Bellman-Ford algorithm. Generally, the Bellman-Ford algorithm computes the shortest paths from a single source vertex to all of the other vertices in a weighted directed graph. A directed graph is one made up of a set of vertices connected by edges, where the edges have a direction associated with them.

Computationally, the basic idea is to model the maximum coverage bivalent vaccine construction problem as a classic graph theory problem where the solution is finding the minimum path in a directed acyclic graph. The computational steps can be summarized as follows:

(4-1) Treat each 9-mer pair as a node, and build edges between adjacent nodes in Step 3;
(4-2) Adding a source node and connect it with all the nodes at the 1st position;
(4-3) Adding a sink node and connect it with all the nodes at the last position;
(4-4) Weight of each edge equals to the frequency of downstream 9-mer pair; and
(4-5) Negating all the weights and finding the optimal path using the Bellman-Ford algorithm.

Step 5: Build Bivalent Vaccine Sequences Based on the Optimal Bivalent 9-Mer Pair Path and Connect Two 9-Mers in Adjacent Positions within the Optimal Bivalent 9-Mer Pair Path if they Share an Overlap of 8 Amino Acids.

In Step 5, a bivalent construct is built by connecting two 9-mers in adjacent positions within the optimal bivalent 9-mer path if they share an overlap of eight amino acids, thereby creating two sequences of connected 9-mers which together form the bivalent construct. The connected adjacent 9-mer pairs all have an 8 amino acid overlap, so they will be assembled into two sequences. For example, one 9-mer pair (AIIIIIIIS (SEQ ID NO: 464), MIIIIIIII (SEQ ID NO: 465)) can be connected with another 9-mer pair (IIIIIIISK (SEQ ID NO: 466), IIIIIIIIR (SEQ ID NO: 467)) and make two sequences (bivalent sequences): AIIIIIIISK (SEQ ID NO: 468) and MIIIIIIIIR (SEQ ID NO: 469).

Figures 5A, 5B, 5C:
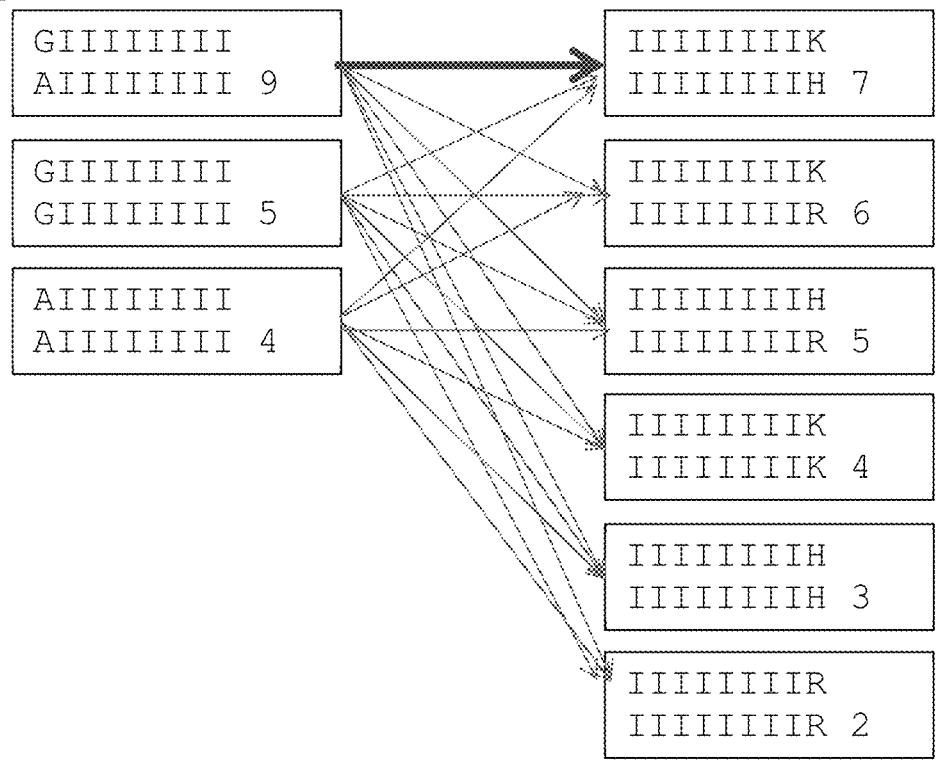
FIGS. 5A-5C.
Figure 7:
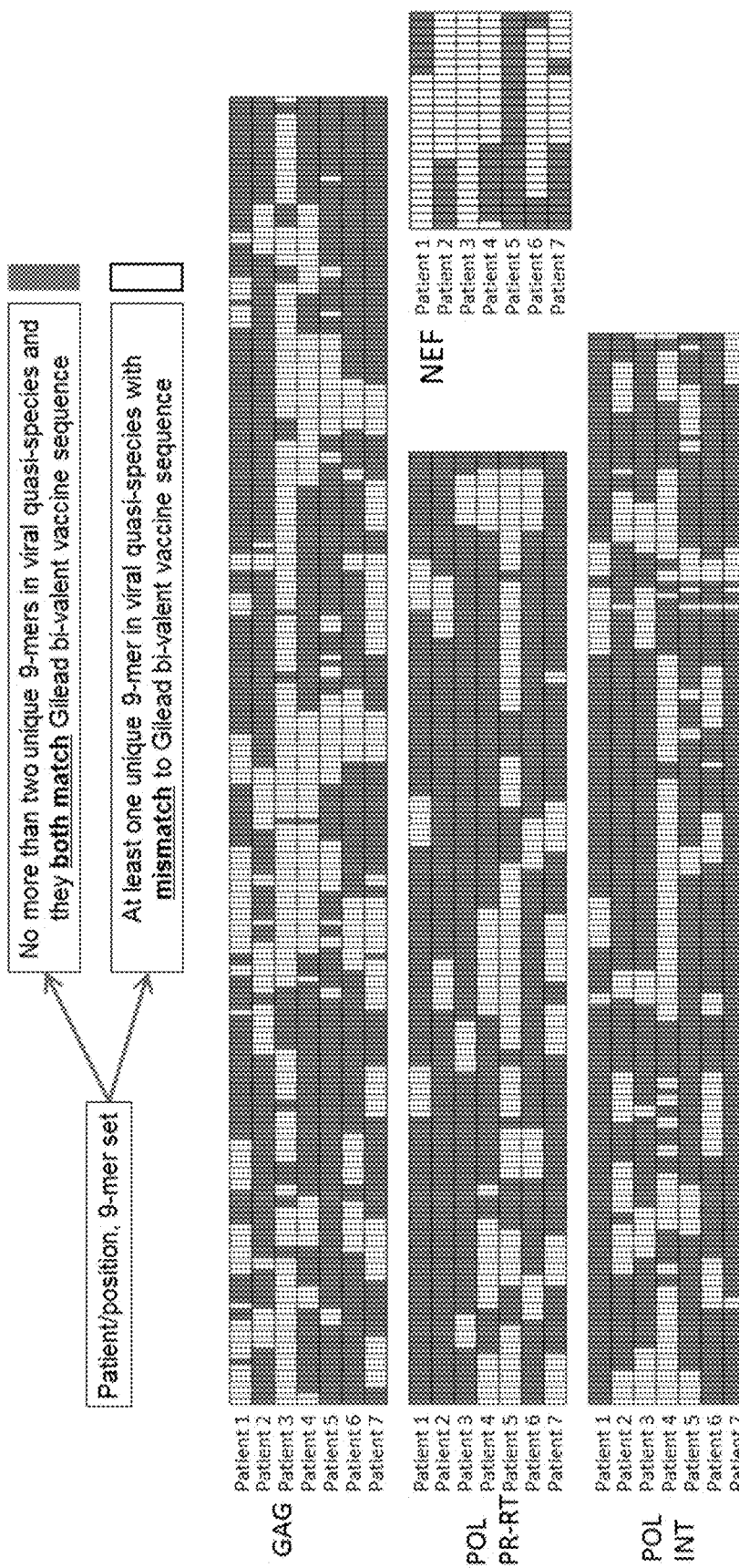
FIG. 7 illustrates intrapatient diversity analysis of HIV-1 proteins. Bivalent vaccine sequences mismatch quasi-species at 21-48% of positions in highly conserved regions.

This method is illustrated graphically in FIGS. 5A-5C. FIG. 5A shows a hypothetical set of 9 source viral sequences having, at the first position, 2 unique 9-mers and at the second adjacent position 3 unique 9-mers. The frequency of each sequence is indicated to the right of the sequence as 'times', e.g., "×5" means that sequence occurs 5 times in the source set. FIG. 5B depicts the building of the positional De Brujin graph in which each node is one bivalent 9-mer pair. Where two bivalent 9-mer pairs in adjacent positions share an overlap of eight amino acids they are connected to build an edge. In this manner the directed acyclic graph is created. FIG. 5C illustrates the finding of the optimal path. As noted above, the optimal path is defined in terms of the sum of the frequencies of all 9-mer pairs. This is accomplished by finding the connection between adjacent 9-mers that provides the highest conservation with reference to the input sequences. Thus, in FIG. 5C, connecting the two 9-mer pairs as shown in the top set of four pairs provides the following bivalent sequences, (SEQ ID NO: 471)
GIIIIIIIK
x0

(SEQ ID NO: 472)
AIIIIIIIH
x0.

Neither of these sequences is present in the source sequences shown in FIG. 5A.

In contrast, connecting the two 9-mer pairs as shown in the bottom set of four pairs in FIG. 5C provides the following bivalent sequences, (SEQ ID NO: 473)
GIIIIIIIH
x3

(SEQ ID NO: 474)
AIIIIIIIK
x4.

Each of these is present, 3 or 4 times, respectively, in the source sequences shown in FIG. 5A. Accordingly, it is these second pair of bivalent sequences that is selected by the algorithm because it maximizes conservation relative to the source sequences.

Computationally, this can be illustrated by the following exemplary cases:

Case 1: if $s_{iu}[2:9]=s_{i+lp}[1:8]$ and $s_{iv}[2:9]=s_{i+lq}[1:8]$, connect $s_{iu}$ with $s_{i+lp}$ and $s_{iv}$ with $s_{i+lq}$;

Case 2: if $s_{iu}[2:9]=s_{i+lq}[1:8]$ and $s_{iv}[2:9]=s_{i+lp}[1:8]$, connect $s_{iu}$ with $s_{i+lq}$ and $s_{iv}$ with $s_{i+lp}$;

Case 3: if $s_{iu}[2:9]=s_{i+lp}[1:8]$ and $s_{iv}[2:9]=s_{i+lq}[1:8]$ and $s_{iu}[2:9]=s_{i+lq}[1:8]$ and $s_{iv}[2:9]=s_{i+lp}[1:8]$, the selection of connection is based on the prevalence of the two connections in natural sequences:

Denote the prevalence of the co-existence of $s_{ix}$ and $s_{i+ly}$ in input sequences as $C_{ixy}$;

If $C_{iup}+C_{ivq}>C_{iuq}+C_{ivp}$, connect $s_{iu}$ with $s_{i+lp}$ and $s_{iv}$ with $s_{i+lq}$;

If $C_{iuq}+C_{ivp}+C_{iup}+C_{ivq}$, connect $s_{iu}$ with $s_{i+lq}$ and $s_{iv}$ with $s_{i+lp}$;

If $C_{iup}+C_{ivq}=C_{iuq}+C_{ivp}$, backtrack and combine the prevalence of the co-existence of 9-mer pairs in positions i−1 and i until the first position. If there is no difference between two different connections, randomly pick one.

This backtrack and co-existence prevalence approach considers prevalence of peptides longer than 9 amino acids and further differentiates the present algorithm from other graph-based methods.

Next, constructed sequences from regions not adjacent to one another in the natural sequence, that is, regions which could not be joined according to the CWA as described above due to their lacking an 8 amino acid overlap, were combined using one of three different linker strategies: 1. direct fusion without any linker; 2. insert 'AAA' linker (SEQ ID NO: 378) between each two conserved regions; 3. direct fusion without any linker for segments within the same protein and insertion of an F2A linker between segments from different proteins.

An overview of the Conserved Walking Analysis (CWA) method is shown in FIGS. 1 and 2. The fusion polypeptides of SEQ ID NOs: 345-350 and the sequences in Table 1, which have polypeptide segments encoding by the HIV-1 Gag, Nef and Pol genes, are exemplary immunogenic fusion polypeptide sequences designed according to this method.

Example 2

Illustrated Implementation of the Conservation Analysis and Conserved Walking Analysis (CWA) Applied to Proteins Encoded by HIV-1 Genes This example describes a similar implementation based on conserved HIV-1 regions of (i) Gag and Nef ("GagNef"), (ii) Pol, or (iii) Pol and Env ("PolEnv").

In Example 1 above, the Conservation algorithm was applied to identify a set of all candidate conserved regions in the protein coding regions of the target genes Gag, Nef, Env and Pol. In this example, we utilized the protein coding regions of (1) Gag and Nef, (2) Pol or (3) Pol and Env to generate three different bivalent constructs, "GagNef," "Pol" and "PolEnv," respectively. As in Steps 1-2 of Example 1 above, we first aligned the source sequences and then applied the Conservation Algorithm to identify a set of all candidate conserved regions in the protein coding regions of the target genes, which were either Gag and Nef, Pol, or Pol and Env. As above, we then we applied further selection criteria based on conservation and known immunogenicity (see, e.g., epitope maps at hiv.lanl.gov/content/immunology/maps/maps.html and Fischer, et al., *Nat Med.* (2007) 13(1): 100-6). In certain sequences including polypeptide segments encoding by the Pol gene, we excluded sequence segments including one or both of the "YMDD" motif (SEQ ID NO: 462) in reverse transcriptase and the "DTG" motif in protease, because they may affect expression the maintenance of enzymatic activity.

Using this modified set of conserved regions, we applied the CWA to build bivalent sequence constructs, as in Steps 3-5 in Example 1.

Some polypeptide segments were connected by a poly-alanine linker (e.g., AA, AAA (SEQ ID NO: 378) or AAY (SEQ ID NO: 379)), chosen for demonstration purposes because it is a small flexible linker that is unlikely to have a significant influence on protein structure. If we determined that it was possible to fuse polypeptide segments without creating a deleterious or undesirable junctional epitope, e.g., such as one that may stimulate T cells that may cross react to self-antigens, a fusion approach was used. If we determined that a deleterious or undesirable junctional epitope may be created, a flexible linker was inserted between polypeptide segments.

For this Example, we applied a further analysis of the junctional regions for possible presentation of deleterious epitopes and arranged the segments to reduce or avoid the creation of such junctional epitopes.

Different arrangements of peptide segments generate different junction 9-mers that can induce different junction responses. We developed a polypeptide segment arrangement tool to examine MHC binding affinities and cross-recognition with human peptides for all the junction 9-mers in each arrangement. Our internally developed polypeptide segment arrangement tool searches different arrangements of peptides and determines the best arrangement with minimal junction response based on in silico prediction results of applying the two analyses described below ((1) in-silico HLA binding analysis and (2) human proteome analysis to identify epitopes that may prime T cells that may recognize self-antigens) on the junctions of 9-mers. The junctional response score between each two adjacent segments is determined by the sum of the number of junction 9-mers that are predicted to have high binding affinities to target HLA alleles and the number of human proteins predicted to have peptides or T cell recognition motifs with any junction 9-mers. The score of each segment arrangement is determined by the sum of the junctional response scores for all the junctional regions in each segment arrangement.

1) When there are less than 15 peptide segments, our internally developed polypeptide segment arrangement tool searches all the possible arrangements and determines the best one with minimal junction response (the lowest segment arrangement score)

2) When there are at least 15 peptide segments, our internally developed polypeptide segment arrangement tool uses a 'greedy' strategy. It first creates all the junctions and then starts from the best junction in terms of predicted junctional response. Next, it searches for the next compatible best junction iteratively and assembles all the peptide segments.

In-Silico MHC Class I (Human HLA) Binding Analysis:

Antigen processing, presentation, and T cell receptor recognition are complex processes that remain incompletely understood. Intracellular and extracellular antigens are processed within endosomal compartments, and the cytoplasm by the proteasome and trafficked to endosomal compartments such as the ER where they peptide fragments interact with MHC molecules. Stable peptide-MHC complexes are trafficked to the cell surface where they can be recognized by a T cell expressing a TCR with the appropriate specificity. One of the most selective steps in antigen processing and presentation is HLA binding. HLA binding affinities can be predicted using various tools such as NetMHC or MHCflurry, or large internal datasets derived from immunopeptidome analyses and confirmed by experimental binding data as well as epitopes defined from patient samples. These tools are publicly available and are described, for example, in Lundegarrd et al., *Nucleic Acids Res.* 2008 Jul. 1; 36(Web Server issue):W509-12 and O'Donnell, et al., *Cell Systems* 2018 7:129-132. In this example we used NetMHC. The default settings were used for all the parameters in NetMHC, along with inputting information for peptide sequences and HLA alleles. Predicted binding affinities with an IC50 value less than 1,000 nM are considered as low binding affinities.

Human Proteome Cross-Recognition Analysis:

Epitopes similar to human peptides may induce tolerogenic responses or responses that may cross-react with self-antigens. We searched all the 9-mers in our vaccine against public human protein databases (e.g., Uniprot, NCBI). If an HIV peptide 9-mer has at least a 5-residue amino acid sequence identity with a human peptide 9-mer, and both are predicted to have high binding affinities to the same alleles, they are considered as cross-conserved 9-mers. We downloaded all the human protein sequences from the UniProt database and built a tool to support efficient search of a given 9-mer against all the human protein 9-mers with up to 4 mismatches (at least 5 matches).

FIG. 8 illustrates the results of human proteome cross-recognition analysis. In this example, we searched HIV-1 peptide 9-mers over human protein databases and identified all the human protein 9-mers sharing a certain number of amino acids (at least 5 tentatively) and are predicted to have high binding affinities (e.g., IC50 of less than about 1000 nM or having a percentile rank within the top 5% in a population of polypeptide segments) to the same alleles based on the in silico MHC class I analysis described herein. Such HIV 9-mers having both high sequence identity (e.g., having have at least 55% (5 of 9 amino acid residues), e.g., at least 65% (6 of 9 amino acid residues), e.g., at least 75% (7 of 9 amino acid residues), e.g., at least 85% (8 of 9 amino acid residues)) to a peptide segment of a human protein and high predicted MHC class I binding affinity are excluded because they may induce tolerogenic responses or responses that may cross-react with human self-antigens (defined herein as "deleterious epitopes.").

Figure 9:
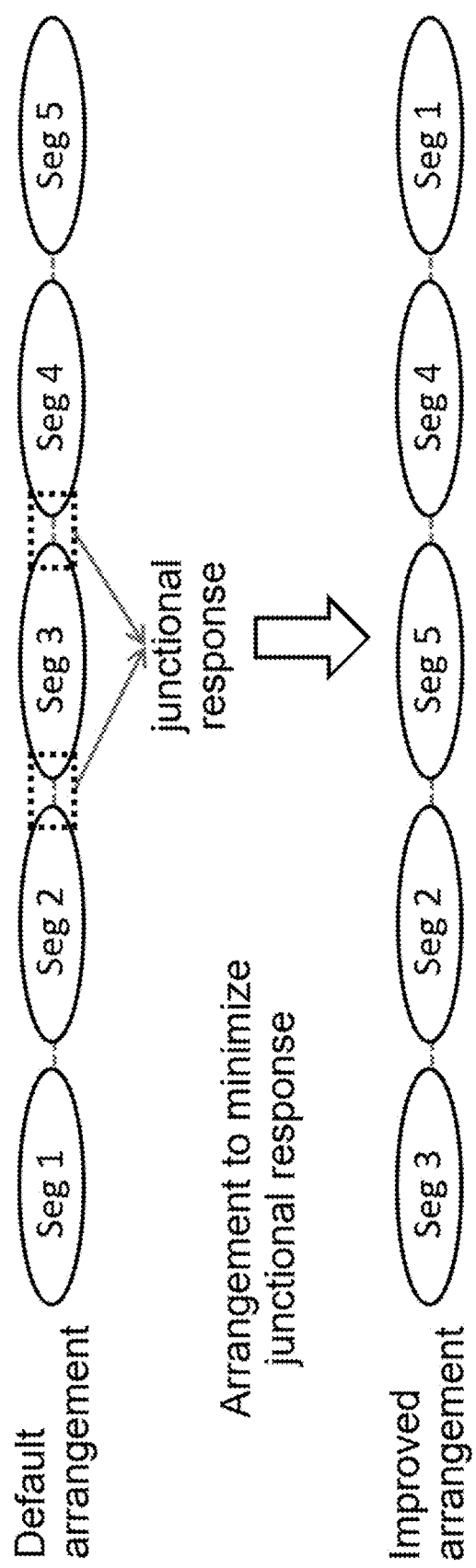
FIG. 9 illustrates how polypeptide segment arrangement analysis can reduce or eliminate possible presentation of deleterious or undesirable epitopes injunction regions.
Figure 11:
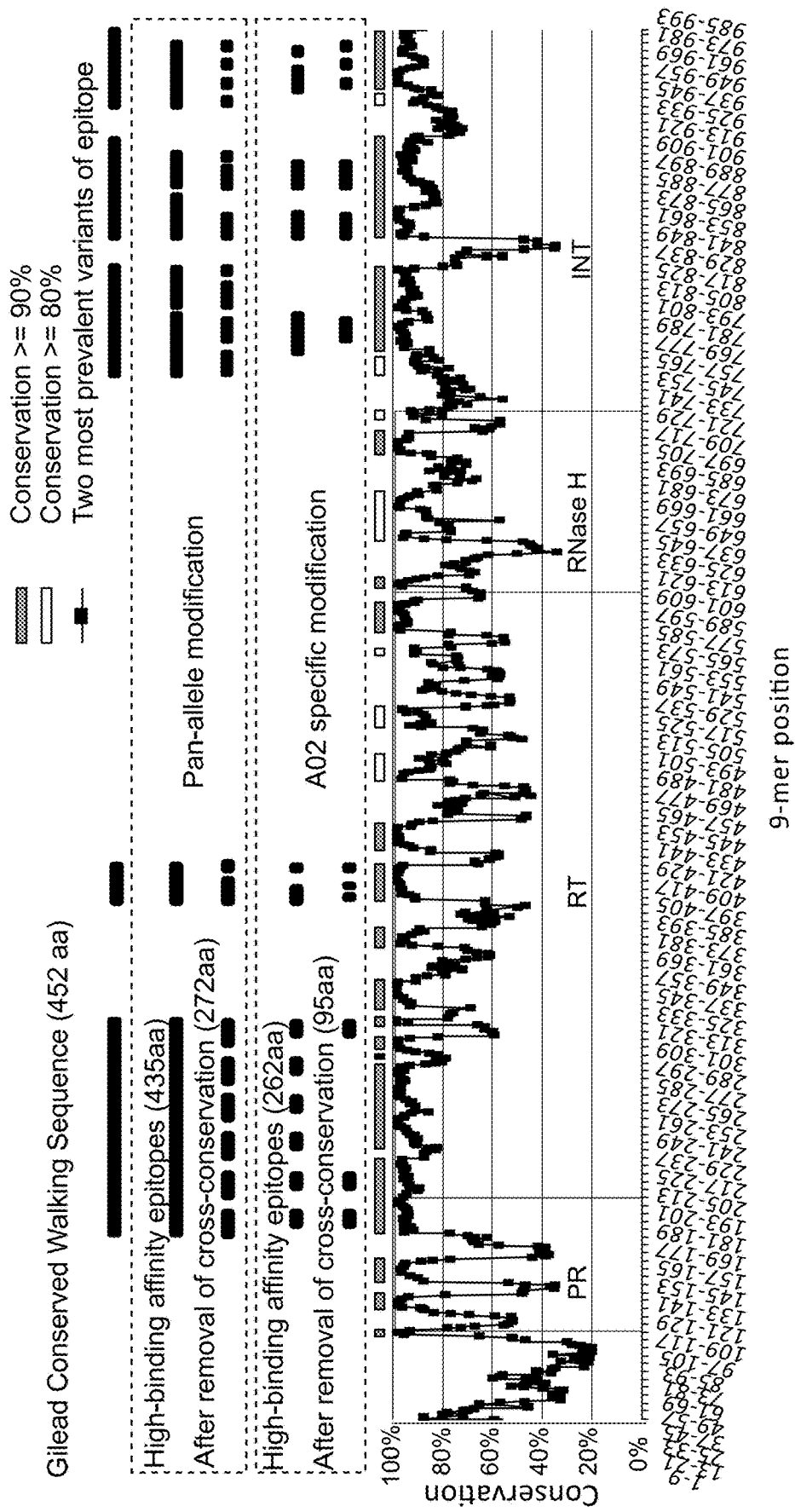
FIG. 11 illustrates incorporating considerations of binding of identified conserved viral protein regions to MHC class I molecules including pan-allele (e.g., HLA supertypes: A01, A02, A03, A24, B07, B08, B27, B44, B58, B62) and particular allele (e.g., A*0201 as a representative human MHC class one allele) analyses.

FIG. 9 illustrates how polypeptide segment arrangement analysis can reduce or eliminate possible presentation of deleterious or undesirable epitopes injunction regions. In the illustrated default arrangement, the junction 9-mers between Seg 2 and Seg3, and between Seg 3 and Seg 4 are predicted to produce junctional sequences that may induce tolerogenic or self-reactive responses in a human (e.g., having either high MHC binding affinity based on in silico HLA binding analysis or cross-recognition with human proteins based on human proteome cross-recognition analysis). We applied an algorithm that searches different arrangements and determines an arrangement that results in reduced or eliminated predicted junctional sequences that may induce tolerogenic or self-reactive responses in a human.

The fusion polypeptides of SEQ ID NOs: 351-366 and 407-410 are exemplary immunogenic fusion polypeptide sequences designed according to this method.

Example 3

MHC Class I Restricted Fusion Polypeptides

A component of improving the design of antigens for T cell vaccines is to define a desirable set of antigens that can be readily presented by the hosts' T cells and prime a T cell response. Short amino acid fragments (8-30aa long), derived from viral antigens are processed and presented on host Human Leukocyte Antigen (HLA) alleles that are defined within the Major Histocompatibility Complex (MHC). These alleles are defined as MHC class I if they present peptides that are recognized by the T cell receptor (TCR) on CD8+ T cells, and MHC class II if the peptide and MHC complex is recognized by TCRs on CD4+ T cells.

This example describes an approach in which a set of MHC class I restricted 9-mers is selected from the bivalent constructs and combined to form a MHC class I restricted vaccine construct. This method is illustrated by designing an immunogenic fusion polypeptide with multiple epitopes predicted to bind to human HLA-A*0201 allele. We selected the human HLA-A*0201 allele to demonstrate the method because it is a very common allele in the United States.

Two approaches were used to generate HLA-A*0201 restricted sequences, a "short peptide" approach and a "long peptide" approach. For the short peptide approach, we applied the in-silico MHC class I binding analysis described in Example 2 to identify any 9-mers in the bivalent sequences that were predicted to have low binding affinity to HLA-A*0201. Low affinity 9-mers (e.g., 9-mers having a predicted MHC class I binding IC50 value of less than 1,000 nM) were removed from the constructs.

Next, as described in Example 2, we performed a human proteome cross-recognition analysis for all the 9-mers in the bivalent construct. We identified any 9-mers sharing at least 5 residues with human peptide sequences and removed them from the constructs.

We subsequently applied our internally developed polypeptide segment arrangement tool described in Example 2 and combined all of the remaining 9-mers in both of the bivalent sequences into a single sequence, arranged in an order to reduce or avoid undesirable junctions. We refer to this as a "beads on a string" approach. In a vaccine construct that is based on single or multiple MHC class I allele binding specificities, induction of a helper CD4+ T cell responses can be achieved by including MHC class II epitopes. These may be class II epitopes defined in the literature and known to be targeted by a large proportion of the population or may be tailored to the individuals own MHC class II alleles (Ranasinghe, *J Virol*, (2012) 86(1):277-83; and Kaufmann, et al., *J Virol*. (2004) 78(9):4463-77).

For the "long peptide" approach, we performed the same steps as described above to arrive at the "short peptide" sequence, except after removing the low affinity MHC class I (here, human HLA-A*0201) binding 9-mers, each of the remaining 9-mers was flanked with the most conserved 8 amino acid segments upstream and downstream to create 25 amino acid long peptides. Then, as with the short peptide approach, all of the 25-mers are combined into a single sequence using a "beads on a string" approach, arranged in an order to reduce or avoid undesirable junctions.

FIG. 10A-B provides a flow diagram illustrating the basic methodology of the "short peptide" and "long peptide" approaches, respectively. The fusion polypeptides of SEQ ID NOs: 367-377 and 411 are exemplary immunogenic fusion polypeptide sequences designed according to this method.

Example 4

Individualized Construct with Deep Sequencing Data Analysis Incorporated

This example describes an approach in which deep sequencing data analysis is included to form an individualized vaccine construct. In this Example, as in Steps 1-2 of Example 1 above, we first aligned the source sequences and then applied the Conservation Algorithm to identify a set of all candidate conserved regions in the protein coding regions of the target genes. In this example, the target genes were Gag, Nef and Pol. We applied the CWA to build bivalent sequences in those regions, as in Steps 3-5 of Example 1.

In addition to the 9-mers derived from downloaded population sequences, we also analyzed deep sequencing data of the target individual to identify intra-patient diversity within those conserved regions. To identify intra-patient 9-mer variants using deep sequencing data, deep sequencing reads were assembled to create subject-specific consensus sequences. The deep sequencing reads were aligned to subject-specific consensus sequence and then alignment was mapped to HXB2 position coordinates based on alignment of subject-specific consensus to HXB2 reference sequence. At each 9-mer position within the conserved regions, corresponding subsequences from all the sequencing reads completely covering that position were extracted converted into 9 amino acid sequences. Only 9-mer variants with prevalence exceeding assay background were included.

Figure 12A:
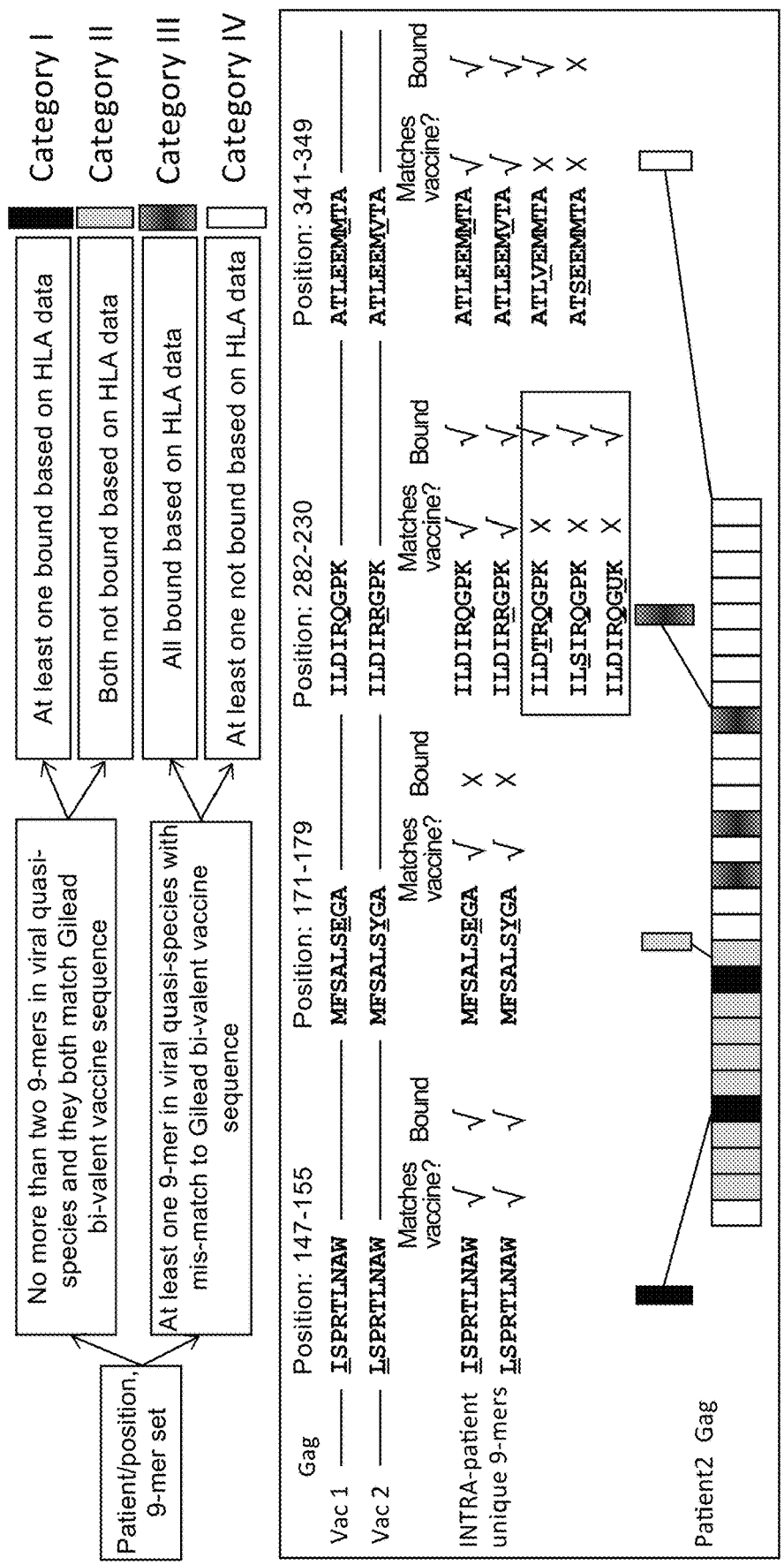
FIGS. 12A-12B.
Figure 12B:
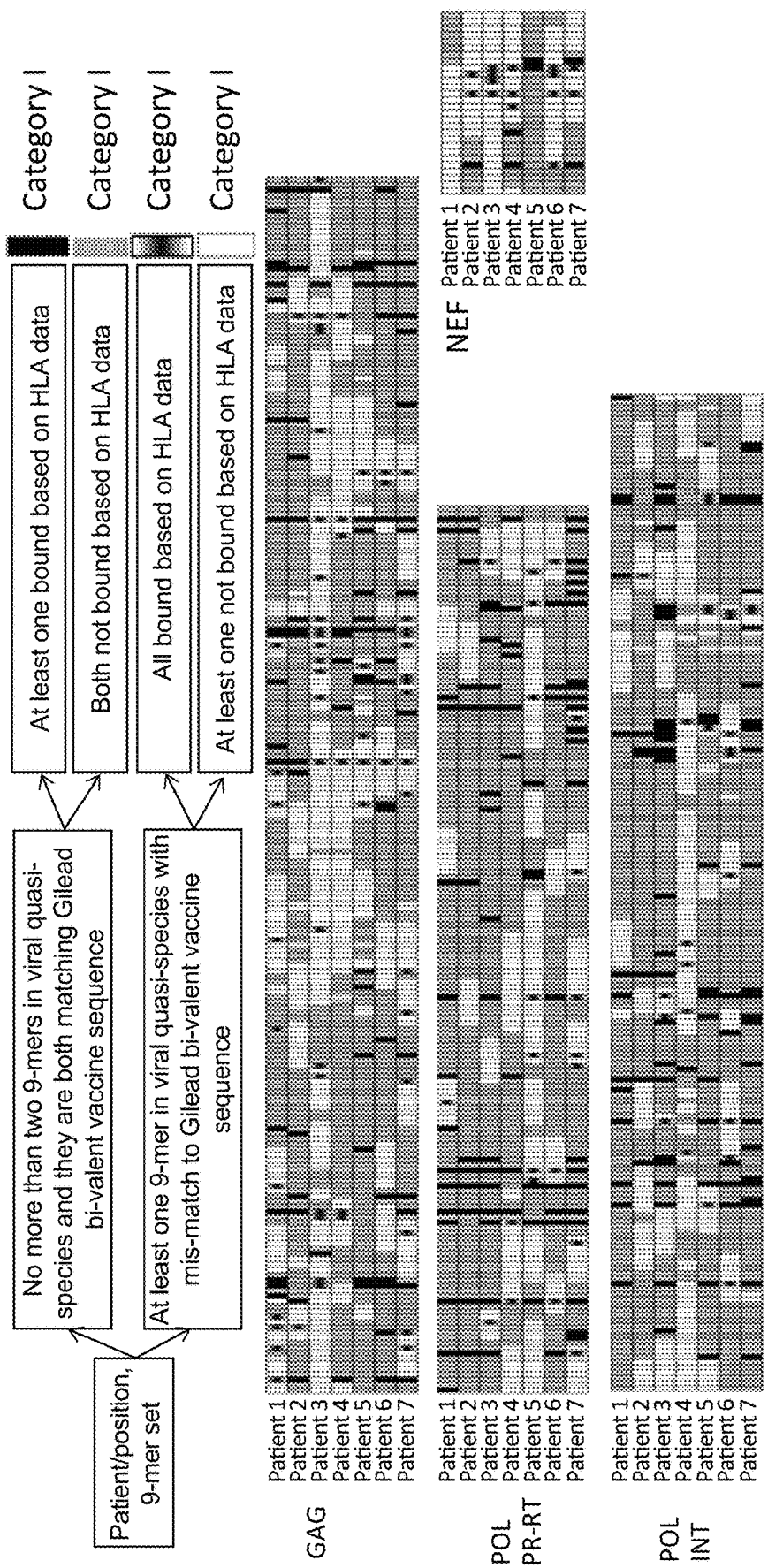
Figure 15:
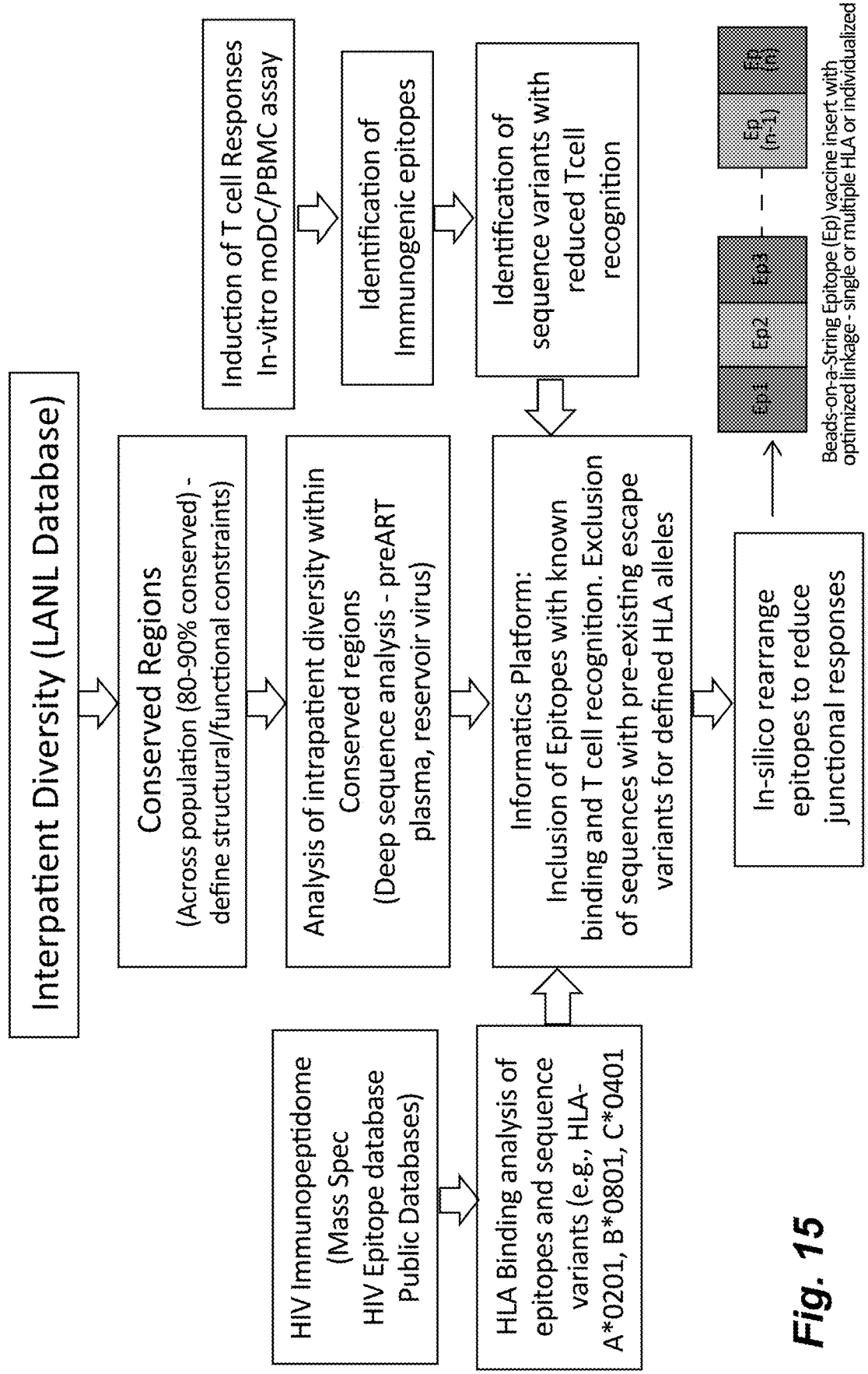
FIG. 15 illustrates rational antiviral immunogen design approach that considers for interpatient and intrapatient viral sequence diversity and host MHC class I and class II molecules binding, and T cell recognition. The approach and resulting immunogens are exemplified herein by immunogens that elicit human immune responses against HIV-1.

For all the 9-mers position within conserved regions, we performed the in-silico HLA prediction analysis and then classified all the positions into four categories (FIG. 6). Positions are classified into Category I (represented by ▌ in FIG. 12A) if all the intra-patient 9-mers match bivalent sequences and at least one of them have high predicted binding affinities. Positions are classified into Category II (represented by ▓ in FIG. 12A) if all the intra-patient 9-mers match bivalent sequences and all of them have low predicted binding affinities. Positions are classified into Category III (represented by ▓ in FIG. 12A) if at least one of the intra-patient 9-mers does match bivalent sequences and all of them have high predicted binding affinities. Positions are classified into Category IV (represented by ⌐ in FIG. 12A) if at least one of the intra-patient 9-mers does match bivalent sequences and at least one of them has low predicted binding affinity.

Next, based on the conserved region position classification results, all the 9-mer variants in Category IV positions are removed and only 9-mers that have high binding affinity (e.g., 9-mers having a predicted MHC class I binding IC50 value of greater than 1,000 nM) to patient HLA allele in other position are kept. Any epitopes that are known to be escape variants (i.e., sequence variants that escape T cell recognition) based on external public HIV databases (hiv.lanl.gov) or internal experimental data are removed. As described in Example 2, we performed a human proteome cross-recognition analysis for all the remaining 9-mers and any 9-mers sharing at least 5 residues with human peptide sequences are removed. Then as described in the "long peptide" approach in Example 3, each of the remaining 9-mers was flanked with the most conserved 8 amino acid segments upstream and downstream to create 25 amino acid long peptides (25-mers). In a final step, we applied our internally developed polypeptide segment arrangement tool described in Example 2 and combined all of the 25-mers into a single sequence ("beads on a string" approach).

FIG. 13 provides a flow diagram illustrating the basic methodology of the individualized construct approach. SEQ ID NO: 422 provides an exemplary immunogenic fusion polypeptide sequence designed according to this method. It is an illustrative individualized construct designed with deep sequencing data analysis incorporated; generated using deep sequencing data from a patient with HLA alleles: A*02:01, A*23:01, B*07:02, B*44:03, C*04:01, and C*07:02.

Example 5

HLA Restricted Construct Improved with Deep Sequencing Data Analysis

This example describes an approach in which deep sequencing data and patient HLA data analyses are included to further improve the HLA restricted vaccine construct described in Example 3. In this Example, as in Steps 1-2 of Example 1 above, we first aligned the source sequences and then applied the Conservation Algorithm to identify a set of all candidate conserved regions in the protein coding regions of the target genes. In this example, the target genes were Gag, Pol and Nef We applied the CWA to build bivalent sequences in those regions, as in Steps 3-5 of Example 1.

In addition to the 9-mers derived from downloaded population sequences, we also analyzed deep sequencing data of four individuals with the same HLA allele (HLA-A*0201) to identify intra-patient diversity within those conserved regions.

As described in Example 4 above, we analyzed deep sequencing data and classified all the conserved region positions into four categories for each individual.

For each of the positions in conserved regions, if it is in Category IV for at least one patient, all the 9-mer variants are removed as this indicates that an escape pathway for that allele has been defined. While in all the other positions, only 9-mers that have high binding affinity to the target HLA allele (HLA-A*0201 in this example) are kept. As described in Example 2, we performed a human proteome cross-recognition analysis for all the remaining 9-mers and any 9-mers sharing at least 5 residues with human peptide sequences are removed. Then as described in the "long peptide" approach in Example 3, each of the remaining 9-mers was flanked with the most conserved 8 amino acid segments upstream and downstream to create 25 amino acid long peptides (25-mers) (see, Assadipour, et al., *Clin Cancer Res*. (2017) 23(15):4347-4353; Zhang, et al., *J Biol Chem*, (2009) 284(14):9184-91). In a final step, we applied our internally developed polypeptide segment arrangement tool described in Example 2 and combined all of the 25-mers into a single sequence ("beads on a string" approach).

FIG. 14 provides a flow diagram illustrating the basic methodology of the HLA restricted construct (e.g., HLA-A*0201 sequence) approach with deep sequencing data analysis incorporated. SEQ ID NO: 423 provides an exemplary immunogenic fusion polypeptide sequence designed according to this method. It is an illustrative HLA restricted construct improved with deep sequencing data analysis; generated using deep sequencing data from four HLA-A*02:01 patients.

Example 6

Viral Expression Vectors Containing Immunogenic Fusion Polypeptides

In this example, we generated viral expression vectors encoding the computationally defined polypeptide segments containing conserved regions of HIV-1 encoded by Gag, Nef and Pol genes as a transgene and confirmed expression of the transgene in mammalian cells. The polypeptide segments containing conserved regions were concatenated or connected by a variety of approaches including direct fusion, linkage of regions by the addition of a proteolytic cleavage site sequence or the addition of a flexible linker between regions. For the purposes of demonstration, we used a polyalanine (AAA) flexible linker (SEQ ID NO: 378), and a proteolytic cleavage site derived from the 2A region of the foot-and-mouth disease virus (FMDV) polyprotein (F2A) (Ryan, et al., *J Gen Virol*, (1991) 72(11):2727-32).

Methods

Construction of Viral Expression Vector Containing Transgene Encoding Fusion Polypeptide Variants.

Ad5/35 vectors expressing an HIV-1 computationally defined vaccine immunogen with various approaches to linkage of conserved HIV-1 sequences, were generated by in vitro recombination using standard methods (Vector Biolabs). Expression cassettes were generated by PCR using synthetic oligonucleotides codon-biased for improved human expression (GeneArt, ThermoFisher Scientific), and placed under the control of the CMV promoter using standard gene cloning techniques. The constructs developed for this evaluation are listed in Table 1 and schematically depicted in FIG. 20.

Evaluation of Target Gene Expression and F2A Cleavage In Vitro.

To improve assembly of viral vectors encoding the vaccine expression cassette, the genes were cloned into vector plasmids (ThermoFisher Scientific) containing restriction sites for cloning target genes and a GFP marker. DNA was transformed into One Shot™ TOP10 competent cells (Invitrogen, Carlsbad, CA) following manufacturer's protocol and plated onto LB agar plate supplemented with 100 μg/ml ampicillin. The plate was incubated overnight at 37° C. A single colony was picked from the plate and inoculated into a 10 ml liquid LB+ampicillin culture and shaken overnight at 37° C. at 250 rpm in an Eppendorf bench top shaker. The bacterial pellet was processed using QIAprep Spin miniprep kit (Qiagen, Germantown, MD) to obtain the plasmid DNA following manufacturer's protocol. Nucleic acid concentration was determined by reading absorbance at 280 nm using NanoDrop™2000 (Thermo Scientific). To evaluate in vitro expression, the expression vectors were transfected into Expi293™ cells according to manufacturer's protocol using ExpiFectamine™ (Invitrogen, Carlsbad, CA). At Day2 post-transfection when the viability of cells was still at >80%, they were evaluated for GFP expression by flow cytometry

TABLE 1

Fusion Polypeptides Expressed from Adenoviral Vectors ("AAA" is SEQ ID NO: 378)

| SEQ ID NO: | HIV-1 Fusion polypeptide | Amino Acid Sequence |
|---|---|---|
| 349 | p17-p24-Pr-RT-Int-RNAseH-nef | LKHIVWASRELERFAVNPGLLETVSQNYPIVQNISPRTLNAWVKVVEEKAFSPEVIPMFSALSEGATPQDLNTMLNTVGGH<br>QAAMQMLKETINEEAAEWDRLHPVHAGPIAPGQMREPRGSDIAGTTSTLQEQIGWMTNNPPIPVGEIYKRWIILGLNKIVR<br>MYSPTSILDIRQGPKEPFRDYVDRFYKTLRAEQASQEVKNWMTETLLVQNANPDCKTILKALGPAATLEEMMTACQGVGGP<br>GHKARVLAEAMSQLPGRWKPKMIGGIGGFIKVRQYDQGTVLVGPTPVNIIGRNLLTQIGCTLNFPISPIETVPVKLKPGMD<br>GPKVKQWPLTEEKIKALVEICTEMEKEGKISKIGPENPYNTPVFAIKKKDSTKWRKLVDFRELNKRTQDFWEVQLGIPHPA<br>GLKKKKSVTVLDVGDAYFSVPLDKDFRKYTAFTIPSWGFTTPDKKHQKEPPFLWMGYELHPDKWTVQPIVAKEIVASCDKC<br>QLKGEAMHGQVDCSPGIWQLDCTHLEGKIILVAVHVASGYIEAEVIPAETGQETAYFLLKLAGRWPVKTTVKAACWWAGIK<br>QEFGIPYNPQSQGVVESMNKELKKIIGQVRDQAEHLKTAVQMAVFIHNFKRKGGIGGYSAGERIVDIIAITKIQNFRVYYR<br>DSRDPLWKGPAKLLWKGEGAVVIQDNSDIKVVPRRKAKIIRDYGKQMAGDDCVASRQDEDEEVGFPVKPQVPLRPMTFKGA<br>LDLSHFLREKGGLEG |
| 345 | p17-p24-AAA-Pr-RT-AAA-Int-RNAseH-AAA-nef | LKHIVWASRELERFAVNPGLLETAAAVSQNYPIVQNAAAISPRTLNAWVKVVEEKAFSPEVIPMFSALSEGATPQDLNTML<br>NTVGGHQAAMQMLKETINEEAAEWDRLHPVHAGPIAPGQMREPRGSDIAGTTSTLQEQIGWMTNNPPIPVGEIYKRWIILG<br>LNKIVRMYSPTSILDIRQGPKEPFRDYVDRFYKTLRAEQASQEVKNWMTETLLVQNANPDCKTILKALGPAATLEEMMTAC<br>QGVGGPGHKARVLAEAMSQAAALPGRWKPKMIGGIGGFIKVRQYDQAAAGTVLVGPTPVNIIGRNLLTQIGCTLNFPISPI<br>ETVPVKLKPGMDGPKVKQWPLTEEKIKALVEICTEMEKEGKISKIGPENPYNTPVFAIKKKDSTKWRKLVDFRELNKRTQD<br>FWEVQLGIPHPAGLKKKKSVTVLDVGDAYFSVPLDKDFRKYTAFTIPSAAAWGFTTPDKKHQKEPPFLWMGYELHPDKWTV<br>QPIAAAVAKEIVASCDKCQLKGEAMHGQVDCSPGIWQLDCTHLEGKIILVAVHVASGYIEAEVIPAETGQETAYFLLKLAG<br>RWPVKTAAATVKAACWWAGIKQEFGIPYNPQSQGVVESMNKELKKIIGQVRDQAEHLKTAVQMAVFIHNFKRKGGIGGYSA<br>GERIVDIIAAAAITKIQNFRVYYRDSRDPLWKGPAKLLWKGEGAVVIQDNSDIKVVPRRKAKIIRDYGKQMAGDDCVASRQ<br>DEDAAAEEVGFPVKPQVPLRPMTFKGALDLSHFLREKGGLEG |
| 347 | p17-p24-F2A-Pr-RT-F2A-Int-RNAseH-F2A-nef | LKHIVWASRELERFAVNPGLLETVSQNYPIVQNISPRTLNAWVKVVEEKAFSPEVIPMFSALSEGATPQDLNTMLNTVGGH<br>QAAMQMLKETINEEAAEWDRLHPVHAGPIAPGQMREPRGSDIAGTTSTLQEQIGWMTNNPPIPVGEIYKRWIILGLNKIVR<br>MYSPTSILDIRQGPKEPFRDYVDRFYKTLRAEQASQEVKNWMTETLLVQNANPDCKTILKALGPAATLEEMMTACQGVGGP<br>GHKARVLAEAMSQRAKRAPVKQTLNFDLLKLAGDVESNPGPLPGRWKPKMIGGIGGFIKVRQYDQGTVLVGPTPVNIIGRN<br>LLTQIGCTLNFPISPIETVPVKLKPGMDGPKVKQWPLTEEKIKALVEICTEMEKEGKISKIGPENPYNTPVFAIKKKDSTK<br>WRKLVDFRELNKRTQDFWEVQLGIPHPAGLKKKKSVTVLDVGDAYFSVPLDKDFRKYTAFTIPSWGFTTPDKKHQKEPPFL<br>WMGYELHPDKWTVQPIVAKEIVASCDKCQLKGEAMHGQVDCSPGIWQLDCTHLEGKIILVAVHVASGYIEAEVIPAETGQE<br>TAYFLLKLAGRWPVKTTVKAACWWAGIKQEFGIPYNPQSQGVVESMNKELKKIIGQVRDQAEHLKTAVQMAVFIHNFKRKG<br>GIGGYSAGERIVDIIAITKIQNFRVYYRDSRDPLWKGPAKLLWKGEGAVVIQDNSDIKVVPRRKAKIIRDYGKQMAGDDCV<br>ASRQDEDRAKRAPVKQTLNFDLLKLAGDVESNPGPEEVGFPVKPQVPLRPMTFKGALDLSHFLREKGGLEG |
| 428 | p17-p24 | LKHIVWASRELERFAVNPGLLETVSQNYPIVQNISPRTLNAWVKVVEEKAFSPEVIPMFSALSEGATPQDLNTMLNTVGGH<br>QAAMQMLKETINEEAAEWDRLHPVHAGPIAPGQMREPRGSDIAGTTSTLQEQIGWMTNNPPIPVGEIYKRWIILGLNKIVR<br>MYSPTSILDIRQGPKEPFRDYVDRFYKTLRAEQASQEVKNWMTETLLVQNANPDCKTILKALGPAATLEEMMTACQGVGGP<br>GHKARVLAEAMSQ |
| 429 | Pr-RT | LPGRWKPKMIGGIGGFIKVRQYDQGTVLVGPTPVNIIGRNLLTQIGCTLNFPISPIETVPVKLKPGMDGPKVKQWPLTEEK<br>IKALVEICTEMEKEGKISKIGPENPYNTPVFAIKKKDSTKWRKLVDFRELNKRTQDFWEVQLGIPHPAGLKKKKSVTVLDV<br>GDAYFSVPLDKDFRKYTAFTIPSWGFTTPDKKHQKEPPFLWMGYELHPDKWTVQPI |
| 151 | Nef | EEVGFPVKPQVPLRPMTFKGALDLSHFLREKGGLEG | or pelleted. The cell lysates were evaluated for HIV-1 gag p24 expression by ELISA or protein expression was determined by western blot immunoprecipitated with anti-Nef antibody to enable detection of the full-length translation product containing the Nef sequence at the C terminus.

Results

Figure 21A:
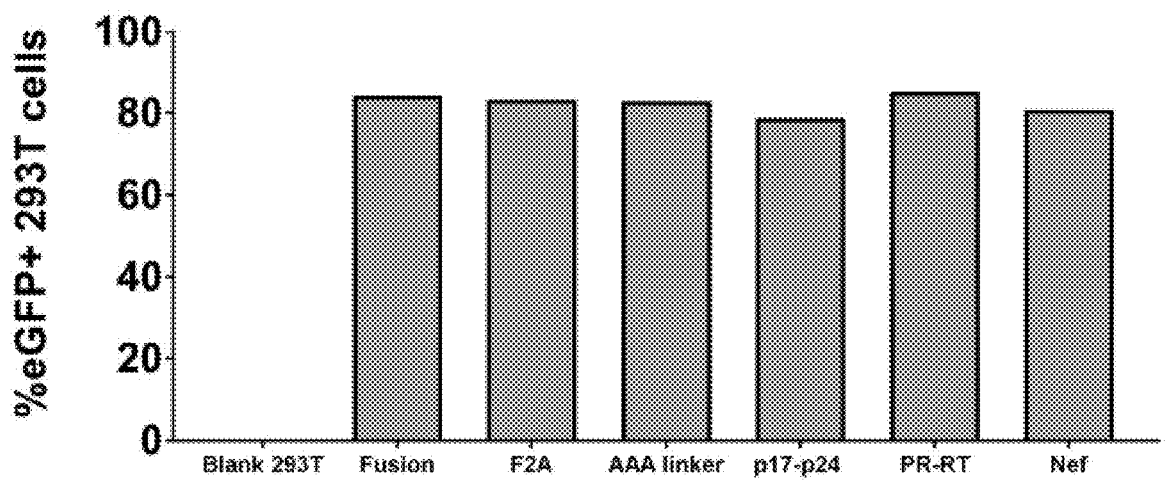
FIGS. 21A-21C. (A) Plasmid DNAs containing the vaccine immunogen each representing different linkage strategies (fusion, F2A cleavage site, AAA linker (SEQ ID NO: 378)) or a fusion segment (e.g., Pol PR-RT) were transfected into Expi293™ cells. Transfection efficiency was determined by evaluation of % GFP expression of transfected Expi293F cells by flow cytometry. Results shown are representative of several independent experiments. (B) All plasmid DNAs contained p24 in the expression cassette. Expression efficiency was assessed by p24 ELISA (C) Translation products of the vaccine transgene constructs. The identity of the translation polypeptide was confirmed by Western blot immunoprecipitation with anti-Nef antibodies (2 µg/mL, 0.5 sec exposure). The uppermost band corresponded to the expected full-length translation product (88 kDa) in the fusion and the AAA linker (SEQ ID NO: 378) containing constructs. The F2A containing translation product was not detected by anti-Nef antibodies, indicating cleavage of the Nef product by absence of the full-length construct. To control for equal loading, the membrane was probed with an antibody against anti-alpha tubulin.
Figure 21B:
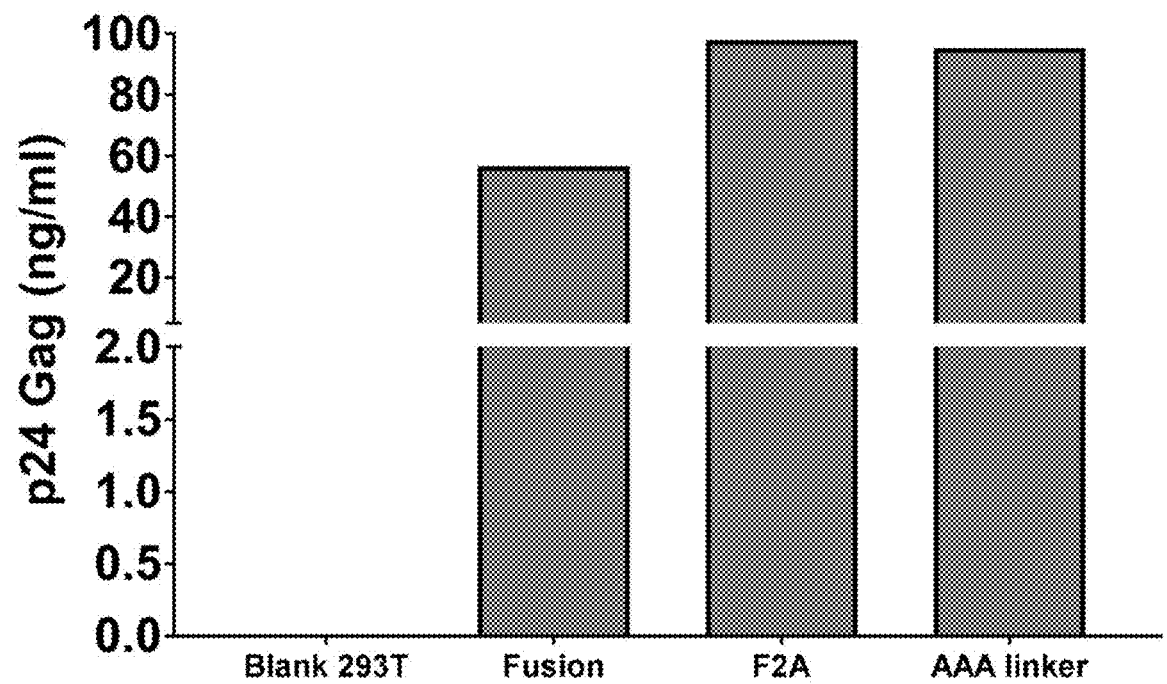
Figure 21C:
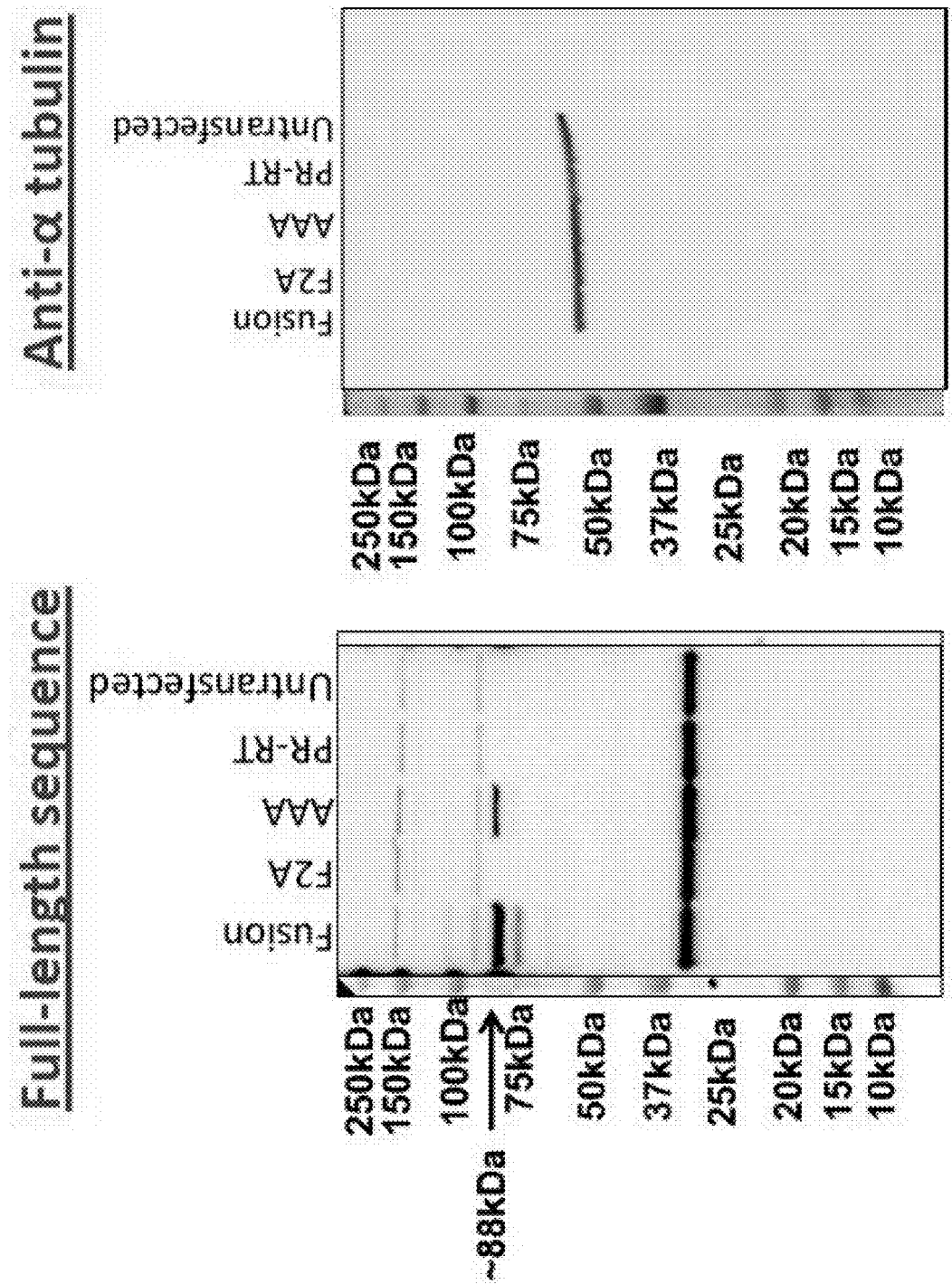

The data depicted in FIGS. 21A-21C demonstrated that the all three approaches to concatenation or connection of conserved region polypeptide segments into fusion polypeptides resulted in the efficient transfection and expression of the polypeptides encoded by the transgene. Evaluation of the translation product indicated that the inclusion of the F2A proteolytic cleavage sequence resulted in appropriate cleavage of the polypeptide (FIG. 21C). We then tested the efficiency of these constructs in various viral vector systems to prime T cell responses in vitro and in vivo.

Example 7

In Vitro Assays Demonstrating Human T Cell Activation Induced by Fusion Polypeptides In this example, we established an in vitro method for testing the efficacy of T cell priming in humans by vaccine constructs in expression vectors. A similar approach is described in, e.g., WO 2015/110397. The application of this method in vaccinology allows evaluation of antigen processing, presentation and priming of T cells in humans of the transgene cassette, as well as the study of immune parameters including adjuvants and immune modulators that may modify the efficacy of priming.

Methods

Monocyte Purification and Maturation of Monocyte Derived Dendritic Cells (moDCs).

Freshly isolated or cryopreserved PBMCs were used in the moDC– based T cell stimulation assays. CD14+ monocytes were purified from PBMCS from individuals with or without HIV, and ART naïve or on ART using the EasySep human anti-CD14 positive selection antibody kit (StemCell Technologies). Flow cytometry was used to confirm the purification of the isolated CD14+ monocytes to >90% prior to the establishment of the culture. To generate immature moDCs, $2 \times 10^6$ purified CD14+ monocytes were cultured in 3 mL of moDC differentiation media, i.e., complete RPMI 1640 containing 10% heat inactivated fetal calf serum, 1% penicillin streptomycin/mL, 0.5 mM HEPES, 800U/mL of GM-CSF (Miltenyi Biotec), and 1000 U of IL-4 (Miltenyi Biotec) in 6 well culture plates. The plates were incubated at 37° C. and 5% $CO_2$ for 6 days and monitored daily to ensure adherence of monocytes. To generate mature moDCs, adherent immature moDC cultures were supplemented with recombinant soluble CD40L (0.5 µg/ml), IFN-γ (1,000U/ml), PGE2 (5 µM), TNF-α (10 ng/ml), IL-6 (100 ng/ml) and IL-1β (10 ng/ml) with an additional 3 ml of moDC differentiation media on day 6 and incubated at 37° C. and 5% $CO_2$ for an additional 48 hrs.

Figure 22:
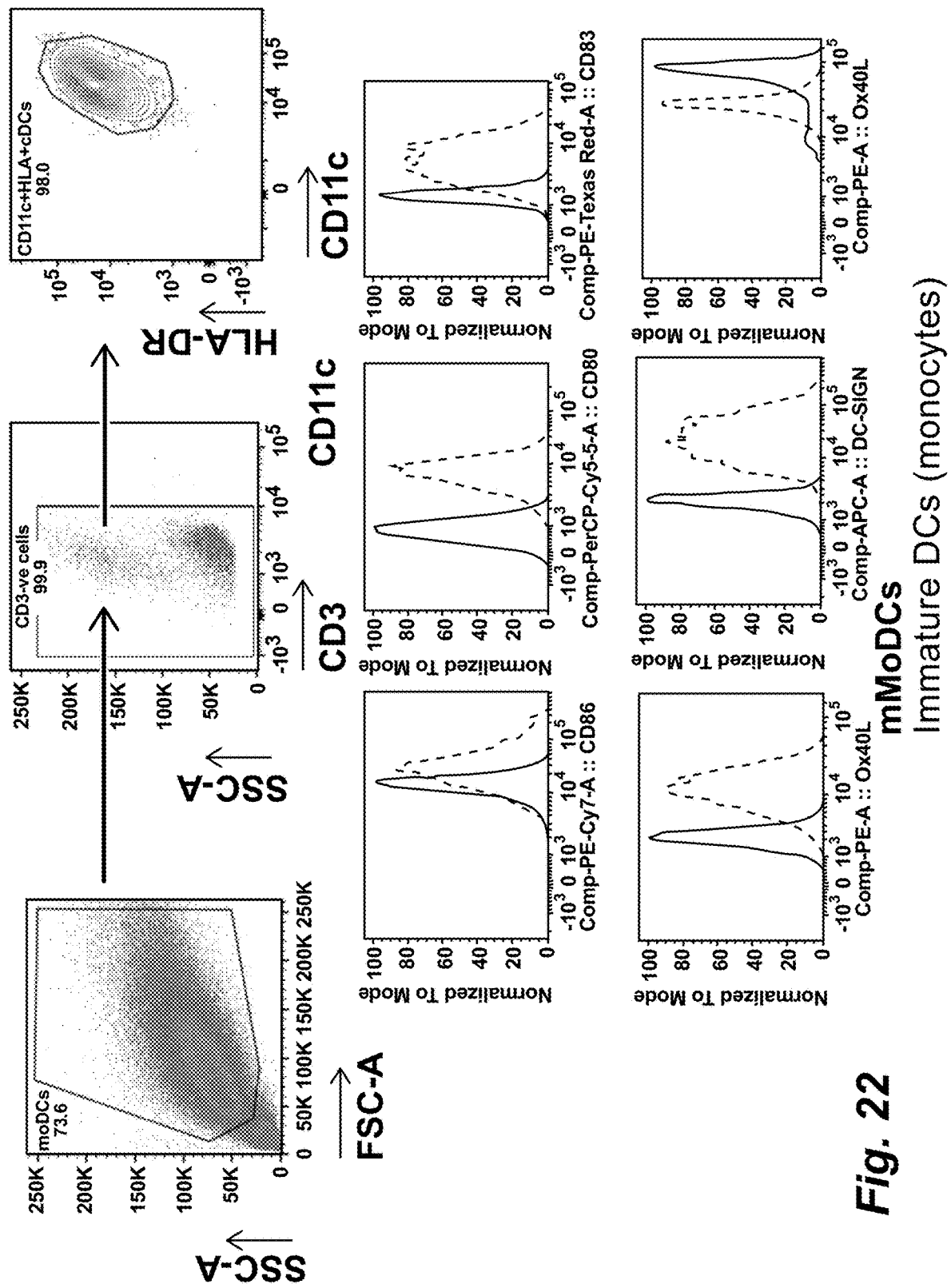
FIG. 22 illustrates a comparison of the differentiation phenotype of immature dendritic cells and mature monocyte derived dendritic cells (mMoDCs). Monocyte derived DCs (MoDCs) were matured in the presence of cytokines for 8 days and analyzed by flow cytometry for the expression of CD11c, HLA-DR, CD14, CD430, DCSIGN, CD83, CD86 and OX40L.

On day 8, adherent mature moDCs were detached using ice-cold PBS and a cell scrapper to manually detach the moDCs. Following this procedure, unattached cells were washed using moDC differentiation media and transferred to a 50 ml Falcon tube. The resulting cell mixture was centrifuged at 1500 rpm for 5 minutes at room temperature. Next, the supernatant was discarded and the cell pellet was resuspended in 5m of moDC differentiation media. A fraction of the mature moDCs were isolated and stained to characterize the differentiation phenotype of the moDCs with antiCD11c+, anti-HLA-DR+, anti-CD14−, anti-CD40+, anti-DCSIGN+, anti-CD83, anti-CD86 and anti-OX40L antibodies. The results are shown in FIG. 22.

Transduction of moDCs with Viral Vector, e.g., Adenovirus (Ad) 5/35 Vectors.

Figure 23:
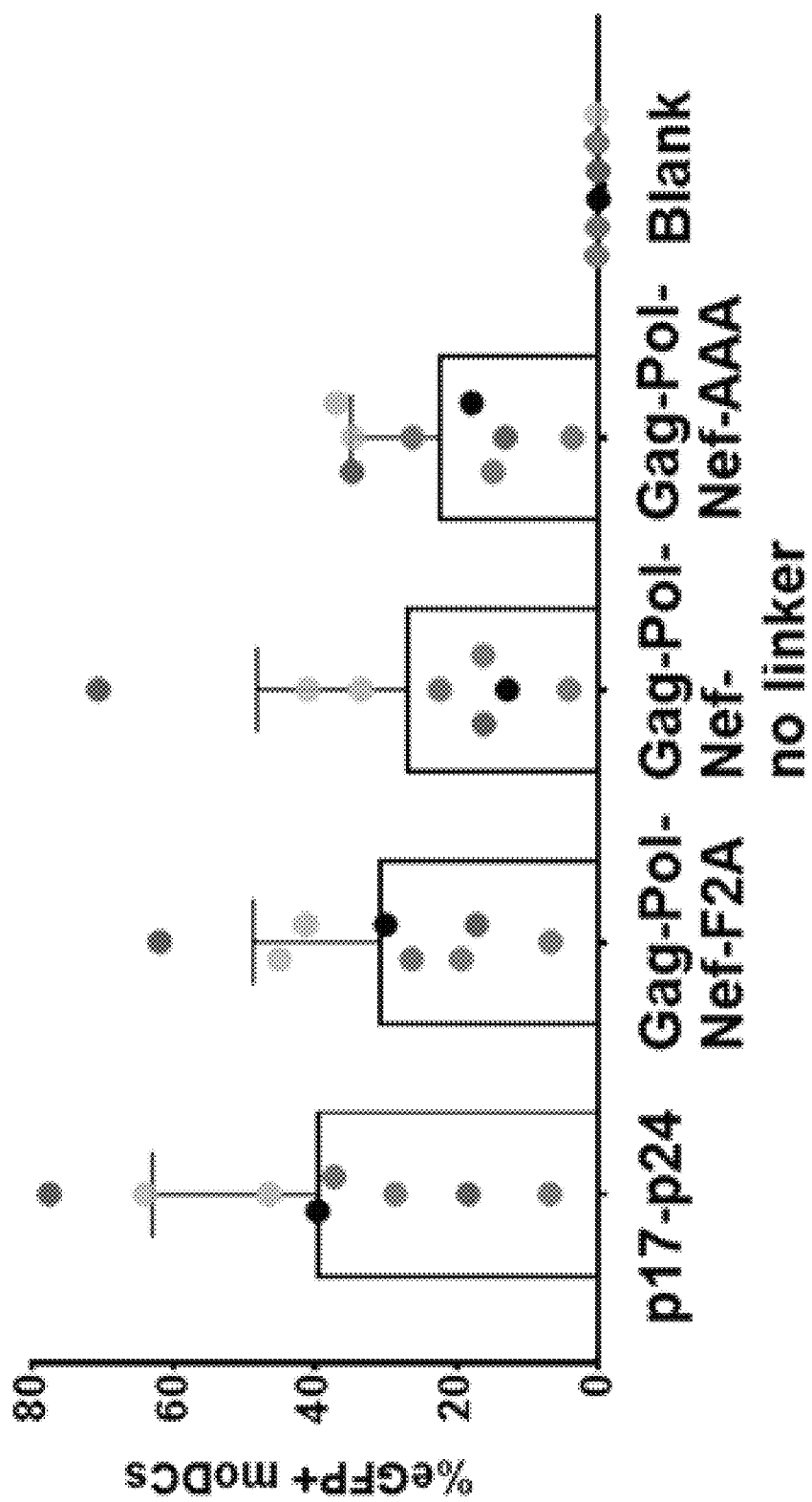
FIG. 23 illustrates representative moDC transduction efficiency using GFP expressing Ad5/35 viral vectors at multiplicity of infection (MOI) of 1000 PFU in eight human donors at day 3 post-transfection. Proportion of cells expressing GFP by flow cytometry is shown on the y-axis. The x-axis represents vaccine immunogen constructs consisting of conserved regions in p17-p24 only (SEQ ID NO: 428) as well as full length Gag-Nef immunogens designed with each of the 3 fusion approaches (F2A (SEQ ID NOs: 347), fusion (SEQ ID NOs: 349) and AAA linker (SEQ ID NOs: 345) ("AAA" disclosed as SEQ ID NO: 378)). The amino acid sequences are provided in Table 1.

The purified moDCs were harvested, washed twice in serum-free media, and re-suspended in X-Vivo 15 (BioWhittaker, Walkersville, MD) at $10^7$/ml. Cells were equilibrated at 37° C. in a water bath for 20-30 min before transduction. Ad5/35 stocks were thawed on ice and added to the moDC suspension at the indicated multiplicity of infection (MOI). Cells were gently mixed and placed immediately in the 37° C. incubator. After 2 hours, warm moDC differentiation media containing GM-CSF and IL-4 were added to dilute the moDCs to a final concentration of $10^5$/ml. 0.5 ml of transduced moDCs were transferred to 48 well plates and maintained at 37° C. in 5% $CO_2$ for an additional 24 h before addition of PBMCs or purified CD8+ T cells. The results are shown in FIG. 23.

Purification of Autologous CD8 or CD4 T Cells and Co-Culture with moDCs.

In experiments requiring the stimulation of CD8+ T cells, the CD8+ fraction was enriched from autologous PBMCs using the human CD8+ T cell enrichment kits (EasySep, StemCell Technologies). Purified CD8+ T cells were co-cultured with vaccine vector transduced autologous moDCs for 7 days (first round) and then non-adherent cells were subsequently transferred to a second culture of freshly transduced autologous moDCs for another 7 days (day 14 second round). In experiments requiring the stimulation of CD4+ T cells, the CD4+ fraction was enriched from autologous PBMCs using the human CD4+ T cell enrichment kits (EasySep, StemCell Technologies). Cells were confirmed to have >90% purity by flow cytometry. Isolated cells were resuspended at $1-5 \times 10^6$/ml cells in 1.0 ml (max. volume) of PBS containing 0.1% FBS in a 15 ml Falcon tube and labeled with cell trace violet (Tag-it violet) following the manufacturer's protocol (Biolegend). Cell-trace violet (CTV)-labeled CD8+ T cells, CD4+ T cells or PBMCs were then enumerated and resuspended at $2 \times 10^6$/ml. $1 \times 10^6$ purified CD8+ T cells, CD4+ T cells or PBMCs were then seeded to each well containing $5 \times 10^4$ moDCs in 48 well culture plates at a moDC: T cell/PBMC ratio of 1:20.

ELISpot Assays.

Figure 24A:
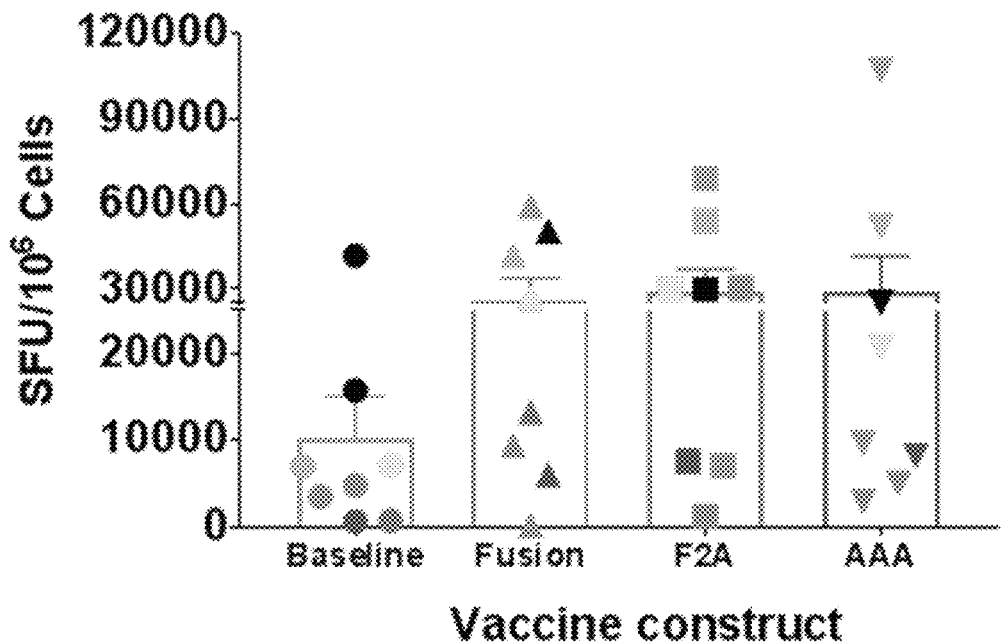
FIGS. 24A-24B illustrate priming of antigen specific T cells by vaccine constructs expressing conserved regions of HIV-1 concatenated or connected by fusion, F2A proteolytic cleavage sequence or an AAA linker (SEQ ID NO: 378). (A) Magnitude of primed responses assessed by IFN-γ ELISpot assay on day 10 following co-culture of PBMCs with vaccine vector transduced autologous moDCs. PBMCs derived from HIV infected donors with pre-existing HIV specific responses at baseline (B) Breadth of responses defined as number of de novo recognized peptide pools (excluding pre-existing baseline responses). No statistical significance was observed among the different groups in this analysis.
Figure 24B:
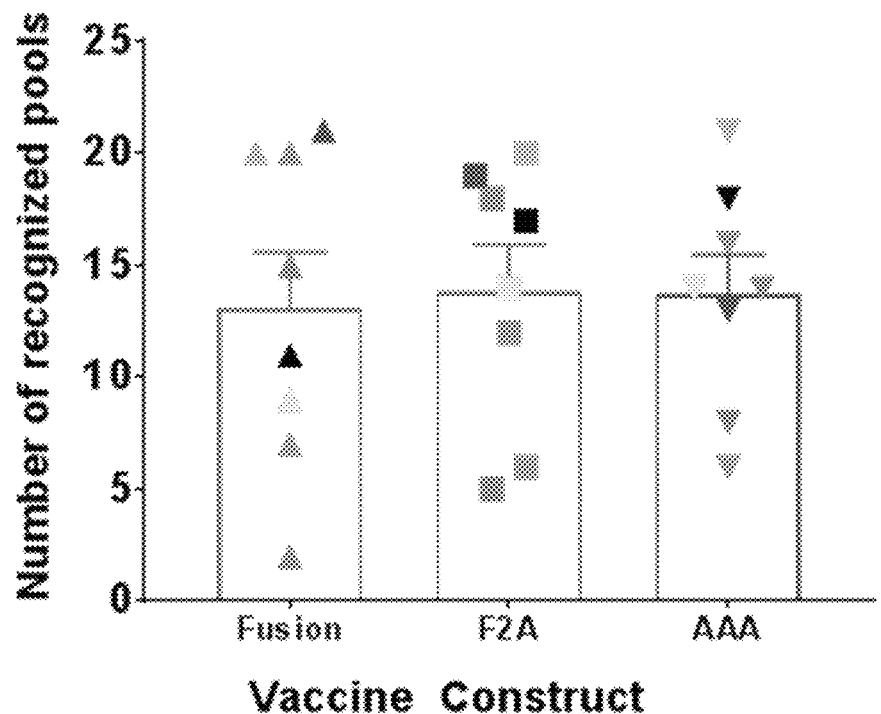

Pre-coated strip ELISpot plates (Cellular Technologies Limited) were used for all ELISpot analyses. Briefly, $5 \times 10^4$ cells from Day 10 moDC-CD8+ T cell/PBMC cultures were seeded to each well. Peptide pools consisting of 15-mer peptides overlapping by 11 amino acids spanning the entire HIV conserved regions were assembled into a matrix with 8-12 aa in each pool and used in IFN-γ ELISpot assays to evaluate vaccine immunogenicity. For positive controls, 50 ng/ml PMA (Sigma) was added. Plates were incubated at 37° C. in 5% $CO_2$ for 24 hours. After 24 hours stimulation, the cells were removed from the plates and the wells were washed three times in PBS prior to three washes with PBS containing 0.05% tween. Biotinylated anti-IFN-γ detection antibody was then added to the plates for 2 hours at room temperature. The plates were then washed three times with PBS containing 0.05% tween prior to the addition of streptavidin-conjugated alkaline phosphatase (AP). Wells were then washed two times with 0.05% tween-PBS and then two times with distilled water prior to the addition of the blue developer solution. The plates were then incubated at room temperature for 15 minutes before the reaction was stopped using tap water. The wells were then dried overnight and spot forming units (SFUs) were counted on an Immunospot ELISpot reader. The settings were identical for all plates and counts were expressed at SFU per $10^6$ PBMCs. The results are shown in FIGS. 24A-B.

In Vitro Peptide Stimulation and Intracellular Cytokine Staining.

Figure 25A:
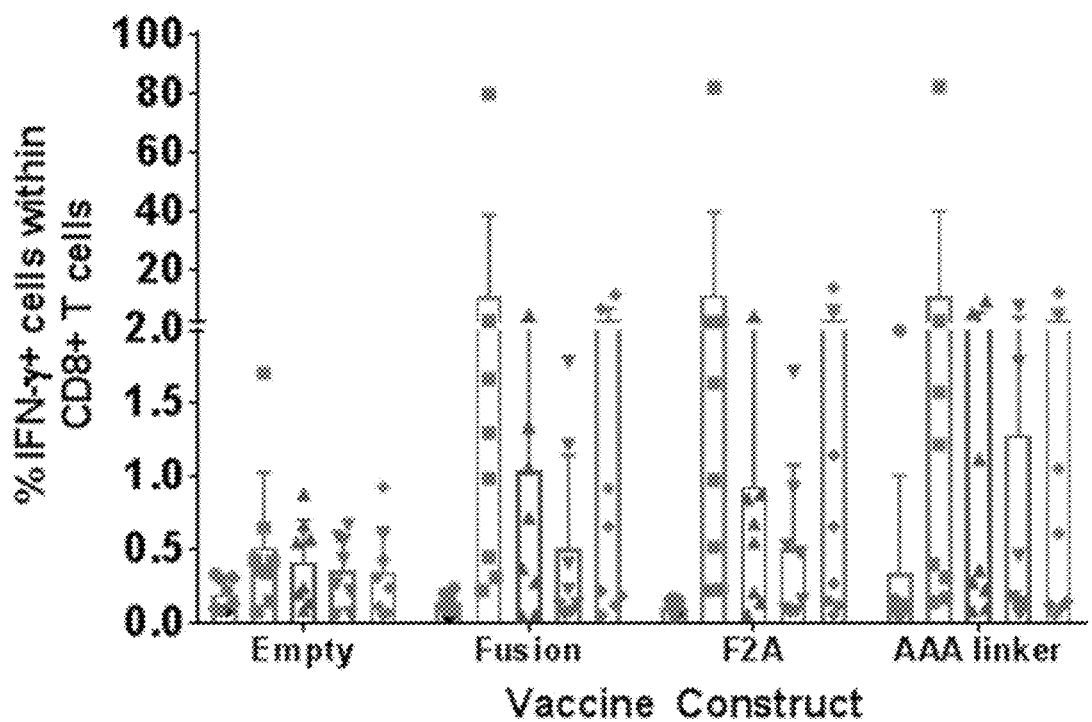
FIGS. 25A-25B illustrate in vitro priming of antigen specific T cells from HIV infected donors. Representative flow cytometry plots showing IFN-γ production by intracellular cytokine staining (ICS) on day 10 following co-culture of PBMCs with vaccine vector transduced autologous moDCs. The x-axis indicates the vaccine construct used for in-vitro priming. Each bar represents stimulation with peptide pools from Gag p17, gag p24, integrase, Pol (protease/RT) and Nef respectively. Percentages of IFN-γ+ T cells are indicated (A) CD8+ T cell responses (B) CD4+ T cells. (•) Gag p17; (■) Gag p24; (▲) INT; (▼) Pol; (♦) Nef. No statistical significance was observed among the different groups in this analysis.
Figure 25B:
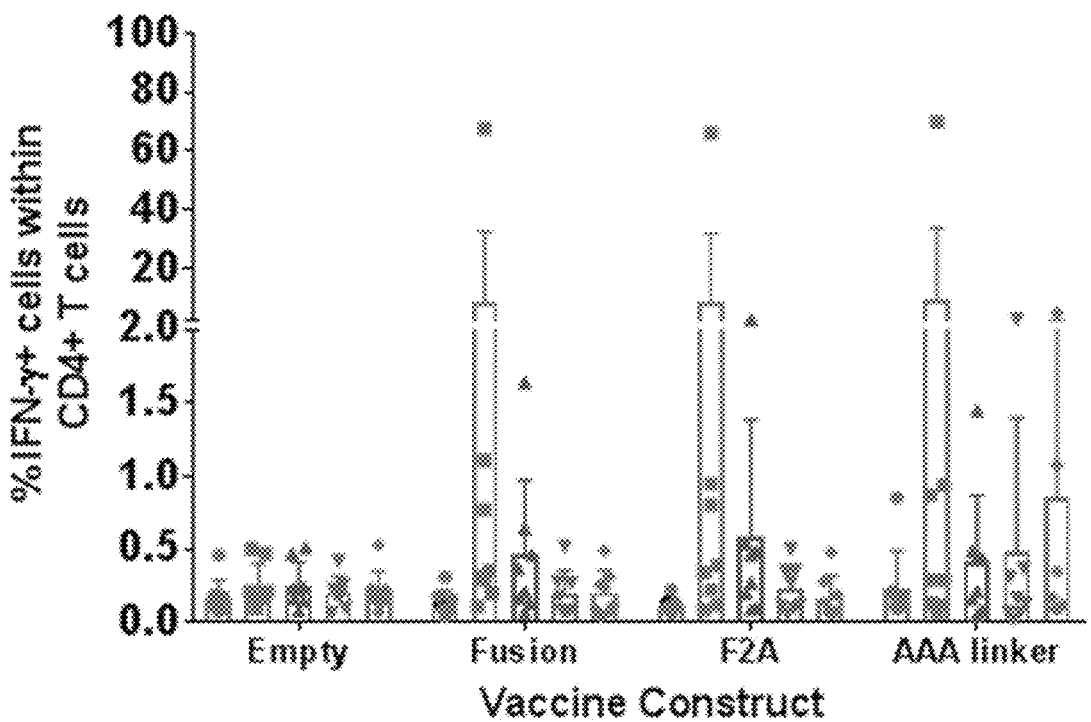

Lymphocytes were incubated at 37° C. for 5 h with 2 µg/ml of the corresponding HIV peptide pools along with anti-CD107a, and GolgiPlug (BD) (1 µl/ml) and monensin (1×) were added during the last 4 h of re-stimulation. This was followed by surface and intracellular staining for cytokine production. The Foxp3 Fixation/Permeabilization Concentrate and Diluent Kit (Thermo Fisher Scientific) was used for intracellular cytokine staining. Briefly, after blocking Fc receptors with 0.5 mg/ml human IgG (BD), 1×10$^6$ cells were incubated with a mixture of fluorescence-conjugated anti-human antibodies for 30 min at 4° C. Stained cells were washed twice using FACS buffer (PBS, 2% FCS, 0.1% NaN$_3$), acquired with an LSR II flow cytometer using FACSDiva software (BD), and analyzed using FlowJo software version 10.2 (TreeStar). Anti-human antibodies were obtained from BioLegend or BD biosciences, anti-PD-1 BV421 or BV605 clone EH12.2H7, anti-CD27 BV711 clone 0323, anti-CD4 BV605 clone OKT4, anti-CCR7 BV785 clone G043H7, anti-CD45RA PE-Cy7 clone H100), anti-CD3 BV650 clone SK7, anti-CD8a BV650 clone RPA-T8. After surface staining, stained cells were incubated with 100 µl of Fix/Perm b 667 buffer for 1 hour. Subsequently, cells were washed twice with 100 µl Perm 77jhy gt buffer each time and were then incubated with a cocktail of antibodies diluted in 100 µl of Perm buffer per 1×10$^6$ cells. A cocktail of fluorophore-conjugated anti human antibodies containing anti-IL-2 PE clone MQ1-17H12, anti-TNF-α PercPcy5.5 clone MAB11 and anti-IFN-γ PE-CF594 clone B27, was added to the cells and stained for an hour. For mouse experiments, anti-IFN-γ PE clone XMG1.2, anti-IL-2 APC-cy7 clone JES6-5H4 and anti-TNF-α BV650 clone MP6-XT22. Permeabilized cells were then washed with 100 µl Perm buffer twice and immediately analyzed on a Fortessa flow cytometer. Results are shown in FIGS. 25A-B.

Results

Monocyte derived DCs matured in the presence of cytokines (GM-CSF, IL-4, CD40L, IFN-γ, PGE2, TNF-α, IL-6 and IL-1β) and transduced with viral vectors containing a vaccine transgene were able to prime autologous vaccine antigen specific T cells in vitro. These responses were of high magnitude and breadth. Patient to patient variability is observed in transduction efficiency of moDCs and may reflect variability in expression of receptors to facilitate uptake of viral vectors as would be anticipated in a heterogeneous human population. The assay may facilitate the preclinical evaluation of vaccine constructs across large numbers of human donors prior to initiation of large-scale vaccine trials.

Human donors who respond to priming with generation of de novo responses made responses of similar magnitude irrespective of the fusion approach used to combine the conserved regions. Donors with high magnitude responses consistently recognized a larger number of pools irrespective of the viral vector construct used to prime T cell responses.

The method primed both CD4+ and CD8+ T cell responses. The immunodominant CD8+ responses were targeted at p24 Gag and Nef while immunodominant CD4+ responses were mostly focused on p24 Gag. There was no significant difference in the magnitude of the response or the regions targeted based on the approach used to combine conserved regions in the design of the vaccine construct. The primed T cells were largely monofunctional with IFN-γ being the primary cytokine with comparable proportions of multifunctional T cell responses across several donors. This likely reflects the viral vectors used (e.g., adenovirus) as well as the in vitro culture techniques.

The results demonstrate strong induction of CD8+ and CD4+ T cell responses by vaccine immunogen in primary human PBMCs. Fusion of conserved regions results in responses of similar magnitude to responses induced by an immunogen with an F2A proteolytic cleavage sequence or an AAA linker (SEQ ID NO: 378). This data supports the use of any of these approaches to fusion of conserved regions. Factors such as packaging limits of a vaccine vector, or reducing or avoiding the generation of junctional responses, are considerations that contribute determining which approach is used for a given set of sequences or viral vector.

Figure 26A:
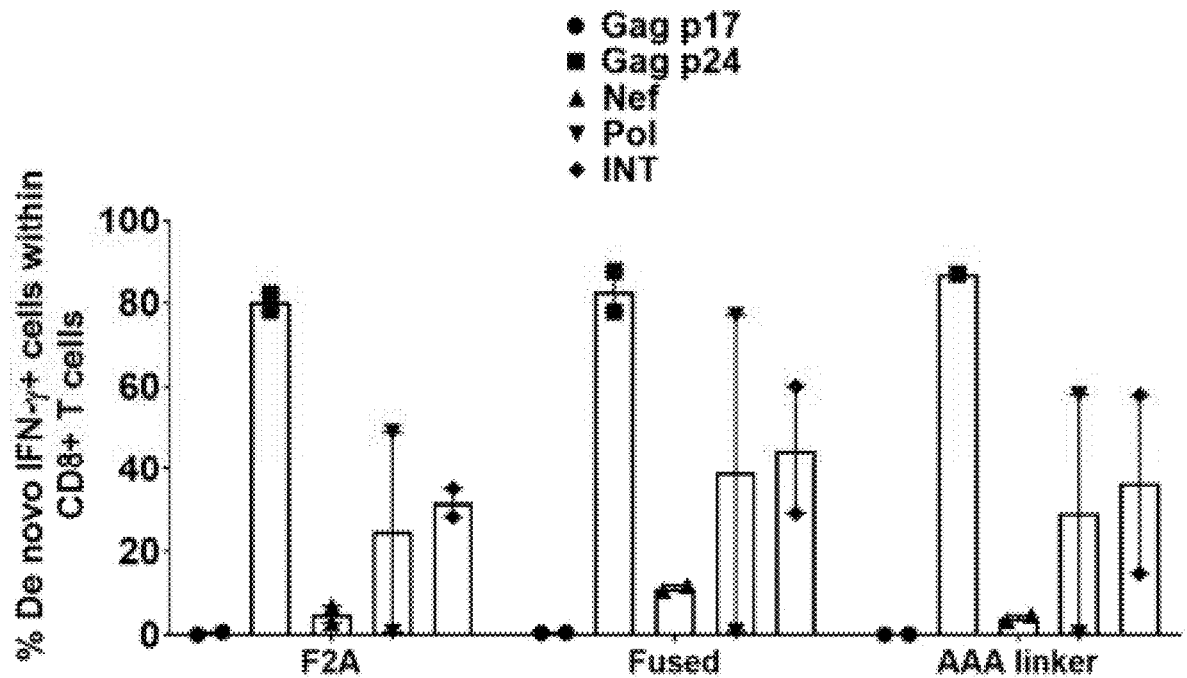
FIGS. 26A-26B illustrate in vitro priming of antigen specific T cells from aviremic and viremic HIV-1 infected donors. Representative figures showing IFN-γ production by intracellular cytokine staining (ICS) on day 7 (first round) and day 14 (second round) following co-culture of PBMCs with autologous moDCs transduced with an adenoviral vector comprising a Gag-Nef immunogen designed according to one of three fusion approaches (F2A (SEQ ID NO: 347), fusion (SEQ ID NO: 349) and AAA linker (SEQ ID NO: 345; "AAA" disclosed as SEQ ID NO: 378) in aviremic (A) and viremic (B) donors. The x-axis indicates the vaccine construct used for in-vitro priming. Each bar represents stimulation with peptide pools from Gag p17, Gag p24, integrase, Pol (protease/RT) and Nef respectively. Percentages of IFN-γ+ T cells are indicated (A) CD8+ T cell responses (B) CD4+ T cells. (•) Gag p17; (■) Gag p24; (▲) INT; (▼) Pol; (♦) Nef.
Figure 26B:
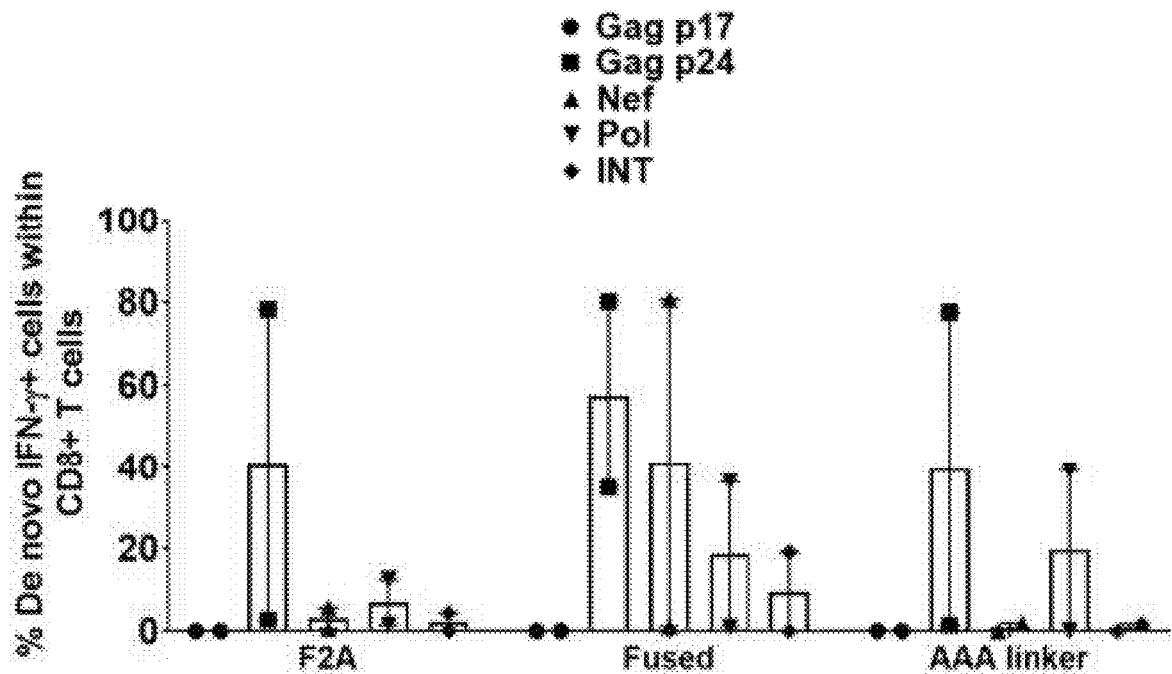

The data are consistent with the conclusion that CD8+ T cells from aviremic and viremic patients that were exposed to two rounds of moDC stimulation had an enhanced magnitude of IFN-γ regardless of the concatenation approach used (FIG. 26A-26B).

The results further demonstrate that the in vitro moDC-T cell priming assay induce both de-novo naïve responses as well as prime pre-existing memory responses and that IFN-γ producing cells express high levels of PD-1 and CTLA-4, suggesting that the responding cells were exhausted as illustrated in FIGS. 30A-30B.

Example 8

In Vivo T Cell Activation Assays

In this example, we evaluated the efficacy of in vivo T cell priming by vaccine constructs in a mouse model and determined the optimal approach to fusing conserved regions within the vaccine construct. To do this, we immunized groups of mice with Ad5/35 vectors expressing computationally defined conserved regions vaccine immunogen sequences with different linkage strategies. We evaluated the magnitude and functional phenotype of those responses to determine the optimal approach to fusion of conserved regions.

Methods

In-Vivo Evaluation of Immunogenicity

Immunizations.

Six or seven-week-old C57BL/6 and Balb/c mice were immunized with either 1×10$^8$ or 1×10$^9$ PFU of Ad5/35 vectors expressing HIV immunogens by intramuscular (i.m.) injections in both hind leg muscles. The vaccine vector was administered in 100 µl of phosphate-buffered saline (PBS) injections (50 µl per quadriceps). Mice were anesthetized with isoflurane prior to vaccine immunization. Animals were housed at the Charles River Laboratories animal facility (North Carolina) and experiments were performed according to approved IACUC protocol.

Homologous Prime-Boost Regimen.

Figure 28A:
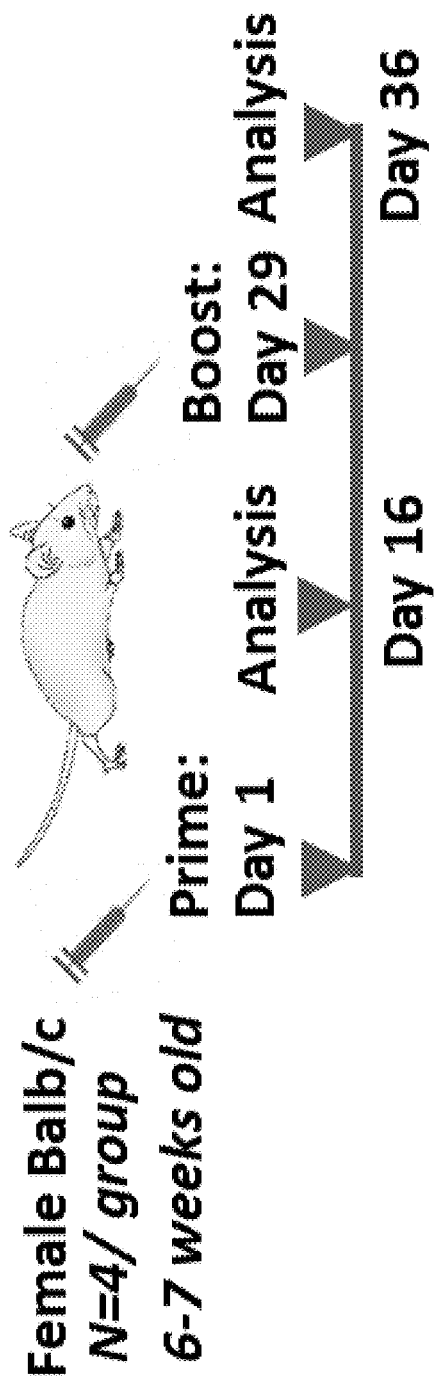
FIGS. 28A-28C illustrate viral vectors expressing HIV-1 antigens elicit high magnitude CD8+ T cell responses following immunization. (A) Immunization and sampling schedule. Groups of Balb/c mice were immunized with Ad5/35 vectors expressing HIV-1 conserved regions sequences concatenated by fusion, F2A proteolytic cleavage sequence or a flexible AAA linker (SEQ ID NO: 378). Mice were immunized in a homologous prime-boost schedule on day 1 and day 29, with analysis of each group on Day 16
Figure 28B:
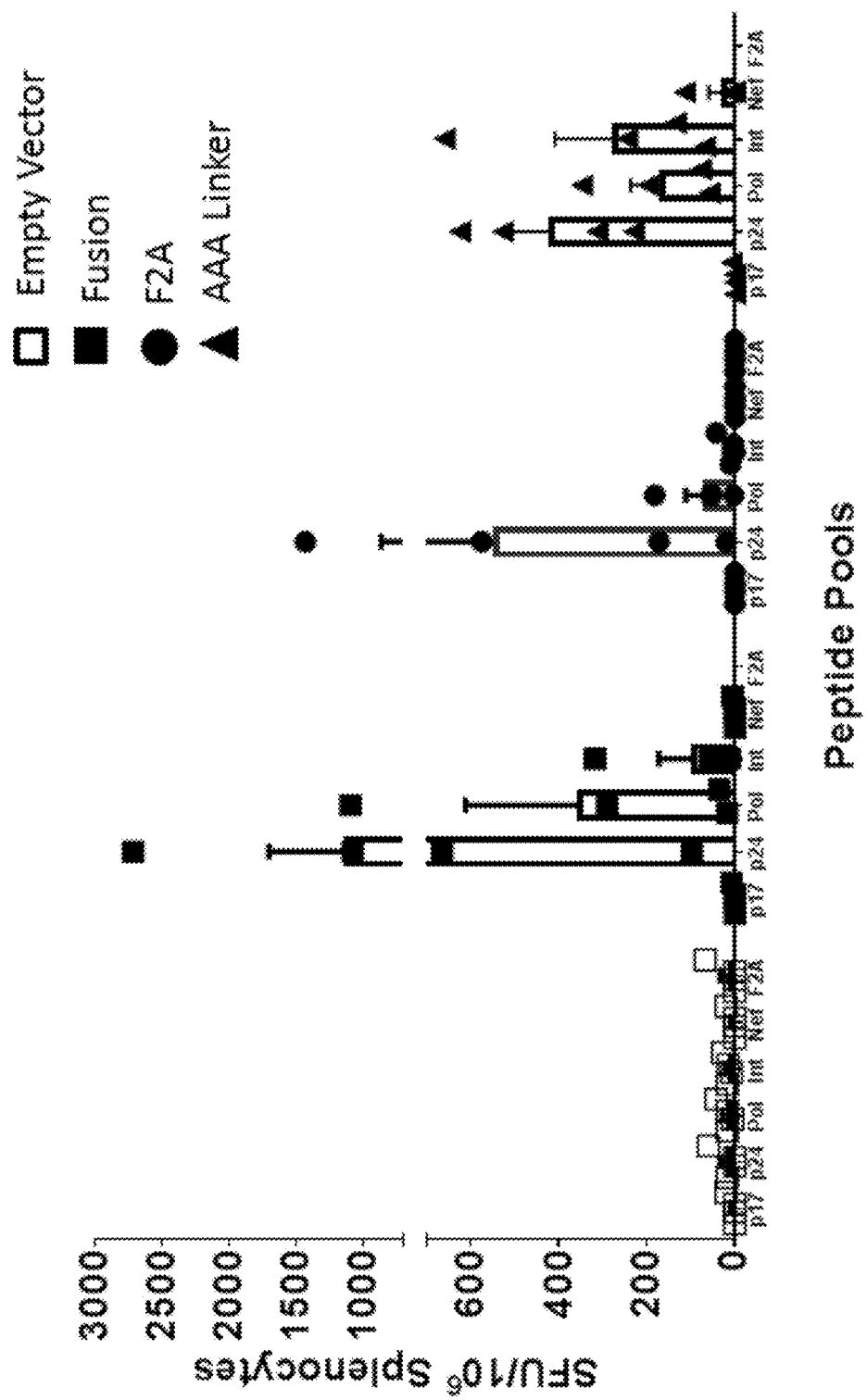
Figure 28C:
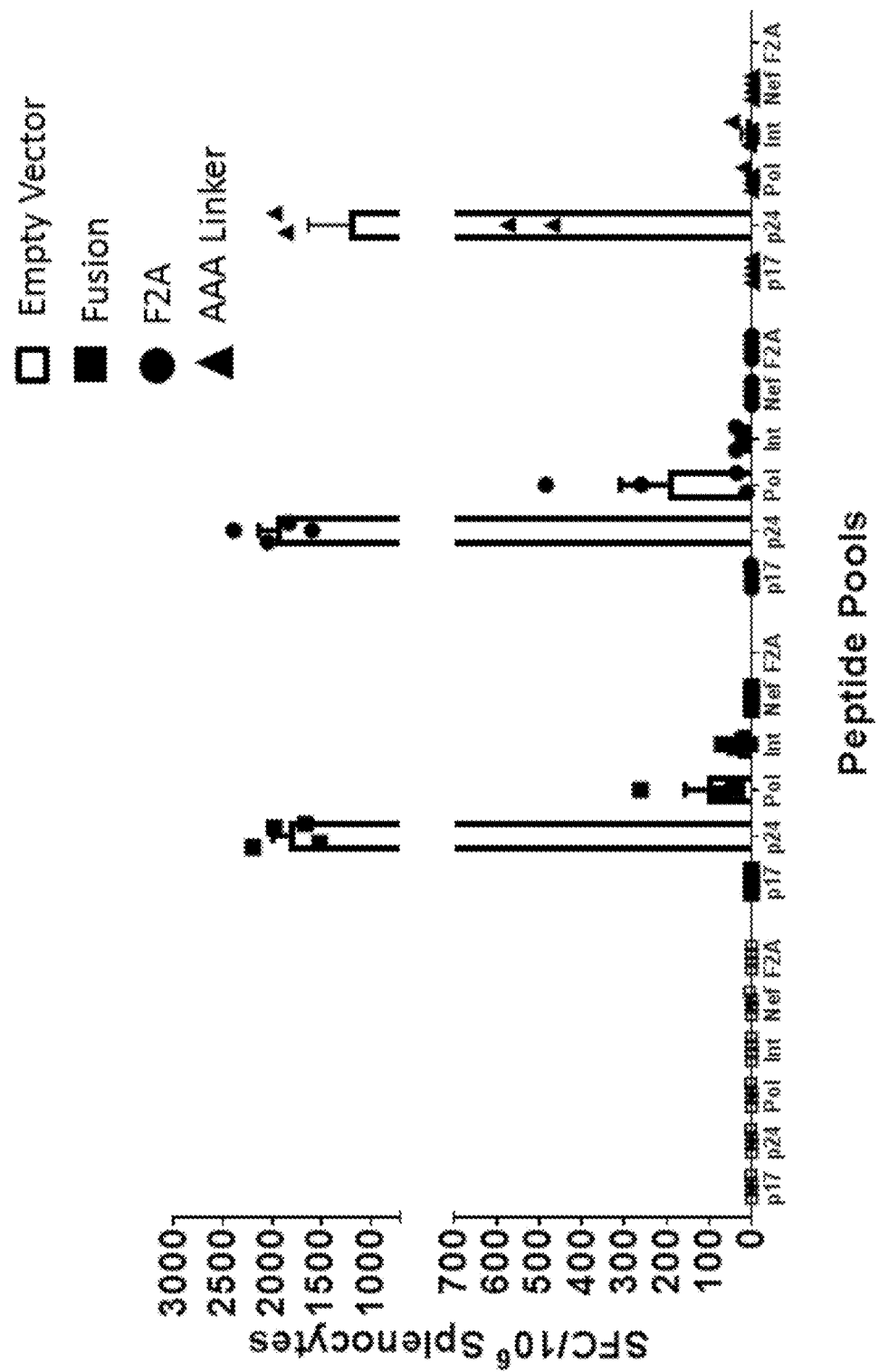

Mice were primed with either 1×10$^8$ or 1×10$^9$ PFU of Ad5/35 vectors expressing HIV immunogens by intramuscular (i.m.) injections in both hind leg muscles and rested for 28 days before homologous boost with vectors expressing identical antigens. Immunogenicity and cellular phenotype were evaluated by analyzing splenocytes by ELISpot assay as previously described (Miyahira, et al., *J Immunol Methods*, (1995) 181(1):45-54), ICS or tetramer staining at various time points. A schematic of the regimen and results are shown in FIGS. 28A-28C.

Flow Cytometry.

Cell counts for prepared single-cell suspensions were determined using a hemacytometer. After blocking Fc receptors with 1:100 anti-CD16+CD32 (Biolegend) (for mouse cells) or 0.5 mg/ml human IgG (BD) (for human cells), 1×10⁶ cells from single-cell suspensions were incubated with a mixture of fluorescence-conjugated anti-mouse or anti-human antibodies for 30 min at 4° C. Stained cells were washed twice using FACS buffer (PBS, 2% FCS, 0.1% NaN₃), acquired with an LSR II flow cytometer using FACSDiva software (BD), and analyzed using FlowJo software version 10.2 (TreeStar). Anti-mouse antibodies were obtained from either Biolegend or BD Biosciences, CD8 AF700 clone 53-6.7, CD4 BV605 clone RM4-5, TCR-β PECF594 clone H57-597, CD27 BV711 clone LG.3A10, CD43 PE-cy7 clone 1B11, KLRG1 PercpCy5.5 clone 2F1 and CD127 BV421 clone SB/199 were used for surface staining. After surface staining, cells were fixed and permeabilized in preparation for intracellular cytokine staining. The Foxp3 Fixation/Permeabilization Concentrate and Diluent Kit (Thermo Fisher Scientific) were used for intracellular cytokine staining. Briefly, 1×10⁶ cells already stained with surface antibodies were incubated with 100 μl of Fix/Perm buffer for 1 hour. Subsequently, cells were washed twice with 100 μl Perm buffer each time and were then incubated with a cocktail of antibodies diluted in 100 μl of Perm buffer per 1×10⁶ cells. A cocktail of fluorophore-conjugated anti mouse anti-IFN-γ PE clone XMG1.2, anti-IL-2 APC-cy7 clone JES6-5H4 and anti-TNF-α BV650 clone MP6-XT22 were used for intracellular cytokine staining. Permeabilized cells were then washed with 100 μl Perm buffer twice and immediately analyzed on a Fortessa flow cytometer.

Anti-mouse antibodies were obtained from either Biolegend or BD Biosciences, CD8 AF700 clone 53-6.7, CD4 BV605 clone RM4-5, TCR-β PECF594 clone H57-597, CD27 BV711 clone LG.3A10, CD43 PE-cy7 clone 1B11, KLRG1 PercpCy5.5 clone 2F1 and CD127 BV421 clone SB/199 were used for surface staining. After surface staining, cells were fixed and permeabilized in preparation for intracellular cytokine staining. The Foxp3 Fixation/Permeabilization Concentrate and Diluent Kit (Thermo Fisher Scientific) were used for intracellular cytokine staining. Briefly, 1×10⁶ cells already stained with surface antibodies were incubated with 100 μl of Fix/Perm buffer for 1 hour. Subsequently, cells were washed twice with 100 μl Perm buffer each time and were then incubated with a cocktail of antibodies diluted in 100 μl of Perm buffer per 1×10⁶ cells. A cocktail of fluorophore-conjugated anti mouse anti-IFN-γ PE clone XMG1.2, anti-IL-2 APC-cy7 clone JES6-5H4 and anti-TNF-α BV650 clone MP6-XT22 were used for intracellular cytokine staining. Permeabilized cells were then washed with 100 μl Perm buffer twice and immediately analyzed on a Fortessa flow cytometer.

Results

Figure 27:
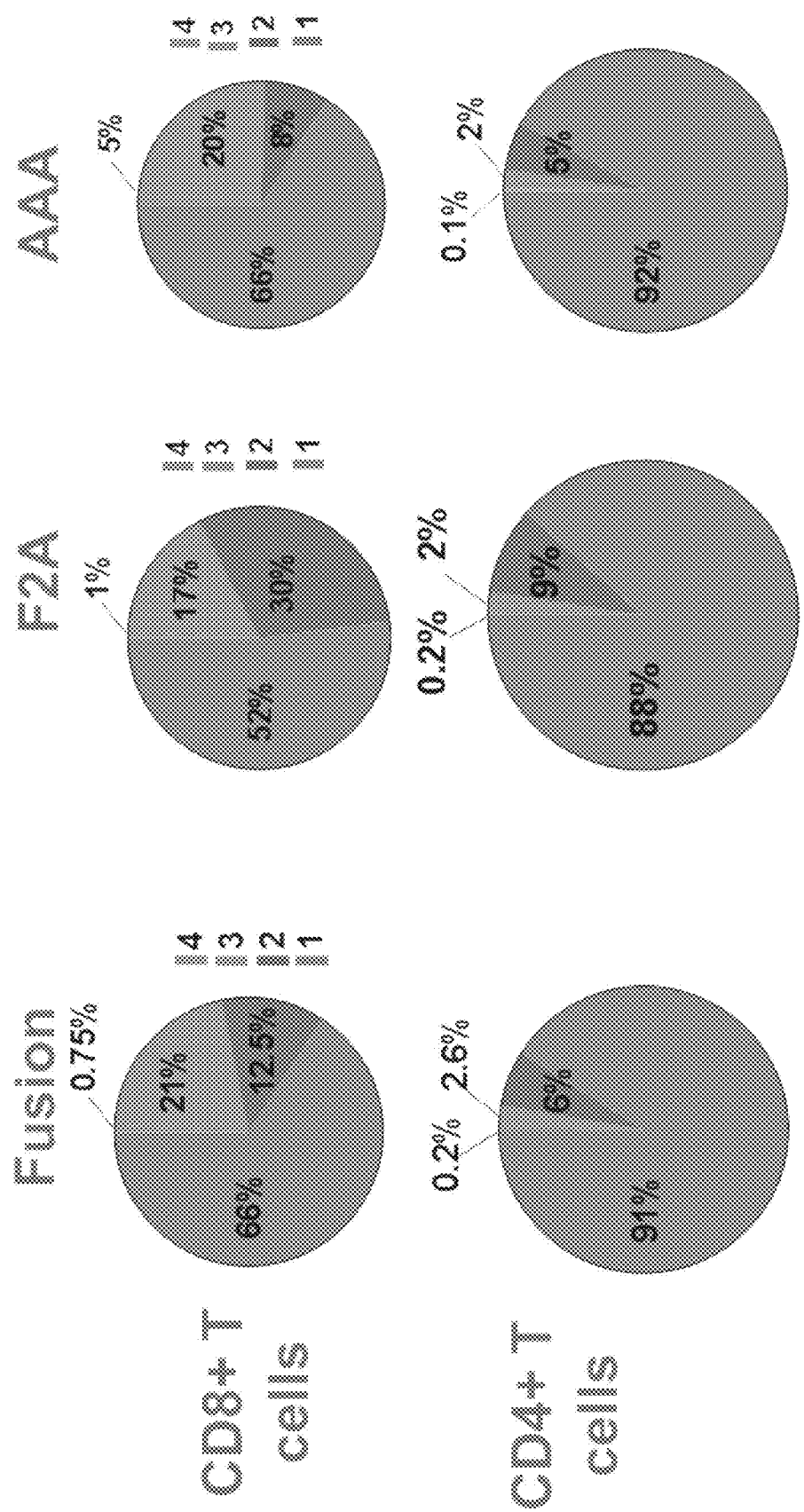
FIG. 27 illustrates profiling of functional characteristics of antigen of antigen specific CD8+ and CD4+ T cells primed using moDCs transduced with vectors containing immunogen expression cassettes with conserved regions concatenated by fusion, F2A proteolytic cleavage sequence or AAA linker (SEQ ID NO: 378). The pie charts depict adjusted multifunctionality (background responses subtracted) characteristics of primed CD8+ or CD4+ T cells (one to four functions—CD107a, IFN-γ, TNF-α and IL-2).

The viral vectors expressing conserved regions of HIV-1 proteins in fusion polypeptides were able to elicit high magnitude responses following prime and boost when expressed in Ad5/35 vectors. No responses were generated to the F2A sequence. The magnitude of the response was peptide pool specific. The Gag p24 response was of the greatest magnitude with weaker responses observed to Pol (PR/RT) and Int, and almost no Nef specific responses observed (FIG. 27B). This reflects the presence of immunodominant epitopes presented by mouse HLA within Gag p24 (Im, et al., *PLoS Pathog*, (2011) 7(5):e1002041). The magnitude of the p24 response was greatest in the mice immunized with the fusion and F2A constructs. Levels of responses changed following homologous boost, with the response to p24 emerging as the dominant response (FIG. 28C). Responses were of similar magnitude in animals vaccinated with all constructs. No significant different was observed in the magnitude of the response in mice vaccinated with a vector where the concatenation of conserved regions was by fusion, F2A or AAA linker (SEQ ID NO: 378). Similar studies were conducted with C57/B16 mice. The overall magnitude of the IFN-γ response was weaker, however following both prime and boost there was no significant difference in the magnitude of the response induced by the different vaccine constructs.

The ability to produce cytokines is a functional measure of effector and memory CD8+ T cells. We evaluated the phenotypic and functional characteristics of CD8+ T cell responses generated following immunization. We observed that following Ad5/35 immunization, T cells with monofunctional characteristics were generated. The dominant monofunctional response identified was the presence of CD107a expression, among the single cytokines IFN-γ, was the most commonly produced. There were not functional differences observed across the groups based on the fusion approach used to design the vector transgene.

The data are consistent with the conclusion that the conserved regions sequences are immunogenic. There was no significant difference in in vivo mouse immunogenicity based on the transgene sequence insert approach to fusing conserved regions.

Example 9

Evaluating the Ability of Leader Sequences to Enhance Immunogenicity of Fusion Polypeptides In this example, our primary objective was to determine if leader or signal sequences could enhance the immunogenicity of the HIV-1 vaccine immunogen. To do this, we designed vaccine constructs with various signal sequences and expressed them in viral vectors, e.g., adenovirus or arenavirus vectors.

Viral vectors can be engineered to express protein sequences that can enhance antigen processing or presentation in both MHC class I and class II pathways. These leader sequences are well known. These sequences are typically short polypeptides with hydrophobic domains, that bind to signal recognition particles and direct the elongating protein to membrane bound structures, e.g., endoplasmic reticulum or lysosomes. These secretory signal sequences may include a secretory polypeptide from tissue plasminogen activator (tPA), GM-CSF signal peptides (SPCore) or from chemokines such as the monocyte chemoattractant protein 3 (MCP3) or C-X-C motif chemokine ligand 10 (CXCL10; a.k.a., IP-10). These are often placed at the N-terminus of the vaccine immunogen expression cassettes. Other signaling sequences may include N-terminal and C-terminal sequences from the lysosomal associated membrane protein 1 or 2 (LAMP-1 or -2) which directs proteins to the lysosomal compartment. The secretory polypeptide from secreted chemokines such as MCP-3 and IP-10 can be fused and engineered onto the N-terminus of the vaccine immunogen. The addition of destabilizing sequences that can promote ubiquination and consequently target a sequence for degradation have been previously described and used in the context of immunization with HIV or SIV immunogens (Tobery, et al., *J Exp Med*, (1997) 185(5):909-20; Townsend, et al., *J Exp Med*, (1988) 168(4):1211-24). An N-terminal β-catenin signal sequence can promote N-terminal ubiquitination promoting degradation by the 26S proteasome (Rosati, et al., *Proc Natl Acad Sci USA*, (2009) 106(37): 15831-6).

Transgenic mice that express human HLA molecules represent a unique in vivo experimental model for evaluating human immune system function. These models have been used to study the role of the human class I or class II restricted T cell repertoire in autoimmune disease, infectious disease, and vaccine development. These mice serve as tools to evaluate vaccine design strategies through epitope identification and to study T cell responses restricted by HLA molecules which can facilitate the development of vaccines targeted against specific ethnic/regional populations, as well as broad populations. The HLA transgenic mouse models generally assume conserved antigen processing and presentation of antigen to generate the appropriate 'human' 8-10 mer CTL epitopes, physiological peptide selection by human class 1 molecules in murine antigen presentation cells, and an appropriate CD8+ T-cell repertoire containing T-cell receptors (TCRs) capable of positive selection on the 'human' epitope-HLA class I complex.

We determined whether the signal sequences could increase the CD8+ and CD4+ T cell responses following immunization of C57/BL6, Balb/c or A*0201 transgenic mice with adenovirus or arenavirus vectors expressing the HIV immunogen with the corresponding leader/signal sequences. We evaluated the phenotype, magnitude and functional characteristics of those responses.

Construction of viral vectors expressing vaccine transgene with various leader sequences. Adenovirus (Ad5/35 or Ad5) or arenavirus vectors expressing computationally defined HIV conserved regions sequences (e.g., SEQ ID NOs: 353-356, 363-366 and 358-372) with various leader sequences were generated. Expression plasmids and viral vectors were synthesized as previously described. Illustrative leader sequences used in the test constructs are summarized in the table below.

TABLE 2

Signal Sequences Expressed with Immunogenic Fusion Polypeptides

| SEQ ID NO: | Source Protein | Signal Sequence |
|---|---|---|
| 393 | CSF2, GM-CSF | MWLQSLLLLGTVACSISV |
| 394 | PLAT, t-PA | MDAMKRGLCCVLLLCGAVFVSAR |
| 398 | CCL7, MCP-3 | MNPSAAVIFCLILLGLSGTQGILDMAQPVGIN TSTTCCYRFINKKIPKQRLESYRRTTSSHCPR EAVIFKTKLDKEICADPTQKWVQDFMKHLDKK TQTPKLASAGA |
| 397 | β-catenin | MRKAAVSHWQQQSYLDSGIHSGATTTAPSLS |
| 399 | lysosomal associated membrane protein 1 (LAMP-1) (N-terminus) | MAPRSARRPLLLLLLLLLLGLMHCASAAMFMV KNGNGTACIMANFSAAFSVNYDTKSGPKNMTL DLPSDATVVLNRSSCGKENTSDPSLVIAFGRG HTLTLNFTRNATRYSVQLMSFVYNLSDTHLFP NASSKEIKTVESITDIRADIDKKYRCVSGTQV HMNNVTVTLHDATIQAYLSNSSFSRGETRCEQ DRPSPTTAPPAPPSPSPSPVPKSPSVDKYNVS GTNGTCLLASMGLQLNLTYERKDNTTVTRLLN INPNKTSASGSCGAHLVTLELHSEGTTVLLFQ FGMNASSSRFFLQGIQLNTlLPDARDPAFKAA NGSLRALQATVGNSYKCNAEEHVRVTKAFSVN IFKVWVQAFKVEGGQFGSVEECLLDENSLEDI |
| 412 | LAMP-1 - C-term | GSEFTLIPIAVGGALAGLVIVLIAYLVGRKRS HAGYQTI |

Methods

In-Vivo Evaluation of Immunogenicity

Immunizations.

Six or seven-week-old Balb/c mice were immunized with $1\times10^9$ PFU of Ad5/35 vectors by intramuscular (i.m.) injections in both hind leg muscles or $1\times10^6$ RCV FFU for replication defective LCMV vectors expressing HIV immunogens by intravenous (i.v.) injections. The Ad5/35 vaccine vectors were administered in 100 μl of phosphate-buffered saline (PBS) injections (50 μl per quadriceps). The LCMV vaccine vectors were administered in a volume of 200 μl formulated in buffer (10 mM Hepes, 150 mM NaCl, 20 mM Glycine, pH 7.4 (±0.2). For stabilization 10% Sorbitol was added. Mice were anesthetized with isoflurane prior to vaccine immunization. Animals were housed at the Charles River Laboratories animal facility (North Carolina) and experiments were performed according to approved IACUC protocol.

ELISpot Assays.

Pre-coated strip ELISpot plates (Cellular Technologies Limited) were used for all ELISpot analyses. Briefly, $2\times10^5$ splenocytes from immunized animals were seeded to each well. Peptide pools consisting of 15-mer peptides overlapping by 11 amino acids spanning the entire HIV or A*0201 conserved regions sequences were used in IFN-γ ELISpot assays to evaluate vaccine immunogenicity. For positive controls, 50 ng/ml PMA (Sigma) was added. Plates were incubated at 37° C. in 5% $CO_2$ for 24 hours. After 24 hours stimulation, the cells were removed from the plates and the wells were washed three times in PBS prior to three washes with PBS containing 0.05% tween. Biotinylated anti-IFN-γ detection antibody was then added to the plates for 2 hours at room temperature. The plates were then washed three times with PBS containing 0.05% tween prior to the addition of streptavidin-conjugated alkaline phosphatase (AP). Wells were then washed two times with 0.05% tween-PBS and then two times with distilled water prior to the addition of the blue developer solution. The plates were then incubated at room temperature for 15 minutes before the reaction was stopped using tap water. The wells were then dried overnight and spot forming cells (SFCs) were counted on an Immunospot ELISpot reader. The settings were identical for all plates and counts were expressed at SFU per $10^6$ splenocytes.

Results

Leader sequences enhanced immunogenicity of the vaccine immunogen in an Ad5/35 vector in A*0201 transgenic mice immunized with a vaccine construct consisting of HIV-1 sequences designed by our algorithm and predicted to bind to HLA-A*0201. The addition of the signal sequences GM-CSF, tPA, MCP-3, β-catenin and LAMP significantly enhanced immunogenicity of the constructs relative to the construct without the leader sequences. In the model with A*0201 transgenic mice MCP-3 was significantly more immunogenic than vectors expressing GM-CSF (p<0.01). See, FIG. 31A.

In addition the full-length conserved regions construct with a GM-CSF leader sequence was (FIG. 31B) was immunogenic in A*0201 mice, with immunodominant responses observed within HIV-1 Gag p24.

The data are consistent with the conclusion that signal sequences can enhance the immunogenicity of Gag p24 epitopes with LCMV replication incompetent vectors following prime and boost immunizations. The data are further consistent with the conclusion that GM-CSF signal sequence enhances the immunogenicity of subdominant antigens such as Pol (FIGS. 32C-32E).

C57/B16 mice transgenic for human leucocyte antigen (HLA) A*0201 antigen-binding domain were used to evaluate immunogenicity of vaccines composed of defined HLA A*0201-restricted cytotoxic T-lymphocyte (CTL) epitopes from HIV conserved region sequences in LCMV replication incompetent vector format with and without GM-CSF leader sequence. Magnitude of IFN-γ responses were evaluated at day 7 after prime and day 5 after boost vaccinations. The data are consistent with the conclusion that immunogenicity of A*0201 epitopes from HIV conserved sequences in a "bead on a string" format is weak. Upon homologous boost, responses with GM-CSF leader sequence were enhanced slightly but were not significant. Gag specific responses in mice vaccinated with HIV conserved sequence showed enhanced responses compared to A*0201 peptide specific responses. Boost and GM-CSF leader sequences further enhanced responses from prime and no leader sequence responses but were not significantly different. The data indicates that the responses in A*0201 transgenic mice are likely driven by C57/BL6 background and the endogenic processing and presentation of A*0201 specific epitopes on HLA A*0201 allele is not optimal. The data are further consistent with the conclusion that signal sequences can enhance the immunogenicity of A*0201 and Gag p24 epitopes with LCMV replication incompetent vectors following prime and boost immunizations (FIGS. 34A-34D).

C57/B16 mice transgenic for human leucocyte antigen (HLA) A*0201 antigen-binding domain were used to evaluate immunogenecity of vaccines composed of defined HLA A*0201-restricted cytotoxic T-lymphocyte (CTL) epitopes from HIV conserved region sequences in Ad5/35 vector format with and without various leader sequences. Magnitude of IFN-γ responses were evaluated at day 16 after prime vaccination. The data are consistent with the conclusion that immunogenicity of A*0201 epitopes from HIV conserved sequences in a "bead on a string" format is weak. In the prescence of leader sequences including, GM-CSF, TPA, MCP-3, β-Catenin and LAMP-1, the responses were enhanced significantly, even though the magnitude of response is smaller. The data are consistent with the conclusion that signal sequences can enhance the immunogenicity of A*0201 epitopes with Ad5/35 vectors following prime immunizations. Responses against Gag P24 and to subdominant antigens such as Pol-1 and Pol-2 in mice vaccinated with HIV conserved sequence as a whole showed enhanced responses compared to A*0201 peptide specific responses. Very minimal to no responses were seen against specific peptide stimulations in Ad5/35 backbone vector primed mice indicating specificity of responses in antigen vaccinated mice. The data indicates that the responses in A*0201 transgenic mice were likely driven by C57/BL6 background and the endogenic processing and presentation of A*0201 specific epitopes on HLA A*0201 allele is not optimal (FIG. 35A-35D).

Example 10

Inducing T Cell Responses with Arenavirus Vectors

In this example, we evaluated approaches for inducing T cell responses following immunization with arenavirus vectors. To do this, we evaluated the immunogenicity of the viral vectors in mouse and non-human primates and describe the magnitude and phenotypic characteristics of the antigen specific responses elicited by immunization.

Construction of Arenavirus Viral Vectors Expressing SIV Antigens.

Adenovirus (Ad5/35 or Ad5) or arenavirus vectors expressing optimally defined SIV full length proteins were designed. Sequences from the SIV sme543 Gag strain (SIV SME543; Genbank Sequence ID: U72748) were used to develop a construct with mammalian codon codon-bias. SIVsme543 Pol construct was developed with the following inactivating mutations introduced: deletion of DTG motif in protease, YMDD sequence (SEQ ID NO: 462) in reverse transcriptase, 473E in RNaseH, and D64, D113 and E150 in integrase (see, e.g., Hansen, et al., Nature, 2011. 473(7348): 523-7; Kulkarni, et al., Vaccine, 2011. 29(39):6742-54; Loeb, et al., Nature, 1989. 340(6232):397-400; Larder, et al., Nature, 1987. 327(6124):716-7; Schatz, et al., FEBS Lett, 1989. 257(2):311-4; and Leavitt, et al., J Biol Chem, 1993. 268(3):2113-9). Due to package insert limitations in the arenavirus the Pol vector was divided into two segments of Pol-1 (protease and reverse transcriptase) and Pol-2 (RNAse H and Integrase). The SIV env sequence includes a truncated gp41. Expression plasmids and viral vectors were synthesized as previously described; 14 vectors in tri-segmented replication attenuated or bi-segmented replication defective arenavirus platforms with either a Lymphocytic choriomeningitis mammarenavirus (LCMV) or Cali mammarenavirus (a.k.a., Pichinde mammarenavirus or Pichinde arenavirus) (PICV) vector backbone were generated. Replication defective arenavirus vectors used are described in WO 2009/083210. Replication attenuated arenavirus vectors used are described in WO 2016075250 (LCMV) and WO 2017/198726 (Pichinde).

Immunizations.

Ten-week-old C57BL/6 mice were immunized with either 1×10⁵ RCV FFU for replication attenuated or 1×10⁶ RCV FFU for replication defective per antigen of LCMV or PICV vectors expressing SIV immunogens by intravenous (i.v.) injections. The vaccine vector was administered in a volume of 200 µl formulated in buffer (10 mM Hepes, 150 mM NaCl, 20 mM Glycine, pH 7.4 (±0.2). For stabilization 10% Sorbitol was added. Mice were anesthetized with isoflurane prior to vaccine immunization. Animals were housed at the WuXi AppTec (Shanghai, China) and experiments were performed in accordance with the regulations of the Association for Assessment and Accreditation of Laboratory Animal Care (AAALAC).

Homologous Prime Boost.

Mice were primed with 1×10⁵ RCV FFU for replication attenuated and 1×10⁶ FFU for replication defective arenavirus vectors either LCMV or PICV expressing SIV immunogens by intravenous (i.v.) injections in the tail vein and rested for 21 days before homologous boost with vectors expressing identical antigens. Immunogenicity and cellular phenotype were evaluated by analyzing splenocytes by ELISpot assay as previously described (Miyahira, et al., J Immunol Methods, 1995. 181(1):45-54), intracellular cytokine staining (ICS) or tetramer staining at various time points, typically on day 7 post prime or day 26 post-boost.

Heterologous Prime Boost.

Mice were primed with 1×10⁵ RCV FFU for replication attenuated and 1×10⁶ FFU for replication defective arenavirus vectors either LCMV or PICV expressing SIV immunogens by intravenous (i.v.) injections in the tail vein and rested for 21 days before heterologous boost with vectors expressing identical antigens. If the initial prime was LCMV the heterologous boost was PICV, and vice versa. Immunogenicity and cellular phenotype were evaluated by analyzing splenocytes by ELISpot assay as previously described (Miyahira, et al., supra), ICS or tetramer staining at various time points, typically on day 7 post prime or day 26 post-boost.

Results

In a single vector prime with a highly immunogenic antigen (SIV gp-140) we observed enhanced priming with LCMV compared to PICV in the same tri-segmented replication attenuated platform (e.g., as described in WO 2016075250 (LCMV) and WO 2017/198726 (Pichinde)). In a prime-boost immunization schedule we observed that a heterologous prime-boost significantly enhanced immunogenicity. This was most evident with less immunogenic antigens such as Pol-1 and Pol-2. No significant difference was observed with vectors expressing gp-140, however, this may reflect saturation of the IFN-γ ELISpot assay. In heterologous prime-boost comparing immunization with replication attenuated arenavirus vectors to replication defective arenavirus vectors, we observed significant enhancement of immunogenicity following multi-vector immunization with the replication attenuated arenavirus vectors compared with replication defective arenavirus vectors.

Enhanced immunogenicity following heterologous prime boost was also confirmed following immunization of non-human primates. These data are consistent with the conclusion that arenavirus vectors expressing SIV/HIV antigens heterologous prime boost enhance immunogenicity. The results are shown in FIGS. 36A-36E.

well. Individual 15-mer peptide pools overlapping by 11 amino acids spanning the entire HIV conserved regions were added to each well and used in IFN-γ ELISpot assays to evaluate vaccine immunogenicity. For positive controls, 50 ng/ml PMA (Sigma) was added. Plates were incubated at 37° C. in 5% $CO_2$ for 24 hours. After 24 hours stimulation, the cells were removed from the plates and the wells were washed three times in PBS prior to three washes with PBS containing 0.05% tween. Biotinylated anti-IFN-γ detection antibody was then added to the plates for 2 hours at room temperature. The plates were then washed three times with PBS containing 0.05% tween prior to the addition of streptavidin-conjugated alkaline phosphatase (AP). Wells were then washed two times with 0.05% tween-PBS and then two times with distilled water prior to the addition of the blue developer solution. The plates were then incubated at room temperature for 15 minutes before the reaction was stopped using tap water. The wells were then dried overnight and spot forming units (SFUs) were counted on an Immunospot ELISpot reader. The settings were identical for all plates and counts were expressed at SFU per $10^6$ PBMCs. The results are shown in FIGS. 37A-37F.

To determine the epitopes within conserved regions vaccine that induce antigen specific T cell responses, we adopted a 384 well ELISpot assay that utilizes individual 15 mers per well rather than peptide pools (FIG. 37B) and completed this analysis on 10 patient samples with different HLA profiles (Table 3).

TABLE 3

Analysis on Ten Patient Samples with Different HLA Profiles

| | HLA | | | | | | Viral | |
|---|---|---|---|---|---|---|---|---|
| | A $1^{st}$ allele | A $2^{nd}$ allele | B $1^{st}$ allele | B $2^{nd}$ allele | C $1^{st}$ allele | C $2^{nd}$ allele | load | Gender |
| LP1408 | A*0101 | A*0201 | B*0702 | B*4101 | Cw*0702 | Cw*1700 | | |
| LP210 | | | | | | | 60 | |
| LP 009-001 | A*25:01 | A*26:01 | B*27:EKN | B*44:AMUT | C*01:02 | C*05:01 | <50 | M |
| LP-014-001 | A02:ANGA | A*03:01 | B*27:EKN | B*44:AMUT | C*01:02 | C*05:01 | <50 | M |
| LP267 | A*03:01 | A*24:02 | B*18:01 | B*41:01 | C*07:01 | C*17:01 | | |
| LP2253 | A*0101 | A*0301 | B*3501 | B*5201 | Cw*0401 | Cw*1202 | | |
| LP237 | A*0201/02:01L | | B*15:01 | | C*03:04 | | 92 | |
| LP270 | A*03:01 | A*33:01 | B*07:02/61/161N | B*44:03 | C*02:02 | C*07:02 | | |
| LP300 | A*24:01:01 | A*11:01:01 | B*07:02 | B*08:01 | C*07:01 | C*07:02 | <50 | M |
| LP301 | A*03:01 | A*32:01 | B*07 | B*40:01 | C*03:04 | C*07:02 | <50 | M |

EKN = 05/13; AMUT = 44:02, 44:02S, 44:19N; ANGA = 02:01/02:01L

Example 11

Mapping Vaccine Specific Epitope Responses

Figure 37A:
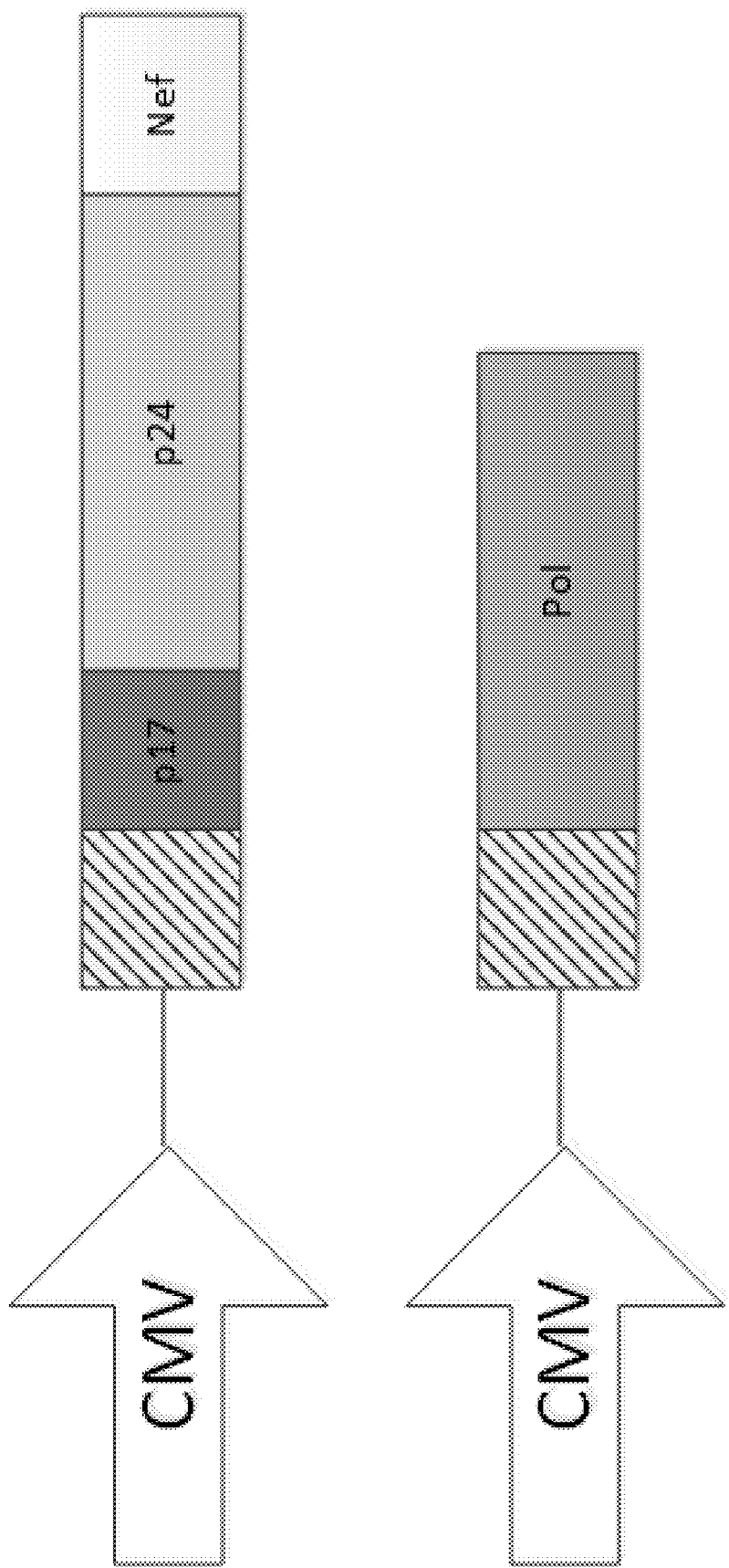
Figure 37B:
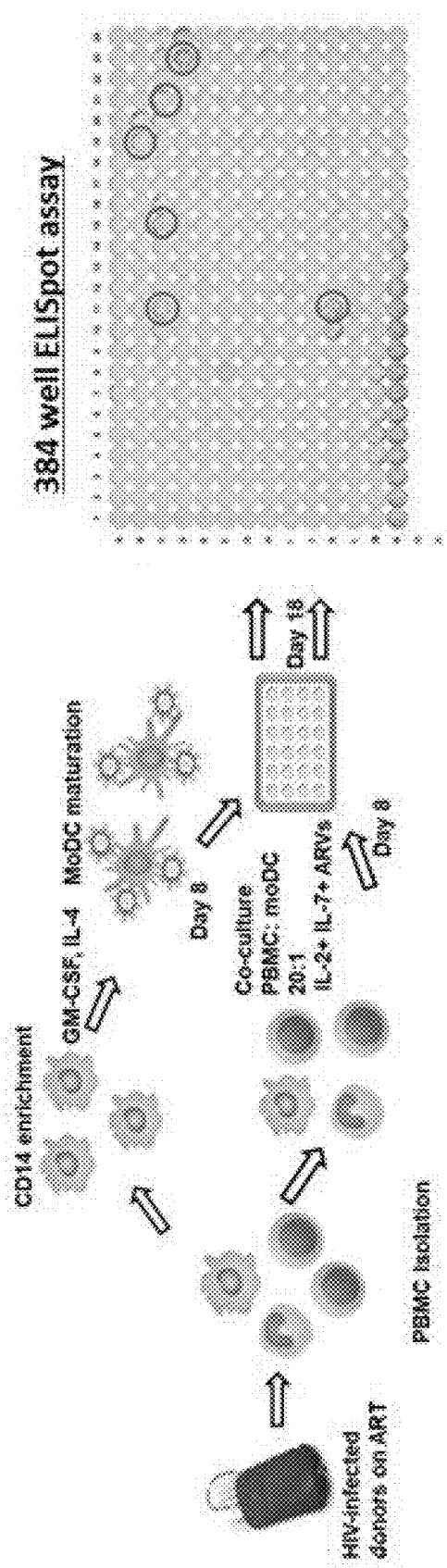

In this example, we used the in vitro T cell priming assay to decode the CD8+ T cell responses to the vaccine immunogen. We focused on determining the epitopes within conserved regions vaccine that induce antigen specific T cell responses and evaluated the impact of pre-existing responses on induction of de novo responses (original antigenic sin). In addition, we also determined if modifications to the immunogen e.g., addition of signal sequences, can modify the breadth of T cell responses generated. Fusion proteins of SEQ ID NOs: 353, 354, 355, 356, 357, 363, 364, 365, 366 and 429 were used in this assay (FIG. 37A).

Methods

ELISpot Assays.

Figure 37C:
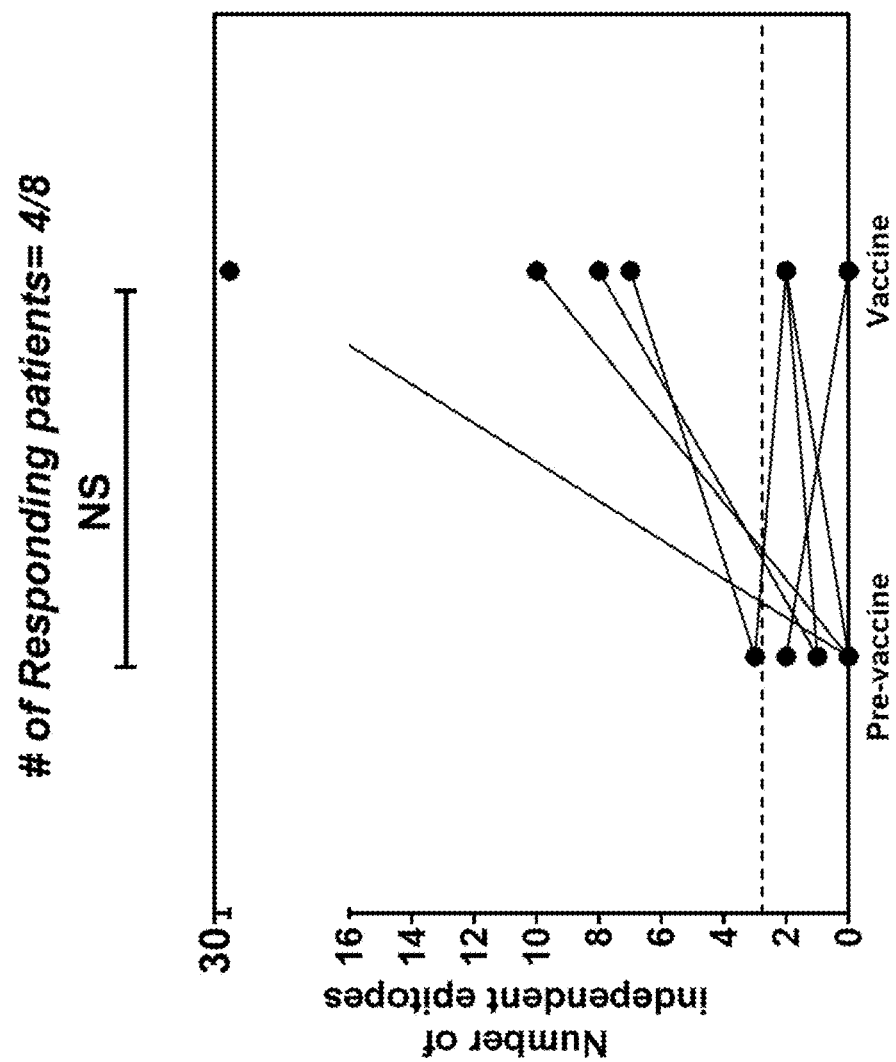
Figure 37D:
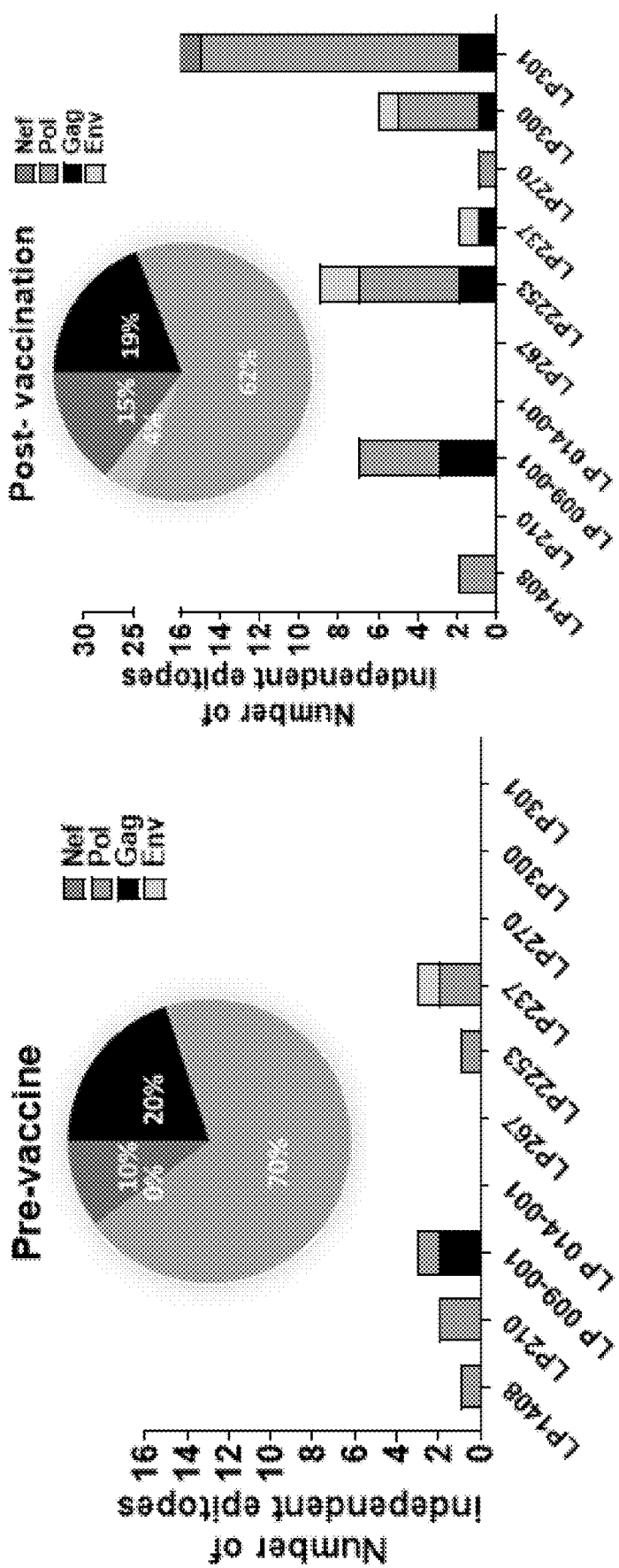
Figure 37E:
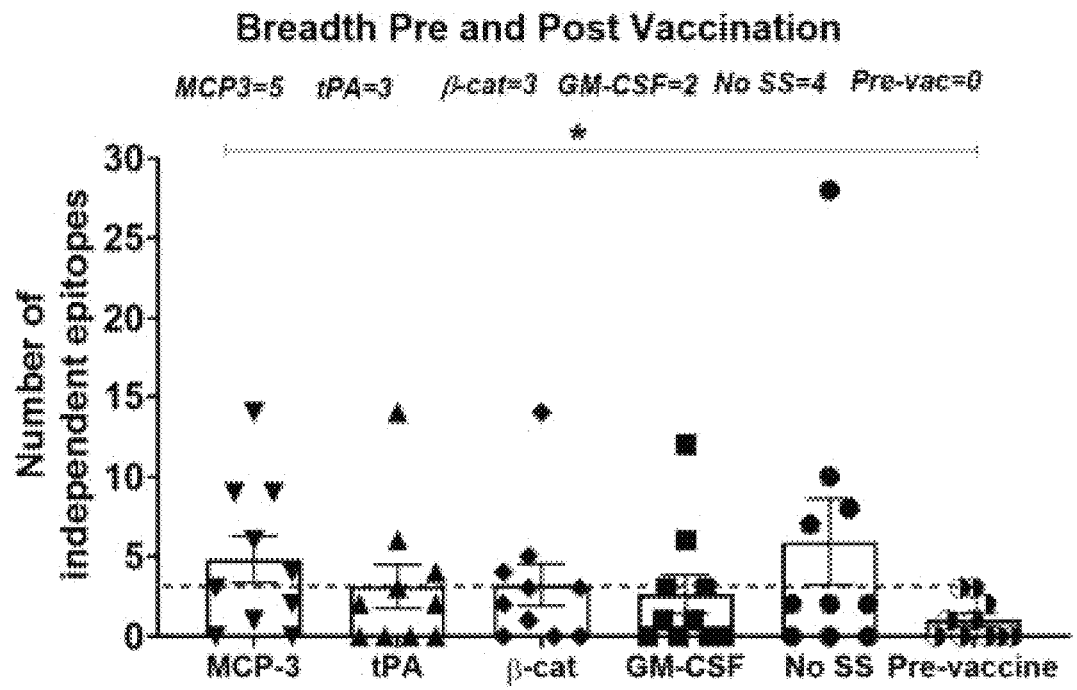
Figure 37F:
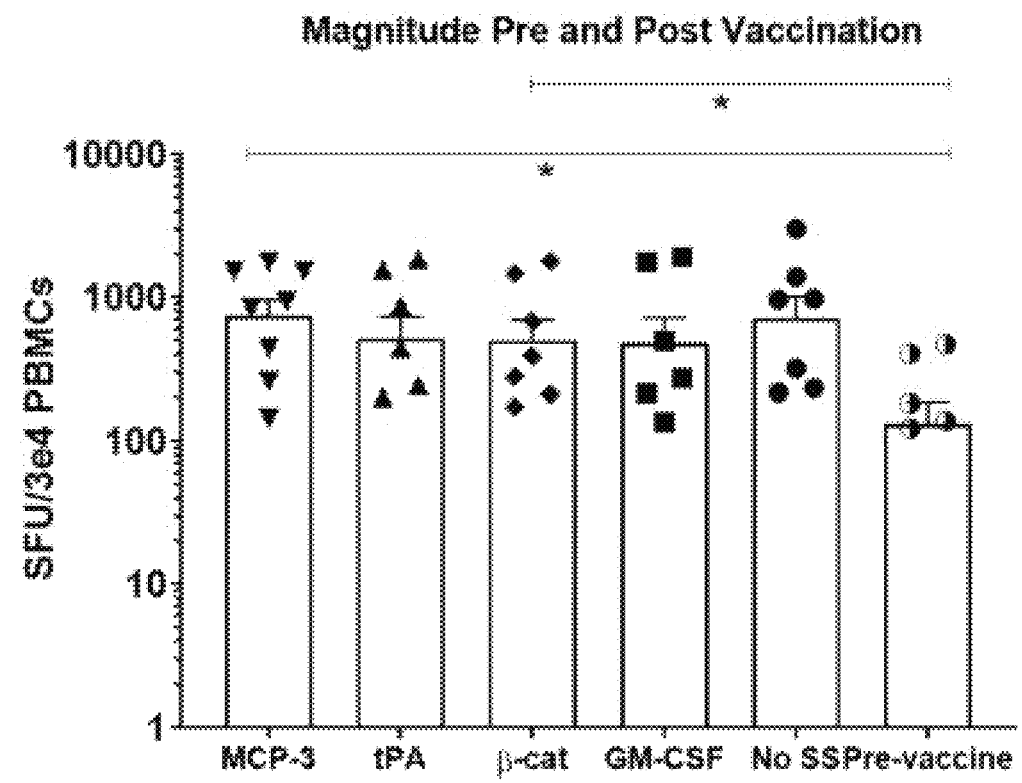

384 ELISpot plates (Cellular Technologies Limited) were coated with capture antibody and used for all epitope mapping experiments. Briefly, $3\times10^4$ cells from Day 10 moDC-CD8+ T cell/PBMC cultures were seeded to each The data are consistent with the conclusion that the conserved regions vaccine constructs expressing Gag-Nef and Pol-Env can prime de novo responses predominantly again Pol epitopes (FIG. 37C-37D). The data further indicates that the presence of signal sequences does not significantly enhance the magnitude or the breadth of the response. However, the presence of MCP-3 may increase the number of responders (defined as ≥3 epitopes recognized given the data from the STEP Trial; see, Janes, et al., *J Infect Dis* (2013) 208(8):1231-1239; ClinicalTrials.gov identifier: NCT00095576). The results are presented in FIGS. 37E-37F.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

<160> NUMBER OF SEQ ID NOS: 519

<210> SEQ ID NO 1
<211> LENGTH: 25
<212> TYPE: PRT
<213> ORGANISM: Human immunodeficiency virus

<400> SEQUENCE: 1

Cys Ser Ala Thr Glu Lys Leu Trp Val Thr Val Tyr Tyr Gly Val Pro
1               5                   10                  15

Val Trp Lys Glu Ala Thr Thr Thr Leu
            20                  25

<210> SEQ ID NO 2
<211> LENGTH: 15
<212> TYPE: PRT
<213> ORGANISM: Human immunodeficiency virus

<400> SEQUENCE: 2

Leu Trp Val Thr Val Tyr Tyr Gly Val Pro Val Trp Lys Glu Ala
1               5                   10                  15

<210> SEQ ID NO 3
<211> LENGTH: 15
<212> TYPE: PRT
<213> ORGANISM: Human immunodeficiency virus

<400> SEQUENCE: 3

Leu Trp Val Thr Ile Tyr Tyr Gly Val Pro Val Trp Lys Asp Ala
1               5                   10                  15

<210> SEQ ID NO 4
<211> LENGTH: 14
<212> TYPE: PRT
<213> ORGANISM: Human immunodeficiency virus

<400> SEQUENCE: 4

Leu Trp Val Thr Val Tyr Tyr Gly Val Pro Val Trp Lys Glu
1               5                   10

<210> SEQ ID NO 5
<211> LENGTH: 14
<212> TYPE: PRT
<213> ORGANISM: Human immunodeficiency virus

<400> SEQUENCE: 5

Leu Trp Val Thr Ile Tyr Tyr Gly Val Pro Val Trp Lys Asp
1               5                   10

<210> SEQ ID NO 6
<211> LENGTH: 9
<212> TYPE: PRT
<213> ORGANISM: Human immunodeficiency virus

<400> SEQUENCE: 6

Val Thr Val Tyr Tyr Gly Val Pro Val
1               5

<210> SEQ ID NO 7
<211> LENGTH: 9
<212> TYPE: PRT
<213> ORGANISM: Human immunodeficiency virus

<400> SEQUENCE: 7

```
Val Thr Ile Tyr Tyr Gly Val Pro Val
1               5
```

```
<210> SEQ ID NO 8
<211> LENGTH: 14
<212> TYPE: PRT
<213> ORGANISM: Human immunodeficiency virus

<400> SEQUENCE: 8

Ala Thr Thr Thr Leu Phe Cys Ala Ser Asp Ala Lys Ala Tyr
1               5                   10
```

```
<210> SEQ ID NO 9
<211> LENGTH: 14
<212> TYPE: PRT
<213> ORGANISM: Human immunodeficiency virus

<400> SEQUENCE: 9

Ala Asn Thr Thr Leu Phe Cys Ala Ser Asp Ala Lys Gly Tyr
1               5                   10
```

```
<210> SEQ ID NO 10
<211> LENGTH: 25
<212> TYPE: PRT
<213> ORGANISM: Human immunodeficiency virus

<400> SEQUENCE: 10

Lys Ala Tyr Asp Thr Glu Val His Asn Val Trp Ala Thr His Ala Cys
1               5                   10                  15

Val Pro Thr Asp Pro Asn Pro Gln Glu
            20                  25
```

```
<210> SEQ ID NO 11
<211> LENGTH: 19
<212> TYPE: PRT
<213> ORGANISM: Human immunodeficiency virus

<400> SEQUENCE: 11

Ala His Asn Val Trp Ala Thr His Ala Cys Val Pro Thr Asp Pro Asn
1               5                   10                  15

Pro Gln Glu
```

```
<210> SEQ ID NO 12
<211> LENGTH: 19
<212> TYPE: PRT
<213> ORGANISM: Human immunodeficiency virus

<400> SEQUENCE: 12

Val His Asn Ile Trp Ala Thr His Ala Cys Val Pro Thr Asp Pro Ser
1               5                   10                  15

Pro Gln Glu
```

```
<210> SEQ ID NO 13
<211> LENGTH: 18
<212> TYPE: PRT
<213> ORGANISM: Human immunodeficiency virus

<400> SEQUENCE: 13

His Asn Val Trp Ala Thr His Ala Cys Val Pro Thr Asp Pro Asn Pro
1               5                   10                  15

Gln Glu
```

```
<210> SEQ ID NO 14
<211> LENGTH: 18
<212> TYPE: PRT
<213> ORGANISM: Human immunodeficiency virus

<400> SEQUENCE: 14

His Asn Ile Trp Ala Thr His Ala Cys Val Pro Thr Asp Pro Ser Pro
1               5                   10                  15

Gln Glu

<210> SEQ ID NO 15
<211> LENGTH: 9
<212> TYPE: PRT
<213> ORGANISM: Human immunodeficiency virus

<400> SEQUENCE: 15

Asn Val Trp Ala Thr His Ala Cys Val
1               5

<210> SEQ ID NO 16
<211> LENGTH: 9
<212> TYPE: PRT
<213> ORGANISM: Human immunodeficiency virus

<400> SEQUENCE: 16

Asn Ile Trp Ala Thr His Ala Cys Val
1               5

<210> SEQ ID NO 17
<211> LENGTH: 23
<212> TYPE: PRT
<213> ORGANISM: Human immunodeficiency virus

<400> SEQUENCE: 17

Asp Ile Ile Ser Leu Trp Asp Gln Ser Leu Lys Pro Cys Val Lys Leu
1               5                   10                  15

Thr Pro Leu Cys Val Thr Leu
            20

<210> SEQ ID NO 18
<211> LENGTH: 23
<212> TYPE: PRT
<213> ORGANISM: Human immunodeficiency virus

<400> SEQUENCE: 18

Asp Ile Ile Ser Leu Trp Asp Glu Ser Leu Lys Pro Cys Val Lys Leu
1               5                   10                  15

Thr Pro Ile Cys Val Thr Leu
            20

<210> SEQ ID NO 19
<211> LENGTH: 25
<212> TYPE: PRT
<213> ORGANISM: Human immunodeficiency virus

<400> SEQUENCE: 19

Asp Gln Ser Leu Lys Pro Cys Val Lys Leu Thr Pro Leu Cys Val Thr
1               5                   10                  15

Leu Asn Cys Thr Asp Leu Arg Asn Thr
            20                  25

<210> SEQ ID NO 20
<211> LENGTH: 25
```

```
<212> TYPE: PRT
<213> ORGANISM: Human immunodeficiency virus

<400> SEQUENCE: 20

Asp Glu Ser Leu Lys Pro Cys Val Lys Leu Thr Pro Ile Cys Val Thr
1               5                   10                  15

Leu Asn Cys Thr Asp Leu Arg Asn Thr
            20                  25

<210> SEQ ID NO 21
<211> LENGTH: 9
<212> TYPE: PRT
<213> ORGANISM: Human immunodeficiency virus

<400> SEQUENCE: 21

Lys Leu Thr Pro Leu Cys Val Thr Leu
1               5

<210> SEQ ID NO 22
<211> LENGTH: 9
<212> TYPE: PRT
<213> ORGANISM: Human immunodeficiency virus

<400> SEQUENCE: 22

Lys Leu Thr Pro Ile Cys Val Thr Leu
1               5

<210> SEQ ID NO 23
<211> LENGTH: 18
<212> TYPE: PRT
<213> ORGANISM: Human immunodeficiency virus

<400> SEQUENCE: 23

Ser Phe Glu Pro Ile Pro Ile His Tyr Cys Ala Pro Ala Gly Phe Ala
1               5                   10                  15

Ile Leu

<210> SEQ ID NO 24
<211> LENGTH: 18
<212> TYPE: PRT
<213> ORGANISM: Human immunodeficiency virus

<400> SEQUENCE: 24

Thr Phe Glu Pro Ile Pro Ile His Tyr Cys Thr Pro Ala Gly Phe Ala
1               5                   10                  15

Ile Leu

<210> SEQ ID NO 25
<211> LENGTH: 9
<212> TYPE: PRT
<213> ORGANISM: Human immunodeficiency virus

<400> SEQUENCE: 25

Pro Ala Gly Phe Ala Ile Leu Lys Cys
1               5

<210> SEQ ID NO 26
<211> LENGTH: 9
<212> TYPE: PRT
<213> ORGANISM: Human immunodeficiency virus

<400> SEQUENCE: 26

Pro Ala Gly Phe Ala Leu Leu Lys Cys
```

<210> SEQ ID NO 27
<211> LENGTH: 25
<212> TYPE: PRT
<213> ORGANISM: Human immunodeficiency virus

<400> SEQUENCE: 27

Gly Thr Gly Pro Cys Thr Asn Val Ser Thr Val Gln Cys Thr His Gly
1               5                   10                  15

Ile Arg Pro Val Val Ser Thr Gln Leu
            20                  25

<210> SEQ ID NO 28
<211> LENGTH: 28
<212> TYPE: PRT
<213> ORGANISM: Human immunodeficiency virus

<400> SEQUENCE: 28

Asn Val Ser Thr Val Gln Cys Thr His Gly Ile Arg Pro Val Val Ser
1               5                   10                  15

Thr Gln Leu Leu Leu Asn Gly Ser Leu Ala Glu Glu
            20                  25

<210> SEQ ID NO 29
<211> LENGTH: 28
<212> TYPE: PRT
<213> ORGANISM: Human immunodeficiency virus

<400> SEQUENCE: 29

Asn Ile Ser Thr Val Gln Cys Thr His Gly Ile Lys Pro Val Val Ser
1               5                   10                  15

Thr Gln Leu Leu Leu Asn Gly Ser Leu Ala Glu Lys
            20                  25

<210> SEQ ID NO 30
<211> LENGTH: 9
<212> TYPE: PRT
<213> ORGANISM: Human immunodeficiency virus

<400> SEQUENCE: 30

Ser Thr Val Gln Cys Thr His Gly Ile
1               5

<210> SEQ ID NO 31
<211> LENGTH: 11
<212> TYPE: PRT
<213> ORGANISM: Human immunodeficiency virus

<400> SEQUENCE: 31

Phe Asn Cys Gly Gly Glu Phe Phe Tyr Cys Asn
1               5                   10

<210> SEQ ID NO 32
<211> LENGTH: 11
<212> TYPE: PRT
<213> ORGANISM: Human immunodeficiency virus

<400> SEQUENCE: 32

Phe Asn Cys Arg Gly Glu Phe Phe Tyr Cys Asn
1               5                   10

<210> SEQ ID NO 33

```
<211> LENGTH: 10
<212> TYPE: PRT
<213> ORGANISM: Human immunodeficiency virus

<400> SEQUENCE: 33

Val Gly Lys Ala Met Tyr Ala Pro Pro Ile
1               5                   10

<210> SEQ ID NO 34
<211> LENGTH: 10
<212> TYPE: PRT
<213> ORGANISM: Human immunodeficiency virus

<400> SEQUENCE: 34

Val Gly Arg Ala Met Tyr Ala Pro Pro Ile
1               5                   10

<210> SEQ ID NO 35
<211> LENGTH: 10
<212> TYPE: PRT
<213> ORGANISM: Human immunodeficiency virus

<400> SEQUENCE: 35

Gly Gly Asp Met Arg Asp Asn Trp Arg Ser
1               5                   10

<210> SEQ ID NO 36
<211> LENGTH: 10
<212> TYPE: PRT
<213> ORGANISM: Human immunodeficiency virus

<400> SEQUENCE: 36

Gly Gly Asn Met Lys Asp Asn Trp Arg Ser
1               5                   10

<210> SEQ ID NO 37
<211> LENGTH: 15
<212> TYPE: PRT
<213> ORGANISM: Human immunodeficiency virus

<400> SEQUENCE: 37

Met Arg Asp Asn Trp Arg Ser Glu Leu Tyr Lys Tyr Lys Val Val
1               5                   10                  15

<210> SEQ ID NO 38
<211> LENGTH: 15
<212> TYPE: PRT
<213> ORGANISM: Human immunodeficiency virus

<400> SEQUENCE: 38

Met Lys Asp Asn Trp Arg Ser Glu Leu Tyr Arg Tyr Lys Val Val
1               5                   10                  15

<210> SEQ ID NO 39
<211> LENGTH: 11
<212> TYPE: PRT
<213> ORGANISM: Human immunodeficiency virus

<400> SEQUENCE: 39

Ala Lys Arg Arg Val Val Gln Arg Glu Lys Arg
1               5                   10

<210> SEQ ID NO 40
<211> LENGTH: 11
<212> TYPE: PRT
```

```
<213> ORGANISM: Human immunodeficiency virus

<400> SEQUENCE: 40

Ala Arg Arg Arg Val Val Gln Arg Glu Lys Arg
1               5                   10

<210> SEQ ID NO 41
<211> LENGTH: 105
<212> TYPE: PRT
<213> ORGANISM: Human immunodeficiency virus

<400> SEQUENCE: 41

Lys Arg Arg Val Val Gln Arg Glu Lys Arg Ala Val Gly Ile Gly Ala
1               5                   10                  15

Met Phe Leu Gly Phe Leu Gly Ala Ala Gly Ser Thr Met Gly Ala Ala
            20                  25                  30

Ser Ile Thr Leu Thr Val Gln Ala Arg Gln Leu Leu Ser Gly Ile Val
        35                  40                  45

Gln Gln Gln Asn Asn Leu Leu Arg Ala Ile Glu Ala Gln Gln His Leu
    50                  55                  60

Leu Gln Leu Thr Val Trp Gly Ile Lys Gln Leu Gln Ala Arg Val Leu
65                  70                  75                  80

Ala Val Glu Arg Tyr Leu Lys Asp Gln Gln Leu Leu Gly Ile Trp Gly
                85                  90                  95

Cys Ser Gly Lys Leu Ile Cys Thr Thr
            100                 105

<210> SEQ ID NO 42
<211> LENGTH: 105
<212> TYPE: PRT
<213> ORGANISM: Human immunodeficiency virus

<400> SEQUENCE: 42

Arg Arg Arg Val Val Gln Arg Glu Lys Arg Ala Ile Gly Leu Gly Ala
1               5                   10                  15

Val Phe Leu Gly Phe Leu Gly Thr Ala Gly Ser Thr Met Gly Ala Ala
            20                  25                  30

Ser Met Thr Leu Thr Val Gln Ala Arg Leu Leu Leu Ser Gly Ile Val
        35                  40                  45

Gln Gln Gln Ser Asn Leu Leu Arg Ala Ile Glu Ala Gln Gln His Met
    50                  55                  60

Leu Gln Leu Thr Val Trp Gly Ile Lys Gln Leu Gln Ala Arg Ile Leu
65                  70                  75                  80

Ala Val Glu Arg Tyr Leu Arg Asp Gln Gln Leu Leu Gly Ile Trp Gly
                85                  90                  95

Cys Ser Gly Arg Leu Ile Cys Thr Thr
            100                 105

<210> SEQ ID NO 43
<211> LENGTH: 16
<212> TYPE: PRT
<213> ORGANISM: Human immunodeficiency virus

<400> SEQUENCE: 43

Phe Leu Gly Phe Leu Gly Ala Ala Gly Ser Thr Met Gly Ala Ala Ser
1               5                   10                  15

<210> SEQ ID NO 44
<211> LENGTH: 16
```

```
<212> TYPE: PRT
<213> ORGANISM: Human immunodeficiency virus

<400> SEQUENCE: 44

Phe Leu Gly Phe Leu Gly Thr Ala Gly Ser Thr Met Gly Ala Ala Ala
1               5                   10                  15

<210> SEQ ID NO 45
<211> LENGTH: 74
<212> TYPE: PRT
<213> ORGANISM: Human immunodeficiency virus

<400> SEQUENCE: 45

Ala Ser Ile Thr Leu Thr Val Gln Ala Arg Gln Leu Leu Ser Gly Ile
1               5                   10                  15

Val Gln Gln Gln Asn Asn Leu Leu Arg Ala Ile Glu Ala Gln Gln His
            20                  25                  30

Leu Leu Gln Leu Thr Val Trp Gly Ile Lys Gln Leu Gln Ala Arg Val
        35                  40                  45

Leu Ala Val Glu Arg Tyr Leu Lys Asp Gln Gln Leu Leu Gly Ile Trp
    50                  55                  60

Gly Cys Ser Gly Lys Leu Ile Cys Thr Thr
65                  70

<210> SEQ ID NO 46
<211> LENGTH: 74
<212> TYPE: PRT
<213> ORGANISM: Human immunodeficiency virus

<400> SEQUENCE: 46

Ala Ser Met Thr Leu Thr Val Gln Ala Arg Leu Leu Leu Ser Gly Ile
1               5                   10                  15

Val Gln Gln Gln Ser Asn Leu Leu Arg Ala Ile Glu Ala Gln Gln His
            20                  25                  30

Met Leu Gln Leu Thr Val Trp Gly Ile Lys Gln Leu Gln Ala Arg Ile
        35                  40                  45

Leu Ala Val Glu Arg Tyr Leu Arg Asp Gln Gln Leu Leu Gly Ile Trp
    50                  55                  60

Gly Cys Ser Gly Arg Leu Ile Cys Thr Thr
65                  70

<210> SEQ ID NO 47
<211> LENGTH: 21
<212> TYPE: PRT
<213> ORGANISM: Human immunodeficiency virus

<400> SEQUENCE: 47

Thr Leu Thr Val Gln Ala Arg Gln Leu Leu Ser Gly Ile Val Gln Gln
1               5                   10                  15

Gln Asn Asn Leu Leu
            20

<210> SEQ ID NO 48
<211> LENGTH: 21
<212> TYPE: PRT
<213> ORGANISM: Human immunodeficiency virus

<400> SEQUENCE: 48

Thr Leu Thr Val Gln Ala Arg Leu Leu Leu Ser Gly Ile Val Gln Gln
1               5                   10                  15
```

Gln Ser Asn Leu Leu
        20

<210> SEQ ID NO 49
<211> LENGTH: 11
<212> TYPE: PRT
<213> ORGANISM: Human immunodeficiency virus

<400> SEQUENCE: 49

Asn Leu Leu Arg Ala Ile Glu Ala Gln Gln His
1               5                   10

<210> SEQ ID NO 50
<211> LENGTH: 11
<212> TYPE: PRT
<213> ORGANISM: Human immunodeficiency virus

<400> SEQUENCE: 50

Asn Leu Leu Lys Ala Ile Glu Ala Gln Gln His
1               5                   10

<210> SEQ ID NO 51
<211> LENGTH: 27
<212> TYPE: PRT
<213> ORGANISM: Human immunodeficiency virus

<400> SEQUENCE: 51

Ala Ile Glu Ala Gln Gln His Leu Leu Gln Leu Thr Val Trp Gly Ile
1               5                   10                  15

Lys Gln Leu Gln Ala Arg Val Leu Ala Val Glu
            20                  25

<210> SEQ ID NO 52
<211> LENGTH: 27
<212> TYPE: PRT
<213> ORGANISM: Human immunodeficiency virus

<400> SEQUENCE: 52

Ala Ile Glu Ala Gln Gln His Met Leu Gln Leu Thr Val Trp Gly Ile
1               5                   10                  15

Lys Gln Leu Gln Ala Arg Ile Leu Ala Val Glu
            20                  25

<210> SEQ ID NO 53
<211> LENGTH: 9
<212> TYPE: PRT
<213> ORGANISM: Human immunodeficiency virus

<400> SEQUENCE: 53

Glu Arg Tyr Leu Lys Asp Gln Gln Leu
1               5

<210> SEQ ID NO 54
<211> LENGTH: 9
<212> TYPE: PRT
<213> ORGANISM: Human immunodeficiency virus

<400> SEQUENCE: 54

Glu Arg Tyr Leu Arg Asp Gln Gln Leu
1               5

<210> SEQ ID NO 55
<211> LENGTH: 9
<212> TYPE: PRT

```
<213> ORGANISM: Human immunodeficiency virus

<400> SEQUENCE: 55

Tyr Leu Lys Asp Gln Gln Leu Leu Gly
1               5

<210> SEQ ID NO 56
<211> LENGTH: 9
<212> TYPE: PRT
<213> ORGANISM: Human immunodeficiency virus

<400> SEQUENCE: 56

Tyr Leu Arg Asp Gln Gln Leu Leu Gly
1               5

<210> SEQ ID NO 57
<211> LENGTH: 25
<212> TYPE: PRT
<213> ORGANISM: Human immunodeficiency virus

<400> SEQUENCE: 57

Tyr Leu Lys Asp Gln Gln Leu Leu Gly Ile Trp Gly Cys Ser Gly Lys
1               5                   10                  15

Leu Ile Cys Thr Thr Ala Val Pro Trp
            20                  25

<210> SEQ ID NO 58
<211> LENGTH: 18
<212> TYPE: PRT
<213> ORGANISM: Human immunodeficiency virus

<400> SEQUENCE: 58

Asp Gln Gln Leu Leu Gly Ile Trp Gly Cys Ser Gly Lys Leu Ile Cys
1               5                   10                  15

Thr Thr

<210> SEQ ID NO 59
<211> LENGTH: 18
<212> TYPE: PRT
<213> ORGANISM: Human immunodeficiency virus

<400> SEQUENCE: 59

Asp Gln Gln Leu Leu Gly Leu Trp Gly Cys Ser Gly Lys Leu Ile Cys
1               5                   10                  15

Pro Thr

<210> SEQ ID NO 60
<211> LENGTH: 9
<212> TYPE: PRT
<213> ORGANISM: Human immunodeficiency virus

<400> SEQUENCE: 60

Gly Ile Trp Gly Cys Ser Gly Lys Leu
1               5

<210> SEQ ID NO 61
<211> LENGTH: 9
<212> TYPE: PRT
<213> ORGANISM: Human immunodeficiency virus

<400> SEQUENCE: 61

Gly Leu Trp Gly Cys Ser Gly Lys Leu
1               5
```

```
<210> SEQ ID NO 62
<211> LENGTH: 11
<212> TYPE: PRT
<213> ORGANISM: Human immunodeficiency virus

<400> SEQUENCE: 62

Trp Leu Trp Tyr Ile Lys Ile Phe Ile Met Ile
1               5                   10

<210> SEQ ID NO 63
<211> LENGTH: 11
<212> TYPE: PRT
<213> ORGANISM: Human immunodeficiency virus

<400> SEQUENCE: 63

Trp Leu Trp Tyr Ile Arg Ile Phe Ile Met Ile
1               5                   10

<210> SEQ ID NO 64
<211> LENGTH: 14
<212> TYPE: PRT
<213> ORGANISM: Human immunodeficiency virus

<400> SEQUENCE: 64

Ile Phe Ile Met Ile Val Gly Gly Leu Ile Gly Leu Arg Ile
1               5                   10

<210> SEQ ID NO 65
<211> LENGTH: 14
<212> TYPE: PRT
<213> ORGANISM: Human immunodeficiency virus

<400> SEQUENCE: 65

Leu Phe Ile Met Ile Val Gly Gly Leu Val Gly Leu Arg Ile
1               5                   10

<210> SEQ ID NO 66
<211> LENGTH: 15
<212> TYPE: PRT
<213> ORGANISM: Human immunodeficiency virus

<400> SEQUENCE: 66

Val Asn Arg Val Arg Gln Gly Tyr Ser Pro Leu Ser Phe Gln Thr
1               5                   10                  15

<210> SEQ ID NO 67
<211> LENGTH: 15
<212> TYPE: PRT
<213> ORGANISM: Human immunodeficiency virus

<400> SEQUENCE: 67

Val Asn Arg Val Arg Lys Gly Tyr Ser Pro Leu Ser Phe Gln Ile
1               5                   10                  15

<210> SEQ ID NO 68
<211> LENGTH: 11
<212> TYPE: PRT
<213> ORGANISM: Human immunodeficiency virus

<400> SEQUENCE: 68

Met Gly Ala Arg Ala Ser Val Leu Ser Gly Gly
1               5                   10
```

```
<210> SEQ ID NO 69
<211> LENGTH: 11
<212> TYPE: PRT
<213> ORGANISM: Human immunodeficiency virus

<400> SEQUENCE: 69

Met Gly Ala Arg Ala Ser Ile Leu Ser Gly Gly
1               5                   10

<210> SEQ ID NO 70
<211> LENGTH: 53
<212> TYPE: PRT
<213> ORGANISM: Human immunodeficiency virus

<400> SEQUENCE: 70

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
                20                  25                  30

His Ile Val Trp Ala Ser Arg Glu Leu Glu Arg Phe Ala Val Asn Pro
            35                  40                  45

Gly Leu Leu Glu Thr
    50

<210> SEQ ID NO 71
<211> LENGTH: 53
<212> TYPE: PRT
<213> ORGANISM: Human immunodeficiency virus

<400> SEQUENCE: 71

Met Gly Ala Arg Ala Ser Ile Leu Ser Gly Gly Lys Leu Asp Lys Trp
1               5                   10                  15

Glu Lys Ile Arg Leu Arg Pro Gly Gly Arg Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr
    50

<210> SEQ ID NO 72
<211> LENGTH: 13
<212> TYPE: PRT
<213> ORGANISM: Human immunodeficiency virus

<400> SEQUENCE: 72

Leu Asp Arg Trp Glu Lys Ile Arg Leu Arg Pro Gly Gly
1               5                   10

<210> SEQ ID NO 73
<211> LENGTH: 13
<212> TYPE: PRT
<213> ORGANISM: Human immunodeficiency virus

<400> SEQUENCE: 73

Leu Asp Lys Trp Glu Lys Ile Arg Leu Arg Pro Met Gly
1               5                   10

<210> SEQ ID NO 74
<211> LENGTH: 9
<212> TYPE: PRT
<213> ORGANISM: Human immunodeficiency virus

<400> SEQUENCE: 74
```

```
Ile Arg Leu Arg Pro Gly Gly Lys Lys
1               5
```

\<210\> SEQ ID NO 75
\<211\> LENGTH: 9
\<212\> TYPE: PRT
\<213\> ORGANISM: Human immunodeficiency virus

\<400\> SEQUENCE: 75

```
Ile Arg Leu Arg Pro Gly Gly Arg Lys
1               5
```

\<210\> SEQ ID NO 76
\<211\> LENGTH: 23
\<212\> TYPE: PRT
\<213\> ORGANISM: Human immunodeficiency virus

\<400\> SEQUENCE: 76

```
Leu Lys His Ile Val Trp Ala Ser Arg Glu Leu Glu Arg Phe Ala Val
1               5                   10                  15

Asn Pro Gly Leu Leu Glu Thr
            20
```

\<210\> SEQ ID NO 77
\<211\> LENGTH: 23
\<212\> TYPE: PRT
\<213\> ORGANISM: Human immunodeficiency virus

\<400\> SEQUENCE: 77

```
Leu Lys His Leu Val Trp Ala Ser Arg Glu Leu Glu Arg Phe Ala Leu
1               5                   10                  15

Asn Pro Gly Leu Leu Glu Thr
            20
```

\<210\> SEQ ID NO 78
\<211\> LENGTH: 15
\<212\> TYPE: PRT
\<213\> ORGANISM: Human immunodeficiency virus

\<400\> SEQUENCE: 78

```
Ala Ser Arg Glu Leu Glu Arg Phe Ala Val Asn Pro Gly Leu Leu
1               5                   10                  15
```

\<210\> SEQ ID NO 79
\<211\> LENGTH: 15
\<212\> TYPE: PRT
\<213\> ORGANISM: Human immunodeficiency virus

\<400\> SEQUENCE: 79

```
Ala Ser Arg Glu Leu Glu Arg Phe Ala Leu Asn Pro Gly Leu Leu
1               5                   10                  15
```

\<210\> SEQ ID NO 80
\<211\> LENGTH: 9
\<212\> TYPE: PRT
\<213\> ORGANISM: Human immunodeficiency virus

\<400\> SEQUENCE: 80

```
Thr Gly Ser Glu Glu Leu Lys Ser Leu
1               5
```

\<210\> SEQ ID NO 81
\<211\> LENGTH: 9

```
<212> TYPE: PRT
<213> ORGANISM: Human immunodeficiency virus

<400> SEQUENCE: 81

Thr Gly Ser Glu Glu Leu Arg Ser Leu
1               5

<210> SEQ ID NO 82
<211> LENGTH: 9
<212> TYPE: PRT
<213> ORGANISM: Human immunodeficiency virus

<400> SEQUENCE: 82

Asp Thr Lys Glu Ala Leu Asp Lys Ile
1               5

<210> SEQ ID NO 83
<211> LENGTH: 9
<212> TYPE: PRT
<213> ORGANISM: Human immunodeficiency virus

<400> SEQUENCE: 83

Asp Thr Lys Glu Ala Leu Glu Lys Ile
1               5

<210> SEQ ID NO 84
<211> LENGTH: 9
<212> TYPE: PRT
<213> ORGANISM: Human immunodeficiency virus

<400> SEQUENCE: 84

Glu Ala Leu Asp Lys Ile Glu Glu Glu
1               5

<210> SEQ ID NO 85
<211> LENGTH: 9
<212> TYPE: PRT
<213> ORGANISM: Human immunodeficiency virus

<400> SEQUENCE: 85

Glu Ala Leu Glu Lys Ile Glu Glu Glu
1               5

<210> SEQ ID NO 86
<211> LENGTH: 10
<212> TYPE: PRT
<213> ORGANISM: Human immunodeficiency virus

<400> SEQUENCE: 86

Val Ser Gln Asn Tyr Pro Ile Val Gln Asn
1               5                   10

<210> SEQ ID NO 87
<211> LENGTH: 10
<212> TYPE: PRT
<213> ORGANISM: Human immunodeficiency virus

<400> SEQUENCE: 87

Val Ser Gln Asn Phe Pro Ile Val Gln Asn
1               5                   10

<210> SEQ ID NO 88
<211> LENGTH: 231
<212> TYPE: PRT
<213> ORGANISM: Human immunodeficiency virus
```

<400> SEQUENCE: 88

```
Pro Ile Val Gln Asn Leu Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Leu His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu
225                 230

<210> SEQ ID NO 89
<211> LENGTH: 231
<212> TYPE: PRT
<213> ORGANISM: Human immunodeficiency virus

<400> SEQUENCE: 89

Pro Ile Val Gln Asn Ile Gln Gly Gln Met Val His Gln Pro Ile Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Thr Ala Leu Ser Glu Gly Ala Thr
        35                  40                  45

Pro His Asp Leu Asn Thr Met Leu Asn Thr Ile Gly Gly His Gln Ala
    50                  55                  60

Ala Met Gln Met Leu Lys Asp Thr Ile Asn Glu Glu Ala Ala Glu Trp
65                  70                  75                  80

Asp Arg Val His Pro Val His Ala Gly Pro Val Ala Pro Gly Gln Met
                85                  90                  95

Arg Asp Pro Arg Gly Ser Asp Ile Ala Gly Thr Thr Ser Asn Leu Gln
            100                 105                 110

Glu Gln Ile Gly Trp Met Thr Ser Asn Pro Pro Ile Pro Val Gly Asp
        115                 120                 125
```

-continued

Ile Tyr Lys Arg Trp Ile Ile Met Gly Leu Asn Lys Ile Val Arg Met
130                 135                 140

Tyr Ser Pro Val Ser Ile Leu Asp Ile Lys Gln Gly Pro Lys Glu Pro
145                 150                 155                 160

Phe Arg Asp Tyr Val Asp Arg Phe Tyr Arg Thr Leu Arg Ala Glu Gln
                165                 170                 175

Ala Ser Gln Asp Val Lys Asn Trp Met Thr Glu Thr Leu Leu Val Gln
            180                 185                 190

Asn Ser Asn Pro Asp Cys Lys Thr Ile Leu Lys Ala Leu Gly Pro Gly
        195                 200                 205

Ala Thr Leu Glu Glu Met Met Ser Ala Cys Gln Gly Val Gly Gly Pro
210                 215                 220

Ser His Lys Ala Arg Val Leu
225                 230

<210> SEQ ID NO 90
<211> LENGTH: 25
<212> TYPE: PRT
<213> ORGANISM: Human immunodeficiency virus

<400> SEQUENCE: 90

Met Val His Gln Ala Ile Ser Pro Arg Thr Leu Asn Ala Trp Val Lys
1               5                   10                  15

Val Val Glu Glu Lys Ala Phe Ser Pro
            20                  25

<210> SEQ ID NO 91
<211> LENGTH: 25
<212> TYPE: PRT
<213> ORGANISM: Human immunodeficiency virus

<400> SEQUENCE: 91

Met Val His Gln Pro Ile Ser Pro Arg Thr Leu Asn Ala Trp Val Lys
1               5                   10                  15

Val Ile Glu Glu Lys Ala Phe Ser Pro
            20                  25

<210> SEQ ID NO 92
<211> LENGTH: 71
<212> TYPE: PRT
<213> ORGANISM: Human immunodeficiency virus

<400> SEQUENCE: 92

Ile Ser Pro Arg Thr Leu Asn Ala Trp Val Lys Val Val Glu Glu Lys
1               5                   10                  15

Ala Phe Ser Pro Glu Val Ile Pro Met Phe Ser Ala Leu Ser Glu Gly
            20                  25                  30

Ala Thr Pro Gln Asp Leu Asn Thr Met Leu Asn Thr Val Gly Gly His
        35                  40                  45

Gln Ala Ala Met Gln Met Leu Lys Glu Thr Ile Asn Glu Glu Ala Ala
    50                  55                  60

Glu Trp Asp Arg Leu His Pro
65                  70

<210> SEQ ID NO 93
<211> LENGTH: 71
<212> TYPE: PRT
<213> ORGANISM: Human immunodeficiency virus

<400> SEQUENCE: 93

Leu Ser Pro Arg Thr Leu Asn Ala Trp Val Lys Val Ile Glu Glu Lys
1               5                   10                  15

Ala Phe Ser Pro Glu Val Ile Pro Met Phe Thr Ala Leu Ser Glu Gly
                20                  25                  30

Ala Thr Pro His Asp Leu Asn Thr Met Leu Asn Thr Ile Gly Gly His
            35                  40                  45

Gln Ala Ala Met Gln Met Leu Lys Asp Thr Ile Asn Glu Glu Ala Ala
    50                  55                  60

Glu Trp Asp Arg Val His Pro
65                  70

<210> SEQ ID NO 94
<211> LENGTH: 223
<212> TYPE: PRT
<213> ORGANISM: Human immunodeficiency virus

<400> SEQUENCE: 94

Ile Ser Pro Arg Thr Leu Asn Ala Trp Val Lys Val Glu Glu Lys
1               5                   10                  15

Ala Phe Ser Pro Glu Val Ile Pro Met Phe Ser Ala Leu Ser Glu Gly
                20                  25                  30

Ala Thr Pro Gln Asp Leu Asn Thr Met Leu Asn Thr Val Gly Gly His
            35                  40                  45

Gln Ala Ala Met Gln Met Leu Lys Glu Thr Ile Asn Glu Glu Ala Ala
    50                  55                  60

Glu Trp Asp Arg Leu His Pro Val His Ala Gly Pro Ile Ala Pro Gly
65                  70                  75                  80

Gln Met Arg Glu Pro Arg Gly Ser Asp Ile Ala Gly Thr Thr Ser Thr
                85                  90                  95

Leu Gln Glu Gln Ile Gly Trp Met Thr Asn Asn Pro Pro Ile Pro Val
            100                 105                 110

Gly Glu Ile Tyr Lys Arg Trp Ile Ile Leu Gly Leu Asn Lys Ile Val
        115                 120                 125

Arg Met Tyr Ser Pro Thr Ser Ile Leu Asp Ile Arg Gln Gly Pro Lys
    130                 135                 140

Glu Pro Phe Arg Asp Tyr Val Asp Arg Phe Tyr Lys Thr Leu Arg Ala
145                 150                 155                 160

Glu Gln Ala Ser Gln Glu Val Lys Asn Trp Met Thr Glu Thr Leu Leu
                165                 170                 175

Val Gln Asn Ala Asn Pro Asp Cys Lys Thr Ile Leu Lys Ala Leu Gly
            180                 185                 190

Pro Ala Ala Thr Leu Glu Glu Met Met Thr Ala Cys Gln Gly Val Gly
        195                 200                 205

Gly Pro Gly His Lys Ala Arg Val Leu Ala Glu Ala Met Ser Gln
    210                 215                 220

<210> SEQ ID NO 95
<211> LENGTH: 223
<212> TYPE: PRT
<213> ORGANISM: Human immunodeficiency virus

<400> SEQUENCE: 95

Leu Ser Pro Arg Thr Leu Asn Ala Trp Val Lys Val Ile Glu Glu Lys
1               5                   10                  15

Ala Phe Ser Pro Glu Val Ile Pro Met Phe Thr Ala Leu Ser Glu Gly

```
                 20                  25                  30

Ala Thr Pro His Asp Leu Asn Thr Met Leu Asn Thr Ile Gly Gly His
             35                  40                  45

Gln Ala Ala Met Gln Met Leu Lys Asp Thr Ile Asn Glu Glu Ala Ala
         50                  55                  60

Glu Trp Asp Arg Val His Pro Val His Ala Gly Pro Val Ala Pro Gly
 65                  70                  75                  80

Gln Met Arg Asp Pro Arg Gly Ser Asp Ile Ala Gly Ser Thr Ser Thr
                 85                  90                  95

Leu Gln Glu Gln Ile Ala Trp Met Thr Asn Asn Pro Pro Ile Pro Val
             100                 105                 110

Gly Asp Ile Tyr Lys Arg Trp Ile Ile Met Gly Leu Asn Lys Ile Val
         115                 120                 125

Arg Met Tyr Ser Pro Val Ser Ile Leu Asp Ile Lys Gln Gly Pro Lys
130                 135                 140

Glu Pro Phe Arg Asp Tyr Val Asp Arg Phe Tyr Arg Thr Leu Arg Ala
145                 150                 155                 160

Glu Gln Ala Ser Gln Asp Val Lys Asn Trp Met Thr Glu Thr Leu Leu
                165                 170                 175

Val Gln Asn Ser Asn Pro Asp Cys Lys Thr Ile Leu Lys Ala Leu Gly
            180                 185                 190

Pro Gly Ala Thr Leu Glu Glu Met Met Ser Ala Cys Gln Gly Val Gly
        195                 200                 205

Gly Pro Ser His Lys Ala Arg Val Leu Ala Glu Ala Met Cys Gln
    210                 215                 220

<210> SEQ ID NO 96
<211> LENGTH: 9
<212> TYPE: PRT
<213> ORGANISM: Human immunodeficiency virus

<400> SEQUENCE: 96

Arg Thr Leu Asn Ala Trp Val Lys Val
1               5

<210> SEQ ID NO 97
<211> LENGTH: 25
<212> TYPE: PRT
<213> ORGANISM: Human immunodeficiency virus

<400> SEQUENCE: 97

Leu Ser Glu Gly Ala Thr Pro Gln Asp Leu Asn Thr Met Leu Asn Thr
1               5                  10                  15

Val Gly Gly His Gln Ala Ala Met Gln
            20                  25

<210> SEQ ID NO 98
<211> LENGTH: 25
<212> TYPE: PRT
<213> ORGANISM: Human immunodeficiency virus

<400> SEQUENCE: 98

Leu Ser Glu Gly Ala Thr Pro His Asp Leu Asn Thr Met Leu Asn Thr
1               5                  10                  15

Ile Gly Gly His Gln Ala Ala Met Gln
            20                  25

<210> SEQ ID NO 99
```

```
<211> LENGTH: 9
<212> TYPE: PRT
<213> ORGANISM: Human immunodeficiency virus

<400> SEQUENCE: 99

Asp Leu Asn Thr Met Leu Asn Thr Val
1               5

<210> SEQ ID NO 100
<211> LENGTH: 9
<212> TYPE: PRT
<213> ORGANISM: Human immunodeficiency virus

<400> SEQUENCE: 100

Asp Leu Asn Thr Met Leu Asn Thr Ile
1               5

<210> SEQ ID NO 101
<211> LENGTH: 27
<212> TYPE: PRT
<213> ORGANISM: Human immunodeficiency virus

<400> SEQUENCE: 101

Pro Gly Gln Met Arg Glu Pro Arg Gly Ser Asp Ile Ala Gly Thr Thr
1               5                   10                  15

Ser Thr Leu Gln Glu Gln Ile Gly Trp Met Thr
            20                  25

<210> SEQ ID NO 102
<211> LENGTH: 27
<212> TYPE: PRT
<213> ORGANISM: Human immunodeficiency virus

<400> SEQUENCE: 102

Pro Gly Gln Met Arg Asp Pro Arg Gly Ser Asp Ile Ala Gly Ser Thr
1               5                   10                  15

Ser Thr Leu Gln Glu Gln Ile Ala Trp Met Thr
            20                  25

<210> SEQ ID NO 103
<211> LENGTH: 33
<212> TYPE: PRT
<213> ORGANISM: Human immunodeficiency virus

<400> SEQUENCE: 103

Asn Pro Pro Ile Pro Val Gly Glu Ile Tyr Lys Arg Trp Ile Ile Leu
1               5                   10                  15

Gly Leu Asn Lys Ile Val Arg Met Tyr Ser Pro Thr Ser Ile Leu Asp
            20                  25                  30

Ile

<210> SEQ ID NO 104
<211> LENGTH: 33
<212> TYPE: PRT
<213> ORGANISM: Human immunodeficiency virus

<400> SEQUENCE: 104

Asn Pro Pro Ile Pro Val Gly Asp Ile Tyr Lys Arg Trp Ile Ile Met
1               5                   10                  15

Gly Leu Asn Lys Ile Val Arg Met Tyr Ser Pro Val Ser Ile Leu Asp
            20                  25                  30

Ile
```

<210> SEQ ID NO 105
<211> LENGTH: 34
<212> TYPE: PRT
<213> ORGANISM: Human immunodeficiency virus

<400> SEQUENCE: 105

Pro Val Gly Glu Ile Tyr Lys Arg Trp Ile Ile Leu Gly Leu Asn Lys
1               5                   10                  15

Ile Val Arg Met Tyr Ser Pro Thr Ser Ile Leu Asp Ile Arg Gln Gly
            20                  25                  30

Pro Lys

<210> SEQ ID NO 106
<211> LENGTH: 34
<212> TYPE: PRT
<213> ORGANISM: Human immunodeficiency virus

<400> SEQUENCE: 106

Pro Val Gly Asp Ile Tyr Lys Arg Trp Ile Ile Met Gly Leu Asn Lys
1               5                   10                  15

Ile Val Arg Met Tyr Ser Pro Val Ser Ile Leu Asp Ile Lys Gln Gly
            20                  25                  30

Pro Lys

<210> SEQ ID NO 107
<211> LENGTH: 18
<212> TYPE: PRT
<213> ORGANISM: Human immunodeficiency virus

<400> SEQUENCE: 107

Trp Ile Ile Leu Gly Leu Asn Lys Ile Val Arg Met Tyr Ser Pro Thr
1               5                   10                  15

Ser Ile

<210> SEQ ID NO 108
<211> LENGTH: 18
<212> TYPE: PRT
<213> ORGANISM: Human immunodeficiency virus

<400> SEQUENCE: 108

Trp Ile Ile Met Gly Leu Asn Lys Ile Val Arg Met Tyr Ser Pro Val
1               5                   10                  15

Ser Ile

<210> SEQ ID NO 109
<211> LENGTH: 34
<212> TYPE: PRT
<213> ORGANISM: Human immunodeficiency virus

<400> SEQUENCE: 109

Ser Ile Leu Asp Ile Arg Gln Gly Pro Lys Glu Pro Phe Arg Asp Tyr
1               5                   10                  15

Val Asp Arg Phe Tyr Lys Thr Leu Arg Ala Glu Gln Ala Ser Gln Glu
            20                  25                  30

Val Lys

<210> SEQ ID NO 110
<211> LENGTH: 34
<212> TYPE: PRT

-continued

<213> ORGANISM: Human immunodeficiency virus

<400> SEQUENCE: 110

Ser Ile Leu Asp Ile Lys Gln Gly Pro Lys Glu Pro Phe Arg Asp Tyr
1               5                   10                  15

Val Asp Arg Phe Tyr Arg Thr Leu Arg Ala Glu Gln Ala Ser Gln Asp
            20                  25                  30

Val Lys

<210> SEQ ID NO 111
<211> LENGTH: 34
<212> TYPE: PRT
<213> ORGANISM: Human immunodeficiency virus

<400> SEQUENCE: 111

Gly Pro Lys Glu Pro Phe Arg Asp Tyr Val Asp Arg Phe Tyr Lys Thr
1               5                   10                  15

Leu Arg Ala Glu Gln Ala Ser Gln Gly Val Lys Asn Trp Met Thr Glu
            20                  25                  30

Thr Leu

<210> SEQ ID NO 112
<211> LENGTH: 34
<212> TYPE: PRT
<213> ORGANISM: Human immunodeficiency virus

<400> SEQUENCE: 112

Gly Pro Lys Glu Pro Phe Arg Asp Tyr Val Asp Arg Phe Tyr Arg Thr
1               5                   10                  15

Leu Arg Ala Glu Gln Ala Ser Gln Asp Val Lys Asn Trp Met Thr Glu
            20                  25                  30

Thr Leu

<210> SEQ ID NO 113
<211> LENGTH: 18
<212> TYPE: PRT
<213> ORGANISM: Human immunodeficiency virus

<400> SEQUENCE: 113

Tyr Val Asp Arg Phe Tyr Lys Thr Leu Arg Ala Glu Gln Ala Ser Gln
1               5                   10                  15

Glu Val

<210> SEQ ID NO 114
<211> LENGTH: 18
<212> TYPE: PRT
<213> ORGANISM: Human immunodeficiency virus

<400> SEQUENCE: 114

Tyr Val Asp Arg Phe Tyr Arg Thr Leu Arg Ala Glu Gln Ala Ser Gln
1               5                   10                  15

Asp Val

<210> SEQ ID NO 115
<211> LENGTH: 59
<212> TYPE: PRT
<213> ORGANISM: Human immunodeficiency virus

<400> SEQUENCE: 115

Gln Glu Val Lys Asn Trp Met Thr Glu Thr Leu Leu Val Gln Asn Ala

```
                1               5                  10                 15
Asn Pro Asp Cys Lys Thr Ile Leu Lys Ala Leu Gly Pro Ala Ala Thr
                20                  25                  30
Leu Glu Glu Met Met Thr Ala Cys Gln Gly Val Gly Pro Gly His
            35                  40                  45
Lys Ala Arg Val Leu Ala Glu Ala Met Ser Gln
        50                  55
```

<210> SEQ ID NO 116
<211> LENGTH: 59
<212> TYPE: PRT
<213> ORGANISM: Human immunodeficiency virus

<400> SEQUENCE: 116

```
Gln Asp Val Lys Asn Trp Met Thr Glu Thr Leu Leu Val Gln Asn Ser
1               5                   10                  15
Asn Pro Asp Cys Lys Thr Ile Leu Lys Ala Leu Gly Pro Gly Ala Thr
                20                  25                  30
Leu Glu Glu Met Met Ser Ala Cys Gln Gly Val Gly Pro Ser His
            35                  40                  45
Lys Ala Arg Val Leu Ala Glu Ala Met Cys Gln
        50                  55
```

<210> SEQ ID NO 117
<211> LENGTH: 25
<212> TYPE: PRT
<213> ORGANISM: Human immunodeficiency virus

<400> SEQUENCE: 117

```
Ile Leu Lys Ala Leu Gly Pro Ala Ala Thr Leu Glu Glu Met Met Thr
1               5                   10                  15
Ala Cys Gln Gly Val Gly Gly Pro Gly
                20                  25
```

<210> SEQ ID NO 118
<211> LENGTH: 25
<212> TYPE: PRT
<213> ORGANISM: Human immunodeficiency virus

<400> SEQUENCE: 118

```
Ile Leu Lys Ala Leu Gly Pro Gly Ala Thr Leu Glu Glu Met Met Ser
1               5                   10                  15
Ala Cys Gln Gly Val Gly Gly Pro Ser
                20                  25
```

<210> SEQ ID NO 119
<211> LENGTH: 25
<212> TYPE: PRT
<213> ORGANISM: Human immunodeficiency virus

<400> SEQUENCE: 119

```
Leu Gly Pro Ala Ala Thr Leu Glu Glu Met Met Thr Ala Cys Gln Gly
1               5                   10                  15
Val Gly Gly Pro Gly His Lys Ala Arg
                20                  25
```

<210> SEQ ID NO 120
<211> LENGTH: 25
<212> TYPE: PRT
<213> ORGANISM: Human immunodeficiency virus

```
<400> SEQUENCE: 120

Leu Gly Pro Gly Ala Thr Leu Glu Glu Met Met Ser Ala Cys Gln Gly
1               5                   10                  15

Val Gly Gly Pro Ser His Lys Ala Arg
            20                  25

<210> SEQ ID NO 121
<211> LENGTH: 9
<212> TYPE: PRT
<213> ORGANISM: Human immunodeficiency virus

<400> SEQUENCE: 121

Ala Thr Leu Glu Glu Met Met Thr Ala
1               5

<210> SEQ ID NO 122
<211> LENGTH: 9
<212> TYPE: PRT
<213> ORGANISM: Human immunodeficiency virus

<400> SEQUENCE: 122

Ala Thr Leu Glu Glu Met Met Ser Ala
1               5

<210> SEQ ID NO 123
<211> LENGTH: 9
<212> TYPE: PRT
<213> ORGANISM: Human immunodeficiency virus

<400> SEQUENCE: 123

Glu Met Met Thr Ala Cys Gln Gly Val
1               5

<210> SEQ ID NO 124
<211> LENGTH: 9
<212> TYPE: PRT
<213> ORGANISM: Human immunodeficiency virus

<400> SEQUENCE: 124

Glu Met Met Ser Ala Cys Gln Gly Val
1               5

<210> SEQ ID NO 125
<211> LENGTH: 10
<212> TYPE: PRT
<213> ORGANISM: Human immunodeficiency virus

<400> SEQUENCE: 125

Lys Cys Phe Asn Cys Gly Lys Glu Gly His
1               5                   10

<210> SEQ ID NO 126
<211> LENGTH: 10
<212> TYPE: PRT
<213> ORGANISM: Human immunodeficiency virus

<400> SEQUENCE: 126

Lys Cys Phe Asn Cys Gly Arg Glu Gly His
1               5                   10

<210> SEQ ID NO 127
<211> LENGTH: 9
<212> TYPE: PRT
<213> ORGANISM: Human immunodeficiency virus
```

<400> SEQUENCE: 127

Ala Arg Asn Cys Arg Ala Pro Arg Lys
1               5

<210> SEQ ID NO 128
<211> LENGTH: 9
<212> TYPE: PRT
<213> ORGANISM: Human immunodeficiency virus

<400> SEQUENCE: 128

Ala Lys Asn Cys Arg Ala Pro Arg Lys
1               5

<210> SEQ ID NO 129
<211> LENGTH: 39
<212> TYPE: PRT
<213> ORGANISM: Human immunodeficiency virus

<400> SEQUENCE: 129

Ala Arg Asn Cys Arg Ala Pro Arg Lys Lys Gly Cys Trp Lys Cys Gly
1               5                   10                  15

Lys Glu Gly His Gln Met Lys Asp Cys Thr Glu Arg Gln Ala Asn Phe
            20                  25                  30

Leu Gly Lys Ile Trp Pro Ser
        35

<210> SEQ ID NO 130
<211> LENGTH: 39
<212> TYPE: PRT
<213> ORGANISM: Human immunodeficiency virus

<400> SEQUENCE: 130

Ala Lys Asn Cys Arg Ala Pro Arg Lys Arg Gly Cys Trp Lys Cys Gly
1               5                   10                  15

Arg Glu Gly His Gln Met Lys Asp Cys Asn Glu Arg Gln Ala Asn Phe
            20                  25                  30

Leu Gly Lys Val Trp Pro Ser
        35

<210> SEQ ID NO 131
<211> LENGTH: 14
<212> TYPE: PRT
<213> ORGANISM: Human immunodeficiency virus

<400> SEQUENCE: 131

Asn Cys Arg Ala Pro Arg Lys Lys Gly Cys Trp Lys Cys Gly
1               5                   10

<210> SEQ ID NO 132
<211> LENGTH: 14
<212> TYPE: PRT
<213> ORGANISM: Human immunodeficiency virus

<400> SEQUENCE: 132

Asn Cys Arg Ala Pro Arg Lys Arg Gly Cys Trp Lys Cys Gly
1               5                   10

<210> SEQ ID NO 133
<211> LENGTH: 19
<212> TYPE: PRT
<213> ORGANISM: Human immunodeficiency virus

```
<400> SEQUENCE: 133

Gly Cys Trp Lys Cys Gly Lys Glu Gly His Gln Met Lys Asp Cys Thr
1               5                   10                  15

Glu Arg Gln

<210> SEQ ID NO 134
<211> LENGTH: 19
<212> TYPE: PRT
<213> ORGANISM: Human immunodeficiency virus

<400> SEQUENCE: 134

Gly Cys Trp Lys Cys Gly Arg Glu Gly His Gln Met Lys Asp Cys Asn
1               5                   10                  15

Glu Arg Gln

<210> SEQ ID NO 135
<211> LENGTH: 17
<212> TYPE: PRT
<213> ORGANISM: Human immunodeficiency virus

<400> SEQUENCE: 135

Lys Asp Cys Thr Glu Arg Gln Ala Asn Phe Leu Gly Lys Ile Trp Pro
1               5                   10                  15

Ser

<210> SEQ ID NO 136
<211> LENGTH: 17
<212> TYPE: PRT
<213> ORGANISM: Human immunodeficiency virus

<400> SEQUENCE: 136

Lys Asp Cys Asn Glu Arg Gln Ala Asn Phe Leu Gly Lys Val Trp Pro
1               5                   10                  15

Ser

<210> SEQ ID NO 137
<211> LENGTH: 16
<212> TYPE: PRT
<213> ORGANISM: Human immunodeficiency virus

<400> SEQUENCE: 137

Arg Gln Ala Asn Phe Leu Gly Lys Ile Trp Pro Ser His Lys Gly Arg
1               5                   10                  15

<210> SEQ ID NO 138
<211> LENGTH: 16
<212> TYPE: PRT
<213> ORGANISM: Human immunodeficiency virus

<400> SEQUENCE: 138

Arg Gln Ala Asn Phe Leu Gly Lys Val Trp Pro Ser His Asn Gly Arg
1               5                   10                  15

<210> SEQ ID NO 139
<211> LENGTH: 12
<212> TYPE: PRT
<213> ORGANISM: Human immunodeficiency virus

<400> SEQUENCE: 139

Lys Gly Arg Pro Gly Asn Phe Leu Gln Ser Arg Pro
1               5                   10
```

<210> SEQ ID NO 140
<211> LENGTH: 12
<212> TYPE: PRT
<213> ORGANISM: Human immunodeficiency virus

<400> SEQUENCE: 140

Asn Gly Arg Pro Gly Asn Phe Leu Gln Asn Arg Pro
1               5                   10

<210> SEQ ID NO 141
<211> LENGTH: 10
<212> TYPE: PRT
<213> ORGANISM: Human immunodeficiency virus

<400> SEQUENCE: 141

Ser Leu Arg Ser Leu Phe Gly Asn Asp Pro
1               5                   10

<210> SEQ ID NO 142
<211> LENGTH: 10
<212> TYPE: PRT
<213> ORGANISM: Human immunodeficiency virus

<400> SEQUENCE: 142

Ser Leu Lys Ser Leu Phe Gly Asn Asp Pro
1               5                   10

<210> SEQ ID NO 143
<211> LENGTH: 9
<212> TYPE: PRT
<213> ORGANISM: Human immunodeficiency virus

<400> SEQUENCE: 143

Ser Leu Phe Gly Asn Asp Pro Ser Ser
1               5

<210> SEQ ID NO 144
<211> LENGTH: 9
<212> TYPE: PRT
<213> ORGANISM: Human immunodeficiency virus

<400> SEQUENCE: 144

Ser Leu Phe Gly Asn Asp Pro Leu Ser
1               5

<210> SEQ ID NO 145
<211> LENGTH: 33
<212> TYPE: PRT
<213> ORGANISM: Human immunodeficiency virus

<400> SEQUENCE: 145

Leu Lys His Ile Val Trp Ala Ser Arg Glu Leu Glu Arg Phe Ala Val
1               5                   10                  15

Asn Pro Gly Leu Leu Glu Thr Val Ser Gln Asn Tyr Pro Ile Val Gln
            20                  25                  30

Asn

<210> SEQ ID NO 146
<211> LENGTH: 33
<212> TYPE: PRT
<213> ORGANISM: Human immunodeficiency virus

<400> SEQUENCE: 146

```
Leu Lys His Leu Val Trp Ala Ser Arg Glu Leu Glu Arg Phe Ala Leu
1               5                   10                  15

Asn Pro Gly Leu Leu Glu Thr Val Ser Gln Asn Phe Pro Ile Val Gln
            20                  25                  30

Asn

<210> SEQ ID NO 147
<211> LENGTH: 9
<212> TYPE: PRT
<213> ORGANISM: Human immunodeficiency virus

<400> SEQUENCE: 147

Gly Val Gly Ala Val Ser Arg Asp Leu
1               5

<210> SEQ ID NO 148
<211> LENGTH: 9
<212> TYPE: PRT
<213> ORGANISM: Human immunodeficiency virus

<400> SEQUENCE: 148

Gly Val Gly Ala Ala Ser Arg Asp Leu
1               5

<210> SEQ ID NO 149
<211> LENGTH: 19
<212> TYPE: PRT
<213> ORGANISM: Human immunodeficiency virus

<400> SEQUENCE: 149

Glu Glu Val Gly Phe Pro Val Arg Pro Gln Val Pro Leu Arg Pro Met
1               5                   10                  15

Thr Tyr Lys

<210> SEQ ID NO 150
<211> LENGTH: 19
<212> TYPE: PRT
<213> ORGANISM: Human immunodeficiency virus

<400> SEQUENCE: 150

Glu Glu Val Gly Phe Pro Val Lys Pro Gln Val Pro Leu Arg Pro Met
1               5                   10                  15

Thr Phe Lys

<210> SEQ ID NO 151
<211> LENGTH: 36
<212> TYPE: PRT
<213> ORGANISM: Human immunodeficiency virus

<400> SEQUENCE: 151

Glu Glu Val Gly Phe Pro Val Lys Pro Gln Val Pro Leu Arg Pro Met
1               5                   10                  15

Thr Phe Lys Gly Ala Leu Asp Leu Ser His Phe Leu Arg Glu Lys Gly
            20                  25                  30

Gly Leu Glu Gly
            35

<210> SEQ ID NO 152
<211> LENGTH: 36
<212> TYPE: PRT
<213> ORGANISM: Human immunodeficiency virus
```

```
<400> SEQUENCE: 152

Glu Glu Val Gly Phe Pro Val Arg Pro Gln Val Pro Leu Arg Pro Met
1               5                   10                  15

Thr Tyr Lys Gly Ala Leu Asp Leu Ser His Phe Leu Lys Glu Lys Gly
            20                  25                  30

Gly Leu Glu Gly
        35

<210> SEQ ID NO 153
<211> LENGTH: 22
<212> TYPE: PRT
<213> ORGANISM: Human immunodeficiency virus

<400> SEQUENCE: 153

Tyr Lys Ala Ala Val Asp Leu Ser His Phe Leu Arg Glu Lys Gly Gly
1               5                   10                  15

Leu Glu Gly Ala Ala Tyr
            20

<210> SEQ ID NO 154
<211> LENGTH: 22
<212> TYPE: PRT
<213> ORGANISM: Human immunodeficiency virus

<400> SEQUENCE: 154

Tyr Lys Gly Ala Leu Asp Leu Ser His Phe Leu Lys Glu Lys Gly Gly
1               5                   10                  15

Leu Glu Gly Ala Ala Tyr
            20

<210> SEQ ID NO 155
<211> LENGTH: 10
<212> TYPE: PRT
<213> ORGANISM: Human immunodeficiency virus

<400> SEQUENCE: 155

Ser His Phe Leu Lys Glu Lys Gly Gly Leu
1               5                   10

<210> SEQ ID NO 156
<211> LENGTH: 10
<212> TYPE: PRT
<213> ORGANISM: Human immunodeficiency virus

<400> SEQUENCE: 156

Ser His Phe Leu Arg Glu Lys Gly Gly Leu
1               5                   10

<210> SEQ ID NO 157
<211> LENGTH: 9
<212> TYPE: PRT
<213> ORGANISM: Human immunodeficiency virus

<400> SEQUENCE: 157

Leu Lys Glu Lys Gly Gly Leu Glu Gly
1               5

<210> SEQ ID NO 158
<211> LENGTH: 9
<212> TYPE: PRT
<213> ORGANISM: Human immunodeficiency virus

<400> SEQUENCE: 158
```

```
Leu Arg Glu Lys Gly Gly Leu Glu Gly
1               5

<210> SEQ ID NO 159
<211> LENGTH: 16
<212> TYPE: PRT
<213> ORGANISM: Human immunodeficiency virus

<400> SEQUENCE: 159

Thr Gln Gly Tyr Phe Pro Asp Trp Gln Asn Tyr Thr Pro Gly Pro Gly
1               5                   10                  15

<210> SEQ ID NO 160
<211> LENGTH: 16
<212> TYPE: PRT
<213> ORGANISM: Human immunodeficiency virus

<400> SEQUENCE: 160

Thr Gln Gly Phe Phe Pro Asp Trp Gln Asn Tyr Thr Pro Glu Pro Gly
1               5                   10                  15

<210> SEQ ID NO 161
<211> LENGTH: 32
<212> TYPE: PRT
<213> ORGANISM: Human immunodeficiency virus

<400> SEQUENCE: 161

Thr Gln Gly Phe Phe Pro Asp Trp Gln Asn Tyr Thr Pro Glu Pro Gly
1               5                   10                  15

Ile Arg Phe Pro Leu Thr Phe Gly Trp Cys Phe Lys Leu Val Pro Leu
            20                  25                  30

<210> SEQ ID NO 162
<211> LENGTH: 32
<212> TYPE: PRT
<213> ORGANISM: Human immunodeficiency virus

<400> SEQUENCE: 162

Thr Gln Gly Tyr Phe Pro Asp Trp Gln Asn Tyr Thr Pro Gly Pro Gly
1               5                   10                  15

Thr Arg Tyr Pro Leu Thr Phe Gly Trp Cys Phe Lys Leu Val Pro Val
            20                  25                  30

<210> SEQ ID NO 163
<211> LENGTH: 19
<212> TYPE: PRT
<213> ORGANISM: Human immunodeficiency virus

<400> SEQUENCE: 163

Glu Pro Gly Ile Arg Phe Pro Leu Thr Phe Gly Trp Cys Phe Lys Leu
1               5                   10                  15

Val Pro Leu

<210> SEQ ID NO 164
<211> LENGTH: 19
<212> TYPE: PRT
<213> ORGANISM: Human immunodeficiency virus

<400> SEQUENCE: 164

Gly Pro Gly Thr Arg Tyr Pro Leu Thr Phe Gly Trp Cys Phe Lys Leu
1               5                   10                  15

Val Pro Val
```

```
<210> SEQ ID NO 165
<211> LENGTH: 25
<212> TYPE: PRT
<213> ORGANISM: Human immunodeficiency virus

<400> SEQUENCE: 165

Gly Pro Gly Ile Arg Tyr Pro Leu Leu Thr Phe Gly Trp Cys Phe Lys
1               5                   10                  15

Leu Pro Val Glu Pro Glu Lys Val Glu
            20                  25

<210> SEQ ID NO 166
<211> LENGTH: 9
<212> TYPE: PRT
<213> ORGANISM: Human immunodeficiency virus

<400> SEQUENCE: 166

Arg Tyr Pro Leu Thr Phe Gly Trp Cys
1               5

<210> SEQ ID NO 167
<211> LENGTH: 9
<212> TYPE: PRT
<213> ORGANISM: Human immunodeficiency virus

<400> SEQUENCE: 167

Arg Phe Pro Leu Thr Phe Gly Trp Cys
1               5

<210> SEQ ID NO 168
<211> LENGTH: 15
<212> TYPE: PRT
<213> ORGANISM: Human immunodeficiency virus

<400> SEQUENCE: 168

Arg Tyr Pro Leu Thr Phe Gly Trp Cys Phe Lys Leu Val Pro Val
1               5                   10                  15

<210> SEQ ID NO 169
<211> LENGTH: 15
<212> TYPE: PRT
<213> ORGANISM: Human immunodeficiency virus

<400> SEQUENCE: 169

Arg Phe Pro Leu Thr Phe Gly Trp Cys Phe Lys Leu Val Pro Leu
1               5                   10                  15

<210> SEQ ID NO 170
<211> LENGTH: 13
<212> TYPE: PRT
<213> ORGANISM: Human immunodeficiency virus

<400> SEQUENCE: 170

Pro Leu Thr Phe Gly Trp Cys Phe Lys Leu Val Pro Val
1               5                   10

<210> SEQ ID NO 171
<211> LENGTH: 13
<212> TYPE: PRT
<213> ORGANISM: Human immunodeficiency virus

<400> SEQUENCE: 171

Pro Leu Cys Phe Gly Trp Cys Phe Lys Leu Val Pro Leu
```

```
<210> SEQ ID NO 172
<211> LENGTH: 9
<212> TYPE: PRT
<213> ORGANISM: Human immunodeficiency virus

<400> SEQUENCE: 172

Leu Thr Phe Gly Trp Cys Phe Lys Leu
1               5

<210> SEQ ID NO 173
<211> LENGTH: 9
<212> TYPE: PRT
<213> ORGANISM: Human immunodeficiency virus

<400> SEQUENCE: 173

Leu Cys Phe Gly Trp Cys Phe Lys Leu
1               5

<210> SEQ ID NO 174
<211> LENGTH: 12
<212> TYPE: PRT
<213> ORGANISM: Human immunodeficiency virus

<400> SEQUENCE: 174

Phe Pro Gln Ile Thr Leu Trp Gln Arg Pro Leu Val
1               5                   10

<210> SEQ ID NO 175
<211> LENGTH: 12
<212> TYPE: PRT
<213> ORGANISM: Human immunodeficiency virus

<400> SEQUENCE: 175

Leu Pro Gln Ile Thr Leu Trp Gln Arg Pro Ile Val
1               5                   10

<210> SEQ ID NO 176
<211> LENGTH: 62
<212> TYPE: PRT
<213> ORGANISM: Human immunodeficiency virus

<400> SEQUENCE: 176

Phe Pro Gln Ile Thr Leu Trp Gln Arg Pro Leu Val Thr Ile Lys Ile
1               5                   10                  15

Gly Gly Gln Leu Lys Glu Ala Leu Leu Asp Thr Gly Ala Asp Asp Thr
            20                  25                  30

Val Leu Glu Glu Met Asn Leu Pro Gly Arg Trp Lys Pro Lys Met Ile
        35                  40                  45

Gly Gly Ile Gly Gly Phe Ile Lys Val Arg Gln Tyr Asp Gln
    50                  55                  60

<210> SEQ ID NO 177
<211> LENGTH: 62
<212> TYPE: PRT
<213> ORGANISM: Human immunodeficiency virus

<400> SEQUENCE: 177

Leu Pro Gln Ile Thr Leu Trp Gln Arg Pro Ile Val Thr Ile Lys Ile
1               5                   10                  15

Gly Gly Gln Ile Lys Glu Ala Leu Leu Asp Thr Gly Ala Asp Asp Thr
            20                  25                  30
```

```
Val Leu Glu Asp Met Asn Leu Pro Gly Lys Trp Lys Pro Lys Met Ile
         35                  40                  45

Gly Gly Ile Gly Gly Phe Ile Lys Val Lys Gln Tyr Asp Gln
         50                  55                  60

<210> SEQ ID NO 178
<211> LENGTH: 20
<212> TYPE: PRT
<213> ORGANISM: Human immunodeficiency virus

<400> SEQUENCE: 178

Gly Gly Gln Leu Lys Glu Ala Leu Leu Asp Thr Gly Ala Asp Asp Thr
1               5                   10                  15

Val Leu Glu Glu
         20

<210> SEQ ID NO 179
<211> LENGTH: 20
<212> TYPE: PRT
<213> ORGANISM: Human immunodeficiency virus

<400> SEQUENCE: 179

Gly Gly Gln Ile Lys Glu Ala Leu Leu Asp Thr Gly Ala Asp Asp Thr
1               5                   10                  15

Val Leu Glu Asp
         20

<210> SEQ ID NO 180
<211> LENGTH: 24
<212> TYPE: PRT
<213> ORGANISM: Human immunodeficiency virus

<400> SEQUENCE: 180

Leu Pro Gly Arg Trp Lys Pro Lys Met Ile Gly Gly Ile Gly Gly Phe
1               5                   10                  15

Ile Lys Val Arg Gln Tyr Asp Gln
         20

<210> SEQ ID NO 181
<211> LENGTH: 24
<212> TYPE: PRT
<213> ORGANISM: Human immunodeficiency virus

<400> SEQUENCE: 181

Leu Pro Gly Lys Trp Lys Pro Lys Met Ile Gly Gly Ile Gly Gly Phe
1               5                   10                  15

Ile Lys Val Lys Gln Tyr Asp Gln
         20

<210> SEQ ID NO 182
<211> LENGTH: 132
<212> TYPE: PRT
<213> ORGANISM: Human immunodeficiency virus

<400> SEQUENCE: 182

Gly Thr Val Leu Val Gly Pro Thr Pro Val Asn Ile Ile Gly Arg Asn
1               5                   10                  15

Leu Leu Thr Gln Ile Gly Cys Thr Leu Asn Phe Pro Ile Ser Pro Ile
         20                  25                  30

Glu Thr Val Pro Val Lys Leu Lys Pro Gly Met Asp Gly Pro Lys Val
         35                  40                  45
```

```
Lys Gln Trp Pro Leu Thr Glu Glu Lys Ile Lys Ala Leu Val Glu Ile
        50                  55                  60

Cys Thr Glu Met Glu Lys Glu Gly Lys Ile Ser Lys Ile Gly Pro Glu
 65                  70                  75                  80

Asn Pro Tyr Asn Thr Pro Val Phe Ala Ile Lys Lys Lys Asp Ser Thr
                 85                  90                  95

Lys Trp Arg Lys Leu Val Asp Phe Arg Glu Leu Asn Lys Arg Thr Gln
            100                 105                 110

Asp Phe Trp Glu Val Gln Leu Gly Ile Pro His Pro Ala Gly Leu Lys
        115                 120                 125

Lys Lys Lys Ser
        130

<210> SEQ ID NO 183
<211> LENGTH: 132
<212> TYPE: PRT
<213> ORGANISM: Human immunodeficiency virus

<400> SEQUENCE: 183

Gly Thr Val Leu Ile Gly Pro Thr Pro Val Asn Ile Ile Gly Arg Asn
 1               5                  10                  15

Leu Leu Thr Gln Leu Gly Cys Thr Leu Asn Phe Pro Ile Ser Pro Ile
            20                  25                  30

Asp Thr Val Pro Val Lys Leu Lys Pro Gly Met Asp Gly Pro Arg Val
         35                  40                  45

Lys Gln Trp Pro Leu Thr Glu Glu Lys Ile Lys Ala Leu Ile Glu Ile
        50                  55                  60

Cys Thr Glu Met Glu Lys Glu Gly Lys Ile Ser Arg Ile Gly Pro Glu
 65                  70                  75                  80

Asn Pro Tyr Asn Thr Pro Ile Phe Ala Ile Lys Lys Lys Asp Gly Thr
                 85                  90                  95

Lys Trp Arg Lys Leu Val Asp Phe Arg Glu Leu Asn Lys Lys Thr Gln
            100                 105                 110

Asp Phe Trp Glu Val Gln Leu Gly Ile Pro His Pro Ser Gly Leu Lys
        115                 120                 125

Lys Lys Lys Ser
        130

<210> SEQ ID NO 184
<211> LENGTH: 149
<212> TYPE: PRT
<213> ORGANISM: Human immunodeficiency virus

<400> SEQUENCE: 184

Gly Thr Val Leu Val Gly Pro Thr Pro Val Asn Ile Ile Gly Arg Asn
 1               5                  10                  15

Leu Leu Thr Gln Ile Gly Cys Thr Leu Asn Phe Pro Ile Ser Pro Ile
            20                  25                  30

Glu Thr Val Pro Val Lys Leu Lys Pro Gly Met Asp Gly Pro Lys Val
         35                  40                  45

Lys Gln Trp Pro Leu Thr Glu Glu Lys Ile Lys Ala Leu Val Glu Ile
        50                  55                  60

Cys Thr Glu Met Glu Lys Glu Gly Lys Ile Ser Lys Ile Gly Pro Glu
 65                  70                  75                  80

Asn Pro Tyr Asn Thr Pro Val Phe Ala Ile Lys Lys Lys Asp Ser Thr
                 85                  90                  95
```

```
Lys Trp Arg Lys Leu Val Asp Phe Arg Glu Leu Asn Lys Arg Thr Gln
            100                 105                 110

Asp Phe Trp Glu Val Gln Leu Gly Ile Pro His Pro Ala Gly Leu Lys
        115                 120                 125

Lys Lys Lys Ser Val Thr Val Leu Asp Val Gly Asp Ala Tyr Phe Ser
    130                 135                 140

Val Pro Leu Asp Lys
145

<210> SEQ ID NO 185
<211> LENGTH: 149
<212> TYPE: PRT
<213> ORGANISM: Human immunodeficiency virus

<400> SEQUENCE: 185

Gly Thr Val Leu Ile Gly Pro Thr Pro Val Asn Ile Ile Gly Arg Asn
1               5                   10                  15

Leu Leu Thr Gln Leu Gly Cys Thr Leu Asn Phe Pro Ile Ser Pro Ile
            20                  25                  30

Asp Thr Val Pro Val Lys Leu Lys Pro Gly Met Asp Gly Pro Arg Val
        35                  40                  45

Lys Gln Trp Pro Leu Thr Glu Glu Lys Ile Lys Ala Leu Ile Glu Ile
    50                  55                  60

Cys Thr Glu Met Glu Lys Glu Gly Lys Ile Ser Arg Ile Gly Pro Glu
65                  70                  75                  80

Asn Pro Tyr Asn Thr Pro Ile Phe Ala Ile Lys Lys Lys Asp Gly Thr
                85                  90                  95

Lys Trp Arg Lys Leu Val Asp Phe Arg Glu Leu Asn Lys Lys Thr Gln
            100                 105                 110

Asp Phe Trp Glu Val Gln Leu Gly Ile Pro His Pro Ser Gly Leu Lys
        115                 120                 125

Lys Lys Lys Ser Val Thr Ile Leu Asp Val Gly Asp Ala Tyr Phe Ser
    130                 135                 140

Ile Pro Leu Asp Lys
145

<210> SEQ ID NO 186
<211> LENGTH: 161
<212> TYPE: PRT
<213> ORGANISM: Human immunodeficiency virus

<400> SEQUENCE: 186

Gly Thr Val Leu Val Gly Pro Thr Pro Val Asn Ile Ile Gly Arg Asn
1               5                   10                  15

Leu Leu Thr Gln Ile Gly Cys Thr Leu Asn Phe Pro Ile Ser Pro Ile
            20                  25                  30

Glu Thr Val Pro Val Lys Leu Lys Pro Gly Met Asp Gly Pro Lys Val
        35                  40                  45

Lys Gln Trp Pro Leu Thr Glu Glu Lys Ile Lys Ala Leu Val Glu Ile
    50                  55                  60

Cys Thr Glu Met Glu Lys Glu Gly Lys Ile Ser Lys Ile Gly Pro Glu
65                  70                  75                  80

Asn Pro Tyr Asn Thr Pro Val Phe Ala Ile Lys Lys Lys Asp Ser Thr
                85                  90                  95

Lys Trp Arg Lys Leu Val Asp Phe Arg Glu Leu Asn Lys Arg Thr Gln
            100                 105                 110
```

```
Asp Phe Trp Glu Val Gln Leu Gly Ile Pro His Pro Ala Gly Leu Lys
        115                 120                 125

Lys Lys Lys Ser Val Thr Val Leu Asp Val Gly Asp Ala Tyr Phe Ser
    130                 135                 140

Val Pro Leu Asp Lys Asp Phe Arg Lys Tyr Thr Ala Phe Thr Ile Pro
145                 150                 155                 160

Ser
```

<210> SEQ ID NO 187
<211> LENGTH: 161
<212> TYPE: PRT
<213> ORGANISM: Human immunodeficiency virus

<400> SEQUENCE: 187

```
Gly Thr Val Leu Ile Gly Pro Thr Pro Val Asn Ile Ile Gly Arg Asn
1               5                   10                  15

Leu Leu Thr Gln Leu Gly Cys Thr Leu Asn Phe Pro Ile Ser Pro Ile
            20                  25                  30

Asp Thr Val Pro Val Lys Leu Lys Pro Gly Met Asp Gly Pro Arg Val
        35                  40                  45

Lys Gln Trp Pro Leu Thr Glu Glu Lys Ile Lys Ala Leu Ile Glu Ile
    50                  55                  60

Cys Thr Glu Met Glu Lys Glu Gly Lys Ile Ser Arg Ile Gly Pro Glu
65                  70                  75                  80

Asn Pro Tyr Asn Thr Pro Ile Phe Ala Ile Lys Lys Lys Asp Gly Thr
                85                  90                  95

Lys Trp Arg Lys Leu Val Asp Phe Arg Glu Leu Asn Lys Lys Thr Gln
            100                 105                 110

Asp Phe Trp Glu Val Gln Leu Gly Ile Pro His Pro Ser Gly Leu Lys
        115                 120                 125

Lys Lys Lys Ser Val Thr Val Leu Asp Ile Gly Asp Ala Tyr Phe Ser
    130                 135                 140

Val Pro Leu Asp Lys Glu Phe Arg Lys Tyr Thr Ala Phe Thr Val Pro
145                 150                 155                 160

Ser
```

<210> SEQ ID NO 188
<211> LENGTH: 192
<212> TYPE: PRT
<213> ORGANISM: Human immunodeficiency virus

<400> SEQUENCE: 188

```
Gly Thr Val Leu Val Gly Pro Thr Pro Val Asn Ile Ile Gly Arg Asn
1               5                   10                  15

Leu Leu Thr Gln Ile Gly Cys Thr Leu Asn Phe Pro Ile Ser Pro Ile
            20                  25                  30

Glu Thr Val Pro Val Lys Leu Lys Pro Gly Met Asp Gly Pro Lys Val
        35                  40                  45

Lys Gln Trp Pro Leu Thr Glu Glu Lys Ile Lys Ala Leu Val Glu Ile
    50                  55                  60

Cys Thr Glu Met Glu Lys Glu Gly Lys Ile Ser Lys Ile Gly Pro Glu
65                  70                  75                  80

Asn Pro Tyr Asn Thr Pro Val Phe Ala Ile Lys Lys Lys Asp Ser Thr
                85                  90                  95

Lys Trp Arg Lys Leu Val Asp Phe Arg Glu Leu Asn Lys Arg Thr Gln
```

```
                100              105              110
Asp Phe Trp Glu Val Gln Leu Gly Ile Pro His Pro Ala Gly Leu Lys
            115              120              125
Lys Lys Lys Ser Val Thr Val Leu Asp Val Gly Asp Ala Tyr Phe Ser
            130              135              140
Val Pro Leu Asp Lys Asp Phe Arg Lys Tyr Thr Ala Phe Thr Ile Pro
145              150              155              160
Ser Ile Asn Asn Glu Thr Pro Gly Ile Arg Tyr Gln Tyr Asn Val Leu
                165              170              175
Pro Gln Gly Trp Lys Gly Ser Pro Ala Ile Phe Gln Ser Ser Met Thr
            180              185              190

<210> SEQ ID NO 189
<211> LENGTH: 192
<212> TYPE: PRT
<213> ORGANISM: Human immunodeficiency virus

<400> SEQUENCE: 189

Gly Thr Val Leu Ile Gly Pro Thr Pro Val Asn Ile Ile Gly Arg Asn
1               5               10                  15
Leu Leu Thr Gln Leu Gly Cys Thr Leu Asn Phe Pro Ile Ser Pro Ile
            20              25              30
Asp Thr Val Pro Val Lys Leu Lys Pro Gly Met Asp Gly Pro Arg Val
        35              40              45
Lys Gln Trp Pro Leu Thr Glu Glu Lys Ile Lys Ala Leu Ile Glu Ile
    50              55              60
Cys Thr Glu Met Glu Lys Glu Gly Lys Ile Ser Arg Ile Gly Pro Glu
65              70              75                  80
Asn Pro Tyr Asn Thr Pro Ile Phe Ala Ile Lys Lys Lys Asp Gly Thr
                85              90                  95
Lys Trp Arg Lys Leu Val Asp Phe Arg Glu Leu Asn Lys Lys Thr Gln
            100              105              110
Asp Phe Trp Glu Val Gln Leu Gly Ile Pro His Pro Ser Gly Leu Lys
            115              120              125
Lys Lys Lys Ser Val Thr Val Leu Asp Ile Gly Asp Ala Tyr Phe Ser
            130              135              140
Val Pro Leu Asp Lys Glu Phe Arg Lys Tyr Thr Ala Phe Thr Val Pro
145              150              155              160
Ser Thr Asn Asn Glu Thr Pro Gly Val Arg Tyr Gln Tyr Asn Val Leu
                165              170              175
Pro Met Gly Trp Lys Gly Ser Pro Ala Ile Phe Gln Cys Ser Met Thr
            180              185              190

<210> SEQ ID NO 190
<211> LENGTH: 25
<212> TYPE: PRT
<213> ORGANISM: Human immunodeficiency virus

<400> SEQUENCE: 190

Asn Leu Leu Thr Gln Ile Gly Cys Thr Leu Asn Phe Pro Ile Ser Pro
1               5               10                  15
Ile Glu Thr Val Pro Val Lys Leu Lys
            20              25

<210> SEQ ID NO 191
<211> LENGTH: 25
<212> TYPE: PRT
```

<213> ORGANISM: Human immunodeficiency virus

<400> SEQUENCE: 191

Asn Leu Leu Thr Gln Leu Gly Cys Thr Leu Asn Phe Pro Ile Ser Pro
1               5                   10                  15

Ile Asp Thr Val Pro Val Lys Leu Lys
            20                  25

<210> SEQ ID NO 192
<211> LENGTH: 9
<212> TYPE: PRT
<213> ORGANISM: Human immunodeficiency virus

<400> SEQUENCE: 192

Thr Leu Asn Phe Pro Ile Ser Pro Ile
1               5

<210> SEQ ID NO 193
<211> LENGTH: 24
<212> TYPE: PRT
<213> ORGANISM: Human immunodeficiency virus

<400> SEQUENCE: 193

Gly Leu Lys Lys Lys Lys Ser Val Thr Val Leu Asp Val Gly Asp Ala
1               5                   10                  15

Tyr Phe Ser Val Pro Leu Asp Lys
            20

<210> SEQ ID NO 194
<211> LENGTH: 24
<212> TYPE: PRT
<213> ORGANISM: Human immunodeficiency virus

<400> SEQUENCE: 194

Gly Leu Lys Lys Asn Lys Ser Val Thr Val Leu Asp Val Gly Asp Ala
1               5                   10                  15

Tyr Phe Ser Ile Pro Leu Asp Lys
            20

<210> SEQ ID NO 195
<211> LENGTH: 12
<212> TYPE: PRT
<213> ORGANISM: Human immunodeficiency virus

<400> SEQUENCE: 195

Asp Phe Arg Lys Tyr Thr Ala Phe Thr Ile Pro Ser
1               5                   10

<210> SEQ ID NO 196
<211> LENGTH: 12
<212> TYPE: PRT
<213> ORGANISM: Human immunodeficiency virus

<400> SEQUENCE: 196

Glu Phe Arg Lys Tyr Thr Ala Phe Thr Val Pro Ser
1               5                   10

<210> SEQ ID NO 197
<211> LENGTH: 25
<212> TYPE: PRT
<213> ORGANISM: Human immunodeficiency virus

<400> SEQUENCE: 197

-continued

Asn Asn Glu Thr Pro Gly Ile Arg Tyr Gln Tyr Asn Val Leu Pro Gln
1               5                   10                  15

Gly Trp Lys Gly Ser Pro Ala Ile Phe
            20                  25

<210> SEQ ID NO 198
<211> LENGTH: 25
<212> TYPE: PRT
<213> ORGANISM: Human immunodeficiency virus

<400> SEQUENCE: 198

Asn Asn Glu Thr Pro Gly Val Arg Tyr Gln Tyr Asn Val Leu Pro Met
1               5                   10                  15

Gly Trp Lys Gly Ser Pro Ala Ile Phe
            20                  25

<210> SEQ ID NO 199
<211> LENGTH: 30
<212> TYPE: PRT
<213> ORGANISM: Human immunodeficiency virus

<400> SEQUENCE: 199

Asn Asn Glu Thr Pro Gly Ile Arg Tyr Gln Tyr Asn Val Leu Pro Gln
1               5                   10                  15

Gly Trp Lys Gly Ser Pro Ala Ile Phe Gln Ser Ser Met Thr
            20                  25                  30

<210> SEQ ID NO 200
<211> LENGTH: 30
<212> TYPE: PRT
<213> ORGANISM: Human immunodeficiency virus

<400> SEQUENCE: 200

Asn Asn Glu Thr Pro Gly Val Arg Tyr Gln Tyr Asn Val Leu Pro Met
1               5                   10                  15

Gly Trp Lys Gly Ser Pro Ala Ile Phe Gln Cys Ser Met Thr
            20                  25                  30

<210> SEQ ID NO 201
<211> LENGTH: 9
<212> TYPE: PRT
<213> ORGANISM: Human immunodeficiency virus

<400> SEQUENCE: 201

Tyr Gln Tyr Asn Val Leu Pro Gln Gly
1               5

<210> SEQ ID NO 202
<211> LENGTH: 9
<212> TYPE: PRT
<213> ORGANISM: Human immunodeficiency virus

<400> SEQUENCE: 202

Tyr Gln Tyr Asn Val Leu Pro Met Gly
1               5

<210> SEQ ID NO 203
<211> LENGTH: 9
<212> TYPE: PRT
<213> ORGANISM: Human immunodeficiency virus

<400> SEQUENCE: 203

Phe Gln Ser Ser Met Thr Lys Ile Leu

```
1               5

<210> SEQ ID NO 204
<211> LENGTH: 9
<212> TYPE: PRT
<213> ORGANISM: Human immunodeficiency virus

<400> SEQUENCE: 204

Phe Gln Cys Ser Met Thr Lys Ile Leu
1               5

<210> SEQ ID NO 205
<211> LENGTH: 10
<212> TYPE: PRT
<213> ORGANISM: Human immunodeficiency virus

<400> SEQUENCE: 205

Ser Met Thr Lys Ile Leu Glu Pro Phe Arg
1               5                   10

<210> SEQ ID NO 206
<211> LENGTH: 10
<212> TYPE: PRT
<213> ORGANISM: Human immunodeficiency virus

<400> SEQUENCE: 206

Ser Met Thr Lys Ile Leu Asp Pro Phe Arg
1               5                   10

<210> SEQ ID NO 207
<211> LENGTH: 9
<212> TYPE: PRT
<213> ORGANISM: Human immunodeficiency virus

<400> SEQUENCE: 207

Ile Leu Glu Pro Phe Arg Lys Gln Asn
1               5

<210> SEQ ID NO 208
<211> LENGTH: 9
<212> TYPE: PRT
<213> ORGANISM: Human immunodeficiency virus

<400> SEQUENCE: 208

Ile Leu Asp Pro Phe Arg Lys Gln Asn
1               5

<210> SEQ ID NO 209
<211> LENGTH: 25
<212> TYPE: PRT
<213> ORGANISM: Human immunodeficiency virus

<400> SEQUENCE: 209

Phe Arg Lys Gln Asn Pro Asp Ile Val Ile Tyr Gln Tyr Met Asp Asp
1               5                   10                  15

Leu Tyr Val Gly Ser Asp Leu Glu Ile
            20                  25

<210> SEQ ID NO 210
<211> LENGTH: 25
<212> TYPE: PRT
<213> ORGANISM: Human immunodeficiency virus

<400> SEQUENCE: 210
```

-continued

```
Lys Gln Asn Pro Asp Ile Val Ile Tyr Gln Tyr Met Asp Asp Leu Tyr
1               5                   10                  15

Val Gly Ser Asp Leu Glu Ile Gly Gln
            20                  25

<210> SEQ ID NO 211
<211> LENGTH: 25
<212> TYPE: PRT
<213> ORGANISM: Human immunodeficiency virus

<400> SEQUENCE: 211

Asn Pro Asp Ile Val Ile Tyr Gln Tyr Met Asp Asp Leu Tyr Val Gly
1               5                   10                  15

Ser Asp Leu Glu Ile Gly Gln His Arg
            20                  25

<210> SEQ ID NO 212
<211> LENGTH: 25
<212> TYPE: PRT
<213> ORGANISM: Human immunodeficiency virus

<400> SEQUENCE: 212

Asn Pro Asp Ile Val Ile Tyr Gln Tyr Val Asp Asp Leu Tyr Val Gly
1               5                   10                  15

Ser Asp Leu Glu Ile Glu Gln His Arg
            20                  25

<210> SEQ ID NO 213
<211> LENGTH: 22
<212> TYPE: PRT
<213> ORGANISM: Human immunodeficiency virus

<400> SEQUENCE: 213

Ile Val Ile Tyr Gln Tyr Met Asp Asp Leu Tyr Val Gly Ser Asp Leu
1               5                   10                  15

Glu Ile Gly Gln His Arg
            20

<210> SEQ ID NO 214
<211> LENGTH: 22
<212> TYPE: PRT
<213> ORGANISM: Human immunodeficiency virus

<400> SEQUENCE: 214

Ile Val Ile Tyr Gln Tyr Val Asp Asp Leu Tyr Val Gly Ser Asp Leu
1               5                   10                  15

Glu Ile Glu Gln His Arg
            20

<210> SEQ ID NO 215
<211> LENGTH: 9
<212> TYPE: PRT
<213> ORGANISM: Human immunodeficiency virus

<400> SEQUENCE: 215

Val Ile Tyr Gln Tyr Met Asp Asp Leu
1               5

<210> SEQ ID NO 216
<211> LENGTH: 9
<212> TYPE: PRT
<213> ORGANISM: Human immunodeficiency virus
```

```
<400> SEQUENCE: 216

Val Ile Tyr Gln Tyr Val Asp Asp Leu
1               5

<210> SEQ ID NO 217
<211> LENGTH: 9
<212> TYPE: PRT
<213> ORGANISM: Human immunodeficiency virus

<400> SEQUENCE: 217

Tyr Gln Tyr Met Asp Asp Leu Tyr Val
1               5

<210> SEQ ID NO 218
<211> LENGTH: 9
<212> TYPE: PRT
<213> ORGANISM: Human immunodeficiency virus

<400> SEQUENCE: 218

Tyr Gln Tyr Val Asp Asp Leu Tyr Val
1               5

<210> SEQ ID NO 219
<211> LENGTH: 9
<212> TYPE: PRT
<213> ORGANISM: Human immunodeficiency virus

<400> SEQUENCE: 219

Tyr Met Asp Asp Leu Tyr Val Gly Ser
1               5

<210> SEQ ID NO 220
<211> LENGTH: 9
<212> TYPE: PRT
<213> ORGANISM: Human immunodeficiency virus

<400> SEQUENCE: 220

Tyr Val Asp Asp Leu Tyr Val Gly Ser
1               5

<210> SEQ ID NO 221
<211> LENGTH: 33
<212> TYPE: PRT
<213> ORGANISM: Human immunodeficiency virus

<400> SEQUENCE: 221

Trp Gly Phe Thr Thr Pro Asp Lys Lys His Gln Lys Glu Pro Pro Phe
1               5                   10                  15

Leu Trp Met Gly Tyr Glu Leu His Pro Asp Lys Trp Thr Val Gln Pro
            20                  25                  30

Ile

<210> SEQ ID NO 222
<211> LENGTH: 33
<212> TYPE: PRT
<213> ORGANISM: Human immunodeficiency virus

<400> SEQUENCE: 222

Trp Gly Leu Thr Thr Pro Asp Lys Lys His Gln Lys Asp Pro Pro Phe
1               5                   10                  15

Leu Trp Met Gly Tyr Glu Leu His Pro Asp Arg Trp Thr Val Gln Pro
            20                  25                  30
```

Ile

<210> SEQ ID NO 223
<211> LENGTH: 65
<212> TYPE: PRT
<213> ORGANISM: Human immunodeficiency virus

<400> SEQUENCE: 223

Trp Gly Phe Thr Thr Pro Asp Lys Lys His Gln Lys Glu Pro Pro Phe
1               5                   10                  15

Leu Trp Met Gly Tyr Glu Leu His Pro Asp Lys Trp Thr Val Gln Pro
            20                  25                  30

Ile Val Leu Pro Glu Lys Asp Ser Trp Thr Val Asn Asp Ile Gln Lys
        35                  40                  45

Leu Val Gly Lys Leu Asn Trp Ala Ser Gln Ile Tyr Pro Gly Ile Lys
    50                  55                  60

Val
65

<210> SEQ ID NO 224
<211> LENGTH: 65
<212> TYPE: PRT
<213> ORGANISM: Human immunodeficiency virus

<400> SEQUENCE: 224

Trp Gly Leu Thr Thr Pro Asp Lys Lys His Gln Lys Asp Pro Pro Phe
1               5                   10                  15

Leu Trp Met Gly Tyr Glu Leu His Pro Asp Arg Trp Thr Val Gln Pro
            20                  25                  30

Ile Glu Leu Pro Glu Lys Glu Ser Trp Thr Val Asn Asp Ile Gln Lys
        35                  40                  45

Leu Ile Gly Lys Leu Asn Trp Ala Ser Gln Ile Tyr Ala Gly Ile Lys
    50                  55                  60

Val
65

<210> SEQ ID NO 225
<211> LENGTH: 25
<212> TYPE: PRT
<213> ORGANISM: Human immunodeficiency virus

<400> SEQUENCE: 225

Lys Lys His Gln Lys Glu Pro Pro Phe Leu Trp Met Gly Tyr Glu Leu
1               5                   10                  15

His Pro Asp Lys Trp Thr Val Gln Pro
            20                  25

<210> SEQ ID NO 226
<211> LENGTH: 25
<212> TYPE: PRT
<213> ORGANISM: Human immunodeficiency virus

<400> SEQUENCE: 226

Lys Lys His Gln Lys Asp Pro Pro Phe Leu Trp Met Gly Tyr Glu Leu
1               5                   10                  15

His Pro Asp Arg Trp Thr Val Gln Pro
            20                  25

<210> SEQ ID NO 227
<211> LENGTH: 25

<212> TYPE: PRT
<213> ORGANISM: Human immunodeficiency virus

<400> SEQUENCE: 227

Pro Pro Phe Leu Trp Met Gly Tyr Glu Leu His Pro Asp Lys Trp Thr
1               5                   10                  15
Val Gln Pro Ile Val Leu Pro Glu Lys
            20                  25

<210> SEQ ID NO 228
<211> LENGTH: 25
<212> TYPE: PRT
<213> ORGANISM: Human immunodeficiency virus

<400> SEQUENCE: 228

Pro Pro Phe Leu Trp Met Gly Tyr Glu Leu His Pro Asp Arg Trp Thr
1               5                   10                  15
Val Gln Pro Ile Glu Leu Pro Glu Lys
            20                  25

<210> SEQ ID NO 229
<211> LENGTH: 9
<212> TYPE: PRT
<213> ORGANISM: Human immunodeficiency virus

<400> SEQUENCE: 229

Phe Leu Trp Met Gly Tyr Glu Leu His
1               5

<210> SEQ ID NO 230
<211> LENGTH: 9
<212> TYPE: PRT
<213> ORGANISM: Human immunodeficiency virus

<400> SEQUENCE: 230

Glu Leu His Pro Asp Lys Trp Thr Val
1               5

<210> SEQ ID NO 231
<211> LENGTH: 9
<212> TYPE: PRT
<213> ORGANISM: Human immunodeficiency virus

<400> SEQUENCE: 231

Glu Leu His Pro Asp Arg Trp Thr Val
1               5

<210> SEQ ID NO 232
<211> LENGTH: 25
<212> TYPE: PRT
<213> ORGANISM: Human immunodeficiency virus

<400> SEQUENCE: 232

Ile Val Leu Pro Glu Lys Asp Ser Trp Thr Val Asn Asp Ile Gln Lys
1               5                   10                  15
Leu Val Gly Lys Leu Asn Trp Ala Ser
            20                  25

<210> SEQ ID NO 233
<211> LENGTH: 25
<212> TYPE: PRT
<213> ORGANISM: Human immunodeficiency virus

<400> SEQUENCE: 233

Ile Glu Leu Pro Glu Lys Glu Ser Trp Thr Val Asn Asp Ile Gln Lys
1               5                   10                  15

Leu Ile Gly Lys Leu Asn Trp Ala Ser
            20                  25

<210> SEQ ID NO 234
<211> LENGTH: 25
<212> TYPE: PRT
<213> ORGANISM: Human immunodeficiency virus

<400> SEQUENCE: 234

Val Leu Pro Glu Lys Asp Ser Trp Thr Val Asn Asp Ile Gln Lys Leu
1               5                   10                  15

Val Gly Lys Leu Asn Trp Ala Ser Gln
            20                  25

<210> SEQ ID NO 235
<211> LENGTH: 25
<212> TYPE: PRT
<213> ORGANISM: Human immunodeficiency virus

<400> SEQUENCE: 235

Glu Leu Pro Glu Lys Glu Ser Trp Thr Val Asn Asp Ile Gln Lys Leu
1               5                   10                  15

Ile Gly Lys Leu Asn Trp Ala Ser Gln
            20                  25

<210> SEQ ID NO 236
<211> LENGTH: 31
<212> TYPE: PRT
<213> ORGANISM: Human immunodeficiency virus

<400> SEQUENCE: 236

Leu Pro Glu Lys Asp Ser Trp Thr Val Asn Asp Ile Gln Lys Leu Val
1               5                   10                  15

Gly Lys Leu Asn Trp Ala Ser Gln Ile Tyr Pro Gly Ile Lys Val
            20                  25                  30

<210> SEQ ID NO 237
<211> LENGTH: 31
<212> TYPE: PRT
<213> ORGANISM: Human immunodeficiency virus

<400> SEQUENCE: 237

Leu Pro Glu Lys Glu Ser Trp Thr Val Asn Asp Ile Gln Lys Leu Ile
1               5                   10                  15

Gly Lys Leu Asn Trp Ala Ser Gln Ile Tyr Ala Gly Ile Lys Val
            20                  25                  30

<210> SEQ ID NO 238
<211> LENGTH: 25
<212> TYPE: PRT
<213> ORGANISM: Human immunodeficiency virus

<400> SEQUENCE: 238

Ser Trp Thr Val Asn Asp Ile Gln Lys Leu Val Gly Lys Leu Asn Trp
1               5                   10                  15

Ala Ser Gln Ile Tyr Pro Gly Ile Lys
            20                  25

<210> SEQ ID NO 239

```
<211> LENGTH: 25
<212> TYPE: PRT
<213> ORGANISM: Human immunodeficiency virus

<400> SEQUENCE: 239

Ser Trp Thr Val Asn Asp Ile Gln Lys Leu Ile Gly Lys Leu Asn Trp
1               5                   10                  15

Ala Ser Gln Ile Tyr Ala Gly Ile Lys
            20                  25

<210> SEQ ID NO 240
<211> LENGTH: 9
<212> TYPE: PRT
<213> ORGANISM: Human immunodeficiency virus

<400> SEQUENCE: 240

Trp Thr Val Asn Asp Ile Gln Lys Leu
1               5

<210> SEQ ID NO 241
<211> LENGTH: 9
<212> TYPE: PRT
<213> ORGANISM: Human immunodeficiency virus

<400> SEQUENCE: 241

Thr Val Asn Asp Ile Gln Lys Leu Val
1               5

<210> SEQ ID NO 242
<211> LENGTH: 9
<212> TYPE: PRT
<213> ORGANISM: Human immunodeficiency virus

<400> SEQUENCE: 242

Thr Val Asn Asp Ile Gln Lys Leu Ile
1               5

<210> SEQ ID NO 243
<211> LENGTH: 9
<212> TYPE: PRT
<213> ORGANISM: Human immunodeficiency virus

<400> SEQUENCE: 243

Lys Leu Val Gly Lys Leu Asn Trp Ala
1               5

<210> SEQ ID NO 244
<211> LENGTH: 9
<212> TYPE: PRT
<213> ORGANISM: Human immunodeficiency virus

<400> SEQUENCE: 244

Lys Leu Ile Gly Lys Leu Asn Trp Ala
1               5

<210> SEQ ID NO 245
<211> LENGTH: 9
<212> TYPE: PRT
<213> ORGANISM: Human immunodeficiency virus

<400> SEQUENCE: 245

Leu Cys Lys Leu Leu Arg Gly Thr Lys
1               5
```

```
<210> SEQ ID NO 246
<211> LENGTH: 9
<212> TYPE: PRT
<213> ORGANISM: Human immunodeficiency virus

<400> SEQUENCE: 246

Leu Cys Lys Leu Leu Arg Gly Ala Lys
1               5

<210> SEQ ID NO 247
<211> LENGTH: 19
<212> TYPE: PRT
<213> ORGANISM: Human immunodeficiency virus

<400> SEQUENCE: 247

Glu Ala Glu Leu Glu Leu Ala Glu Asn Arg Glu Ile Leu Lys Glu Pro
1               5                   10                  15

Val His Gly

<210> SEQ ID NO 248
<211> LENGTH: 19
<212> TYPE: PRT
<213> ORGANISM: Human immunodeficiency virus

<400> SEQUENCE: 248

Glu Ala Glu Ile Glu Leu Ala Glu Asn Arg Glu Ile Leu Arg Glu Pro
1               5                   10                  15

Val His Gly

<210> SEQ ID NO 249
<211> LENGTH: 12
<212> TYPE: PRT
<213> ORGANISM: Human immunodeficiency virus

<400> SEQUENCE: 249

Glu Pro Val His Gly Val Tyr Tyr Asp Pro Ser Lys
1               5                   10

<210> SEQ ID NO 250
<211> LENGTH: 12
<212> TYPE: PRT
<213> ORGANISM: Human immunodeficiency virus

<400> SEQUENCE: 250

Glu Pro Val His Gly Ala Tyr Tyr Asp Pro Ser Lys
1               5                   10

<210> SEQ ID NO 251
<211> LENGTH: 22
<212> TYPE: PRT
<213> ORGANISM: Human immunodeficiency virus

<400> SEQUENCE: 251

Gly Gln Trp Thr Tyr Gln Ile Tyr Gln Glu Pro Phe Lys Asn Leu Lys
1               5                   10                  15

Thr Gly Lys Tyr Ala Arg
            20

<210> SEQ ID NO 252
<211> LENGTH: 22
<212> TYPE: PRT
<213> ORGANISM: Human immunodeficiency virus

<400> SEQUENCE: 252
```

```
Gly Gln Trp Ser Tyr Gln Ile Tyr Gln Glu Pro Tyr Lys Asn Leu Lys
1               5                   10                  15

Thr Gly Lys Tyr Ala Lys
            20

<210> SEQ ID NO 253
<211> LENGTH: 16
<212> TYPE: PRT
<213> ORGANISM: Human immunodeficiency virus

<400> SEQUENCE: 253

Ala His Thr Asn Asp Val Lys Gln Leu Thr Glu Ala Val Gln Lys Ile
1               5                   10                  15

<210> SEQ ID NO 254
<211> LENGTH: 16
<212> TYPE: PRT
<213> ORGANISM: Human immunodeficiency virus

<400> SEQUENCE: 254

Ala His Thr Asn Asp Val Arg Gln Leu Thr Glu Ala Val Gln Lys Val
1               5                   10                  15

<210> SEQ ID NO 255
<211> LENGTH: 10
<212> TYPE: PRT
<213> ORGANISM: Human immunodeficiency virus

<400> SEQUENCE: 255

Ile Val Ile Trp Gly Lys Thr Pro Lys Phe
1               5                   10

<210> SEQ ID NO 256
<211> LENGTH: 10
<212> TYPE: PRT
<213> ORGANISM: Human immunodeficiency virus

<400> SEQUENCE: 256

Ile Val Ile Trp Gly Lys Ile Pro Lys Phe
1               5                   10

<210> SEQ ID NO 257
<211> LENGTH: 13
<212> TYPE: PRT
<213> ORGANISM: Human immunodeficiency virus

<400> SEQUENCE: 257

Pro Lys Phe Lys Leu Pro Ile Gln Lys Glu Thr Trp Glu
1               5                   10

<210> SEQ ID NO 258
<211> LENGTH: 13
<212> TYPE: PRT
<213> ORGANISM: Human immunodeficiency virus

<400> SEQUENCE: 258

Pro Lys Phe Arg Leu Pro Ile Gln Lys Glu Thr Trp Asp
1               5                   10

<210> SEQ ID NO 259
<211> LENGTH: 65
<212> TYPE: PRT
<213> ORGANISM: Human immunodeficiency virus
```

```
<400> SEQUENCE: 259

Pro Lys Phe Lys Leu Pro Ile Gln Lys Glu Thr Trp Glu Thr Trp Trp
1               5                   10                  15

Thr Glu Tyr Trp Gln Ala Thr Trp Ile Pro Glu Trp Glu Phe Val Asn
            20                  25                  30

Thr Pro Pro Leu Val Lys Leu Trp Tyr Gln Leu Glu Lys Glu Pro Ile
        35                  40                  45

Val Gly Ala Glu Thr Phe Tyr Val Asp Gly Ala Ala Asn Arg Glu Thr
    50                  55                  60

Lys
65

<210> SEQ ID NO 260
<211> LENGTH: 65
<212> TYPE: PRT
<213> ORGANISM: Human immunodeficiency virus

<400> SEQUENCE: 260

Pro Lys Phe Arg Leu Pro Ile Gln Lys Glu Thr Trp Asp Thr Trp Trp
1               5                   10                  15

Thr Asp Tyr Trp Gln Ala Thr Trp Ile Pro Glu Trp Glu Phe Thr Asn
            20                  25                  30

Thr Pro Pro Leu Val Lys Leu Trp Tyr Gln Leu Glu Thr Glu Pro Ile
        35                  40                  45

Ala Gly Val Glu Thr Phe Tyr Val Asp Gly Ala Ser Asn Arg Glu Thr
    50                  55                  60

Lys
65

<210> SEQ ID NO 261
<211> LENGTH: 25
<212> TYPE: PRT
<213> ORGANISM: Human immunodeficiency virus

<400> SEQUENCE: 261

Trp Glu Thr Trp Trp Thr Glu Tyr Trp Gln Ala Thr Trp Ile Pro Glu
1               5                   10                  15

Trp Glu Phe Val Asn Thr Pro Pro Leu
            20                  25

<210> SEQ ID NO 262
<211> LENGTH: 25
<212> TYPE: PRT
<213> ORGANISM: Human immunodeficiency virus

<400> SEQUENCE: 262

Trp Asp Thr Trp Trp Thr Asp Tyr Trp Gln Ala Thr Trp Ile Pro Glu
1               5                   10                  15

Trp Glu Phe Thr Asn Thr Pro Pro Leu
            20                  25

<210> SEQ ID NO 263
<211> LENGTH: 31
<212> TYPE: PRT
<213> ORGANISM: Human immunodeficiency virus

<400> SEQUENCE: 263

Glu Tyr Trp Gln Ala Thr Trp Ile Pro Glu Trp Glu Phe Val Asn Thr
1               5                   10                  15
```

Pro Pro Leu Val Lys Leu Trp Tyr Gln Leu Glu Lys Glu Pro Ile
            20                  25                  30

<210> SEQ ID NO 264
<211> LENGTH: 31
<212> TYPE: PRT
<213> ORGANISM: Human immunodeficiency virus

<400> SEQUENCE: 264

Asp Tyr Trp Gln Ala Thr Trp Ile Pro Glu Trp Glu Phe Thr Asn Thr
1               5                   10                  15

Pro Pro Leu Val Lys Leu Trp Tyr Gln Leu Glu Thr Glu Pro Ile
            20                  25                  30

<210> SEQ ID NO 265
<211> LENGTH: 9
<212> TYPE: PRT
<213> ORGANISM: Human immunodeficiency virus

<400> SEQUENCE: 265

Trp Gln Ala Thr Trp Ile Pro Glu Trp
1               5

<210> SEQ ID NO 266
<211> LENGTH: 16
<212> TYPE: PRT
<213> ORGANISM: Human immunodeficiency virus

<400> SEQUENCE: 266

Gly Ala Glu Thr Phe Tyr Val Asp Gly Ala Ala Asn Arg Glu Thr Lys
1               5                   10                  15

<210> SEQ ID NO 267
<211> LENGTH: 16
<212> TYPE: PRT
<213> ORGANISM: Human immunodeficiency virus

<400> SEQUENCE: 267

Gly Val Glu Thr Phe Tyr Val Asp Gly Ala Ser Asn Arg Glu Thr Lys
1               5                   10                  15

<210> SEQ ID NO 268
<211> LENGTH: 13
<212> TYPE: PRT
<213> ORGANISM: Human immunodeficiency virus

<400> SEQUENCE: 268

Thr Asp Thr Thr Asn Gln Lys Thr Glu Leu Gln Ala Ile
1               5                   10

<210> SEQ ID NO 269
<211> LENGTH: 13
<212> TYPE: PRT
<213> ORGANISM: Human immunodeficiency virus

<400> SEQUENCE: 269

Ala Asp Thr Thr Asn Gln Lys Thr Glu Leu His Ala Ile
1               5                   10

<210> SEQ ID NO 270
<211> LENGTH: 9
<212> TYPE: PRT
<213> ORGANISM: Human immunodeficiency virus

<400> SEQUENCE: 270

Ala Ile His Leu Ala Leu Gln Asp Ser
1               5

<210> SEQ ID NO 271
<211> LENGTH: 9
<212> TYPE: PRT
<213> ORGANISM: Human immunodeficiency virus

<400> SEQUENCE: 271

Ala Ile Tyr Leu Ala Leu Gln Asp Ser
1               5

<210> SEQ ID NO 272
<211> LENGTH: 33
<212> TYPE: PRT
<213> ORGANISM: Human immunodeficiency virus

<400> SEQUENCE: 272

Leu Ala Leu Gln Asp Ser Gly Leu Glu Val Asn Ile Val Thr Asp Ser
1               5                   10                  15

Gln Tyr Ala Leu Gly Ile Ile Gln Ala Gln Pro Asp Lys Ser Glu Ser
            20                  25                  30

Glu

<210> SEQ ID NO 273
<211> LENGTH: 33
<212> TYPE: PRT
<213> ORGANISM: Human immunodeficiency virus

<400> SEQUENCE: 273

Leu Ala Leu Gln Asp Ser Gly Ser Glu Val Asn Ile Val Thr Asp Ser
1               5                   10                  15

Gln Tyr Ala Ile Gly Ile Ile Gln Ala Gln Pro Asp Arg Ser Glu Ser
            20                  25                  30

Glu

<210> SEQ ID NO 274
<211> LENGTH: 25
<212> TYPE: PRT
<213> ORGANISM: Human immunodeficiency virus

<400> SEQUENCE: 274

Gln Asp Ser Gly Leu Glu Val Asn Ile Val Thr Asp Ser Gln Tyr Ala
1               5                   10                  15

Leu Gly Ile Ile Gln Ala Gln Pro Asp
            20                  25

<210> SEQ ID NO 275
<211> LENGTH: 25
<212> TYPE: PRT
<213> ORGANISM: Human immunodeficiency virus

<400> SEQUENCE: 275

Gln Asp Ser Gly Ser Glu Val Asn Ile Val Thr Asp Ser Gln Tyr Ala
1               5                   10                  15

Ile Gly Ile Ile Gln Ala Gln Pro Asp
            20                  25

<210> SEQ ID NO 276
<211> LENGTH: 9
<212> TYPE: PRT

<213> ORGANISM: Human immunodeficiency virus

<400> SEQUENCE: 276

Ile Val Thr Asp Ser Gln Tyr Ala Leu
1 5

<210> SEQ ID NO 277
<211> LENGTH: 9
<212> TYPE: PRT
<213> ORGANISM: Human immunodeficiency virus

<400> SEQUENCE: 277

Ile Val Thr Asp Ser Gln Tyr Ala Ile
1 5

<210> SEQ ID NO 278
<211> LENGTH: 9
<212> TYPE: PRT
<213> ORGANISM: Human immunodeficiency virus

<400> SEQUENCE: 278

Val Ser Gln Ile Ile Glu Gln Leu Ile
1 5

<210> SEQ ID NO 279
<211> LENGTH: 9
<212> TYPE: PRT
<213> ORGANISM: Human immunodeficiency virus

<400> SEQUENCE: 279

Val Asn Gln Ile Ile Glu Gln Leu Ile
1 5

<210> SEQ ID NO 280
<211> LENGTH: 10
<212> TYPE: PRT
<213> ORGANISM: Human immunodeficiency virus

<400> SEQUENCE: 280

Gln Ile Ile Glu Gln Leu Ile Lys Lys Glu
1 5 10

<210> SEQ ID NO 281
<211> LENGTH: 10
<212> TYPE: PRT
<213> ORGANISM: Human immunodeficiency virus

<400> SEQUENCE: 281

Gln Ile Ile Glu Gln Leu Ile Asn Lys Glu
1 5 10

<210> SEQ ID NO 282
<211> LENGTH: 26
<212> TYPE: PRT
<213> ORGANISM: Human immunodeficiency virus

<400> SEQUENCE: 282

Lys Glu Lys Val Tyr Leu Ala Trp Val Pro Ala His Lys Gly Ile Gly
1 5 10 15

Gly Asn Glu Gln Val Asp Lys Leu Val Ser
20 25

<210> SEQ ID NO 283
<211> LENGTH: 26

```
<212> TYPE: PRT
<213> ORGANISM: Human immunodeficiency virus

<400> SEQUENCE: 283

Lys Glu Lys Ile Tyr Leu Ala Trp Val Pro Ala His Lys Gly Ile Gly
1               5                   10                  15

Gly Asn Glu Gln Ile Asp Lys Leu Val Ser
            20                  25

<210> SEQ ID NO 284
<211> LENGTH: 16
<212> TYPE: PRT
<213> ORGANISM: Human immunodeficiency virus

<400> SEQUENCE: 284

Gly Ile Arg Lys Val Leu Phe Leu Asp Gly Ile Asp Lys Ala Gln Glu
1               5                   10                  15

<210> SEQ ID NO 285
<211> LENGTH: 16
<212> TYPE: PRT
<213> ORGANISM: Human immunodeficiency virus

<400> SEQUENCE: 285

Gly Ile Arg Arg Val Leu Phe Leu Asp Gly Ile Glu Lys Ala Gln Asp
1               5                   10                  15

<210> SEQ ID NO 286
<211> LENGTH: 9
<212> TYPE: PRT
<213> ORGANISM: Human immunodeficiency virus

<400> SEQUENCE: 286

His Glu Lys Tyr His Ser Asn Trp Arg
1               5

<210> SEQ ID NO 287
<211> LENGTH: 9
<212> TYPE: PRT
<213> ORGANISM: Human immunodeficiency virus

<400> SEQUENCE: 287

His Glu Lys Tyr His Asn Asn Trp Arg
1               5

<210> SEQ ID NO 288
<211> LENGTH: 9
<212> TYPE: PRT
<213> ORGANISM: Human immunodeficiency virus

<400> SEQUENCE: 288

Met Ala Ser Asp Phe Asn Leu Pro Pro
1               5

<210> SEQ ID NO 289
<211> LENGTH: 9
<212> TYPE: PRT
<213> ORGANISM: Human immunodeficiency virus

<400> SEQUENCE: 289

Met Ala Ser Asp Phe Asn Ile Pro Pro
1               5

<210> SEQ ID NO 290
```

```
<211> LENGTH: 13
<212> TYPE: PRT
<213> ORGANISM: Human immunodeficiency virus

<400> SEQUENCE: 290

Phe Asn Leu Pro Pro Val Val Ala Lys Glu Ile Val Ala
1               5                   10

<210> SEQ ID NO 291
<211> LENGTH: 13
<212> TYPE: PRT
<213> ORGANISM: Human immunodeficiency virus

<400> SEQUENCE: 291

Phe Asn Leu Pro Pro Ile Val Ala Lys Glu Ile Val Ala
1               5                   10

<210> SEQ ID NO 292
<211> LENGTH: 87
<212> TYPE: PRT
<213> ORGANISM: Human immunodeficiency virus

<400> SEQUENCE: 292

Phe Asn Leu Pro Pro Val Val Ala Lys Glu Ile Val Ala Ser Cys Asp
1               5                   10                  15

Lys Cys Gln Leu Lys Gly Glu Ala Met His Gly Gln Val Asp Cys Ser
            20                  25                  30

Pro Gly Ile Trp Gln Leu Asp Cys Thr His Leu Glu Gly Lys Ile Ile
        35                  40                  45

Leu Val Ala Val His Val Ala Ser Gly Tyr Ile Glu Ala Glu Val Ile
    50                  55                  60

Pro Ala Glu Thr Gly Gln Glu Thr Ala Tyr Phe Leu Leu Lys Leu Ala
65                  70                  75                  80

Gly Arg Trp Pro Val Lys Thr
                85

<210> SEQ ID NO 293
<211> LENGTH: 87
<212> TYPE: PRT
<213> ORGANISM: Human immunodeficiency virus

<400> SEQUENCE: 293

Phe Asn Leu Pro Pro Ile Val Ala Lys Glu Ile Val Ala Cys Cys Asp
1               5                   10                  15

Lys Cys Gln Leu Lys Gly Glu Ala Ile His Gly Gln Val Asp Cys Ser
            20                  25                  30

Pro Gly Val Trp Gln Leu Asp Cys Thr His Leu Glu Gly Lys Val Ile
        35                  40                  45

Leu Val Ala Val His Val Ala Ser Gly Tyr Ile Glu Ala Glu Ile Ile
    50                  55                  60

Pro Thr Glu Thr Gly Gln Glu Thr Ala Tyr Phe Ile Leu Lys Leu Ala
65                  70                  75                  80

Gly Arg Trp Pro Val Thr Thr
                85

<210> SEQ ID NO 294
<211> LENGTH: 81
<212> TYPE: PRT
<213> ORGANISM: Human immunodeficiency virus

<400> SEQUENCE: 294
```

Val Ala Lys Glu Ile Val Ala Ser Cys Asp Lys Cys Gln Leu Lys Gly
1               5                   10                  15

Glu Ala Met His Gly Gln Val Asp Cys Ser Pro Gly Ile Trp Gln Leu
                20                  25                  30

Asp Cys Thr His Leu Glu Gly Lys Ile Ile Leu Val Ala Val His Val
            35                  40                  45

Ala Ser Gly Tyr Ile Glu Ala Glu Val Ile Pro Ala Glu Thr Gly Gln
        50                  55                  60

Glu Thr Ala Tyr Phe Leu Leu Lys Leu Ala Gly Arg Trp Pro Val Lys
65                  70                  75                  80

Thr

<210> SEQ ID NO 295
<211> LENGTH: 81
<212> TYPE: PRT
<213> ORGANISM: Human immunodeficiency virus

<400> SEQUENCE: 295

Val Ala Lys Glu Ile Val Ala Cys Cys Asp Lys Cys Gln Leu Lys Gly
1               5                   10                  15

Glu Ala Ile His Gly Gln Val Asp Cys Ser Pro Gly Val Trp Gln Leu
                20                  25                  30

Asp Cys Thr His Leu Glu Gly Lys Val Ile Leu Val Ala Val His Val
            35                  40                  45

Ala Ser Gly Tyr Met Glu Ala Glu Val Ile Pro Thr Glu Thr Gly Gln
        50                  55                  60

Glu Thr Ala Tyr Phe Ile Leu Lys Leu Ala Gly Arg Trp Pro Val Thr
65                  70                  75                  80

Thr

<210> SEQ ID NO 296
<211> LENGTH: 25
<212> TYPE: PRT
<213> ORGANISM: Human immunodeficiency virus

<400> SEQUENCE: 296

Gln Leu Lys Gly Glu Ala Met His Gly Gln Val Asp Cys Ser Pro Gly
1               5                   10                  15

Ile Trp Gln Leu Asp Cys Thr His Leu
            20                  25

<210> SEQ ID NO 297
<211> LENGTH: 25
<212> TYPE: PRT
<213> ORGANISM: Human immunodeficiency virus

<400> SEQUENCE: 297

Gln Leu Lys Gly Glu Ala Ile His Gly Gln Val Asp Cys Ser Pro Gly
1               5                   10                  15

Val Trp Gln Leu Asp Cys Thr His Leu
            20                  25

<210> SEQ ID NO 298
<211> LENGTH: 9
<212> TYPE: PRT
<213> ORGANISM: Human immunodeficiency virus

<400> SEQUENCE: 298

```
Gly Gln Val Asp Cys Ser Pro Gly Ile
1               5

<210> SEQ ID NO 299
<211> LENGTH: 9
<212> TYPE: PRT
<213> ORGANISM: Human immunodeficiency virus

<400> SEQUENCE: 299

Gly Gln Val Asp Cys Ser Pro Gly Val
1               5

<210> SEQ ID NO 300
<211> LENGTH: 25
<212> TYPE: PRT
<213> ORGANISM: Human immunodeficiency virus

<400> SEQUENCE: 300

Gln Val Asp Cys Ser Pro Gly Ile Trp Gln Leu Asp Cys Thr His Leu
1               5                   10                  15

Glu Gly Lys Ile Ile Leu Val Ala Val
            20                  25

<210> SEQ ID NO 301
<211> LENGTH: 25
<212> TYPE: PRT
<213> ORGANISM: Human immunodeficiency virus

<400> SEQUENCE: 301

Gln Val Asp Cys Ser Pro Gly Val Trp Gln Leu Asp Cys Thr His Leu
1               5                   10                  15

Glu Gly Lys Val Ile Leu Val Ala Val
            20                  25

<210> SEQ ID NO 302
<211> LENGTH: 9
<212> TYPE: PRT
<213> ORGANISM: Human immunodeficiency virus

<400> SEQUENCE: 302

Trp Gln Leu Asp Cys Thr His Leu Glu
1               5

<210> SEQ ID NO 303
<211> LENGTH: 25
<212> TYPE: PRT
<213> ORGANISM: Human immunodeficiency virus

<400> SEQUENCE: 303

Ser Asn Phe Thr Ser Thr Thr Val Lys Ala Ala Cys Trp Trp Ala Gly
1               5                   10                  15

Ile Lys Gln Glu Phe Gly Ile Pro Tyr
            20                  25

<210> SEQ ID NO 304
<211> LENGTH: 25
<212> TYPE: PRT
<213> ORGANISM: Human immunodeficiency virus

<400> SEQUENCE: 304

Ser Asn Phe Thr Ser Thr Ala Val Lys Ala Ala Cys Trp Trp Ala Gly
1               5                   10                  15

Val Lys Gln Glu Phe Gly Ile Pro Tyr
```

```
            20                  25

<210> SEQ ID NO 305
<211> LENGTH: 80
<212> TYPE: PRT
<213> ORGANISM: Human immunodeficiency virus

<400> SEQUENCE: 305

Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp Ile Ile
65                  70                  75                  80

<210> SEQ ID NO 306
<211> LENGTH: 80
<212> TYPE: PRT
<213> ORGANISM: Human immunodeficiency virus

<400> SEQUENCE: 306

Ala Val Lys Ala Ala Cys Trp Trp Ala Gly Val Lys Gln Glu Phe Gly
1               5                   10                  15

Ile Pro Tyr His Pro Gln Ser Gln Gly Val Val Glu Ser Met Asn Asn
            20                  25                  30

Glu Leu Lys Lys Ile Ile Gly Gln Ile Arg Asp Gln Ala Glu Gln Leu
        35                  40                  45

Lys Thr Ala Val Gln Met Ala Val Leu Ile His Asn Phe Lys Arg Lys
    50                  55                  60

Gly Gly Ile Gly Glu Tyr Ser Ala Gly Glu Arg Ile Ile Asp Ile Ile
65                  70                  75                  80

<210> SEQ ID NO 307
<211> LENGTH: 81
<212> TYPE: PRT
<213> ORGANISM: Human immunodeficiency virus

<400> SEQUENCE: 307

Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp Ile Ile
65                  70                  75                  80

Ala

<210> SEQ ID NO 308
<211> LENGTH: 81
<212> TYPE: PRT
<213> ORGANISM: Human immunodeficiency virus
```

```
<400> SEQUENCE: 308

Ala Val Lys Ala Ala Cys Trp Trp Ala Gly Val Lys Gln Glu Phe Gly
1               5                   10                  15

Ile Pro Tyr His Pro Gln Ser Gln Gly Val Val Glu Ser Met Asn Asn
                20                  25                  30

Glu Leu Lys Lys Ile Ile Gly Gln Ile Arg Asp Gln Ala Glu Gln Leu
            35                  40                  45

Lys Thr Ala Val Gln Met Ala Val Leu Ile His Asn Phe Lys Arg Lys
    50                  55                  60

Gly Gly Ile Gly Glu Tyr Ser Ala Gly Glu Arg Ile Ile Asp Ile Ile
65                  70                  75                  80

Ala

<210> SEQ ID NO 309
<211> LENGTH: 164
<212> TYPE: PRT
<213> ORGANISM: Human immunodeficiency virus

<400> SEQUENCE: 309

Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
                20                  25                  30

Glu Leu Lys Lys Ile Ile Gly Gln Val Arg Asp Gln Ala Glu His Leu
            35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp Ile Ile
65                  70                  75                  80

Ala Thr Asp Ile Gln Thr Lys Glu Leu Gln Lys Gln Ile Thr Lys Ile
                85                  90                  95

Gln Asn Phe Arg Val Tyr Tyr Arg Asp Ser Arg Asp Pro Leu Trp Lys
                100                 105                 110

Gly Pro Ala Lys Leu Leu Trp Lys Gly Glu Gly Ala Val Val Ile Gln
            115                 120                 125

Asp Asn Ser Asp Ile Lys Val Val Pro Arg Arg Lys Ala Lys Ile Ile
    130                 135                 140

Arg Asp Tyr Gly Lys Gln Met Ala Gly Asp Asp Cys Val Ala Ser Arg
145                 150                 155                 160

Gln Asp Glu Asp

<210> SEQ ID NO 310
<211> LENGTH: 164
<212> TYPE: PRT
<213> ORGANISM: Human immunodeficiency virus

<400> SEQUENCE: 310

Ala Val Lys Ala Ala Cys Trp Trp Ala Gly Val Lys Gln Glu Phe Gly
1               5                   10                  15

Ile Pro Tyr Asn Thr Gln Ser Gln Gly Val Val Glu Ser Met Asn Asn
                20                  25                  30

Glu Leu Lys Lys Ile Ile Gly Gln Ile Arg Asp Gln Ala Glu His Leu
            35                  40                  45

Lys Thr Ala Val Gln Met Ala Val Leu Ile His Asn Phe Lys Arg Lys
    50                  55                  60
```

```
Gly Gly Ile Gly Glu Tyr Ser Ala Gly Glu Arg Ile Asp Ile Ile
 65                  70                  75                  80

Ala Thr Asp Ile Gln Thr Arg Glu Leu Gln Lys Gln Ile Thr Lys Leu
                 85                  90                  95

Gln Asn Phe Arg Val Tyr Tyr Arg Asp Asn Arg Asp Pro Leu Trp Lys
            100                 105                 110

Gly Pro Ala Arg Leu Leu Trp Lys Gly Glu Gly Ala Val Val Ile Gln
        115                 120                 125

Asp Asn Ser Glu Ile Lys Val Val Pro Arg Arg Lys Val Lys Ile Ile
    130                 135                 140

Arg Asp Tyr Gly Lys Arg Met Ala Gly Asp Asp Cys Val Ala Gly Arg
145                 150                 155                 160

Gln Asp Glu Asp

<210> SEQ ID NO 311
<211> LENGTH: 9
<212> TYPE: PRT
<213> ORGANISM: Human immunodeficiency virus

<400> SEQUENCE: 311

Lys Ala Ala Cys Trp Trp Ala Gly Ile
1               5

<210> SEQ ID NO 312
<211> LENGTH: 9
<212> TYPE: PRT
<213> ORGANISM: Human immunodeficiency virus

<400> SEQUENCE: 312

Lys Ala Ala Cys Trp Trp Ala Gly Val
1               5

<210> SEQ ID NO 313
<211> LENGTH: 9
<212> TYPE: PRT
<213> ORGANISM: Human immunodeficiency virus

<400> SEQUENCE: 313

Asp Ile Ile Ala Thr Asp Ile Gln Thr
1               5

<210> SEQ ID NO 314
<211> LENGTH: 9
<212> TYPE: PRT
<213> ORGANISM: Human immunodeficiency virus

<400> SEQUENCE: 314

Asp Ile Ile Ala Ser Asp Ile Gln Thr
1               5

<210> SEQ ID NO 315
<211> LENGTH: 9
<212> TYPE: PRT
<213> ORGANISM: Human immunodeficiency virus

<400> SEQUENCE: 315

Asp Ile Gln Thr Lys Glu Leu Gln Lys
1               5

<210> SEQ ID NO 316
<211> LENGTH: 9
<212> TYPE: PRT
```

<213> ORGANISM: Human immunodeficiency virus

<400> SEQUENCE: 316

Asp Ile Gln Thr Arg Glu Leu Gln Lys
1               5

<210> SEQ ID NO 317
<211> LENGTH: 9
<212> TYPE: PRT
<213> ORGANISM: Human immunodeficiency virus

<400> SEQUENCE: 317

Gln Thr Lys Glu Leu Gln Lys Gln Ile
1               5

<210> SEQ ID NO 318
<211> LENGTH: 9
<212> TYPE: PRT
<213> ORGANISM: Human immunodeficiency virus

<400> SEQUENCE: 318

Gln Thr Arg Glu Leu Gln Lys Gln Ile
1               5

<210> SEQ ID NO 319
<211> LENGTH: 73
<212> TYPE: PRT
<213> ORGANISM: Human immunodeficiency virus

<400> SEQUENCE: 319

Ala Ile Thr Lys Ile Gln Asn Phe Arg Val Tyr Tyr Arg Asp Ser Arg
1               5                   10                  15

Asp Pro Leu Trp Lys Gly Pro Ala Lys Leu Leu Trp Lys Gly Glu Gly
            20                  25                  30

Ala Val Val Ile Gln Asp Asn Ser Asp Ile Lys Val Val Pro Arg Arg
        35                  40                  45

Lys Ala Lys Ile Ile Arg Asp Tyr Gly Lys Gln Met Ala Gly Asp Asp
    50                  55                  60

Cys Val Ala Ser Arg Gln Asp Glu Asp
65                  70

<210> SEQ ID NO 320
<211> LENGTH: 73
<212> TYPE: PRT
<213> ORGANISM: Human immunodeficiency virus

<400> SEQUENCE: 320

Ala Ile Thr Lys Leu Gln Asn Phe Arg Val Tyr Tyr Arg Asp Asn Arg
1               5                   10                  15

Asp Pro Leu Trp Lys Gly Pro Ala Arg Leu Leu Trp Lys Gly Glu Gly
            20                  25                  30

Ala Val Val Ile Gln Asp Asn Ser Glu Ile Lys Val Val Pro Arg Arg
        35                  40                  45

Lys Val Lys Ile Ile Arg Asp Tyr Gly Lys Arg Met Ala Gly Asp Asp
    50                  55                  60

Cys Val Ala Gly Arg Gln Asp Glu Asp
65                  70

<210> SEQ ID NO 321
<211> LENGTH: 72
<212> TYPE: PRT

```
<213> ORGANISM: Human immunodeficiency virus

<400> SEQUENCE: 321

Ile Thr Lys Ile Gln Asn Phe Arg Val Tyr Tyr Arg Asp Ser Arg Asp
1               5                   10                  15

Pro Leu Trp Lys Gly Pro Ala Lys Leu Leu Trp Lys Gly Glu Gly Ala
            20                  25                  30

Val Val Ile Gln Asp Asn Ser Asp Ile Lys Val Val Pro Arg Arg Lys
        35                  40                  45

Ala Lys Ile Ile Arg Asp Tyr Gly Lys Gln Met Ala Gly Asp Asp Cys
    50                  55                  60

Val Ala Ser Arg Gln Asp Glu Asp
65                  70

<210> SEQ ID NO 322
<211> LENGTH: 72
<212> TYPE: PRT
<213> ORGANISM: Human immunodeficiency virus

<400> SEQUENCE: 322

Ile Thr Lys Leu Gln Asn Phe Arg Val Tyr Tyr Arg Asp Asn Arg Asp
1               5                   10                  15

Pro Leu Trp Lys Gly Pro Ala Arg Leu Leu Trp Lys Gly Glu Gly Ala
            20                  25                  30

Val Val Ile Gln Asp Asn Ser Glu Ile Lys Val Val Pro Arg Arg Lys
        35                  40                  45

Val Lys Ile Ile Arg Asp Tyr Gly Lys Arg Met Ala Gly Asp Asp Cys
    50                  55                  60

Val Ala Gly Arg Gln Asp Glu Asp
65                  70

<210> SEQ ID NO 323
<211> LENGTH: 25
<212> TYPE: PRT
<213> ORGANISM: Human immunodeficiency virus

<400> SEQUENCE: 323

Val Tyr Tyr Arg Asp Ser Arg Asp Pro Leu Trp Lys Gly Pro Ala Lys
1               5                   10                  15

Leu Leu Trp Lys Gly Glu Gly Ala Val
            20                  25

<210> SEQ ID NO 324
<211> LENGTH: 25
<212> TYPE: PRT
<213> ORGANISM: Human immunodeficiency virus

<400> SEQUENCE: 324

Val Tyr Tyr Arg Asp Asn Arg Asp Pro Leu Trp Lys Gly Pro Ala Arg
1               5                   10                  15

Leu Leu Trp Lys Gly Glu Gly Ala Val
            20                  25

<210> SEQ ID NO 325
<211> LENGTH: 25
<212> TYPE: PRT
<213> ORGANISM: Human immunodeficiency virus

<400> SEQUENCE: 325

Asp Pro Leu Trp Lys Gly Pro Ala Lys Leu Leu Trp Lys Gly Glu Gly
```

```
                1               5                  10                  15
Ala Val Val Ile Gln Asp Asn Ser Asp
            20                  25

<210> SEQ ID NO 326
<211> LENGTH: 25
<212> TYPE: PRT
<213> ORGANISM: Human immunodeficiency virus

<400> SEQUENCE: 326

Asp Pro Leu Trp Lys Gly Pro Ala Arg Leu Leu Trp Lys Gly Glu Gly
1               5                   10                  15

Ala Val Val Ile Gln Asp Asn Ser Glu
            20                  25

<210> SEQ ID NO 327
<211> LENGTH: 9
<212> TYPE: PRT
<213> ORGANISM: Human immunodeficiency virus

<400> SEQUENCE: 327

Pro Leu Trp Lys Gly Pro Ala Lys Leu
1               5

<210> SEQ ID NO 328
<211> LENGTH: 9
<212> TYPE: PRT
<213> ORGANISM: Human immunodeficiency virus

<400> SEQUENCE: 328

Pro Leu Trp Lys Gly Pro Ala Arg Leu
1               5

<210> SEQ ID NO 329
<211> LENGTH: 25
<212> TYPE: PRT
<213> ORGANISM: Human immunodeficiency virus

<400> SEQUENCE: 329

Pro Leu Trp Lys Gly Pro Ala Lys Leu Leu Trp Lys Gly Glu Gly Ala
1               5                   10                  15

Val Val Ile Gln Asp Asn Ser Asp Ile
            20                  25

<210> SEQ ID NO 330
<211> LENGTH: 25
<212> TYPE: PRT
<213> ORGANISM: Human immunodeficiency virus

<400> SEQUENCE: 330

Pro Leu Trp Lys Gly Pro Ala Arg Leu Leu Trp Lys Gly Glu Gly Ala
1               5                   10                  15

Val Val Ile Gln Asp Asn Ser Glu Ile
            20                  25

<210> SEQ ID NO 331
<211> LENGTH: 9
<212> TYPE: PRT
<213> ORGANISM: Human immunodeficiency virus

<400> SEQUENCE: 331

Lys Leu Leu Trp Lys Gly Glu Gly Ala
1               5
```

<210> SEQ ID NO 332
<211> LENGTH: 9
<212> TYPE: PRT
<213> ORGANISM: Human immunodeficiency virus

<400> SEQUENCE: 332

Arg Leu Leu Trp Lys Gly Glu Gly Ala
1               5

<210> SEQ ID NO 333
<211> LENGTH: 9
<212> TYPE: PRT
<213> ORGANISM: Human immunodeficiency virus

<400> SEQUENCE: 333

Leu Leu Trp Lys Gly Glu Gly Ala Val
1               5

<210> SEQ ID NO 334
<211> LENGTH: 24
<212> TYPE: PRT
<213> ORGANISM: Human immunodeficiency virus

<400> SEQUENCE: 334

Ala Lys Ile Ile Arg Asp Tyr Gly Lys Gln Met Ala Gly Asp Asp Cys
1               5                   10                  15

Val Ala Ser Arg Gln Asp Glu Asp
            20

<210> SEQ ID NO 335
<211> LENGTH: 24
<212> TYPE: PRT
<213> ORGANISM: Human immunodeficiency virus

<400> SEQUENCE: 335

Val Lys Ile Ile Arg Asp Tyr Gly Lys Arg Met Ala Gly Asp Asp Cys
1               5                   10                  15

Val Ala Gly Arg Gln Asp Glu Asp
            20

<210> SEQ ID NO 336
<211> LENGTH: 9
<212> TYPE: PRT
<213> ORGANISM: Human immunodeficiency virus

<400> SEQUENCE: 336

Lys Gln Met Ala Gly Asp Asp Cys Val
1               5

<210> SEQ ID NO 337
<211> LENGTH: 9
<212> TYPE: PRT
<213> ORGANISM: Human immunodeficiency virus

<400> SEQUENCE: 337

Lys Arg Met Ala Gly Asp Asp Cys Val
1               5

<210> SEQ ID NO 338
<211> LENGTH: 25
<212> TYPE: PRT
<213> ORGANISM: Human immunodeficiency virus

```
<400> SEQUENCE: 338

Tyr Leu Arg Asp Gln Gln Leu Leu Gly Leu Trp Gly Cys Ser Gly Lys
1               5                   10                  15

Leu Ile Cys Pro Thr Ala Val Pro Trp
            20                  25

<210> SEQ ID NO 339
<211> LENGTH: 26
<212> TYPE: PRT
<213> ORGANISM: Human immunodeficiency virus

<400> SEQUENCE: 339

Pro Val Gly Glu Ile Tyr Lys Arg Trp Ile Ile Leu Gly Leu Asn Lys
1               5                   10                  15

Ile Val Arg Met Tyr Ser Pro Thr Ser Ile
            20                  25

<210> SEQ ID NO 340
<211> LENGTH: 26
<212> TYPE: PRT
<213> ORGANISM: Human immunodeficiency virus

<400> SEQUENCE: 340

Pro Val Gly Asp Ile Tyr Lys Arg Trp Ile Ile Met Gly Leu Asn Lys
1               5                   10                  15

Ile Val Arg Met Tyr Ser Pro Val Ser Ile
            20                  25

<210> SEQ ID NO 341
<211> LENGTH: 26
<212> TYPE: PRT
<213> ORGANISM: Human immunodeficiency virus

<400> SEQUENCE: 341

Gly Pro Lys Glu Pro Phe Arg Asp Tyr Val Asp Arg Phe Tyr Lys Thr
1               5                   10                  15

Leu Arg Ala Glu Gln Ala Ser Gln Glu Val
            20                  25

<210> SEQ ID NO 342
<211> LENGTH: 26
<212> TYPE: PRT
<213> ORGANISM: Human immunodeficiency virus

<400> SEQUENCE: 342

Gly Pro Lys Glu Pro Phe Arg Asp Tyr Val Asp Arg Phe Tyr Arg Thr
1               5                   10                  15

Leu Arg Ala Glu Gln Ala Ser Gln Asp Val
            20                  25

<210> SEQ ID NO 343
<211> LENGTH: 25
<212> TYPE: PRT
<213> ORGANISM: Human immunodeficiency virus

<400> SEQUENCE: 343

Phe Arg Lys Gln Asn Pro Asp Ile Val Ile Tyr Gln Tyr Val Asp Asp
1               5                   10                  15

Leu Tyr Val Gly Ser Asp Leu Glu Ile
            20                  25
```

```
<210> SEQ ID NO 344
<211> LENGTH: 25
<212> TYPE: PRT
<213> ORGANISM: Human immunodeficiency virus

<400> SEQUENCE: 344

Lys Gln Asn Pro Asp Ile Val Ile Tyr Gln Tyr Val Asp Asp Leu Tyr
1               5                   10                  15

Val Gly Ser Asp Leu Glu Ile Glu Gln
            20                  25

<210> SEQ ID NO 345
<211> LENGTH: 771
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Leu Lys His Ile Val Trp Ala Ser Arg Glu Leu Glu Arg Phe Ala Val
1               5                   10                  15

Asn Pro Gly Leu Leu Glu Thr Ala Ala Ala Val Ser Gln Asn Tyr Pro
            20                  25                  30

Ile Val Gln Asn Ala Ala Ala Ile Ser Pro Arg Thr Leu Asn Ala Trp
        35                  40                  45

Val Lys Val Val Glu Glu Lys Ala Phe Ser Pro Glu Val Ile Pro Met
50                  55                  60

Phe Ser Ala Leu Ser Glu Gly Ala Thr Pro Gln Asp Leu Asn Thr Met
65                  70                  75                  80

Leu Asn Thr Val Gly Gly His Gln Ala Ala Met Gln Met Leu Lys Glu
                85                  90                  95

Thr Ile Asn Glu Glu Ala Ala Glu Trp Asp Arg Leu His Pro Val His
            100                 105                 110

Ala Gly Pro Ile Ala Pro Gly Gln Met Arg Glu Pro Arg Gly Ser Asp
        115                 120                 125

Ile Ala Gly Thr Thr Ser Thr Leu Gln Glu Gln Ile Gly Trp Met Thr
130                 135                 140

Asn Asn Pro Pro Ile Pro Val Gly Glu Ile Tyr Lys Arg Trp Ile Ile
145                 150                 155                 160

Leu Gly Leu Asn Lys Ile Val Arg Met Tyr Ser Pro Thr Ser Ile Leu
                165                 170                 175

Asp Ile Arg Gln Gly Pro Lys Glu Pro Phe Arg Asp Tyr Val Asp Arg
            180                 185                 190

Phe Tyr Lys Thr Leu Arg Ala Glu Gln Ala Ser Gln Glu Val Lys Asn
        195                 200                 205

Trp Met Thr Glu Thr Leu Leu Val Gln Asn Ala Asn Pro Asp Cys Lys
210                 215                 220

Thr Ile Leu Lys Ala Leu Gly Pro Ala Ala Thr Leu Glu Glu Met Met
225                 230                 235                 240

Thr Ala Cys Gln Gly Val Gly Gly Pro Gly His Lys Ala Arg Val Leu
                245                 250                 255

Ala Glu Ala Met Ser Gln Ala Ala Leu Pro Gly Arg Trp Lys Pro
            260                 265                 270

Lys Met Ile Gly Gly Ile Gly Gly Phe Ile Lys Val Arg Gln Tyr Asp
        275                 280                 285

Gln Ala Ala Ala Gly Thr Val Leu Val Gly Pro Thr Pro Val Asn Ile
```

```
                  290                 295                 300
Ile Gly Arg Asn Leu Leu Thr Gln Ile Gly Cys Thr Leu Asn Phe Pro
305                 310                 315                 320

Ile Ser Pro Ile Glu Thr Val Pro Val Lys Leu Lys Pro Gly Met Asp
                325                 330                 335

Gly Pro Lys Val Lys Gln Trp Pro Leu Thr Glu Glu Lys Ile Lys Ala
                340                 345                 350

Leu Val Glu Ile Cys Thr Glu Met Glu Lys Glu Gly Lys Ile Ser Lys
                355                 360                 365

Ile Gly Pro Glu Asn Pro Tyr Asn Thr Pro Val Phe Ala Ile Lys Lys
            370                 375                 380

Lys Asp Ser Thr Lys Trp Arg Lys Leu Val Asp Phe Arg Glu Leu Asn
385                 390                 395                 400

Lys Arg Thr Gln Asp Phe Trp Glu Val Gln Leu Gly Ile Pro His Pro
                405                 410                 415

Ala Gly Leu Lys Lys Lys Lys Ser Val Thr Val Leu Asp Val Gly Asp
                420                 425                 430

Ala Tyr Phe Ser Val Pro Leu Asp Lys Asp Phe Arg Lys Tyr Thr Ala
                435                 440                 445

Phe Thr Ile Pro Ser Ala Ala Ala Trp Gly Phe Thr Thr Pro Asp Lys
450                 455                 460

Lys His Gln Lys Glu Pro Pro Phe Leu Trp Met Gly Tyr Glu Leu His
465                 470                 475                 480

Pro Asp Lys Trp Thr Val Gln Pro Ile Ala Ala Val Ala Lys Glu
                485                 490                 495

Ile Val Ala Ser Cys Asp Lys Cys Gln Leu Lys Gly Glu Ala Met His
                500                 505                 510

Gly Gln Val Asp Cys Ser Pro Gly Ile Trp Gln Leu Asp Cys Thr His
                515                 520                 525

Leu Glu Gly Lys Ile Ile Leu Val Ala Val His Val Ala Ser Gly Tyr
            530                 535                 540

Ile Glu Ala Glu Val Ile Pro Ala Glu Thr Gly Gln Glu Thr Ala Tyr
545                 550                 555                 560

Phe Leu Leu Lys Leu Ala Gly Arg Trp Pro Val Lys Thr Ala Ala Ala
                565                 570                 575

Thr Val Lys Ala Ala Cys Trp Trp Ala Gly Ile Lys Gln Glu Phe Gly
                580                 585                 590

Ile Pro Tyr Asn Pro Gln Ser Gln Gly Val Val Glu Ser Met Asn Lys
            595                 600                 605

Glu Leu Lys Lys Ile Ile Gly Gln Val Arg Asp Gln Ala Glu His Leu
            610                 615                 620

Lys Thr Ala Val Gln Met Ala Val Phe Ile His Asn Phe Lys Arg Lys
625                 630                 635                 640

Gly Gly Ile Gly Gly Tyr Ser Ala Gly Glu Arg Ile Val Asp Ile Ile
                645                 650                 655

Ala Ala Ala Ala Ile Thr Lys Ile Gln Asn Phe Arg Val Tyr Tyr Arg
                660                 665                 670

Asp Ser Arg Asp Pro Leu Trp Lys Gly Pro Ala Lys Leu Leu Trp Lys
                675                 680                 685

Gly Glu Gly Ala Val Val Ile Gln Asp Asn Ser Asp Ile Lys Val Val
            690                 695                 700

Pro Arg Arg Lys Ala Lys Ile Ile Arg Asp Tyr Gly Lys Gln Met Ala
705                 710                 715                 720
```

```
Gly Asp Asp Cys Val Ala Ser Arg Gln Asp Glu Asp Ala Ala Ala Glu
                725                 730                 735

Glu Val Gly Phe Pro Val Lys Pro Gln Val Pro Leu Arg Pro Met Thr
            740                 745                 750

Phe Lys Gly Ala Leu Asp Leu Ser His Phe Leu Arg Glu Lys Gly Gly
        755                 760                 765

Leu Glu Gly
    770

<210> SEQ ID NO 346
<211> LENGTH: 771
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Leu Lys His Leu Val Trp Ala Ser Arg Glu Leu Glu Arg Phe Ala Leu
1               5                   10                  15

Asn Pro Gly Leu Leu Glu Thr Ala Ala Ala Val Ser Gln Asn Phe Pro
            20                  25                  30

Ile Val Gln Asn Ala Ala Ala Leu Ser Pro Arg Thr Leu Asn Ala Trp
        35                  40                  45

Val Lys Val Ile Glu Glu Lys Ala Phe Ser Pro Glu Val Ile Pro Met
    50                  55                  60

Phe Thr Ala Leu Ser Glu Gly Ala Thr Pro His Asp Leu Asn Thr Met
65                  70                  75                  80

Leu Asn Thr Ile Gly Gly His Gln Ala Ala Met Gln Met Leu Lys Asp
                85                  90                  95

Thr Ile Asn Glu Glu Ala Ala Glu Trp Asp Arg Val His Pro Val His
            100                 105                 110

Ala Gly Pro Val Ala Pro Gly Gln Met Arg Asp Pro Arg Gly Ser Asp
        115                 120                 125

Ile Ala Gly Ser Thr Ser Thr Leu Gln Glu Gln Ile Ala Trp Met Thr
    130                 135                 140

Asn Asn Pro Pro Ile Pro Val Gly Asp Ile Tyr Lys Arg Trp Ile Ile
145                 150                 155                 160

Met Gly Leu Asn Lys Ile Val Arg Met Tyr Ser Pro Val Ser Ile Leu
                165                 170                 175

Asp Ile Lys Gln Gly Pro Lys Glu Pro Phe Arg Asp Tyr Val Asp Arg
            180                 185                 190

Phe Tyr Arg Thr Leu Arg Ala Glu Gln Ala Ser Gln Asp Val Lys Asn
        195                 200                 205

Trp Met Thr Glu Thr Leu Leu Val Gln Asn Ser Asn Pro Asp Cys Lys
    210                 215                 220

Thr Ile Leu Lys Ala Leu Gly Pro Gly Ala Thr Leu Glu Glu Met Met
225                 230                 235                 240

Ser Ala Cys Gln Gly Val Gly Gly Pro Ser His Lys Ala Arg Val Leu
                245                 250                 255

Ala Glu Ala Met Cys Gln Ala Ala Leu Pro Gly Lys Trp Lys Pro
            260                 265                 270

Lys Met Ile Gly Gly Ile Gly Gly Phe Ile Lys Val Lys Gln Tyr Asp
        275                 280                 285

Gln Ala Ala Ala Gly Thr Val Leu Ile Gly Pro Thr Pro Val Asn Ile
```

```
              290                 295                 300
Ile Gly Arg Asn Leu Leu Thr Gln Leu Gly Cys Thr Leu Asn Phe Pro
305                 310                 315                 320

Ile Ser Pro Ile Asp Thr Val Pro Val Lys Leu Lys Pro Gly Met Asp
                325                 330                 335

Gly Pro Arg Val Lys Gln Trp Pro Leu Thr Glu Glu Lys Ile Lys Ala
                340                 345                 350

Leu Ile Glu Ile Cys Thr Glu Met Glu Lys Glu Gly Lys Ile Ser Arg
                355                 360                 365

Ile Gly Pro Glu Asn Pro Tyr Asn Thr Pro Ile Phe Ala Ile Lys Lys
                370                 375                 380

Lys Asp Gly Thr Lys Trp Arg Lys Leu Val Asp Phe Arg Glu Leu Asn
385                 390                 395                 400

Lys Lys Thr Gln Asp Phe Trp Glu Val Gln Leu Gly Ile Pro His Pro
                405                 410                 415

Ser Gly Leu Lys Lys Lys Ser Val Thr Val Leu Asp Ile Gly Asp
                420                 425                 430

Ala Tyr Phe Ser Val Pro Leu Asp Lys Glu Phe Arg Lys Tyr Thr Ala
                435                 440                 445

Phe Thr Val Pro Ser Ala Ala Trp Gly Leu Thr Thr Pro Asp Lys
                450                 455                 460

Lys His Gln Lys Asp Pro Pro Phe Leu Trp Met Gly Tyr Glu Leu His
465                 470                 475                 480

Pro Asp Arg Trp Thr Val Gln Pro Ile Ala Ala Val Ala Lys Glu
                485                 490                 495

Ile Val Ala Cys Cys Asp Lys Cys Gln Leu Lys Gly Glu Ala Ile His
                500                 505                 510

Gly Gln Val Asp Cys Ser Pro Gly Val Trp Gln Leu Asp Cys Thr His
                515                 520                 525

Leu Glu Gly Lys Val Ile Leu Val Ala Val His Val Ala Ser Gly Tyr
530                 535                 540

Met Glu Ala Glu Val Ile Pro Thr Glu Thr Gly Gln Glu Thr Ala Tyr
545                 550                 555                 560

Phe Ile Leu Lys Leu Ala Gly Arg Trp Pro Val Thr Thr Ala Ala Ala
                565                 570                 575

Ala Val Lys Ala Ala Cys Trp Trp Ala Gly Val Lys Gln Glu Phe Gly
                580                 585                 590

Ile Pro Tyr His Pro Gln Ser Gln Gly Val Val Glu Ser Met Asn Asn
                595                 600                 605

Glu Leu Lys Lys Ile Ile Gly Gln Ile Arg Asp Gln Ala Glu Gln Leu
                610                 615                 620

Lys Thr Ala Val Gln Met Ala Val Leu Ile His Asn Phe Lys Arg Lys
625                 630                 635                 640

Gly Gly Ile Gly Glu Tyr Ser Ala Gly Glu Arg Ile Ile Asp Ile Ile
                645                 650                 655

Ala Ala Ala Ala Ile Thr Lys Leu Gln Asn Phe Arg Val Tyr Tyr Arg
                660                 665                 670

Asp Asn Arg Asp Pro Leu Trp Lys Gly Pro Ala Arg Leu Leu Trp Lys
                675                 680                 685

Gly Glu Gly Ala Val Val Ile Gln Asp Asn Ser Glu Ile Lys Val Val
                690                 695                 700

Pro Arg Arg Lys Val Lys Ile Ile Arg Asp Tyr Gly Lys Arg Met Ala
705                 710                 715                 720
```

Gly Asp Asp Cys Val Ala Gly Arg Gln Asp Glu Asp Ala Ala Ala Glu
            725                 730                 735

Glu Val Gly Phe Pro Val Arg Pro Gln Val Pro Leu Arg Pro Met Thr
        740                 745                 750

Tyr Lys Gly Ala Leu Asp Leu Ser His Phe Leu Lys Glu Lys Gly Gly
    755                 760                 765

Leu Glu Gly
    770

<210> SEQ ID NO 347
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Leu Lys His Ile Val Trp Ala Ser Arg Glu Leu Glu Arg Phe Ala Val
1               5                   10                  15

Asn Pro Gly Leu Leu Glu Thr Val Ser Gln Asn Tyr Pro Ile Val Gln
            20                  25                  30

Asn Ile Ser Pro Arg Thr Leu Asn Ala Trp Val Lys Val Val Glu Glu
        35                  40                  45

Lys Ala Phe Ser Pro Glu Val Ile Pro Met Phe Ser Ala Leu Ser Glu
    50                  55                  60

Gly Ala Thr Pro Gln Asp Leu Asn Thr Met Leu Asn Thr Val Gly Gly
65                  70                  75                  80

His Gln Ala Ala Met Gln Met Leu Lys Glu Thr Ile Asn Glu Glu Ala
                85                  90                  95

Ala Glu Trp Asp Arg Leu His Pro Val His Ala Gly Pro Ile Ala Pro
            100                 105                 110

Gly Gln Met Arg Glu Pro Arg Gly Ser Asp Ile Ala Gly Thr Thr Ser
        115                 120                 125

Thr Leu Gln Glu Gln Ile Gly Trp Met Thr Asn Asn Pro Pro Ile Pro
    130                 135                 140

Val Gly Glu Ile Tyr Lys Arg Trp Ile Ile Leu Gly Leu Asn Lys Ile
145                 150                 155                 160

Val Arg Met Tyr Ser Pro Thr Ser Ile Leu Asp Ile Arg Gln Gly Pro
                165                 170                 175

Lys Glu Pro Phe Arg Asp Tyr Val Asp Arg Phe Tyr Lys Thr Leu Arg
            180                 185                 190

Ala Glu Gln Ala Ser Gln Glu Val Lys Asn Trp Met Thr Glu Thr Leu
        195                 200                 205

Leu Val Gln Asn Ala Asn Pro Asp Cys Lys Thr Ile Leu Lys Ala Leu
    210                 215                 220

Gly Pro Ala Ala Thr Leu Glu Glu Met Met Thr Ala Cys Gln Gly Val
225                 230                 235                 240

Gly Gly Pro Gly His Lys Ala Arg Val Leu Ala Glu Ala Met Ser Gln
                245                 250                 255

Arg Ala Lys Arg Ala Pro Val Lys Gln Thr Leu Asn Phe Asp Leu Leu
            260                 265                 270

Lys Leu Ala Gly Asp Val Glu Ser Asn Pro Gly Pro Leu Pro Gly Arg
        275                 280                 285

Trp Lys Pro Lys Met Ile Gly Gly Ile Gly Gly Phe Ile Lys Val Arg

```
            290                 295                 300

Gln Tyr Asp Gln Gly Thr Val Leu Val Gly Pro Thr Val Asn Ile
305                 310                 315                 320

Ile Gly Arg Asn Leu Leu Thr Gln Ile Gly Cys Thr Leu Asn Phe Pro
                325                 330                 335

Ile Ser Pro Ile Glu Thr Val Pro Val Lys Leu Lys Pro Gly Met Asp
                340                 345                 350

Gly Pro Lys Val Lys Gln Trp Pro Leu Thr Glu Glu Lys Ile Lys Ala
                355                 360                 365

Leu Val Glu Ile Cys Thr Glu Met Glu Lys Glu Gly Lys Ile Ser Lys
            370                 375                 380

Ile Gly Pro Glu Asn Pro Tyr Asn Thr Pro Val Phe Ala Ile Lys Lys
385                 390                 395                 400

Lys Asp Ser Thr Lys Trp Arg Lys Leu Val Asp Phe Arg Glu Leu Asn
                405                 410                 415

Lys Arg Thr Gln Asp Phe Trp Glu Val Gln Leu Gly Ile Pro His Pro
                420                 425                 430

Ala Gly Leu Lys Lys Lys Ser Val Thr Val Leu Asp Val Gly Asp
            435                 440                 445

Ala Tyr Phe Ser Val Pro Leu Asp Lys Asp Phe Arg Lys Tyr Thr Ala
            450                 455                 460

Phe Thr Ile Pro Ser Trp Gly Phe Thr Thr Pro Asp Lys Lys His Gln
465                 470                 475                 480

Lys Glu Pro Pro Phe Leu Trp Met Gly Tyr Glu Leu His Pro Asp Lys
                485                 490                 495

Trp Thr Val Gln Pro Ile Val Ala Lys Glu Ile Val Ala Ser Cys Asp
                500                 505                 510

Lys Cys Gln Leu Lys Gly Glu Ala Met His Gly Gln Val Asp Cys Ser
            515                 520                 525

Pro Gly Ile Trp Gln Leu Asp Cys Thr His Leu Glu Gly Lys Ile Ile
            530                 535                 540

Leu Val Ala Val His Val Ala Ser Gly Tyr Ile Glu Ala Glu Val Ile
545                 550                 555                 560

Pro Ala Glu Thr Gly Gln Glu Thr Ala Tyr Phe Leu Leu Lys Leu Ala
                565                 570                 575

Gly Arg Trp Pro Val Lys Thr Thr Val Lys Ala Ala Cys Trp Trp Ala
                580                 585                 590

Gly Ile Lys Gln Glu Phe Gly Ile Pro Tyr Asn Pro Gln Ser Gln Gly
            595                 600                 605

Val Val Glu Ser Met Asn Lys Glu Leu Lys Lys Ile Ile Gly Gln Val
            610                 615                 620

Arg Asp Gln Ala Glu His Leu Lys Thr Ala Val Gln Met Ala Val Phe
625                 630                 635                 640

Ile His Asn Phe Lys Arg Lys Gly Gly Ile Gly Gly Tyr Ser Ala Gly
                645                 650                 655

Glu Arg Ile Val Asp Ile Ile Ala Ile Thr Lys Ile Gln Asn Phe Arg
                660                 665                 670

Val Tyr Tyr Arg Asp Ser Arg Asp Pro Leu Trp Lys Gly Pro Ala Lys
                675                 680                 685

Leu Leu Trp Lys Gly Glu Gly Ala Val Val Ile Gln Asp Asn Ser Asp
            690                 695                 700

Ile Lys Val Val Pro Arg Arg Lys Ala Lys Ile Ile Arg Asp Tyr Gly
705                 710                 715                 720
```

```
Lys Gln Met Ala Gly Asp Asp Cys Val Ala Ser Arg Gln Asp Glu Asp
                725                 730                 735

Arg Ala Lys Arg Ala Pro Val Lys Gln Thr Leu Asn Phe Asp Leu Leu
            740                 745                 750

Lys Leu Ala Gly Asp Val Glu Ser Asn Pro Gly Pro Glu Glu Val Gly
        755                 760                 765

Phe Pro Val Lys Pro Gln Val Pro Leu Arg Pro Met Thr Phe Lys Gly
    770                 775                 780

Ala Leu Asp Leu Ser His Phe Leu Arg Glu Lys Gly Gly Leu Glu Gly
785                 790                 795                 800
```

<210> SEQ ID NO 348
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

```
Leu Lys His Leu Val Trp Ala Ser Arg Glu Leu Glu Arg Phe Ala Leu
1               5                   10                  15

Asn Pro Gly Leu Leu Glu Thr Val Ser Gln Asn Phe Pro Ile Val Gln
            20                  25                  30

Asn Leu Ser Pro Arg Thr Leu Asn Ala Trp Val Lys Val Ile Glu Glu
        35                  40                  45

Lys Ala Phe Ser Pro Glu Val Ile Pro Met Phe Thr Ala Leu Ser Glu
50                  55                  60

Gly Ala Thr Pro His Asp Leu Asn Thr Met Leu Asn Thr Ile Gly Gly
65                  70                  75                  80

His Gln Ala Ala Met Gln Met Leu Lys Asp Thr Ile Asn Glu Glu Ala
                85                  90                  95

Ala Glu Trp Asp Arg Val His Pro Val His Ala Gly Pro Val Ala Pro
            100                 105                 110

Gly Gln Met Arg Asp Pro Arg Gly Ser Asp Ile Ala Gly Ser Thr Ser
        115                 120                 125

Thr Leu Gln Glu Gln Ile Ala Trp Met Thr Asn Asn Pro Pro Ile Pro
130                 135                 140

Val Gly Asp Ile Tyr Lys Arg Trp Ile Ile Met Gly Leu Asn Lys Ile
145                 150                 155                 160

Val Arg Met Tyr Ser Pro Val Ser Ile Leu Asp Ile Lys Gln Gly Pro
                165                 170                 175

Lys Glu Pro Phe Arg Asp Tyr Val Asp Arg Phe Tyr Arg Thr Leu Arg
            180                 185                 190

Ala Glu Gln Ala Ser Gln Asp Val Lys Asn Trp Met Thr Glu Thr Leu
        195                 200                 205

Leu Val Gln Asn Ser Asn Pro Asp Cys Lys Thr Ile Leu Lys Ala Leu
210                 215                 220

Gly Pro Gly Ala Thr Leu Glu Glu Met Met Ser Ala Cys Gln Gly Val
225                 230                 235                 240

Gly Gly Pro Ser His Lys Ala Arg Val Leu Ala Glu Ala Met Cys Gln
                245                 250                 255

Arg Ala Lys Arg Ala Pro Val Lys Gln Thr Leu Asn Phe Asp Leu Leu
            260                 265                 270

Lys Leu Ala Gly Asp Val Glu Ser Asn Pro Gly Pro Leu Pro Gly Lys
```

```
            275                 280                 285
Trp Lys Pro Lys Met Ile Gly Ile Gly Gly Phe Ile Lys Val Lys
290                 295                 300

Gln Tyr Asp Gln Gly Thr Val Leu Ile Gly Pro Thr Pro Val Asn Ile
305             310                 315                 320

Ile Gly Arg Asn Leu Leu Thr Gln Leu Gly Cys Thr Leu Asn Phe Pro
                325                 330                 335

Ile Ser Pro Ile Asp Thr Val Pro Val Lys Leu Lys Pro Gly Met Asp
                340                 345                 350

Gly Pro Arg Val Lys Gln Trp Pro Leu Thr Glu Glu Lys Ile Lys Ala
                355                 360                 365

Leu Ile Glu Ile Cys Thr Glu Met Glu Lys Glu Gly Lys Ile Ser Arg
370                 375                 380

Ile Gly Pro Glu Asn Pro Tyr Asn Thr Pro Ile Phe Ala Ile Lys Lys
385                 390                 395                 400

Lys Asp Gly Thr Lys Trp Arg Lys Leu Val Asp Phe Arg Glu Leu Asn
                405                 410                 415

Lys Lys Thr Gln Asp Phe Trp Glu Val Gln Leu Gly Ile Pro His Pro
                420                 425                 430

Ser Gly Leu Lys Lys Lys Lys Ser Val Thr Val Leu Asp Ile Gly Asp
                435                 440                 445

Ala Tyr Phe Ser Val Pro Leu Asp Lys Glu Phe Arg Lys Tyr Thr Ala
450                 455                 460

Phe Thr Val Pro Ser Trp Gly Leu Thr Thr Pro Asp Lys Lys His Gln
465                 470                 475                 480

Lys Asp Pro Pro Phe Leu Trp Met Gly Tyr Glu Leu His Pro Asp Arg
                485                 490                 495

Trp Thr Val Gln Pro Ile Val Ala Lys Glu Ile Val Ala Cys Cys Asp
                500                 505                 510

Lys Cys Gln Leu Lys Gly Glu Ala Ile His Gly Gln Val Asp Cys Ser
                515                 520                 525

Pro Gly Val Trp Gln Leu Asp Cys Thr His Leu Glu Gly Lys Val Ile
530                 535                 540

Leu Val Ala Val His Val Ala Ser Gly Tyr Met Glu Ala Glu Val Ile
545                 550                 555                 560

Pro Thr Glu Thr Gly Gln Glu Thr Ala Tyr Phe Ile Leu Lys Leu Ala
                565                 570                 575

Gly Arg Trp Pro Val Thr Thr Ala Val Lys Ala Ala Cys Trp Trp Ala
                580                 585                 590

Gly Val Lys Gln Glu Phe Gly Ile Pro Tyr His Pro Gln Ser Gln Gly
                595                 600                 605

Val Val Glu Ser Met Asn Asn Glu Leu Lys Lys Ile Ile Gly Gln Ile
610                 615                 620

Arg Asp Gln Ala Glu Gln Leu Lys Thr Ala Val Gln Met Ala Val Leu
625                 630                 635                 640

Ile His Asn Phe Lys Arg Lys Gly Gly Ile Gly Glu Tyr Ser Ala Gly
                645                 650                 655

Glu Arg Ile Ile Asp Ile Ala Ile Thr Lys Leu Gln Asn Phe Arg
                660                 665                 670

Val Tyr Tyr Arg Asp Asn Arg Asp Pro Leu Trp Lys Gly Pro Ala Arg
                675                 680                 685

Leu Leu Trp Lys Gly Glu Gly Ala Val Val Ile Gln Asp Asn Ser Glu
690                 695                 700
```

```
Ile Lys Val Val Pro Arg Arg Lys Val Lys Ile Ile Arg Asp Tyr Gly
705                 710                 715                 720

Lys Arg Met Ala Gly Asp Asp Cys Val Ala Gly Arg Gln Asp Glu Asp
            725                 730                 735

Arg Ala Lys Arg Ala Pro Val Lys Gln Thr Leu Asn Phe Asp Leu Leu
        740                 745                 750

Lys Leu Ala Gly Asp Val Glu Ser Asn Pro Gly Pro Glu Glu Val Gly
    755                 760                 765

Phe Pro Val Arg Pro Gln Val Pro Leu Arg Pro Met Thr Tyr Lys Gly
770                 775                 780

Ala Leu Asp Leu Ser His Phe Leu Lys Glu Lys Gly Gly Leu Glu Gly
785                 790                 795                 800

<210> SEQ ID NO 349
<211> LENGTH: 744
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Leu Lys His Ile Val Trp Ala Ser Arg Glu Leu Glu Arg Phe Ala Val
1               5                   10                  15

Asn Pro Gly Leu Leu Glu Thr Val Ser Gln Asn Tyr Pro Ile Val Gln
            20                  25                  30

Asn Ile Ser Pro Arg Thr Leu Asn Ala Trp Val Lys Val Val Glu Glu
        35                  40                  45

Lys Ala Phe Ser Pro Glu Val Ile Pro Met Phe Ser Ala Leu Ser Glu
    50                  55                  60

Gly Ala Thr Pro Gln Asp Leu Asn Thr Met Leu Asn Thr Val Gly Gly
65                  70                  75                  80

His Gln Ala Ala Met Gln Met Leu Lys Glu Thr Ile Asn Glu Glu Ala
                85                  90                  95

Ala Glu Trp Asp Arg Leu His Pro Val His Ala Gly Pro Ile Ala Pro
            100                 105                 110

Gly Gln Met Arg Glu Pro Arg Gly Ser Asp Ile Ala Gly Thr Thr Ser
        115                 120                 125

Thr Leu Gln Glu Gln Ile Gly Trp Met Thr Asn Asn Pro Pro Ile Pro
    130                 135                 140

Val Gly Glu Ile Tyr Lys Arg Trp Ile Ile Leu Gly Leu Asn Lys Ile
145                 150                 155                 160

Val Arg Met Tyr Ser Pro Thr Ser Ile Leu Asp Ile Arg Gln Gly Pro
                165                 170                 175

Lys Glu Pro Phe Arg Asp Tyr Val Asp Arg Phe Tyr Lys Thr Leu Arg
            180                 185                 190

Ala Glu Gln Ala Ser Gln Glu Val Lys Asn Trp Met Thr Glu Thr Leu
        195                 200                 205

Leu Val Gln Asn Ala Asn Pro Asp Cys Lys Thr Ile Leu Lys Ala Leu
    210                 215                 220

Gly Pro Ala Ala Thr Leu Glu Glu Met Met Thr Ala Cys Gln Gly Val
225                 230                 235                 240

Gly Gly Pro Gly His Lys Ala Arg Val Leu Ala Glu Ala Met Ser Gln
                245                 250                 255

Leu Pro Gly Arg Trp Lys Pro Lys Met Ile Gly Gly Ile Gly Gly Phe
```

-continued

```
                260                 265                 270
Ile Lys Val Arg Gln Tyr Asp Gln Gly Thr Val Leu Val Gly Pro Thr
            275                 280                 285

Pro Val Asn Ile Ile Gly Arg Asn Leu Leu Thr Gln Ile Gly Cys Thr
        290                 295                 300

Leu Asn Phe Pro Ile Ser Pro Ile Glu Thr Val Pro Val Lys Leu Lys
305                 310                 315                 320

Pro Gly Met Asp Gly Pro Lys Val Lys Gln Trp Pro Leu Thr Glu Glu
                325                 330                 335

Lys Ile Lys Ala Leu Val Glu Ile Cys Thr Glu Met Glu Lys Glu Gly
            340                 345                 350

Lys Ile Ser Lys Ile Gly Pro Glu Asn Pro Tyr Asn Thr Pro Val Phe
        355                 360                 365

Ala Ile Lys Lys Lys Asp Ser Thr Lys Trp Arg Lys Leu Val Asp Phe
    370                 375                 380

Arg Glu Leu Asn Lys Arg Thr Gln Asp Phe Trp Glu Val Gln Leu Gly
385                 390                 395                 400

Ile Pro His Pro Ala Gly Leu Lys Lys Lys Ser Val Thr Val Leu
                405                 410                 415

Asp Val Gly Asp Ala Tyr Phe Ser Val Pro Leu Asp Lys Asp Phe Arg
            420                 425                 430

Lys Tyr Thr Ala Phe Thr Ile Pro Ser Trp Gly Phe Thr Thr Pro Asp
        435                 440                 445

Lys Lys His Gln Lys Glu Pro Pro Phe Leu Trp Met Gly Tyr Glu Leu
    450                 455                 460

His Pro Asp Lys Trp Thr Val Gln Pro Ile Val Ala Lys Glu Ile Val
465                 470                 475                 480

Ala Ser Cys Asp Lys Cys Gln Leu Lys Gly Glu Ala Met His Gly Gln
                485                 490                 495

Val Asp Cys Ser Pro Gly Ile Trp Gln Leu Asp Cys Thr His Leu Glu
            500                 505                 510

Gly Lys Ile Ile Leu Val Ala Val His Val Ala Ser Gly Tyr Ile Glu
        515                 520                 525

Ala Glu Val Ile Pro Ala Glu Thr Gly Gln Glu Thr Ala Tyr Phe Leu
    530                 535                 540

Leu Lys Leu Ala Gly Arg Trp Pro Val Lys Thr Thr Val Lys Ala Ala
545                 550                 555                 560

Cys Trp Trp Ala Gly Ile Lys Gln Glu Phe Gly Ile Pro Tyr Asn Pro
                565                 570                 575

Gln Ser Gln Gly Val Val Glu Ser Met Asn Lys Glu Leu Lys Lys Ile
            580                 585                 590

Ile Gly Gln Val Arg Asp Gln Ala Glu His Leu Lys Thr Ala Val Gln
        595                 600                 605

Met Ala Val Phe Ile His Asn Phe Lys Arg Lys Gly Gly Ile Gly Gly
    610                 615                 620

Tyr Ser Ala Gly Glu Arg Ile Val Asp Ile Ile Ala Ile Thr Lys Ile
625                 630                 635                 640

Gln Asn Phe Arg Val Tyr Tyr Arg Asp Ser Arg Asp Pro Leu Trp Lys
                645                 650                 655

Gly Pro Ala Lys Leu Leu Trp Lys Gly Glu Gly Ala Val Val Ile Gln
            660                 665                 670

Asp Asn Ser Asp Ile Lys Val Val Pro Arg Arg Lys Ala Lys Ile Ile
        675                 680                 685
```

```
Arg Asp Tyr Gly Lys Gln Met Ala Gly Asp Asp Cys Val Ala Ser Arg
        690                 695                 700

Gln Asp Glu Asp Glu Val Gly Phe Pro Val Lys Pro Gln Val Pro
705                 710                 715                 720

Leu Arg Pro Met Thr Phe Lys Gly Ala Leu Asp Leu Ser His Phe Leu
                725                 730                 735

Arg Glu Lys Gly Gly Leu Glu Gly
            740

<210> SEQ ID NO 350
<211> LENGTH: 744
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Leu Lys His Leu Val Trp Ala Ser Arg Glu Leu Glu Arg Phe Ala Leu
1               5                   10                  15

Asn Pro Gly Leu Leu Glu Thr Val Ser Gln Asn Phe Pro Ile Val Gln
            20                  25                  30

Asn Leu Ser Pro Arg Thr Leu Asn Ala Trp Val Lys Val Ile Glu Glu
        35                  40                  45

Lys Ala Phe Ser Pro Glu Val Ile Pro Met Phe Thr Ala Leu Ser Glu
    50                  55                  60

Gly Ala Thr Pro His Asp Leu Asn Thr Met Leu Asn Thr Ile Gly Gly
65                  70                  75                  80

His Gln Ala Ala Met Gln Met Leu Lys Asp Thr Ile Asn Glu Glu Ala
                85                  90                  95

Ala Glu Trp Asp Arg Val His Pro Val His Ala Gly Pro Val Ala Pro
            100                 105                 110

Gly Gln Met Arg Asp Pro Arg Gly Ser Asp Ile Ala Gly Ser Thr Ser
        115                 120                 125

Thr Leu Gln Glu Gln Ile Ala Trp Met Thr Asn Asn Pro Pro Ile Pro
130                 135                 140

Val Gly Asp Ile Tyr Lys Arg Trp Ile Ile Met Gly Leu Asn Lys Ile
145                 150                 155                 160

Val Arg Met Tyr Ser Pro Val Ser Ile Leu Asp Ile Lys Gln Gly Pro
                165                 170                 175

Lys Glu Pro Phe Arg Asp Tyr Val Asp Arg Phe Tyr Arg Thr Leu Arg
            180                 185                 190

Ala Glu Gln Ala Ser Gln Asp Val Lys Asn Trp Met Thr Glu Thr Leu
        195                 200                 205

Leu Val Gln Asn Ser Asn Pro Asp Cys Lys Thr Ile Leu Lys Ala Leu
210                 215                 220

Gly Pro Gly Ala Thr Leu Glu Glu Met Met Ser Ala Cys Gln Gly Val
225                 230                 235                 240

Gly Gly Pro Ser His Lys Ala Arg Val Leu Ala Glu Ala Met Cys Gln
                245                 250                 255

Leu Pro Gly Lys Trp Lys Pro Lys Met Ile Gly Gly Ile Gly Gly Phe
            260                 265                 270

Ile Lys Val Lys Gln Tyr Asp Gln Gly Thr Val Leu Ile Gly Pro Thr
        275                 280                 285

Pro Val Asn Ile Ile Gly Arg Asn Leu Leu Thr Gln Leu Gly Cys Thr
```

```
                290                 295                 300
Leu Asn Phe Pro Ile Ser Pro Ile Asp Thr Val Pro Val Lys Leu Lys
305                 310                 315                 320

Pro Gly Met Asp Gly Pro Arg Val Lys Gln Trp Pro Leu Thr Glu Glu
                325                 330                 335

Lys Ile Lys Ala Leu Ile Glu Ile Cys Thr Glu Met Glu Lys Glu Gly
                340                 345                 350

Lys Ile Ser Arg Ile Gly Pro Glu Asn Pro Tyr Asn Thr Pro Ile Phe
                355                 360                 365

Ala Ile Lys Lys Lys Asp Gly Thr Lys Trp Arg Lys Leu Val Asp Phe
370                 375                 380

Arg Glu Leu Asn Lys Lys Thr Gln Asp Phe Trp Glu Val Gln Leu Gly
385                 390                 395                 400

Ile Pro His Pro Ser Gly Leu Lys Lys Lys Ser Val Thr Val Leu
                405                 410                 415

Asp Ile Gly Asp Ala Tyr Phe Ser Val Pro Leu Asp Lys Glu Phe Arg
                420                 425                 430

Lys Tyr Thr Ala Phe Thr Val Pro Ser Trp Gly Leu Thr Thr Pro Asp
                435                 440                 445

Lys Lys His Gln Lys Asp Pro Pro Phe Leu Trp Met Gly Tyr Glu Leu
450                 455                 460

His Pro Asp Arg Trp Thr Val Gln Pro Ile Val Ala Lys Glu Ile Val
465                 470                 475                 480

Ala Cys Cys Asp Lys Cys Gln Leu Lys Gly Glu Ala Ile His Gly Gln
                485                 490                 495

Val Asp Cys Ser Pro Gly Val Trp Gln Leu Asp Cys Thr His Leu Glu
                500                 505                 510

Gly Lys Val Ile Leu Val Ala Val His Val Ala Ser Gly Tyr Met Glu
                515                 520                 525

Ala Glu Val Ile Pro Thr Glu Thr Gly Gln Glu Thr Ala Tyr Phe Ile
                530                 535                 540

Leu Lys Leu Ala Gly Arg Trp Pro Val Thr Thr Ala Val Lys Ala Ala
545                 550                 555                 560

Cys Trp Trp Ala Gly Val Lys Gln Glu Phe Gly Ile Pro Tyr His Pro
                565                 570                 575

Gln Ser Gln Gly Val Val Glu Ser Met Asn Asn Glu Leu Lys Lys Ile
                580                 585                 590

Ile Gly Gln Ile Arg Asp Gln Ala Glu Gln Leu Lys Thr Ala Val Gln
                595                 600                 605

Met Ala Val Leu Ile His Asn Phe Lys Arg Lys Gly Gly Ile Gly Glu
610                 615                 620

Tyr Ser Ala Gly Glu Arg Ile Ile Asp Ile Ala Ile Thr Lys Leu
625                 630                 635                 640

Gln Asn Phe Arg Val Tyr Tyr Arg Asp Asn Arg Asp Pro Leu Trp Lys
                645                 650                 655

Gly Pro Ala Arg Leu Leu Trp Lys Gly Glu Gly Ala Val Val Ile Gln
                660                 665                 670

Asp Asn Ser Glu Ile Lys Val Val Pro Arg Arg Lys Val Lys Ile Ile
                675                 680                 685

Arg Asp Tyr Gly Lys Arg Met Ala Gly Asp Asp Cys Val Ala Gly Arg
                690                 695                 700

Gln Asp Glu Asp Glu Glu Val Gly Phe Pro Val Arg Pro Gln Val Pro
705                 710                 715                 720
```

```
Leu Arg Pro Met Thr Tyr Lys Gly Ala Leu Asp Leu Ser His Phe Leu
            725                 730                 735

Lys Glu Lys Gly Gly Leu Glu Gly
            740

<210> SEQ ID NO 351
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ala Ala Ile Ser Pro Arg Thr Leu Asn Ala Trp
    50                  55                  60

Val Lys Val Val Glu Glu Lys Ala Phe Ser Pro Glu Val Ile Pro Met
65              70                  75                  80

Phe Ser Ala Leu Ser Glu Gly Ala Thr Pro Gln Asp Leu Asn Thr Met
                85                  90                  95

Leu Asn Thr Val Gly Gly His Gln Ala Ala Met Gln Met Leu Lys Glu
            100                 105                 110

Thr Ile Asn Glu Glu Ala Ala Glu Trp Asp Arg Leu His Pro Val His
        115                 120                 125

Ala Gly Pro Ile Ala Pro Gly Gln Met Arg Glu Pro Arg Gly Ser Asp
    130                 135                 140

Ile Ala Gly Thr Thr Ser Thr Leu Gln Glu Gln Ile Gly Trp Met Thr
145             150                 155                 160

Asn Asn Pro Pro Ile Pro Val Gly Glu Ile Tyr Lys Arg Trp Ile Ile
                165                 170                 175

Leu Gly Leu Asn Lys Ile Val Arg Met Tyr Ser Pro Thr Ser Ile Leu
            180                 185                 190

Asp Ile Arg Gln Gly Pro Lys Glu Pro Phe Arg Asp Tyr Val Asp Arg
        195                 200                 205

Phe Tyr Lys Thr Leu Arg Ala Glu Gln Ala Ser Gln Glu Val Lys Asn
    210                 215                 220

Trp Met Thr Glu Thr Leu Leu Val Gln Asn Ala Asn Pro Asp Cys Lys
225             230                 235                 240

Thr Ile Leu Lys Ala Leu Gly Pro Ala Ala Thr Leu Glu Glu Met Met
                245                 250                 255

Thr Ala Cys Gln Gly Val Gly Gly Pro Gly His Lys Ala Arg Val Leu
            260                 265                 270

Ala Glu Ala Met Ser Gln Glu Val Gly Phe Pro Val Lys Pro Gln
        275                 280                 285

Val Pro Leu Arg Pro Met Thr Phe Lys Gly Ala Leu Asp Leu Ser His
    290                 295                 300

Phe Leu Arg Glu Lys Gly Gly Leu Glu Gly Thr Gln Gly Phe Phe Pro
305             310                 315                 320

Asp Trp Gln Asn Tyr Thr Pro Glu Pro Gly Ile Arg Phe Pro Leu Thr
```

Phe Gly Trp Cys Phe Lys Leu Val Pro Leu
            340                 345

<210> SEQ ID NO 352
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Leu Ser Pro Arg Thr Leu Asn Ala Trp Val Lys Val Ile Glu Glu Lys
1               5                   10                  15

Ala Phe Ser Pro Glu Val Ile Pro Met Phe Thr Ala Leu Ser Glu Gly
            20                  25                  30

Ala Thr Pro His Asp Leu Asn Thr Met Leu Asn Thr Ile Gly Gly His
        35                  40                  45

Gln Ala Ala Met Gln Met Leu Lys Asp Thr Ile Asn Glu Glu Ala Ala
    50                  55                  60

Glu Trp Asp Arg Val His Pro Val His Ala Gly Pro Val Ala Pro Gly
65                  70                  75                  80

Gln Met Arg Asp Pro Arg Gly Ser Asp Ile Ala Gly Ser Thr Ser Thr
                85                  90                  95

Leu Gln Glu Gln Ile Ala Trp Met Thr Asn Asn Pro Pro Ile Pro Val
            100                 105                 110

Gly Asp Ile Tyr Lys Arg Trp Ile Ile Met Gly Leu Asn Lys Ile Val
        115                 120                 125

Arg Met Tyr Ser Pro Val Ser Ile Leu Asp Ile Lys Gln Gly Pro Lys
    130                 135                 140

Glu Pro Phe Arg Asp Tyr Val Asp Arg Phe Tyr Arg Thr Leu Arg Ala
145                 150                 155                 160

Glu Gln Ala Ser Gln Asp Val Lys Asn Trp Met Thr Glu Thr Leu Leu
                165                 170                 175

Val Gln Asn Ser Asn Pro Asp Cys Lys Thr Ile Leu Lys Ala Leu Gly
            180                 185                 190

Pro Gly Ala Thr Leu Glu Glu Met Met Ser Ala Cys Gln Gly Val Gly
        195                 200                 205

Gly Pro Ser His Lys Ala Arg Val Leu Ala Glu Ala Met Cys Gln Met
    210                 215                 220

Gly Ala Arg Ala Ser Ile Leu Ser Gly Gly Lys Leu Asp Lys Trp Glu
225                 230                 235                 240

Lys Ile Arg Leu Arg Pro Gly Gly Arg Lys Lys Tyr Lys Leu Lys His
                245                 250                 255

Ile Val Trp Ala Ser Arg Glu Leu Glu Arg Phe Ala Val Asn Pro Gly
            260                 265                 270

Leu Leu Glu Thr Glu Glu Val Gly Phe Pro Val Arg Pro Gln Val Pro
        275                 280                 285

Leu Arg Pro Met Thr Tyr Lys Gly Ala Leu Asp Leu Ser His Phe Leu
    290                 295                 300

Lys Glu Lys Gly Gly Leu Glu Gly Thr Gln Gly Tyr Phe Pro Asp Trp
305                 310                 315                 320

Gln Asn Tyr Thr Pro Gly Pro Gly Thr Arg Tyr Pro Leu Thr Phe Gly
                325                 330                 335

Trp Cys Phe Lys Leu Val Pro Val
            340

<210> SEQ ID NO 353
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Met Trp Leu Gln Ser Leu Leu Leu Gly Thr Val Ala Cys Ser Ile
1               5                   10                  15

Ser Val Met Gly Ala Arg Ala Ser Val Leu Ser Gly Gly Glu Leu Asp
            20                  25                  30

Arg Trp Glu Lys Ile Arg Leu Arg Pro Gly Gly Lys Lys Lys Tyr Arg
        35                  40                  45

Leu Lys His Ile Val Trp Ala Ser Arg Glu Leu Glu Arg Phe Ala Val
    50                  55                  60

Asn Pro Gly Leu Leu Glu Thr Leu Lys His Ile Val Trp Ala Ser Arg
65                  70                  75                  80

Glu Leu Glu Arg Phe Ala Val Asn Pro Gly Leu Leu Glu Thr Ala Ala
                85                  90                  95

Ile Ser Pro Arg Thr Leu Asn Ala Trp Val Lys Val Glu Glu Lys
            100                 105                 110

Ala Phe Ser Pro Glu Val Ile Pro Met Phe Ser Ala Leu Ser Glu Gly
        115                 120                 125

Ala Thr Pro Gln Asp Leu Asn Thr Met Leu Asn Thr Val Gly Gly His
    130                 135                 140

Gln Ala Ala Met Gln Met Leu Lys Glu Thr Ile Asn Glu Glu Ala Ala
145                 150                 155                 160

Glu Trp Asp Arg Leu His Pro Val His Ala Gly Pro Ile Ala Pro Gly
                165                 170                 175

Gln Met Arg Glu Pro Arg Gly Ser Asp Ile Ala Gly Thr Thr Ser Thr
            180                 185                 190

Leu Gln Glu Gln Ile Gly Trp Met Thr Asn Asn Pro Pro Ile Pro Val
        195                 200                 205

Gly Glu Ile Tyr Lys Arg Trp Ile Ile Leu Gly Leu Asn Lys Ile Val
    210                 215                 220

Arg Met Tyr Ser Pro Thr Ser Ile Leu Asp Ile Arg Gln Gly Pro Lys
225                 230                 235                 240

Glu Pro Phe Arg Asp Tyr Val Asp Arg Phe Tyr Lys Thr Leu Arg Ala
                245                 250                 255

Glu Gln Ala Ser Gln Glu Val Lys Asn Trp Met Thr Glu Thr Leu Leu
            260                 265                 270

Val Gln Asn Ala Asn Pro Asp Cys Lys Thr Ile Leu Lys Ala Leu Gly
        275                 280                 285

Pro Ala Ala Thr Leu Glu Glu Met Met Thr Ala Cys Gln Gly Val Gly
    290                 295                 300

Gly Pro Gly His Lys Ala Arg Val Leu Ala Glu Ala Met Ser Gln Glu
305                 310                 315                 320

Glu Val Gly Phe Pro Val Lys Pro Gln Val Pro Leu Arg Pro Met Thr
                325                 330                 335

Phe Lys Gly Ala Leu Asp Leu Ser His Phe Leu Arg Glu Lys Gly Gly
            340                 345                 350

```
Leu Glu Gly Thr Gln Gly Phe Phe Pro Asp Gln Asn Tyr Thr Pro Glu
            355                 360                 365

Pro Gly Ile Arg Phe Pro Leu Thr Phe Gly Trp Cys Phe Lys Leu Val
    370                 375                 380

Pro Leu
385

<210> SEQ ID NO 354
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Met Asp Ala Met Lys Arg Gly Leu Cys Cys Val Leu Leu Leu Cys Gly
1               5                   10                  15

Ala Val Phe Val Ser Ala Arg Met Gly Ala Arg Ala Ser Val Leu Ser
            20                  25                  30

Gly Gly Glu Leu Asp Arg Trp Glu Lys Ile Arg Leu Arg Pro Gly Gly
        35                  40                  45

Lys Lys Lys Tyr Arg Leu Lys His Ile Val Trp Ala Ser Arg Glu Leu
    50                  55                  60

Glu Arg Phe Ala Val Asn Pro Gly Leu Leu Glu Thr Leu Lys His Ile
65                  70                  75                  80

Val Trp Ala Ser Arg Glu Leu Glu Arg Phe Ala Val Asn Pro Gly Leu
                85                  90                  95

Leu Glu Thr Ala Ala Ile Ser Pro Arg Thr Leu Asn Ala Trp Val Lys
            100                 105                 110

Val Val Glu Glu Lys Ala Phe Ser Pro Glu Val Ile Pro Met Phe Ser
        115                 120                 125

Ala Leu Ser Glu Gly Ala Thr Pro Gln Asp Leu Asn Thr Met Leu Asn
    130                 135                 140

Thr Val Gly Gly His Gln Ala Ala Met Gln Met Leu Lys Glu Thr Ile
145                 150                 155                 160

Asn Glu Glu Ala Ala Glu Trp Asp Arg Leu His Pro Val His Ala Gly
                165                 170                 175

Pro Ile Ala Pro Gly Gln Met Arg Glu Pro Arg Gly Ser Asp Ile Ala
            180                 185                 190

Gly Thr Thr Ser Thr Leu Gln Glu Gln Ile Gly Trp Met Thr Asn Asn
        195                 200                 205

Pro Pro Ile Pro Val Gly Glu Ile Tyr Lys Arg Trp Ile Ile Leu Gly
    210                 215                 220

Leu Asn Lys Ile Val Arg Met Tyr Ser Pro Thr Ser Ile Leu Asp Ile
225                 230                 235                 240

Arg Gln Gly Pro Lys Glu Pro Phe Arg Asp Tyr Val Asp Arg Phe Tyr
                245                 250                 255

Lys Thr Leu Arg Ala Glu Gln Ala Ser Gln Glu Val Lys Asn Trp Met
            260                 265                 270

Thr Glu Thr Leu Leu Val Gln Asn Ala Asn Pro Asp Cys Lys Thr Ile
        275                 280                 285

Leu Lys Ala Leu Gly Pro Ala Ala Thr Leu Glu Glu Met Met Thr Ala
    290                 295                 300

Cys Gln Gly Val Gly Gly Pro Gly His Lys Ala Arg Val Leu Ala Glu
```

```
                305                 310                 315                 320
Ala Met Ser Gln Glu Glu Val Gly Phe Pro Val Lys Pro Gln Val Pro
                    325                 330                 335

Leu Arg Pro Met Thr Phe Lys Gly Ala Leu Asp Leu Ser His Phe Leu
                340                 345                 350

Arg Glu Lys Gly Gly Leu Glu Gly Thr Gln Gly Phe Phe Pro Asp Gln
                355                 360                 365

Asn Tyr Thr Pro Glu Pro Gly Ile Arg Phe Pro Leu Thr Phe Gly Trp
            370                 375                 380

Cys Phe Lys Leu Val Pro Leu
385                 390

<210> SEQ ID NO 355
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Met Asn Pro Ser Ala Ala Val Ile Phe Cys Leu Ile Leu Leu Gly Leu
1               5                   10                  15

Ser Gly Thr Gln Gly Ile Leu Asp Met Ala Gln Pro Val Gly Ile Asn
            20                  25                  30

Thr Ser Thr Thr Cys Cys Tyr Arg Phe Ile Asn Lys Lys Ile Pro Lys
        35                  40                  45

Gln Arg Leu Glu Ser Tyr Arg Arg Thr Thr Ser Ser His Cys Pro Arg
    50                  55                  60

Glu Ala Val Ile Phe Lys Thr Lys Leu Asp Lys Glu Ile Cys Ala Asp
65                  70                  75                  80

Pro Thr Gln Lys Trp Val Gln Asp Phe Met Lys His Leu Asp Lys Lys
                85                  90                  95

Thr Gln Thr Pro Lys Leu Ala Ser Ala Gly Ala Met Gly Ala Arg Ala
            100                 105                 110

Ser Val Leu Ser Gly Gly Glu Leu Asp Arg Trp Glu Lys Ile Arg Leu
        115                 120                 125

Arg Pro Gly Gly Lys Lys Lys Tyr Arg Leu Lys His Ile Val Trp Ala
    130                 135                 140

Ser Arg Glu Leu Glu Arg Phe Ala Val Asn Pro Gly Leu Leu Glu Thr
145                 150                 155                 160

Leu Lys His Ile Val Trp Ala Ser Arg Glu Leu Glu Arg Phe Ala Val
                165                 170                 175

Asn Pro Gly Leu Leu Glu Thr Ala Ala Ile Ser Pro Arg Thr Leu Asn
            180                 185                 190

Ala Trp Val Lys Val Val Glu Glu Lys Ala Phe Ser Pro Glu Val Ile
        195                 200                 205

Pro Met Phe Ser Ala Leu Ser Glu Gly Ala Thr Pro Gln Asp Leu Asn
    210                 215                 220

Thr Met Leu Asn Thr Val Gly Gly His Gln Ala Ala Met Gln Met Leu
225                 230                 235                 240

Lys Glu Thr Ile Asn Glu Glu Ala Ala Glu Trp Asp Arg Leu His Pro
                245                 250                 255

Val His Ala Gly Pro Ile Ala Pro Gly Gln Met Arg Glu Pro Arg Gly
            260                 265                 270
```

```
Ser Asp Ile Ala Gly Thr Thr Ser Thr Leu Gln Glu Gln Ile Gly Trp
            275                 280                 285

Met Thr Asn Asn Pro Pro Ile Pro Val Gly Glu Ile Tyr Lys Arg Trp
        290                 295                 300

Ile Ile Leu Gly Leu Asn Lys Ile Val Arg Met Tyr Ser Pro Thr Ser
305                 310                 315                 320

Ile Leu Asp Ile Arg Gln Gly Pro Lys Glu Pro Phe Arg Asp Tyr Val
                325                 330                 335

Asp Arg Phe Tyr Lys Thr Leu Arg Ala Glu Gln Ala Ser Gln Glu Val
            340                 345                 350

Lys Asn Trp Met Thr Glu Thr Leu Leu Val Gln Asn Ala Asn Pro Asp
        355                 360                 365

Cys Lys Thr Ile Leu Lys Ala Leu Gly Pro Ala Ala Thr Leu Glu Glu
370                 375                 380

Met Met Thr Ala Cys Gln Gly Val Gly Gly Pro Gly His Lys Ala Arg
385                 390                 395                 400

Val Leu Ala Glu Ala Met Ser Gln Glu Val Gly Phe Pro Val Lys
                405                 410                 415

Pro Gln Val Pro Leu Arg Pro Met Thr Phe Lys Gly Ala Leu Asp Leu
            420                 425                 430

Ser His Phe Leu Arg Glu Lys Gly Gly Leu Glu Gly Thr Gln Gly Phe
        435                 440                 445

Phe Pro Asp Gln Asn Tyr Thr Pro Glu Pro Gly Ile Arg Phe Pro Leu
    450                 455                 460

Thr Phe Gly Trp Cys Phe Lys Leu Val Pro Leu
465                 470                 475

<210> SEQ ID NO 356
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Met Arg Lys Ala Ala Val Ser His Trp Gln Gln Ser Tyr Leu Asp
1               5                   10                  15

Ser Gly Ile His Ser Gly Ala Thr Thr Thr Ala Pro Ser Leu Ser Met
            20                  25                  30

Gly Ala Arg Ala Ser Val Leu Ser Gly Gly Glu Leu Asp Arg Trp Glu
        35                  40                  45

Lys Ile Arg Leu Arg Pro Gly Gly Lys Lys Tyr Arg Leu Lys His
    50                  55                  60

Ile Val Trp Ala Ser Arg Glu Leu Glu Arg Phe Ala Val Asn Pro Gly
65                  70                  75                  80

Leu Leu Glu Thr Leu Lys His Ile Val Trp Ala Ser Arg Glu Leu Glu
                85                  90                  95

Arg Phe Ala Val Asn Pro Gly Leu Leu Glu Thr Ala Ala Ile Ser Pro
            100                 105                 110

Arg Thr Leu Asn Ala Trp Val Lys Val Val Glu Glu Lys Ala Phe Ser
        115                 120                 125

Pro Glu Val Ile Pro Met Phe Ser Ala Leu Ser Glu Gly Ala Thr Pro
    130                 135                 140

Gln Asp Leu Asn Thr Met Leu Asn Thr Val Gly Gly His Gln Ala Ala
145                 150                 155                 160
```

```
Met Gln Met Leu Lys Glu Thr Ile Asn Glu Glu Ala Ala Glu Trp Asp
                165                 170                 175

Arg Leu His Pro Val His Ala Gly Pro Ile Ala Pro Gly Gln Met Arg
            180                 185                 190

Glu Pro Arg Gly Ser Asp Ile Ala Gly Thr Thr Ser Thr Leu Gln Glu
        195                 200                 205

Gln Ile Gly Trp Met Thr Asn Asn Pro Pro Ile Pro Val Gly Glu Ile
    210                 215                 220

Tyr Lys Arg Trp Ile Ile Leu Gly Leu Asn Lys Ile Val Arg Met Tyr
225                 230                 235                 240

Ser Pro Thr Ser Ile Leu Asp Ile Arg Gln Gly Pro Lys Glu Pro Phe
                245                 250                 255

Arg Asp Tyr Val Asp Arg Phe Tyr Lys Thr Leu Arg Ala Glu Gln Ala
            260                 265                 270

Ser Gln Glu Val Lys Asn Trp Met Thr Glu Thr Leu Leu Val Gln Asn
        275                 280                 285

Ala Asn Pro Asp Cys Lys Thr Ile Leu Lys Ala Leu Gly Pro Ala Ala
    290                 295                 300

Thr Leu Glu Glu Met Met Thr Ala Cys Gln Gly Val Gly Gly Pro Gly
305                 310                 315                 320

His Lys Ala Arg Val Leu Ala Glu Ala Met Ser Gln Glu Glu Val Gly
                325                 330                 335

Phe Pro Val Lys Pro Gln Val Pro Leu Arg Pro Met Thr Phe Lys Gly
            340                 345                 350

Ala Leu Asp Leu Ser His Phe Leu Arg Glu Lys Gly Gly Leu Glu Gly
        355                 360                 365

Thr Gln Gly Phe Phe Pro Asp Gln Asn Tyr Thr Pro Glu Pro Gly Ile
    370                 375                 380

Arg Phe Pro Leu Thr Phe Gly Trp Cys Phe Lys Leu Val Pro Leu
385                 390                 395

<210> SEQ ID NO 357
<211> LENGTH: 854
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Gly Thr Val Leu Val Gly Pro Thr Pro Val Asn Ile Ile Gly Arg Asn
1               5                   10                  15

Leu Leu Thr Gln Ile Gly Cys Thr Leu Asn Phe Pro Ile Ser Pro Ile
            20                  25                  30

Glu Thr Val Pro Val Lys Leu Lys Pro Gly Met Asp Gly Pro Lys Val
        35                  40                  45

Lys Gln Trp Pro Leu Thr Glu Glu Lys Ile Lys Ala Leu Val Glu Ile
    50                  55                  60

Cys Thr Glu Met Glu Lys Glu Gly Lys Ile Ser Lys Ile Gly Pro Glu
65                  70                  75                  80

Asn Pro Tyr Asn Thr Pro Val Phe Ala Ile Lys Lys Lys Asp Ser Thr
                85                  90                  95

Lys Trp Arg Lys Leu Val Asp Phe Arg Glu Leu Asn Lys Arg Thr Gln
            100                 105                 110

Asp Phe Trp Glu Val Gln Leu Gly Ile Pro His Pro Ala Gly Leu Lys
```

```
            115                 120                 125
Lys Lys Lys Ser Val Thr Val Leu Asp Val Gly Asp Ala Tyr Phe Ser
            130                 135                 140

Val Pro Leu Asp Lys Asp Phe Arg Lys Tyr Thr Ala Phe Thr Ile Pro
145                 150                 155                 160

Ser Ile Asn Asn Glu Thr Pro Gly Ile Arg Tyr Gln Tyr Asn Val Leu
                165                 170                 175

Pro Gln Gly Trp Lys Gly Ser Pro Ala Ile Phe Gln Ser Ser Met Thr
                180                 185                 190

Thr Val Lys Ala Ala Cys Trp Trp Ala Gly Ile Lys Gln Glu Phe Gly
                195                 200                 205

Ile Pro Tyr Asn Pro Gln Ser Gln Gly Val Val Glu Ser Met Asn Lys
            210                 215                 220

Glu Leu Lys Lys Ile Ile Gly Gln Val Arg Asp Gln Ala Glu His Leu
225                 230                 235                 240

Lys Thr Ala Val Gln Met Ala Val Phe Ile His Asn Phe Lys Arg Lys
                245                 250                 255

Gly Gly Ile Gly Gly Tyr Ser Ala Gly Glu Arg Ile Val Asp Ile Ile
                260                 265                 270

Asn Val Ser Thr Val Gln Cys Thr His Gly Ile Arg Pro Val Val Ser
            275                 280                 285

Thr Gln Leu Leu Leu Asn Gly Ser Leu Ala Glu Glu Lys Arg Arg Val
            290                 295                 300

Val Gln Arg Glu Lys Arg Ala Val Gly Ile Gly Ala Met Phe Leu Gly
305                 310                 315                 320

Phe Leu Gly Ala Ala Gly Ser Thr Met Gly Ala Ala Ser Ile Thr Leu
                325                 330                 335

Thr Val Gln Ala Arg Gln Leu Leu Ser Gly Ile Val Gln Gln Gln Asn
                340                 345                 350

Asn Leu Leu Arg Ala Ile Glu Ala Gln Gln His Leu Leu Gln Leu Thr
            355                 360                 365

Val Trp Gly Ile Lys Gln Leu Gln Ala Arg Val Leu Ala Val Glu Arg
            370                 375                 380

Tyr Leu Lys Asp Gln Gln Leu Leu Gly Ile Trp Gly Cys Ser Gly Lys
385                 390                 395                 400

Leu Ile Cys Thr Thr Val Ala Lys Glu Ile Val Ala Ser Cys Asp Lys
                405                 410                 415

Cys Gln Leu Lys Gly Glu Ala Met His Gly Gln Val Asp Cys Ser Pro
                420                 425                 430

Gly Ile Trp Gln Leu Asp Cys Thr His Leu Glu Gly Lys Ile Ile Leu
            435                 440                 445

Val Ala Val His Val Ala Ser Gly Tyr Ile Glu Ala Glu Val Ile Pro
            450                 455                 460

Ala Glu Thr Gly Gln Glu Thr Ala Tyr Phe Leu Leu Lys Leu Ala Gly
465                 470                 475                 480

Arg Trp Pro Val Lys Thr Leu Trp Val Thr Val Tyr Tyr Gly Val Pro
                485                 490                 495

Val Trp Lys Glu Ala Ala Phe Pro Gln Ile Thr Leu Trp Gln Arg Pro
                500                 505                 510

Leu Val Thr Ile Lys Ile Gly Gly Gln Leu Lys Glu Ala Leu Leu Asp
                515                 520                 525

Thr Gly Ala Asp Asp Thr Val Leu Glu Glu Met Asn Leu Pro Gly Arg
            530                 535                 540
```

-continued

Trp Lys Pro Lys Met Ile Gly Gly Ile Gly Gly Phe Ile Lys Val Arg
545                 550                 555                 560

Gln Tyr Asp Gln Ala Ala Ala His Asn Val Trp Ala Thr His Ala
            565                 570                 575

Cys Val Pro Thr Asp Pro Asn Pro Gln Glu Ala Ile Thr Lys Ile Gln
                580                 585                 590

Asn Phe Arg Val Tyr Tyr Arg Asp Ser Arg Asp Pro Leu Trp Lys Gly
            595                 600                 605

Pro Ala Lys Leu Leu Trp Lys Gly Glu Gly Ala Val Val Ile Gln Asp
            610                 615                 620

Asn Ser Asp Ile Lys Val Val Pro Arg Arg Lys Ala Lys Ile Ile Arg
625                 630                 635                 640

Asp Tyr Gly Lys Gln Met Ala Gly Asp Asp Cys Val Ala Ser Arg Gln
                645                 650                 655

Asp Glu Asp Pro Lys Phe Lys Leu Pro Ile Gln Lys Glu Thr Trp Glu
            660                 665                 670

Thr Trp Trp Thr Glu Tyr Trp Gln Ala Thr Trp Ile Pro Glu Trp Glu
            675                 680                 685

Phe Val Asn Thr Pro Pro Leu Val Lys Leu Trp Tyr Gln Leu Glu Lys
            690                 695                 700

Glu Pro Ile Val Gly Ala Glu Thr Phe Tyr Val Asp Gly Ala Ala Asn
705                 710                 715                 720

Arg Glu Thr Lys Ala Ala Lys Glu Lys Val Tyr Leu Ala Trp Val Pro
                725                 730                 735

Ala His Lys Gly Ile Gly Gly Asn Glu Gln Val Asp Lys Leu Val Ser
            740                 745                 750

Trp Gly Phe Thr Thr Pro Asp Lys Lys His Gln Lys Glu Pro Pro Phe
            755                 760                 765

Leu Trp Met Gly Tyr Glu Leu His Pro Asp Lys Trp Thr Val Gln Pro
            770                 775                 780

Ile Val Leu Pro Glu Lys Asp Ser Trp Thr Val Asn Asp Ile Gln Lys
785                 790                 795                 800

Leu Val Gly Lys Leu Asn Trp Ala Ser Gln Ile Tyr Pro Gly Ile Lys
                805                 810                 815

Val Ile Val Ile Tyr Gln Tyr Met Asp Asp Leu Tyr Val Gly Ser Asp
            820                 825                 830

Leu Glu Ile Gly Gln His Arg Met Arg Asp Asn Trp Arg Ser Glu Leu
            835                 840                 845

Tyr Lys Tyr Lys Val Val
            850

<210> SEQ ID NO 358
<211> LENGTH: 849
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Ala Val Lys Ala Ala Cys Trp Trp Ala Gly Val Lys Gln Glu Phe Gly
1               5                   10                  15

Ile Pro Tyr His Pro Gln Ser Gln Gly Val Val Glu Ser Met Asn Asn
            20                  25                  30

Glu Leu Lys Lys Ile Ile Gly Gln Ile Arg Asp Gln Ala Glu Gln Leu

```
              35                  40                  45
Lys Thr Ala Val Gln Met Ala Val Leu Ile His Asn Phe Lys Arg Lys
 50                  55                  60

Gly Gly Ile Gly Glu Tyr Ser Ala Gly Glu Arg Ile Ile Asp Ile Ile
 65                  70                  75                  80

Arg Arg Arg Val Val Gln Arg Glu Lys Arg Ala Ile Gly Leu Gly Ala
                     85                  90                  95

Val Phe Leu Gly Phe Leu Gly Thr Ala Gly Ser Thr Met Gly Ala Ala
                    100                 105                 110

Ser Met Thr Leu Thr Val Gln Ala Arg Leu Leu Leu Ser Gly Ile Val
                    115                 120                 125

Gln Gln Gln Ser Asn Leu Leu Arg Ala Ile Glu Ala Gln Gln His Met
                    130                 135                 140

Leu Gln Leu Thr Val Trp Gly Ile Lys Gln Leu Gln Ala Arg Ile Leu
145                 150                 155                 160

Ala Val Glu Arg Tyr Leu Arg Asp Gln Gln Leu Leu Gly Ile Trp Gly
                    165                 170                 175

Cys Ser Gly Arg Leu Ile Cys Thr Thr Val Ala Lys Glu Ile Val Ala
                    180                 185                 190

Cys Cys Asp Lys Cys Gln Leu Lys Gly Glu Ala Ile His Gly Gln Val
                    195                 200                 205

Asp Cys Ser Pro Gly Val Trp Gln Leu Asp Cys Thr His Leu Glu Gly
                    210                 215                 220

Lys Val Ile Leu Val Ala Val His Val Ala Ser Gly Tyr Met Glu Ala
225                 230                 235                 240

Glu Val Ile Pro Thr Glu Thr Gly Gln Glu Thr Ala Tyr Phe Ile Leu
                    245                 250                 255

Lys Leu Ala Gly Arg Trp Pro Val Thr Thr Asn Ile Ser Thr Val Gln
                    260                 265                 270

Cys Thr His Gly Ile Lys Pro Val Val Ser Thr Gln Leu Leu Leu Asn
                    275                 280                 285

Gly Ser Leu Ala Glu Lys Trp Gly Leu Thr Thr Pro Asp Lys Lys His
                    290                 295                 300

Gln Lys Asp Pro Pro Phe Leu Trp Met Gly Tyr Glu Leu His Pro Asp
305                 310                 315                 320

Arg Trp Thr Val Gln Pro Ile Glu Leu Pro Glu Lys Glu Ser Trp Thr
                    325                 330                 335

Val Asn Asp Ile Gln Lys Leu Ile Gly Lys Leu Asn Trp Ala Ser Gln
                    340                 345                 350

Ile Tyr Ala Gly Ile Lys Val Ile Val Ile Tyr Gln Tyr Val Asp Asp
                    355                 360                 365

Leu Tyr Val Gly Ser Asp Leu Glu Ile Glu Gln His Arg Pro Lys Phe
                    370                 375                 380

Arg Leu Pro Ile Gln Lys Glu Thr Trp Asp Thr Trp Thr Asp Tyr
385                 390                 395                 400

Trp Gln Ala Thr Trp Ile Pro Glu Trp Glu Phe Thr Asn Thr Pro Pro
                    405                 410                 415

Leu Val Lys Leu Trp Tyr Gln Leu Glu Thr Gly Pro Ile Ala Gly Val
                    420                 425                 430

Glu Thr Phe Tyr Val Asp Gly Ala Ser Asn Arg Glu Thr Lys Leu Pro
                    435                 440                 445

Gln Ile Thr Leu Trp Gln Arg Pro Ile Val Thr Ile Lys Ile Gly Gly
                    450                 455                 460
```

```
Gln Ile Lys Glu Ala Leu Leu Asp Thr Gly Ala Asp Thr Val Leu
465                 470                 475                 480

Glu Asp Met Asn Leu Pro Gly Lys Trp Lys Pro Lys Met Ile Gly Gly
            485                 490                 495

Ile Gly Gly Phe Ile Lys Val Lys Gln Tyr Asp Gln Ala Ala Leu Trp
                500                 505                 510

Val Thr Ile Tyr Tyr Gly Val Pro Val Trp Lys Asp Val His Asn Ile
            515                 520                 525

Trp Ala Thr His Ala Cys Val Pro Thr Asp Pro Ser Pro Gln Glu Ala
            530                 535                 540

Ile Thr Lys Leu Gln Asn Phe Arg Val Tyr Tyr Arg Asp Asn Arg Asp
545                 550                 555                 560

Pro Leu Trp Lys Gly Pro Ala Arg Leu Leu Trp Lys Gly Glu Gly Ala
                565                 570                 575

Val Val Ile Gln Asp Asn Ser Glu Ile Lys Val Val Pro Arg Arg Lys
            580                 585                 590

Val Lys Ile Ile Arg Asp Tyr Gly Lys Arg Met Ala Gly Asp Asp Cys
            595                 600                 605

Val Ala Gly Arg Gln Asp Glu Asp Gly Thr Val Leu Ile Gly Pro Thr
            610                 615                 620

Pro Val Asn Ile Ile Gly Arg Asn Leu Leu Thr Gln Leu Gly Cys Thr
625                 630                 635                 640

Leu Asn Phe Pro Ile Ser Pro Ile Asp Thr Val Pro Val Lys Leu Lys
                645                 650                 655

Pro Gly Met Asp Gly Pro Arg Val Lys Gln Trp Pro Leu Thr Glu Glu
            660                 665                 670

Lys Ile Lys Ala Leu Ile Glu Ile Cys Thr Glu Met Glu Lys Glu Gly
            675                 680                 685

Lys Ile Ser Arg Ile Gly Pro Glu Asn Pro Tyr Asn Thr Pro Ile Phe
            690                 695                 700

Ala Ile Lys Lys Lys Asp Gly Thr Lys Trp Arg Lys Leu Val Asp Phe
705                 710                 715                 720

Arg Glu Leu Asn Lys Lys Thr Gln Asp Phe Trp Glu Val Gln Leu Gly
                725                 730                 735

Ile Pro His Pro Ser Gly Leu Lys Lys Lys Lys Ser Val Thr Val Leu
            740                 745                 750

Asp Ile Gly Asp Ala Tyr Phe Ser Val Pro Leu Asp Lys Glu Phe Arg
            755                 760                 765

Lys Tyr Thr Ala Phe Thr Val Pro Ser Thr Asn Asn Glu Thr Pro Gly
            770                 775                 780

Val Arg Tyr Gln Tyr Asn Val Leu Pro Met Gly Trp Lys Gly Ser Pro
785                 790                 795                 800

Ala Ile Phe Gln Cys Ser Met Thr Lys Glu Lys Ile Tyr Leu Ala Trp
                805                 810                 815

Val Pro Ala His Lys Gly Ile Gly Gly Asn Glu Gln Ile Asp Lys Leu
            820                 825                 830

Val Ser Met Lys Asp Asn Trp Arg Ser Glu Leu Tyr Arg Tyr Lys Val
            835                 840                 845

Val

<210> SEQ ID NO 359
<211> LENGTH: 486
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 359

```
Gly Thr Val Leu Val Gly Pro Thr Pro Val Asn Ile Ile Gly Arg Asn
1               5                   10                  15

Leu Leu Thr Gln Ile Gly Cys Thr Leu Asn Phe Pro Ile Ser Pro Ile
            20                  25                  30

Glu Thr Val Pro Val Lys Leu Lys Pro Gly Met Asp Gly Pro Lys Val
        35                  40                  45

Lys Gln Trp Pro Leu Thr Glu Glu Lys Ile Lys Ala Leu Val Glu Ile
    50                  55                  60

Cys Thr Glu Met Glu Lys Glu Gly Lys Ile Ser Lys Ile Gly Pro Glu
65                  70                  75                  80

Asn Pro Tyr Asn Thr Pro Val Phe Ala Ile Lys Lys Lys Asp Ser Thr
                85                  90                  95

Lys Trp Arg Lys Leu Val Asp Phe Arg Glu Leu Asn Lys Arg Thr Gln
            100                 105                 110

Asp Phe Trp Glu Val Gln Leu Gly Ile Pro His Pro Ala Gly Leu Lys
        115                 120                 125

Lys Lys Lys Ser Val Thr Val Leu Asp Val Gly Asp Ala Tyr Phe Ser
    130                 135                 140

Val Pro Leu Asp Lys Asp Phe Arg Lys Tyr Thr Ala Phe Thr Ile Pro
145                 150                 155                 160

Ser Ile Asn Asn Glu Thr Pro Gly Ile Arg Tyr Gln Tyr Asn Val Leu
                165                 170                 175

Pro Gln Gly Trp Lys Gly Ser Pro Ala Ile Phe Gln Ser Ser Met Thr
            180                 185                 190

Thr Val Lys Ala Ala Cys Trp Trp Ala Gly Ile Lys Gln Glu Phe Gly
        195                 200                 205

Ile Pro Tyr Asn Pro Gln Ser Gln Gly Val Val Glu Ser Met Asn Lys
    210                 215                 220

Glu Leu Lys Lys Ile Ile Gly Gln Val Arg Asp Gln Ala Glu His Leu
225                 230                 235                 240

Lys Thr Ala Val Gln Met Ala Val Phe Ile His Asn Phe Lys Arg Lys
                245                 250                 255

Gly Gly Ile Gly Gly Tyr Ser Ala Gly Glu Arg Ile Val Asp Ile Ile
            260                 265                 270

Asn Val Ser Thr Val Gln Cys Thr His Gly Ile Arg Pro Val Val Ser
        275                 280                 285

Thr Gln Leu Leu Leu Asn Gly Ser Leu Ala Glu Glu Lys Arg Arg Val
    290                 295                 300

Val Gln Arg Glu Lys Arg Ala Val Gly Ile Gly Ala Met Phe Leu Gly
305                 310                 315                 320

Phe Leu Gly Ala Ala Gly Ser Thr Met Gly Ala Ala Ser Ile Thr Leu
                325                 330                 335

Thr Val Gln Ala Arg Gln Leu Leu Ser Gly Ile Val Gln Gln Gln Asn
            340                 345                 350

Asn Leu Leu Arg Ala Ile Glu Ala Gln Gln His Leu Leu Gln Leu Thr
        355                 360                 365

Val Trp Gly Ile Lys Gln Leu Gln Ala Arg Val Leu Ala Val Glu Arg
    370                 375                 380
```

Tyr Leu Lys Asp Gln Gln Leu Leu Gly Ile Trp Gly Cys Ser Gly Lys
385                 390                 395                 400

Leu Ile Cys Thr Thr Val Ala Lys Glu Ile Val Ala Ser Cys Asp Lys
            405                 410                 415

Cys Gln Leu Lys Gly Glu Ala Met His Gly Gln Val Asp Cys Ser Pro
        420                 425                 430

Gly Ile Trp Gln Leu Asp Cys Thr His Leu Glu Gly Lys Ile Ile Leu
        435                 440                 445

Val Ala Val His Val Ala Ser Gly Tyr Ile Glu Ala Glu Val Ile Pro
    450                 455                 460

Ala Glu Thr Gly Gln Glu Thr Ala Tyr Phe Leu Leu Lys Leu Ala Gly
465                 470                 475                 480

Arg Trp Pro Val Lys Thr
                485

<210> SEQ ID NO 360
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Leu Trp Val Thr Val Tyr Tyr Gly Val Pro Val Trp Lys Glu Ala Ala
1               5                   10                  15

Phe Pro Gln Ile Thr Leu Trp Gln Arg Pro Leu Val Thr Ile Lys Ile
            20                  25                  30

Gly Gly Gln Leu Lys Glu Ala Leu Leu Asp Thr Gly Ala Asp Asp Thr
        35                  40                  45

Val Leu Glu Glu Met Asn Leu Pro Gly Arg Trp Lys Pro Lys Met Ile
    50                  55                  60

Gly Gly Ile Gly Gly Phe Ile Lys Val Arg Gln Tyr Asp Gln Ala Ala
65                  70                  75                  80

Ala Ala His Asn Val Trp Ala Thr His Ala Cys Val Pro Thr Asp Pro
                85                  90                  95

Asn Pro Gln Glu Ala Ile Thr Lys Ile Gln Asn Phe Arg Val Tyr Tyr
            100                 105                 110

Arg Asp Ser Arg Asp Pro Leu Trp Lys Gly Pro Ala Lys Leu Leu Trp
        115                 120                 125

Lys Gly Glu Gly Ala Val Val Ile Gln Asp Asn Ser Asp Ile Lys Val
130                 135                 140

Val Pro Arg Arg Lys Ala Lys Ile Ile Arg Asp Tyr Gly Lys Gln Met
145                 150                 155                 160

Ala Gly Asp Asp Cys Val Ala Ser Arg Gln Asp Glu Asp Pro Lys Phe
                165                 170                 175

Lys Leu Pro Ile Gln Lys Glu Thr Trp Glu Thr Trp Trp Thr Glu Tyr
            180                 185                 190

Trp Gln Ala Thr Trp Ile Pro Glu Trp Glu Phe Val Asn Thr Pro Pro
        195                 200                 205

Leu Val Lys Leu Trp Tyr Gln Leu Glu Lys Glu Pro Ile Val Gly Ala
    210                 215                 220

Glu Thr Phe Tyr Val Asp Gly Ala Ala Asn Arg Glu Thr Lys Ala Ala
225                 230                 235                 240

Lys Glu Lys Val Tyr Leu Ala Trp Val Pro Ala His Lys Gly Ile Gly
                245                 250                 255

```
Gly Asn Glu Gln Val Asp Lys Leu Val Ser Trp Gly Phe Thr Thr Pro
            260                 265                 270

Asp Lys Lys His Gln Lys Glu Pro Pro Phe Leu Trp Met Gly Tyr Glu
            275                 280                 285

Leu His Pro Asp Lys Trp Thr Val Gln Pro Ile Val Leu Pro Glu Lys
            290                 295                 300

Asp Ser Trp Thr Val Asn Asp Ile Gln Lys Leu Val Gly Lys Leu Asn
305                 310                 315                 320

Trp Ala Ser Gln Ile Tyr Pro Gly Ile Lys Val Ile Val Ile Tyr Gln
            325                 330                 335

Tyr Met Asp Asp Leu Tyr Val Gly Ser Asp Leu Glu Ile Gly Gln His
            340                 345                 350

Arg Met Arg Asp Asn Trp Arg Ser Glu Leu Tyr Lys Tyr Lys Val Val
            355                 360                 365

<210> SEQ ID NO 361
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Ala Val Lys Ala Ala Cys Trp Trp Ala Gly Val Lys Gln Glu Phe Gly
1               5                   10                  15

Ile Pro Tyr His Pro Gln Ser Gln Gly Val Val Glu Ser Met Asn Asn
            20                  25                  30

Glu Leu Lys Lys Ile Ile Gly Gln Ile Arg Asp Gln Ala Glu Gln Leu
        35                  40                  45

Lys Thr Ala Val Gln Met Ala Val Leu Ile His Asn Phe Lys Arg Lys
    50                  55                  60

Gly Gly Ile Gly Glu Tyr Ser Ala Gly Glu Arg Ile Ile Asp Ile Ile
65                  70                  75                  80

Arg Arg Arg Val Val Gln Arg Glu Lys Arg Ala Ile Gly Leu Gly Ala
                85                  90                  95

Val Phe Leu Gly Phe Leu Gly Thr Ala Gly Ser Thr Met Gly Ala Ala
            100                 105                 110

Ser Met Thr Leu Thr Val Gln Ala Arg Leu Leu Leu Ser Gly Ile Val
        115                 120                 125

Gln Gln Gln Ser Asn Leu Leu Arg Ala Ile Glu Ala Gln Gln His Met
    130                 135                 140

Leu Gln Leu Thr Val Trp Gly Ile Lys Gln Leu Gln Ala Arg Ile Leu
145                 150                 155                 160

Ala Val Glu Arg Tyr Leu Arg Asp Gln Gln Leu Leu Gly Ile Trp Gly
                165                 170                 175

Cys Ser Gly Arg Leu Ile Cys Thr Thr Val Ala Lys Glu Ile Val Ala
            180                 185                 190

Cys Cys Asp Lys Cys Gln Leu Lys Gly Glu Ala Ile His Gly Gln Val
        195                 200                 205

Asp Cys Ser Pro Gly Val Trp Gln Leu Asp Cys Thr His Leu Glu Gly
    210                 215                 220

Lys Val Ile Leu Val Ala Val His Val Ala Ser Gly Tyr Met Glu Ala
225                 230                 235                 240

Glu Val Ile Pro Thr Glu Thr Gly Gln Glu Thr Ala Tyr Phe Ile Leu
```

```
                    245                 250                 255
Lys Leu Ala Gly Arg Trp Pro Val Thr Thr Asn Ile Ser Thr Val Gln
            260                 265                 270

Cys Thr His Gly Ile Lys Pro Val Ser Thr Gln Leu Leu Leu Asn
        275                 280                 285

Gly Ser Leu Ala Glu Lys Trp Gly Leu Thr Thr Pro Asp Lys Lys His
    290                 295                 300

Gln Lys Asp Pro Pro Phe Leu Trp Met Gly Tyr Glu Leu His Pro Asp
305                 310                 315                 320

Arg Trp Thr Val Gln Pro Ile Glu Leu Pro Glu Lys Glu Ser Trp Thr
                325                 330                 335

Val Asn Asp Ile Gln Lys Leu Ile Gly Lys Leu Asn Trp Ala Ser Gln
            340                 345                 350

Ile Tyr Ala Gly Ile Lys Val Ile Val Ile Tyr Gln Tyr Val Asp Asp
        355                 360                 365

Leu Tyr Val Gly Ser Asp Leu Glu Ile Glu Gln His Arg Pro Lys Phe
    370                 375                 380

Arg Leu Pro Ile Gln Lys Glu Thr Trp Asp Thr Trp Thr Asp Tyr
385                 390                 395                 400

Trp Gln Ala Thr Trp Ile Pro Glu Trp Glu Phe Thr Asn Thr Pro Pro
                405                 410                 415

Leu Val Lys Leu Trp Tyr Gln Leu Glu Thr Glu Pro Ile Ala Gly Val
            420                 425                 430

Glu Thr Phe Tyr Val Asp Gly Ala Ser Asn Arg Glu Thr Lys Leu Pro
        435                 440                 445

Gln Ile Thr Leu Trp Gln Arg Pro Ile Val Thr Ile Lys Ile Gly Gly
    450                 455                 460

Gln Ile Lys Glu Ala Leu Leu Asp Thr Gly Ala Asp Asp Thr Val Leu
465                 470                 475                 480

Glu Asp Met Asn Leu Pro Gly Lys Trp Lys Pro Lys Met Ile Gly Gly
                485                 490                 495

Ile Gly Gly Phe Ile Lys Val Lys Gln Tyr Asp Gln Ala Ala
            500                 505                 510

<210> SEQ ID NO 362
<211> LENGTH: 339
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Leu Trp Val Thr Ile Tyr Tyr Gly Val Pro Val Trp Lys Asp Val His
1               5                   10                  15

Asn Ile Trp Ala Thr His Ala Cys Val Pro Thr Asp Pro Ser Pro Gln
            20                  25                  30

Glu Ala Ile Thr Lys Leu Gln Asn Phe Arg Val Tyr Tyr Arg Asp Asn
        35                  40                  45

Arg Asp Pro Leu Trp Lys Gly Pro Ala Arg Leu Leu Trp Lys Gly Glu
    50                  55                  60

Gly Ala Val Val Ile Gln Asp Asn Ser Glu Ile Lys Val Val Pro Arg
65                  70                  75                  80

Arg Lys Val Lys Ile Ile Arg Asp Tyr Gly Lys Arg Met Ala Gly Asp
                85                  90                  95
```

Asp Cys Val Ala Gly Arg Gln Asp Glu Asp Gly Thr Val Leu Ile Gly
            100                 105                 110

Pro Thr Pro Val Asn Ile Ile Gly Arg Asn Leu Leu Thr Gln Leu Gly
        115                 120                 125

Cys Thr Leu Asn Phe Pro Ile Ser Pro Ile Asp Thr Val Pro Val Lys
    130                 135                 140

Leu Lys Pro Gly Met Asp Gly Pro Arg Val Lys Gln Trp Pro Leu Thr
145                 150                 155                 160

Glu Glu Lys Ile Lys Ala Leu Ile Glu Ile Cys Thr Glu Met Glu Lys
                165                 170                 175

Glu Gly Lys Ile Ser Arg Ile Gly Pro Glu Asn Pro Tyr Asn Thr Pro
            180                 185                 190

Ile Phe Ala Ile Lys Lys Lys Asp Gly Thr Lys Trp Arg Lys Leu Val
        195                 200                 205

Asp Phe Arg Glu Leu Asn Lys Lys Thr Gln Asp Phe Trp Glu Val Gln
    210                 215                 220

Leu Gly Ile Pro His Pro Ser Gly Leu Lys Lys Lys Ser Val Thr
225                 230                 235                 240

Val Leu Asp Ile Gly Asp Ala Tyr Phe Ser Val Pro Leu Asp Lys Glu
                245                 250                 255

Phe Arg Lys Tyr Thr Ala Phe Thr Val Pro Ser Thr Asn Asn Glu Thr
            260                 265                 270

Pro Gly Val Arg Tyr Gln Tyr Asn Val Leu Pro Met Gly Trp Lys Gly
        275                 280                 285

Ser Pro Ala Ile Phe Gln Cys Ser Met Thr Lys Glu Lys Ile Tyr Leu
    290                 295                 300

Ala Trp Val Pro Ala His Lys Gly Ile Gly Gly Asn Glu Gln Ile Asp
305                 310                 315                 320

Lys Leu Val Ser Met Lys Asp Asn Trp Arg Ser Glu Leu Tyr Arg Tyr
                325                 330                 335

Lys Val Val

<210> SEQ ID NO 363
<211> LENGTH: 872
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Met Trp Leu Gln Ser Leu Leu Leu Leu Gly Thr Val Ala Cys Ser Ile
1               5                   10                  15

Ser Val Gly Thr Val Leu Val Gly Pro Thr Pro Val Asn Ile Ile Gly
            20                  25                  30

Arg Asn Leu Leu Thr Gln Ile Gly Cys Thr Leu Asn Phe Pro Ile Ser
        35                  40                  45

Pro Ile Glu Thr Val Pro Val Lys Leu Lys Pro Gly Met Asp Gly Pro
    50                  55                  60

Lys Val Lys Gln Trp Pro Leu Thr Glu Glu Lys Ile Lys Ala Leu Val
65                  70                  75                  80

Glu Ile Cys Thr Glu Met Glu Lys Glu Gly Lys Ile Ser Lys Ile Gly
                85                  90                  95

Pro Glu Asn Pro Tyr Asn Thr Pro Val Phe Ala Ile Lys Lys Lys Asp
            100                 105                 110

```
Ser Thr Lys Trp Arg Lys Leu Val Asp Phe Arg Glu Leu Asn Lys Arg
            115                 120                 125

Thr Gln Asp Phe Trp Glu Val Gln Leu Gly Ile Pro His Pro Ala Gly
130                 135                 140

Leu Lys Lys Lys Lys Ser Val Thr Val Leu Asp Val Gly Asp Ala Tyr
145                 150                 155                 160

Phe Ser Val Pro Leu Asp Lys Asp Phe Arg Lys Tyr Thr Ala Phe Thr
                165                 170                 175

Ile Pro Ser Ile Asn Asn Glu Thr Pro Gly Ile Arg Tyr Gln Tyr Asn
            180                 185                 190

Val Leu Pro Gln Gly Trp Lys Gly Ser Pro Ala Ile Phe Gln Ser Ser
        195                 200                 205

Met Thr Thr Val Lys Ala Ala Cys Trp Trp Ala Gly Ile Lys Gln Glu
    210                 215                 220

Phe Gly Ile Pro Tyr Asn Pro Gln Ser Gln Gly Val Val Glu Ser Met
225                 230                 235                 240

Asn Lys Glu Leu Lys Lys Ile Ile Gly Gln Val Arg Asp Gln Ala Glu
                245                 250                 255

His Leu Lys Thr Ala Val Gln Met Ala Val Phe Ile His Asn Phe Lys
            260                 265                 270

Arg Lys Gly Gly Ile Gly Gly Tyr Ser Ala Gly Glu Arg Ile Val Asp
        275                 280                 285

Ile Ile Asn Val Ser Thr Val Gln Cys Thr His Gly Ile Arg Pro Val
    290                 295                 300

Val Ser Thr Gln Leu Leu Leu Asn Gly Ser Leu Ala Glu Glu Lys Arg
305                 310                 315                 320

Arg Val Val Gln Arg Glu Lys Arg Ala Val Gly Ile Gly Ala Met Phe
                325                 330                 335

Leu Gly Phe Leu Gly Ala Ala Gly Ser Thr Met Gly Ala Ala Ser Ile
            340                 345                 350

Thr Leu Thr Val Gln Ala Arg Gln Leu Leu Ser Gly Ile Val Gln Gln
        355                 360                 365

Gln Asn Asn Leu Leu Arg Ala Ile Glu Ala Gln Gln His Leu Leu Gln
370                 375                 380

Leu Thr Val Trp Gly Ile Lys Gln Leu Gln Ala Arg Val Leu Ala Val
385                 390                 395                 400

Glu Arg Tyr Leu Lys Asp Gln Gln Leu Leu Gly Ile Trp Gly Cys Ser
                405                 410                 415

Gly Lys Leu Ile Cys Thr Thr Val Ala Lys Glu Ile Val Ala Ser Cys
            420                 425                 430

Asp Lys Cys Gln Leu Lys Gly Glu Ala Met His Gly Gln Val Asp Cys
        435                 440                 445

Ser Pro Gly Ile Trp Gln Leu Asp Cys Thr His Leu Glu Gly Lys Ile
    450                 455                 460

Ile Leu Val Ala Val His Val Ala Ser Gly Tyr Ile Glu Ala Glu Val
465                 470                 475                 480

Ile Pro Ala Glu Thr Gly Gln Glu Thr Ala Tyr Phe Leu Leu Lys Leu
                485                 490                 495

Ala Gly Arg Trp Pro Val Lys Thr Leu Trp Val Thr Val Tyr Tyr Gly
            500                 505                 510

Val Pro Val Trp Lys Glu Ala Ala Phe Pro Gln Ile Thr Leu Trp Gln
        515                 520                 525

Arg Pro Leu Val Thr Ile Lys Ile Gly Gly Gln Leu Lys Glu Ala Leu
```

```
                530             535             540
Leu Asp Thr Gly Ala Asp Asp Thr Val Leu Glu Glu Met Asn Leu Pro
545                 550                 555                 560

Gly Arg Trp Lys Pro Lys Met Ile Gly Gly Ile Gly Gly Phe Ile Lys
                565                 570                 575

Val Arg Gln Tyr Asp Gln Ala Ala Ala His Asn Val Trp Ala Thr
                580                 585                 590

His Ala Cys Val Pro Thr Asp Pro Asn Pro Gln Glu Ala Ile Thr Lys
                595                 600                 605

Ile Gln Asn Phe Arg Val Tyr Tyr Arg Asp Ser Arg Asp Pro Leu Trp
                610                 615                 620

Lys Gly Pro Ala Lys Leu Leu Trp Lys Gly Glu Gly Ala Val Val Ile
625                 630                 635                 640

Gln Asp Asn Ser Asp Ile Lys Val Val Pro Arg Arg Lys Ala Lys Ile
                645                 650                 655

Ile Arg Asp Tyr Gly Lys Gln Met Ala Gly Asp Asp Cys Val Ala Ser
                660                 665                 670

Arg Gln Asp Glu Asp Pro Lys Phe Lys Leu Pro Ile Gln Lys Glu Thr
                675                 680                 685

Trp Glu Thr Trp Trp Thr Glu Tyr Trp Gln Ala Thr Trp Ile Pro Glu
                690                 695                 700

Trp Glu Phe Val Asn Thr Pro Pro Leu Val Lys Leu Trp Tyr Gln Leu
705                 710                 715                 720

Glu Lys Glu Pro Ile Val Gly Ala Glu Thr Phe Tyr Val Asp Gly Ala
                725                 730                 735

Ala Asn Arg Glu Thr Lys Ala Ala Lys Glu Lys Val Tyr Leu Ala Trp
                740                 745                 750

Val Pro Ala His Lys Gly Ile Gly Gly Asn Glu Gln Val Asp Lys Leu
                755                 760                 765

Val Ser Trp Gly Phe Thr Thr Pro Asp Lys Lys His Gln Lys Glu Pro
770                 775                 780

Pro Phe Leu Trp Met Gly Tyr Glu Leu His Pro Asp Lys Trp Thr Val
785                 790                 795                 800

Gln Pro Ile Val Leu Pro Glu Lys Asp Ser Trp Thr Val Asn Asp Ile
                805                 810                 815

Gln Lys Leu Val Gly Lys Leu Asn Trp Ala Ser Gln Ile Tyr Pro Gly
                820                 825                 830

Ile Lys Val Ile Val Ile Tyr Gln Tyr Met Asp Asp Leu Tyr Val Gly
                835                 840                 845

Ser Asp Leu Glu Ile Gly Gln His Arg Met Arg Asp Asn Trp Arg Ser
850                 855                 860

Glu Leu Tyr Lys Tyr Lys Val Val
865                 870

<210> SEQ ID NO 364
<211> LENGTH: 877
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Met Asp Ala Met Lys Arg Gly Leu Cys Cys Val Leu Leu Leu Cys Gly
1               5                   10                  15
```

-continued

```
Ala Val Phe Val Ser Ala Arg Gly Thr Val Leu Val Gly Pro Thr Pro
            20                  25                  30
Val Asn Ile Ile Gly Arg Asn Leu Leu Thr Gln Ile Gly Cys Thr Leu
        35                  40                  45
Asn Phe Pro Ile Ser Pro Ile Glu Thr Val Pro Val Lys Leu Lys Pro
    50                  55                  60
Gly Met Asp Gly Pro Lys Val Lys Gln Trp Pro Leu Thr Glu Glu Lys
65                  70                  75                  80
Ile Lys Ala Leu Val Glu Ile Cys Thr Glu Met Glu Lys Glu Gly Lys
                85                  90                  95
Ile Ser Lys Ile Gly Pro Glu Asn Pro Tyr Asn Thr Pro Val Phe Ala
            100                 105                 110
Ile Lys Lys Lys Asp Ser Thr Lys Trp Arg Lys Leu Val Asp Phe Arg
        115                 120                 125
Glu Leu Asn Lys Arg Thr Gln Asp Phe Trp Glu Val Gln Leu Gly Ile
    130                 135                 140
Pro His Pro Ala Gly Leu Lys Lys Lys Ser Val Thr Val Leu Asp
145                 150                 155                 160
Val Gly Asp Ala Tyr Phe Ser Val Pro Leu Asp Lys Asp Phe Arg Lys
                165                 170                 175
Tyr Thr Ala Phe Thr Ile Pro Ser Ile Asn Asn Glu Thr Pro Gly Ile
            180                 185                 190
Arg Tyr Gln Tyr Asn Val Leu Pro Gln Gly Trp Lys Gly Ser Pro Ala
        195                 200                 205
Ile Phe Gln Ser Ser Met Thr Thr Val Lys Ala Ala Cys Trp Trp Ala
    210                 215                 220
Gly Ile Lys Gln Glu Phe Gly Ile Pro Tyr Asn Pro Gln Ser Gln Gly
225                 230                 235                 240
Val Val Glu Ser Met Asn Lys Glu Leu Lys Lys Ile Ile Gly Gln Val
                245                 250                 255
Arg Asp Gln Ala Glu His Leu Lys Thr Ala Val Gln Met Ala Val Phe
            260                 265                 270
Ile His Asn Phe Lys Arg Lys Gly Gly Ile Gly Gly Tyr Ser Ala Gly
        275                 280                 285
Glu Arg Ile Val Asp Ile Ile Asn Val Ser Thr Val Gln Cys Thr His
    290                 295                 300
Gly Ile Arg Pro Val Val Ser Thr Gln Leu Leu Leu Asn Gly Ser Leu
305                 310                 315                 320
Ala Glu Glu Lys Arg Arg Val Val Gln Arg Glu Lys Arg Ala Val Gly
                325                 330                 335
Ile Gly Ala Met Phe Leu Gly Phe Leu Gly Ala Ala Gly Ser Thr Met
            340                 345                 350
Gly Ala Ala Ser Ile Thr Leu Thr Val Gln Ala Arg Gln Leu Leu Ser
        355                 360                 365
Gly Ile Val Gln Gln Gln Asn Asn Leu Leu Arg Ala Ile Glu Ala Gln
    370                 375                 380
Gln His Leu Leu Gln Leu Thr Val Trp Gly Ile Lys Gln Leu Gln Ala
385                 390                 395                 400
Arg Val Leu Ala Val Glu Arg Tyr Leu Lys Asp Gln Gln Leu Leu Gly
                405                 410                 415
Ile Trp Gly Cys Ser Gly Lys Leu Ile Cys Thr Thr Val Ala Lys Glu
            420                 425                 430
Ile Val Ala Ser Cys Asp Lys Cys Gln Leu Lys Gly Glu Ala Met His
```

-continued

```
            435                 440                 445
Gly Gln Val Asp Cys Ser Pro Gly Ile Trp Gln Leu Asp Cys Thr His
450                 455                 460

Leu Glu Gly Lys Ile Ile Leu Val Ala Val His Val Ala Ser Gly Tyr
465                 470                 475                 480

Ile Glu Ala Glu Val Ile Pro Ala Glu Thr Gly Gln Glu Thr Ala Tyr
                485                 490                 495

Phe Leu Leu Lys Leu Ala Gly Arg Trp Pro Val Lys Thr Leu Trp Val
                500                 505                 510

Thr Val Tyr Tyr Gly Val Pro Val Trp Lys Glu Ala Ala Phe Pro Gln
            515                 520                 525

Ile Thr Leu Trp Gln Arg Pro Leu Val Thr Ile Lys Ile Gly Gly Gln
530                 535                 540

Leu Lys Glu Ala Leu Leu Asp Thr Gly Ala Asp Asp Thr Val Leu Glu
545                 550                 555                 560

Glu Met Asn Leu Pro Gly Arg Trp Lys Pro Lys Met Ile Gly Gly Ile
                565                 570                 575

Gly Gly Phe Ile Lys Val Arg Gln Tyr Asp Gln Ala Ala Ala His
                580                 585                 590

Asn Val Trp Ala Thr His Ala Cys Val Pro Thr Asp Pro Asn Pro Gln
            595                 600                 605

Glu Ala Ile Thr Lys Ile Gln Asn Phe Arg Val Tyr Tyr Arg Asp Ser
610                 615                 620

Arg Asp Pro Leu Trp Lys Gly Pro Ala Lys Leu Leu Trp Lys Gly Glu
625                 630                 635                 640

Gly Ala Val Val Ile Gln Asp Asn Ser Asp Ile Lys Val Val Pro Arg
                645                 650                 655

Arg Lys Ala Lys Ile Ile Arg Asp Tyr Gly Lys Gln Met Ala Gly Asp
                660                 665                 670

Asp Cys Val Ala Ser Arg Gln Asp Glu Asp Pro Lys Phe Lys Leu Pro
            675                 680                 685

Ile Gln Lys Glu Thr Trp Glu Thr Trp Trp Thr Glu Tyr Trp Gln Ala
            690                 695                 700

Thr Trp Ile Pro Glu Trp Glu Phe Val Asn Thr Pro Pro Leu Val Lys
705                 710                 715                 720

Leu Trp Tyr Gln Leu Glu Lys Glu Pro Ile Val Gly Ala Glu Thr Phe
                725                 730                 735

Tyr Val Asp Gly Ala Ala Asn Arg Glu Thr Lys Ala Ala Lys Glu Lys
                740                 745                 750

Val Tyr Leu Ala Trp Val Pro Ala His Lys Gly Ile Gly Gly Asn Glu
            755                 760                 765

Gln Val Asp Lys Leu Val Ser Trp Gly Phe Thr Thr Pro Asp Lys Lys
            770                 775                 780

His Gln Lys Glu Pro Pro Phe Leu Trp Met Gly Tyr Glu Leu His Pro
785                 790                 795                 800

Asp Lys Trp Thr Val Gln Pro Ile Val Leu Pro Glu Lys Asp Ser Trp
                805                 810                 815

Thr Val Asn Asp Ile Gln Lys Leu Val Gly Lys Leu Asn Trp Ala Ser
                820                 825                 830

Gln Ile Tyr Pro Gly Ile Lys Val Ile Val Tyr Gln Tyr Met Asp
            835                 840                 845

Asp Leu Tyr Val Gly Ser Asp Leu Glu Ile Gly Gln His Arg Met Arg
850                 855                 860
```

Asp Asn Trp Arg Ser Glu Leu Tyr Lys Tyr Lys Val Val
865                 870                 875

<210> SEQ ID NO 365
<211> LENGTH: 961
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Met Asn Pro Ser Ala Val Ile Phe Cys Leu Ile Leu Gly Leu
1               5                   10                  15

Ser Gly Thr Gln Gly Ile Leu Asp Met Ala Gln Pro Val Gly Ile Asn
            20                  25                  30

Thr Ser Thr Thr Cys Cys Tyr Arg Phe Ile Asn Lys Lys Ile Pro Lys
                35                  40                  45

Gln Arg Leu Glu Ser Tyr Arg Arg Thr Ser Ser His Cys Pro Arg
50                  55                  60

Glu Ala Val Ile Phe Lys Thr Lys Leu Asp Lys Glu Ile Cys Ala Asp
65                  70                  75                  80

Pro Thr Gln Lys Trp Val Gln Asp Phe Met Lys His Leu Asp Lys Lys
                85                  90                  95

Thr Gln Thr Pro Lys Leu Ala Ser Ala Gly Ala Gly Thr Val Leu Val
            100                 105                 110

Gly Pro Thr Pro Val Asn Ile Ile Gly Arg Asn Leu Leu Thr Gln Ile
        115                 120                 125

Gly Cys Thr Leu Asn Phe Pro Ile Ser Pro Ile Glu Thr Val Pro Val
    130                 135                 140

Lys Leu Lys Pro Gly Met Asp Gly Pro Lys Val Lys Gln Trp Pro Leu
145                 150                 155                 160

Thr Glu Glu Lys Ile Lys Ala Leu Val Glu Ile Cys Thr Glu Met Glu
                165                 170                 175

Lys Glu Gly Lys Ile Ser Lys Ile Gly Pro Glu Asn Pro Tyr Asn Thr
            180                 185                 190

Pro Val Phe Ala Ile Lys Lys Lys Asp Ser Thr Lys Trp Arg Lys Leu
        195                 200                 205

Val Asp Phe Arg Glu Leu Asn Lys Arg Thr Gln Asp Phe Trp Glu Val
    210                 215                 220

Gln Leu Gly Ile Pro His Pro Ala Gly Leu Lys Lys Lys Ser Val
225                 230                 235                 240

Thr Val Leu Asp Val Gly Asp Ala Tyr Phe Ser Val Pro Leu Asp Lys
                245                 250                 255

Asp Phe Arg Lys Tyr Thr Ala Phe Thr Ile Pro Ser Ile Asn Asn Glu
            260                 265                 270

Thr Pro Gly Ile Arg Tyr Gln Tyr Asn Val Leu Pro Gln Gly Trp Lys
        275                 280                 285

Gly Ser Pro Ala Ile Phe Gln Ser Ser Met Thr Thr Val Lys Ala Ala
    290                 295                 300

Cys Trp Trp Ala Gly Ile Lys Gln Glu Phe Gly Ile Pro Tyr Asn Pro
305                 310                 315                 320

Gln Ser Gln Gly Val Val Glu Ser Met Asn Lys Glu Leu Lys Lys Ile
                325                 330                 335

Ile Gly Gln Val Arg Asp Gln Ala Glu His Leu Lys Thr Ala Val Gln

```
                340                 345                 350
Met Ala Val Phe Ile His Asn Phe Lys Arg Lys Gly Ile Gly Gly
            355                 360                 365
Tyr Ser Ala Gly Glu Arg Ile Val Asp Ile Ile Asn Val Ser Thr Val
            370                 375                 380
Gln Cys Thr His Gly Ile Arg Pro Val Val Ser Thr Gln Leu Leu Leu
385                 390                 395                 400
Asn Gly Ser Leu Ala Glu Glu Lys Arg Arg Val Val Gln Arg Glu Lys
                405                 410                 415
Arg Ala Val Gly Ile Gly Ala Met Phe Leu Gly Phe Leu Gly Ala Ala
                420                 425                 430
Gly Ser Thr Met Gly Ala Ala Ser Ile Thr Leu Thr Val Gln Ala Arg
                435                 440                 445
Gln Leu Leu Ser Gly Ile Val Gln Gln Gln Asn Asn Leu Leu Arg Ala
            450                 455                 460
Ile Glu Ala Gln Gln His Leu Leu Gln Leu Thr Val Trp Gly Ile Lys
465                 470                 475                 480
Gln Leu Gln Ala Arg Val Leu Ala Val Glu Arg Tyr Leu Lys Asp Gln
                485                 490                 495
Gln Leu Leu Gly Ile Trp Gly Cys Ser Gly Lys Leu Ile Cys Thr Thr
            500                 505                 510
Val Ala Lys Glu Ile Val Ala Ser Cys Asp Lys Cys Gln Leu Lys Gly
            515                 520                 525
Glu Ala Met His Gly Gln Val Asp Cys Ser Pro Gly Ile Trp Gln Leu
            530                 535                 540
Asp Cys Thr His Leu Glu Gly Lys Ile Ile Leu Val Ala Val His Val
545                 550                 555                 560
Ala Ser Gly Tyr Ile Glu Ala Glu Val Ile Pro Ala Glu Thr Gly Gln
                565                 570                 575
Glu Thr Ala Tyr Phe Leu Leu Lys Leu Ala Gly Arg Trp Pro Val Lys
                580                 585                 590
Thr Leu Trp Val Thr Val Tyr Tyr Gly Val Pro Val Trp Lys Glu Ala
                595                 600                 605
Ala Phe Pro Gln Ile Thr Leu Trp Gln Arg Pro Leu Val Thr Ile Lys
            610                 615                 620
Ile Gly Gly Gln Leu Lys Glu Ala Leu Leu Asp Thr Gly Ala Asp Asp
625                 630                 635                 640
Thr Val Leu Glu Glu Met Asn Leu Pro Gly Arg Trp Lys Pro Lys Met
                645                 650                 655
Ile Gly Gly Ile Gly Gly Phe Ile Lys Val Arg Gln Tyr Asp Gln Ala
            660                 665                 670
Ala Ala His Asn Val Trp Ala Thr His Ala Cys Val Pro Thr Asp
            675                 680                 685
Pro Asn Pro Gln Glu Ala Ile Thr Lys Ile Gln Asn Phe Arg Val Tyr
            690                 695                 700
Tyr Arg Asp Ser Arg Asp Pro Leu Trp Lys Gly Pro Ala Lys Leu Leu
705                 710                 715                 720
Trp Lys Gly Glu Gly Ala Val Val Ile Gln Asp Asn Ser Asp Ile Lys
                725                 730                 735
Val Val Pro Arg Arg Lys Ala Lys Ile Ile Arg Asp Tyr Gly Lys Gln
            740                 745                 750
Met Ala Gly Asp Asp Cys Val Ala Ser Arg Gln Asp Glu Asp Pro Lys
            755                 760                 765
```

```
Phe Lys Leu Pro Ile Gln Lys Glu Thr Trp Glu Trp Trp Thr Glu
    770                 775                 780
Tyr Trp Gln Ala Thr Trp Ile Pro Glu Trp Glu Phe Val Asn Thr Pro
785                 790                 795                 800
Pro Leu Val Lys Leu Trp Tyr Gln Leu Glu Lys Glu Pro Ile Val Gly
                805                 810                 815
Ala Glu Thr Phe Tyr Val Asp Gly Ala Ala Asn Arg Glu Thr Lys Ala
            820                 825                 830
Ala Lys Glu Lys Val Tyr Leu Ala Trp Val Pro Ala His Lys Gly Ile
        835                 840                 845
Gly Gly Asn Glu Gln Val Asp Lys Leu Val Ser Trp Gly Phe Thr Thr
    850                 855                 860
Pro Asp Lys Lys His Gln Lys Glu Pro Pro Phe Leu Trp Met Gly Tyr
865                 870                 875                 880
Glu Leu His Pro Asp Lys Trp Thr Val Gln Pro Ile Val Leu Pro Glu
                885                 890                 895
Lys Asp Ser Trp Thr Val Asn Asp Ile Gln Lys Leu Val Gly Lys Leu
            900                 905                 910
Asn Trp Ala Ser Gln Ile Tyr Pro Gly Ile Lys Val Ile Val Ile Tyr
        915                 920                 925
Gln Tyr Met Asp Asp Leu Tyr Val Gly Ser Asp Leu Glu Ile Gly Gln
    930                 935                 940
His Arg Met Arg Asp Asn Trp Arg Ser Glu Leu Tyr Lys Tyr Lys Val
945                 950                 955                 960
Val

<210> SEQ ID NO 366
<211> LENGTH: 885
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Met Arg Lys Ala Ala Val Ser His Trp Gln Gln Gln Ser Tyr Leu Asp
1               5                   10                  15
Ser Gly Ile His Ser Gly Ala Thr Thr Thr Ala Pro Ser Leu Ser Gly
            20                  25                  30
Thr Val Leu Val Gly Pro Thr Pro Val Asn Ile Ile Gly Arg Asn Leu
        35                  40                  45
Leu Thr Gln Ile Gly Cys Thr Leu Asn Phe Pro Ile Ser Pro Ile Glu
    50                  55                  60
Thr Val Pro Val Lys Leu Lys Pro Gly Met Asp Gly Pro Lys Val Lys
65                  70                  75                  80
Gln Trp Pro Leu Thr Glu Glu Lys Ile Lys Ala Leu Val Glu Ile Cys
                85                  90                  95
Thr Glu Met Glu Lys Glu Gly Lys Ile Ser Lys Ile Gly Pro Glu Asn
            100                 105                 110
Pro Tyr Asn Thr Pro Val Phe Ala Ile Lys Lys Asp Ser Thr Lys
        115                 120                 125
Trp Arg Lys Leu Val Asp Phe Arg Glu Leu Asn Lys Arg Thr Gln Asp
    130                 135                 140
Phe Trp Glu Val Gln Leu Gly Ile Pro His Pro Ala Gly Leu Lys Lys
145                 150                 155                 160
```

```
Lys Lys Ser Val Thr Val Leu Asp Val Gly Asp Ala Tyr Phe Ser Val
            165                 170                 175

Pro Leu Asp Lys Asp Phe Arg Lys Tyr Thr Ala Phe Thr Ile Pro Ser
        180                 185                 190

Ile Asn Asn Glu Thr Pro Gly Ile Arg Tyr Gln Tyr Asn Val Leu Pro
            195                 200                 205

Gln Gly Trp Lys Gly Ser Pro Ala Ile Phe Gln Ser Ser Met Thr Thr
    210                 215                 220

Val Lys Ala Ala Cys Trp Trp Ala Gly Ile Lys Gln Glu Phe Gly Ile
225                 230                 235                 240

Pro Tyr Asn Pro Gln Ser Gln Gly Val Val Glu Ser Met Asn Lys Glu
                245                 250                 255

Leu Lys Lys Ile Ile Gly Gln Val Arg Asp Gln Ala Glu His Leu Lys
            260                 265                 270

Thr Ala Val Gln Met Ala Val Phe Ile His Asn Phe Lys Arg Lys Gly
        275                 280                 285

Gly Ile Gly Gly Tyr Ser Ala Gly Glu Arg Ile Val Asp Ile Ile Asn
    290                 295                 300

Val Ser Thr Val Gln Cys Thr His Gly Ile Arg Pro Val Val Ser Thr
305                 310                 315                 320

Gln Leu Leu Leu Asn Gly Ser Leu Ala Glu Glu Lys Arg Arg Val Val
                325                 330                 335

Gln Arg Glu Lys Arg Ala Val Gly Ile Gly Ala Met Phe Leu Gly Phe
            340                 345                 350

Leu Gly Ala Ala Gly Ser Thr Met Gly Ala Ala Ser Ile Thr Leu Thr
        355                 360                 365

Val Gln Ala Arg Gln Leu Leu Ser Gly Ile Val Gln Gln Gln Asn Asn
    370                 375                 380

Leu Leu Arg Ala Ile Glu Ala Gln Gln His Leu Leu Gln Leu Thr Val
385                 390                 395                 400

Trp Gly Ile Lys Gln Leu Gln Ala Arg Val Leu Ala Val Glu Arg Tyr
                405                 410                 415

Leu Lys Asp Gln Gln Leu Leu Gly Ile Trp Gly Cys Ser Gly Lys Leu
            420                 425                 430

Ile Cys Thr Thr Val Ala Lys Glu Ile Val Ala Ser Cys Asp Lys Cys
        435                 440                 445

Gln Leu Lys Gly Glu Ala Met His Gly Gln Val Asp Cys Ser Pro Gly
    450                 455                 460

Ile Trp Gln Leu Asp Cys Thr His Leu Glu Gly Lys Ile Ile Leu Val
465                 470                 475                 480

Ala Val His Val Ala Ser Gly Tyr Ile Glu Ala Glu Val Ile Pro Ala
                485                 490                 495

Glu Thr Gly Gln Glu Thr Ala Tyr Phe Leu Leu Lys Leu Ala Gly Arg
            500                 505                 510

Trp Pro Val Lys Thr Leu Trp Val Thr Val Tyr Tyr Gly Val Pro Val
        515                 520                 525

Trp Lys Glu Ala Ala Phe Pro Gln Ile Thr Leu Trp Gln Arg Pro Leu
    530                 535                 540

Val Thr Ile Lys Ile Gly Gly Gln Leu Lys Glu Ala Leu Leu Asp Thr
545                 550                 555                 560

Gly Ala Asp Asp Thr Val Leu Glu Glu Met Asn Leu Pro Gly Arg Trp
                565                 570                 575
```

```
Lys Pro Lys Met Ile Gly Gly Ile Gly Gly Phe Ile Lys Val Arg Gln
                580                 585                 590

Tyr Asp Gln Ala Ala Ala Ala His Asn Val Trp Ala Thr His Ala Cys
            595                 600                 605

Val Pro Thr Asp Pro Asn Pro Gln Glu Ala Ile Thr Lys Ile Gln Asn
610                 615                 620

Phe Arg Val Tyr Tyr Arg Asp Ser Arg Asp Pro Leu Trp Lys Gly Pro
625                 630                 635                 640

Ala Lys Leu Leu Trp Lys Gly Glu Gly Ala Val Val Ile Gln Asp Asn
                645                 650                 655

Ser Asp Ile Lys Val Val Pro Arg Arg Lys Ala Lys Ile Ile Arg Asp
            660                 665                 670

Tyr Gly Lys Gln Met Ala Gly Asp Asp Cys Val Ala Ser Arg Gln Asp
        675                 680                 685

Glu Asp Pro Lys Phe Lys Leu Pro Ile Gln Lys Glu Thr Trp Glu Thr
    690                 695                 700

Trp Trp Thr Glu Tyr Trp Gln Ala Thr Trp Ile Pro Glu Trp Glu Phe
705                 710                 715                 720

Val Asn Thr Pro Pro Leu Val Lys Leu Trp Tyr Gln Leu Glu Lys Glu
                725                 730                 735

Pro Ile Val Gly Ala Glu Thr Phe Tyr Val Asp Gly Ala Ala Asn Arg
            740                 745                 750

Glu Thr Lys Ala Ala Lys Glu Lys Val Tyr Leu Ala Trp Val Pro Ala
        755                 760                 765

His Lys Gly Ile Gly Gly Asn Glu Gln Val Asp Lys Leu Val Ser Trp
    770                 775                 780

Gly Phe Thr Thr Pro Asp Lys Lys His Gln Lys Glu Pro Pro Phe Leu
785                 790                 795                 800

Trp Met Gly Tyr Glu Leu His Pro Asp Lys Trp Thr Val Gln Pro Ile
                805                 810                 815

Val Leu Pro Glu Lys Asp Ser Trp Thr Val Asn Asp Ile Gln Lys Leu
            820                 825                 830

Val Gly Lys Leu Asn Trp Ala Ser Gln Ile Tyr Pro Gly Ile Lys Val
        835                 840                 845

Ile Val Ile Tyr Gln Tyr Met Asp Asp Leu Tyr Val Gly Ser Asp Leu
    850                 855                 860

Glu Ile Gly Gln His Arg Met Arg Asp Asn Trp Arg Ser Glu Leu Tyr
865                 870                 875                 880

Lys Tyr Lys Val Val
                885

<210> SEQ ID NO 367
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Tyr Gln Tyr Asn Val Leu Pro Gln Gly Ala Ser Arg Glu Leu Glu Arg
1               5                   10                  15

Phe Ala Val Asn Pro Gly Leu Leu Trp Ile Ile Leu Gly Leu Asn Lys
            20                  25                  30

Ile Val Arg Met Tyr Ser Pro Thr Ser Ile Ala Ala Arg Thr Leu Asn
        35                  40                  45
```

```
Ala Trp Val Lys Val Phe Leu Trp Met Gly Tyr Glu Leu His Leu Thr
 50                  55                  60

Phe Gly Trp Cys Phe Lys Leu Pro Leu Trp Lys Gly Pro Ala Lys Leu
 65                  70                  75                  80

Val Thr Val Tyr Tyr Gly Val Pro Val Ala Ala Leu Trp Lys Gly
                 85                  90                  95

Glu Gly Ala Val Ala Ala Ala Lys Leu Val Gly Lys Leu Asn Trp Ala
                100                 105                 110

Lys Leu Leu Trp Lys Gly Glu Gly Ala Thr Leu Asn Phe Pro Ile Ser
             115                 120                 125

Pro Ile Trp Gln Ala Thr Trp Ile Pro Glu Trp Lys Ala Ala Cys Trp
130                 135                 140

Trp Ala Gly Ile Arg Gln Ala Asn Phe Leu Gly Lys Ile Trp Pro Ser
145                 150                 155                 160

His Lys Gly Arg Asn Val Trp Ala Thr His Ala Cys Val Ala Ala Glu
                165                 170                 175

Met Met Thr Ala Cys Gln Gly Val Ser Thr Val Gln Cys Thr His Gly
            180                 185                 190

Ile Ala Ala Lys Gln Met Ala Gly Asp Cys Val Ala Trp Gln
        195                 200                 205

Leu Asp Cys Thr His Leu Glu Tyr Lys Ala Ala Val Asp Leu Ser His
210                 215                 220

Phe Leu Arg Glu Lys Gly Gly Leu Glu Gly Ala Ala Tyr Tyr Met Asp
225                 230                 235                 240

Asp Leu Tyr Val Gly Ser Gly Gln Val Asp Cys Ser Pro Gly Ile Ala
                245                 250                 255

Thr Leu Glu Glu Met Met Thr Ala Glu Leu His Pro Asp Lys Trp Thr
            260                 265                 270

Val Trp Thr Val Asn Asp Ile Gln Lys Leu Gly Ile Trp Gly Cys Ser
        275                 280                 285

Gly Lys Leu Thr Val Asn Asp Ile Gln Lys Leu Val Ile Val Thr Asp
    290                 295                 300

Ser Gln Tyr Ala Leu Tyr Val Asp Arg Phe Tyr Lys Thr Leu Arg Ala
305                 310                 315                 320

Glu Gln Ala Ser Gln Glu Val Asp Leu Asn Thr Met Leu Asn Thr Val
                325                 330                 335

Lys Leu Thr Pro Leu Cys Val Thr Leu Tyr Gln Tyr Met Asp Asp Leu
            340                 345                 350

Tyr Val Val Ile Tyr Gln Tyr Met Asp Asp Leu
        355                 360

<210> SEQ ID NO 368
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Met Trp Leu Gln Ser Leu Leu Leu Leu Gly Thr Val Ala Cys Ser Ile
 1               5                  10                  15

Ser Val Tyr Gln Tyr Asn Val Leu Pro Gln Gly Ala Ser Arg Glu Leu
                20                  25                  30

Glu Arg Phe Ala Val Asn Pro Gly Leu Leu Trp Ile Ile Leu Gly Leu
```

35                  40                  45
Asn Lys Ile Val Arg Met Tyr Ser Pro Thr Ser Ile Ala Ala Arg Thr
        50                  55                  60

Leu Asn Ala Trp Val Lys Val Phe Leu Trp Met Gly Tyr Glu Leu His
65                  70                  75                  80

Leu Thr Phe Gly Trp Cys Phe Lys Leu Pro Leu Trp Lys Gly Pro Ala
                85                  90                  95

Lys Leu Val Thr Val Tyr Tyr Gly Val Pro Val Ala Ala Leu Leu Trp
                100                 105                 110

Lys Gly Glu Gly Ala Val Ala Ala Lys Leu Val Gly Lys Leu Asn
        115                 120                 125

Trp Ala Lys Leu Leu Trp Lys Gly Glu Gly Ala Thr Leu Asn Phe Pro
        130                 135                 140

Ile Ser Pro Ile Trp Gln Ala Thr Trp Ile Pro Glu Trp Lys Ala Ala
145                 150                 155                 160

Cys Trp Trp Ala Gly Ile Arg Gln Ala Asn Phe Leu Gly Lys Ile Trp
                165                 170                 175

Pro Ser His Lys Gly Arg Asn Val Trp Ala Thr His Ala Cys Val Ala
                180                 185                 190

Ala Glu Met Met Thr Ala Cys Gln Gly Val Ser Thr Val Gln Cys Thr
        195                 200                 205

His Gly Ile Ala Ala Lys Gln Met Ala Gly Asp Asp Cys Val Ala Ala
        210                 215                 220

Trp Gln Leu Asp Cys Thr His Leu Glu Tyr Lys Ala Ala Val Asp Leu
225                 230                 235                 240

Ser His Phe Leu Arg Glu Lys Gly Gly Leu Glu Gly Ala Ala Tyr Tyr
                245                 250                 255

Met Asp Asp Leu Tyr Val Gly Ser Gly Gln Val Asp Cys Ser Pro Gly
                260                 265                 270

Ile Ala Thr Leu Glu Glu Met Met Thr Ala Glu Leu His Pro Asp Lys
        275                 280                 285

Trp Thr Val Trp Thr Val Asn Asp Ile Gln Lys Leu Gly Ile Trp Gly
        290                 295                 300

Cys Ser Gly Lys Leu Thr Val Asn Asp Ile Gln Lys Leu Val Ile Val
305                 310                 315                 320

Thr Asp Ser Gln Tyr Ala Leu Tyr Val Asp Arg Phe Tyr Lys Thr Leu
                325                 330                 335

Arg Ala Glu Gln Ala Ser Gln Glu Val Asp Leu Asn Thr Met Leu Asn
                340                 345                 350

Thr Val Lys Leu Thr Pro Leu Cys Val Thr Leu Tyr Gln Tyr Met Asp
        355                 360                 365

Asp Leu Tyr Val Val Ile Tyr Gln Tyr Met Asp Asp Leu
        370                 375                 380

<210> SEQ ID NO 369
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Met Asp Ala Met Lys Arg Gly Leu Cys Cys Val Leu Leu Leu Cys Gly
1               5                   10                  15

Ala Val Phe Val Ser Ala Arg Tyr Gln Tyr Asn Val Leu Pro Gln Gly
            20                  25                  30

Ala Ser Arg Glu Leu Glu Arg Phe Ala Val Asn Pro Gly Leu Leu Trp
        35                  40                  45

Ile Ile Leu Gly Leu Asn Lys Ile Val Arg Met Tyr Ser Pro Thr Ser
    50                  55                  60

Ile Ala Ala Arg Thr Leu Asn Ala Trp Val Lys Val Phe Leu Trp Met
65                  70                  75                  80

Gly Tyr Glu Leu His Leu Thr Phe Gly Trp Cys Phe Lys Leu Pro Leu
                85                  90                  95

Trp Lys Gly Pro Ala Lys Leu Val Thr Val Tyr Tyr Gly Val Pro Val
            100                 105                 110

Ala Ala Leu Leu Trp Lys Gly Glu Gly Ala Val Ala Ala Lys Leu
        115                 120                 125

Val Gly Lys Leu Asn Trp Ala Lys Leu Leu Trp Lys Gly Glu Gly Ala
    130                 135                 140

Thr Leu Asn Phe Pro Ile Ser Pro Ile Trp Gln Ala Thr Trp Ile Pro
145                 150                 155                 160

Glu Trp Lys Ala Ala Cys Trp Trp Ala Gly Ile Arg Gln Ala Asn Phe
                165                 170                 175

Leu Gly Lys Ile Trp Pro Ser His Lys Gly Arg Asn Val Trp Ala Thr
            180                 185                 190

His Ala Cys Val Ala Ala Glu Met Met Thr Ala Cys Gln Gly Val Ser
        195                 200                 205

Thr Val Gln Cys Thr His Gly Ile Ala Ala Lys Gln Met Ala Gly Asp
210                 215                 220

Asp Cys Val Ala Ala Trp Gln Leu Asp Cys Thr His Leu Glu Tyr Lys
225                 230                 235                 240

Ala Ala Val Asp Leu Ser His Phe Leu Arg Glu Lys Gly Gly Leu Glu
                245                 250                 255

Gly Ala Ala Tyr Tyr Met Asp Asp Leu Tyr Val Gly Ser Gly Gln Val
            260                 265                 270

Asp Cys Ser Pro Gly Ile Ala Thr Leu Glu Glu Met Met Thr Ala Glu
        275                 280                 285

Leu His Pro Asp Lys Trp Thr Val Trp Thr Val Asn Asp Ile Gln Lys
290                 295                 300

Leu Gly Ile Trp Gly Cys Ser Gly Lys Leu Thr Val Asn Asp Ile Gln
305                 310                 315                 320

Lys Leu Val Ile Val Thr Asp Ser Gln Tyr Ala Leu Tyr Val Asp Arg
                325                 330                 335

Phe Tyr Lys Thr Leu Arg Ala Glu Gln Ala Ser Gln Glu Val Asp Leu
            340                 345                 350

Asn Thr Met Leu Asn Thr Val Lys Leu Thr Pro Leu Cys Val Thr Leu
        355                 360                 365

Tyr Gln Tyr Met Asp Asp Leu Tyr Val Val Ile Tyr Gln Tyr Met Asp
370                 375                 380

Asp Leu
385

<210> SEQ ID NO 370
<211> LENGTH: 470
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 370

```
Met Asn Pro Ser Ala Val Ile Phe Cys Leu Ile Leu Leu Gly Leu
1               5                   10                  15

Ser Gly Thr Gln Gly Ile Leu Asp Met Ala Gln Pro Val Gly Ile Asn
            20                  25                  30

Thr Ser Thr Thr Cys Cys Tyr Arg Phe Ile Asn Lys Lys Ile Pro Lys
            35                  40                  45

Gln Arg Leu Glu Ser Tyr Arg Arg Thr Thr Ser Ser His Cys Pro Arg
    50                  55                  60

Glu Ala Val Ile Phe Lys Thr Lys Leu Asp Lys Glu Ile Cys Ala Asp
65                  70                  75                  80

Pro Thr Gln Lys Trp Val Gln Asp Phe Met Lys His Leu Asp Lys Lys
                85                  90                  95

Thr Gln Thr Pro Lys Leu Ala Ser Ala Gly Ala Tyr Gln Tyr Asn Val
            100                 105                 110

Leu Pro Gln Gly Ala Ser Arg Glu Leu Glu Arg Phe Ala Val Asn Pro
        115                 120                 125

Gly Leu Leu Trp Ile Ile Leu Gly Leu Asn Lys Ile Val Arg Met Tyr
130                 135                 140

Ser Pro Thr Ser Ile Ala Ala Arg Thr Leu Asn Ala Trp Val Lys Val
145                 150                 155                 160

Phe Leu Trp Met Gly Tyr Glu Leu His Leu Thr Phe Gly Trp Cys Phe
                165                 170                 175

Lys Leu Pro Leu Trp Lys Gly Pro Ala Lys Leu Val Thr Val Tyr Tyr
            180                 185                 190

Gly Val Pro Val Ala Ala Leu Leu Trp Lys Gly Glu Gly Ala Val Ala
        195                 200                 205

Ala Ala Lys Leu Val Gly Lys Leu Asn Trp Ala Lys Leu Leu Trp Lys
210                 215                 220

Gly Glu Gly Ala Thr Leu Asn Phe Pro Ile Ser Pro Ile Trp Gln Ala
225                 230                 235                 240

Thr Trp Ile Pro Glu Trp Lys Ala Ala Cys Trp Trp Ala Gly Ile Arg
                245                 250                 255

Gln Ala Asn Phe Leu Gly Lys Ile Trp Pro Ser His Lys Gly Arg Asn
            260                 265                 270

Val Trp Ala Thr His Ala Cys Val Ala Ala Glu Met Met Thr Ala Cys
        275                 280                 285

Gln Gly Val Ser Thr Val Gln Cys Thr His Gly Ile Ala Ala Lys Gln
290                 295                 300

Met Ala Gly Asp Asp Cys Val Ala Ala Trp Gln Leu Asp Cys Thr His
305                 310                 315                 320

Leu Glu Tyr Lys Ala Ala Val Asp Leu Ser His Phe Leu Arg Glu Lys
                325                 330                 335

Gly Gly Leu Glu Gly Ala Ala Tyr Tyr Met Asp Asp Leu Tyr Val Gly
            340                 345                 350

Ser Gly Gln Val Asp Cys Ser Pro Gly Ile Ala Thr Leu Glu Glu Met
        355                 360                 365

Met Thr Ala Glu Leu His Pro Asp Lys Trp Thr Val Trp Thr Val Asn
370                 375                 380

Asp Ile Gln Lys Leu Gly Ile Trp Gly Cys Ser Gly Lys Leu Thr Val
385                 390                 395                 400
```

```
Asn Asp Ile Gln Lys Leu Val Ile Val Thr Asp Ser Gln Tyr Ala Leu
                405                 410                 415

Tyr Val Asp Arg Phe Tyr Lys Thr Leu Arg Ala Glu Gln Ala Ser Gln
            420                 425                 430

Glu Val Asp Leu Asn Thr Met Leu Asn Thr Val Lys Leu Thr Pro Leu
            435                 440                 445

Cys Val Thr Leu Tyr Gln Tyr Met Asp Asp Leu Tyr Val Val Ile Tyr
            450                 455                 460

Gln Tyr Met Asp Asp Leu
465                 470

<210> SEQ ID NO 371
<211> LENGTH: 394
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Met Arg Lys Ala Ala Val Ser His Trp Gln Gln Gln Ser Tyr Leu Asp
1               5                   10                  15

Ser Gly Ile His Ser Gly Ala Thr Thr Thr Ala Pro Ser Leu Ser Tyr
            20                  25                  30

Gln Tyr Asn Val Leu Pro Gln Gly Ala Ser Arg Glu Leu Glu Arg Phe
        35                  40                  45

Ala Val Asn Pro Gly Leu Leu Trp Ile Leu Gly Leu Asn Lys Ile
    50                  55                  60

Val Arg Met Tyr Ser Pro Thr Ser Ile Ala Ala Arg Thr Leu Asn Ala
65                  70                  75                  80

Trp Val Lys Val Phe Leu Trp Met Gly Tyr Glu Leu His Leu Thr Phe
                85                  90                  95

Gly Trp Cys Phe Lys Leu Pro Leu Trp Lys Gly Pro Ala Lys Leu Val
            100                 105                 110

Thr Val Tyr Tyr Gly Val Pro Val Ala Leu Leu Trp Lys Gly Glu
        115                 120                 125

Gly Ala Val Ala Ala Lys Leu Val Gly Lys Leu Asn Trp Ala Lys
    130                 135                 140

Leu Leu Trp Lys Gly Glu Gly Ala Thr Leu Asn Phe Pro Ile Ser Pro
145                 150                 155                 160

Ile Trp Gln Ala Thr Trp Ile Pro Glu Trp Lys Ala Ala Cys Trp Trp
                165                 170                 175

Ala Gly Ile Arg Gln Ala Asn Phe Leu Gly Lys Ile Trp Pro Ser His
            180                 185                 190

Lys Gly Arg Asn Val Trp Ala Thr His Ala Cys Val Ala Ala Glu Met
        195                 200                 205

Met Thr Ala Cys Gln Gly Val Ser Thr Val Gln Cys Thr His Gly Ile
    210                 215                 220

Ala Ala Lys Gln Met Ala Gly Asp Asp Cys Val Ala Ala Trp Gln Leu
225                 230                 235                 240

Asp Cys Thr His Leu Glu Tyr Lys Ala Ala Val Asp Leu Ser His Phe
                245                 250                 255

Leu Arg Glu Lys Gly Gly Leu Glu Gly Ala Ala Tyr Tyr Met Asp Asp
            260                 265                 270

Leu Tyr Val Gly Ser Gly Gln Val Asp Cys Ser Pro Gly Ile Ala Thr
        275                 280                 285
```

```
Leu Glu Glu Met Met Thr Ala Glu Leu His Pro Asp Lys Trp Thr Val
    290                 295                 300

Trp Thr Val Asn Asp Ile Gln Lys Leu Gly Ile Trp Gly Cys Ser Gly
305                 310                 315                 320

Lys Leu Thr Val Asn Asp Ile Gln Lys Leu Val Ile Val Thr Asp Ser
                325                 330                 335

Gln Tyr Ala Leu Tyr Val Asp Arg Phe Tyr Lys Thr Leu Arg Ala Glu
            340                 345                 350

Gln Ala Ser Gln Glu Val Asp Leu Asn Thr Met Leu Asn Thr Val Lys
        355                 360                 365

Leu Thr Pro Leu Cys Val Thr Leu Tyr Gln Tyr Met Asp Asp Leu Tyr
370                 375                 380

Val Val Ile Tyr Gln Tyr Met Asp Asp Leu
385                 390
```

<210> SEQ ID NO 372
<211> LENGTH: 928
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 372

```
Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
        50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
```

```
                   245                 250                 255
Ile Asn Pro Asn Lys Thr Ser Ala Ser Gly Ser Cys Gly Ala His Leu
                260                 265                 270
Val Thr Leu Glu Leu His Ser Glu Gly Thr Thr Val Leu Leu Phe Gln
                275                 280                 285
Phe Gly Met Asn Ala Ser Ser Ser Arg Phe Phe Leu Gln Gly Ile Gln
                290                 295                 300
Leu Asn Thr Leu Leu Pro Asp Ala Arg Asp Pro Ala Phe Lys Ala Ala
305                 310                 315                 320
Asn Gly Ser Leu Arg Ala Leu Gln Ala Thr Val Gly Asn Ser Tyr Lys
                325                 330                 335
Cys Asn Ala Glu Glu His Val Arg Val Thr Lys Ala Phe Ser Val Asn
                340                 345                 350
Ile Phe Lys Val Trp Val Gln Ala Phe Lys Val Glu Gly Gly Gln Phe
                355                 360                 365
Gly Ser Val Glu Glu Cys Leu Leu Asp Glu Asn Ser Leu Glu Asp Ile
                370                 375                 380
Arg Thr Leu Asn Ala Trp Val Lys Val Arg Glu Lys Arg Asp Leu Asn
385                 390                 395                 400
Thr Met Leu Asn Thr Val Arg Glu Lys Arg Trp Ile Ile Leu Gly Leu
                405                 410                 415
Asn Lys Ile Arg Glu Lys Arg Tyr Val Asp Arg Phe Tyr Lys Thr Leu
                420                 425                 430
Arg Glu Lys Arg Ala Thr Leu Glu Glu Met Met Thr Ala Arg Glu Lys
                435                 440                 445
Arg Glu Met Met Thr Ala Cys Gln Gly Val Arg Glu Lys Arg Thr Leu
                450                 455                 460
Asn Phe Pro Ile Ser Pro Ile Arg Glu Lys Arg Tyr Gln Tyr Asn Val
465                 470                 475                 480
Leu Pro Gln Gly Arg Glu Lys Arg Val Ile Tyr Gln Tyr Met Asp Asp
                485                 490                 495
Leu Arg Glu Lys Arg Tyr Gln Tyr Met Asp Asp Leu Tyr Val Arg Glu
                500                 505                 510
Lys Arg Tyr Met Asp Asp Leu Tyr Val Gly Ser Arg Glu Lys Arg Phe
                515                 520                 525
Leu Trp Met Gly Tyr Glu Leu His Arg Glu Lys Arg Glu Leu His Pro
                530                 535                 540
Asp Lys Trp Thr Val Arg Glu Lys Arg Trp Thr Val Asn Asp Ile Gln
545                 550                 555                 560
Lys Leu Arg Glu Lys Arg Thr Val Asn Asp Ile Gln Lys Leu Val Arg
                565                 570                 575
Glu Lys Arg Lys Leu Val Gly Lys Leu Asn Trp Ala Arg Glu Lys Arg
                580                 585                 590
Trp Gln Ala Thr Trp Ile Pro Glu Trp Arg Glu Lys Arg Ile Val Thr
                595                 600                 605
Asp Ser Gln Tyr Ala Leu Arg Glu Lys Arg Gly Gln Val Asp Cys Ser
                610                 615                 620
Pro Gly Ile Arg Glu Lys Arg Trp Gln Leu Asp Cys Thr His Leu Glu
625                 630                 635                 640
Arg Glu Lys Arg Lys Ala Ala Cys Trp Trp Ala Gly Ile Arg Glu Lys
                645                 650                 655
Arg Pro Leu Trp Lys Gly Pro Ala Lys Leu Arg Glu Lys Arg Lys Leu
                660                 665                 670
```

```
Leu Trp Lys Gly Glu Gly Ala Arg Glu Lys Arg Leu Leu Trp Lys Gly
            675                 680                 685

Glu Gly Ala Val Arg Glu Lys Arg Lys Gln Met Ala Gly Asp Asp Cys
    690                 695                 700

Val Arg Glu Lys Arg Val Thr Val Tyr Tyr Gly Val Pro Val Arg Glu
705                 710                 715                 720

Lys Arg Asn Val Trp Ala Thr His Ala Cys Val Arg Glu Lys Arg Lys
                725                 730                 735

Leu Thr Pro Leu Cys Val Thr Leu Arg Glu Lys Arg Ser Thr Val Gln
            740                 745                 750

Cys Thr His Gly Ile Arg Glu Lys Arg Gly Ile Trp Gly Cys Ser Gly
            755                 760                 765

Lys Leu Arg Glu Lys Arg Leu Thr Phe Gly Trp Cys Phe Lys Leu Arg
770                 775                 780

Glu Lys Arg Ala Ser Arg Glu Leu Glu Arg Phe Ala Val Asn Pro Gly
785                 790                 795                 800

Leu Leu Arg Glu Lys Arg Trp Ile Ile Leu Gly Leu Asn Lys Ile Val
                805                 810                 815

Arg Met Tyr Ser Pro Thr Ser Ile Arg Glu Lys Arg Tyr Val Asp Arg
            820                 825                 830

Phe Tyr Lys Thr Leu Arg Ala Glu Gln Ala Ser Gln Glu Val Arg Glu
            835                 840                 845

Lys Arg Arg Gln Ala Asn Phe Leu Gly Lys Ile Trp Pro Ser His Lys
850                 855                 860

Gly Arg Arg Glu Lys Arg Tyr Lys Ala Ala Val Asp Leu Ser His Phe
865                 870                 875                 880

Leu Arg Glu Lys Gly Gly Leu Glu Gly Ser Glu Phe Thr Leu Ile
                885                 890                 895

Pro Ile Ala Val Gly Gly Ala Leu Ala Gly Leu Val Ile Val Leu Ile
            900                 905                 910

Ala Tyr Leu Val Gly Arg Lys Arg Ser His Ala Gly Tyr Gln Thr Ile
            915                 920                 925

<210> SEQ ID NO 373
<211> LENGTH: 847
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Ala Ser Arg Glu Leu Glu Arg Phe Ala Val Asn Pro Gly Leu Leu Gln
1               5                   10                  15

Leu Lys Gly Glu Ala Met His Gly Gln Val Asp Cys Ser Pro Gly Ile
            20                  25                  30

Trp Gln Leu Asp Cys Thr His Leu Cys Ser Ala Thr Glu Lys Leu Trp
        35                  40                  45

Val Thr Val Tyr Tyr Gly Val Pro Val Trp Lys Glu Ala Thr Thr Thr
    50                  55                  60

Leu Pro Val Gly Glu Ile Tyr Lys Arg Trp Ile Ile Leu Gly Leu Asn
65                  70                  75                  80

Lys Ile Val Arg Met Tyr Ser Pro Thr Ser Ile Asn Asn Glu Thr Pro
                85                  90                  95

Gly Ile Arg Tyr Gln Tyr Asn Val Leu Pro Gln Gly Trp Lys Gly Ser
```

```
                100             105                 110
Pro Ala Ile Phe Ala Ala Pro Leu Trp Lys Gly Pro Ala Lys Leu Leu
            115                 120             125

Trp Lys Gly Glu Gly Ala Val Val Ile Gln Asp Asn Ser Asp Ile Ala
        130                 135             140

Ala Ile Val Leu Pro Glu Lys Asp Ser Trp Thr Val Asn Asp Ile Gln
145                 150             155                 160

Lys Leu Val Gly Lys Leu Asn Trp Ala Ser Val Tyr Tyr Arg Asp Ser
                165                 170             175

Arg Asp Pro Leu Trp Lys Gly Pro Ala Lys Leu Leu Trp Lys Gly Glu
            180                 185             190

Gly Ala Val Ser Asn Phe Thr Ser Thr Val Lys Ala Ala Cys Trp
        195                 200             205

Trp Ala Gly Ile Lys Gln Glu Phe Gly Ile Pro Tyr Val Leu Pro Glu
        210                 215             220

Lys Asp Ser Trp Thr Val Asn Asp Ile Gln Lys Leu Val Gly Lys Leu
225                 230             235                 240

Asn Trp Ala Ser Gln Met Val His Gln Ala Ile Ser Pro Arg Thr Leu
                245                 250             255

Asn Ala Trp Val Lys Val Val Glu Glu Lys Ala Phe Ser Pro Ala Ala
            260                 265             270

Trp Glu Thr Trp Trp Thr Glu Tyr Trp Gln Ala Thr Trp Ile Pro Glu
        275                 280             285

Trp Glu Phe Val Asn Thr Pro Pro Leu Gln Asp Ser Gly Leu Glu Val
        290                 295             300

Asn Ile Val Thr Asp Ser Gln Tyr Ala Leu Gly Ile Ile Gln Ala Gln
305                 310             315                 320

Pro Asp Ser Trp Thr Val Asn Asp Ile Gln Lys Leu Val Gly Lys Leu
                325                 330             335

Asn Trp Ala Ser Gln Ile Tyr Pro Gly Ile Lys Asn Pro Asp Ile Val
            340                 345             350

Ile Tyr Gln Tyr Met Asp Asp Leu Tyr Val Gly Ser Asp Leu Glu Ile
        355                 360             365

Gly Gln His Arg Ala Ala Asp Pro Leu Trp Lys Gly Pro Ala Lys Leu
        370                 375             380

Leu Trp Lys Gly Glu Gly Ala Val Val Ile Gln Asp Asn Ser Asp Arg
385                 390             395                 400

Gln Ala Asn Phe Leu Gly Lys Ile Trp Pro Ser His Lys Gly Arg Ala
                405                 410             415

Ala Pro Pro Phe Leu Trp Met Gly Tyr Glu Leu His Pro Asp Lys Trp
            420                 425             430

Thr Val Gln Pro Ile Val Leu Pro Glu Lys Phe Arg Lys Gln Asn Pro
        435                 440             445

Asp Ile Val Ile Tyr Gln Tyr Met Asp Asp Leu Tyr Val Gly Ser Asp
450                 455             460

Leu Glu Ile Asn Leu Leu Thr Gln Ile Gly Cys Thr Leu Asn Phe Pro
465                 470             475                 480

Ile Ser Pro Ile Glu Thr Val Pro Val Lys Leu Lys Gly Pro Lys Glu
                485                 490             495

Pro Phe Arg Asp Tyr Val Asp Arg Phe Tyr Lys Thr Leu Arg Ala Glu
            500                 505             510

Gln Ala Ser Gln Glu Val Tyr Leu Lys Asp Gln Leu Leu Gly Ile
        515                 520             525
```

Trp Gly Cys Ser Gly Lys Leu Ile Cys Thr Thr Ala Val Pro Trp Ala
            530                 535                 540

Ala Ala Lys Lys His Gln Lys Glu Pro Pro Phe Leu Trp Met Gly Tyr
545                 550                 555                 560

Glu Leu His Pro Asp Lys Trp Thr Val Gln Pro Gly Thr Gly Pro Cys
            565                 570                 575

Thr Asn Val Ser Thr Val Gln Cys Thr His Gly Ile Arg Pro Val Val
            580                 585                 590

Ser Thr Gln Leu Lys Gln Asn Pro Asp Ile Val Ile Tyr Gln Tyr Met
            595                 600                 605

Asp Asp Leu Tyr Val Gly Ser Asp Leu Glu Ile Gly Gln Leu Gly Pro
610                 615                 620

Ala Ala Thr Leu Glu Glu Met Met Thr Ala Cys Gln Gly Val Gly Gly
625                 630                 635                 640

Pro Gly His Lys Ala Arg Asp Gln Ser Leu Lys Pro Cys Val Lys Leu
            645                 650                 655

Thr Pro Leu Cys Val Thr Leu Asn Cys Thr Asp Leu Arg Asn Thr Gly
            660                 665                 670

Pro Gly Ile Arg Tyr Pro Leu Leu Thr Phe Gly Trp Cys Phe Lys Leu
            675                 680                 685

Pro Val Glu Pro Glu Lys Val Glu Ala Lys Ile Ile Arg Asp Tyr Gly
690                 695                 700

Lys Gln Met Ala Gly Asp Asp Cys Val Ala Ser Arg Gln Asp Glu Asp
705                 710                 715                 720

Ile Leu Lys Ala Leu Gly Pro Ala Ala Thr Leu Glu Glu Met Met Thr
            725                 730                 735

Ala Cys Gln Gly Val Gly Gly Pro Gly Tyr Lys Ala Ala Val Asp Leu
            740                 745                 750

Ser His Phe Leu Arg Glu Lys Gly Gly Leu Glu Gly Ala Ala Tyr Ala
            755                 760                 765

Ala Lys Ala Tyr Asp Thr Glu Val His Asn Val Trp Ala Thr His Ala
770                 775                 780

Cys Val Pro Thr Asp Pro Asn Pro Gln Glu Ala Ala Leu Ser Glu
785                 790                 795                 800

Gly Ala Thr Pro Gln Asp Leu Asn Thr Met Leu Asn Thr Val Gly Gly
            805                 810                 815

His Gln Ala Ala Met Gln Gln Val Asp Cys Ser Pro Gly Ile Trp Gln
            820                 825                 830

Leu Asp Cys Thr His Leu Glu Gly Lys Ile Ile Leu Val Ala Val
            835                 840                 845

<210> SEQ ID NO 374
<211> LENGTH: 865
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Met Trp Leu Gln Ser Leu Leu Leu Leu Gly Thr Val Ala Cys Ser Ile
1               5                   10                  15

Ser Val Ala Ser Arg Glu Leu Glu Arg Phe Ala Val Asn Pro Gly Leu
            20                  25                  30

Leu Gln Leu Lys Gly Glu Ala Met His Gly Gln Val Asp Cys Ser Pro

-continued

```
                35                  40                  45
Gly Ile Trp Gln Leu Asp Cys Thr His Leu Cys Ser Ala Thr Glu Lys
 50                  55                  60

Leu Trp Val Thr Val Tyr Tyr Gly Val Pro Val Trp Lys Glu Ala Thr
 65                  70                  75                  80

Thr Thr Leu Pro Val Gly Glu Ile Tyr Lys Arg Trp Ile Ile Leu Gly
                 85                  90                  95

Leu Asn Lys Ile Val Arg Met Tyr Ser Pro Thr Ser Ile Asn Asn Glu
                100                 105                 110

Thr Pro Gly Ile Arg Tyr Gln Tyr Asn Val Leu Pro Gln Gly Trp Lys
                115                 120                 125

Gly Ser Pro Ala Ile Phe Ala Ala Pro Leu Trp Lys Gly Pro Ala Lys
                130                 135                 140

Leu Leu Trp Lys Gly Glu Gly Ala Val Val Ile Gln Asp Asn Ser Asp
145                 150                 155                 160

Ile Ala Ala Ile Val Leu Pro Glu Lys Asp Ser Trp Thr Val Asn Asp
                165                 170                 175

Ile Gln Lys Leu Val Gly Lys Leu Asn Trp Ala Ser Val Tyr Tyr Arg
                180                 185                 190

Asp Ser Arg Asp Pro Leu Trp Lys Gly Pro Ala Lys Leu Leu Trp Lys
                195                 200                 205

Gly Glu Gly Ala Val Ser Asn Phe Thr Ser Thr Thr Val Lys Ala Ala
210                 215                 220

Cys Trp Trp Ala Gly Ile Lys Gln Glu Phe Gly Ile Pro Tyr Val Leu
225                 230                 235                 240

Pro Glu Lys Asp Ser Trp Thr Val Asn Asp Ile Gln Lys Leu Val Gly
                245                 250                 255

Lys Leu Asn Trp Ala Ser Gln Met Val His Gln Ala Ile Ser Pro Arg
                260                 265                 270

Thr Leu Asn Ala Trp Val Lys Val Val Glu Glu Lys Ala Phe Ser Pro
                275                 280                 285

Ala Ala Trp Glu Thr Trp Trp Thr Glu Tyr Trp Gln Ala Thr Trp Ile
290                 295                 300

Pro Glu Trp Glu Phe Val Asn Thr Pro Pro Leu Gln Asp Ser Gly Leu
305                 310                 315                 320

Glu Val Asn Ile Val Thr Asp Ser Gln Tyr Ala Leu Gly Ile Ile Gln
                325                 330                 335

Ala Gln Pro Asp Ser Trp Thr Val Asn Asp Ile Gln Lys Leu Val Gly
                340                 345                 350

Lys Leu Asn Trp Ala Ser Gln Ile Tyr Pro Gly Ile Lys Asn Pro Asp
                355                 360                 365

Ile Val Ile Tyr Gln Tyr Met Asp Asp Leu Tyr Val Gly Ser Asp Leu
                370                 375                 380

Glu Ile Gly Gln His Arg Ala Ala Asp Pro Leu Trp Lys Gly Pro Ala
385                 390                 395                 400

Lys Leu Leu Trp Lys Gly Glu Gly Ala Val Val Ile Gln Asp Asn Ser
                405                 410                 415

Asp Arg Gln Ala Asn Phe Leu Gly Lys Ile Trp Pro Ser His Lys Gly
                420                 425                 430

Arg Ala Ala Pro Pro Phe Leu Trp Met Gly Tyr Glu Leu His Pro Asp
                435                 440                 445

Lys Trp Thr Val Gln Pro Ile Val Leu Pro Glu Lys Phe Arg Lys Gln
450                 455                 460
```

```
Asn Pro Asp Ile Val Ile Tyr Gln Tyr Met Asp Asp Leu Tyr Val Gly
465                 470                 475                 480

Ser Asp Leu Glu Ile Asn Leu Leu Thr Gln Ile Gly Cys Thr Leu Asn
                485                 490                 495

Phe Pro Ile Ser Pro Ile Glu Thr Val Pro Val Lys Leu Lys Gly Pro
            500                 505                 510

Lys Glu Pro Phe Arg Asp Tyr Val Asp Arg Phe Tyr Lys Thr Leu Arg
        515                 520                 525

Ala Glu Gln Ala Ser Gln Glu Val Tyr Leu Lys Asp Gln Gln Leu Leu
    530                 535                 540

Gly Ile Trp Gly Cys Ser Gly Lys Leu Ile Cys Thr Thr Ala Val Pro
545                 550                 555                 560

Trp Ala Ala Lys Lys His Gln Lys Glu Pro Pro Phe Leu Trp Met
                565                 570                 575

Gly Tyr Glu Leu His Pro Asp Lys Trp Thr Val Gln Pro Gly Thr Gly
                580                 585                 590

Pro Cys Thr Asn Val Ser Thr Val Gln Cys Thr His Gly Ile Arg Pro
            595                 600                 605

Val Val Ser Thr Gln Leu Lys Gln Asn Pro Asp Ile Val Ile Tyr Gln
610                 615                 620

Tyr Met Asp Asp Leu Tyr Val Gly Ser Asp Leu Glu Ile Gly Gln Leu
625                 630                 635                 640

Gly Pro Ala Ala Thr Leu Glu Glu Met Met Thr Ala Cys Gln Gly Val
                645                 650                 655

Gly Gly Pro Gly His Lys Ala Arg Asp Gln Ser Leu Lys Pro Cys Val
            660                 665                 670

Lys Leu Thr Pro Leu Cys Val Thr Leu Asn Cys Thr Asp Leu Arg Asn
            675                 680                 685

Thr Gly Pro Gly Ile Arg Tyr Pro Leu Leu Thr Phe Gly Trp Cys Phe
        690                 695                 700

Lys Leu Pro Val Glu Pro Glu Lys Val Glu Ala Lys Ile Ile Arg Asp
705                 710                 715                 720

Tyr Gly Lys Gln Met Ala Gly Asp Asp Cys Val Ala Ser Arg Gln Asp
                725                 730                 735

Glu Asp Ile Leu Lys Ala Leu Gly Pro Ala Ala Thr Leu Glu Glu Met
                740                 745                 750

Met Thr Ala Cys Gln Gly Val Gly Gly Pro Gly Tyr Lys Ala Ala Val
            755                 760                 765

Asp Leu Ser His Phe Leu Arg Glu Lys Gly Gly Leu Glu Gly Ala Ala
        770                 775                 780

Tyr Ala Ala Lys Ala Tyr Asp Thr Glu Val His Asn Val Trp Ala Thr
785                 790                 795                 800

His Ala Cys Val Pro Thr Asp Pro Asn Pro Gln Glu Ala Ala Leu
            805                 810                 815

Ser Glu Gly Ala Thr Pro Gln Asp Leu Asn Thr Met Leu Asn Thr Val
                820                 825                 830

Gly Gly His Gln Ala Ala Met Gln Gln Val Asp Cys Ser Pro Gly Ile
            835                 840                 845

Trp Gln Leu Asp Cys Thr His Leu Glu Gly Lys Ile Ile Leu Val Ala
        850                 855                 860

Val
865
```

```
<210> SEQ ID NO 375
<211> LENGTH: 870
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375
```

| | | | | | | | | | | | | | | |
|---|---|---|---|---|---|---|---|---|---|---|---|---|---|---|
| Met | Asp | Ala | Met | Lys | Arg | Gly | Leu | Cys | Cys | Val | Leu | Leu | Cys | Gly |
| 1 | | | | 5 | | | | | 10 | | | | | 15 |
| Ala | Val | Phe | Val | Ser | Ala | Arg | Ala | Ser | Arg | Glu | Leu | Glu | Arg | Phe | Ala |
| | | | 20 | | | | | 25 | | | | | 30 | | |
| Val | Asn | Pro | Gly | Leu | Leu | Gln | Leu | Lys | Gly | Glu | Ala | Met | His | Gly | Gln |
| | | | 35 | | | | 40 | | | | | 45 | | | |
| Val | Asp | Cys | Ser | Pro | Gly | Ile | Trp | Gln | Leu | Asp | Cys | Thr | His | Leu | Cys |
| | 50 | | | | | 55 | | | | | 60 | | | | |
| Ser | Ala | Thr | Glu | Lys | Leu | Trp | Val | Thr | Val | Tyr | Tyr | Gly | Val | Pro | Val |
| 65 | | | | | 70 | | | | | 75 | | | | | 80 |
| Trp | Lys | Glu | Ala | Thr | Thr | Thr | Leu | Pro | Val | Gly | Glu | Ile | Tyr | Lys | Arg |
| | | | | 85 | | | | | 90 | | | | | 95 | |
| Trp | Ile | Ile | Leu | Gly | Leu | Asn | Lys | Ile | Val | Arg | Met | Tyr | Ser | Pro | Thr |
| | | | 100 | | | | | 105 | | | | | 110 | | |
| Ser | Ile | Asn | Asn | Glu | Thr | Pro | Gly | Ile | Arg | Tyr | Gln | Tyr | Asn | Val | Leu |
| | | | 115 | | | | | 120 | | | | | 125 | | |
| Pro | Gln | Gly | Trp | Lys | Gly | Ser | Pro | Ala | Ile | Phe | Ala | Ala | Pro | Leu | Trp |
| | 130 | | | | | 135 | | | | | 140 | | | | |
| Lys | Gly | Pro | Ala | Lys | Leu | Leu | Trp | Lys | Gly | Glu | Gly | Ala | Val | Val | Ile |
| 145 | | | | | 150 | | | | | 155 | | | | | 160 |
| Gln | Asp | Asn | Ser | Asp | Ile | Ala | Ala | Ile | Val | Leu | Pro | Glu | Lys | Asp | Ser |
| | | | | 165 | | | | | 170 | | | | | 175 | |
| Trp | Thr | Val | Asn | Asp | Ile | Gln | Lys | Leu | Val | Gly | Lys | Leu | Asn | Trp | Ala |
| | | | 180 | | | | | 185 | | | | | 190 | | |
| Ser | Val | Tyr | Tyr | Arg | Asp | Ser | Arg | Asp | Pro | Leu | Trp | Lys | Gly | Pro | Ala |
| | | | 195 | | | | | 200 | | | | | 205 | | |
| Lys | Leu | Leu | Trp | Lys | Gly | Glu | Gly | Ala | Val | Ser | Asn | Phe | Thr | Ser | Thr |
| | 210 | | | | | 215 | | | | | 220 | | | | |
| Thr | Val | Lys | Ala | Ala | Cys | Trp | Trp | Ala | Gly | Ile | Lys | Gln | Glu | Phe | Gly |
| 225 | | | | | 230 | | | | | 235 | | | | | 240 |
| Ile | Pro | Tyr | Val | Leu | Pro | Glu | Lys | Asp | Ser | Trp | Thr | Val | Asn | Asp | Ile |
| | | | | 245 | | | | | 250 | | | | | 255 | |
| Gln | Lys | Leu | Val | Gly | Lys | Leu | Asn | Trp | Ala | Ser | Gln | Met | Val | His | Gln |
| | | | 260 | | | | | 265 | | | | | 270 | | |
| Ala | Ile | Ser | Pro | Arg | Thr | Leu | Asn | Ala | Trp | Val | Lys | Val | Glu | Glu |
| | | | 275 | | | | | 280 | | | | | 285 | | |
| Lys | Ala | Phe | Ser | Pro | Ala | Ala | Trp | Glu | Thr | Trp | Thr | Glu | Tyr | Trp |
| | 290 | | | | | 295 | | | | | 300 | | | | |
| Gln | Ala | Thr | Trp | Ile | Pro | Glu | Trp | Glu | Phe | Val | Asn | Thr | Pro | Pro | Leu |
| 305 | | | | | 310 | | | | | 315 | | | | | 320 |
| Gln | Asp | Ser | Gly | Leu | Glu | Val | Asn | Ile | Val | Thr | Asp | Ser | Gln | Tyr | Ala |
| | | | | 325 | | | | | 330 | | | | | 335 | |
| Leu | Gly | Ile | Ile | Gln | Ala | Gln | Pro | Asp | Ser | Trp | Thr | Val | Asn | Asp | Ile |
| | | | 340 | | | | | 345 | | | | | 350 | | |
| Gln | Lys | Leu | Val | Gly | Lys | Leu | Asn | Trp | Ala | Ser | Gln | Ile | Tyr | Pro | Gly |
| | | | 355 | | | | | 360 | | | | | 365 | | |

```
Ile Lys Asn Pro Asp Ile Val Ile Tyr Gln Tyr Met Asp Asp Leu Tyr
    370                 375                 380

Val Gly Ser Asp Leu Glu Ile Gly Gln His Arg Ala Ala Asp Pro Leu
385                 390                 395                 400

Trp Lys Gly Pro Ala Lys Leu Leu Trp Lys Gly Glu Gly Ala Val Val
                405                 410                 415

Ile Gln Asp Asn Ser Asp Arg Gln Ala Asn Phe Leu Gly Lys Ile Trp
                420                 425                 430

Pro Ser His Lys Gly Arg Ala Ala Pro Pro Phe Leu Trp Met Gly Tyr
            435                 440                 445

Glu Leu His Pro Asp Lys Trp Thr Val Gln Pro Ile Val Leu Pro Glu
    450                 455                 460

Lys Phe Arg Lys Gln Asn Pro Asp Ile Val Ile Tyr Gln Tyr Met Asp
465                 470                 475                 480

Asp Leu Tyr Val Gly Ser Asp Leu Glu Ile Asn Leu Leu Thr Gln Ile
                485                 490                 495

Gly Cys Thr Leu Asn Phe Pro Ile Ser Pro Ile Glu Thr Val Pro Val
                500                 505                 510

Lys Leu Lys Gly Pro Lys Glu Pro Phe Arg Asp Tyr Val Asp Arg Phe
            515                 520                 525

Tyr Lys Thr Leu Arg Ala Glu Gln Ala Ser Gln Glu Val Tyr Leu Lys
    530                 535                 540

Asp Gln Gln Leu Leu Gly Ile Trp Gly Cys Ser Gly Lys Leu Ile Cys
545                 550                 555                 560

Thr Thr Ala Val Pro Trp Ala Ala Lys Lys His Gln Lys Glu Pro
                565                 570                 575

Pro Phe Leu Trp Met Gly Tyr Glu Leu His Pro Asp Lys Trp Thr Val
            580                 585                 590

Gln Pro Gly Thr Gly Pro Cys Thr Asn Val Ser Thr Val Gln Cys Thr
    595                 600                 605

His Gly Ile Arg Pro Val Val Ser Thr Gln Leu Lys Gln Asn Pro Asp
    610                 615                 620

Ile Val Ile Tyr Gln Tyr Met Asp Asp Leu Tyr Val Gly Ser Asp Leu
625                 630                 635                 640

Glu Ile Gly Gln Leu Gly Pro Ala Ala Thr Leu Glu Glu Met Met Thr
                645                 650                 655

Ala Cys Gln Gly Val Gly Gly Pro Gly His Lys Ala Arg Asp Gln Ser
                660                 665                 670

Leu Lys Pro Cys Val Lys Leu Thr Pro Leu Cys Val Thr Leu Asn Cys
            675                 680                 685

Thr Asp Leu Arg Asn Thr Gly Pro Gly Ile Arg Tyr Pro Leu Leu Thr
    690                 695                 700

Phe Gly Trp Cys Phe Lys Leu Pro Val Glu Pro Glu Lys Val Glu Ala
705                 710                 715                 720

Lys Ile Ile Arg Asp Tyr Gly Lys Gln Met Ala Gly Asp Asp Cys Val
                725                 730                 735

Ala Ser Arg Gln Asp Glu Asp Ile Leu Lys Ala Leu Gly Pro Ala Ala
                740                 745                 750

Thr Leu Glu Glu Met Met Thr Ala Cys Gln Gly Val Gly Gly Pro Gly
            755                 760                 765

Tyr Lys Ala Ala Val Asp Leu Ser His Phe Leu Arg Glu Lys Gly Gly
    770                 775                 780
```

```
Leu Glu Gly Ala Ala Tyr Ala Ala Lys Ala Tyr Asp Thr Glu Val His
785                 790                 795                 800

Asn Val Trp Ala Thr His Ala Cys Val Pro Thr Asp Pro Asn Pro Gln
                805                 810                 815

Glu Ala Ala Ala Leu Ser Glu Gly Ala Thr Pro Gln Asp Leu Asn Thr
            820                 825                 830

Met Leu Asn Thr Val Gly Gly His Gln Ala Ala Met Gln Gln Val Asp
        835                 840                 845

Cys Ser Pro Gly Ile Trp Gln Leu Asp Cys Thr His Leu Glu Gly Lys
    850                 855                 860

Ile Ile Leu Val Ala Val
865                 870

<210> SEQ ID NO 376
<211> LENGTH: 954
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Met Asn Pro Ser Ala Ala Val Ile Phe Cys Leu Ile Leu Leu Gly Leu
1               5                   10                  15

Ser Gly Thr Gln Gly Ile Leu Asp Met Ala Gln Pro Val Gly Ile Asn
            20                  25                  30

Thr Ser Thr Thr Cys Cys Tyr Arg Phe Ile Asn Lys Lys Ile Pro Lys
        35                  40                  45

Gln Arg Leu Glu Ser Tyr Arg Arg Thr Thr Ser Ser His Cys Pro Arg
    50                  55                  60

Glu Ala Val Ile Phe Lys Thr Lys Leu Asp Lys Glu Ile Cys Ala Asp
65                  70                  75                  80

Pro Thr Gln Lys Trp Val Gln Asp Phe Met Lys His Leu Asp Lys Lys
                85                  90                  95

Thr Gln Thr Pro Lys Leu Ala Ser Ala Gly Ala Ala Ser Arg Glu Leu
            100                 105                 110

Glu Arg Phe Ala Val Asn Pro Gly Leu Leu Gln Leu Lys Gly Glu Ala
        115                 120                 125

Met His Gly Gln Val Asp Cys Ser Pro Gly Ile Trp Gln Leu Asp Cys
    130                 135                 140

Thr His Leu Cys Ser Ala Thr Glu Lys Leu Trp Val Thr Val Tyr Tyr
145                 150                 155                 160

Gly Val Pro Val Trp Lys Glu Ala Thr Thr Thr Leu Pro Val Gly Glu
                165                 170                 175

Ile Tyr Lys Arg Trp Ile Ile Leu Gly Leu Asn Lys Ile Val Arg Met
            180                 185                 190

Tyr Ser Pro Thr Ser Ile Asn Asn Glu Thr Pro Gly Ile Arg Tyr Gln
        195                 200                 205

Tyr Asn Val Leu Pro Gln Gly Trp Lys Gly Ser Pro Ala Ile Phe Ala
    210                 215                 220

Ala Pro Leu Trp Lys Gly Pro Ala Lys Leu Leu Trp Lys Gly Glu Gly
225                 230                 235                 240

Ala Val Val Ile Gln Asp Asn Ser Asp Ile Ala Ala Ile Val Leu Pro
                245                 250                 255

Glu Lys Asp Ser Trp Thr Val Asn Asp Ile Gln Lys Leu Val Gly Lys
            260                 265                 270
```

```
Leu Asn Trp Ala Ser Val Tyr Tyr Arg Asp Ser Arg Asp Pro Leu Trp
        275                 280                 285

Lys Gly Pro Ala Lys Leu Leu Trp Lys Gly Glu Gly Ala Val Ser Asn
        290                 295                 300

Phe Thr Ser Thr Thr Val Lys Ala Ala Cys Trp Trp Ala Gly Ile Lys
305                 310                 315                 320

Gln Glu Phe Gly Ile Pro Tyr Val Leu Pro Glu Lys Asp Ser Trp Thr
                325                 330                 335

Val Asn Asp Ile Gln Lys Leu Val Gly Lys Leu Asn Trp Ala Ser Gln
                340                 345                 350

Met Val His Gln Ala Ile Ser Pro Arg Thr Leu Asn Ala Trp Val Lys
            355                 360                 365

Val Val Glu Glu Lys Ala Phe Ser Pro Ala Ala Trp Glu Thr Trp Trp
        370                 375                 380

Thr Glu Tyr Trp Gln Ala Thr Trp Ile Pro Glu Trp Glu Phe Val Asn
385                 390                 395                 400

Thr Pro Pro Leu Gln Asp Ser Gly Leu Glu Val Asn Ile Val Thr Asp
                405                 410                 415

Ser Gln Tyr Ala Leu Gly Ile Ile Gln Ala Gln Pro Asp Ser Trp Thr
                420                 425                 430

Val Asn Asp Ile Gln Lys Leu Val Gly Lys Leu Asn Trp Ala Ser Gln
            435                 440                 445

Ile Tyr Pro Gly Ile Lys Asn Pro Asp Ile Val Ile Tyr Gln Tyr Met
        450                 455                 460

Asp Asp Leu Tyr Val Gly Ser Asp Leu Glu Ile Gly Gln His Arg Ala
465                 470                 475                 480

Ala Asp Pro Leu Trp Lys Gly Pro Ala Lys Leu Leu Trp Lys Gly Glu
                485                 490                 495

Gly Ala Val Val Ile Gln Asp Asn Ser Asp Arg Gln Ala Asn Phe Leu
                500                 505                 510

Gly Lys Ile Trp Pro Ser His Lys Gly Arg Ala Ala Pro Pro Phe Leu
        515                 520                 525

Trp Met Gly Tyr Glu Leu His Pro Asp Lys Trp Thr Val Gln Pro Ile
        530                 535                 540

Val Leu Pro Glu Lys Phe Arg Lys Gln Asn Pro Asp Ile Val Ile Tyr
545                 550                 555                 560

Gln Tyr Met Asp Asp Leu Tyr Val Gly Ser Asp Leu Glu Ile Asn Leu
                565                 570                 575

Leu Thr Gln Ile Gly Cys Thr Leu Asn Phe Pro Ile Ser Pro Ile Glu
            580                 585                 590

Thr Val Pro Val Lys Leu Lys Gly Pro Lys Glu Pro Phe Arg Asp Tyr
        595                 600                 605

Val Asp Arg Phe Tyr Lys Thr Leu Arg Ala Glu Gln Ala Ser Gln Glu
        610                 615                 620

Val Tyr Leu Lys Asp Gln Gln Leu Leu Gly Ile Trp Gly Cys Ser Gly
625                 630                 635                 640

Lys Leu Ile Cys Thr Thr Ala Val Pro Trp Ala Ala Lys Lys His
                645                 650                 655

Gln Lys Glu Pro Pro Phe Leu Trp Met Gly Tyr Glu Leu His Pro Asp
            660                 665                 670

Lys Trp Thr Val Gln Pro Gly Thr Gly Pro Cys Thr Asn Val Ser Thr
        675                 680                 685
```

```
Val Gln Cys Thr His Gly Ile Arg Pro Val Val Ser Thr Gln Leu Lys
    690                 695                 700

Gln Asn Pro Asp Ile Val Ile Tyr Gln Tyr Met Asp Asp Leu Tyr Val
705                 710                 715                 720

Gly Ser Asp Leu Glu Ile Gly Gln Leu Gly Pro Ala Ala Thr Leu Glu
                725                 730                 735

Glu Met Met Thr Ala Cys Gln Gly Val Gly Pro Gly His Lys Ala
            740                 745                 750

Arg Asp Gln Ser Leu Lys Pro Cys Val Lys Leu Thr Pro Leu Cys Val
                755                 760                 765

Thr Leu Asn Cys Thr Asp Leu Arg Asn Thr Gly Pro Gly Ile Arg Tyr
770                 775                 780

Pro Leu Leu Thr Phe Gly Trp Cys Phe Lys Leu Pro Val Glu Pro Glu
785                 790                 795                 800

Lys Val Glu Ala Lys Ile Ile Arg Asp Tyr Gly Lys Gln Met Ala Gly
                805                 810                 815

Asp Asp Cys Val Ala Ser Arg Gln Asp Glu Asp Ile Leu Lys Ala Leu
            820                 825                 830

Gly Pro Ala Ala Thr Leu Glu Glu Met Met Thr Ala Cys Gln Gly Val
                835                 840                 845

Gly Gly Pro Gly Tyr Lys Ala Ala Val Asp Leu Ser His Phe Leu Arg
    850                 855                 860

Glu Lys Gly Gly Leu Glu Gly Ala Ala Tyr Ala Ala Lys Ala Tyr Asp
865                 870                 875                 880

Thr Glu Val His Asn Val Trp Ala Thr His Ala Cys Val Pro Thr Asp
                885                 890                 895

Pro Asn Pro Gln Glu Ala Ala Ala Leu Ser Glu Gly Ala Thr Pro Gln
            900                 905                 910

Asp Leu Asn Thr Met Leu Asn Thr Val Gly Gly His Gln Ala Ala Met
                915                 920                 925

Gln Gln Val Asp Cys Ser Pro Gly Ile Trp Gln Leu Asp Cys Thr His
    930                 935                 940

Leu Glu Gly Lys Ile Ile Leu Val Ala Val
945                 950

<210> SEQ ID NO 377
<211> LENGTH: 878
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Met Arg Lys Ala Ala Val Ser His Trp Gln Gln Gln Ser Tyr Leu Asp
1               5                   10                  15

Ser Gly Ile His Ser Gly Ala Thr Thr Thr Ala Pro Ser Leu Ser Ala
            20                  25                  30

Ser Arg Glu Leu Glu Arg Phe Ala Val Asn Pro Gly Leu Leu Gln Leu
        35                  40                  45

Lys Gly Glu Ala Met His Gly Gln Val Asp Cys Ser Pro Gly Ile Trp
    50                  55                  60

Gln Leu Asp Cys Thr His Leu Cys Ser Ala Thr Glu Lys Leu Trp Val
65                  70                  75                  80

Thr Val Tyr Tyr Gly Val Pro Val Trp Lys Glu Ala Thr Thr Thr Leu
                85                  90                  95
```

```
Pro Val Gly Glu Ile Tyr Lys Arg Trp Ile Ile Leu Gly Leu Asn Lys
            100                 105                 110

Ile Val Arg Met Tyr Ser Pro Thr Ser Ile Asn Asn Glu Thr Pro Gly
            115                 120                 125

Ile Arg Tyr Gln Tyr Asn Val Leu Pro Gln Gly Trp Lys Gly Ser Pro
        130                 135                 140

Ala Ile Phe Ala Ala Pro Leu Trp Lys Gly Pro Ala Lys Leu Leu Trp
145                 150                 155                 160

Lys Gly Glu Gly Ala Val Ile Gln Asp Asn Ser Asp Ile Ala Ala
                165                 170                 175

Ile Val Leu Pro Glu Lys Asp Ser Trp Thr Val Asn Asp Ile Gln Lys
            180                 185                 190

Leu Val Gly Lys Leu Asn Trp Ala Ser Val Tyr Tyr Arg Asp Ser Arg
        195                 200                 205

Asp Pro Leu Trp Lys Gly Pro Ala Lys Leu Leu Trp Lys Gly Glu Gly
    210                 215                 220

Ala Val Ser Asn Phe Thr Ser Thr Val Lys Ala Ala Cys Trp Trp
225                 230                 235                 240

Ala Gly Ile Lys Gln Glu Phe Gly Ile Pro Tyr Val Leu Pro Glu Lys
            245                 250                 255

Asp Ser Trp Thr Val Asn Asp Ile Gln Lys Leu Val Gly Lys Leu Asn
            260                 265                 270

Trp Ala Ser Gln Met Val His Gln Ala Ile Ser Pro Arg Thr Leu Asn
        275                 280                 285

Ala Trp Val Lys Val Val Glu Lys Ala Phe Ser Pro Ala Ala Trp
        290                 295                 300

Glu Thr Trp Trp Thr Glu Tyr Trp Gln Ala Thr Trp Ile Pro Glu Trp
305                 310                 315                 320

Glu Phe Val Asn Thr Pro Pro Leu Gln Asp Ser Gly Leu Glu Val Asn
            325                 330                 335

Ile Val Thr Asp Ser Gln Tyr Ala Leu Gly Ile Ile Gln Ala Gln Pro
            340                 345                 350

Asp Ser Trp Thr Val Asn Asp Ile Gln Lys Leu Val Gly Lys Leu Asn
        355                 360                 365

Trp Ala Ser Gln Ile Tyr Pro Gly Ile Lys Asn Pro Asp Ile Val Ile
        370                 375                 380

Tyr Gln Tyr Met Asp Asp Leu Tyr Val Gly Ser Asp Leu Glu Ile Gly
385                 390                 395                 400

Gln His Arg Ala Ala Asp Pro Leu Trp Lys Gly Pro Ala Lys Leu Leu
            405                 410                 415

Trp Lys Gly Glu Gly Ala Val Ile Gln Asp Asn Ser Asp Arg Gln
        420                 425                 430

Ala Asn Phe Leu Gly Lys Ile Trp Pro Ser His Lys Gly Arg Ala Ala
            435                 440                 445

Pro Pro Phe Leu Trp Met Gly Tyr Glu Leu His Pro Asp Lys Trp Thr
        450                 455                 460

Val Gln Pro Ile Val Leu Pro Glu Lys Phe Arg Lys Gln Asn Pro Asp
465                 470                 475                 480

Ile Val Ile Tyr Gln Tyr Met Asp Asp Leu Tyr Val Gly Ser Asp Leu
            485                 490                 495

Glu Ile Asn Leu Leu Thr Gln Ile Gly Cys Thr Leu Asn Phe Pro Ile
            500                 505                 510
```

Ser Pro Ile Glu Thr Val Pro Val Lys Leu Lys Gly Pro Lys Glu Pro
515                 520                 525

Phe Arg Asp Tyr Val Asp Arg Phe Tyr Lys Thr Leu Arg Ala Glu Gln
530                 535                 540

Ala Ser Gln Glu Val Tyr Leu Lys Asp Gln Gln Leu Leu Gly Ile Trp
545                 550                 555                 560

Gly Cys Ser Gly Lys Leu Ile Cys Thr Thr Ala Val Pro Trp Ala Ala
                565                 570                 575

Ala Lys Lys His Gln Lys Glu Pro Pro Phe Leu Trp Met Gly Tyr Glu
                580                 585                 590

Leu His Pro Asp Lys Trp Thr Val Gln Pro Gly Thr Gly Pro Cys Thr
                595                 600                 605

Asn Val Ser Thr Val Gln Cys Thr His Gly Ile Arg Pro Val Val Ser
610                 615                 620

Thr Gln Leu Lys Gln Asn Pro Asp Ile Val Ile Tyr Gln Tyr Met Asp
625                 630                 635                 640

Asp Leu Tyr Val Gly Ser Asp Leu Glu Ile Gly Gln Leu Gly Pro Ala
                645                 650                 655

Ala Thr Leu Glu Glu Met Met Thr Ala Cys Gln Gly Val Gly Gly Pro
                660                 665                 670

Gly His Lys Ala Arg Asp Gln Ser Leu Lys Pro Cys Val Lys Leu Thr
                675                 680                 685

Pro Leu Cys Val Thr Leu Asn Cys Thr Asp Leu Arg Asn Thr Gly Pro
690                 695                 700

Gly Ile Arg Tyr Pro Leu Leu Thr Phe Gly Trp Cys Phe Lys Leu Pro
705                 710                 715                 720

Val Glu Pro Glu Lys Val Glu Ala Lys Ile Ile Arg Asp Tyr Gly Lys
                725                 730                 735

Gln Met Ala Gly Asp Asp Cys Val Ala Ser Arg Gln Asp Glu Asp Ile
                740                 745                 750

Leu Lys Ala Leu Gly Pro Ala Ala Thr Leu Glu Glu Met Met Thr Ala
                755                 760                 765

Cys Gln Gly Val Gly Gly Pro Gly Tyr Lys Ala Ala Val Asp Leu Ser
770                 775                 780

His Phe Leu Arg Glu Lys Gly Gly Leu Glu Gly Ala Ala Tyr Ala Ala
785                 790                 795                 800

Lys Ala Tyr Asp Thr Glu Val His Asn Val Trp Ala Thr His Ala Cys
                805                 810                 815

Val Pro Thr Asp Pro Asn Pro Gln Glu Ala Ala Leu Ser Glu Gly
                820                 825                 830

Ala Thr Pro Gln Asp Leu Asn Thr Met Leu Asn Thr Val Gly Gly His
                835                 840                 845

Gln Ala Ala Met Gln Gln Val Asp Cys Ser Pro Gly Ile Trp Gln Leu
850                 855                 860

Asp Cys Thr His Leu Glu Gly Lys Ile Ile Leu Val Ala Val
865                 870                 875

<210> SEQ ID NO 378
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

```
Ala Ala Ala
1

<210> SEQ ID NO 379
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ala Ala Tyr
1

<210> SEQ ID NO 380
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 380

Ala Ala Xaa
1

<210> SEQ ID NO 381
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Arg Ala Lys Arg
1

<210> SEQ ID NO 382
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Arg Glu Lys Arg
1

<210> SEQ ID NO 383
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Arg Arg Lys Arg
1
```

```
<210> SEQ ID NO 384
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ala Thr Asn Phe Ser Leu Leu Lys Gln Ala Gly Asp Val Glu Glu Asn
1               5                   10                  15

Pro Gly Pro

<210> SEQ ID NO 385
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 386
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Arg Ala Lys Arg Ala Pro Val Lys Gln Thr Leu Asn Phe Asp Leu Leu
1               5                   10                  15

Lys Leu Ala Gly Asp Val Glu Ser Asn Pro Gly Pro
            20                  25

<210> SEQ ID NO 387
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gln Cys Thr Asn Tyr Ala Leu Leu Lys Leu Ala Gly Asp Val Glu Ser
1               5                   10                  15

Asn Pro Gly Pro
            20

<210> SEQ ID NO 388
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Glu Gly Arg Gly Ser Leu Leu Thr Cys Gly Asp Val Glu Glu Asn Pro
1               5                   10                  15
```

Gly Pro

<210> SEQ ID NO 389
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Val His Ala Gly Pro Ile Ala
1               5

<210> SEQ ID NO 390
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Val His Ala Gly Pro Val Ala
1               5

<210> SEQ ID NO 391
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Gly Ala Leu Asp Ile
1               5

<210> SEQ ID NO 392
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gly Ala Leu Asp Leu
1               5

<210> SEQ ID NO 393
<211> LENGTH: 18
<212> TYPE: PRT
<213> ORGANISM: Unknown
<220> FEATURE:
<223> OTHER INFORMATION: Description of Unknown:
      GM-CSF sequence

<400> SEQUENCE: 393

Met Trp Leu Gln Ser Leu Leu Leu Leu Gly Thr Val Ala Cys Ser Ile
1               5                   10                  15

Ser Val

<210> SEQ ID NO 394
<211> LENGTH: 23
<212> TYPE: PRT

```
<213> ORGANISM: Unknown
<220> FEATURE:
<223> OTHER INFORMATION: Description of Unknown:
      Tissue-type plasminogen activator (t-PA) sequence

<400> SEQUENCE: 394

Met Asp Ala Met Lys Arg Gly Leu Cys Cys Val Leu Leu Leu Cys Gly
1               5                   10                  15

Ala Val Phe Val Ser Ala Arg
            20

<210> SEQ ID NO 395
<211> LENGTH: 16
<212> TYPE: PRT
<213> ORGANISM: Unknown
<220> FEATURE:
<223> OTHER INFORMATION: Description of Unknown:
      Invariant chain (CD74) sequence

<400> SEQUENCE: 395

Met His Arg Arg Arg Ser Arg Ser Cys Arg Glu Asp Gln Lys Pro Val
1               5                   10                  15

<210> SEQ ID NO 396
<211> LENGTH: 17
<212> TYPE: PRT
<213> ORGANISM: Unknown
<220> FEATURE:
<223> OTHER INFORMATION: Description of Unknown:
      Serum albumin sequence

<400> SEQUENCE: 396

Lys Trp Val Thr Phe Ile Ser Leu Leu Phe Leu Phe Ser Ser Ala Tyr
1               5                   10                  15

Ser

<210> SEQ ID NO 397
<211> LENGTH: 31
<212> TYPE: PRT
<213> ORGANISM: Unknown
<220> FEATURE:
<223> OTHER INFORMATION: Description of Unknown:
      Beta-catenin sequence

<400> SEQUENCE: 397

Met Arg Lys Ala Ala Val Ser His Trp Gln Gln Gln Ser Tyr Leu Asp
1               5                   10                  15

Ser Gly Ile His Ser Gly Ala Thr Thr Thr Ala Pro Ser Leu Ser
            20                  25                  30

<210> SEQ ID NO 398
<211> LENGTH: 107
<212> TYPE: PRT
<213> ORGANISM: Unknown
<220> FEATURE:
<223> OTHER INFORMATION: Description of Unknown:
      MCP-3 sequence

<400> SEQUENCE: 398

Met Asn Pro Ser Ala Ala Val Ile Phe Cys Leu Ile Leu Leu Gly Leu
1               5                   10                  15

Ser Gly Thr Gln Gly Ile Leu Asp Met Ala Gln Pro Val Gly Ile Asn
            20                  25                  30

Thr Ser Thr Thr Cys Cys Tyr Arg Phe Ile Asn Lys Lys Ile Pro Lys
        35                  40                  45
```

```
Gln Arg Leu Glu Ser Tyr Arg Arg Thr Thr Ser Ser His Cys Pro Arg
     50                  55                  60

Glu Ala Val Ile Phe Lys Thr Lys Leu Asp Lys Glu Ile Cys Ala Asp
 65                  70                  75                  80

Pro Thr Gln Lys Trp Val Gln Asp Phe Met Lys His Leu Asp Lys Lys
                 85                  90                  95

Thr Gln Thr Pro Lys Leu Ala Ser Ala Gly Ala
            100                 105

<210> SEQ ID NO 399
<211> LENGTH: 384
<212> TYPE: PRT
<213> ORGANISM: Unknown
<220> FEATURE:
<223> OTHER INFORMATION: Description of Unknown:
      Lysosomal-associated membrane glycoprotein-1
      (LAMP-1) sequence

<400> SEQUENCE: 399

Met Ala Pro Arg Ser Ala Arg Arg Pro Leu Leu Leu Leu Leu Leu Leu
 1               5                  10                  15

Leu Leu Leu Gly Leu Met His Cys Ala Ser Ala Ala Met Phe Met Val
             20                  25                  30

Lys Asn Gly Asn Gly Thr Ala Cys Ile Met Ala Asn Phe Ser Ala Ala
             35                  40                  45

Phe Ser Val Asn Tyr Asp Thr Lys Ser Gly Pro Lys Asn Met Thr Leu
 50                  55                  60

Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
            115                 120                 125

Asn Ala Ser Ser Lys Glu Ile Lys Thr Val Glu Ser Ile Thr Asp Ile
        130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
            195                 200                 205

Pro Ser Pro Val Pro Lys Ser Pro Ser Val Asp Lys Tyr Asn Val Ser
        210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
            275                 280                 285
```

Phe Gly Met Asn Ala Ser Ser Ser Arg Phe Phe Leu Gln Gly Ile Gln
    290                 295                 300

Leu Asn Thr Leu Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Asp Ile
    370                 375                 380

<210> SEQ ID NO 400
<211> LENGTH: 76
<212> TYPE: PRT
<213> ORGANISM: Unknown
<220> FEATURE:
<223> OTHER INFORMATION: Description of Unknown:
      Polyubiquitin B/C (UBB/UBC) sequence

<400> SEQUENCE: 400

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 401
<211> LENGTH: 17
<212> TYPE: PRT
<213> ORGANISM: Unknown
<220> FEATURE:
<223> OTHER INFORMATION: Description of Unknown:
      Calreticulin (CALR) sequence

<400> SEQUENCE: 401

Met Leu Leu Ser Val Pro Leu Leu Leu Gly Leu Leu Gly Leu Ala Val
1               5                   10                  15

Ala

<210> SEQ ID NO 402
<211> LENGTH: 16
<212> TYPE: PRT
<213> ORGANISM: Vesicular stomatitis virus

<400> SEQUENCE: 402

Met Lys Cys Leu Leu Tyr Leu Ala Phe Leu Phe Ile Gly Val Asn Cys
1               5                   10                  15

<210> SEQ ID NO 403
<211> LENGTH: 856
<212> TYPE: PRT
<213> ORGANISM: Human immunodeficiency virus

<400> SEQUENCE: 403

-continued

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
        130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
```

```
              420                 425                 430
Ala Met Tyr Ala Pro Pro Ile Ser Gly Gln Ile Arg Cys Ser Ser Asn
            435                 440                 445
Ile Thr Gly Leu Leu Leu Thr Arg Asp Gly Gly Asn Ser Asn Asn Glu
            450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
                485                 490                 495
Ala Pro Thr Lys Ala Lys Arg Val Val Gln Arg Glu Lys Arg Ala
                500                 505                 510
Val Gly Ile Gly Ala Leu Phe Leu Gly Phe Leu Gly Ala Ala Gly Ser
            515                 520                 525
Thr Met Gly Ala Ala Ser Met Thr Leu Thr Val Gln Ala Arg Gln Leu
            530                 535                 540
Leu Ser Gly Ile Val Gln Gln Asn Asn Leu Leu Arg Ala Ile Glu
545                 550                 555                 560
Ala Gln Gln His Leu Leu Gln Leu Thr Val Trp Gly Ile Lys Gln Leu
                565                 570                 575
Gln Ala Arg Ile Leu Ala Val Glu Arg Tyr Leu Lys Asp Gln Gln Leu
                580                 585                 590
Leu Gly Ile Trp Gly Cys Ser Gly Lys Leu Ile Cys Thr Thr Ala Val
                595                 600                 605
Pro Trp Asn Ala Ser Trp Ser Asn Lys Ser Leu Glu Gln Ile Trp Asn
                610                 615                 620
His Thr Thr Trp Met Glu Trp Asp Arg Glu Ile Asn Asn Tyr Thr Ser
625                 630                 635                 640
Leu Ile His Ser Leu Ile Glu Glu Ser Gln Asn Gln Glu Lys Asn
                645                 650                 655
Glu Gln Glu Leu Leu Glu Leu Asp Lys Trp Ala Ser Leu Trp Asn Trp
                660                 665                 670
Phe Asn Ile Thr Asn Trp Leu Trp Tyr Ile Lys Leu Phe Ile Met Ile
                675                 680                 685
Val Gly Gly Leu Val Gly Leu Arg Ile Val Phe Ala Val Leu Ser Ile
            690                 695                 700
Val Asn Arg Val Arg Gln Gly Tyr Ser Pro Leu Ser Phe Gln Thr His
705                 710                 715                 720
Leu Pro Thr Pro Arg Gly Pro Asp Arg Pro Glu Gly Ile Glu Glu Glu
                725                 730                 735
Gly Gly Glu Arg Asp Arg Asp Arg Ser Ile Arg Leu Val Asn Gly Ser
                740                 745                 750
Leu Ala Leu Ile Trp Asp Asp Leu Arg Ser Leu Cys Leu Phe Ser Tyr
            755                 760                 765
His Arg Leu Arg Asp Leu Leu Leu Ile Val Thr Arg Ile Val Glu Leu
            770                 775                 780
Leu Gly Arg Arg Gly Trp Glu Ala Leu Lys Tyr Trp Trp Asn Leu Leu
785                 790                 795                 800
Gln Tyr Trp Ser Gln Glu Leu Lys Asn Ser Ala Val Ser Leu Leu Asn
                805                 810                 815
Ala Thr Ala Ile Ala Val Ala Glu Gly Thr Asp Arg Val Ile Glu Val
                820                 825                 830
Val Gln Gly Ala Cys Arg Ala Ile Arg His Ile Pro Arg Arg Ile Arg
                835                 840                 845
```

```
Gln Gly Leu Glu Arg Ile Leu Leu
    850                 855

<210> SEQ ID NO 404
<211> LENGTH: 500
<212> TYPE: PRT
<213> ORGANISM: Human immunodeficiency virus

<400> SEQUENCE: 404

Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
```

```
                    355                 360                 365
Gln Val Thr Asn Ser Ala Thr Ile Met Met Gln Arg Gly Asn Phe Arg
            370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
            405                 410                 415

Gly Lys Glu Gly His Gln Met Lys Asp Cys Thr Glu Arg Gln Ala Asn
        420                 425                 430

Phe Leu Gly Lys Ile Trp Pro Ser Tyr Lys Gly Arg Pro Gly Asn Phe
            435                 440                 445

Leu Gln Ser Arg Pro Glu Pro Thr Ala Pro Pro Glu Glu Ser Phe Arg
        450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
            485                 490                 495

Pro Ser Ser Gln
            500

<210> SEQ ID NO 405
<211> LENGTH: 206
<212> TYPE: PRT
<213> ORGANISM: Human immunodeficiency virus

<400> SEQUENCE: 405

Met Gly Gly Lys Trp Ser Lys Ser Ser Val Ile Gly Trp Pro Thr Val
1               5                   10                  15

Arg Glu Arg Met Arg Arg Ala Glu Pro Ala Ala Asp Arg Val Gly Ala
            20                  25                  30

Ala Ser Arg Asp Leu Glu Lys His Gly Ala Ile Thr Ser Ser Asn Thr
        35                  40                  45

Ala Ala Thr Asn Ala Ala Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
            85                  90                  95

Leu Glu Gly Leu Ile His Ser Gln Arg Arg Gln Asp Ile Leu Asp Leu
        100                 105                 110

Trp Ile Tyr His Thr Gln Gly Tyr Phe Pro Asp Trp Gln Asn Tyr Thr
    115                 120                 125

Pro Gly Pro Gly Val Arg Tyr Pro Leu Thr Phe Gly Trp Cys Tyr Lys
130                 135                 140

Leu Val Pro Val Glu Pro Asp Lys Ile Glu Glu Ala Asn Lys Gly Glu
145                 150                 155                 160

Asn Thr Ser Leu Leu His Pro Val Ser Leu His Gly Met Asp Asp Pro
            165                 170                 175

Glu Arg Glu Val Leu Glu Trp Arg Phe Asp Ser Arg Leu Ala Phe His
        180                 185                 190

His Val Ala Arg Glu Leu His Pro Glu Tyr Phe Lys Asn Cys
    195                 200                 205

<210> SEQ ID NO 406
<211> LENGTH: 1003
```

```
<212> TYPE: PRT
<213> ORGANISM: Human immunodeficiency virus

<400> SEQUENCE: 406
```

| | | | | | | | | | | | | | | |
|---|---|---|---|---|---|---|---|---|---|---|---|---|---|---|
| Phe | Phe | Arg | Glu | Asp | Leu | Ala | Phe | Leu | Gln | Gly | Lys | Ala | Arg | Glu | Phe |
| 1 | | | | 5 | | | | | 10 | | | | | 15 | |

Ser Ser Glu Gln Thr Arg Ala Asn Ser Pro Thr Arg Arg Glu Leu Gln
                20                  25                  30

Val Trp Gly Arg Asp Asn Asn Ser Pro Ser Glu Ala Gly Ala Asp Arg
            35                  40                  45

Gln Gly Thr Val Ser Phe Asn Phe Pro Gln Val Thr Leu Trp Gln Arg
 50                  55                  60

Pro Leu Val Thr Ile Lys Ile Gly Gly Gln Leu Lys Glu Ala Leu Leu
 65                  70                  75                  80

Asp Thr Gly Ala Asp Asp Thr Val Leu Glu Glu Met Ser Leu Pro Gly
                85                  90                  95

Arg Trp Lys Pro Lys Met Ile Gly Gly Ile Gly Gly Phe Ile Lys Val
            100                 105                 110

Arg Gln Tyr Asp Gln Ile Leu Ile Glu Ile Cys Gly His Lys Ala Ile
        115                 120                 125

Gly Thr Val Leu Val Gly Pro Thr Pro Val Asn Ile Ile Gly Arg Asn
130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
            260                 265                 270

Val Pro Leu Asp Glu Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
290                 295                 300

Pro Gln Gly Trp Lys Gly Ser Pro Ala Ile Phe Gln Ser Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Leu Thr Thr Pro Asp Lys Lys His Gln Lys Glu Pro Pro Phe Leu Trp
370                 375                 380

Met Gly Tyr Glu Leu His Pro Asp Lys Trp Thr Val Gln Pro Ile Val
385                 390                 395                 400

```
Leu Pro Glu Lys Asp Ser Trp Thr Val Asn Asp Ile Gln Lys Leu Val
                405                 410                 415
Gly Lys Leu Asn Trp Ala Ser Gln Ile Tyr Pro Gly Ile Lys Val Arg
            420                 425                 430
Gln Leu Cys Lys Leu Leu Arg Gly Thr Lys Ala Leu Thr Glu Val Ile
        435                 440                 445
Pro Leu Thr Glu Glu Ala Glu Leu Glu Leu Ala Glu Asn Arg Glu Ile
    450                 455                 460
Leu Lys Glu Pro Val His Gly Val Tyr Tyr Asp Pro Ser Lys Asp Leu
465                 470                 475                 480
Ile Ala Glu Ile Gln Lys Gln Gly Gln Gly Gln Trp Thr Tyr Gln Ile
                485                 490                 495
Tyr Gln Glu Pro Phe Lys Asn Leu Lys Thr Gly Lys Tyr Ala Arg Met
            500                 505                 510
Arg Gly Ala His Thr Asn Asp Val Lys Gln Leu Thr Glu Ala Val Gln
        515                 520                 525
Lys Ile Thr Thr Glu Ser Ile Val Ile Trp Gly Lys Thr Pro Lys Phe
    530                 535                 540
Lys Leu Pro Ile Gln Lys Glu Thr Trp Glu Thr Trp Trp Thr Glu Tyr
545                 550                 555                 560
Trp Gln Ala Thr Trp Ile Pro Glu Trp Glu Phe Val Asn Thr Pro Pro
                565                 570                 575
Leu Val Lys Leu Trp Tyr Gln Leu Glu Lys Glu Pro Ile Val Gly Ala
            580                 585                 590
Glu Thr Phe Tyr Val Asp Gly Ala Ala Asn Arg Glu Thr Lys Leu Gly
        595                 600                 605
Lys Ala Gly Tyr Val Thr Asn Arg Gly Arg Gln Lys Val Val Thr Leu
    610                 615                 620
Thr Asp Thr Thr Asn Gln Lys Thr Glu Leu Gln Ala Ile Tyr Leu Ala
625                 630                 635                 640
Leu Gln Asp Ser Gly Leu Glu Val Asn Ile Val Thr Asp Ser Gln Tyr
                645                 650                 655
Ala Leu Gly Ile Ile Gln Ala Gln Pro Asp Gln Ser Glu Ser Glu Leu
            660                 665                 670
Val Asn Gln Ile Ile Glu Gln Leu Ile Lys Lys Glu Lys Val Tyr Leu
        675                 680                 685
Ala Trp Val Pro Ala His Lys Gly Ile Gly Gly Asn Glu Gln Val Asp
    690                 695                 700
Lys Leu Val Ser Ala Gly Ile Arg Lys Val Leu Phe Leu Asp Gly Ile
705                 710                 715                 720
Asp Lys Ala Gln Asp Glu His Glu Lys Tyr His Ser Asn Trp Arg Ala
                725                 730                 735
Met Ala Ser Asp Phe Asn Leu Pro Pro Val Val Ala Lys Glu Ile Val
            740                 745                 750
Ala Ser Cys Asp Lys Cys Gln Leu Lys Gly Glu Ala Met His Gly Gln
        755                 760                 765
Val Asp Cys Ser Pro Gly Ile Trp Gln Leu Asp Cys Thr His Leu Glu
    770                 775                 780
Gly Lys Val Ile Leu Val Ala Val His Val Ala Ser Gly Tyr Ile Glu
785                 790                 795                 800
Ala Glu Val Ile Pro Ala Glu Thr Gly Gln Glu Thr Ala Tyr Phe Leu
                805                 810                 815
```

-continued

```
Leu Lys Leu Ala Gly Arg Trp Pro Val Lys Thr Ile His Thr Asp Asn
            820                 825                 830

Gly Ser Asn Phe Thr Gly Ala Thr Val Arg Ala Ala Cys Trp Trp Ala
        835                 840                 845

Gly Ile Lys Gln Glu Phe Gly Ile Pro Tyr Asn Pro Gln Ser Gln Gly
    850                 855                 860

Val Val Glu Ser Met Asn Lys Glu Leu Lys Lys Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
            900                 905                 910

Glu Arg Ile Val Asp Ile Ile Ala Thr Asp Ile Gln Thr Lys Glu Leu
        915                 920                 925

Gln Lys Gln Ile Thr Lys Ile Gln Asn Phe Arg Val Tyr Tyr Arg Asp
    930                 935                 940

Ser Arg Asn Pro Leu Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln  Asp Glu Asp
            995                 1000
```

<210> SEQ ID NO 407
<211> LENGTH: 670
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

```
Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp Ile Ile
65                  70                  75                  80

Ala Ile Thr Lys Ile Gln Asn Phe Arg Val Tyr Tyr Arg Asp Ser Arg
                85                  90                  95

Asp Pro Leu Trp Lys Gly Pro Ala Lys Leu Leu Trp Lys Gly Glu Gly
            100                 105                 110

Ala Val Val Ile Gln Asp Asn Ser Asp Ile Lys Val Val Pro Arg Arg
        115                 120                 125

Lys Ala Lys Ile Ile Arg Asp Tyr Gly Lys Gln Met Ala Gly Asp Asp
    130                 135                 140

Cys Val Ala Ser Arg Gln Asp Glu Asp Pro Lys Phe Lys Leu Pro Ile
145                 150                 155                 160

Gln Lys Glu Thr Trp Glu Thr Trp Trp Thr Glu Tyr Trp Gln Ala Thr
                165                 170                 175
```

```
Trp Ile Pro Glu Trp Glu Phe Val Asn Thr Pro Leu Val Lys Leu
            180                 185                 190

Trp Tyr Gln Leu Glu Lys Glu Pro Ile Val Gly Ala Glu Thr Phe Tyr
        195                 200                 205

Val Asp Gly Ala Ala Asn Arg Glu Thr Lys Ala Ala Lys Glu Lys Val
210                 215                 220

Tyr Leu Ala Trp Val Pro Ala His Lys Gly Ile Gly Gly Asn Glu Gln
225                 230                 235                 240

Val Asp Lys Leu Val Ser Trp Gly Phe Thr Thr Pro Asp Lys Lys His
            245                 250                 255

Gln Lys Glu Pro Pro Phe Leu Trp Met Gly Tyr Glu Leu His Pro Asp
            260                 265                 270

Lys Trp Thr Val Gln Pro Ile Val Leu Pro Glu Lys Asp Ser Trp Thr
            275                 280                 285

Val Asn Asp Ile Gln Lys Leu Val Gly Lys Leu Asn Trp Ala Ser Gln
            290                 295                 300

Ile Tyr Pro Gly Ile Lys Val Ile Val Ile Tyr Gln Tyr Met Asp Asp
305                 310                 315                 320

Leu Tyr Val Gly Ser Asp Leu Glu Ile Gly Gln His Arg Val Ala Lys
            325                 330                 335

Glu Ile Val Ala Ser Cys Asp Lys Cys Gln Leu Lys Gly Glu Ala Met
            340                 345                 350

His Gly Gln Val Asp Cys Ser Pro Gly Ile Trp Gln Leu Asp Cys Thr
            355                 360                 365

His Leu Glu Gly Lys Ile Ile Leu Val Ala Val His Val Ala Ser Gly
            370                 375                 380

Tyr Ile Glu Ala Glu Val Ile Pro Ala Glu Thr Gly Gln Glu Thr Ala
385                 390                 395                 400

Tyr Phe Leu Leu Lys Leu Ala Gly Arg Trp Pro Val Lys Thr Ala Ala
            405                 410                 415

Phe Pro Gln Ile Thr Leu Trp Gln Arg Pro Leu Val Thr Ile Lys Ile
            420                 425                 430

Gly Gly Gln Leu Lys Glu Ala Leu Leu Asp Thr Gly Ala Asp Asp Thr
            435                 440                 445

Val Leu Glu Glu Met Asn Leu Pro Gly Arg Trp Lys Pro Lys Met Ile
450                 455                 460

Gly Gly Ile Gly Gly Phe Ile Lys Val Arg Gln Tyr Asp Gln Gly Thr
465                 470                 475                 480

Val Leu Val Gly Pro Thr Pro Val Asn Ile Ile Gly Arg Asn Leu Leu
            485                 490                 495

Thr Gln Ile Gly Cys Thr Leu Asn Phe Pro Ile Ser Pro Ile Glu Thr
            500                 505                 510

Val Pro Val Lys Leu Lys Pro Gly Met Asp Gly Pro Lys Val Lys Gln
            515                 520                 525

Trp Pro Leu Thr Glu Glu Lys Ile Lys Ala Leu Val Glu Ile Cys Thr
            530                 535                 540

Glu Met Glu Lys Glu Gly Lys Ile Ser Lys Ile Gly Pro Glu Asn Pro
545                 550                 555                 560

Tyr Asn Thr Pro Val Phe Ala Ile Lys Lys Lys Asp Ser Thr Lys Trp
            565                 570                 575

Arg Lys Leu Val Asp Phe Arg Glu Leu Asn Lys Arg Thr Gln Asp Phe
            580                 585                 590
```

```
Trp Glu Val Gln Leu Gly Ile Pro His Pro Ala Gly Leu Lys Lys Lys
            595                 600                 605

Lys Ser Val Thr Val Leu Asp Val Gly Asp Ala Tyr Phe Ser Val Pro
    610                 615                 620

Leu Asp Lys Asp Phe Arg Lys Tyr Thr Ala Phe Thr Ile Pro Ser Ile
625                 630                 635                 640

Asn Asn Glu Thr Pro Gly Ile Arg Tyr Gln Tyr Asn Val Leu Pro Gln
                645                 650                 655

Gly Trp Lys Gly Ser Pro Ala Ile Phe Gln Ser Ser Met Thr
            660                 665                 670

<210> SEQ ID NO 408
<211> LENGTH: 669
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Ala Val Lys Ala Ala Cys Trp Trp Ala Gly Val Lys Gln Glu Phe Gly
1               5                   10                  15

Ile Pro Tyr His Pro Gln Ser Gln Gly Val Val Glu Ser Met Asn Asn
            20                  25                  30

Glu Leu Lys Lys Ile Ile Gly Gln Ile Arg Asp Gln Ala Glu Gln Leu
        35                  40                  45

Lys Thr Ala Val Gln Met Ala Val Leu Ile His Asn Phe Lys Arg Lys
    50                  55                  60

Gly Gly Ile Gly Glu Tyr Ser Ala Gly Glu Arg Ile Ile Asp Ile Ile
65              70                  75                  80

Val Ala Lys Glu Ile Val Ala Cys Cys Asp Lys Cys Gln Leu Lys Gly
                85                  90                  95

Glu Ala Ile His Gly Gln Val Asp Cys Ser Pro Gly Val Trp Gln Leu
            100                 105                 110

Asp Cys Thr His Leu Glu Gly Lys Val Ile Leu Val Ala Val His Val
        115                 120                 125

Ala Ser Gly Tyr Met Glu Ala Glu Val Ile Pro Thr Glu Thr Gly Gln
    130                 135                 140

Glu Thr Ala Tyr Phe Ile Leu Lys Leu Ala Gly Arg Trp Pro Val Thr
145                 150                 155                 160

Thr Trp Gly Leu Thr Thr Pro Asp Lys Lys His Gln Lys Asp Pro Pro
                165                 170                 175

Phe Leu Trp Met Gly Tyr Glu Leu His Pro Asp Arg Trp Thr Val Gln
            180                 185                 190

Pro Ile Glu Leu Pro Glu Lys Glu Ser Trp Thr Val Asn Asp Ile Gln
        195                 200                 205

Lys Leu Ile Gly Lys Leu Asn Trp Ala Ser Gln Ile Tyr Ala Gly Ile
    210                 215                 220

Lys Val Ile Val Ile Tyr Gln Tyr Val Asp Asp Leu Tyr Val Gly Ser
225                 230                 235                 240

Asp Leu Glu Ile Glu Gln His Arg Leu Pro Gln Ile Thr Leu Trp Gln
                245                 250                 255

Arg Pro Ile Val Thr Ile Lys Ile Gly Gly Gln Ile Lys Glu Ala Leu
            260                 265                 270

Leu Asp Thr Gly Ala Asp Asp Thr Val Leu Glu Asp Met Asn Leu Pro
        275                 280                 285
```

```
Gly Lys Trp Lys Pro Lys Met Ile Gly Gly Ile Gly Gly Phe Ile Lys
            290                 295                 300

Val Lys Gln Tyr Asp Gln Pro Lys Phe Arg Leu Pro Ile Gln Lys Glu
305                 310                 315                 320

Thr Trp Asp Thr Trp Thr Asp Tyr Trp Gln Ala Thr Trp Ile Pro
                325                 330                 335

Glu Trp Glu Phe Thr Asn Thr Pro Pro Leu Val Lys Leu Trp Tyr Gln
            340                 345                 350

Leu Glu Thr Glu Pro Ile Ala Gly Val Glu Thr Phe Tyr Val Asp Gly
            355                 360                 365

Ala Ser Asn Arg Glu Thr Lys Ala Ala Tyr Ala Ile Thr Lys Leu Gln
370                 375                 380

Asn Phe Arg Val Tyr Tyr Arg Asp Asn Arg Asp Pro Leu Trp Lys Gly
385                 390                 395                 400

Pro Ala Arg Leu Leu Trp Lys Gly Gly Ala Val Val Ile Gln Asp
            405                 410                 415

Asn Ser Glu Ile Lys Val Val Pro Arg Arg Lys Val Lys Ile Ile Arg
            420                 425                 430

Asp Tyr Gly Lys Arg Met Ala Gly Asp Cys Val Ala Gly Arg Gln
            435                 440                 445

Asp Glu Asp Gly Thr Val Leu Ile Gly Pro Thr Pro Val Asn Ile Ile
450                 455                 460

Gly Arg Asn Leu Leu Thr Gln Leu Gly Cys Thr Leu Asn Phe Pro Ile
465                 470                 475                 480

Ser Pro Ile Asp Thr Val Pro Val Lys Leu Lys Pro Gly Met Asp Gly
                485                 490                 495

Pro Arg Val Lys Gln Trp Pro Leu Thr Glu Glu Lys Ile Lys Ala Leu
            500                 505                 510

Ile Glu Ile Cys Thr Glu Met Glu Lys Glu Gly Lys Ile Ser Arg Ile
            515                 520                 525

Gly Pro Glu Asn Pro Tyr Asn Thr Pro Ile Phe Ala Ile Lys Lys Lys
530                 535                 540

Asp Gly Thr Lys Trp Arg Lys Leu Val Asp Phe Arg Glu Leu Asn Lys
545                 550                 555                 560

Lys Thr Gln Asp Phe Trp Glu Val Gln Leu Gly Ile Pro His Pro Ser
                565                 570                 575

Gly Leu Lys Lys Lys Ser Val Thr Val Leu Asp Ile Gly Asp Ala
            580                 585                 590

Tyr Phe Ser Val Pro Leu Asp Lys Glu Phe Arg Lys Tyr Thr Ala Phe
            595                 600                 605

Thr Val Pro Ser Thr Asn Asn Glu Thr Pro Gly Val Arg Tyr Gln Tyr
            610                 615                 620

Asn Val Leu Pro Met Gly Trp Lys Gly Ser Pro Ala Ile Phe Gln Cys
625                 630                 635                 640

Ser Met Thr Lys Glu Lys Ile Tyr Leu Ala Trp Val Pro Ala His Lys
                645                 650                 655

Gly Ile Gly Gly Asn Glu Gln Ile Asp Lys Leu Val Ser
            660                 665

<210> SEQ ID NO 409
<211> LENGTH: 648
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 409

Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp Ile Ile
65                  70                  75                  80

Val Ala Lys Glu Ile Val Ala Ser Cys Asp Lys Cys Gln Leu Lys Gly
                85                  90                  95

Glu Ala Met His Gly Gln Val Asp Cys Ser Pro Gly Ile Trp Gln Leu
            100                 105                 110

Asp Cys Thr His Leu Glu Gly Lys Ile Ile Leu Val Ala Val His Val
        115                 120                 125

Ala Ser Gly Tyr Ile Glu Ala Glu Val Ile Pro Ala Glu Thr Gly Gln
    130                 135                 140

Glu Thr Ala Tyr Phe Leu Leu Lys Leu Ala Gly Arg Trp Pro Val Lys
145                 150                 155                 160

Thr Ala Ile Thr Lys Ile Gln Asn Phe Arg Val Tyr Tyr Arg Asp Ser
                165                 170                 175

Arg Asp Pro Leu Trp Lys Gly Pro Ala Lys Leu Leu Trp Lys Gly Glu
            180                 185                 190

Gly Ala Val Val Ile Gln Asp Asn Ser Asp Ile Lys Val Val Pro Arg
        195                 200                 205

Arg Lys Ala Lys Ile Ile Arg Asp Tyr Gly Lys Gln Met Ala Gly Asp
    210                 215                 220

Asp Cys Val Ala Ser Arg Gln Asp Glu Asp Pro Lys Phe Lys Leu Pro
225                 230                 235                 240

Ile Gln Lys Glu Thr Trp Glu Thr Trp Trp Thr Glu Tyr Trp Gln Ala
                245                 250                 255

Thr Trp Ile Pro Glu Trp Glu Phe Val Asn Thr Pro Pro Leu Val Lys
            260                 265                 270

Leu Trp Tyr Gln Leu Glu Lys Glu Pro Ile Val Gly Ala Glu Thr Phe
        275                 280                 285

Tyr Val Asp Gly Ala Ala Asn Arg Glu Thr Lys Ala Ala Lys Glu Lys
    290                 295                 300

Val Tyr Leu Ala Trp Val Pro Ala His Lys Gly Ile Gly Gly Asn Glu
305                 310                 315                 320

Gln Val Asp Lys Leu Val Ser Trp Gly Phe Thr Thr Pro Asp Lys Lys
                325                 330                 335

His Gln Lys Glu Pro Pro Phe Leu Trp Met Gly Tyr Glu Leu His Pro
            340                 345                 350

Asp Lys Trp Thr Val Gln Pro Ile Val Leu Pro Glu Lys Asp Ser Trp
        355                 360                 365

Thr Val Asn Asp Ile Gln Lys Leu Val Gly Lys Leu Asn Trp Ala Ser
    370                 375                 380

Gln Ile Tyr Pro Gly Ile Lys Val Ala Ala Phe Pro Gln Ile Thr Leu
385                 390                 395                 400

```
Trp Gln Arg Pro Leu Val Thr Ile Lys Ile Gly Gly Gln Leu Lys Glu
                405                 410                 415

Ala Leu Leu Asp Thr Gly Ala Asp Asp Thr Val Leu Glu Glu Met Asn
            420                 425                 430

Leu Pro Gly Arg Trp Lys Pro Lys Met Ile Gly Gly Ile Gly Gly Phe
        435                 440                 445

Ile Lys Val Arg Gln Tyr Asp Gln Gly Thr Val Leu Val Gly Pro Thr
    450                 455                 460

Pro Val Asn Ile Ile Gly Arg Asn Leu Leu Thr Gln Ile Gly Cys Thr
465                 470                 475                 480

Leu Asn Phe Pro Ile Ser Pro Ile Glu Thr Val Pro Val Lys Leu Lys
                485                 490                 495

Pro Gly Met Asp Gly Pro Lys Val Lys Gln Trp Pro Leu Thr Glu Glu
            500                 505                 510

Lys Ile Lys Ala Leu Val Glu Ile Cys Thr Glu Met Glu Lys Glu Gly
        515                 520                 525

Lys Ile Ser Lys Ile Gly Pro Glu Asn Pro Tyr Asn Thr Pro Val Phe
    530                 535                 540

Ala Ile Lys Lys Lys Asp Ser Thr Lys Trp Arg Lys Leu Val Asp Phe
545                 550                 555                 560

Arg Glu Leu Asn Lys Arg Thr Gln Asp Phe Trp Glu Val Gln Leu Gly
                565                 570                 575

Ile Pro His Pro Ala Gly Leu Lys Lys Lys Ser Val Thr Val Leu
            580                 585                 590

Asp Val Gly Asp Ala Tyr Phe Ser Val Pro Leu Asp Lys Asp Phe Arg
        595                 600                 605

Lys Tyr Thr Ala Phe Thr Ile Pro Ser Ile Asn Asn Glu Thr Pro Gly
    610                 615                 620

Ile Arg Tyr Gln Tyr Asn Val Leu Pro Gln Gly Trp Lys Gly Ser Pro
625                 630                 635                 640

Ala Ile Phe Gln Ser Ser Met Thr
                645

<210> SEQ ID NO 410
<211> LENGTH: 650
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Ala Val Lys Ala Ala Cys Trp Trp Ala Gly Val Lys Gln Glu Phe Gly
1               5                   10                  15

Ile Pro Tyr His Pro Gln Ser Gln Gly Val Val Glu Ser Met Asn Asn
            20                  25                  30

Glu Leu Lys Lys Ile Ile Gly Gln Ile Arg Asp Gln Ala Glu Gln Leu
        35                  40                  45

Lys Thr Ala Val Gln Met Ala Val Leu Ile His Asn Phe Lys Arg Lys
    50                  55                  60

Gly Gly Ile Gly Glu Tyr Ser Ala Gly Glu Arg Ile Ile Asp Ile Ile
65                  70                  75                  80

Trp Gly Leu Thr Thr Pro Asp Lys Lys His Gln Lys Asp Pro Pro Phe
                85                  90                  95

Leu Trp Met Gly Tyr Glu Leu His Pro Asp Arg Trp Thr Val Gln Pro
```

```
                100             105             110
Ile Glu Leu Pro Glu Lys Glu Ser Trp Thr Val Asn Asp Ile Gln Lys
            115                 120                 125

Leu Ile Gly Lys Leu Asn Trp Ala Ser Gln Ile Tyr Ala Gly Ile Lys
            130                 135             140

Val Ala Ala Tyr Val Ala Lys Glu Ile Val Ala Cys Cys Asp Lys Cys
145                 150                 155                 160

Gln Leu Lys Gly Glu Ala Ile His Gly Gln Val Asp Cys Ser Pro Gly
                165                 170                 175

Val Trp Gln Leu Asp Cys Thr His Leu Glu Gly Lys Val Ile Leu Val
            180                 185                 190

Ala Val His Val Ala Ser Gly Tyr Met Glu Ala Glu Val Ile Pro Thr
            195                 200                 205

Glu Thr Gly Gln Glu Thr Ala Tyr Phe Ile Leu Lys Leu Ala Gly Arg
            210                 215                 220

Trp Pro Val Thr Thr Leu Pro Gln Ile Thr Leu Trp Gln Arg Pro Ile
225                 230                 235                 240

Val Thr Ile Lys Ile Gly Gly Gln Ile Lys Glu Ala Leu Leu Asp Thr
                245                 250                 255

Gly Ala Asp Asp Thr Val Leu Glu Asp Met Asn Leu Pro Gly Lys Trp
            260                 265                 270

Lys Pro Lys Met Ile Gly Gly Ile Gly Gly Phe Ile Lys Val Lys Gln
            275                 280                 285

Tyr Asp Gln Pro Lys Phe Arg Leu Pro Ile Gln Lys Glu Thr Trp Asp
            290                 295                 300

Thr Trp Trp Thr Asp Tyr Trp Gln Ala Thr Trp Ile Pro Glu Trp Glu
305                 310                 315                 320

Phe Thr Asn Thr Pro Pro Leu Val Lys Leu Trp Tyr Gln Leu Glu Thr
                325                 330                 335

Glu Pro Ile Ala Gly Val Glu Thr Phe Tyr Val Asp Gly Ala Ser Asn
            340                 345                 350

Arg Glu Thr Lys Ala Ala Tyr Ala Ile Thr Lys Leu Gln Asn Phe Arg
            355                 360                 365

Val Tyr Tyr Arg Asp Asn Arg Asp Pro Leu Trp Lys Gly Pro Ala Arg
            370                 375                 380

Leu Leu Trp Lys Gly Glu Gly Ala Val Val Ile Gln Asp Asn Ser Glu
385                 390                 395                 400

Ile Lys Val Val Pro Arg Arg Lys Val Lys Ile Ile Arg Asp Tyr Gly
                405                 410                 415

Lys Arg Met Ala Gly Asp Asp Cys Val Ala Gly Arg Gln Asp Glu Asp
            420                 425                 430

Gly Thr Val Leu Ile Gly Pro Thr Pro Val Asn Ile Ile Gly Arg Asn
            435                 440                 445

Leu Leu Thr Gln Leu Gly Cys Thr Leu Asn Phe Pro Ile Ser Pro Ile
            450                 455                 460

Asp Thr Val Pro Val Lys Leu Lys Pro Gly Met Asp Gly Pro Arg Val
465                 470                 475                 480

Lys Gln Trp Pro Leu Thr Glu Glu Lys Ile Lys Ala Leu Ile Glu Ile
                485                 490                 495

Cys Thr Glu Met Glu Lys Glu Gly Lys Ile Ser Arg Ile Gly Pro Glu
            500                 505                 510

Asn Pro Tyr Asn Thr Pro Ile Phe Ala Ile Lys Lys Lys Asp Gly Thr
            515                 520                 525
```

```
Lys Trp Arg Lys Leu Val Asp Phe Arg Glu Leu Asn Lys Lys Thr Gln
                530                 535                 540

Asp Phe Trp Glu Val Gln Leu Gly Ile Pro His Pro Ser Gly Leu Lys
545                 550                 555                 560

Lys Lys Lys Ser Val Thr Val Leu Asp Ile Gly Asp Ala Tyr Phe Ser
                565                 570                 575

Val Pro Leu Asp Lys Glu Phe Arg Lys Tyr Thr Ala Phe Thr Val Pro
                580                 585                 590

Ser Thr Asn Asn Glu Thr Pro Gly Val Arg Tyr Gln Tyr Asn Val Leu
                595                 600                 605

Pro Met Gly Trp Lys Gly Ser Pro Ala Ile Phe Gln Cys Ser Met Thr
610                 615                 620

Lys Glu Lys Ile Tyr Leu Ala Trp Val Pro Ala His Lys Gly Ile Gly
625                 630                 635                 640

Gly Asn Glu Gln Ile Asp Lys Leu Val Ser
                645                 650

<210> SEQ ID NO 411
<211> LENGTH: 768
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Gln Leu Lys Gly Glu Ala Met His Gly Gln Val Asp Cys Ser Pro Gly
1               5                   10                  15

Ile Trp Gln Leu Asp Cys Thr His Leu Cys Ser Ala Thr Glu Lys Leu
                20                  25                  30

Trp Val Thr Val Tyr Tyr Gly Val Pro Val Trp Lys Glu Ala Thr Thr
            35                  40                  45

Thr Leu Ala Ser Arg Glu Leu Glu Arg Phe Ala Val Asn Pro Gly Leu
        50                  55                  60

Leu Asn Asn Glu Thr Pro Gly Ile Arg Tyr Gln Tyr Asn Val Leu Pro
65                  70                  75                  80

Gln Gly Trp Lys Gly Ser Pro Ala Ile Phe Pro Val Gly Glu Ile Tyr
                85                  90                  95

Lys Arg Trp Ile Ile Leu Gly Leu Asn Lys Ile Val Arg Met Tyr Ser
                100                 105                 110

Pro Thr Ser Ile Ala Ala Pro Pro Phe Leu Trp Met Gly Tyr Glu Leu
            115                 120                 125

His Pro Asp Lys Trp Thr Val Gln Pro Ile Val Leu Pro Glu Lys Trp
        130                 135                 140

Glu Thr Trp Trp Thr Glu Tyr Trp Gln Ala Thr Trp Ile Pro Glu Trp
145                 150                 155                 160

Glu Phe Val Asn Thr Pro Pro Leu Gln Asp Ser Gly Leu Glu Val Asn
                165                 170                 175

Ile Val Thr Asp Ser Gln Tyr Ala Leu Gly Ile Ile Gln Ala Gln Pro
                180                 185                 190

Asp Ser Trp Thr Val Asn Asp Ile Gln Lys Leu Val Gly Lys Leu Asn
            195                 200                 205

Trp Ala Ser Gln Ile Tyr Pro Gly Ile Lys Ala Ala Asp Pro Leu Trp
        210                 215                 220

Lys Gly Pro Ala Lys Leu Leu Trp Lys Gly Glu Gly Ala Val Val Ile
```

```
                225                 230                 235                 240
            Gln Asp Asn Ser Asp Arg Gln Ala Asn Phe Leu Gly Lys Ile Trp Pro
                            245                 250                 255
            Ser His Lys Gly Arg Pro Leu Trp Lys Gly Pro Ala Lys Leu Leu Trp
                            260                 265                 270
            Lys Gly Glu Gly Ala Val Val Ile Gln Asp Asn Ser Asp Ile Ala Ala
                            275                 280                 285
            Ser Asn Phe Thr Ser Thr Thr Val Lys Ala Ala Cys Trp Trp Ala Gly
                            290                 295                 300
            Ile Lys Gln Glu Phe Gly Ile Pro Tyr Val Leu Pro Glu Lys Asp Ser
            305                 310                 315                 320
            Trp Thr Val Asn Asp Ile Gln Lys Leu Val Gly Lys Leu Asn Trp Ala
                            325                 330                 335
            Ser Gln Met Val His Gln Ala Ile Ser Pro Arg Thr Leu Asn Ala Trp
                            340                 345                 350
            Val Lys Val Val Glu Glu Lys Ala Phe Ser Pro Ile Val Leu Pro Glu
                            355                 360                 365
            Lys Asp Ser Trp Thr Val Asn Asp Ile Gln Lys Leu Val Gly Lys Leu
                            370                 375                 380
            Asn Trp Ala Ser Gly Thr Gly Pro Cys Thr Asn Val Ser Thr Val Gln
            385                 390                 395                 400
            Cys Thr His Gly Ile Arg Pro Val Val Ser Thr Gln Leu Tyr Leu Lys
                            405                 410                 415
            Asp Gln Gln Leu Leu Gly Ile Trp Gly Cys Ser Gly Lys Leu Ile Cys
                            420                 425                 430
            Thr Thr Ala Val Pro Trp Ala Ala Lys Lys His Gln Lys Glu Pro
                            435                 440                 445
            Pro Phe Leu Trp Met Gly Tyr Glu Leu His Pro Asp Lys Trp Thr Val
                            450                 455                 460
            Gln Pro Val Tyr Tyr Arg Asp Ser Arg Asp Pro Leu Trp Lys Gly Pro
            465                 470                 475                 480
            Ala Lys Leu Leu Trp Lys Gly Glu Gly Ala Val Asn Leu Leu Thr Gln
                            485                 490                 495
            Ile Gly Cys Thr Leu Asn Phe Pro Ile Ser Pro Ile Glu Thr Val Pro
                            500                 505                 510
            Val Lys Leu Lys Gly Pro Lys Glu Pro Phe Arg Asp Tyr Val Asp Arg
                            515                 520                 525
            Phe Tyr Lys Thr Leu Arg Ala Glu Gln Ala Ser Gln Glu Val Leu Gly
                            530                 535                 540
            Pro Ala Ala Thr Leu Glu Glu Met Met Thr Ala Cys Gln Gly Val Gly
            545                 550                 555                 560
            Gly Pro Gly His Lys Ala Arg Asp Gln Ser Leu Lys Pro Cys Val Lys
                            565                 570                 575
            Leu Thr Pro Leu Cys Val Thr Leu Asn Cys Thr Asp Leu Arg Asn Thr
                            580                 585                 590
            Gly Pro Gly Ile Arg Tyr Pro Leu Leu Thr Phe Gly Trp Cys Phe Lys
                            595                 600                 605
            Leu Pro Val Glu Pro Glu Lys Val Glu Ala Lys Ile Ile Arg Asp Tyr
                            610                 615                 620
            Gly Lys Gln Met Ala Gly Asp Cys Val Ala Ser Arg Gln Asp Glu
            625                 630                 635                 640
            Asp Ile Leu Lys Ala Leu Gly Pro Ala Ala Thr Leu Glu Glu Met Met
                            645                 650                 655
```

```
Thr Ala Cys Gln Gly Val Gly Pro Gly Tyr Lys Ala Ala Val Asp
            660                 665                 670

Leu Ser His Phe Leu Arg Glu Lys Gly Gly Leu Glu Gly Ala Ala Tyr
        675                 680                 685

Ala Ala Lys Ala Tyr Asp Thr Glu Val His Asn Val Trp Ala Thr His
        690                 695                 700

Ala Cys Val Pro Thr Asp Pro Asn Pro Gln Glu Ala Ala Leu Ser
705                 710                 715                 720

Glu Gly Ala Thr Pro Gln Asp Leu Asn Thr Met Leu Asn Thr Val Gly
                725                 730                 735

Gly His Gln Ala Ala Met Gln Gln Val Asp Cys Ser Pro Gly Ile Trp
            740                 745                 750

Gln Leu Asp Cys Thr His Leu Glu Gly Lys Ile Ile Leu Val Ala Val
        755                 760                 765

<210> SEQ ID NO 412
<211> LENGTH: 39
<212> TYPE: PRT
<213> ORGANISM: Unknown
<220> FEATURE:
<223> OTHER INFORMATION: Description of Unknown:
      LAMP-1 C-terminal sequence

<400> SEQUENCE: 412

Gly Ser Glu Phe Thr Leu Ile Pro Ile Ala Val Gly Gly Ala Leu Ala
1               5                   10                  15

Gly Leu Val Ile Val Leu Ile Ala Tyr Leu Val Gly Arg Lys Arg Ser
            20                  25                  30

His Ala Gly Tyr Gln Thr Ile
        35

<210> SEQ ID NO 413
<211> LENGTH: 21
<212> TYPE: PRT
<213> ORGANISM: Unknown
<220> FEATURE:
<223> OTHER INFORMATION: Description of Unknown:
      CXCL10, IP-10 sequence

<400> SEQUENCE: 413

Met Asn Gln Thr Ala Ile Leu Ile Cys Cys Leu Ile Phe Leu Thr Leu
1               5                   10                  15

Ser Gly Ile Gln Gly
            20

<210> SEQ ID NO 414
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 414
atgggagcta gagctagcgt gctgagcgga ggagaactcg atcgctggga aaagatcaga      60
ctgagaccag gaggcaagaa gaagtacaga ctgaagcaca tcgtctgggc ttctagagaa    120
ctggaaagat cgccgtgaa tccaggactg ctggaaacac tgaagcacat tgtctgggct    180
agcagagaac tggagagatt tgccgtgaat ccaggactgc tggaaacagc agctatctct    240
cctagaacac tgaacgcttg ggtgaaagtg gtggaggaaa aggcctttag cccagaagtg    300
```

```
atccctatgt ttagcgccct gtcagaagga gctacacctc aggatctgaa caccatgctg      360
aacacagtgg gaggacatca ggcagctatg cagatgctga aggagacaat taacgaagaa      420
gccgccgagt gggatagact gcatccagtg cacgcaggac ctattgctcc aggacagatg      480
agagagccta gaggaagcga tatcgcagga acaaacatcta cactgcagga gcagatcggt      540
tggatgacca ataatcctcc tatcccagtg ggcgaaatct ataagcgctg gatcatcctg      600
ggactgaaca agatcgtgag gatgtacagc cctaccagca tcctggatat cagacaggga      660
cctaaggagc ctttcagaga ttacgtggac aggttctaca agacactgag agccgaacag      720
gcttctcagg aggtgaagaa ttggatgacc gagacactgc tggtgcagaa cgctaatcca      780
gattgcaaga caattctgaa agctctggga ccagccgcta cactggaaga tgatgatgacc     840 gcttgtcagg gagtggggagg accaggacat aaagctagag tgctggcaga agccatgtct     900
caggaagaag tgggattccc agtgaaacct caggtgcctc tgagacctat gacctttaag      960
ggagctctgg acctgtctca cttcctgaga gaaaagggag gactgaaagg aacacaggga     1020 ttttttcccag atcagaatta cacaccagag ccaggaatca gattccctct gacattcggt     1080
tggtgcttca aactggtgcc tctg                                            1104
```

<210> SEQ ID NO 415
<211> LENGTH: 2562
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 415

```
ggaacagtgc tggtgggacc tactccagtg aatatcatcg aaggaaccct gctgacacag       60
attggttgta ccctgaactt ccctatctct cctatcgaga cagtgccagt gaaactgaag      120
ccaggaatgg atggacctaa agtcaagcag tggcctctga cagaagagaa gatcaaagcc      180
ctggtggaga tttgcaccga gatggagaag gagggaaaga tcagcaagat cggcccagag      240
aatccttaca cacccccagt gttcgccatc aagaagaagg atagcaccaa gtggagaaag      300
ctggtggatt tcagggagct gaacaagaga acccaggatt tttgggaggt gcagctgggt      360
attccacatc ctgccggact gaaaaagaag aaaagcgtga cagtgctgga cgtgggagac      420
gcttatttca gcgtgcctct ggataaggac ttcagaaagt acaccgcctt caccatccct      480
tctatcaaca acgagacccc aggaatcaga taccagtaca acgtgctgcc tcaaggttgg      540
aaaggatctc cagccatctt tcagagcagc atgacaacag tgaaggcagc ttgttggtgg      600
gcaggaatta gcaggagtt cggcatccct tacaatcctc agtctcaggg agtggtggaa      660
tctatgaaca aggagctgaa gaagatcatc ggacaggtga gagatcaggc cgaacatctg      720
aagacagcag tgcaaatggc cgtgttcatc cacaacttca gagaaagggg cggcattgga      780
ggctattctg ccggagagag aattgtggac atcatcaacg tgtcaacagt ccagtgtaca      840
cacggaatca gaccagtcgt gtctacacaa ctgctgctga acggatctct ggccgaagag      900
aagagaagag tggtgcagag agagaaaaga gcagtgggaa tcgagctat gtttctggga      960 tttctgggcg cagcaggatc tacaatggga gcagcttcta tcacactgac agtgcaggct     1020
agacaactgc tgagcggaat tgtgcagcag cagaataacc tgctgagagc tatcgaagct     1080
cagcaacatc tgctgcaact caccgtctgg ggaattaagc aactgcaagc tagagtgctg     1140
gcagtggaaa gatacctgaa ggatcagcaa ctgctgggaa tttggggttg ctcaggcaag     1200
```

```
ctgatttgca caaccgtggc caaagagatt gtggcttctt gcgacaagtg tcagctgaaa      1260
ggagaagcta tgcacggaca gtggattgt tctccaggaa tttggcagct ggattgtaca       1320
cacctggagg gaaagattat tctggtggca gtgcacgtgg ccagcggata tattgaagcc     1380
gaggtgattc cagcagaaac aggacaggaa acagccattt ttctcctgaa actggcaggt    1440
aggtggccag tgaaaaccct ctgggtgaca gtgtactacg gagtcccagt ctggaaagaa    1500
gcagctttcc ctcagattac tctctggcag agacctctgg tgacaatcaa gatcggcgga    1560
cagctgaaag aagctctgct ggatacagga gcagacgata cagtgctgga gaaatgaac     1620 ctgccaggta gatggaagcc taagatgatc ggaggcatcg gaggattcat caaggtgaga    1680
cagtacgacc aagcagcagc agctcataac gtctgggcta cacacgcttg cgtgcctaca    1740
gatcctaatc ctcaggaagc catcaccaag atccagaatt tcagggtgta ctacagggac    1800
agcagagatc ctctctggaa aggaccagct aaactgctgt ggaaaggaga aggagcagtg    1860
gtgatccagg ataacagcga catcaaggtg gtgcctagaa gaaaggccaa gatcatcagg    1920
gactacggaa agcaaatggc aggagacgat tgcgtggctt ctagacagga cgaggatccc    1980
aagttcaagc tgcctattca gaaggagact tgggagactt ggtggacaga gtattggcaa    2040
gcaacttgga tccccgagtg ggaatttgtg aatacccctc ctctggtcaa gctctggtat    2100
cagctggaaa aggagcctat cgtgggagcc gaaacatttt acgtggacgg agcagctaat    2160
agagagacaa agccgccaa ggagaaagtg tatctggctt gggtgccagc tcataaagga     2220
atcggaggaa acgagcaggt ggataaactg gtgtcttggg gctttaccac accagataag    2280
aagcaccaga aggagccacc atttctctgg atgggatacg aactgcaccc agataagtgg    2340
acagtccagc ctattgtgct gccagaaaag gactcttgga cagtgaacga catccagaaa    2400
ctggtgggaa agctgaattg gcctctcag atctacccag gcatcaaggt gatcgtgatc     2460
taccagtaca tggacgatct gtacgtggga tcagatctgg agatcggaca gcacagaatg    2520
agggacaatt ggagaagcga gctgtacaag tacaaggtgg tg                       2562
```

<210> SEQ ID NO 416
<211> LENGTH: 1144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 416

```
taccagtata acgtgctgcc tcagggagct tctagagaac tggagagatt cgcagtgaac       60
ccaggactcc tctggattat cctgggactg aacaagatcg tgaggatgta ctctcctacc     120
tctattgccg ctagaacact gaacgcttgg gtgaaggtct tcctctggat gggatacgaa     180
ctgcatctga cctttggttg gtgctttaag ctccctctct ggaaaggacc agctaagctg     240
gtgacagtgt attacggagt gccagtgcca gctctcctct ggaaaggaga aggagcagtg    300
gcagcagcta aactggtggg aaagctgaat tgggccaaac tcctctggaa gggagaagga   360
gccaccctga ttttcctat cagccctatt tggcaggcta cttggattcc agagtggaaa     420
gcagcttgtt ggtgggcagg aatcagacag gccaacttcc tgggcaagat ttggccttct    480
cacaaaggaa gaaacgtctg ggctacacac gcttgcgtgg cagcagaaat gatgacagct    540 tgtcaggag tgtctacagt ccagtgtaca cacggaatcg cagctaaaca gatggcagga    600
gacgattgcg tggcagcttg gcagctggat tgtacacacc tggagtacaa ggcagcagtg    660
```

```
gatctgtctc actttctgag agaaaaagga ggactggaag gagcagctta ctacatggac    720
gatctgtacg tgggatcagg acaggtggat tgttcaccag gaatcgctac actggaggaa    780
atgatgaccg cagaactgca tccagataag tggaccgtct ggacagtgaa cgatatccag    840
aagctgggca tttggggttg tagcggaaaa ctgaccgtga acgatatcca gaagctggtg    900
atcgtgaccg attctcagta cgctctgtac gtggacagat tctacaagac cctgtacgtg    960
gacaggttct acaagacact gagagccgaa caggcttctc aggaagtgga tctgaacacc   1020
atgctgaaca ccgtgaaact gacacctctc tgcgtgacac tgtatcagta catggacgac   1080
ctgtacgtgg tgatctacca gtacatggac gatctctgga tcatcctggg actgaacaag   1140
atcg                                                                1144
```

<210> SEQ ID NO 417
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 417

```
agaacactga acgcttgggt gaaggtgaga gagaagagag acctgaacac catgctgaac     60
accgtgagag aaaagaggtg gatcatcctg ggactgaaca agatcaggga gaagaggtac    120
gtggacaggt tctacaagac actgagagag aagagagcca cactggaaga tgatgatgacc   180 gctagagaga agagagagat gatgaccgct tgtcagggag tgagagagaa gagaaccctg    240
aacttcccca tctctcctat cagggagaag aggtaccagt acaacgtgct gcctcaggga    300
agagaaaaga gagtgatcta ccagtacatg gacgacctga gagagaagag gtaccagtac    360
atggacgatc tgtacgtgag ggagaagaga tacatggacg acctgtacgt gggatcaaga    420
gagaagagat tcctctggat gggctacgag ctgcatagag agaagagaga gctgcaccca    480
gataagtgga cagtgagaga aaagcgctgg acagtgaacg acatccagaa gctgagagag    540
aagaggacag tgaacgacat ccagaagctg gtgagagaga agaggaagct ggtgggaaaa    600
ctgaattggg ctagggaaaa aaggtggcag gctacttgga ttccagagtg gagagagaag    660
aggatcgtga cagatagcca gtacgctctg agagagaaaa gaggacaggt ggattgctct    720
ccaggaatca gagagaagag atggcagctg gattgtacac acctggagag agagaagagg    780
aaagcagctt gttggtgggc aggaattcgg gaaaaaagac ctctctggaa aggaccagcc    840
aagctgagag agaagagaaa actcctctgg aagggcgaag gagctagaga aaagagactc    900
ctctggaaag gagaaggcgc agtgagagag aagagaaaac agatggccgg agacgattgc    960
gtgagagaaa gagagtgac cgtgtattac ggagtgccag tgagagaaaa gagaaacgtc   1020
tgggctacac acgcttgcgt gagagagaag agaaagctga cacctctgtg cgtgacactg    1080
agagaaaaga gaagcaccgt gcagtgtaca cacggaatta gggagaagag aggcatttgg   1140
ggttgttcag gaaagctgag agagaagagg ctgacattcg gttggtgttt caagctgagg   1200
gagaagagag cctctagaga actggagaga ttcgcagtga atccaggact gctgagagaa   1260
aagcgctgga ttatcctggg actgaacaag atcgtgagga tgtacagccc tacaagcatc   1320
agagaagaga ggtacgtgga cagattctac aagaccctga gagccgaaca ggcatctcag   1380
gaagtgagag agaagagaag gcaggctaac ttcctgggaa agatttggcc tagccacaag   1440
ggaagaagag agaagagata caaggccgca gtggatctgt ctcactttct gagagagaaa    1500
```

```
ggaggactgg aaggagga                                                  1518
```

<210> SEQ ID NO 418
<211> LENGTH: 2784
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 418

```
atggctccta gaagcgctag aagacctctg ctgctgctgc tgctgctgct gctgctggga    60
ctgatgcatt gcgcttcagc agctatgttc atggtgaaga acggcaacgg aacagcttgt   120
atcatggcca atttcagcgc cgcttttagc gtgaattacg acaccaagag cggacctaag   180
aacatgacac tggatctgcc ttcagacgct acagtggtgc tgaatagaag ctcttgcgga   240
aaggagaata cctccgatcc ttctctggtg atcgcttttg cagaggaca cacactgaca    300
ctgaacttca ccagaaacgc caccagatac tcagtgcagc tgatgagctt cgtgtacaac   360
ctgagcgata cccatctgtt tcctaacgct agcagcaagg agatcaagac agtggagtct   420
atcaccgaca tcagagccga tatcgacaag aaataccgct gcgtgtcagg aacacaggtg   480
cacatgaaca acgtgacagt gacactgcac gacgccacaa ttcaggccta tctgagcaat   540
agcagcttta gcagaggcga aactaggtgt gagcaggata gaccttctcc tacaacagct   600
cctccagctc ctccttctcc ttctcctcct ccagtgccta aatctcctag cgtggataag   660
tacaacgtga gcggaacaaa cggcacttgt ctgctggctt ctatgggact gcagctgaat   720
ctgacatacg agaggaagga caacaccaca gtgacaagac tgctgaacat caaccccaac   780
aaaacaagcg ctagcggatc ttgcggagct catctggtga cactggaact gcattcagag   840
ggaacaacag tgctgctgtt tcagttcgga atgaacgcct cagcagcag attcttcctg    900
cagggtattc agctgaatac actgctgcca gatgctagag atccagcctt taaagccgct   960
aatggatctc tgagagctct gcaggctaca gtgggaaata gctacaagtg caacgccgaa  1020
gaacacgtga gtgacaaa agccttcagc gtgaacatct taaggtctg ggtgcaggca     1080
tttaaagtgg agggaggcca gtttggaagc gtcgaagagt gtctgctgga cgaaaatagc  1140
ctggaagaca tcagaacact gaacgcttgg gtgaaggtga gagagaagag agacctgaac  1200
accatgctga acaccgtgag agaaaagagg tggatcatcc tgggactgaa caagatcagg  1260
gagaagaggt acgtggacag gttctacaag acactgagag agaagagagc cacactggaa  1320
gagatgatga ccgctagaga agagagagag atgatgaccg cttgtcaggg agtgagagag  1380
aagagaaccc tgaacttccc catctctcct atcaggaga agaggtacca gtacaacgtg   1440
ctgcctcagg gaagagaaaa gagagtgatc taccagtaca tggacgacct gagagagaag  1500
aggtaccagt acatggacga tctgtacgtg agggagaaga gatacatgga cgacctgtac  1560
gtgggatcaa gagagaagag attcctctgg atgggctacg agctgcatag agagaagaga  1620
gagctgcacc cagataagtg gacagtgaga gaaaagcgct ggacagtgaa cgacatccag  1680
aagctgagag agaagaggac agtgaacgac atccagaagc tggtgagaga agaggaag    1740
ctggtgggaa aactgaattg gctagggaa aaaggtggc aggctacttg gattccagag    1800
tggagagaga agaggatcgt gacagatagc cagtacgctc tgagagagaa aagaggacag  1860
gtggattgct ctccaggaat cagagagaag agatggcagc tggattgtac acacctggag  1920
agagagaaga ggaaagcagc ttgttggtgg gcaggaattc gggaaaaaag acctctctgg  1980
```

-continued

```
aaaggaccag ccaagctgag agagaagaga aaactcctct ggaagggcga aggagctaga    2040
gaaaagagac tcctctggaa aggagaaggc gcagtgagag agaagagaaa acagatggcc    2100
ggagacgatt gcgtgagaga aaagagagtg accgtgtatt acggagtgcc agtgagagaa    2160
aagagaaacg tctgggctac acacgcttgc gtgagagaga agagaaagct gacacctctg    2220
tgcgtgacac tgagagaaaa gagaagcacc gtgcagtgta cacacggaat tagggagaag    2280
agaggcattt ggggttgttc aggaaagctg agagagaaga ggctgacatt cggttggtgt    2340
ttcaagctga gggagaagag agcctctaga gaactggaga gattcgcagt gaatccagga    2400
ctgctgagag aaaagcgctg gattatcctg ggactgaaca agatcgtgag gatgtacagc    2460
cctacaagca tcagagagaa gaggtacgtg gacagattct acaagaccct gagagccgaa    2520
caggcatctc aggaagtgag agagaagaga aggcaggcta acttcctggg aaagatttgg    2580
cctagccaca agggaagaag agagaagaga tacaaggccg cagtggatct gtctcacttt    2640
ctgagagaga aaggaggact ggaaggagga agcgagttta ccctgattcc aattgccgtg    2700
ggaggagctc tggcaggact ggtgattgtg ctgatcgcat acctggtggg aagaaagaga    2760
tctcacgccg gatatcagac catc                                           2784
```

<210> SEQ ID NO 419
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Gly Gly Ser
1

<210> SEQ ID NO 420
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Gly Ser Gly
1

<210> SEQ ID NO 421
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gly Gly Gly Ser
1

<210> SEQ ID NO 422
<211> LENGTH: 706
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

```
Ile Cys Gly His Lys Ala Ile Gly Thr Val Leu Val Gly Pro Thr Pro
1               5                   10                  15

Val Asn Ile Ile Gly Arg Asn Leu Leu Thr Gln Leu Gly Cys Thr Leu
            20                  25                  30

Asn Phe Pro Ile Ser Pro Ile Glu Thr Val Pro Val Lys Leu Lys Pro
        35                  40                  45

Gly Met Asp Gly Pro Lys Val Lys Gln Trp Pro Leu Thr Glu Glu Lys
50                  55                  60

Ile Lys Ala Leu Asp Pro Leu Trp Lys Gly Pro Ala Lys Leu Leu Trp
65                  70                  75                  80

Lys Gly Glu Gly Ala Val Val Ile Gln Asp Asn Ser Asp Ile Lys Val
                85                  90                  95

Val Pro Arg Arg Lys Ala Lys Ile Ile Arg Asp Tyr Gly Lys Gln Met
            100                 105                 110

Ala Ala Ala Tyr Ser Asp Ile Ala Gly Thr Thr Ser Thr Leu Gln Glu
        115                 120                 125

Gln Ile Thr Trp Met Thr Asn Asn Pro Pro Ile Pro Val Gly Glu Ile
130                 135                 140

Tyr Lys Arg Trp Ile Ile Leu Gly Leu Asn Lys Ile Val Arg Met Tyr
145                 150                 155                 160

Ser Pro Val Ser Ile Leu Asp Ile Arg Gln Gly Pro Lys Glu Pro Phe
                165                 170                 175

Arg Asp Tyr Val Asp Arg Phe Tyr Lys Thr Leu Arg Ala Glu Gln Ala
            180                 185                 190

Ser Gln Glu Val Lys Asn Trp Met Thr Glu Thr Leu Leu Val Gln Asn
        195                 200                 205

Ala Asn Pro Asp Cys Lys Thr Ile Leu Lys Ala Leu Gly Pro Ala Ala
210                 215                 220

Thr Leu Glu Glu Met Met Thr Ala Cys Gln Gly Val Gly Gly Pro Gly
225                 230                 235                 240

His Lys Ala Arg Val Leu Ala Glu Ala Met Ser Gln Val Thr Asn Ser
                245                 250                 255

Ala Thr Leu Asn Lys Arg Thr Gln Asp Phe Trp Glu Val Gln Leu Gly
            260                 265                 270

Ile Pro His Pro Ala Gly Leu Lys Lys Lys Ser Asn Phe Thr Ser
        275                 280                 285

Thr Thr Val Lys Ala Ala Cys Trp Trp Ala Gly Ile Lys Gln Glu Phe
290                 295                 300

Gly Ile Pro Tyr Asn Pro Gln Ser Ala Tyr Phe Ser Val Pro Leu Asp
305                 310                 315                 320

Lys Glu Phe Arg Lys Tyr Thr Ala Phe Thr Ile Pro Ser Ile Asn Asn
                325                 330                 335

Glu Asp Thr Val Leu Glu Glu Met Asn Leu Pro Gly Lys Trp Lys Pro
            340                 345                 350

Lys Met Ile Gly Gly Ile Gly Gly Phe Ile Lys Val Arg Gln Tyr Asp
        355                 360                 365

Gln Ile Ser Lys Ile Gly Pro Glu Asn Pro Tyr Asn Thr Pro Ile Phe
370                 375                 380

Ala Ile Lys Lys Lys Asp Ser Thr Lys Trp Ala Ala Gly Lys Lys Lys
385                 390                 395                 400

Tyr Arg Leu Lys His Leu Val Trp Val Ser Arg Glu Leu Glu Arg Phe
```

```
            405                 410                 415
Ala Val Asn Pro Gly Lys Lys Tyr Arg Leu Lys His Leu Val
        420                 425                 430

Trp Ala Ser Arg Glu Leu Glu Arg Phe Ala Val Asn Pro Gly Ala Glu
        435                 440                 445

His Leu Lys Thr Ala Val Gln Met Ala Val Phe Ile His Asn Phe Lys
        450                 455                 460

Arg Lys Gly Gly Ile Gly Gly Ala Gly Gln Met Val His Gln Ala
465                 470                 475                 480

Ile Ser Pro Arg Thr Leu Asn Ala Trp Val Lys Val Glu Glu Lys
                485                 490                 495

Ala Phe Ser Pro Glu Val Ile Pro Met Phe Ser Ala Leu Ala Glu Gly
            500                 505                 510

Ala Thr Pro Gln Asp Leu Asn Thr Met Leu Asn Thr Val Gly Gly His
            515                 520                 525

Gln Ala Arg Trp Ile Ile Leu Gly Leu Asn Lys Thr Val Arg Met Tyr
            530                 535                 540

Ser Pro Val Ser Ile Leu Asp Ile Arg Gln Gly Pro Lys Glu Pro Phe
545                 550                 555                 560

Arg Asp Tyr Val Asp Arg Phe Tyr Lys Thr Leu Arg Ala Glu Gln Ala
                565                 570                 575

Ser Gln Glu Val Lys Asn Trp Met Thr Glu Thr Leu Leu Val Gln Asn
            580                 585                 590

Ala Asn Pro Asp Cys Lys Thr Ile Leu Lys Ala Leu Gly Pro Ala Ala
            595                 600                 605

Thr Leu Glu Glu Met Met Thr Ala Cys Gln Gly Val Gly Gly Pro Gly
610                 615                 620

His Lys Ala Arg Val Leu Ala Glu Ala Met Ser Gln Val Thr Asn Ser
625                 630                 635                 640

Ala Thr Gln Leu Lys Gly Glu Ala Met His Gly Gln Val Asp Cys Ser
            645                 650                 655

Pro Gly Ile Trp Gln Leu Asp Cys Thr His Leu Glu Gly Lys Val Ile
            660                 665                 670

Leu Val Ala Val His Val Ala Ser Gly Tyr Ile Glu Ala Glu Val Ile
    675                 680                 685

Pro Ala Glu Thr Gly Gln Glu Thr Ala Tyr Phe Leu Leu Lys Leu Ala
        690                 695                 700

Gly Arg
705

<210> SEQ ID NO 423
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Ser Asn Phe Thr Ser Thr Thr Val Lys Val Ala Cys Trp Trp Ala Gly
1               5                   10                  15

Ile Lys Gln Glu Phe Gly Ile Pro Tyr Ala Ala Ser Asn Phe Thr Ser
            20                  25                  30

Thr Thr Val Lys Ala Ala Cys Trp Trp Ala Gly Val Lys Gln Glu Phe
        35                  40                  45
```

```
Gly Ile Pro Tyr Ala Ala Ser Asn Phe Thr Ser Thr Thr Val Lys Ala
    50                  55                  60

Ala Cys Trp Trp Ala Gly Ile Lys Gln Glu Phe Gly Ile Pro Tyr Pro
65                  70                  75                  80

Leu Arg Pro Met Thr Tyr Lys Ala Ala Val Asp Leu Ser His Phe Leu
                85                  90                  95

Lys Glu Lys Gly Gly Leu Glu Gly Pro Leu Arg Pro Met Thr Tyr Lys
                100                 105                 110

Ala Ala Val Asp Leu Ser Phe Phe Leu Lys Glu Lys Gly Gly Leu Glu
            115                 120                 125

Gly Pro Leu Arg Pro Met Thr Tyr Lys Gly Ala Phe Asp Leu Ser Phe
    130                 135                 140

Phe Leu Lys Glu Lys Gly Gly Leu Glu Gly Pro Leu Arg Pro Met Thr
145                 150                 155                 160

Tyr Lys Ala Ala Phe Asp Leu Ser Phe Phe Leu Lys Glu Lys Gly Gly
                165                 170                 175

Leu Glu Gly Pro Leu Arg Pro Met Thr Tyr Lys Ala Ala Phe Asp Leu
            180                 185                 190

Ser His Phe Leu Lys Glu Lys Gly Gly Leu Glu Gly Pro Leu Arg Pro
    195                 200                 205

Met Thr Tyr Lys Gly Ala Leu Asp Leu Ser His Phe Leu Lys Glu Lys
    210                 215                 220

Gly Gly Leu Glu Gly Gln Leu Lys Gly Glu Ala Met His Gly Gln Val
225                 230                 235                 240

Asp Cys Ser Pro Gly Ile Trp Gln Leu Asp Cys Thr His Leu Glu Glu
                245                 250                 255

Lys Ile Ile Leu Val Ala Val His Val Ala Ser Gly Tyr Ile Glu Ala
                260                 265                 270

Glu Val Ile Pro Ala Glu Thr Gly Gln Glu Thr Ala Tyr Met Val His
            275                 280                 285

Gln Ala Ile Ser Pro Arg Thr Leu Asn Ala Trp Val Lys Val Val Glu
    290                 295                 300

Glu Lys Ala Phe Ser Pro Leu Asp Cys Thr His Leu Glu Gly Lys Val
305                 310                 315                 320

Ile Leu Val Ala Val His Val Ala Ser Gly Tyr Ile Glu Ala Glu Ile
                325                 330                 335

Cys Gly His Lys Ala Ile Gly Thr Val Leu Val Gly Pro Thr Pro Val
                340                 345                 350

Asn Ile Ile Gly Arg Asn Leu Leu Thr Gln Ile Gly Cys Thr Leu Asn
            355                 360                 365

Phe Pro Ile Ser Pro Ile Glu Thr Val Pro Val Lys Leu Lys Asp Pro
    370                 375                 380

Leu Trp Lys Gly Pro Ala Lys Leu Leu Trp Lys Gly Glu Gly Ala Val
385                 390                 395                 400

Val Ile Gln Asp Asn Ser Asp Ile Asp Pro Leu Trp Lys Gly Pro Ala
                405                 410                 415

Lys Leu Leu Trp Lys Gly Glu Gly Val Val Ile Gln Asp Asn Ser
                420                 425                 430

Asp Ile Met Val His Gln Ala Ile Ser Pro Arg Thr Leu Asn Ala Leu
            435                 440                 445

Val Lys Val Val Glu Glu Lys Ala Phe Ser Pro Ile Cys Gly His Lys
    450                 455                 460

Ala Ile Gly Thr Val Leu Val Gly Ser Thr Pro Val Asn Ile Ile Gly
```

```
                465                 470                 475                 480

Arg Asn Leu Leu

<210> SEQ ID NO 424
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Ile Arg Thr Leu Asn Ala Trp Val Lys Val Arg Glu Lys Arg Asp Leu
1               5                   10                  15

Asn Thr Met Leu Asn Thr Val Arg Glu Lys Arg Trp Ile Ile Leu Gly
            20                  25                  30

Leu Asn Lys Ile Arg Glu Lys Arg Tyr Val Asp Arg Phe Tyr Lys Thr
        35                  40                  45

Leu Arg Glu Lys Arg Ala Thr Leu Glu Glu Met Met Thr Ala Arg Glu
    50                  55                  60

Lys Arg Glu Met Met Thr Ala Cys Gln Gly Val Arg Glu Lys Arg Thr
65                  70                  75                  80

Leu Asn Phe Pro Ile Ser Pro Ile Arg Glu Lys Arg Tyr Gln Tyr Asn
                85                  90                  95

Val Leu Pro Gln Gly Arg Glu Lys Arg Val Ile Tyr Gln Tyr Met Asp
            100                 105                 110

Asp Leu Arg Glu Lys Arg Tyr Gln Tyr Met Asp Asp Leu Tyr Val Arg
        115                 120                 125

Glu Lys Arg Tyr Met Asp Asp Leu Tyr Val Gly Ser Arg Glu Lys Arg
    130                 135                 140

Phe Leu Trp Met Gly Tyr Glu Leu His Arg Glu Lys Arg Glu Leu His
145                 150                 155                 160

Pro Asp Lys Trp Thr Val Arg Glu Lys Arg Trp Thr Val Asn Asp Ile
                165                 170                 175

Gln Lys Leu Arg Glu Lys Arg Thr Val Asn Asp Ile Gln Lys Leu Val
            180                 185                 190

Arg Glu Lys Arg Lys Leu Val Gly Lys Leu Asn Trp Ala Arg Glu Lys
        195                 200                 205

Arg Trp Gln Ala Thr Trp Ile Pro Glu Trp Arg Glu Lys Arg Ile Val
    210                 215                 220

Thr Asp Ser Gln Tyr Ala Leu Arg Glu Lys Arg Gly Gln Val Asp Cys
225                 230                 235                 240

Ser Pro Gly Ile Arg Glu Lys Arg Trp Gln Leu Asp Cys Thr His Leu
                245                 250                 255

Glu Arg Glu Lys Arg Lys Ala Ala Cys Trp Trp Ala Gly Ile Arg Glu
            260                 265                 270

Lys Arg Pro Leu Trp Lys Gly Pro Ala Lys Leu Arg Glu Lys Arg Lys
        275                 280                 285

Leu Leu Trp Lys Gly Glu Gly Ala Arg Glu Lys Arg Leu Leu Trp Lys
    290                 295                 300

Gly Glu Gly Ala Val Arg Glu Lys Arg Lys Gln Met Ala Gly Asp Asp
305                 310                 315                 320

Cys Val Arg Glu Lys Arg Val Thr Val Tyr Tyr Gly Val Pro Val Arg
                325                 330                 335

Glu Lys Arg Asn Val Trp Ala Thr His Ala Cys Val Arg Glu Lys Arg
```

-continued

```
                340                 345                 350
Lys Leu Thr Pro Leu Cys Val Thr Leu Arg Glu Lys Arg Ser Thr Val
            355                 360                 365

Gln Cys Thr His Gly Ile Arg Glu Lys Arg Gly Ile Trp Gly Cys Ser
        370                 375                 380

Gly Lys Leu Arg Glu Lys Arg Leu Thr Phe Gly Trp Cys Phe Lys Leu
385                 390                 395                 400

Arg Glu Lys Arg Ala Ser Arg Glu Leu Glu Arg Phe Ala Val Asn Pro
                405                 410                 415

Gly Leu Arg Glu Lys Arg Trp Ile Ile Leu Gly Leu Asn Lys Ile
            420                 425                 430

Val Arg Met Tyr Ser Pro Thr Ser Ile Arg Glu Lys Arg Tyr Val Asp
        435                 440                 445

Arg Phe Tyr Lys Thr Leu Arg Ala Glu Gln Ala Ser Gln Glu Val Arg
    450                 455                 460

Glu Lys Arg Arg Gln Ala Asn Phe Leu Gly Lys Ile Trp Pro Ser His
465                 470                 475                 480

Lys Gly Arg Arg Glu Lys Arg Tyr Lys Ala Ala Val Asp Leu Ser His
                485                 490                 495

Phe Leu Arg Glu Lys Gly Gly Leu Glu Gly
            500                 505

<210> SEQ ID NO 425
<211> LENGTH: 80
<212> TYPE: PRT
<213> ORGANISM: Human immunodeficiency virus

<400> SEQUENCE: 425

Ala Val Lys Ala Ala Cys Trp Trp Ala Gly Val Lys Gln Glu Phe Gly
1               5                   10                  15

Ile Pro Tyr Asn Thr Gln Ser Gln Gly Val Val Glu Ser Met Asn Asn
            20                  25                  30

Glu Leu Lys Lys Ile Ile Gly Gln Ile Arg Asp Gln Ala Glu His Leu
        35                  40                  45

Lys Thr Ala Val Gln Met Ala Val Leu Ile His Asn Phe Lys Arg Lys
    50                  55                  60

Gly Gly Ile Gly Glu Tyr Ser Ala Gly Glu Arg Ile Ile Asp Ile Ile
65                  70                  75                  80

<210> SEQ ID NO 426
<211> LENGTH: 81
<212> TYPE: PRT
<213> ORGANISM: Human immunodeficiency virus

<400> SEQUENCE: 426

Ala Val Lys Ala Ala Cys Trp Trp Ala Gly Val Lys Gln Glu Phe Gly
1               5                   10                  15

Ile Pro Tyr Asn Thr Gln Ser Gln Gly Val Val Glu Ser Met Asn Asn
            20                  25                  30

Glu Leu Lys Lys Ile Ile Gly Gln Ile Arg Asp Gln Ala Glu His Leu
        35                  40                  45

Lys Thr Ala Val Gln Met Ala Val Leu Ile His Asn Phe Lys Arg Lys
    50                  55                  60

Gly Gly Ile Gly Glu Tyr Ser Ala Gly Glu Arg Ile Ile Asp Ile Ile
65                  70                  75                  80

Ala
```

<210> SEQ ID NO 427
<211> LENGTH: 81
<212> TYPE: PRT
<213> ORGANISM: Human immunodeficiency virus

<400> SEQUENCE: 427

Val Ala Lys Glu Ile Val Ala Cys Cys Asp Lys Cys Gln Leu Lys Gly
1               5                   10                  15
Glu Ala Ile His Gly Gln Val Asp Cys Ser Pro Gly Val Trp Gln Leu
            20                  25                  30
Asp Cys Thr His Leu Glu Gly Lys Val Ile Leu Val Ala Val His Val
        35                  40                  45
Ala Ser Gly Tyr Ile Glu Ala Glu Ile Ile Pro Thr Glu Thr Gly Gln
    50                  55                  60
Glu Thr Ala Tyr Phe Ile Leu Lys Leu Ala Gly Arg Trp Pro Val Thr
65                  70                  75                  80
Thr

<210> SEQ ID NO 428
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Leu Lys His Ile Val Trp Ala Ser Arg Glu Leu Glu Arg Phe Ala Val
1               5                   10                  15
Asn Pro Gly Leu Leu Glu Thr Val Ser Gln Asn Tyr Pro Ile Val Gln
            20                  25                  30
Asn Ile Ser Pro Arg Thr Leu Asn Ala Trp Val Lys Val Val Glu Glu
        35                  40                  45
Lys Ala Phe Ser Pro Glu Val Ile Pro Met Phe Ser Ala Leu Ser Glu
    50                  55                  60
Gly Ala Thr Pro Gln Asp Leu Asn Thr Met Leu Asn Thr Val Gly Gly
65                  70                  75                  80
His Gln Ala Ala Met Gln Met Leu Lys Glu Thr Ile Asn Glu Glu Ala
            85                  90                  95
Ala Glu Trp Asp Arg Leu His Pro Val His Ala Gly Pro Ile Ala Pro
        100                 105                 110
Gly Gln Met Arg Glu Pro Arg Gly Ser Asp Ile Ala Gly Thr Thr Ser
    115                 120                 125
Thr Leu Gln Glu Gln Ile Gly Trp Met Thr Asn Asn Pro Pro Ile Pro
130                 135                 140
Val Gly Glu Ile Tyr Lys Arg Trp Ile Ile Leu Gly Leu Asn Lys Ile
145                 150                 155                 160
Val Arg Met Tyr Ser Pro Thr Ser Ile Leu Asp Ile Arg Gln Gly Pro
            165                 170                 175
Lys Glu Pro Phe Arg Asp Tyr Val Asp Arg Phe Tyr Lys Thr Leu Arg
        180                 185                 190
Ala Glu Gln Ala Ser Gln Glu Val Lys Asn Trp Met Thr Glu Thr Leu
    195                 200                 205
Leu Val Gln Asn Ala Asn Pro Asp Cys Lys Thr Ile Leu Lys Ala Leu
    210                 215                 220

```
Gly Pro Ala Ala Thr Leu Glu Glu Met Met Thr Ala Cys Gln Gly Val
225                 230                 235                 240

Gly Gly Pro Gly His Lys Ala Arg Val Leu Ala Glu Ala Met Ser Gln
            245                 250                 255
```

<210> SEQ ID NO 429
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

```
Leu Pro Gly Arg Trp Lys Pro Lys Met Ile Gly Gly Ile Gly Gly Phe
1               5                   10                  15

Ile Lys Val Arg Gln Tyr Asp Gln Gly Thr Val Leu Val Gly Pro Thr
            20                  25                  30

Pro Val Asn Ile Ile Gly Arg Asn Leu Leu Thr Gln Ile Gly Cys Thr
        35                  40                  45

Leu Asn Phe Pro Ile Ser Pro Ile Glu Thr Val Pro Val Lys Leu Lys
50                  55                  60

Pro Gly Met Asp Gly Pro Lys Val Lys Gln Trp Pro Leu Thr Glu Glu
65                  70                  75                  80

Lys Ile Lys Ala Leu Val Glu Ile Cys Thr Glu Met Glu Lys Glu Gly
                85                  90                  95

Lys Ile Ser Lys Ile Gly Pro Glu Asn Pro Tyr Asn Thr Pro Val Phe
            100                 105                 110

Ala Ile Lys Lys Lys Asp Ser Thr Lys Trp Arg Lys Leu Val Asp Phe
        115                 120                 125

Arg Glu Leu Asn Lys Arg Thr Gln Asp Phe Trp Glu Val Gln Leu Gly
130                 135                 140

Ile Pro His Pro Ala Gly Leu Lys Lys Lys Ser Val Thr Val Leu
145                 150                 155                 160

Asp Val Gly Asp Ala Tyr Phe Ser Val Pro Leu Asp Lys Asp Phe Arg
                165                 170                 175

Lys Tyr Thr Ala Phe Thr Ile Pro Ser Trp Gly Phe Thr Thr Pro Asp
            180                 185                 190

Lys Lys His Gln Lys Glu Pro Pro Phe Leu Trp Met Gly Tyr Glu Leu
        195                 200                 205

His Pro Asp Lys Trp Thr Val Gln Pro Ile
210                 215
```

<210> SEQ ID NO 430
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
        35                  40                  45
```

Gly Leu Leu Glu Thr Leu Lys His Ile Val Trp Ala Ser Arg Glu Leu
 50                  55                  60

Glu Arg Phe Ala Val Asn Pro Gly Leu Leu Glu Thr Ala Ala Ile Ser
 65                  70                  75                  80

Pro Arg Thr Leu Asn Ala Trp Val Lys Val Val Glu Glu Lys Ala Phe
                 85                  90                  95

Ser Pro Glu Val Ile Pro Met Phe Ser Ala Leu Ser Glu Gly Ala Thr
            100                 105                 110

Pro Gln Asp Leu Asn Thr Met Leu Asn Thr Val Gly Gly His Gln Ala
        115                 120                 125

Ala Met Gln Met Leu Lys Glu Thr Ile Asn Glu Glu Ala Ala Glu Trp
130                 135                 140

Asp Arg Leu His Pro Val His Ala Gly Pro Ile Ala Pro Gly Gln Met
145                 150                 155                 160

Arg Glu Pro Arg Gly Ser Asp Ile Ala Gly Thr Thr Ser Thr Leu Gln
                165                 170                 175

Glu Gln Ile Gly Trp Met Thr Asn Asn Pro Pro Ile Pro Val Gly Glu
            180                 185                 190

Ile Tyr Lys Arg Trp Ile Ile Leu Gly Leu Asn Lys Ile Val Arg Met
        195                 200                 205

Tyr Ser Pro Thr Ser Ile Leu Asp Ile Arg Gln Gly Pro Lys Glu Pro
210                 215                 220

Phe Arg Asp Tyr Val Asp Arg Phe Tyr Lys Thr Leu Arg Ala Glu Gln
225                 230                 235                 240

Ala Ser Gln Glu Val Lys Asn Trp Met Thr Glu Thr Leu Leu Val Gln
                245                 250                 255

Asn Ala Asn Pro Asp Cys Lys Thr Ile Leu Lys Ala Leu Gly Pro Ala
            260                 265                 270

Ala Thr Leu Glu Glu Met Met Thr Ala Cys Gln Gly Val Gly Gly Pro
        275                 280                 285

Gly His Lys Ala Arg Val Leu Ala Glu Ala Met Ser Gln Glu Glu Val
290                 295                 300

Gly Phe Pro Val Lys Pro Gln Val Pro Leu Arg Pro Met Thr Phe Lys
305                 310                 315                 320

Gly Ala Leu Asp Leu Ser His Phe Leu Arg Glu Lys Gly Gly Leu Glu
                325                 330                 335

Gly Thr Gln Gly Phe Phe Pro Asp Gln Asn Tyr Thr Pro Glu Pro Gly
            340                 345                 350

Ile Arg Phe Pro Leu Thr Phe Gly Trp Cys Phe Lys Leu Val Pro Leu
        355                 360                 365

<210> SEQ ID NO 431
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Tyr Gln Tyr Asn Val Leu Pro Gln Gly Ala Ser Arg Glu Leu Glu Arg
 1                   5                  10                  15

Phe Ala Val Asn Pro Gly Leu Leu Trp Ile Ile Leu Gly Leu Asn Lys
                 20                  25                  30

Ile Val Arg Met Tyr Ser Pro Thr Ser Ile Ala Ala Arg Thr Leu Asn
            35                  40                  45

```
Ala Trp Val Lys Val Phe Leu Trp Met Gly Tyr Glu Leu His Leu Thr
    50                  55                  60
Phe Gly Trp Cys Phe Lys Leu Pro Leu Trp Lys Gly Pro Ala Lys Leu
 65                  70                  75                  80
Val Thr Val Tyr Tyr Gly Val Pro Val Ala Ala Leu Leu Trp Lys Gly
                85                  90                  95
Glu Gly Ala Val Ala Ala Lys Leu Val Gly Lys Leu Asn Trp Ala
            100                 105                 110
Lys Leu Leu Trp Lys Gly Glu Gly Ala Thr Leu Asn Phe Pro Ile Ser
                115                 120                 125
Pro Ile Trp Gln Ala Thr Trp Ile Pro Glu Trp Lys Ala Ala Cys Trp
        130                 135                 140
Trp Ala Gly Ile Arg Gln Ala Asn Phe Leu Gly Lys Ile Trp Pro Ser
145                 150                 155                 160
His Lys Gly Arg Asn Val Trp Ala Thr His Ala Cys Val Ala Ala Glu
                165                 170                 175
Met Met Thr Ala Cys Gln Gly Val Ser Thr Val Gln Cys Thr His Gly
            180                 185                 190
Ile Ala Ala Lys Gln Met Ala Gly Asp Cys Val Ala Ala Trp Gln
        195                 200                 205
Leu Asp Cys Thr His Leu Glu Tyr Lys Ala Ala Val Asp Leu Ser His
    210                 215                 220
Phe Leu Arg Glu Lys Gly Gly Leu Glu Gly Ala Ala Tyr Tyr Met Asp
225                 230                 235                 240
Asp Leu Tyr Val Gly Ser Gly Gln Val Asp Cys Ser Pro Gly Ile Ala
                245                 250                 255
Thr Leu Glu Glu Met Met Thr Ala Glu Leu His Pro Asp Lys Trp Thr
            260                 265                 270
Val Trp Thr Val Asn Asp Ile Gln Lys Leu Gly Ile Trp Gly Cys Ser
        275                 280                 285
Gly Lys Leu Thr Val Asn Asp Ile Gln Lys Leu Val Ile Val Thr Asp
    290                 295                 300
Ser Gln Tyr Ala Leu Tyr Val Asp Arg Phe Tyr Lys Thr Leu Tyr Val
305                 310                 315                 320
Asp Arg Phe Tyr Lys Thr Leu Arg Ala Glu Gln Ala Ser Gln Glu Val
                325                 330                 335
Asp Leu Asn Thr Met Leu Asn Thr Val Lys Leu Thr Pro Leu Cys Val
            340                 345                 350
Thr Leu Tyr Gln Tyr Met Asp Asp Leu Tyr Val Val Ile Tyr Gln Tyr
        355                 360                 365
Met Asp Asp Leu Trp Ile Ile Leu Gly Leu Asn Lys Ile
    370                 375                 380

<210> SEQ ID NO 432
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 432

Met Trp Leu Gln Ser Leu Leu Leu Leu Gly Thr Val Ala Cys Ser Ile
 1               5                  10                  15

Ser Val Tyr Gln Tyr Asn Val Leu Pro Gln Gly Ala Ser Arg Glu Leu
```

```
                20                  25                  30
Glu Arg Phe Ala Val Asn Pro Gly Leu Leu Trp Ile Ile Leu Gly Leu
             35                  40                  45

Asn Lys Ile Val Arg Met Tyr Ser Pro Thr Ser Ile Ala Ala Arg Thr
 50                  55                  60

Leu Asn Ala Trp Val Lys Val Phe Leu Trp Met Gly Tyr Glu Leu His
 65                  70                  75                  80

Leu Thr Phe Gly Trp Cys Phe Lys Leu Pro Leu Trp Lys Gly Pro Ala
                 85                  90                  95

Lys Leu Val Thr Val Tyr Tyr Gly Val Pro Val Ala Ala Leu Leu Trp
                100                 105                 110

Lys Gly Glu Gly Ala Val Ala Ala Lys Leu Val Gly Lys Leu Asn
            115                 120                 125

Trp Ala Lys Leu Leu Trp Lys Gly Glu Gly Ala Thr Leu Asn Phe Pro
            130                 135                 140

Ile Ser Pro Ile Trp Gln Ala Thr Trp Ile Pro Glu Trp Lys Ala Ala
145                 150                 155                 160

Cys Trp Trp Ala Gly Ile Arg Gln Ala Asn Phe Leu Gly Lys Ile Trp
                165                 170                 175

Pro Ser His Lys Gly Arg Asn Val Trp Ala Thr His Ala Cys Val Ala
                180                 185                 190

Ala Glu Met Met Thr Ala Cys Gln Gly Val Ser Thr Val Gln Cys Thr
            195                 200                 205

His Gly Ile Ala Ala Lys Gln Met Ala Gly Asp Asp Cys Val Ala Ala
            210                 215                 220

Trp Gln Leu Asp Cys Thr His Leu Glu Tyr Lys Ala Ala Val Asp Leu
225                 230                 235                 240

Ser His Phe Leu Arg Glu Lys Gly Gly Leu Glu Gly Ala Ala Tyr Tyr
                245                 250                 255

Met Asp Asp Leu Tyr Val Gly Ser Gly Gln Val Asp Cys Ser Pro Gly
                260                 265                 270

Ile Ala Thr Leu Glu Glu Met Met Thr Ala Glu Leu His Pro Asp Lys
                275                 280                 285

Trp Thr Val Trp Thr Val Asn Asp Ile Gln Lys Leu Gly Ile Trp Gly
            290                 295                 300

Cys Ser Gly Lys Leu Thr Val Asn Asp Ile Gln Lys Leu Val Ile Val
305                 310                 315                 320

Thr Asp Ser Gln Tyr Ala Leu Tyr Val Asp Arg Phe Tyr Lys Thr Leu
                325                 330                 335

Tyr Val Asp Arg Phe Tyr Lys Thr Leu Arg Ala Glu Gln Ala Ser Gln
                340                 345                 350

Glu Val Asp Leu Asn Thr Met Leu Asn Thr Val Lys Leu Thr Pro Leu
            355                 360                 365

Cys Val Thr Leu Tyr Gln Tyr Met Asp Asp Leu Tyr Val Val Ile Tyr
            370                 375                 380

Gln Tyr Met Asp Asp Leu Trp Ile Ile Leu Gly Leu Asn Lys Ile
385                 390                 395

<210> SEQ ID NO 433
<211> LENGTH: 404
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 433

Met Asp Ala Met Lys Arg Gly Leu Cys Cys Val Leu Leu Leu Cys Gly
1               5                   10                  15

Ala Val Phe Val Ser Ala Arg Tyr Gln Tyr Asn Val Leu Pro Gln Gly
            20                  25                  30

Ala Ser Arg Glu Leu Glu Arg Phe Ala Val Asn Pro Gly Leu Leu Trp
        35                  40                  45

Ile Ile Leu Gly Leu Asn Lys Ile Val Arg Met Tyr Ser Pro Thr Ser
50                  55                  60

Ile Ala Ala Arg Thr Leu Asn Ala Trp Val Lys Val Phe Leu Trp Met
65                  70                  75                  80

Gly Tyr Glu Leu His Leu Thr Phe Gly Trp Cys Phe Lys Leu Pro Leu
                85                  90                  95

Trp Lys Gly Pro Ala Lys Leu Val Thr Val Tyr Tyr Gly Val Pro Val
            100                 105                 110

Ala Ala Leu Leu Trp Lys Gly Glu Gly Ala Val Ala Ala Lys Leu
        115                 120                 125

Val Gly Lys Leu Asn Trp Ala Lys Leu Leu Trp Lys Gly Glu Gly Ala
130                 135                 140

Thr Leu Asn Phe Pro Ile Ser Pro Ile Trp Gln Ala Thr Trp Ile Pro
145                 150                 155                 160

Glu Trp Lys Ala Ala Cys Trp Trp Ala Gly Ile Arg Gln Ala Asn Phe
                165                 170                 175

Leu Gly Lys Ile Trp Pro Ser His Lys Gly Arg Asn Val Trp Ala Thr
            180                 185                 190

His Ala Cys Val Ala Ala Glu Met Met Thr Ala Cys Gln Gly Val Ser
        195                 200                 205

Thr Val Gln Cys Thr His Gly Ile Ala Ala Lys Gln Met Ala Gly Asp
210                 215                 220

Asp Cys Val Ala Ala Trp Gln Leu Asp Cys Thr His Leu Glu Tyr Lys
225                 230                 235                 240

Ala Ala Val Asp Leu Ser His Phe Leu Arg Glu Lys Gly Gly Leu Glu
                245                 250                 255

Gly Ala Ala Tyr Tyr Met Asp Asp Leu Tyr Val Gly Ser Gly Gln Val
            260                 265                 270

Asp Cys Ser Pro Gly Ile Ala Thr Leu Glu Glu Met Thr Ala Glu
        275                 280                 285

Leu His Pro Asp Lys Trp Thr Val Trp Thr Val Asn Asp Ile Gln Lys
            290                 295                 300

Leu Gly Ile Trp Gly Cys Ser Gly Lys Leu Thr Val Asn Asp Ile Gln
305                 310                 315                 320

Lys Leu Val Ile Val Thr Asp Ser Gln Tyr Ala Leu Tyr Val Asp Arg
                325                 330                 335

Phe Tyr Lys Thr Leu Tyr Val Asp Arg Phe Tyr Lys Thr Leu Arg Ala
            340                 345                 350

Glu Gln Ala Ser Gln Glu Val Asp Leu Asn Thr Met Leu Asn Thr Val
        355                 360                 365

Lys Leu Thr Pro Leu Cys Val Thr Leu Tyr Gln Tyr Met Asp Asp Leu
            370                 375                 380

Tyr Val Val Ile Tyr Gln Tyr Met Asp Asp Leu Trp Ile Ile Leu Gly
385                 390                 395                 400

Leu Asn Lys Ile

<210> SEQ ID NO 434
<211> LENGTH: 488
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 434

```
Met Asn Pro Ser Ala Ala Val Ile Phe Cys Leu Ile Leu Leu Gly Leu
1               5                   10                  15

Ser Gly Thr Gln Gly Ile Leu Asp Met Ala Gln Pro Val Gly Ile Asn
            20                  25                  30

Thr Ser Thr Thr Cys Cys Tyr Arg Phe Ile Asn Lys Lys Ile Pro Lys
        35                  40                  45

Gln Arg Leu Glu Ser Tyr Arg Arg Thr Thr Ser Ser His Cys Pro Arg
    50                  55                  60

Glu Ala Val Ile Phe Lys Thr Lys Leu Asp Lys Glu Ile Cys Ala Asp
65                  70                  75                  80

Pro Thr Gln Lys Trp Val Gln Asp Phe Met Lys His Leu Asp Lys Lys
                85                  90                  95

Thr Gln Thr Pro Lys Leu Ala Ser Ala Gly Ala Tyr Gln Tyr Asn Val
            100                 105                 110

Leu Pro Gln Gly Ala Ser Arg Glu Leu Glu Arg Phe Ala Val Asn Pro
        115                 120                 125

Gly Leu Leu Trp Ile Ile Leu Gly Leu Asn Lys Ile Val Arg Met Tyr
    130                 135                 140

Ser Pro Thr Ser Ile Ala Ala Arg Thr Leu Asn Ala Trp Val Lys Val
145                 150                 155                 160

Phe Leu Trp Met Gly Tyr Glu Leu His Leu Thr Phe Gly Trp Cys Phe
                165                 170                 175

Lys Leu Pro Leu Trp Lys Gly Pro Ala Lys Leu Val Thr Val Tyr Tyr
            180                 185                 190

Gly Val Pro Val Ala Ala Leu Leu Trp Lys Gly Glu Gly Ala Val Ala
        195                 200                 205

Ala Ala Lys Leu Val Gly Lys Leu Asn Trp Ala Lys Leu Leu Trp Lys
    210                 215                 220

Gly Glu Gly Ala Thr Leu Asn Phe Pro Ile Ser Pro Ile Trp Gln Ala
225                 230                 235                 240

Thr Trp Ile Pro Glu Trp Lys Ala Ala Cys Trp Trp Ala Gly Ile Arg
                245                 250                 255

Gln Ala Asn Phe Leu Gly Lys Ile Trp Pro Ser His Lys Gly Arg Asn
            260                 265                 270

Val Trp Ala Thr His Ala Cys Val Ala Ala Glu Met Met Thr Ala Cys
        275                 280                 285

Gln Gly Val Ser Thr Val Gln Cys Thr His Gly Ile Ala Ala Lys Gln
    290                 295                 300

Met Ala Gly Asp Asp Cys Val Ala Ala Trp Gln Leu Asp Cys Thr His
305                 310                 315                 320

Leu Glu Tyr Lys Ala Ala Val Asp Leu Ser His Phe Leu Arg Glu Lys
                325                 330                 335

Gly Gly Leu Glu Gly Ala Ala Tyr Tyr Met Asp Asp Leu Tyr Val Gly
            340                 345                 350

Ser Gly Gln Val Asp Cys Ser Pro Gly Ile Ala Thr Leu Glu Glu Met
```

```
                355                 360                 365
Met Thr Ala Glu Leu His Pro Asp Lys Trp Thr Val Trp Thr Val Asn
            370                 375                 380

Asp Ile Gln Lys Leu Gly Ile Trp Gly Cys Ser Gly Lys Leu Thr Val
385                 390                 395                 400

Asn Asp Ile Gln Lys Leu Val Ile Val Thr Asp Ser Gln Tyr Ala Leu
                405                 410                 415

Tyr Val Asp Arg Phe Tyr Lys Thr Leu Tyr Val Asp Arg Phe Tyr Lys
                420                 425                 430

Thr Leu Arg Ala Glu Gln Ala Ser Gln Glu Val Asp Leu Asn Thr Met
            435                 440                 445

Leu Asn Thr Val Lys Leu Thr Pro Leu Cys Val Thr Leu Tyr Gln Tyr
            450                 455                 460

Met Asp Asp Leu Tyr Val Val Ile Tyr Gln Tyr Met Asp Asp Leu Trp
465                 470                 475                 480

Ile Ile Leu Gly Leu Asn Lys Ile
                485
```

<210> SEQ ID NO 435
<211> LENGTH: 412
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 435

```
Met Arg Lys Ala Ala Val Ser His Trp Gln Gln Gln Ser Tyr Leu Asp
1               5                   10                  15

Ser Gly Ile His Ser Gly Ala Thr Thr Thr Ala Pro Ser Leu Ser Tyr
            20                  25                  30

Gln Tyr Asn Val Leu Pro Gln Gly Ala Ser Arg Glu Leu Glu Arg Phe
        35                  40                  45

Ala Val Asn Pro Gly Leu Leu Trp Ile Ile Leu Gly Leu Asn Lys Ile
    50                  55                  60

Val Arg Met Tyr Ser Pro Thr Ser Ile Ala Ala Arg Thr Leu Asn Ala
65                  70                  75                  80

Trp Val Lys Val Phe Leu Trp Met Gly Tyr Glu Leu His Leu Thr Phe
                85                  90                  95

Gly Trp Cys Phe Lys Leu Pro Leu Trp Lys Gly Pro Ala Lys Leu Val
            100                 105                 110

Thr Val Tyr Tyr Gly Val Pro Val Ala Ala Leu Leu Trp Lys Gly Glu
        115                 120                 125

Gly Ala Val Ala Ala Lys Leu Val Gly Lys Leu Asn Trp Ala Lys
    130                 135                 140

Leu Leu Trp Lys Gly Glu Gly Ala Thr Leu Asn Phe Pro Ile Ser Pro
145                 150                 155                 160

Ile Trp Gln Ala Thr Trp Ile Pro Glu Trp Lys Ala Ala Cys Trp Trp
                165                 170                 175

Ala Gly Ile Arg Gln Ala Asn Phe Leu Gly Lys Ile Trp Pro Ser His
            180                 185                 190

Lys Gly Arg Asn Val Trp Ala Thr His Ala Cys Val Ala Ala Glu Met
        195                 200                 205

Met Thr Ala Cys Gln Gly Val Ser Thr Val Gln Cys Thr His Gly Ile
    210                 215                 220
```

```
Ala Ala Lys Gln Met Ala Gly Asp Asp Cys Val Ala Trp Gln Leu
225                 230                 235                 240

Asp Cys Thr His Leu Glu Tyr Lys Ala Ala Val Asp Leu Ser His Phe
            245                 250                 255

Leu Arg Glu Lys Gly Gly Leu Glu Gly Ala Ala Tyr Tyr Met Asp Asp
        260                 265                 270

Leu Tyr Val Gly Ser Gly Gln Val Asp Cys Ser Pro Gly Ile Ala Thr
    275                 280                 285

Leu Glu Glu Met Met Thr Ala Glu Leu His Pro Asp Lys Trp Thr Val
    290                 295                 300

Trp Thr Val Asn Asp Ile Gln Lys Leu Gly Ile Trp Gly Cys Ser Gly
305                 310                 315                 320

Lys Leu Thr Val Asn Asp Ile Gln Lys Leu Val Ile Val Thr Asp Ser
                325                 330                 335

Gln Tyr Ala Leu Tyr Val Asp Arg Phe Tyr Lys Thr Leu Tyr Val Asp
            340                 345                 350

Arg Phe Tyr Lys Thr Leu Arg Ala Glu Gln Ala Ser Gln Glu Val Asp
        355                 360                 365

Leu Asn Thr Met Leu Asn Thr Val Lys Leu Thr Pro Leu Cys Val Thr
    370                 375                 380

Leu Tyr Gln Tyr Met Asp Asp Leu Tyr Val Val Ile Tyr Gln Tyr Met
385                 390                 395                 400

Asp Asp Leu Trp Ile Ile Leu Gly Leu Asn Lys Ile
                405                 410

<210> SEQ ID NO 436
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Asp Tyr Lys Asp Asp Asp Asp Lys Leu
1               5

<210> SEQ ID NO 437
<211> LENGTH: 27
<212> TYPE: PRT
<213> ORGANISM: Human immunodeficiency virus

<400> SEQUENCE: 437

Met Arg Val Lys Glu Lys Tyr Gln His Leu Trp Arg Trp Gly Trp Arg
1               5                   10                  15

Trp Gly Thr Met Leu Leu Gly Met Leu Met Ile
            20                  25

<210> SEQ ID NO 438
<211> LENGTH: 6
<212> TYPE: PRT
<213> ORGANISM: Human immunodeficiency virus

<400> SEQUENCE: 438

Phe Cys Ala Ser Asp Ala
1               5

<210> SEQ ID NO 439
<211> LENGTH: 29
<212> TYPE: PRT
```

```
<213> ORGANISM: Human immunodeficiency virus

<400> SEQUENCE: 439

Val Val Leu Val Asn Val Thr Glu Asn Phe Asn Met Trp Lys Asn Asp
1               5                   10                  15

Met Val Glu Gln Met His Glu Asp Ile Ile Ser Leu Trp
            20                  25

<210> SEQ ID NO 440
<211> LENGTH: 96
<212> TYPE: PRT
<213> ORGANISM: Human immunodeficiency virus

<400> SEQUENCE: 440

Asn Thr Asn Ser Ser Gly Arg Met Ile Met Glu Lys Gly Glu Ile
1               5                   10                  15

Lys Asn Cys Ser Phe Asn Ile Ser Thr Ser Ile Arg Gly Lys Val Gln
            20                  25                  30

Lys Glu Tyr Ala Phe Phe Tyr Lys Leu Asp Ile Ile Pro Ile Asp Asn
        35                  40                  45

Asp Thr Thr Ser Tyr Lys Leu Thr Ser Cys Asn Thr Ser Val Ile Thr
    50                  55                  60

Gln Ala Cys Pro Lys Val Ser Phe Glu Pro Ile Pro Ile His Tyr Cys
65                  70                  75                  80

Ala Pro Ala Gly Phe Ala Ile Leu Lys Cys Asn Asn Lys Thr Phe Asn
                85                  90                  95

<210> SEQ ID NO 441
<211> LENGTH: 206
<212> TYPE: PRT
<213> ORGANISM: Human immunodeficiency virus

<400> SEQUENCE: 441

Glu Val Val Ile Arg Ser Val Asn Phe Thr Asp Asn Ala Lys Thr Ile
1               5                   10                  15

Ile Val Gln Leu Asn Thr Ser Val Glu Ile Asn Cys Thr Arg Pro Asn
            20                  25                  30

Asn Asn Thr Arg Lys Arg Ile Arg Ile Gln Arg Gly Pro Gly Arg Ala
        35                  40                  45

Phe Val Thr Ile Gly Lys Ile Gly Asn Met Arg Gln Ala His Cys Asn
    50                  55                  60

Ile Ser Arg Ala Lys Trp Asn Asn Thr Leu Lys Gln Ile Ala Ser Lys
65                  70                  75                  80

Leu Arg Glu Gln Phe Gly Asn Asn Lys Thr Ile Ile Phe Lys Gln Ser
                85                  90                  95

Ser Gly Gly Asp Pro Glu Ile Val Thr His Ser Phe Asn Cys Gly Gly
                100                 105                 110

Glu Phe Phe Tyr Cys Asn Ser Thr Gln Leu Phe Asn Ser Thr Trp Phe
                115                 120                 125

Asn Ser Thr Trp Ser Thr Glu Gly Ser Asn Asn Thr Glu Gly Ser Asp
        130                 135                 140

Thr Ile Thr Leu Pro Cys Arg Ile Lys Gln Ile Ile Asn Met Trp Gln
145                 150                 155                 160

Lys Val Gly Lys Ala Met Tyr Ala Pro Pro Ile Ser Gly Gln Ile Arg
                165                 170                 175

Cys Ser Ser Asn Ile Thr Gly Leu Leu Leu Thr Arg Asp Gly Gly Asn
                180                 185                 190
```

```
Ser Asn Asn Glu Ser Glu Ile Phe Arg Pro Gly Gly Gly Asp
        195                 200                 205

<210> SEQ ID NO 442
<211> LENGTH: 12
<212> TYPE: PRT
<213> ORGANISM: Human immunodeficiency virus

<400> SEQUENCE: 442

Lys Ile Glu Pro Leu Gly Val Ala Pro Thr Lys Ala
1               5                   10

<210> SEQ ID NO 443
<211> LENGTH: 246
<212> TYPE: PRT
<213> ORGANISM: Human immunodeficiency virus

<400> SEQUENCE: 443

Asn Ala Ser Trp Ser Asn Lys Ser Leu Glu Gln Ile Trp Asn His Thr
1               5                   10                  15

Thr Trp Met Glu Trp Asp Arg Glu Ile Asn Asn Tyr Thr Ser Leu Ile
            20                  25                  30

His Ser Leu Ile Glu Glu Ser Gln Asn Gln Glu Lys Asn Glu Gln
        35                  40                  45

Glu Leu Leu Glu Leu Asp Lys Trp Ala Ser Leu Trp Asn Trp Phe Asn
50                  55                  60

Ile Thr Asn Trp Leu Trp Tyr Ile Lys Leu Phe Ile Met Ile Val Gly
65                  70                  75                  80

Gly Leu Val Gly Leu Arg Ile Val Phe Ala Val Leu Ser Ile Val Asn
            85                  90                  95

Arg Val Arg Gln Gly Tyr Ser Pro Leu Ser Phe Gln Thr His Leu Pro
        100                 105                 110

Thr Pro Arg Gly Pro Asp Arg Pro Glu Gly Ile Glu Glu Glu Gly Gly
        115                 120                 125

Glu Arg Asp Arg Asp Arg Ser Ile Arg Leu Val Asn Gly Ser Leu Ala
130                 135                 140

Leu Ile Trp Asp Asp Leu Arg Ser Leu Cys Leu Phe Ser Tyr His Arg
145                 150                 155                 160

Leu Arg Asp Leu Leu Leu Ile Val Thr Arg Ile Val Glu Leu Leu Gly
                165                 170                 175

Arg Arg Gly Trp Glu Ala Leu Lys Tyr Trp Trp Asn Leu Leu Gln Tyr
            180                 185                 190

Trp Ser Gln Glu Leu Lys Asn Ser Ala Val Ser Leu Leu Asn Ala Thr
        195                 200                 205

Ala Ile Ala Val Ala Glu Gly Thr Asp Arg Val Ile Glu Val Val Gln
        210                 215                 220

Gly Ala Cys Arg Ala Ile Arg His Ile Pro Arg Arg Ile Arg Gln Gly
225                 230                 235                 240

Leu Glu Arg Ile Leu Leu
                245

<210> SEQ ID NO 444
<211> LENGTH: 30
<212> TYPE: PRT
<213> ORGANISM: Human immunodeficiency virus

<400> SEQUENCE: 444
```

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys
            20                  25                  30
```

<210> SEQ ID NO 445
<211> LENGTH: 74
<212> TYPE: PRT
<213> ORGANISM: Human immunodeficiency virus

<400> SEQUENCE: 445

```
Ser Glu Gly Cys Arg Gln Ile Leu Gly Gln Leu Gln Pro Ser Leu Gln
1               5                   10                  15

Thr Gly Ser Glu Glu Leu Arg Ser Leu Tyr Asn Thr Val Ala Thr Leu
            20                  25                  30

Tyr Cys Val His Gln Arg Ile Glu Ile Lys Asp Thr Lys Glu Ala Leu
                35                  40                  45

Asp Lys Ile Glu Glu Glu Gln Asn Lys Ser Lys Lys Lys Ala Gln Gln
    50                  55                  60

Ala Ala Ala Asp Thr Gly His Ser Asn Gln
65                  70
```

<210> SEQ ID NO 446
<211> LENGTH: 9
<212> TYPE: PRT
<213> ORGANISM: Human immunodeficiency virus

<400> SEQUENCE: 446

```
Ile Gln Gly Gln Met Val His Gln Ala
1               5
```

<210> SEQ ID NO 447
<211> LENGTH: 59
<212> TYPE: PRT
<213> ORGANISM: Human immunodeficiency virus

<400> SEQUENCE: 447

```
Val Thr Asn Ser Ala Thr Ile Met Met Gln Arg Gly Asn Phe Arg Asn
1               5                   10                  15

Gln Arg Lys Ile Val Lys Cys Phe Asn Cys Gly Lys Glu Gly His Thr
            20                  25                  30

Ala Arg Asn Cys Arg Ala Pro Arg Lys Lys Gly Cys Trp Lys Cys Gly
                35                  40                  45

Lys Glu Gly His Gln Met Lys Asp Cys Thr Glu
    50                  55
```

<210> SEQ ID NO 448
<211> LENGTH: 56
<212> TYPE: PRT
<213> ORGANISM: Human immunodeficiency virus

<400> SEQUENCE: 448

```
Pro Gly Asn Phe Leu Gln Ser Arg Pro Glu Pro Thr Ala Pro Pro Glu
1               5                   10                  15

Glu Ser Phe Arg Ser Gly Val Glu Thr Thr Thr Pro Pro Gln Lys Gln
            20                  25                  30

Glu Pro Ile Asp Lys Glu Leu Tyr Pro Leu Thr Ser Leu Arg Ser Leu
                35                  40                  45

Phe Gly Asn Asp Pro Ser Ser Gln
    50                  55
```

<210> SEQ ID NO 449
<211> LENGTH: 63
<212> TYPE: PRT
<213> ORGANISM: Human immunodeficiency virus

<400> SEQUENCE: 449

Met Gly Gly Lys Trp Ser Lys Ser Ser Val Ile Gly Trp Pro Thr Val
1               5                   10                  15

Arg Glu Arg Met Arg Arg Ala Glu Pro Ala Ala Asp Arg Val Gly Ala
                20                  25                  30

Ala Ser Arg Asp Leu Glu Lys His Gly Ala Ile Thr Ser Ser Asn Thr
            35                  40                  45

Ala Ala Thr Asn Ala Ala Cys Ala Trp Leu Glu Ala Gln Glu Glu
        50                  55                  60

<210> SEQ ID NO 450
<211> LENGTH: 17
<212> TYPE: PRT
<213> ORGANISM: Human immunodeficiency virus

<400> SEQUENCE: 450

Leu Ile His Ser Gln Arg Arg Gln Asp Ile Leu Asp Leu Trp Ile Tyr
1               5                   10                  15

His

<210> SEQ ID NO 451
<211> LENGTH: 76
<212> TYPE: PRT
<213> ORGANISM: Human immunodeficiency virus

<400> SEQUENCE: 451

Pro Gly Val Arg Tyr Pro Leu Thr Phe Gly Trp Cys Tyr Lys Leu Val
1               5                   10                  15

Pro Val Glu Pro Asp Lys Ile Glu Glu Ala Asn Lys Gly Glu Asn Thr
                20                  25                  30

Ser Leu Leu His Pro Val Ser Leu His Gly Met Asp Asp Pro Glu Arg
            35                  40                  45

Glu Val Leu Glu Trp Arg Phe Asp Ser Arg Leu Ala Phe His His Val
        50                  55                  60

Ala Arg Glu Leu His Pro Glu Tyr Phe Lys Asn Cys
65                  70                  75

<210> SEQ ID NO 452
<211> LENGTH: 55
<212> TYPE: PRT
<213> ORGANISM: Human immunodeficiency virus

<400> SEQUENCE: 452

Phe Phe Arg Glu Asp Leu Ala Phe Leu Gln Gly Lys Ala Arg Glu Phe
1               5                   10                  15

Ser Ser Glu Gln Thr Arg Ala Asn Ser Pro Thr Arg Arg Glu Leu Gln
                20                  25                  30

Val Trp Gly Arg Asp Asn Asn Ser Pro Ser Glu Ala Gly Ala Asp Arg
            35                  40                  45

Gln Gly Thr Val Ser Phe Asn
        50                  55

<210> SEQ ID NO 453

-continued

```
<211> LENGTH: 11
<212> TYPE: PRT
<213> ORGANISM: Human immunodeficiency virus

<400> SEQUENCE: 453

Ile Leu Ile Glu Ile Cys Gly His Lys Ala Ile
1               5                   10

<210> SEQ ID NO 454
<211> LENGTH: 5
<212> TYPE: PRT
<213> ORGANISM: Human immunodeficiency virus

<400> SEQUENCE: 454

Lys Ile Leu Glu Pro
1               5

<210> SEQ ID NO 455
<211> LENGTH: 12
<212> TYPE: PRT
<213> ORGANISM: Human immunodeficiency virus

<400> SEQUENCE: 455

Thr Lys Ile Glu Glu Leu Arg Gln His Leu Leu Arg
1               5                   10

<210> SEQ ID NO 456
<211> LENGTH: 109
<212> TYPE: PRT
<213> ORGANISM: Human immunodeficiency virus

<400> SEQUENCE: 456

Gln Leu Cys Lys Leu Leu Arg Gly Thr Lys Ala Leu Thr Glu Val Ile
1               5                   10                  15

Pro Leu Thr Glu Glu Ala Glu Leu Glu Leu Ala Glu Asn Arg Glu Ile
                20                  25                  30

Leu Lys Glu Pro Val His Gly Val Tyr Tyr Asp Pro Ser Lys Asp Leu
            35                  40                  45

Ile Ala Glu Ile Gln Lys Gln Gly Gln Gly Gln Trp Thr Tyr Gln Ile
    50                  55                  60

Tyr Gln Glu Pro Phe Lys Asn Leu Lys Thr Gly Lys Tyr Ala Arg Met
65                  70                  75                  80

Arg Gly Ala His Thr Asn Asp Val Lys Gln Leu Thr Glu Ala Val Gln
                85                  90                  95

Lys Ile Thr Thr Glu Ser Ile Val Ile Trp Gly Lys Thr
            100                 105

<210> SEQ ID NO 457
<211> LENGTH: 35
<212> TYPE: PRT
<213> ORGANISM: Human immunodeficiency virus

<400> SEQUENCE: 457

Leu Gly Lys Ala Gly Tyr Val Thr Asn Arg Gly Arg Gln Lys Val Val
1               5                   10                  15

Thr Leu Thr Asp Thr Thr Asn Gln Lys Thr Glu Leu Gln Ala Ile Tyr
                20                  25                  30

Leu Ala Leu
        35

<210> SEQ ID NO 458
```

```
<211> LENGTH: 16
<212> TYPE: PRT
<213> ORGANISM: Human immunodeficiency virus

<400> SEQUENCE: 458

Gln Ser Glu Ser Glu Leu Val Asn Gln Ile Ile Glu Gln Leu Ile Lys
1               5                   10                  15

<210> SEQ ID NO 459
<211> LENGTH: 37
<212> TYPE: PRT
<213> ORGANISM: Human immunodeficiency virus

<400> SEQUENCE: 459

Gly Ile Arg Lys Val Leu Phe Leu Asp Gly Ile Asp Lys Ala Gln Asp
1               5                   10                  15

Glu His Glu Lys Tyr His Ser Asn Trp Arg Ala Met Ala Ser Asp Phe
            20                  25                  30

Asn Leu Pro Pro Val
        35

<210> SEQ ID NO 460
<211> LENGTH: 6
<212> TYPE: PRT
<213> ORGANISM: Human immunodeficiency virus

<400> SEQUENCE: 460

Ile His Thr Asp Asn Gly
1               5

<210> SEQ ID NO 461
<211> LENGTH: 10
<212> TYPE: PRT
<213> ORGANISM: Human immunodeficiency virus

<400> SEQUENCE: 461

Thr Asp Ile Gln Thr Lys Glu Leu Gln Lys
1               5                   10

<210> SEQ ID NO 462
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Tyr Met Asp Asp
1

<210> SEQ ID NO 463
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Tyr Val Asp Asp
1

<210> SEQ ID NO 464
<211> LENGTH: 9
```

```
-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Ala Ile Ile Ile Ile Ile Ile Ile Ser
1               5

<210> SEQ ID NO 465
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Met Ile Ile Ile Ile Ile Ile Ile Ile
1               5

<210> SEQ ID NO 466
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Ile Ile Ile Ile Ile Ile Ile Ser Lys
1               5

<210> SEQ ID NO 467
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Ile Ile Ile Ile Ile Ile Ile Ile Arg
1               5

<210> SEQ ID NO 468
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Ala Ile Ile Ile Ile Ile Ile Ile Ser Lys
1               5                   10

<210> SEQ ID NO 469
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Met Ile Ile Ile Ile Ile Ile Ile Ile Arg
```

```
1               5                  10
```

<210> SEQ ID NO 470
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This sequence may encompass 2-4 residues

<400> SEQUENCE: 470

```
Ala Ala Ala Ala
1
```

<210> SEQ ID NO 471
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

```
Gly Ile Ile Ile Ile Ile Ile Ile Ile Lys
1               5                  10
```

<210> SEQ ID NO 472
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

```
Ala Ile Ile Ile Ile Ile Ile Ile Ile His
1               5                  10
```

<210> SEQ ID NO 473
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

```
Gly Ile Ile Ile Ile Ile Ile Ile Ile His
1               5                  10
```

<210> SEQ ID NO 474
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

```
Ala Ile Ile Ile Ile Ile Ile Ile Ile Lys
1               5                  10
```

<210> SEQ ID NO 475
<211> LENGTH: 27

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Gln Asn Leu Gln Gly Gln Met Val His Gln Ala Ile Ser Pro Arg Thr
1               5                   10                  15

Leu Asn Ala Trp Val Lys Val Val Lys Ala Phe
            20                  25

<210> SEQ ID NO 476
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Gln Asn Leu Gln Gly Gln Met Val His Gln Ala Ile Ser Pro Arg Thr
1               5                   10                  15

Leu Asn Ala Trp Val Lys Val Glu Lys Ala Phe
            20                  25

<210> SEQ ID NO 477
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Gln Asn Leu Gln Gly Gln Met Val His Gln Ala Ile Ser Pro Arg Thr
1               5                   10                  15

Leu Asn Ala Trp Val Lys Ile Val Lys Ala Phe
            20                  25

<210> SEQ ID NO 478
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Gln Asn Ile Gln Gly Gln Met Val His Gln Ala Ile Ser Pro Arg Thr
1               5                   10                  15

Leu Asn Ala Trp Val Lys Ile Glu Lys Ala Phe
            20                  25

<210> SEQ ID NO 479
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Gln Asn Ile Gln Gly Gln Met Val His Gln Ala Ile Ser Pro Arg Thr
1               5                   10                  15
```

```
Leu Asn Ala Trp Val Lys Val Val Lys Ala Phe
            20                  25

<210> SEQ ID NO 480
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Pro Asn Ile Gln Gly Gln Met Val His Gln Ala Ile Ser Pro Arg Thr
1               5                   10                  15

Leu Asn Ala Trp Val Lys Ile Val Lys Ala Phe
            20                  25

<210> SEQ ID NO 481
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Gln Asn Leu Gln Gly Gln Met Val His
1               5

<210> SEQ ID NO 482
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Gln Asn Ile Gln Gly Gln Met Val His
1               5

<210> SEQ ID NO 483
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Pro Asn Ile Gln Gly Gln Met Val His
1               5

<210> SEQ ID NO 484
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Gly Ile Ile Ile Ile Ile Ile Ile Ile Arg
1               5                   10

<210> SEQ ID NO 485
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Gly Ile Ile Ile Ile Ile Ile Ile Ile
1               5

<210> SEQ ID NO 486
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Ala Ile Ile Ile Ile Ile Ile Ile Ile
1               5

<210> SEQ ID NO 487
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Ile Ile Ile Ile Ile Ile Ile Ile Lys
1               5

<210> SEQ ID NO 488
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Ile Ile Ile Ile Ile Ile Ile Ile His
1               5

<210> SEQ ID NO 489
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Gln Ala Ile Ser Pro Arg Thr Leu Asn
1               5

<210> SEQ ID NO 490
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Gln Asn Leu Gln Gly Gln Met Val His Gln Ala Thr Ser Pro Arg Thr
```

```
                1               5                  10                  15
Leu Asn Ala Trp Val Lys Val Val Lys Ala Phe
            20                  25

<210> SEQ ID NO 491
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Gln Ala Thr Ser Pro Arg Thr Leu Asn
1               5

<210> SEQ ID NO 492
<211> LENGTH: 9
<212> TYPE: PRT
<213> ORGANISM: Human immunodeficiency virus

<400> SEQUENCE: 492

His Pro Pro Gln Ala Gly Pro Val Ala
1               5

<210> SEQ ID NO 493
<211> LENGTH: 9
<212> TYPE: PRT
<213> ORGANISM: Homo sapiens

<400> SEQUENCE: 493

Val Pro Leu Gln Ala Gly Pro Val Gln
1               5

<210> SEQ ID NO 494
<211> LENGTH: 9
<212> TYPE: PRT
<213> ORGANISM: Homo sapiens

<400> SEQUENCE: 494

Met Pro Gly Gln Ala Gly Pro Val Gly
1               5

<210> SEQ ID NO 495
<211> LENGTH: 9
<212> TYPE: PRT
<213> ORGANISM: Homo sapiens

<400> SEQUENCE: 495

Gln Tyr Arg Gln Ala Gly Pro Val Ile
1               5

<210> SEQ ID NO 496
<211> LENGTH: 9
<212> TYPE: PRT
<213> ORGANISM: Homo sapiens

<400> SEQUENCE: 496

Thr Ala Thr Gln Ala Gly Leu Val Phe
1               5

<210> SEQ ID NO 497
<211> LENGTH: 9
<212> TYPE: PRT
<213> ORGANISM: Homo sapiens
```

<400> SEQUENCE: 497

His Thr Lys Gln Ala Gly Leu Val Val
1               5

<210> SEQ ID NO 498
<211> LENGTH: 9
<212> TYPE: PRT
<213> ORGANISM: Homo sapiens

<400> SEQUENCE: 498

Gly Thr Arg Gln Ala Gly Leu Val Ala
1               5

<210> SEQ ID NO 499
<211> LENGTH: 9
<212> TYPE: PRT
<213> ORGANISM: Human immunodeficiency virus

<400> SEQUENCE: 499

Ile Ser Pro Arg Thr Leu Asn Ala Trp
1               5

<210> SEQ ID NO 500
<211> LENGTH: 9
<212> TYPE: PRT
<213> ORGANISM: Human immunodeficiency virus

<400> SEQUENCE: 500

Met Phe Ser Ala Leu Ser Glu Gly Ala
1               5

<210> SEQ ID NO 501
<211> LENGTH: 9
<212> TYPE: PRT
<213> ORGANISM: Human immunodeficiency virus

<400> SEQUENCE: 501

Ile Leu Asp Ile Arg Gln Gly Pro Lys
1               5

<210> SEQ ID NO 502
<211> LENGTH: 9
<212> TYPE: PRT
<213> ORGANISM: Human immunodeficiency virus

<400> SEQUENCE: 502

Leu Ser Pro Arg Thr Leu Asn Ala Trp
1               5

<210> SEQ ID NO 503
<211> LENGTH: 9
<212> TYPE: PRT
<213> ORGANISM: Human immunodeficiency virus

<400> SEQUENCE: 503

Met Phe Ser Ala Leu Ser Tyr Gly Ala
1               5

<210> SEQ ID NO 504
<211> LENGTH: 9
<212> TYPE: PRT
<213> ORGANISM: Human immunodeficiency virus

<400> SEQUENCE: 504

```
Ile Leu Asp Ile Arg Arg Gly Pro Lys
1               5

<210> SEQ ID NO 505
<211> LENGTH: 9
<212> TYPE: PRT
<213> ORGANISM: Human immunodeficiency virus

<400> SEQUENCE: 505

Ala Thr Leu Glu Glu Met Val Thr Ala
1               5

<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Ile Leu Asp Thr Arg Gln Gly Pro Lys
1               5

<210> SEQ ID NO 507
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Ala Thr Leu Val Glu Met Met Thr Ala
1               5

<210> SEQ ID NO 508
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Ile Leu Ser Ile Arg Gln Gly Pro Lys
1               5

<210> SEQ ID NO 509
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Ala Thr Ser Glu Glu Met Met Thr Ala
1               5

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<221> NAME/KEY: MOD_RES
<222> LOCATION: (8)..(8)
<223> OTHER INFORMATION: Any amino acid

<400> SEQUENCE: 510

Ile Leu Asp Ile Arg Gln Gly Xaa Lys
1               5

<210> SEQ ID NO 511
<211> LENGTH: 109
<212> TYPE: PRT
<213> ORGANISM: Human immunodeficiency virus

<400> SEQUENCE: 511

Lys Arg Arg Val Val Gln Arg Glu Lys Arg Ala Val Gly Ile Gly Ala
1               5                   10                  15

Met Phe Leu Gly Phe Leu Gly Ala Ala Gly Ser Thr Met Gly Ala Ala
                20                  25                  30

Ser Ile Thr Leu Thr Val Gln Ala Arg Gln Leu Leu Ser Gly Ile Val
            35                  40                  45

Gln Gln Gln Asn Asn Leu Leu Arg Ala Ile Glu Ala Gln Gln His Leu
    50                  55                  60

Leu Gln Leu Thr Val Trp Gly Ile Lys Gln Leu Gln Ala Arg Val Leu
65                  70                  75                  80

Ala Val Glu Arg Tyr Leu Lys Asp Gln Gln Leu Leu Gly Ile Trp Gly
                85                  90                  95

Cys Ser Gly Lys Leu Ile Cys Thr Thr Ala Val Pro Trp
            100                 105

<210> SEQ ID NO 512
<211> LENGTH: 21
<212> TYPE: PRT
<213> ORGANISM: Human immunodeficiency virus

<400> SEQUENCE: 512

Tyr Leu Lys Asp Gln Gln Leu Leu Gly Ile Trp Gly Cys Ser Gly Lys
1               5                   10                  15

Leu Ile Cys Thr Thr
            20

<210> SEQ ID NO 513
<211> LENGTH: 35
<212> TYPE: PRT
<213> ORGANISM: Human immunodeficiency virus

<400> SEQUENCE: 513

Glu Glu Val Gly Phe Pro Val Lys Pro Gln Val Pro Leu Arg Pro Met
1               5                   10                  15

Thr Phe Lys Gly Ala Leu Asp Leu Ser His Phe Leu Arg Glu Lys Gly
                20                  25                  30

Gly Leu Glu
        35

<210> SEQ ID NO 514
<211> LENGTH: 14
<212> TYPE: PRT
<213> ORGANISM: Human immunodeficiency virus

<400> SEQUENCE: 514

Thr Gln Gly Phe Phe Pro Asp Trp Gln Asn Tyr Thr Pro Glu

```
<210> SEQ ID NO 515
<211> LENGTH: 18
<212> TYPE: PRT
<213> ORGANISM: Human immunodeficiency virus

<400> SEQUENCE: 515

Pro Gly Ile Arg Phe Pro Leu Thr Phe Gly Trp Cys Phe Lys Leu Val
1               5                   10                  15

Pro Leu

<210> SEQ ID NO 516
<211> LENGTH: 21
<212> TYPE: PRT
<213> ORGANISM: Human immunodeficiency virus

<400> SEQUENCE: 516

Val Thr Val Leu Asp Val Gly Asp Ala Tyr Phe Ser Val Pro Leu Asp
1               5                   10                  15

Lys Asp Phe Arg Lys
            20

<210> SEQ ID NO 517
<211> LENGTH: 8
<212> TYPE: PRT
<213> ORGANISM: Human immunodeficiency virus

<400> SEQUENCE: 517

Tyr Thr Ala Phe Thr Ile Pro Ser
1               5

<210> SEQ ID NO 518
<211> LENGTH: 8
<212> TYPE: PRT
<213> ORGANISM: Human immunodeficiency virus

<400> SEQUENCE: 518

Val Ile Tyr Gln Tyr Met Asp Asp
1               5

<210> SEQ ID NO 519
<211> LENGTH: 78
<212> TYPE: PRT
<213> ORGANISM: Human immunodeficiency virus

<400> SEQUENCE: 519

Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp
65                  70                  75
```

What is claimed is:

1. A fusion polypeptide comprising an amino acid sequence of any one of SEQ ID NOs: 345-350, or a sequence that is at least 90%, 91%, 92%, 93%, 94%, 95%, 96%, 97%, 98%, or 99% identical to the full length of any one of SEQ ID NOs: 345-350, wherein the full-length of the fusion polypeptide comprises polypeptide segments encoded by HIV-1 genes Gag, Nef and Pol, is at least about 700 amino acids and up to about 800 amino acids in length, and wherein the fusion polypeptide is capable of inducing, promoting or stimulating proliferation and/or activation of one or more cell types selected from monocyte-derived dendritic cells (DCs), CD8+ T cells and CD4+ T cells.

2. The fusion polypeptide of claim 1, wherein the fusion polypeptide does not comprise and HIV-1 Pol polypeptide segment comprising the amino acid sequence YMDD (SEQ ID NO: 462) or YVDD (SEQ ID NO: 463).

3. The fusion polypeptide of claim 1, comprising an N-terminal signal peptide or leader sequence.

4. The fusion polypeptide of claim 3, wherein the signal peptide or leader sequence is from a source protein selected from the group consisting of: colony stimulating factor 2 (CSF2, GM-CSF), tissue type plasminogen activator (PLAT, t-PA), C-C motif chemokine ligand 7 (CCL7, MCP-3), C-X-C motif chemokine ligand 10 (CXCL10, IP-10), catenin beta 1 (CTNNB1), CD74 (p33; DHLAG; HLADG; Ia-GAMMA, invariant chain), serum albumin (ALB), polyubiquitin B/C (UBB/UBC), calreticulin (CALR), vesicular stomatitis virus G protein (VSV-G), lysosomal associated membrane protein 1 (LAMP-1) and lysosomal associated membrane protein 2 (LAMP-2).

5. A polynucleotide encoding one or more fusion polypeptides of claim 1.

6. An expression cassette, comprising a polynucleotide of claim 5 operably linked to one or more regulatory sequences.

7. A vector comprising one or more polynucleotides of claim 5.

8. The vector of claim 7, wherein the vector is a plasmid vector, a bacterial vector or a viral vector.

9. A host cell comprising one or more polynucleotides of claim 5.

10. An immunogenic composition comprising one or more of the fusion polypeptides of claim 1, and a pharmaceutically acceptable carrier.

11. A pharmaceutical composition comprising one or more of the fusion polypeptides of claim 1, and a pharmaceutically acceptable carrier.

12. The pharmaceutical composition of claim 11, comprising two or more fusion polypeptides.

* * * * *